(12) United States Patent
Ishizuka et al.

(10) Patent No.: US 8,178,681 B2
(45) Date of Patent: May 15, 2012

(54) 3-CARBAMOYL-2-PYRIDONE DERIVATIVES

(75) Inventors: Natsuki Ishizuka, Osaka (JP);
Yoshiharu Hiramatsu, Osaka (JP);
Yasuhiko Fujii, Osaka (JP); Yoshikazu Fukui, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 1186 days.

(21) Appl. No.: 11/628,804

(22) PCT Filed: Oct. 28, 2005

(86) PCT No.: PCT/JP2005/020248
§ 371 (c)(1),
(2), (4) Date: Aug. 29, 2007

(87) PCT Pub. No.: WO2006/046778
PCT Pub. Date: May 4, 2006

(65) Prior Publication Data
US 2008/0103139 A1    May 1, 2008

(30) Foreign Application Priority Data

Oct. 28, 2004 (JP) .................................. 2004-313947
May 31, 2005 (JP) .................................. 2005-159995

(51) Int. Cl.
*C07D 221/04*    (2006.01)
*C07D 213/62*    (2006.01)
*A61K 31/54*    (2006.01)
*A61K 31/435*    (2006.01)

(52) U.S. Cl. ...................... 546/183; 546/295; 514/227.2; 514/235.2

(58) Field of Classification Search .................. None
See application file for complete search history.

(56) References Cited

U.S. PATENT DOCUMENTS

| | | | |
|---|---|---|---|
| 7,420,030 B2 * | 9/2008 | Arap et al. ..................... 530/300 |
| 2003/0191069 A1 | 10/2003 | Inaba et al. | |
| 2003/0232855 A1 | 12/2003 | Iwamura et al. | |
| 2004/0077643 A1 | 4/2004 | Ogawa et al. | |
| 2004/0082619 A1 * | 4/2004 | Tada et al. ..................... 514/340 |
| 2005/0009902 A1 | 1/2005 | Miyaji et al. | |
| 2005/0101590 A1 | 5/2005 | Yasui et al. | |

FOREIGN PATENT DOCUMENTS

| WO | WO 99/02499 | 1/1999 |
|---|---|---|
| WO | WO 00/66104 | 11/2000 |
| WO | WO 01/21577 A2 | 3/2001 |
| WO | WO 02/39997 A2 | 5/2002 |
| WO | WO 02/053543 A1 | 7/2002 |
| WO | WO 02/065997 A1 | 8/2002 |
| WO | WO 03/007901 A1 | 1/2003 |
| WO | WO 03/049727 A1 | 6/2003 |
| WO | WO 03/070277 A1 | 8/2003 |
| WO | WO 2004/103974 A1 | 12/2004 |
| WO | WO 2004/104000 A1 | 12/2004 |
| WO | WO 2005/014533 A2 | 2/2005 |
| WO | WO 2005/023771 A1 | 3/2005 |
| WO | WO 2005/074939 A1 | 8/2005 |
| WO | WO 2005/099688 A2 | 10/2005 |

OTHER PUBLICATIONS

P. H. Reggio "Endocannabinoid structure-activity relationships for interaction at the cannabinoid receptors" Prostaglandins, Leukotrienes and Essential Fatty Acids 2002, 66, 143-160.*
Vippagunta et al., "Crystalline Solids", 48 Adv. Drug Delivery Rev. 3-26 (2001).*
International Preliminary Report on Patentability issued in PCT/JP2005/020248, from the International Bureau of WIPO dated May 10, 2007, 10 pages.
Munro, et al., "Molecular characterization of a peripheral receptor for cannabinoids", Letters To Nature, vol. 365, pp. 61-65, (Sep. 2, 1993).
"Japanese dermatology association's atopic dermatitis treatment guideline, 2004 revised edition", Japanese skin society magazine, pp. 135-142, (2004).

* cited by examiner

*Primary Examiner* — Janet L. Andres
*Assistant Examiner* — Timothy R Rozof
(74) *Attorney, Agent, or Firm* — Finnegan, Henderson, Farabow, Garrett & Dunner LLP

(57) ABSTRACT

The present invention provides compounds having an agonistic activity to the cannabinoid receptor, which is represented by the formula (I):

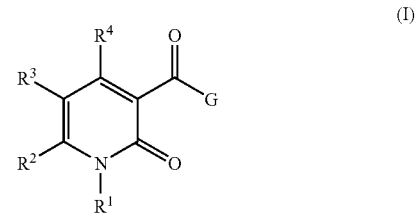

wherein $R^1$ is optionally substituted C1-C8 alkyl and the like; $R^2$ is C1-C6 alkyl; $R^3$ is C1-C6 alkyl and the like; or $R^2$ and $R^3$ taken together with may form an optionally substituted 5 to 10 membered non-aromatic carbon ring; $R^4$ is hydrogen and the like; G is a group selected from the groups shown by the formula an the like:

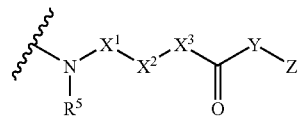

wherein $R^5$ is hydrogen and the like; $X^1$ is a single bond and the like; $X^2$ is optionally substituted C1-C8 alkylene that may be replaced by one or two groups of —O—, or —N($R^6$)—, wherein $R^6$ is hydrogen and the like, and the like; $X^3$ is a single bond and the like;
a pharmaceutically acceptable salt or a solvate thereof, and pharmaceutical compositions, atopic dermatitis treating agents, and anti-pruritus agents, especially anti-pruritus agents for oral used and for external application, which each contains the said compound as an active ingredient.

5 Claims, No Drawings

3-CARBAMOYL-2-PYRIDONE DERIVATIVES

TECHNICAL FIELD

The present invention relates to 3-carbamoyl-2-pyridone derivatives having an agonistic activity to the cannabinoid receptor, its pharmaceutical-compositions, and its medicine applications.

BACKGROUND ART

Cannabinoid (CB) was discovered as the main active substance contained in marijuana in 1960 and its main behavior was an activity in the central nervous system bringing about illusion, euphoria, sensory confusion of time and space, and the like by being ingested.

It has been found that a seven times transmembrane G protein bonded cannabinoid type 1 (CB1) receptor exists in the central nervous system such as the brain in 1990, and besides agonists to the receptor take part in the adjustment of a higher-order function of the brain by restrainedly controlling the neurotransmitter discharge with the signal transmission system in the cell such as controlling adenylate cyclase activity, controlling N— and P/Q types Ca $2^+$ channels, activating voltage gated K+ channel, and activating MAP kinase activity through the receptor, it has been also found that the receptor exists also in peripheral tissues and has minor activities in non-nervous systems such as an anti-inflammatory activity, and the alleviation of hypotonia bulbi and muscular spasm. Further, a cannabinoid type 2 receptor (CB2) was found to be distributed over immune tissues such as the spleen and agonists to this receptor were found to surpress an activation of immunocyte or inflammatory cells to exhibit an immunosuppressive activity, an anti-inflammatory activity and analgesic activity (Non-patent literature 1). From these facts, the application of agonists to the cannabinoid receptors to medicines has become to be examined widely.

As applications as medicines of agonists to the cannabinoid receptors, the medical treatment for an allergic disease of quinolone derivatives (Patent literatures 1, 2, 3, 4, and 5), 3,4-dihydroisoquinoline derivatives (Patent literature 6), pyridone derivatives (Patent literature 7), and further quinolone derivatives (Patent literature 8) have been described. Moreover, an anti-pruritic activity is disclosed in Patent literatures 10 and 11.

Itching is a kind of biological reaction, and peripheral itching and central itching are known. For example, sweet itches including inflammatory reactions such as an edema, atopic dermatitis, hives, senile xerosis, and contact dermatitis are peripheral itching caused when nerve endings (itching receptors) of sensory nerve fibers existing in the epidermal-dermal junction are activated by a chemical, physical, or electric stimulus and the like. On the other hand, refractory pruritus such as systemic pruritus of a renal failure patient, which is derived from the hemodialysis, is thought to be central itching that is caused by an opioid peptide uniting with the receptor.

Medicines presently used as an anti-pruritus agent include, for example, diphenhydramine and crotamiton. The former is not effective in other itching though it is effective in the edema and hives that histamine took part as an antihistaminic. Moreover, though the latter adds anti-inflammatory activity by adding a steroid drug and is used as ointment for itching of eczema and the like, the action mechanism is uncertain.

By the way, atopic dermatitis is a cutaneous disease being accompanied by very strong pruritus and skin inflammation in the background of the atopic disposition and accompanied by the decrease in the barrier function, and the wax and wane are repeated. At present, as for medicines that soothe the inflammation and the effectiveness is proven, there are only two kinds, that is, steroids for internal use and for external application, and calcineurin inhibitory medicines that are called the immunosuppressive activity agents or immuno-regulation agents for external use such as tacrolimus and eridale. However, there are severe faults such as the existence of steroid refractory patients, various systemic and locality side effects, and rebounds in the steroid. Moreover, though the immunoregulation agent for external use, the action mechanism of which is quite different from the steroid for external application, is highly effective especially for exanthemata in the face and the cervical region, it has peculiar skin stimulation and is a taboo for using especially in epidermolysis surface seen in atopic dermatitis and the like, and an advanced specialty and attention are demanded when using it. These medicines to the atopic dermatitis are symptomatic treatment medicines which aim at moderate solution of the symptom, and not those which aim at the treatment going back even the cause (Non-patent literature 2).

On the other hand, itching is understood as a sense which causes the impulse of wanting to scratch, and scratching off, a blow, and the like, which are accompanied by itching, are often the most complicating factors of atopic dermatitis. That is, if pruritus can be controlled, not only itching, which is the most suffering of the patient, can be softened to improve QOL (Quality of life), but also an indirect effect that an exanthema is improved by controlling scratching off can be expected. For these reasons, the development of a safe anti-pruritus agent that enables the loss in quantity or cessation of the symptomatic treatment medicine and is strong and can endure the chronic administration is waited for.

As one mode of such a medicine, a medicine for external application that acts only on the applied region and can avoid the systemic action by the internal use is cited. That is, compared with oral agents that the medicines are absorbed from an alimentary canal, an endermic liniment for external application becomes possible to absorb the medicine directly from the disorder affected part by the noninvasive zero-order discharge, to avoid the first-pass effect in the liver, to avoid dosage dependent systemic side effects, and to control medicinal concentration in the disorder affected part for long periods of time, and the merit of the medicine is considered that it can be used safely for cutaneous diseases often seen especially in elderly people, sick people, and infants. In fact, though the steroid drug has a strong anti-inflammatory activity and an anti-pruritic activity that accompanies it, it is not used as an oral medicine except for the remission of extremely severe symptoms. On the one hand, it is well known that the skin has a remarkably strong barrier function for a lot of medicines, so that effective medicines in oral administration are not necessarily effective even in dermal administration.

The present inventors have eagerly made progress in their studies, resulting in finding that the application of a 3-carbamoyl-2-pyridone derivative shown in the following on the skin of the disorder affected part makes the derivative act directly to the cannabinoid receptor existing in the periphery to reveal excellent anti-pruritic activity.

Though pyridone derivatives similar to the said compounds of the present invention are commercially available from Interbioscreen Corp., Interchim Corp., Asinex Corp., and Ambinter Sarl Corp. as reagents, pharmacological activity on these compounds has not described.

Patent Literature 1

International Publication No. 99/02499 Pamphlet

Patent Literature 2

International Publication No. 00/40562 Pamphlet

Patent Literature 3

International Publication No. 2004/103974 Pamphlet

Patent Literature 4

International Publication No. 04/103974 Pamphlet

Patent Literature 5

International Publication No. 04/104000 Pamphlet

Patent Literature 6

International Publication No. 02/10135 Pamphlet

Patent Literature 7

International Publication No. 02/053543 Pamphlet

Patent Literature 8

International Publication No. 03/061699 Pamphlet

Patent Literature 9

International Publication No. 02/065997 Pamphlet

Patent Literature 10

International Publication No. 03/035109 Pamphlet

Patent Literature 11

International Publication No. 03/070277 Pamphlet

Non-Patent Literature 1

Nature, 1993, vol. 365, p. 61-65

Non-Patent Literature 2

Japanese dermatology association's atopic dermatitis treatment guideline, 2004 revised edition, "Japanese skin society magazine", 2004, p. 114-135

DISCLOSURE OF INVENTION

Compounds having an agonistic activity to the cannabinoid receptor, particularly compounds being excellent in transdermal absorbency or oral absorbency will be offered. Especially, pharmaceutical compositions, atopic dermatitis therapeutic drugs, and anti-pruritus agents, especially anti-pruritus agents for oral used and for external application, which contain the said compound as an active ingredient, will be offered.

The present inventors found 3-carbamoyl-2-pyridone derivatives shown in the following, which have a strong agonistic activity to the cannabinoid receptor, are low in inhibition activity for enzyme (CYP), are low in the central nerve side effects, are excellent in photostability, and/or have excellent transdermal absorbency or oral absorbency. Moreover, the pharmaceutical composition, which contains the said compound as an active ingredient, was found to be effective as an atopic dermatitis therapeutic drug, an anti-pruritus agent, especially anti-pruritus agents for oral use and for external application.

That is, the present invention relates to: 1) a compound of the formula (I):

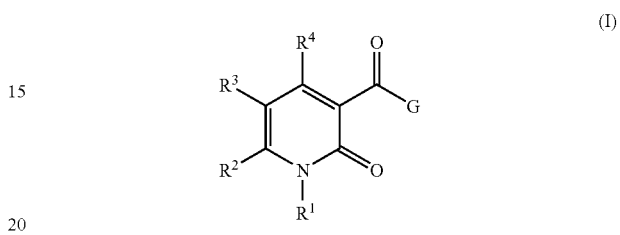

wherein, $R^1$ is C1-C8 alkyl optionally substituted with one to three substituents selected from substituent group A, C2-C8 alkenyl, or C2-C8 alkynyl;

$R^2$ is C1-C6 alkyl or C1-C6 alkoxy C1-C6 alkyl;

$R^3$ is C1-C6 alkyl or C1-C6 alkoxy; or $R^2$ and $R^3$ taken together with the adjacent carbon atoms may form an optionally substituted non-aromatic 5 to 10 membered carbon ring which may be replaced by one group selected from —O—, —S—, —SO—, and —SO$_2$—;

$R^4$ is hydrogen or hydroxy;

G is a group represented by formula:

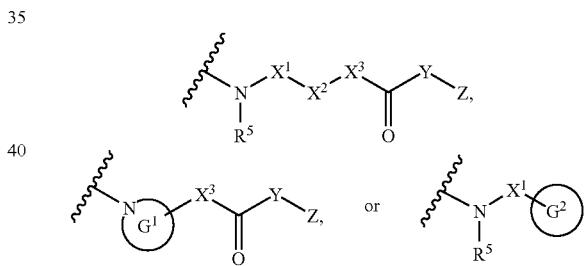

wherein $R^5$ is hydrogen or C1-C6 alkyl;

$X^1$ is a single bond, C1-C4 alkylene optionally substituted with one to three substituents selected from substituents group B, C2-C4 alkenylene optionally substituted with one to three substituents selected from substituent group B, or C2-C4 alkynylene optionally substituted with one to three substituents selected from substituent group B;

$X^2$ is C1-C8 alkylene which may be replaced by one or two groups of —O— or —NR$^6$— wherein R$^6$ is hydrogen, C1-C8 alkyl, or benzyl, and optionally substituted with one to three substituents selected from substituent group B, C3-C8 cycloalkanediyl optionally substituted with one or two substituents selected from substituent group C, C3-C8 cycloalkenediyl optionally substituted with one or two substituents selected from substituent group C, aryldiyl optionally substituted with one or two substituents selected from substituent group C, heteroaryldiyl optionally substituted with one or two substituents selected from substituent group C, or non-aromatic heterocyclediyl optionally substituted with one or two substituents selected from substituent group C;

X³ is a single bond, C1-C4 alkylene which may be replaced by a heteroatom, and optionally substituted with one to three substituents selected from substituent group B, C2-C4 alkenylene optionally substituted with one to three substituents selected from substituent group B, C2-C4 alkynylene optionally substituted with one to three substituents selected from substituent group B, or carbonyl;

the group represented by formula:

is a group selected from the groups represented by the formulas:

wherein $R^a$ is C1-C8 alkyl and n is 0, 1, or 2;

the group represented by formula:

is a group selected from the groups represented by the formulas:

wherein $R^b$ is hydrogen or C1-C8 alkyl; p is 0, 1, or 2; q is an integer of 1 to 4; Y is —O—, —S—, —N($R^6$)— wherein $R^6$ is hydrogen or C1-C8 alkyl optionally substituted with one to three substituents selected from substituent group D, or a group selected from the groups represented by formulas:

wherein $R^7$ is C1-C8 alkyl; m is 1 or 2;

Z is hydrogen, C1-C8 alkyl optionally substituted with one to three substituents selected from substituent group D, C3-C12 cycloalkyl optionally substituted with one or two substituents selected from substituent group C, hydroxy, C1-C8 alkoxy, halo C1-C8 alkoxy, amino optionally substituted with one or two substituents selected from substituent group E, C1-C8 alkylsulfonyl, C6-C14 arylsulfony optionally substituted with one to three substituents selected from substituent group F, C6-C14 aryl optionally substituted with one to three substituents selected from substituent group F, heteroaryl optionally substituted with one to three substituents selected from substituent group F, non-aromatic heterocyclic group optionally substituted with one to three substituents selected from substituent group E, a group represented by the formula: —C(NH₂)—NR⁸—CO—NR⁸R⁹ wherein R⁸ and R⁹ is each independently hydrogen or C1-C8 alkyl, or a group represented by the formula: —C(=W)—R¹⁰ wherein R¹⁰ is C1-C8 alkyl, hydroxy C1-C8 alkyl, C1-C8 alkoxy, C1-C8 alkylthio, amino optionally substituted with one or two substituents selected from substituent group E, hydrazino optionally substituted with one or two substituents selected from substituent group E, C6-C14 aryl optionally substituted with one to three substituents selected from substituent group F, heteroaryl optionally substituted with one to three substituents selected from substituent group F, or non-aromatic heterocyclic group optionally substituted with one to three substituents selected from substituent group E; W is an oxygen atom or a sulfur atom;

substituent group A: halogen, C3-C8 cycloalkyl, hydroxy, C1-C8 alkoxy, halo C1-C8 alkoxy, oxo, amino optionally substituted with one or two substituents selected from substituent group E, cyano, azide, nitro, C6-C14 aryl optionally substituted with one to three substituents selected from substituent group F, heteroaryl optionally substituted with one to three substituents selected from substituent group F, non-aromatic heterocyclic group optionally substituted with one to three substituents selected from substituent group F, and a group represented by the formula: —C(=O)—R¹¹ wherein R¹¹ is hydrogen, C1-C8 alkyl, C1-C8 alkoxy, C1-C8 alkylthio, amino optionally substituted with one or two substituents selected from substituent group E, C6-C14 aryl optionally substituted with one to three substituents selected from substituent group F, heteroaryl optionally substituted with one to three substituents selected from substituent group F, or non-aromatic heterocyclic group optionally substituted with one to three substituents selected from substituent group F;

substituent group B: halogen, C1-C8 alkyl optionally substituted with one to three substituents selected from substituent group A, C3-C8 cycloalkyl, C2-C8 alkenyl, C2-C8 alkylene which may be replaced by one group of —O—, hydroxy, C1-C8 alkoxy, C1-C8 alkylthio, halo C1-C8 alkoxy, oxo, amino optionally substituted with one or two substituents selected from substituent group E, cyano, azide, nitro, C6-C14 aryl optionally substituted with one to three substituents selected from substituent group F, heteroaryl optionally substituted with one to three substituents selected from substituent group F, non-aromatic heterocyclic group optionally substituted with one to three substituents selected from substituent group F, and a group represented by the formula: —C(=O)—R$^{12}$ wherein R$^{12}$ is hydrogen, C1-C8 alkyl, C1-C8 alkoxy, C1-C8 alkylthio, amino optionally substituted with one or two substituents selected from substituent group E, C6-C14 aryl optionally substituted with one to three substituents selected from substituent group F, heteroaryl optionally substituted with one to three substituents selected from substituent group F, or non-aromatic heterocyclic group optionally substituted with one to three substituents selected from substituent group F;

substituent group C: halogen, C1-C8 alkyl, halo C1-C8 alkyl, C1-C8 alkoxy, halo C1-C8 alkoxy, oxo, cyano, azide, nitro, and phenyl;

substituent group D: halogen, C1-C8 alkyl, halo C1-C8 alkyl, C3-C8 cycloalkyl, hydroxy, C1-C8 alkoxy, hydroxy C1-C8 alkoxy, C1-C8 alkylthio, halo C1-C8 alkoxy, oxo, amino optionally substituted with one or two substituents selected from substituent group E, carboxy, cyano, azide, nitro, tri(C1-C8 alkyl)ammonium, di(C1-C8 alkyl)benzyl ammonium, C6-C14 aryl optionally substituted with one to three substituents selected from substituent group F, heteroaryl optionally substituted with one to three substituents selected from substituent group F, non-aromatic heterocyclic group optionally substituted with one to three substituents selected from substituent group F, a group represented by the formula: —C(=O)—R$^{13}$ wherein R$^{13}$ is hydrogen, C1-C8 alkyl, C1-C8 alkoxy, C1-C8 alkylthio, amino optionally substituted with one or two substituents selected from substituent group E, C6-C14 aryl optionally substituted with one to three substituents selected from substituent group F, heteroaryl optionally substituted with one to three substituents selected from substituent group F, or non-aromatic heterocyclic group optionally substituted with one to three substituents selected from substituent group F, and a group represented by the formula: —O—C(=O)—R$^{14}$ wherein R$^{14}$ is C1-C8 alkyl, C3-C8 cycloalkyl, C1-C8 alkoxy, C3-C8 cycloalkyloxy, C6-C14 aryloxy optionally substituted with one to three substituents selected from substituent group F, heteroaryloxy optionally substituted with one to three substituents selected from substituent group F, amino optionally substituted with one or two substituents selected from substituent group E, piperidino, C6-C14 aryl optionally substituted with one to three substituents selected from substituent group F, heteroaryl optionally substituted with one to three substituents selected from substituent group F, or non-aromatic heterocyclic group optionally substituted with one to three substituents selected from substituent group F;

substituent group E: C1-C8 alkyl, (C1-C8 alkyl)carbonyl, (C1-C8 alkoxy)carbonyl, (C6-C14 aryl)carbonyl, heteroaryl carbonyl, (amino optionally substituted with one or two groups of C1-C8 alkyl or C6-C14 aryl)carbonyl, C1-C8 alkylsulfonyl, C6-C14 arylsulfonyl, and heteroarylsulfonyl;

substituent group F: halogen, C1-C8 alkyl, halo C1-C8 alkyl, hydroxy, C1-C8 alkoxy, halo C1-C8 alkoxy, methylenedioxy, benzyloxy, carbamoyl optionally substituted with one or two C1-C8 alkyl, cyano, azide, nitro, oxo, and phenyl;

provided that, when —X$^1$—X$^2$—X$^3$—C(=O)—Y—Z is a group represented by the formula (II):

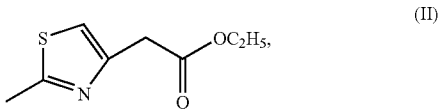

R$^2$ and R$^3$ do not form 6 membered non-aromatic carbon ring taken together with the adjacent carbon atoms;
a pharmaceutically acceptable salt or a solvate thereof,
2) the compound according to 1), wherein R$^1$ is C1-C5 alkyl optionally substituted with one to three substituents selected from substituent group A or C4-C5 alkenyl, a pharmaceutically acceptable salt or a solvate thereof, 3) the compound according to 1), wherein R$^1$ is n-butyl, isopentyl, 3-methyl-2-butenyl, 4,4,4-trifluorobutyl, 2-methyoxyethyl, cyclohexylmethyl, or (phenyl optionally substituted with one to three substituents selected from substituent group F) methyl, a pharmaceutically acceptable salt or a solvate thereof,
4) the compound according to any one of 1) to 3), wherein R$^2$ is C1-C4 alkyl, or C1-C4 allyloxy C1-C4 alkyl, and R$^3$ is C1-C4 alkyl or C1-C4 allyloxy, a pharmaceutically acceptable salt or a solvate thereof,
5) the compound according to any one of 1) to 3), wherein R$^2$ is ethyl, n-propyl, isopropyl, or methyloxymethyl, and R$^3$ is methyl, ethyl, or methyloxy, a pharmaceutically acceptable salt or a solvate thereof,
6) the compound according to any one of 1) to 3), wherein R$^2$ and R$^3$ taken together with the adjacent carbon atoms form a non-aromatic 7 to 10 membered carbon ring optionally substituted with C1-C4 alkyl, a pharmaceutically acceptable salt or a solvate thereof,
7) the compound according to any one of 1) to 3), wherein R$^2$ and R$^3$ taken together with the adjacent carbon atoms form a non-aromatic 8 membered carbon ring, a pharmaceutically acceptable salt or a solvate thereof,
8) the compound according to any one of 1) to 7), wherein R$^4$ is hydrogen, a pharmaceutically acceptable salt or a solvate thereof,
9) the compound according to any one of 1) to 8), wherein R$^5$ is hydrogen, a pharmaceutically acceptable salt or a solvate thereof,
10) the compound according to any 1) to 9), wherein X$^1$ and X$^3$ are a single bond, and X$^2$ is straight-chain C1-C4 alkylene optionally substituted with one to two substituents selected from substituent group B, a pharmaceutically acceptable salt or a solvate thereof,
11) the compound according to any one of 1) to 9), wherein X$^1$ and X$^3$ each is independently a single bond or C1-C3 alkylene, and X$^2$ is C3-C8 cycloalkanediyl optionally substituted with one to two substituents selected from substituent group C, a pharmaceutically acceptable salt or a solvate thereof,
12) the compound according to any one of 1) to 9), wherein X$^1$ is a single bond, X$^3$ is C1-C3 alkylene or C2-C3 alkenylene, and X$^2$ is heteroaryldiyl optionally substituted with one to two substituents selected from substituent group C, a pharmaceutically acceptable salt or a solvate thereof,
13) the compound according to any one of 1) to 12), wherein Y is —O—, Z is hydrogen or C1-C8 alkyl optionally substituted with one to three substituents selected from substituent group D, a pharmaceutically acceptable salt or a solvate thereof,
14) the compound according to any one of 1) to 12), wherein Y is —N(R$^6$)— wherein R$^6$ is as defined in 1), a pharmaceutically acceptable salt or a solvate thereof, 15) the compound according to any one of 1) to 12), wherein Y is a group represented by the formula:

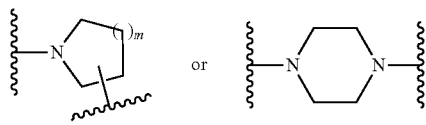

wherein m is as defined in 1), a pharmaceutically acceptable salt or a solvate thereof, 16) a compound of the formula (II)

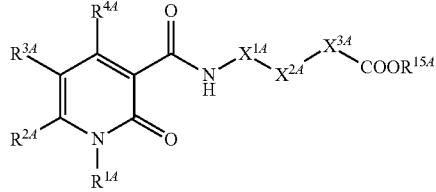
(II)

wherein $R^{1A}$ is C1-C6 alkyl optionally substituted with one to three substituents selected from substituent group G, C3-C6 alkenyl, or C3-C6 alkynyl;
$R^{2A}$ is C1-C4 alkyl or C1-C4 alkoxy C1-C4 alkyl;
$R^{3A}$ is C1-C4 alkyl or C1-C4 alkoxy; or
$R^{2A}$ and $R^{3A}$ taken together with the adjacent carbon atoms may form an optionally substituted non-aromatic 5 to 10 membered carbon ring;
$R^{4A}$ is hydrogen or hydroxy;
$R^{15A}$ is hydrogen or C1-C4 alkyl;
$X^{1A}$ is a single bond or C1-C3 alkylene;
$X^{2A}$ is straight-chain C1-C4 alkylene optionally substituted with one to two substituents selected from substituent group H, C3-C8 cycloalkanediyl optionally substituted with one to two substituents selected from substituent group I, or heteroaryldiyl optionally substituted with one to two substituents selected from substituent group I;
$X^{3A}$ is a single bond, C1-C3 alkylene, or C2-C3 alkenylene;
substituent group G: halogen, C3-C8 cycloalkyl, C1-C8 alkoxy, haloC1-C8 alkoxy, cyano, azide, C6-C14 aryl optionally substituted with one to three substituents selected from substituent group J, and heteroaryl optionally substituted with one to three substituents selected from substituent group J;
substituent group H: halogen, C1-C8 alkyl optionally substituted with one to three substituents selected from substituent group G, C3-C8 cycloalkyl, C2-C8 alkenyl, C2-C8 alkylene which may be replaced by one group of —O—, C1-C8 alkoxy, C1-C8 alkylthio, halo C1-C8 alkoxy, C6-C14 aryl optionally substituted with one to three substituents selected from substituent group J, heteroaryl optionally substituted with one to three substituents selected from substituent group J, and non-aromatic heterocyclic group optionally substituted with one to three substituents selected from substituent group J;
substituent group I: halogen, C1-C8 alkyl, and phenyl;
substituent group J: halogen, C1-C8 alkyl, halo C1-C8 alkyl, C1-C8 alkoxy, halo C1-C8 alkoxy, cyano, nitro, and phenyl;
a pharmaceutically acceptable salt or a solvate thereof, 17) the compound according to 16) wherein the group represented by the formula:

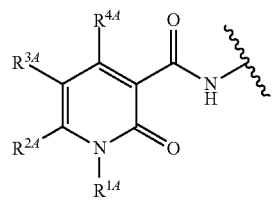

is a group selected from the groups represented by the formulas:

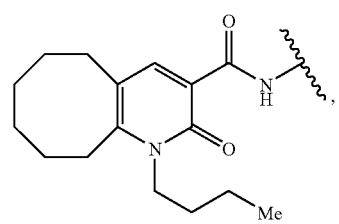

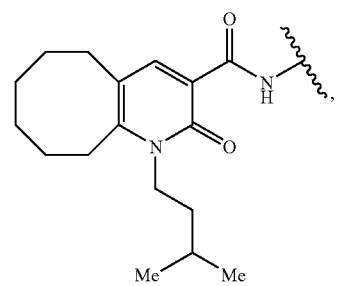

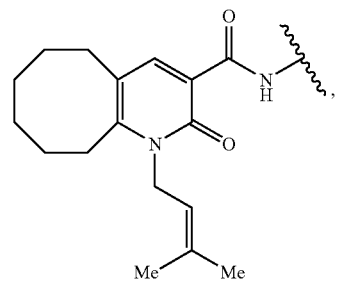

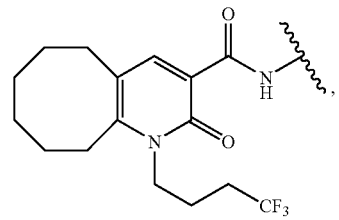

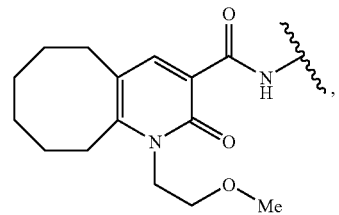

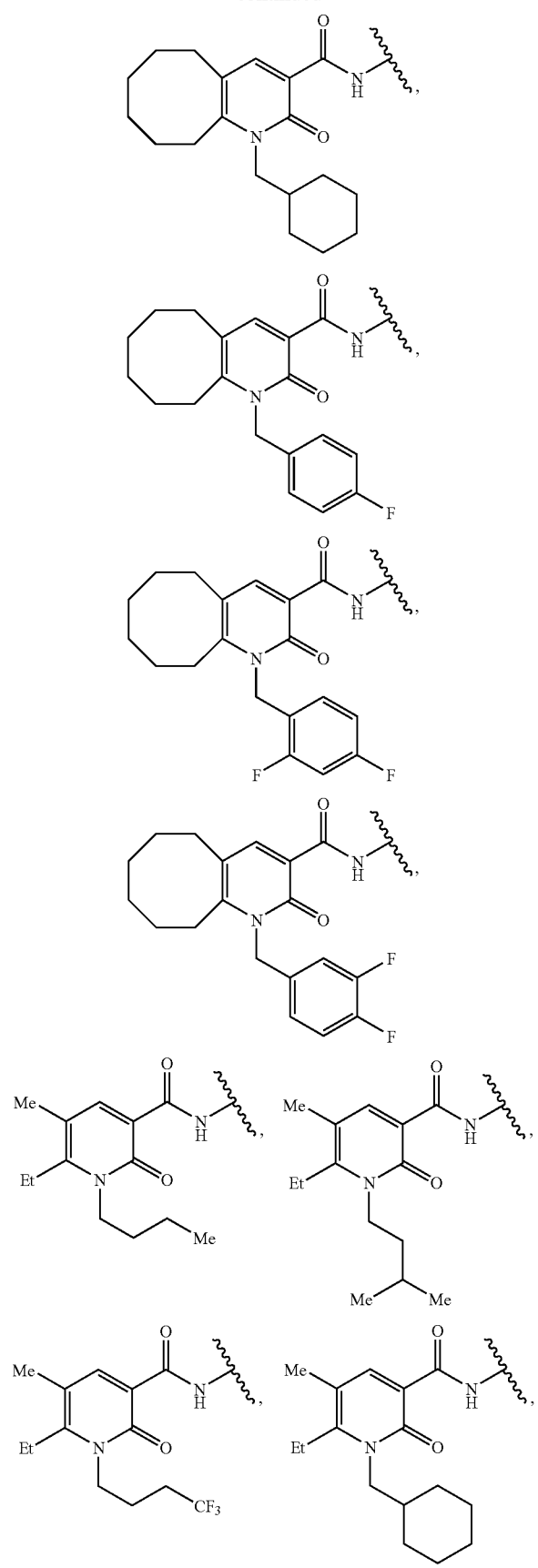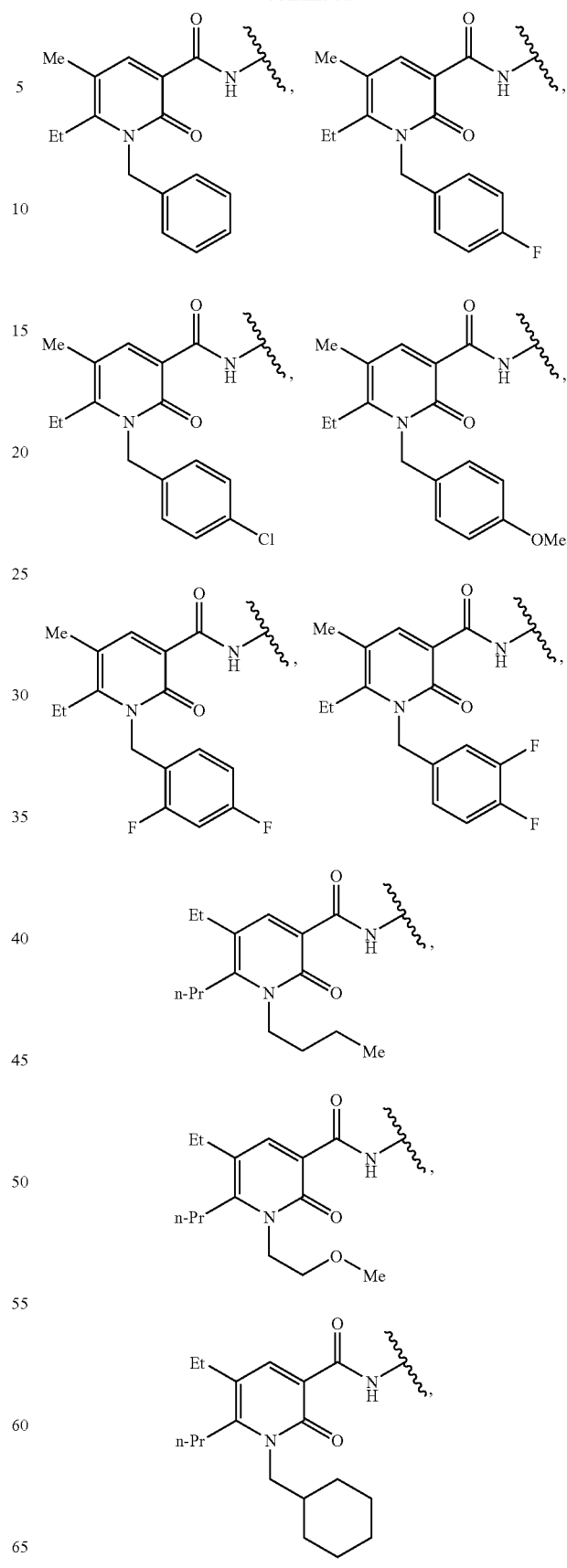

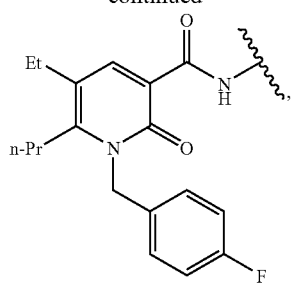
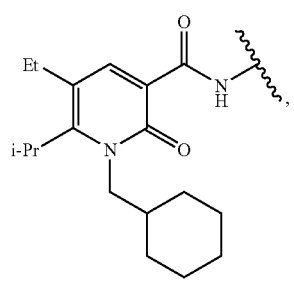
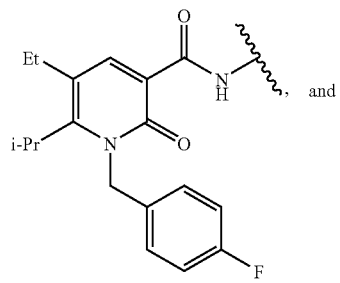, and
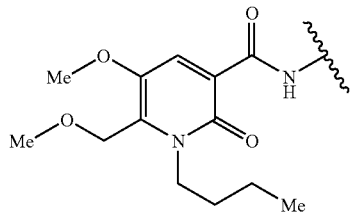
wherein Me is methyl; Et is ethyl; n-Pr is n-propyl; i-Pr is isopropyl, the group represented by the formula:
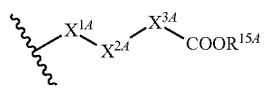
is a group selected from the groups represented by the formulas:
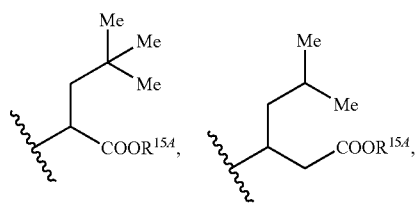
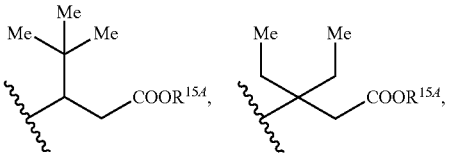
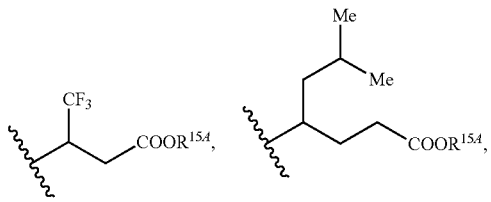
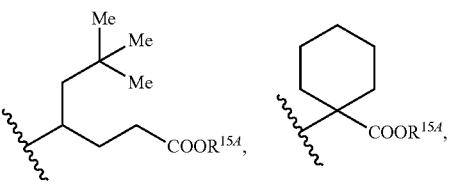
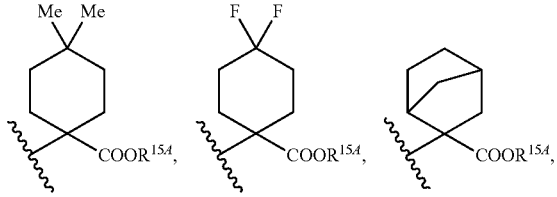
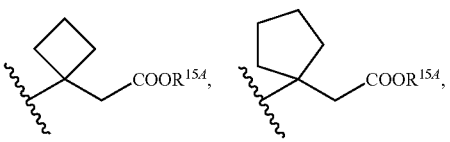
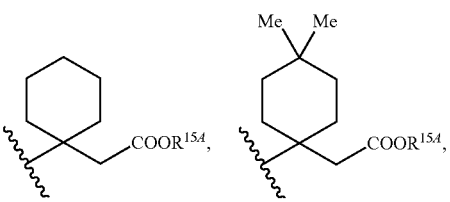
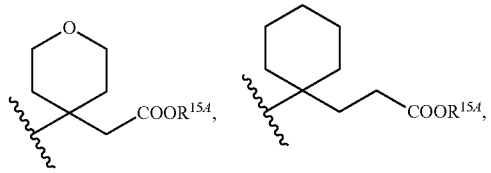
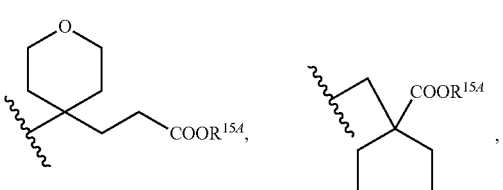
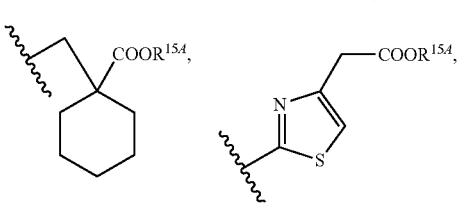

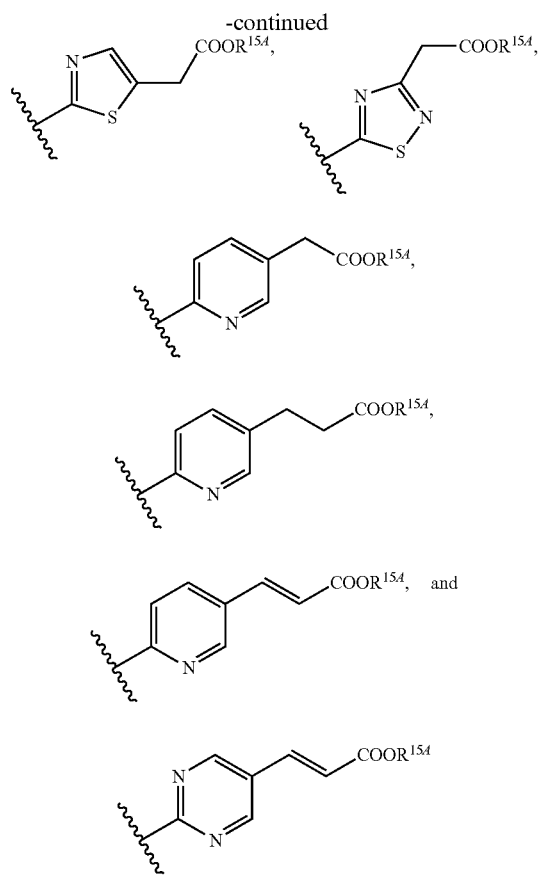

wherein Me is methyl; Et is ethyl; n-Pr is n-propyl; i-Pr is isopropyl; $R^{15A}$ is as defined in 16);

a pharmaceutically acceptable salt or a solvate thereof, 18) the compound according to 17), wherein $R^{15A}$ is hydrogen, a pharmaceutically acceptable salt or a solvate thereof, 19) a pharmaceutical composition containing the compound according to any one of 1) to 18) as an active ingredient, 20) the pharmaceutical composition according to 19), which is an atopic dermatitis treating agent, 21) the pharmaceutical composition according to 19), which is an anti-pruritus agent, 22) use of a compound, and a pharmaceutically acceptable salt or a solvate thereof according to any one of 1) to 18) for preparation of a medicament for preventing and/or treating atopic dermatitis, 23) a method of preventing and/or treating atopic dermatitis in a mammal including human, which comprises administrating to said mammal a therapeutically effective amount of the compound, and a pharmaceutically acceptable salt or a solvate thereof according to any one of 1) to 18), thereby alleviating its symptoms, 24) use of the compound, and a pharmaceutically acceptable salt or solvates according to any one of 1) to 18) for preparation of medicament for preventing and/or treating itching, 25) a method of alleviating itching a mammal including human, which comprises administrating to said mammal a therapeutically effective amount of the compound and a pharmaceutically acceptable salt or a solvate thereof according to any one of 1) to 18), and 26) a compound of the formula:

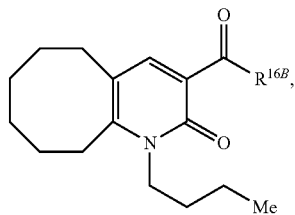

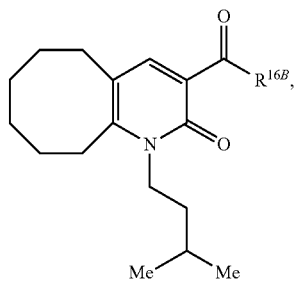

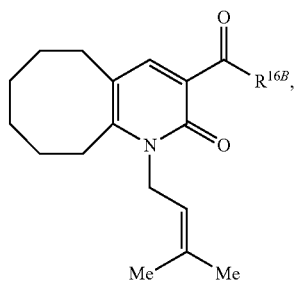

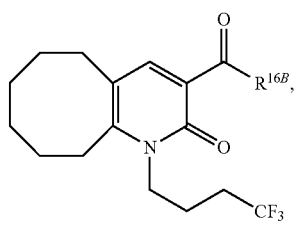

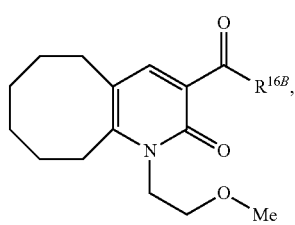

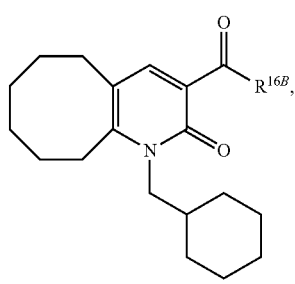

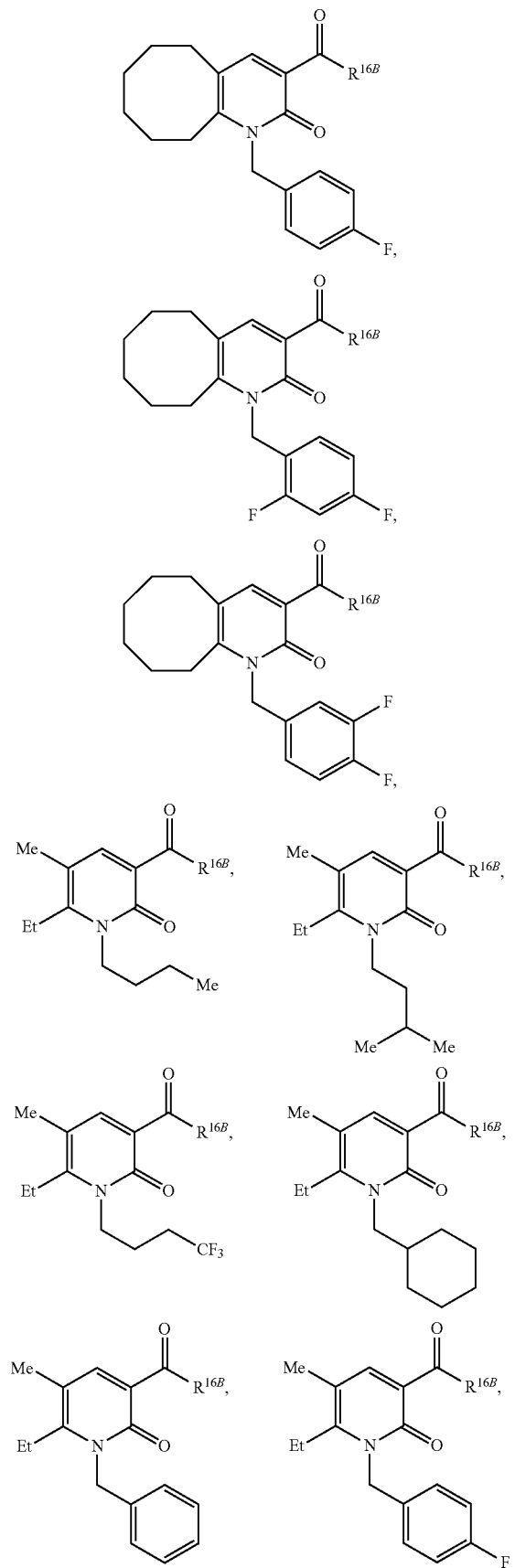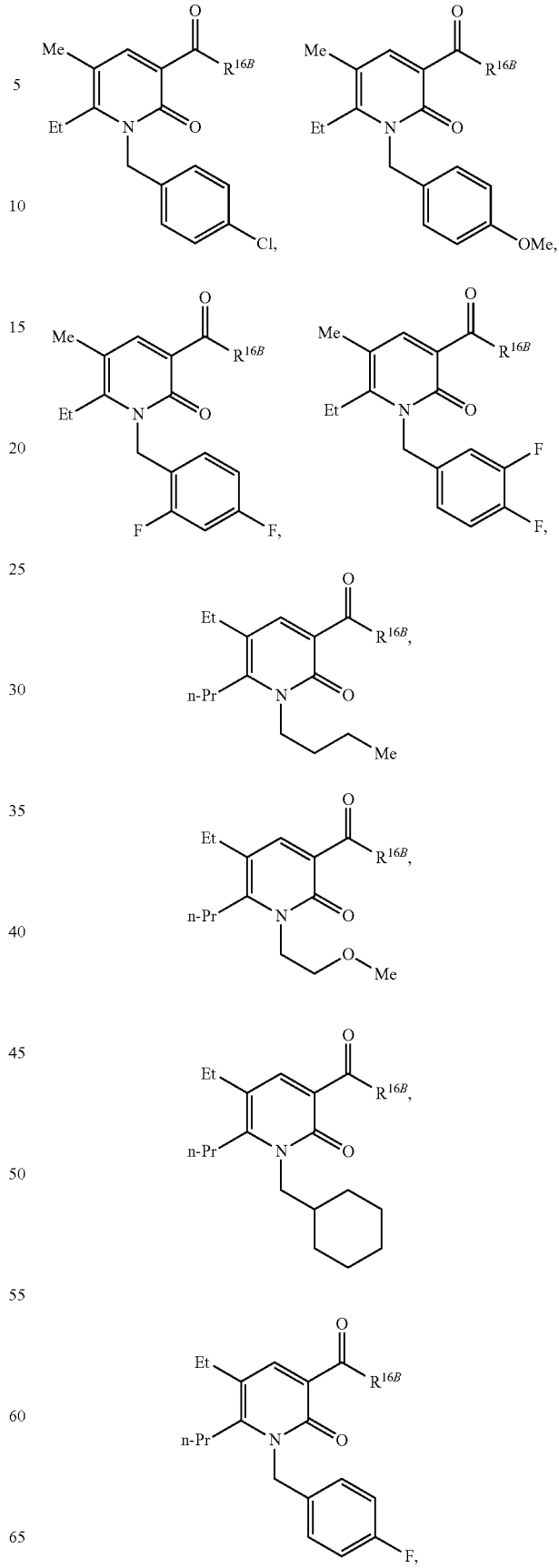

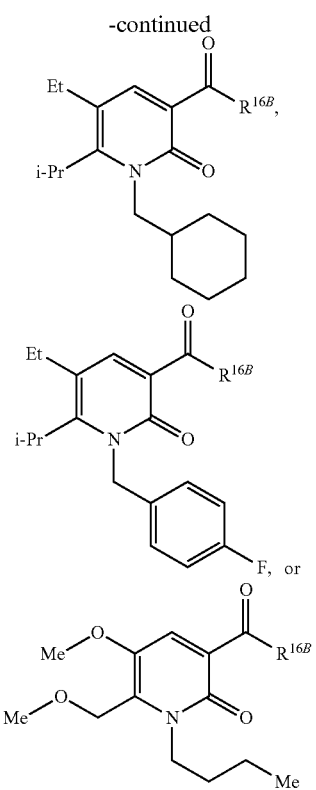

wherein $R^{16B}$ is hydroxy, C1-C4 alkyloxy, or chloro;
and a pharmaceutically acceptable salt or a solvate thereof.

Moreover, the following inventions are included in the present invention. The invention relates to {1} a compound of the formula (BB):

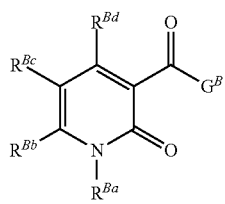

(BB)

wherein $R^{Ba}$ is C1-C8 alkyl is optionally substituted with one to three substituents selected from substituent group A, C2-C8 alkenyl, or C2-C8 alkynyl;
$R^{Bb}$ is C1-C6 alkyl;
$R^{Bc}$ is C1-C6 alkyl or C1-C6 alkoxy; or
$R^{Bb}$ and $R^{Bc}$ may together with adjacent carbon atoms form an optionally substituted non-aromatic 5 to 10 membered carbon ring which may be replaced by one group selected from —O—, —S—, —SO—, and —SO$_2$—;
$R^{Bd}$ is hydrogen or hydroxy;
$G^B$ is a group represented by the formula:

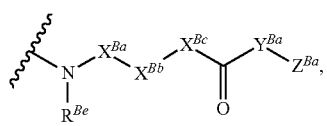

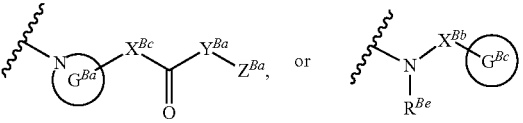

wherein $R^{Be}$ is hydrogen or C1-C6 alkyl;
$X^{Ba}$ is a single bond or C1-C4 alkylene optionally substituted with one to three substituents selected from substituent group B;
$X^{Bb}$ is C1-C8 alkylene which may be replaced by one or two groups of —O— or —NR$^{Bf}$— wherein $R^{Bf}$ is hydrogen, C1-C8 alkyl, or benzyl, and optionally substituted with one to three substituents selected from substituent group $B^{Bb}$, C3-C8 cycloalkanediyl optionally substituted with one or two substituents selected from substituent group $C^{Bc}$, C3-C8 cycloalkenediyl optionally substituted with one or two substituents selected from substituent group $C^{Bc}$, aryldiyl optionally substituted with one or two substituents selected from substituent group C, heteroaryldiyl optionally substituted with one or two substituents selected from substituent group $C^{Bc}$, or non-aromatic heterocyclediyl optionally substituted with one or two substituents selected from substituent group $C^{Bc}$;
$X^{Bc}$ is a single bond, C1-C4 alkylene which may de replaced by heteroatom, and optionally substituted with one to three substituents selected from substituent group $B^{Bb}$, C2-C4 alkenylene optionally substituted with one to three substituents selected from substituent group $B^{Bb}$, or carbonyl;
ring $G^{Ba}$ is a group selected from the groups represented by the formulas:

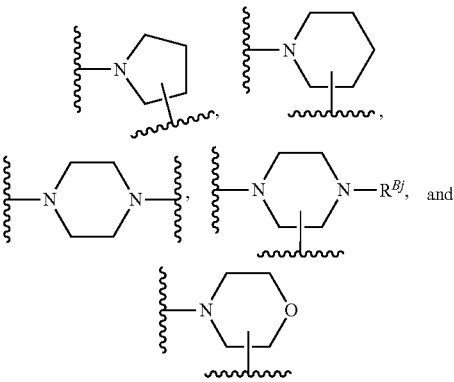

wherein $R^{Bj}$ is C1-C8 alkyl; n is 0, 1, or 2;
ring $G^{Bb}$ is a group selected from the groups represented by the formulas:

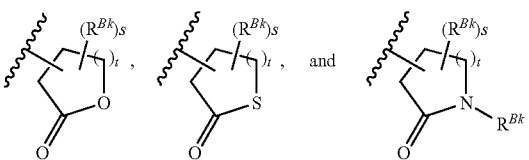

wherein $R^{Bk}$ is hydrogen or C1-C8 alkyl; s is 0, 1, or 2; t is an integer of 1 to 4; $Y^{Ba}$ is —O—, —S—, —N(R$^{Bz}$)— wherein $R^{Bz}$ is hydrogen or C1-C8 alkyl optionally substituted with one to three substituents selected from substituents group $D^{Bd}$, or a group selected from the groups represented by the formulas:

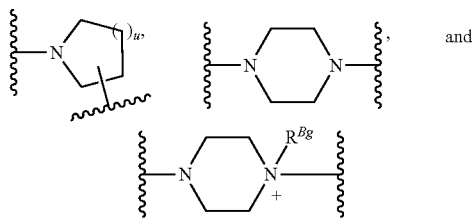

wherein $R^{Bg}$ is C1-C8 alkyl; m is 1 or 2;
$Z^{Ba}$ is a group shown by hydrogen, C1-C8 alkyl optionally substituted with one to three substituents selected from substituent group $D^{Bd}$, C3-C12 cycloalkyl optionally substituted with one or two substituents selected from substituent group $C^{Bc}$, hydroxy, C1-C8 alkoxy, halo C1-C8 alkoxy, amino optionally substituted with one or two substituents selected from substituent group $E^{Be}$, C1-C8 alkylsulfonyl, C6-C14 arylsulfonyl optionally substituted with one to three substituents selected from substituent group $F^{Bf}$, C6-C14 aryl optionally substituted with one to three substituents selected from substituent group $F^{Bf}$, heteroaryl optionally substituted with one to three substituents selected from substituent group $F^{Bf}$, non-aromatic heterocycle groups optionally substituted with one to three substituents selected from substituent group $E^{Be}$, a group represented by the formula: —C(NH$_2$)—NR$^{Bha}$—CO—NR$^{Bhb}$R$^{Bi}$ wherein R$^{Bha}$, R$^{Bhb}$, and R$^{Bi}$ each is independently hydrogen or C1-C8 alkyl, or a group represented by the formula: —C(=W$^{Ba}$)—R$^{B1}$ wherein R$^{B1}$ is C1-C8 alkyl optionally substituted with one to two substituents selected from substituent group $D^{Bd}$, hydroxy C1-C8 alkyl, C1-C8 alkoxy, C1-C8 alkylthio, amino optionally substituted with one or two substituents selected from substituent group $E^{Be}$, hydrazino optionally substituted with one or two substituents selected from substituent group $E^{Be}$, C6-C14 aryl optionally substituted with one to three substituents selected from substituent group $F^{Bf}$, heteroaryl optionally substituted with one to three substituents selected from substituent group $F^{Bf}$, or non-aromatic heterocycle groups optionally substituted with one to three substituents selected from substituent group $E^{Be}$; $W^{Ba}$ is an oxygen atom or a sulfur atom;
substituent group $A^{Be}$: halogen, C3 to C8 cycloalkyl, hydroxy, C1-C8 alkoxy, halo C1-C8 alkoxy, oxo, amino optionally substituted with one or two substituents selected from substituent group $E^{Be}$, cyano, azide, nitro, C1-C8 alkylsulfonyl, C6-C14 arylsulfonyl optionally substituted with one to three substituents selected from substituent group $F^{Bf}$, heteroarylsulfonyl optionally substituted with one to three substituents selected from substituent group $F^{Bf}$, C6-C14 aryl optionally substituted with one to three substituents selected from substituent group $F^{Bf}$, heteroaryl optionally substituted with one to three substituents selected from substituent group $F^{Bf}$, non-aromatic heterocycle groups optionally substituted with one to three substituents selected from substituent group $F^{Bf}$, and a group represented by the formula: —C(=O)—R$^{Bm}$ wherein R$^{Bm}$ is hydrogen, C1-C8 alkyl, C1-C8 alkoxy, C1-C8 alkylthio, amino optionally substituted with one or two substituents selected from substituent group $E^{Be}$, C6-C14 aryl optionally substituted with one to three substituents selected from substituent group $F^{Bf}$, heteroaryl optionally substituted with one to three substituents selected from substituent group $F^{Bf}$, or non-aromatic heterocycle groups optionally substituted with one to three substituents selected from substituent group $F^{Bf}$;

substituent group $B^{Bb}$: halogen, C3-C8 cycloalkyl, C2-C8 alkenyl, C2-C8 alkylene, hydroxy, C1-C8 alkoxy, C1-C8 alkylthio, halo C1-C8 alkoxy, oxo, amino optionally substituted with one or two substituents selected from substituent group $E^{Be}$, cyano, azide, nitro, C6-C14 aryl optionally substituted with one to three substituents selected from substituent group $F^{Bf}$, or heteroaryl optionally substituted with one to three substituents selected from substituent group $F^{Bf}$, non-aromatic heterocycle groups optionally substituted with one to three substituents selected from substituent group $F^{Bf}$, and a group represented by the formula: —C(=O)—R$^{Bn}$ wherein R$^{Bn}$ is hydrogen, C1-C8 alkyl, C1-C8 alkoxy, C1-C8 alkylthio, amino optionally substituted with one or two substituents selected from substituent group $E^{Be}$, C6-C14 aryl optionally substituted with one to three substituents selected from substituent group $F^{Bf}$, heteroaryl optionally substituted with one to three substituents selected from substituent group $F^{Bf}$, or non-aromatic heterocycle groups optionally substituted with one to three substituents selected from substituent group $F^{Bf}$;
substituent group $C^{Bc}$: halogen, C1-C8 alkyl, halo C1-C8 alkyl, C1-C8 alkoxy, halo C1-C8 alkoxy, oxo, cyano, azide, nitro, and phenyl;
substituent group $D^{Bd}$: halogen, C1-C8 alkyl, halo C1-C8 alkyl, C3 to C8 cycloalkyl, hydroxy, C1-C8 alkoxy, hydroxy C1-C8 alkoxy, C1-C8 alkylthio, halo C1-C8 alkoxy, oxo, amino optionally substituted with one or two substituents selected from substituent group $E^{Be}$, carboxy, cyano, azide, nitro, tri(C1-C8 alkyl)ammonium, di(C1-C8 alkyl)benzylammonium, C6-C14 aryl optionally substituted with one to three substituents selected from substituent group $F^{Bf}$, heteroaryl optionally substituted with one to three substituents selected from substituent group $F^{Bf}$, non-aromatic heterocycle groups optionally substituted with one to three substituents selected from substituent group $F^{Bf}$, a group represented by the formula: —(=O)—$^{13}$ wherein R$^{13}$ is hydrogen, C1-C8 alkyl, C1-C8 alkoxy, C1-C8 alkylthio, amino optionally substituted with one or two substituents selected from substituent group E, C6-C14 aryl optionally substituted with one to three substituents selected from substituent group F, heteroaryl optionally substituted with one to three substituents selected from substituent group F, or non-aromatic heterocycle groups optionally substituted with one to three substituents selected from substituent group F, and a group represented by the formula: —C(=O)—R$^{Bp}$ wherein R$^{Bp}$ is C1-C8 alkyl, C3-C8 cycloalkyl, C1-C8 alkoxy, C3-C8 cycloalkyloxy, C6-C14 aryloxy optionally substituted with one to three substituents selected from substituent group $F^{Bf}$, heteroaryloxy optionally substituted with one to three substituents selected from substituent group $F^{Bf}$, amino optionally substituted with one or two substituents selected from substituent group $E^{Be}$, piperidino, C6-C14 aryl optionally substituted with one to three substituents selected from substituent group $F^{Bf}$, heteroaryl optionally substituted with one to three substituents selected from substituent group $F^{Bf}$, or non-aromatic heterocycle groups optionally substituted with one to three substituents selected from substituent group $F^{Bf}$;
substituent group $E^{Be}$: C1-C8 alkyl, (C1-C8 alkyl)carbonyl, (C1-C8 alkoxy)carbonyl, (C6-C14 aryl)carbonyl, heteroarylcarbonyl, (amino optionally substituted with one or two C1-C8 alkyl or C6-C14 aryl)carbonyl, C1-C8 alkylsulfonyl, C6-C14 arylsulfonyl, and heteroarylsulfonyl;
substituent group $F^{Bf}$: halogen, C1-C8 alkyl, halo C1-C8 alkyl, hydroxy, C1-C8 alkoxy, halo C1-C8 alkoxy, methylenedioxy, benzyloxy, carbamoyl optionally substituted with one or two C1-C8 alkyl, cyano, azide, nitro, oxo, and phenyl;

provided that, when —$X^{Ba}$—$X^{Bb}$—$X^{Bc}$—C(=)—$Y^{Ba}$—$Z^{Be}$ is a group represented by the formula (BB),

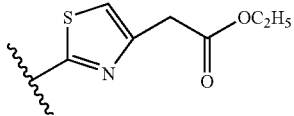
(BB)

$R^{Bb}$ and $R^{Bc}$ do not form 6 membered non-aromatic carbon ring taken together with the adjacent carbon atoms;
a pharmaceutically acceptable salt or a solvate thereof,
{2} the compound according to {1}, wherein $R^{Ba}$ is C1-C4 alkyl optionally substituted with one to three substituents selected from substituent group $A^{Ba}$, a pharmaceutically acceptable salt or a solvate thereof,
{3} the compound according to {1} or {2}, wherein $R^{Ba}$ is n-butyl, cyclohexylmethyl, or (phenyl optionally substituted with one to three substituents selected from substituent group $F^{Bf}$)methyl, a pharmaceutically acceptable salt or a solvate thereof,
{4} the compound according to any to {1} to {3}, wherein $R^{Bb}$ and $R^{Bc}$ each is independently C1-C4 alkyl, a pharmaceutically acceptable salt or a solvate thereof,
{5} the compound according to any one of {1} to {3}, wherein $R^{Bb}$ and $R^{Bc}$ taken together with the adjacent carbon atoms form a non-aromatic 7 to 10 membered carbon ring optionally substituted with C1-C4 alkyl, a pharmaceutically acceptable salt or a solvate thereof,
{6} the compound according to any one of {1} to {5}, wherein $R^{Bd}$ is hydrogen, a pharmaceutically acceptable salt or a solvate thereof,
{7} the compound according to any one of {1} to {6}, wherein $R^{Be}$ is hydrogen, a pharmaceutically acceptable salt or a solvate thereof,
{8} the compound according to any one of {1} to {7}, wherein $X^{Ba}$ and $X^{Bc}$ are single bonds, and $X^{Bb}$ is straight chain C1-C4 alkylene optionally substituted with one substituent selected from C1-C6 alkyl optionally substituted with one substituent selected from substituent group $B^{Bb}$ and substituent group $B^{Bb}$, a pharmaceutically acceptable salt or a solvate thereof, {9} the compound according to any one of {1} to {7}, wherein $X^{Bb}$ is heteroaryldiyl optionally substituted with one to two substituents selected from substituents group $C^{Bc}$, a pharmaceutically acceptable salt or a solvate thereof,
{10} the compound according to any one of {1} to {9}, wherein $Y^{Ba}$ is —O—, and $Z^{Ba}$ is hydrogen or C1-C8 alkyl optionally substituted with one to three substituents selected from substituent group D, a pharmaceutically acceptable salt or a solvate thereof,
{11} the compound according to any one of {1} to {9}, wherein $Y^{Ba}$ is —N($R^{Bz}$)—wherein $R^{Bz}$ is as defined in {1}, a pharmaceutically acceptable salt or a solvate thereof,
{12} the compound according to any one of {1} to {9}, wherein $Y^{Ba}$ is a group represented by the formula:

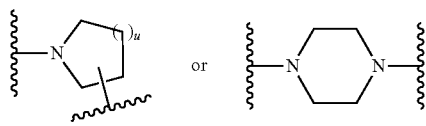

wherein u is as defined in {1};
a pharmaceutically acceptable salt or a solvate thereof,
{13} a pharmaceutical composition containing the compound according to any one of {1} to {12} as an active ingredient,
{14} the pharmaceutical composition according to {13} which is useful as an anti-pruritus agent,
{15} the pharmaceutical composition according to {13} which is useful as an antiasthmatic agent,
{16} the pharmaceutical-composition according to {1} which is useful as a chronic obstructive pulmonary disease therapeutic agent.

Moreover, the following inventions are included in the present invention. The invention relates to [1] a compound of the formula (A):

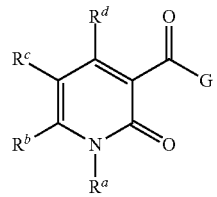
(A)

wherein $R^a$ is C1-C8 alkyl is optionally substituted with one to three pieces of substituents selected from substituents group $A^a$, C2-C8 alkenyl, or C2-C8 alkynyl;
$R^b$ is C1-C6 alkyl;
$R^c$ is C1-C6 alkyl or C1-C6 alkoxy; or
$R^b$ and $R^c$ taken together with the adjacent carbon atoms may form a 5 to 10 membered cycloalkene having one double bond, which may be replaced by one group selected from —O—, —S—, —SO—, and —SO$_2$— in the ring;
$R^d$ is hydrogen or hydroxy;
G is a group represented by the formula:

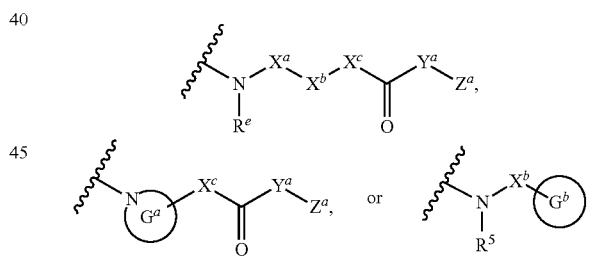

wherein $R^e$ is hydrogen or C1-C6 alkyl;
$X^a$ is a single bond or C1-C4 alkylene;
$X^b$ is C1-C8 alkylene which may be replaced by one or two groups of —O—, or —N($R^f$)— wherein $R^f$ is hydrogen and C1-C8 alkyl or aralkyl, and optionally substituted with one to three substituents selected from substituents group $B^b$, C3-C8 cycloalkanediyl optionally substituted with one or two substituents selected from substituent group $C^c$, C3-C8 cycloalkenediyl optionally substituted with one or two substituents selected from substituent group $C^c$, aryldiyl optionally substituted with one or two substituents selected from substituent group $C^c$, heteroaryldiyl optionally substituted with one or two substituents selected from substituent group $C^c$, or non-aromatic heterocyclediyl optionally substituted with one or two substituents selected from substituent group $C^c$;
$X^c$ is a single bond, C1-C4 alkylene, C2-C4 alkenylene, C2-C4 alkynylene, or carbonyl;

ring G$^a$ is a group selected from the groups represented by the formulas:

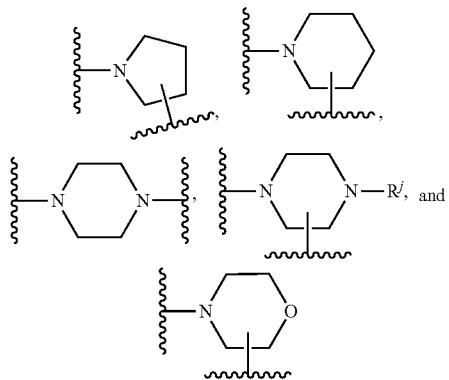

wherein R$^j$ is hydrogen or C1-C8 alkyl;
ring G$^b$ is a group represented by the formula:

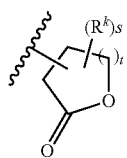

wherein R$^k$ is C1-C8 alkyl; s is 0, 1, or 2; t is an integer of 1 to 4;
Y$^a$ is —O—, —S—, —N(R$^z$)— wherein R$^z$ is hydrogen or C1-C8 alkyl optionally substituted with one to three substituents selected from substituent group D$^d$, or a group selected from the groups represented by the formulas:

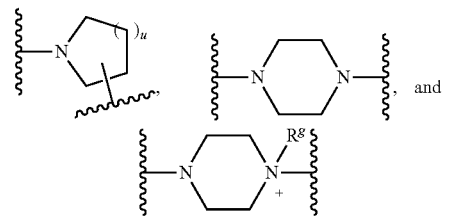

wherein R$^g$ is C1-C8 alkyl; u is 1 or 2;
Z$^a$ is hydrogen, C1-C8 alkyl optionally substituted with one to three substituents selected from substituent group D$^d$, amino optionally substituted with one or two substituents selected from substituent group E$^e$, C1-C8 alkylsulfonyl, C6-C14 arylsulfonyl optionally substituted with one to three substituents selected from substituent group F$^f$, C6-C14 aryl optionally substituted with one to three substituents selected from substituent group F$^f$, heteroaryl optionally substituted with one to three substituents selected from substituent group F$^f$, non-aromatic heterocycle groups optionally substituted with one to three substituents selected from substituent group E$^e$, a group represented by the formula: —C(NH$_2$)—NR$^{ha}$—CO—NR$^{hb}$R$^i$ wherein R$^{ha}$, R$^{hb}$, and R$^i$ each is independently hydrogen or C1-C8 alkyl, or a group represented by the formula: —C(=W$^a$)—R$^l$ wherein R$^l$ is C1-C8 alkyl optionally substituted with one or two substituents selected from substituent group D$^d$, hydroxy C1-C8 alkyl, C1-C8 alkoxy, C1-C8 alkylthio, amino optionally substituted with one or two substituents selected from substituent group E$^e$, hydrazino optionally substituted with one or two substituents selected from substituent group E$^e$, C6-C14 aryl optionally substituted with one to three substituents selected from substituent group F$^f$, heteroaryl optionally substituted with one to three substituents selected from substituent group F$^f$, or non-aromatic heterocycle groups optionally substituted with one to three substituents selected from substituent group E$^e$; W$^a$ is an oxygen atom or a sulfur atom;

substituent group A$^a$: halogen, C3-C8 cycloalkyl, hydroxy, C1-C8 alkoxy, halo C1-C8 alkoxy, amino optionally substituted with one or two substituents selected from substituent group E$^e$, cyano, azide, nitro, C1-C8 alkylsulfonyl, C6-C14 arylsulfonyl optionally substituted with one to three substituents selected from substituent group F$^f$, heteroarylsulfonyl optionally substituted with one to three substituents selected from substituent group F$^f$, C6-C14 aryl optionally substituted with one to three substituents selected from substituent group F$^f$, heteroaryl optionally substituted with one to three substituents selected from substituent group F$^f$, non-aromatic heterocycle groups optionally substituted with one to three substituents selected from substituent group F$^f$, and a group represented by the formula: —C(=O)—R$^m$ wherein R$^m$ is hydrogen, C1-C8 alkyl, C1-C8 alkoxy, C1-C8 alkylthio, amino optionally substituted with one or two substituents selected from substituent group E$^e$, C6-C14 aryl optionally substituted with one to three substituents selected from substituent group F$^f$, heteroaryl optionally substituted with one to three substituents selected from substituent group F$^f$, or non-aromatic heterocycle groups optionally substituted with one to three substituents selected from substituent group F$^f$;

substituent group B$^b$: halogen, C3-C8 cycloalkyl, C2-C8 alkenyl, C2-C8 alkylene, hydroxy, C1-C8 alkoxy, C1-C8 alkylthio, halo C1-C8 alkoxy, amino optionally substituted with one or two substituents selected from substituent group E$^e$, cyano, azide, nitro, C6-C14 aryl optionally substituted with one to three substituents selected from substituent group F$^f$, or heteroaryl optionally substituted with one to three pieces of substituents selected from substituent group F$^f$, non-aromatic heterocycle groups optionally substituted with one to three substituents selected from substituent group F$^f$, and a group represented by the formula: —C(=O)—R$^n$ wherein R$^n$ is hydrogen, C1-C8 alkyl, C1-C8 alkoxy, C1-C8 alkylthio, amino optionally substituted with one or two substituents selected from substituent group E$^e$, C6-C14 aryl optionally substituted with one to three substituents selected from substituent group F$^f$, heteroaryl optionally substituted with one to three substituents selected from substituent group F$^f$, or non-aromatic heterocycle groups optionally substituted with one to three substituents selected from substituent group F;

substituent group C$^c$: halogen, C1-C8 alkyl, halo C1-C8 alkyl, C1-C8 alkoxy, halo C1-C8 alkoxy, cyano, azide, nitro, and phenyl;

substituent group D$^d$: halogen, C1-C8 alkyl, halo C1-C8 alkyl, C3-C8 cycloalkyl, hydroxy, C1-C8 alkoxy, hydroxy C1-C8 alkoxy, C1-C8 alkylthio, halo C1-C8 alkoxy, amino optionally substituted with one or two substituents selected from substituent group E$^e$, carboxy, cyano, azide, nitro, tri (C1-C8 alkyl)ammonium, di(C1-C8 alkyl)benzyl ammonium, C6-C14 aryl optionally substituted with one to three substituents selected from substituent group F$^f$, heteroaryl optionally substituted with one to three substituents selected from substituent group F$^f$, non-aromatic heterocycle groups optionally substituted with one to three substituents selected from substituent group F$^f$, a group represented by the formula: —C(=O)—R$^p$ wherein R$^p$ is hydrogen, C1-C8 alkyl, C1-C8 alkoxy, C1-C8 alkylthio, amino optionally substituted with one or two substituents selected from substituent group $E^e$, C6-C14 aryl optionally substituted with one to three substituents selected from substituent group $F^f$, heteroaryl optionally substituted with one to three substituents selected from substituent group $F^f$, or non-aromatic heterocycle groups optionally substituted with one to three substituents selected from substituent group $F^f$, and a group represented by the formula: —O—C(=O)—$R^q$ wherein $R^q$ is C1-C8 alkyl, C3-C8 cycloalkyl, C1-C8 alkoxy, C3-C8 cycloalkyloxy, C6-C14 aryloxy optionally substituted with one to three substituents selected from substituent group $F^f$, heteroaryloxy optionally substituted with one to three substituents selected from substituent group $F^f$, amino optionally substituted with one or two substituents selected from substituent group $E^e$, piperidino, C6-C14 aryl optionally substituted with one to three of substituents selected from substituent group $F^f$, heteroaryl optionally substituted with one to three substituents selected from substituent group $F^f$, or non-aromatic heterocycle groups optionally substituted with one to three substituents selected from substituent group $F^f$;

substituent group $E^e$: C1-C8 alkyl, (C1-C8 alkyl)carbonyl, (C1-C8 alkoxy)carbonyl, (C6-C14 aryl)carbonyl, heteroarylcarbony, amino carbonyl optionally substituted with one or two C1-C8 alkyl or C6-C14 aryl, C1-C8 alkylsulfonyl, C6-C14 arylsulfony, and heteroarylsulfonyl;

substituent group $F^f$: halogen, C1-C8 alkyl, halo C1-C8 alkyl, hydroxy, C1-C8 alkoxy, halo C1-C8 alkoxy, methylenedioxy, benzyloxy, carbamoyl optionally substituted with one or two C1-C8 alkyl, cyano, azide, nitro, oxo, and phenyl;

however, when —$X^a$—$X^b$—$X^c$—C(=O)—$Y^a$—$Z^a$ is a group represented by the formula (B):

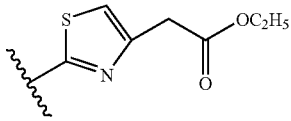

(B)

the case where $R^b$ and $R^c$ do not form 6 membered non-aromatic carbon ring taken together with the adjacent carbon atoms;

a pharmaceutically acceptable salt or a solvate thereof,

[2] the compound according to [1], wherein $R^a$ is C1-C4 alkyl optionally substituted with one to three substituents selected from substituents group $A^a$, a pharmaceutically acceptable salt or a solvate thereof,

[3] the compound according to [1] or [2], wherein $R^a$ is n-butyl, cyclohexylmethyl, or phenylmethyl optionally substituted with one to three substituents selected from substituent group $F^f$, a pharmaceutically acceptable salt or a solvate thereof,

[4] the compound according to [1] to [3], wherein $R^b$ and $R^c$ each is independently C1-C4 alkyl, a pharmaceutically acceptable salt or a solvate thereof,

[5] the compound according to any one of [1] to [3], wherein $R^b$ and $R^c$ taken together with the adjacent carbon atoms form 7 to 10 membered cycloalkene, a pharmaceutically acceptable salt or a solvate thereof,

[6] the compound according to any one of [1] to [5], wherein $R^4$ is hydrogen, a pharmaceutically acceptable salt or a solvate thereof,

[7] the compound according to any one of [1] to [6], wherein $R^e$ is hydrogen, a pharmaceutically acceptable salt or a solvate thereof,

[8] the compound according to any one of [1] to [7], wherein $X^a$ and $X^c$ are single bonds, and $X^b$ is C1-C4 alkylene optionally substituted with one substituent selected from C1-C6 alkyl optionally substituted with a group selected from substituent group $B^b$ and one substituent selected from substituent $B^b$, a pharmaceutically acceptable salt or a solvate thereof,

[9] the compound according to any one of [1] to [7], wherein $X^b$ is heteroaryldiyl optionally substituted with one to two substituents selected from substituent group C, a pharmaceutically acceptable salt or a solvate thereof,

[10] the compound according to any one of [1] to [9], wherein $Y^a$ is —O—, and $Z^a$ is hydrogen or C1-C8 alkyl optionally substituted with one to three substituents selected from substituent group D, a pharmaceutically acceptable salt or a solvate thereof,

[11] the compound according to any one of [1] to [9], wherein $Y^a$ is —N($R^z$)— wherein $R^z$ is as defined in [1], a pharmaceutically acceptable salt or a solvate thereof,

[12] the compound according to any one of [1] to [9], wherein $Y^a$ is a group represented by the formula:

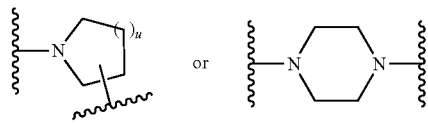

wherein u is as defined in [1];

a pharmaceutically acceptable salt or a solvate thereof,

[13] a pharmaceutical composition containing the compound according to any one of [1] to [12] as an active ingredient,

[14] an anti-pruroitus agent containing the compound according to any one of [1] to [12] as an active ingredient.

The meaning of each term will be explained below. Each term is used in the united meaning in the present description, and is used in the same meaning when used alone or when used being combined with other terms.

The term "halogen" includes the fluorine atom, the chlorine atom, the bromine atom, and the iodine atom.

The term "heteroatoms" includes the nitrogen atom, an oxygen atom, and a sulfur atom.

The term "alkyl" includes a C1-C10 straight or branched alkyl. For example, methyl, ethyl, n-propyl, isopropyl, n-butyl, isobutyl, sec-butyl, t-butyl, n-pentyl, isopentyl, neo-pentyl, n-hexyl, n-heptyl, n-octyl, n-nonyl, n-decyl, and the like can be listed. When the number of carbons is specified, the "alkyl", which has the number of carbons within the ranges of the number, is meant.

The term "haloalkyl" includes a C1-C10 straight or branched alkyl in which one or more halogen are replaced at optional positions that can be replaced. For example, chloromethyl, dichloromethyl, difluoromethyl, trifluoromethyl, chloroethyl (e.g., 2-chloroethyl and the like), dichloroethyl (e.g., 1,2-dichloroethyl, 2,2-dichloroethyl and the like), chloropropyl (e.g., 2-chloropropyl, 3-chloropropyl and the like), and the like can be listed. When the number of carbons is specified, the "haloalkyl", which has the number of carbons within the ranges of the number, is meant.

The term "hydroxyalkyl" includes a C1-C10 straight or branched alkyl in which one or more hydroxy groups are replaced at optional positions that can be replaced. For example, hydroxymethyl, 2-hydroxyethyl, 3-hydroxypropyl, 4-hydroxybutyl, 5-hydroxypentyl, 6-hydroxyhexyl, 7-hydroxyheptyl, 8-hydroxyoctyl, and the like can be listed. When the number of carbons is specified, the "hydroxyalkyl", which has the number of carbons within the ranges of the number, is meant.

The alkyl of "alkylthio" is as defined the above "alkyl". As "alkylthio", for example, methylthio, ethylthio, n-propylthio, isopropylthio, n-butylthio, isobutylthio, sec-butylthio, t-butylthio, n-pentylthio, n-hexylthio, and the like can be listed. When the number of carbons is specified, the "alkylthio", which has the number of carbons within the ranges of the number, is meant.

The alkyl of "alkylcarbonyl" is as defined the above "alkyl". As "alkylcarbonyl", for example, acetyl, propionyl, butyryl, isobutyryl, valeryl, isovaleryl, pivaloyl, hexanoyl, octanoyl, lauroyl, and the like can be listed. When the number of carbons is specified, the "alkylcarbonyl", which has the number of carbons within the ranges of the number, is meant.

The alkyl of "alkylsulfonyl" is as defined the above "alkyl". As alkylsulfonyl, for example, methanesulfonyl, ethanesulfonyl, and the like can be listed. When the number of carbons is specified, the "alkylsulfonyl", which has the number of carbons within the ranges of the number, is meant.

The term "cycloalkyl" includes a C3-C12 cycloalkyl. For example, cyclopropyl, cyclobutyl, cyclopentyl, cyclohexyl, cycloheptyl, cyclooctyl, and the like can be listed. When the number of carbons is specified, the "cycloalkyl", which has the number of carbons within the ranges of the number, is meant.

The term "alkenyl" includes a C2-C10 straight or branched alkyl containing one or more double bonds. For example, vinyl, 1-propenyl, allyl, isopropenyl, 1-butenyl, 2-butenyl, 3-butenyl, 2-pentenyl, 1,3-butadienyl, 3-methyl-2-butenyl, and the like can be listed. When the number of carbons is specified, the "alkenyl", which has the number of carbons within the ranges of the number, is meant.

The term "alkynyl" includes a C2-C10 straight or branched alkyl containing one or more triple bonds. For example, ethynyl, propargyl, and the like can be listed. When the number of carbons is specified, the "alkynyl", which has the number of carbons within the ranges of the number, is meant.

The alkyl of "alkoxy" is as defined the above "alkyl". As alkoxy, for example, methoxy, ethoxy, n-propoxy, isopropoxy, n-butoxy, isobutoxy, sec-butoxy, t-butoxy, n-pentyloxy, n-hexyloxy, n-heptyloxy, n-octyloxy, and the like can be listed. When the number of carbons is specified, the "alkoxy", which has the number of carbons within the ranges of the number, is meant.

The term "haloalkoxy" includes the above-mentioned alkoxy in which one or more halogen are replaced at optional positions that can be replaced. For example, dichloromethoxy, difluoromethoxy, trifluoromethoxy, trifluoroethoxy (2,2,2-trifluoroethoxy and the like), and the like can be listed. When the number of carbons is specified, the "haloalkoxy", which has the number of carbons within the ranges of the number, is meant.

The cycloalkyl of "cycloalkyloxy" is as defined the above "cycloalkyl". As "cycloalkyloxy", for example, cyclopropyloxy, cyclobutyloxy, cyclopentyloxy, cyclohexyloxy, cycloheptyloxy, cyclooctyloxy, and the like can be listed. When the number of carbons is specified, the "cycloalkyl", which has the number of carbons within the ranges of the number, is meant.

The alkyl of "alkoxycarbonyl" is as defined the above "alkoxy". As "alkoxycarbonyl", for example, methoxycarbonyl, ethoxycarbonyl, n-propoxycarbonyl, i-propoxycarbonyl, n-butoxycarbonyl, i-butoxycarbonyl, n-hexyloxycarbonyl, n-heptyloxycarbonyl, n-octyloxycarbonyl, and the like can be listed. When the number of carbons is specified, the "alkoxycarbonyl", which has the number of carbons within the ranges of the number, is meant.

The term "alkylene" includes a C1-C10 straight or branched alkylene. For example, methylene, ethylene, 1-methylethylene, 1-ethylethylene, 1,1-dimethylethylene, 1,2-dimethylethylene, 1,1-diethylethylene, 1,2-diethylethylene, 1-ethyl-2-methylethylene, trimethylene, 1-methyltrimethylene, 2-methyltrimethylene, 1,1-dimethyltrimethylene, 1,2-dimethyltrimethylene, 2,2-dimethyltrimethylene, 1-ethyltrimethylene, 2-ethyltrimethylene, 1,1-diethyltrimethylene, 1,2-diethyltrimethylene, 2,2-diethyltrimethylene, 2,2-di-n-propyltrimethylene, 2-ethyl-2-methyltrimethylene, tetramethylene, 1-methyltetramethylene, 2-methyltetramethylene, 1,1-dimethyltetramethylene, 1,2-dimethyltetramethylene, 2,2-dimethyltetramethylene, pentamethylene, hexamethylene, heptamethylene, octamethylene, nonamethylene, decamethylene, and the like can be listed. When the number of carbons is specified, the "alkylene", which has the number of carbons within the ranges of the number, is meant.

The term "straight alkylene" includes a straight alkylene that is not branched. For example, methylene, ethylene, trimethylene, tetramethylene, pentamethylene, hexamethylene, heptamethylene, octamethylene, nonamethylene, decamethylene, and the like can be listed. When the number of carbons is specified, the "straight alkylene", which has the number of carbons within the ranges of the number, is meant.

The term "alkenylene" includes a C2-C10 straight or branched alkylene having one or more double bonds. For example, vinylene, 1-propenylene, allylene, isopropenylene, 1-butenylene, 2-butenylene, 3-butenylene, 2-pentenylene, 1,3-butadienylene, 3-methyl-2-butenylene, and the like can be listed. When the number of carbons is specified, the "alkenylene", which has the number of carbons within the ranges of the number, is meant.

The term "alkynylene" includes a C2-C10 straight or branched alkylene having one or more triple bonds. For example, ethynylene, 1-propynylene, and the like can be listed. When the number of carbons is specified, the "alkynylene", which has the number of carbons within the ranges of the number, is meant.

The term "cycloalkanediyl" includes a C3-C10 monocyclic or bicyclic cycloalkanediyl. For example, cyclopropanediyl, cyclobutanediyl, cyclopentanediyl, cyclohexanediyl, cycloheptanediyl, cyclooctanediyl, bicyclo[2,2,2]octanediyl, bicyclo[2,2,1]heptanediyl, adamantyldiyl, and the like can be listed. The same carbon atom may have two bonding hands. For example, cyclohexane-1,1-diyl and the like can be listed. When the number of carbons is specified, the "cycloalkanediyl", which has members within the ranges of the number, is meant.

The term "cycloalkenediyl" includes a C3-C10 cycloalkenediyl. For example, cyclopropenediyl, cyclobutenediyl, cyclopentenediyl, cyclohexenediyl, cycloheptenediyl, cyclooctenediyl, and the like can be listed. If it is possible, the same carbon atom may have two bonding hand. For example, 2-cyclohexene-1,1-diyl and the like can be listed. When the number of carbons is specified, the "cycloalkenediyl", which has members within the ranges of the number, is meant.

The term "aryl" includes a C6-14 aryl. For example, phenyl, naphthyl, anthryl, phenanthryl, and the like can be listed. When the number of carbons is specified, the "aryl", which has members within the ranges of the number, is meant.

The term "aralkyl" includes a group in which the above "alkyl" is replaced with the above "aryl". For example, benzyl, phenylethyl (e.g., 1-phenylethyl, 2-phenylethy), phenylpropyl (1-phenylpropyl, 2-phenylpropyl, 3-phenylpropyl, and the like), naphthylmethyl (e.g., 1-naphthylmethyl, 2-naphthylmethyl, and the like) can be listed.

The term "aryldiyl" includes a C6-C14 aryldiyl. For example, phenylene, naphthylene, anthrylene, phenanthrylene, and the like can be listed. When the number of carbons is specified, the "aryldiyl", which has members within the ranges of the number, is meant.

The aryl of "aryloxy" is as defined the above "aryl". As "aryloxy", for example, phenoxy, naphthoxy (e.g., 1-naphthoxy, 2-naphthoxy, and the like), anthryloxy (e.g., 1-anthryloxy, 2-anthryloxy, and the like), phenanthryloxy (e.g., 1-phenanthryloxy, 2-phenanthryloxy, and the like), and the like can be listed. When the number of carbons is specified, the "aryloxy", which has members within the ranges of the number, is meant.

The aryl of "arylcarbonyl" is as defined the above "aryl". As "arylcarbonyl", for example, benzoyl, naphthoyl, and the like can be listed. When the number of carbons is specified, the "arylcarbonyl", which has members within the ranges of the number, is meant.

The aryl of "arylsulfonyl" is as defined the above "aryl". As "arylsulfonyl", for example, phenylsulfonyl, naphthylsulfonyl, and the like can be listed. When the number of carbons is specified, the "arylsulfonyl", which has the number of carbons within the ranges of the number, is meant.

The term "heteroaryl" includes a C1-C9 heteroaryl having one to four nitrogen atom(s), oxygen atom(s), and/or sulfur atom(s), for example, furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazoly, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl, quinoxalyl (e.g., 2-quinoxalyl, 5-quinoxalyl, 6-quinoxalyl), cinnolyl (e.g., 3-cinnolyl, 4-cinnolyl, 5-cinnolyl, 6-cinnolyl, 7-cinnolyl, 8-cinnolyl), quinazolyl (e.g., 2-quinazolyl, 4-quinazolyl, 5-quinazolyl, 6-quinazolyl, 7-quinazolyl, 8-quinazolyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl), phenothiadinyl (e.g., 1-phenothiadinyl, 2-phenothiadinyl, 3-phenothiadinyl, 4-phenothiadinyl) or the like.

The term "heteroaryldiyl" includes a C1-C9 heteroaryldiyl having one to four nitrogen atom(s), oxygen atom(s), and/or sulfur atom(s), for example, furandiyl, thiophenediyl, pyrrolediyl, imidazolediyl, pyrazolediyl, triazolediyl, tetrazolediyl, oxazolediyl, isoxazolediyl, thiazolediyl, thiadiazolediyl, isothiazolediyl, pyridinediyl, pyridazinediyl, pyrimidinediyl, furazandiyl, pyrazinediyl, oxadiazolediyl, benzofurandiyl, benzothiophenediyl, benzimidazolediyl, dibenzofurandiyl, benzoxazolediyl, quinoxalinediyl, cinnolinediyl, quinazolinediyl, quinolinediyl, phthalazinediyl, isoquinolinediyl, purinediyl, pteridinediyl, carbazolunediyl, phenanthridinediyl, acridinediyl, indolinediyl, isoindolinediyl, phenazinediyl, phenothiadinediyl, or the like.

As preferable heteroaryldiyl of $X^2$, thiazole-1,4-diyl, thiazole-1,5-diyl, thiazole-3,5-diyl, pyridine-2,5-diyl, pyrimidine-2,5-diyl, and the like can be listed.

The heteroaryl of "heteroarylcarbonyl" is as defined the above "heteroaryl". As "heteroarylcarbonyl", for example, pyridylcarbonyl and the like can be listed.

The heteroaryl of "heteroarylsulfonyl" is as defined the above "heteroaryl". As "heteroarylsulfonyl", for example, furylsulfonyl, thienylsulfonyl, pyrrolylsulfonyl, imidazolylsulfonyl, pyrazolylsulfonyl, triazolylsulfonyl, tetrazolylsulfonyl, oxazolylsulfonyl, isoxazolylsulfonyl, thiazolylsulfonyl, thiadiazolylsulfonyl, isothiazolylsulfonyl, pyridylsulfonyl, pyridazinylsulfonyl, pyrimidinylsulfonyl, furazanylsulfonyl, pyrazinylsulfonyl, oxadiazoltlsulfonyl, benzofurylsulfonyl, benzothienylsulfonyl, benzimidazolylsulfonyl, dibenzofurylsulfonyl, benzoxazolylsulfonyl, quinoxalylsulfonyl, cinnolylsulfonyl, quinazolylsulfonyl, quinolylsulfonyl, phthalazinylsulfonyl, isoquinolylsulfonyl, purylsulfonyl, pteridinylsulfonyl, carbazolylsulfonyl, phenanthridinylsulfonyl, acridinylsulfonyl, indolylsulfonyl, isoindolylsulfonyl, phenazinylsulfonyl, phenothiadinylsulfonyl, or the like can be listed.

The term "non-aromatic heterocyclic group" includes a C1-C9 non-aromatic ring having one to four nitrogen atom(s), oxygen atom(s), and/or sulfur atom(s), for example, oxirane, 1-pyrrolinyl, 2-pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperazino, 2-piperazinyl, 2-morpholinyl, 3-morpholinyl, morpholino, tetrahydrofuranyl, tetrahydropyranyl, tetrahydrothiopyranyl, or the like.

The term "non-aromatic heterocyclediyl" includes a C1-C9 non-aromatic ring diyl having one to four nitrogen atom(s), oxygen atom(s), and/or sulfur atom(s), for example, pyrrolinediyl, pyrrolidinediyl, imidazolinediyl, imidazolidinediyl, pyrazolinediyl, pyrazolidinediyl, piperidinediyl, piperazinediyl, morpholinediyl, tetrahydropyrandiyl, or the like.

As "5-10 membered cycloalkene having one double bond, which may contain a group selected from —O—, —S—, —SO—, and —$SO_2$— in the ring", for example, cyclopentene, dihydropyran, dihydrothiopyran, dihydrothiopyran-1-oxide, dihydrothiopyran-1,1-dioxide, cyclohexene, cycloheptene, cyclooctene, cyclononene, cyclodecene, and the like can be listed. 7 to 10 membered cycloalkene is preferable, and, for example, cycloheptene, cyclooctene, cyclononene, and cyclodecene can be listed.

"Optionally substituted alkyl", "Optionally substituted: aryl", "Optionally substituted: heteroaryl", "Optionally substituted: non-aromatic heterocycle group", "Optionally substituted: alkylene", "Optionally substituted: aryloxy", "Optionally substituted: heteroaryloxy", "Optionally substituted: arylsulfonyl", "optionally replaced heteroarylsulfonyl", "Optionally substituted: cycloalkanediyl", "Optionally substituted: cycloalkenediyl", "Optionally substituted: aryldiyl", "Optionally substituted: heteroaryldiyl", "optionally replace non-aromatic heterocyclediyl", "Optionally substituted: amino", "Optionally substituted: hydrazine" include being unsubstituted or having a substituents.

When substituents are possessed, arbitrary positions, which can be replaced, may be replaced respectively with the same substituents or the different substituents of one or more possible numbers.

The substituents include, for example, hydroxy, carboxy, halogen (fluorine atom, chlorine atom, bromine atom, iodine atom), haloalkyl (e.g., $CF_3$, $CH_2CF_3$, $CH_2CCl_3$, and the like), haloalkoxy, alkyl (e.g., methyl, ethyl, isopropyl, t-butyl, and the like), alkenyl (e.g., binyl), formyl, acyl (e.g., acetyl, propionyl, butyryl, pivaloyl, benzoyl, pyridinecarbonyl, cyclopentanecarbonyl, cyclohexanecarbonyl, and the like), alkynyl (e.g., ethynyl), cycloalkyl (e.g., cyclopropyl, cyclobutyl, cyclopentyl, cyclohexyl, and the like), alkylene (e.g., trimethylene, pentamethylene, hexamethylene, and the like), alkenylene (e.g., 2-propene-1,3-diyl, 3-pentene-1,5-diyl, 3-hexene-1,6-diyl, and the like), alkoxy (e.g., methoxy, ethoxy, propoxy, butoxy, and the like), alkoxycarbonyl (e.g., methoxycarbonyl, ethoxycarbonyl, t-butoxycarbonyl, and the like), nitro, nitroso, oxo, Optionally substituted: amino (e.g., amino, alkylamino (e.g., methylamino, ethylamino, dimethylamino, and the like), formylamino, acylamino (e.g., acetylamino, benzoylamino, and the like)), azide, aryl (e.g., phenyl and the like), aryloxy (e.g., phenoxy), cyano, isocyano, isocyanate, thiocyanate, isothiocyanate, mercapto, alkylthio (e.g., methylthio, ethylthio, and the like), alkylsulfonyl (e.g., methanesulfonyl, ethanesulfonyl), arylsulfonyl (e.g., benzenesulfonyl and the like), Optionally substituted: carbamoyl, sulfamoyl, formyloxy, haloformyl, oxalo, mercapto, thioformyl, thiocarboxy, dithiocarboxy, thiocarbamoyl, sulfino, sulfo, sulfoamino, hydrazine, ureido, amidino, guanidino, formyloxy, thioxo, alkoxyalkoxy, alkylthioalkoxy, and the like.

When the number of the substituents or the kinds of the substituents are specified, it means that the substitution may be carried out within the specified range.

A preferable compound of the formula (I) is such a compound that has each of the following partial structures of a) to r) independently, or has them in any one of their possible combination. a) $R^1$ is C1-C5 alkyl is optionally substituted with one to three substituents selected from the above-mentioned substituent group A or C4-C5 alkenyl, b) $R^1$ is C1-C5 alkyl optionally substituted with one to three substituents selected from the above-mentioned substituent group A, c) $R^1$ is n-butyl, isopentyl, 3-methyl-2-butenyl, 4,4,4-trifluorobutyl, 2-methyloxyethyl, cyclohexylmethyl, or (phenyl optionally substituted with one to three substituents selected from the above-mentioned substituent group F) methyl, d) $R^2$ is C1-C4 alkyl or C1-C4 alkyloxy C1-C4 alkyl, e) $R^2$ is C1-C4 alkyl, f) $R^3$ is C1-C4 alkyl or C1-C4 alkyloxy, g) $R^3$ is C1-C4 alkyl, h) $R^2$ and $R^3$ taken together with the adjacent carbon atoms form a 7 to 10 membered cycloalkene, i) $R^2$ and $R^3$ taken together with the adjacent carbon atoms form a 8 membered cycloalkene, j) $R^4$ is hydrogen or a hydroxy group, k) $R^4$ is hydrogen, l) $R^5$ is hydrogen, m) $X^1$ and $X^3$ are single bonds, and $X^2$ is C1-C4 alkylene optionally substituted with one to two substituents selected from the above-mentioned substituent group B, n) $X^1$ and $X^3$ each is independently a single bond or C1-C3 alkylene, and $X^2$ is C3-C8 cycloalkanediyl optionally substituted with one to two substituents selected from the above-mentioned substituent group C, o) $X^1$ is a single bond, $X^3$ is C1-C3 alkylene or C2-C3 alkenylene, $X^2$ is heteroaryldiyl optionally substituted with one to two substituents selected from the above-mentioned substituent group C, p) Y is —O—, and Z is hydrogen or C1-C8 alkyl optionally substituted with one to three substituents selected from the above-mentioned substituent group D, q) Y is —N($R^6$)— wherein $R^6$ is as defined the above, r) Y is preferable to be a group represented by the formula:

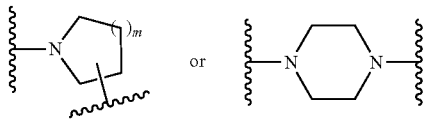

wherein m is as defined above, but it is not limited to these.

Preferable combinations will be specifically illustrated as follows.

(R1, R2, R3, R4, R5, (X1, X2, X3), (Y, Z)) is preferable to be, (a, d, f, j, l, m, p), (a, d, f, j, l, n, p), (a, d, f, j, l, o, p), (a, d, f, k, l, m, p), (a, d, f, k, l, n, p), (a, d, f, k, l, o, p), (a, d, g, j, l, m, p), (a, d, g, j, l, n, p), (a, d, g, j, l, o, p), (a, d, g, k, l, m, p), (a, d, g, k, l, n, p), (a, d, g, k, l, o, p), (a, e, f, j, l, m, p), (a, e, f, j, l, n, p), (a, e, f, j, l, o, p), (a, e, f, k, l, m, p), (a, e, f, k, l, n, p), (a, e, f, k, l, o, p), (a, e, g, j, l, m, p), (a, e, g, j, l, n, p), (a, e, g, j, l, o, p), (a, e, g, k, l, m, p), (a, e, g, k, l, n, p) (a, e, g, k, l, o, p), (b, d, f, j, l, m, p), (b, d, f, j, l, n, p), (b, d, f, j, l, o, p), (b, d, f, k, l, m, p), (b, d, f, k, l, n, p), (b, d, f, k, l, o, p), (b, d, g, j, l, m, p), (b, d, g, j, l, n, p), (b, d, g, j, l, o, p), (b, d, g, k, l, m, p), (b, d, g, k, l, n, p), (b, d, g, k, l, o, p), (b, e, f, j, l, m, p), (b, e, f, j, l, n, p), (b, e, f, j, l, o, p), (b, e, f, k, l, m, p), (b, e, f, k, l, n, p), (b, e, f, k, l, o, p), (b, e, g, j, l, m, p), (b, e, g, j, l, n, p), (b, e, g, j, l, o, p), (b, e, g, k, l, m, p), (b, e, g, k, l, n, p), (b, e, g, k, l, o, p), (c, d, f, j, l, m, p), (c, d, f, j, l, n, p), (c, d, f, j, l, o, p), (c, d, f, k, l, m, p), (c, d, f, k, l, n, p), (c, d, f, k, l, o, p), (c, d, g, j, l, m, p), (c, d, g, j, l, n, p), (c, d, g, j, l, o, p), (c, d, g, k, l, m, p), (c, d, g, k, l, n, p), (c, d, g, k, l, o, p), (c, e, f, j, l, m, p), (c, e, f, j, l, n, p), (c, e, f, j, l, o, p), (c, e, f, k, l, m, p), (c, e, f, k, l, n, p), (c, e, f, k, l, o, p), (c, e, g, j, l, m, p), (c, e, g, j, l, n, p), (c, e, g, j, l, o, p), (c, e, g, k, l, m, p), (c, e, g, k, l, n, p), or (c, e, g, k, l, o, p), (R1, R2, R3, R4, R5, (X1, X2, X3), Y) is preferable to be (a, d, f, j, l, m, q), (a, d, f, j, l, m, r), (a, d, f, j, l, n, q), (a, d, f, j, l, n, r), (a, d, f, j, l, o, q), (a, d, f, j, l, o, r), (a, d, f, k, l, m, q), (a, d, f, k, l, m, r), (a, d, f, k, l, n, q), (a, d, f, k, l, n, r), (a, d, f, k, l, o, q), (a, d, f, k, l, o, r), (a, d, g, j, l, m, q), (a, d, g, j, l, m, r), (a, d, g, j, l, n, q), (a, d, g, j, l, n, r), (a, d, g, j, l, o, q), (a, d, g, j, l, o, r), (a, d, g, k, l, m, q), (a, d, g, k, l, m, r), (a, d, g, k, l, n, q), (a, d, g, k, l, n, r), (a, d, g, k, l, o, q), (a, d, g, k, l, o, r), (a, e, f, j, l, m, q), (a, e, f, j, l, m, r), (a, e, f, j, l, n, q), (a, e, f, j, l, n, r), (a, e, f, j, l, o, q), (a, e, f, j, l, o, r), (a, e, f, k, l, m, q), (a, e, f, k, l, m, r), (a, e, f, k, l, n, q), (a, e, f, k, l, n, r), (a, e, f, k, l, o, q), (a, e, f, k, l, o, r), (a, e, g, j, l, m, q), (a, e, g, j, l, m, r), (a, e, j, l, n, q), (a, e, g, j, l, n, r), (a, e, g, j, l, o, q), (a, e, g, j, l, o, r), (a, e, g, k, l, m, q), (a, e, g, k, l, m, r), (a, e, g, k, l, n, q), (a, e, g, k, l, n, r), (a, e, g, k, l, o, q), (a, e, g, k, l, o, r), (b, d, f, j, l, m, q), (b, d, f, j, l, m, r), (b, d, f, j, l, n, q), (b, d, f, j, l, n, r), (b, d, f, j, l, o, q), (b, d, f, j, l, o, r), (b, d, f, k, l, m, q), (b, d, f, k, l, m, r), (b, d, f, k, l, n, q), (b, d, f, k, l, n, r), (b, d, f, k, l, o, q), (b, d, f, k, l, o, r), (b, d, g, j, l, m, q), (b, d, g, j, l, m, r), (b, d, g, j, l, n, q), (b, d, g, j, l, n, r), (b, d, g, j, l, o, q), (b, d, g, j, l, o, r), (b, d, g, k, l, m, q), (b, d, g, k, l, m, r), (b, d, g, k, l, n, q), (b, d, g, k, l, n, r), (b, d, g, k, l, o, q), (b, d, g, k, l, o, r), (b, e, f, j, l, m, q), (b, e, f, j, l, m, r), (b, e, f, j, l, n, q), (b, e, f, j, l, n, r), (b, e, f, j, l, o, q), (b, e, f, j, l, o, r), (b, e, f, k, l, m, q), (b, e, f, k, l, m, r), (b, e, f, k, l, n, q), (b, e, f, k, l, n, r), (b, e, f, k, l, o, q), (b, e, f, k, l, o, r), (b, e, g, j, l, m, q), (b, e, g, j, l, m, r), (b, e, g, j, l, n, q), (b, e, g, j, l, n, r), (b, e, g, j, l, o, q), (b, e, g, j, l, o, r), (b, e, g, k, l, m, q), (b, e, g, k, l, m, r), (b, e, g, k, l, n, q), (b, e, g, k, l, n, r), (b, e, g, k, l, o, q), (b, e, g, k, l, o, r), (c, d, f, j, l, m, q), (c, d, f, j, l, m, r), (c, d, f, j, l, n, q), (c, d, f, j, l, n, r), (c, d, f, j, l, o, q), (c, d, f, j, l, o, r), (c, d, f, k, l, m, q), (c, d, f, k, l, m, r), (c, d, f, k, l, n, q), (c, d, f, k, l, n, r), (c, d, f, k, l, o, q), (c, d, f, k, l, o, r), (c, d, g, j, l, m, q), (c, d, g, j, l, m, r), (c, d, g, j, l, n, q), (c, d, g, j, l, n, r), (c, d, g, j, l, o, q), (c, d, g, j, l, o, r), (c, d, g, k, l, m, q), (c, d, g, k, l, m, r), (c, d, g, k, l, n, q), (c, d, g, k, l, n, r), (c, d, g, k, l, o, q), (c, d, g, k, l, o, r), (c, e, f, j, l, m, q), (c, e, f, j, l, m, r), (c, e, f, j, l, n, q), (c, e, f, j, l, n, r), (c, e, f, j, l, o, q), (c, e, f, j, l, o, r), (c, e, f, k, l, m, q), (c, e, f, k, l, m, r), (c, e, f, k, l, n, q), (c, e, f, k, l, n, r), (c, e, f, k, l, o, q), (c, e, f, k, l, o, r), (c, e, g, j, l, m, q), (c, e, g, j, l, m, r), (c, e, g, j, l, n, q), (c, e, g, j, l, n, r), (c, e, g, j, l, o, q), (c, e, g, j, l, o, r), (c, e, g, k, l, m, q), (c, e, g, k, l, r), (c, e, g, k, l, n, q), (c, e, g, k, l, n, r), (c, e, g, k, l, o, q), or (c, e, g, k, l, o, r), (R1, (R2-R3), R4, R5, (X1, X2, X3), (Y, Z)) is preferable to be (a, h, j, l, m, p), (a, h, j, l, n, p), (a, h, j, l, o, p), (a, h, k, l, m, p), (a, h, k, l, n, p), (a, h, k, l, o, p), (a, i, j, l, m, p), (a, i, j, l, n, p), (a, i, j, l, o, p), (a, i, k, l, m, p), (a, i, k, l, n, p), (a, i, k, l, o, p), (b, h, j, l, m, p), (b, h, j, l, n, p), (b, h, j, l, o, p), (b, h, k, l, m, p), (b, h, k, l, n, p), (b, h, k, l, o, p), (b, i, j, l, m, p), (b, i, j, l, n, p), (b, i, j, l, o, p), (b, i, k, l, m, p), (b, i, k, l, n, p), (b, i, k, l, o, p), (c, h, j, l, m, p), (c, h, j, l, n, p), (c, h, j, l, o, p), (c, h, k, l, p), (c, h, k, l, n, p), (c, h, k, l, o, p), (c, i, j, l, m, p), (c, i, j, l, n, p), (c, i, j, l, o, p), (c, i, k, l, m, p), (c, i, k, l, n, p), or (c, i, k, l, o, p), or, (R1, (R2-R3), R4, R5, (X1, X2, X3), Y) is preferable to be (a, h, j, l, m, q), (a, h, j, l, m, r), (a, h, j, l, n, q), (a, h, j, l, n, r), (a, h, j, l, o, q), (a, h, j, l, o, r), (a, h, k, l, m, q), (a, h, k, l, r), (a, h, k, l, n, q), (a, h, k, l, n, r), (a, h, k, l, o, q), (a, h, k, l, o, r), (a, i, j, l, m, q), (a, i, j, l, m, r), (a, i, j, l, n, q), (a, i, j, l, n, r), (a, i, j, l, o, q), (a, i, j, l, o, r), (a, i, k, l, m, q), (a, i, k, l, m, r), (a, i, k, l, n, q), (a, i, k, l, n, r), (a, i, k, l, o, q), (a, i, k, l, o, r), (b, h, j, l, m, q), (b, h, j, l, m, r), (b, h, j, l, n, q), (b, h, j, l, n, r), (b, h, j, l, o, q), (b, h, j, l, o, r), (b, h, k, l, m, q), (b, h, k, l, m, r), (b, h, k, l, n, q), (b, h, k, l, n, r), (b, h, k, l, o, q), (b, h, k, l, o, r), (b, i, j, l, in, q), (b, i, j, l, m, r), (b, i, j, l, n, q), (b, i, j, l, n, r), (b, i, j, l, o, q), (b, i, j, l, o, r), (b, i, k, l, m, q), (b, i, k, l, m, r), (b, i, k, l, n, q), (b, i, k, l, n, r), (b, i, k, l, o, q), (b, i, k, l, o, r), (c, h, j, l, m, q), (c, h, j, l, m, r), (c, h, j, l, n, q), (c, h, j, l, n, r), (c, h, j, l, o, q), (c, h, j, l, o, r), (c, h, k, l, m, q), (c, h, k, l, m, r), (c, h, k, l, n, q), (c, h, k, l, n, r), (c, h, k, l, o, q), (c, h, k, l, o, r), (c, i, j, l, m, q), (c, i, j, l, m, r), (c, i, j, l, n, q), (c, i, j, l, n, r), (c, i, j, l, o, q), (c, i, j, l, o, r), (c, i, k, l, m, q), (c, i, k, l, m, r), (c, i, k, l, n, q), (c, i, k, l, n, r), (c, i, k, l, o, q), or (c, i, k, l, o, r).

Moreover, in the formula (II), a compound having a possible combination of partial structure A and partial structure B shown below is preferable.

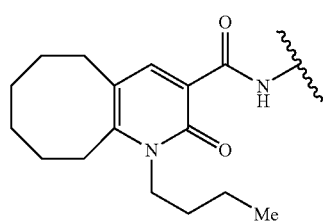
(A-1)

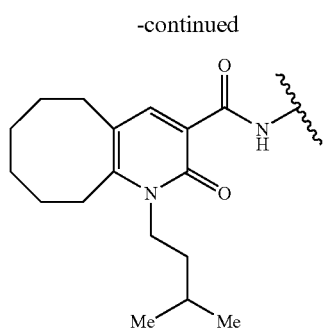
(A-2)

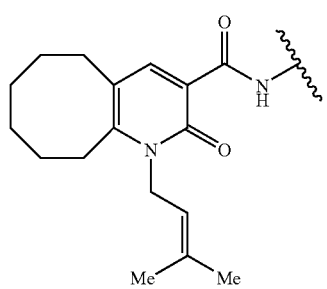
(A-3)

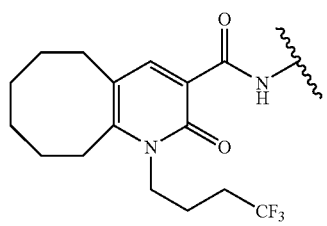
(A-4)

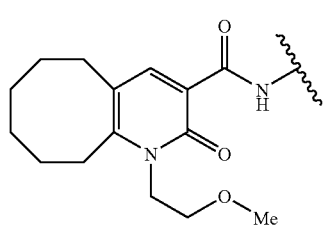
(A-5)

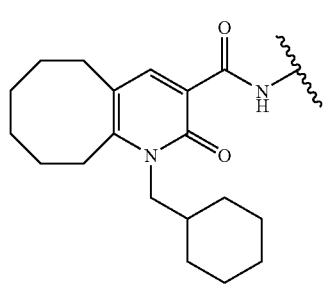
(A-6)

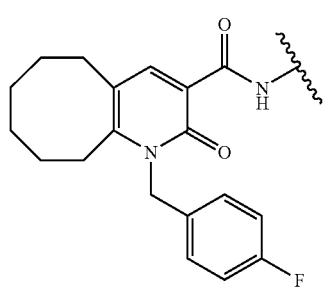
(A-7)

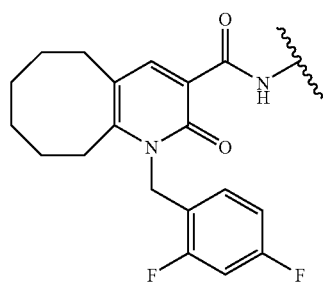
(A-8)
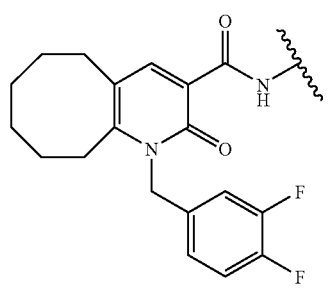
(A-9)
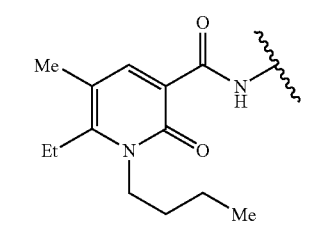
(B-1)
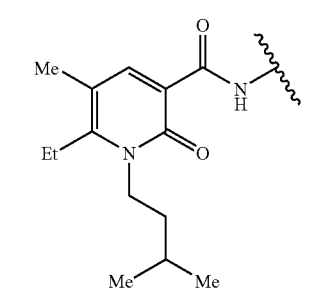
(B-2)
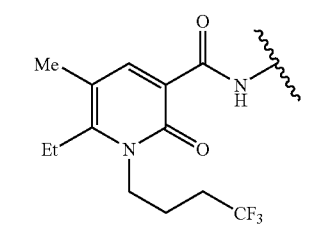
(B-4)
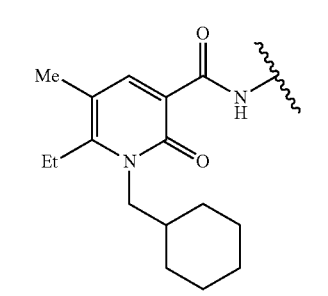
(B-6)
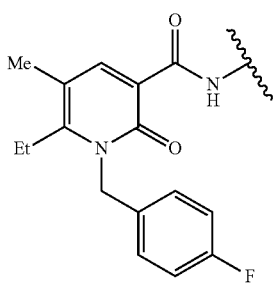
(B-7)
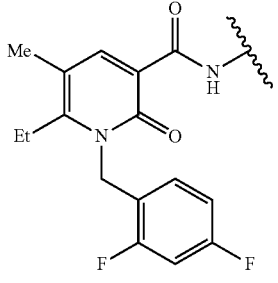
(B-8)
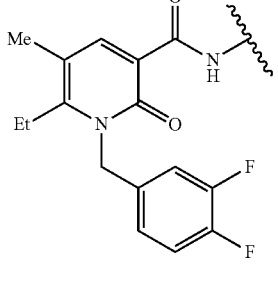
(B-9)
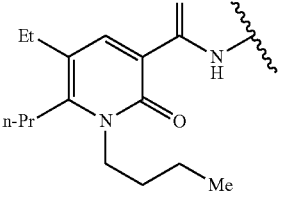
(C-1)
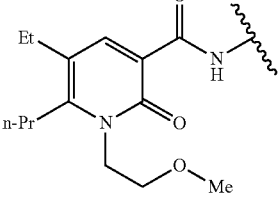
(C-5)
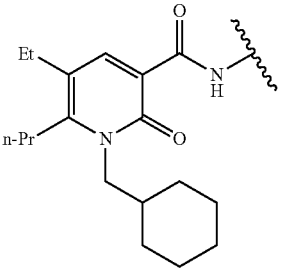
(C-6)

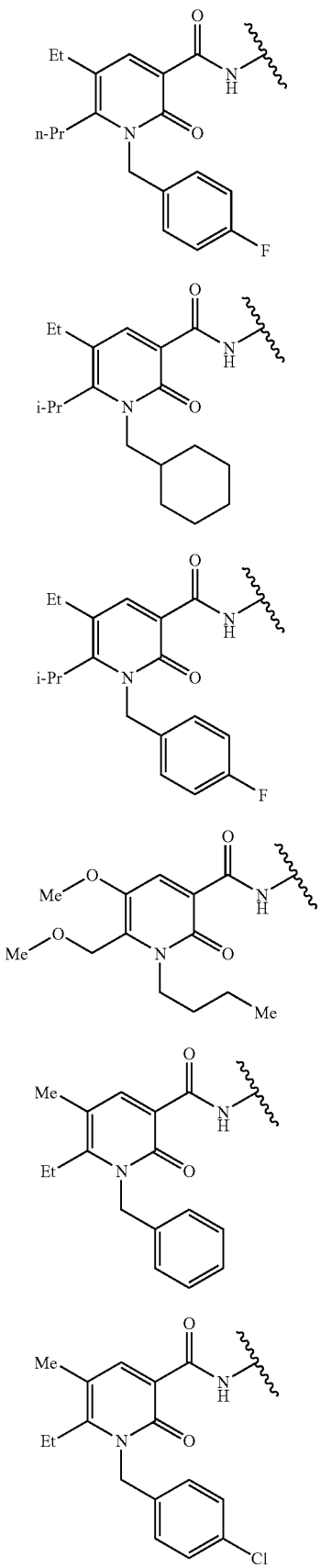
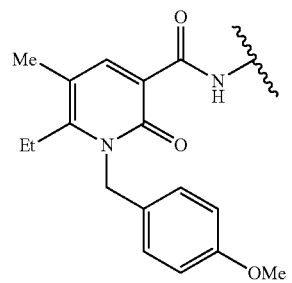
(B-13)
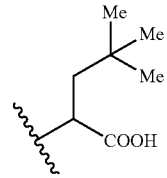
(N-1)
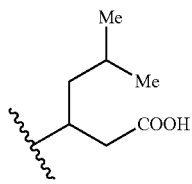
(Q-1)
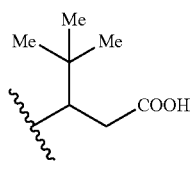
(Q-2)
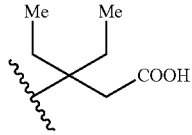
(Q-3)
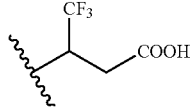
(Q-4)
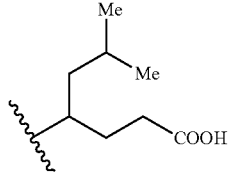
(R-1)
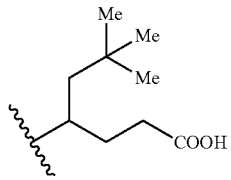
(R-2)

-continued
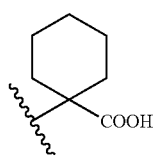 (S-1)
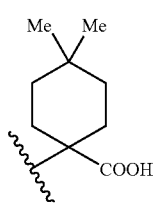 (S-2)
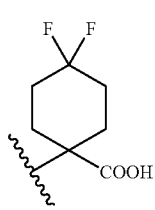 (S-3)
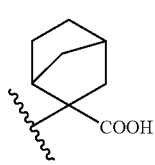 (S-4)
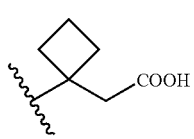 (T-1)
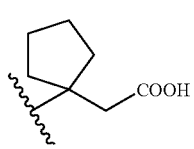 (T-2)
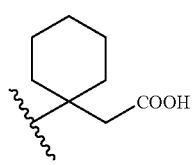 (T-3)
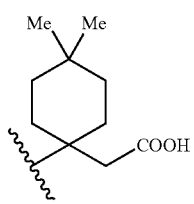 (T-4)
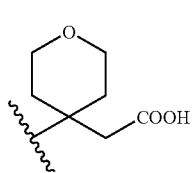 (T-5)
-continued
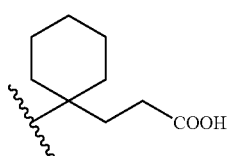 (U-1)
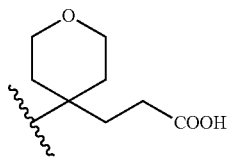 (U-2)
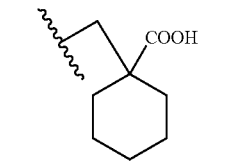 (V-1)
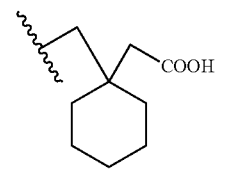 (W-1)
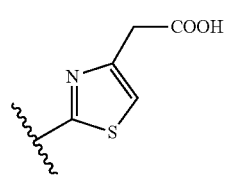 (X-1)
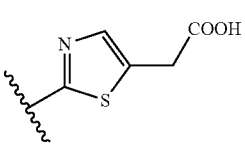 (X-2)
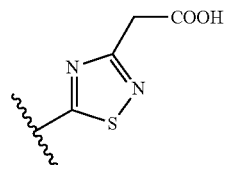 (X-3)
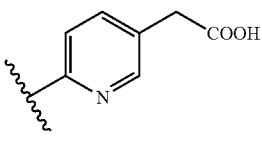 (X-4)
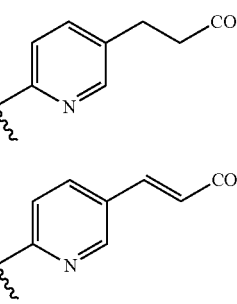 (Y-1)
(Z-1)

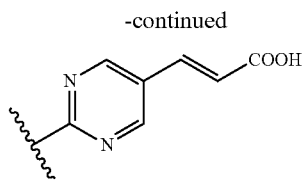
(Z-2)

Specifically, a preferable compound has the combination of (partial structure A, partial structure B) of (A-1, N-1), (A-1, Q-1), (A-1, Q-2), (A-1, Q-3), (A-1, Q-4), (A-1, R-1), (A-1, R-2), (A-1, S-1), (A-1, S-2), (A-1, S-3), (A-1, S-4), (A-1, T-1), (A-1, T-2), (A-1, T-3), (A-1, T-4), (A-1, T-5), (A-1, U-1), (A-1, U-2), (A-1, V-1), (A-1, W-1), (A-1, X-1), (A-1, X-2), (A-1, X-3), (A-1, X-4), (A-1, Y-1), (A-1, Z-1), (A-1, Z-2), (A-2, N-1), (A-2, Q-1), (A-2, Q-2), (A-2, Q-3), (A-2, Q-4), (A-2, R-1), (A-2, R-2), (A-2, S-1), (A-2, S-2), (A-2, S-3), (A-2, S-4), (A-2, T-1), (A-2, T-2), (A-2, T-3), (A-2, T-4), (A-2, T-5), (A-2, U-1), (A-2, U-2), (A-2, V-1), (A-2, W-1), (A-2, X-1), (A-2, X-2), (A-2, X-3), (A-2, X-4), (A-2, Y-1), (A-2, Z-1), (A-2, Z-2), (A-3, N-1), (A-3, Q-1), (A-3, Q-2), (A-3, Q-3), (A-3, Q-4), (A-3, R-1), (A-3, R-2), (A-3, S-1), (A-3, S-2), (A-3, S-3), (A-3, S-4), (A-3, T-1), (A-3, T-2), (A-3, T-3), (A-3, T-4), (A-3, T-5), (A-3, U-1), (A-3, U-2), (A-3, V-1), (A-3, W-1), (A-3, X-1), (A-3, X-2), (A-3, X-3), (A-3, X-4), (A-3, Y-1), (A-3, Z-1), (A-3, Z-2), (A-4, N-1), (A-4, Q-1), (A-4, Q-2), (A-4, Q-3), (A-4, Q-4), (A-4, R-1), (A-4, R-2), (A-4, S-1), (A-4, S-2), (A-4, S-3), (A-4, S-4), (A-4, T-1), (A-4, T-2), (A-4, T-3), (A-4, T-4), (A-4, T-5), (A-4, U-1), (A-4, U-2), (A-4, V-1), (A-4, W-1), (A-4, X-1), (A-4, X-2), (A-4, X-3), (A-4, X-4), (A-4, Y-1), (A-4, Z-1), (A-4, Z-2), (A-5, N-1), (A-5, Q-1), (A-5, Q-2), (A-5, Q-3), (A-5, Q-4), (A-5, R-1), (A-5, R-2), (A-5, S-1), (A-5, S-2), (A-5, S-3), (A-5, S-4), (A-5, T-1), (A-5, T-2), (A-5, T-3), (A-5, T-4), (A-5, T-5), (A-5, U-1), (A-5, U-2), (A-5, V-1), (A-5, W-1), (A-5, X-1), (A-5, X-2), (A-5, X-3), (A-5, X-4), (A-5, Y-1), (A-5, Z-1), (A-5, Z-2), (A-6, N-1), (A-6, Q-1), (A-6, Q-2), (A-6, Q-3), (A-6, Q-4), (A-6, R-1), (A-6, R-2), (A-6, S-1), (A-6, S-2), (A-6, S-3), (A-6, S-4), (A-6, T-1), (A-6, T-2), (A-6, T-3), (A-6, T-4), (A-6, T-5), (A-6, U-1), (A-6, U-2), (A-6, V-1), (A-6, W-1), (A-6, X-1), (A-6, X-2), (A-6, X-3), (A-6, X-4), (A-6, Y-1), (A-6, Z-1), (A-6, Z-2), (A-7, N-1), (A-7, Q-1), (A-7, Q-2), (A-7, Q-3), (A-7, Q-4), (A-7, R-1), (A-7, R-2), (A-7, S-1), (A-7, S-2), (A-7, S-3), (A-7, S-4), (A-7, T-1), (A-7, T-2), (A-7, T-3), (A-7, T-4), (A-7, T-5), (A-7, U-1), (A-7, U-2), (A-7, V-1), (A-7, W-1), (A-7, X-1), (A-7, X-2), (A-7, X-3), (A-7, X-4), (A-7, Y-1), (A-7, Z-1), (A-7, Z-2), (A-8, N-1), (A-8, Q-1), (A-8, Q-2), (A-8, Q-3), (A-8, Q-4), (A-8, R-1), (A-8, R-2), (A-8, S-1), (A-8, S-2), (A-8, S-3), (A-8, S-4), (A-8, T-1), (A-8, T-2), (A-8, T-3), (A-8, T-4), (A-8, T-5), (A-8, U-1), (A-8, U-2), (A-8, V-1), (A-8, W-1), (A-8, X-1), (A-8, X-2), (A-8, X-3), (A-8, X-4), (A-8, Y-1), (A-8, Z-1), (A-8, Z-2), (A-9, N-1), (A-9, Q-1), (A-9, Q-2), (A-9, Q-3), (A-9, Q-4), (A-9, R-1), (A-9, R-2), (A-9, S-1), (A-9, S-2), (A-9, S-3), (A-9, S-4), (A-9, T-1), (A-9, T-2), (A-9, T-3), (A-9, T-4), (A-9, T-5), (A-9, U-1), (A-9, U-2), (A-9, V-1), (A-9, W-1), (A-9, X-1), (A-9, X-2), (A-9, X-3), (A-9, X-4), (A-9, Y-1), (A-9, Z-1), (A-9, Z-2), (B-1, N-1), (B-1, Q-1), (B-1, Q-2), (B-1, Q-3), (B-1, Q-4), (B-1, R-1), (B-1, R-2), (B-1, S-1), (B-1, S-2), (B-1, S-3), (B-1, S-4), (B-1, T-1), (B-1, T-2), (B-1, T-3), (B-1, T-4), (B-1, T-5), (B-1, U-1), (B-1, U-2), (B-1, V-1), (B-1, W-1), (B-1, X-1), (B-1, X-2), (B-1, X-3), (B-1, X-4), (B-1, Y-1), (B-1, Z-1), (B-1, Z-2), (B-2, N-1), (B-2, Q-1), (B-2, Q-2), (B-2, Q-3), (B-2, Q-4), (B-2, R-1), (B-2, R-2), (B-2, S-1), (B-2, S-2), (B-2, S-3), (B-2, S-4), (B-2, T-1), (B-2, T-2), (B-2, T-3), (B-2, T-4), (B-2, T-5), (B-2, U-1), (B-2, U-2), (B-2, V-1), (B-2, W-1), (B-2, X-1), (B-2, X-2), (B-2, X-3), (B-2, X-4), (B-2, Y-1), (B-2, Z-1), (B-2, Z-2), (B-3, N-1), (B-3, Q-1), (B-3, Q-2), (B-3, Q-3), (B-3, Q-4), (B-3, R-1), (B-3, R-2), (B-3, S-1), (B-3, S-2), (B-3, S-3), (B-3, S-4), (B-3, T-1), (B-3, T-2), (B-3, T-3), (B-3, T-4), (B-3, T-5), (B-3, U-1), (B-3, U-2), (B-3, V-1), (B-3, W-1), (B-3, X-1), (B-3, X-2), (B-3, X-3), (B-3, X-4), (B-3, Y-1), (B-3, Z-1), (B-3, Z-2), (B-4, N-1), (B-4, Q-1), (B-4, Q-2), (B-4, Q-3), (B-4, Q-4), (B-4, R-1), (B-4, R-2), (B-4, S-1), (B-4, S-2), (B-4, S-3), (B-4, S-4), (B-4, T-1), (B-4, T-2), (B-4, T-3), (B-4, T-4), (B-4, T-5), (B-4, U-1), (B-4, U-2), (B-4, V-1), (B-4, W-1), (B-4, X-1), (B-4, X-2), (B-4, X-3), (B-4, X-4), (B-4, Y-1), (B-4, Z-1), (B-4, Z-2), (B-5, N-1), (B-5, Q-1), (B-5, Q-2), (B-5, Q-3), (B-5, Q-4), (B-5, R-1), (B-5, R-2), (B-5, S-1), (B-5, S-2), (B-5, S-3), (B-5, S-4), (B-5, T-1), (B-5, T-2), (B-5, T-3), (B-5, T-4), (B-5, T-5), (B-5, U-1), (B-5, U-2), (B-5, V-1), (B-5, W-1), (B-5, X-1), (B-5, X-2), (B-5, X-3), (B-5, X-4), (B-5, Y-1), (B-5, Z-1), (B-5, Z-2), (B-6, N-1), (B-6, Q-1), (B-6, Q-2), (B-6, Q-3), (B-6, Q-4), (B-6, R-1), (B-6, R-2), (B-6, S-1), (B-6, S-2), (B-6, S-3), (B-6, S-4), (B-6, T-1), (B-6, T-2), (B-6, T-3), (B-6, T-4), (B-6, T-5), (B-6, U-1), (B-6, U-2), (B-6, V-1), (B-6, W-1), (B-6, X-1), (B-6, X-2), (B-6, X-3), (B-6, X-4), (B-6, Y-1), (B-6, Z-1), (B-6, Z-2), (B-7, N-1), (B-7, Q-1), (B-7, Q-2), (B-7, Q-3), (B-7, Q-4), (B-7, R-1), (B-7, R-2), (B-7, S-1), (B-7, S-2), (B-7, S-3), (B-7, S-4), (B-7, T-1), (B-7, T-2), (B-7, T-3), (B-7, T-4), (B-7, T-5), (B-7, U-1), (B-7, U-2), (B-7, V-1), (B-7, W-1), (B-7, X-1), (B-7, X-2), (B-7, X-3), (B-7, X-4), (B-7, Y-1), (B-7, Z-1), (B-7, Z-2), (B-8, N-1), (B-8, Q-1), (B-8, Q-2), (B-8, Q-3), (B-8, Q-4), (B-8, R-1), (B-8, R-2), (B-8, S-1), (B-8, S-2), (B-8, S-3), (B-8, S-4), (B-8, T-1), (B-8, T-2), (B-8, T-3), (B-8, T-4), (B-8, T-5), (B-8, U-1), (B-8, U-2), (B-8, V-1), (B-8, W-1), (B-8, X-1), (B-8, X-2), (B-8, X-3), (B-8, X-4), (B-8, Y-1), (B-8, Z-1), (B-8, Z-2), (B-9, N-1), (B-9, Q-1), (B-9, Q-2), (B-9, Q-3), (B-9, Q-4), (B-9, R-1), (B-9, R-2), (B-9, S-1), (B-9, S-2), (B-9, S-3), (B-9, S-4), (B-9, T-1), (B-9, T-2), (B-9, T-3), (B-9, T-4), (B-9, T-5), (B-9, U-1), (B-9, U-2), (B-9, V-1), (B-9, W-1), (B-9, X-1), (B-9, X-2), (B-9, X-3), (B-9, X-4), (B-9, Y-1), (B-9, Z-1), (B-9, Z-2), (C-1, N-1), (C-1, Q-1), (C-1, Q-2), (C-1, Q-3), (C-1, Q-4), (C-1, R-1), (C-1, R-2), (C-1, S-1) (C-1, S-2), (C-1, S-3), (C-1, S-4), (C-1, T-1), (C-1, T-2), (C-1, T-3), (C-1, T-4), (C-1, T-5), (C-1, U-1), (C-1, U-2), (C-1, V-1), (C-1, W-1), (C-1, X-1), (C-1, X-2), (C-1, X-3), (C-1, X-4), (C-1, Y-1), (C-1, Z-1), (C-1, Z-2), (C-5, N-1), (C-5, Q-1), (C-5, Q-2), (C-5, Q-3), (C-5, Q-4), (C-5, R-1), (C-5, R-2), (C-5, S-1), (C-5, S-2), (C-5, S-3), (C-5, S-4), (C-5, T-1), (C-5, T-2), (C-5, T-3), (C-5, T-4), (C-5, T-5), (C-5, U-1), (C-5, U-2), (C-5, V-1), (C-5, W-1), (C-5, X-1), (C-5, X-2), (C-5, X-3), (C-5, X-4), (C-5, Y-1), (C-5, Z-1), (C-5, Z-2), (C-6, N-1), (C-6, Q-1), (C-6, Q-2), (C-6, Q-3), (C-6, Q-4), (C-6, R-1), (C-6, R-2), (C-6, S-1), (C-6, S-2), (C-6, S-3), (C-6, S-4), (C-6, T-1), (C-6, T-2), (C-6, T-3), (C-6, T-4), (C-6, T-5), (C-6, U-1), (C-6, U-2), (C-6, V-1), (C-6, W-1), (C-6, X-1), (C-6, X-2), (C-6, X-3), (C-6, X-4), (C-6, Y-1), (C-6, Z-1), (C-6, Z-2), (C-7, N-1), (C-7, Q-1), (C-7, Q-2), (C-7, Q-3), (C-7, Q-4), (C-7, R-1), (C-7, R-2), (C-7, S-1), (C-7, S-2), (C-7, S-3), (C-7, S-4), (C-7, T-1), (C-7, T-2), (C-7, T-3), (C-7, T-4), (C-7, T-5), (C-7, U-1), (C-7, U-2), (C-7, V-1), (C-7, W-1), (C-7, X-1), (C-7, X-2), (C-7, X-3), (C-7, X-4), (C-7, Y-1), (C-7, Z-1), (C-7, Z-2), (D-6, N-1), (D-6, Q-1), (D-6, Q-2), (D-6, Q-3), (D-6, Q-4), (D-6, R-1), (D-6, R-2), (D-6, S-1), (D-6, S-2), (D-6, S-3), (D-6, S-4), (D-6, T-1), (D-6, T-2), (D-6, T-3), (D-6, T-4), (D-6, T-5), (D-6, U-1), (D-6, U-2), (D-6, V-1), (D-6, W-1), (D-6, X-1), (D-6, X-2), (D-6, X-3), (D-6, X-4), (D-6, Y-1), (D-6, Z-1), (D-6, Z-2), (D-7, N-1), (D-7, Q-1), (D-7, Q-2), (D-7, Q-3), (D-7, Q-4), (D-7, R-1), (D-7, R-2), (D-7, S-1), (D-7, S-2), (D-7, S-3), (D-7, S-4), (D-7, T-1), (D-7, T-2), (D-7, T-3), (D-7, T-4), (D-7, T-5), (D-7, U-1), (D-7, U-2), (D-7, V-1), (D-7, W-1), (D-7, X-1), (D-7, X-2), (D-7, X-3), (D-7, X-4), (D-7, Y-1), (D-7, Z-1), (D-7, Z-2), (E-1, N-1), (E-1, Q-1), (E-1, Q-2), (E-1, Q-3), (E-1, Q-4), (E-1, R-1), (E-1, R-2), (E-1, S-1), (E-1, S-2), (E-1, S-3), (E-1, S-4), (E-1, T-1), (E-1, T-2), (E-1, T-3), (E-1, T-4), (E-1, T-5), (E-1, U-1), (E-1, U-2), (E-1, V-1), (E-1, W-1), (E-1, X-1), (E-1, X-2), (E-1, X-3), (E-1, X-4), (E-1, Y-1), (E-1, Z-1), (E-1, Z-2), (B-11, N-1), (B-11, Q-1), (B-11, Q-2), (B-11, Q-3), (B-11, Q-4), (B-11, R-1), (B-11, R-2), (B-11, S-1), (B-11, S-2), (B-11, S-3), (B-11, S-4), (B-11, T-1), (B-11, T-2), (B-11, T-3), (B-11, T-4), (B-11, T-5), (B-11, U-1), (B-11, U-2), (B-11, V-1), (B-11, W-1), (B-11, X-1), (B-11, X-2), (B-11, X-3), (B-11, X-4), (B-11, Y-1), (B-11, Z-1), (B-11, Z-2), (B-12, N-1), (B-12, Q-1), (B-12, Q-2), (B-12, Q-3), (B-12, Q-4), (B-12, R-1), (B-12, R-2), (B-12, S-1), (B-12, S-2), (B-12, S-3), (B-12, S-4), (B-12, T-1), (B-12, T-2), (B-12, T-3), (B-12, T-4), (B-12, T-5), (B-12, U-1), (B-12, U-2), (B-12, V-1), (B-12, W-1), (B-12, X-1), (B-12, X-2), (B-12, X-3), (B-12, X-4), (B-12, Y-1), (B-12, Z-1), (B-12, Z-2), (B-13, N-1), (B-13, Q-1), (B-13, Q-2), (B-13, Q-3), (B-13, Q-4), (B-13, R-1), (B-13, R-2), (B-13, S-1), (B-13, S-2), (B-13, S-3), (B-13, S-4), (B-13, T-1), (B-13, T-2), (B-13, T-3), (B-13, T-4), (B-13, T-5), (B-13, U-1), (B-13, U-2), (B-13, V-1), (B-13, W-1), (B-13, X-1), (B-13, X-2), (B-13, X-3), (B-13, X-4), (B-13, Y-1), (B-13, Z-1), or (B-13, Z-2).

Preferable compounds will be illustrated as follows.
(1) methyl 3-methyl-2-{[2-oxo-1-(2-oxo-ethyl)-1,2,5,6,7,8,9,10-octahydro-cycloocta[b]pyridine-3-carbonyl]-amino}-butyrate,
(2) 5-[(1-cyclohexylmethyl-2-oxo-1,2,5,6,7,8,9,10-octahydro-cycloocta[b]pyridine-3-carbonyl)-amino]-valeric acid,
(3) (E)-3-[(1-cyclohexylmethyl-2-oxo-1,2,5,6,7,8,9,10-octahydro-cycloocta[b]pyridine-3-carbonyl)-amino]-4-hexene acid,
(4) methyl 2-{[5,6-dimethyl-1-(2-morpholine-4-yl-ethyl)-2-oxo-1,2-dihydropyridine-3-carbonyl]-amino}-3-methyl-butyrate,
(5) 1-[(1-cyclohexylmethyl-6-ethyl-5-methyl-2-oxo-1,2-dihydropyridine-3-carbonyl)-amino]-cyclohexane carboxylic acid,
(6) methyl {2-[(1-cyclohexylmethyl-2-oxo-1,2,5,6,7,8,9,10-octahydro-cycloocta[b]pyridine-3-carbonyl)-amino]-acetoxy}-(2,2-dimethyl-[1,3]dioxolan-4-yl)-acetate,
(7) methyl 2-[(1-butyl-5,6-dimethyl-2-oxo-1,2-dihydroxy-pyridine-3-carbonyl)-amino]-4-methylsulphanyl-butyrate,
(8) methyl 4-{[2-oxo-1-(tetrahydro-furan-2-ylmethyl)-1,2,5,6,7,8,9,10-octahydro-cycloocta[b]pyridine-3-carbonyl]-amino}-cyclohexanecarboxylate,
(9) 1-[(1-cyclohexylmethyl-4-hydroxy-2-oxo-1,2,5,6,7,8,9,10-octahydro-cycloocta[b]pyridine-3-carbonyl)-amino]-cyclohexanecarboxylic acid,
(10) 2-{[1-(4-cyano-benzyl)-2-oxo-1,2,5,6,7,8,9,10-octahydro-cycloocta[b]pyridine-3-carbonyl]-amino}-cyclohexanecarboxylic acid,
(11) 2-{[1-(4-fluorobenzyl)-2-oxo-1,2,5,6,7,8,9,10-octahydro-cycloocta[b]pyridine-3-carbonyl]-amino}-3,3-dimethyl-butyric acid,
(12) {[1-(2-methoxy-ethyl)-2-oxo-1,2,5,6,7,8,9,10-octahydro-cycloocta[b]pyridine-3-carbonyl]-amino}-phenylacetic acid,
(13) 2-{[1-(4-fluorobenzyl)-2-oxo-1,2,5,6,7,8,9,10-octahydro-cycloocta[b]pyridine-3-carbonyl]-amino}-3-methyl-butyric acid,
(14) 4-{2-[(1-cyclohexylmethyl-2-oxo-1,2,5,6,7,8,9,10-octahydro-cycloocta[b]pyridine-3-carbonyl)-amino]-2-methyl-propionyl}-1,1-dimethyl-piperazine-1-ium,
(15) 3-[(1-cyclohexylmethyl-2-oxo-1,2,5,6,7,8,9,10-octahydro-cycloocta[b]pyridine-3-carbonyl)-amino]-4,4,4-trifluoro-butyric acid,
(16) ({2-[(1-cyclohexylmethyl-2-oxo-1,2,5,6,7,8,9,10-octahydro-cycloocta[b]pyridine-3-carbonyl)-amino]-2-methyl-propionyl}-methyl-amino)-acetic acid,
(17) 2-[(1-cyclohexylmethyl-2-oxo-1,2,5,6,7,8,9,10-octahydro-cycloocta[b]pyridine-3-carbonyl)-amino]-cyclopent-1-en-carboxylic acid,
(18) 1-{[6-ethyl-1-(4-fluorobenzyl)-5-methyl-2-oxo-1,2-dihydropyridine-3-carbonyl]-amino}-cyclohexanecarboxylic acid,
(19) {[1-(4-cyano-butyl)-2-oxo-1,2,5,6,7,8,9,10-octahydro-cycloocta[b]pyridine-3-carbonyl]-amino}-phenylacetic acid,
(20) 1-cyclohexylmethyl-2-oxo-1,2,5,6,7,8,9,10-octahydro-cycloocta[b]pyridine-3-carboxylic acid 1,1-dimethyl-2-oxo-2-[N'-carbamoylhydrazino]-ethyl}-amide,
(21) [(1-cyclohexylmethyl-6-ethyl-5-methyl-2-oxo-1,2-dihydropyridine-3-carbonyl)-amino]-phenylacetic acid,
(22) methyl {[1-(2-chloro-benzyl)-5,6-dimethyl-2-oxo-1,2-dihydropyridine-3-carbonyl]-amino}-phenyl acetate,
(23) 1-cyclohexylmethyl-2-oxo-1,2,5,6,7,8,9,10-octahydro-cycloocta[b]pyridine-3-carboxylic acid {1-methyl-1-[(pyridine-3-carbothioyl)-carbamoyl]-ethyl}-amide,
(24) 2-[(1-cyclohexylmethyl-2-oxo-1,2,5,6,7,8,9,10-octahydro-cycloocta[b]pyridine-3-carbonyl)-amino]-2-methyl-propionic acid 2-phenyl-[1,3]dioxane-5-yl ester,
(25) methyl biphenyl-4-yl-[(1-cyclohexylmethyl-2-oxo-1,2,5,6,7,8,9,10-octahydro-cycloocta[b]pyridine-3-carbonyl)-amino]-acetate,
(26) 2-[(1-cyclohexylmethyl-2-oxo-1,2,5,6,7,8,9,10-octahydro-cycloocta[b]pyridine-3-carbonyl)-amino]-3-phenyl-propionic acid,
(27) 2-[(1-butyl-2-oxo-1,2,5,6,7,8,9,10-octahydro-cycloocta[b]pyridine-3-carbonyl)-amino]-cyclohexanecarboxylic acid,
(28) {[1-(2-cyano-ethyl)-2-oxo-1,2,5,6,7,8,9,10-octahydro-cycloocta[b]pyridine-3-carbonyl]-amino}-phenylacetic acid,
(29) 1-[(1-butyl-5-ethyl-2-oxo-6-propyl-1,2-dihydropyridine-3-carbonyl)-amino]-cyclohexanecarboxylic acid,
(30) dimethyl 2-[(1-cyclohexylmethyl-5,6-dimethyl-2-oxo-1,2-dihydropyridine-3-carbonyl)-amino]-succinate,
(31) 4-[(1-cyclohexylmethyl-2-oxo-1,2,5,6,7,8,9,10-octahydro-cycloocta[b]pyridine-3-carbonyl)-amino]-cyclohexanecarboxylic acid,
(32) methyl 1-{[1-(1-ethyl-pyrrolidine-2-2-ylmethyl)-2-oxo-1,2,5,6,7,8,9,10-octahydro-cycloocta[b]pyridine-3-carbonyl]-amino}-cyclohexanecarboxylate,
(33) 2-[(1-benzo[1,3]dioxol-5-ylmethyl-2-oxo-1,2,5,6,7,8,9,10-octahydro-cycloocta[b]pyridine-3-carbonyl)-amino]-3-methyl-butyric acid,
(34) 1-cyclohexylmethyl-2-oxo-1,2,5,6,7,8,9,10-octahydro-cycloocta[b]pyridine-3-carboxylic acid (1-{[2-(3,4-dimethoxy-phenyl)-ethyl]-methylcarbamoyl}-1-methyl-ethyl)-amide,
(35) 1-cyclohexylmethyl-2-oxo-1,2,5,6,7,8,9,10-octahydro-cycloocta[b]pyridine-3-carboxylic acid {1-[2-(3,4-dimethoxy-phenyl)-ethylcarbamoyl]-1-methyl-ethyl}-amide,
(36) 2-[(1-cyclohexylmethyl-2-oxo-1,2,5,6,7,8,9,10-octahydro-cycloocta[b]pyridine-3-carbonyl)-amino]-3,3-dimethyl-butyric acid,

(37) methyl {[1-(4-methoxybenzyl)-5,6-dimethyl-2-oxo-1,2-dihydropyridine-3-carbonyl]-amino}-phenyl acetate,
(38) ethyl 2-[(1-butyl-5,6-dimethyl-2-oxo-1,2-dihydroxypyridine-3-carbonyl)-amino]-cyclohexanecarboxylate,
(39) 1-[(1-cyclohexylmethyl-2-oxo-1,2,5,6,7,8,9,10-octahydro-cycloocta[b]pyridine-3-carbonyl)-amino]-cyclopropanecarboxylic acid,
(40) ethyl 2-[(1-butyl-5,6-dimethyl-2-oxo-1,2-dihydropyridine-3-carbonyl)-amino]-cyclopentanecarboxylate,
(41) 2-[(1-butyl-4-hydroxy-2-oxo-1,2,5,6,7,8,9,10-octahydro-cycloocta[b]pyridine-3-carbonyl)-amino]-cyclohexanecarboxylic acid,
(42) 2-[(1-cyclohexylmethyl-2-oxo-1,2,5,6,7,8,9,10-octahydro-cycloocta[b]pyridine-3-carbonyl)-amino]-3-methyl-butyric acid,
(43) diethyl 2-[(1-cyclohexylmethyl-5,6-dimethyl-2-oxo-1,2-dihydropyridine-3-carbonyl)-amino]-glutarate,
(44) methyl [(1-butyl-5-ethyl-2-oxo-6-propyl-1,2-dihydropyridine-3-carbonyl)-amino]-phenyl acetate,
(45) 2-[(1-cyclohexylmethyl-2-oxo-1,2,5,6,7,8,9,10-octahydro-cycloocta[b]pyridine-3-carbonyl)-amino]-3-methyl-butyric acid,
(46) methyl 2-[(1-cyclohexylmethyl-5,6-dimethyl-2-oxo-1,2-dihydropyridine-3-carbonyl)-amino]-3-phenyl-propionate,
(47) 1-cyclohexylmethyl-2-oxo-1,2,5,6,7,8,9,10-octahydro-cycloocta[b]pyridine-3-carboxylic acid [1-methyl-1-(morpholine-4-ylcarbamoyl)-ethyl]-amide,
(48) {[6-ethyl-1-(4-fluoro-benzyl)-5-methyl-2-oxo-1,2-dihydropyridine-3-carbonyl]-amino}-phenylacetic acid,
(49) 2-{[1-(4-fluorobenzyl)-2-oxo-1,2,5,6,7,8,9,10-octahydro-cycloocta[b]pyridine-3-carbonyl]-amino}-3-methyl-butyric acid,
(50) {2-[(1-cyclohexylmethyl-2-oxo-1,2,5,6,7,8,9,10-octahydro-cycloocta[b]pyridine-3-carbonyl)-amino]-thiazole-4-yl}-acetic acid,
(51) methyl [(1-butyl-2-oxo-2,5,6,7,8,9-hexahydroquinoline-1H-cyclohepta[b]pyridine-3-carbonyl)-amino]-phenyl acetate,
(52) methyl {[1-(3-chloro-benzyl)-5,6-dimethyl-2-oxo-1,2-dihydropyridine-3-carbonyl]-amino}-phenyl acetate,
(53) {[1-(4-cyano-benzyl)-2-oxo-1,2,5,6,7,8,9,10-octahydro-cycloocta[b]pyridine-3-carbonyl]-amino}-phenylacetic acid,
(54) methyl (benzyl-{2-[(1-cyclohexylmethyl-2-oxo-1,2,5,6,7,8,9,10-octahydro-cycloocta[b]pyridine-3-carbonyl)-amino]-ethyl}-amino)-acetate,
(55) methyl 3-[(1-butyl-2-oxo-1,2,5,6,7,8-hexahydroquinoline-3-carbonyl)-amino]-3-phenyl-propionate,
(56) 1-cyclohexylmethyl-2-oxo-1,2,5,6,7,8,9,10-octahydro-cycloocta[b]pyridine-3-carboxylic acid {1-[2-(4-methoxy-phenyl)-ethylcarbamoyl]-1-methyl-ethyl}-amide,
(57) 1-cyclohexylmethyl-2-oxo-1,2,5,6,7,8,9,10-octahydro-cycloocta[b]pyridine-3-carboxylic acid [1-(2-benzo[1,3]dioxol-5-yl-ethylcarbamoyl)-1-methyl-ethyl]-amide,
(58) [(1-butyl-2-oxo-1,2,5,6,7,8,9,10,11,12-decahydrocyclodeca[b]pyridine-3-carbonyl)-amino]-phenylacetic acid,
(59) methyl [(1-cyclohexylmethyl-2-oxo-1,2,5,6,7,8-hexahydroquinoline-3-carbonyl)-amino]-(4-methoxyphenyl)-acetate,
(60) methyl 2-{[1-(3-methoxycarbonyamino-propyl)-2-oxo-1,2,5,6,7,8,9,10-octahydro-cycloocta[b]pyridine-3-carbonyl]-amino}-2-methyl-propionate,
(61) 1-cyclohexylmethyl-2-oxo-1,2,5,6,7,8,9,10-octahydro-cycloocta[b]pyridine-3-carboxylic acid (1-methyl-1-thiobenzoylcarbamoyl-ethyl)-amide,
(62) 1-cyclohexylmethyl-2-oxo-1,2,5,6,7,8,9,10-octahydro-cycloocta[b]pyridine-3-carboxylic acid {1,1-dimethyl-2-oxo-2-[(pyridine-2-carbonyl)-amino]-ethyl}-amide,
(63) methyl 2-{[1-(1-ethyl-pyrrolidine-2-2-ylmethyl)-2-oxo-1,2,5,6,7,8,9,10-octahydro-cycloocta[b]pyridine-3-carbonyl]-amino}-3-methyl-butyrate,
(64) 1-cyclohexylmethyl-2-oxo-1,2,5,6,7,8,9,10-octahydro-cycloocta[b]pyridine-3-carboxylic acid {2-[4-(2-hydroxy-ethyl)-piperazine-1-yl]-1,1-dimethyl-2-oxo-ethyl}-amide,
(65) methyl [(1-cyclohexylmethyl-2-oxo-1,2,5,6,7,8-hexahydroquinoline-3-carbonyl)-amino]-(4-hydroxyphenyl)-acetate,
(66) [(1-cyclohexylmethyl-2-oxo-1,2,5,6,7,8,9,10-octahydro-cycloocta[b]pyridine-3-carbonyl)-amino]-(4-hydroxy-phenyl)-acetic acid,
(67) methyl {[1-(2-methoxy-ethyl)-2-oxo-1,2,5,6,7,8,9,10-octahydro-cycloocta[b]pyridine-3-carbonyl]-amino}-phenyl acetate,
(68) [(1-cyclohexylmethyl-2-oxo-1,2,5,6,7,8,9,10-decahydrocycloocta[b]pyridine-3-carbonyl)-amino]-acetic acid 2-pyridine-2-yl-ethyl ester
(69) 1-{[1-(4-fluorobenzyl)-2-oxo-1,2,5,6,7,8,9,10-octahydro-cycloocta[b]pyridine-3-carbonyl]-amino}-cyclohexanecarboxylic acid,
(70) 1-cyclohexylmethyl-2-oxo-1,2,5,6,7,8,9,10-octahydro-cycloocta[b]pyridine-3-carboxylic acid [1-methyl-1-(methylcarbamoylmethyl-carbamoyl)-ethyl]-amide,
(71) methyl 2-[(1-heptyl-5,6-dimethyl-2-oxo-1,2-dihydropyridine-3-carbonyl)-amino]-3-methyl-butyrate,
(72) methyl {[5,6-dimethyl-2-oxo-1-(4-trifluoromethyl-benzyl)-1,2-dihydropyridine-3-carbonyl]-amino}-phenyl acetate,
(73) methyl 2-{[1-(3-acetylamino-propyl)-2-oxo-1,2,5,6,7,8,9,10-octahydro-cycloocta[b]pyridine-3-carbonyl]-amino}-2-methyl-propionate,
(74) ethyl 2-{[1-(3-methoxycarnonyamino-propyl)-2-oxo-1,2,5,6,7,8,9,10-octahydro-cycloocta[b]pyridine-3-carbonyl]-amino}-cyclohexanecarboxylate,
(75) methyl {2-[(1-cyclohexylmethyl-2-oxo-1,2,5,6,7,8,9,10-octahydro-cycloocta[b]pyridine-3-carbonyl)-amino]-ethylamino}-acetate,
(76) 2-[(1-cyclohexylmethyl-2-oxo-1,2,5,6,7,8,9,10-octahydro-cycloocta[b]pyridine-3-carbonyl)-amino]-4-methyl-thiazole-5-carboxylic acid,
(77) 4-[(1-cyclohexylmethyl-2-oxo-1,2,5,6,7,8,9,10-octahydro-cycloocta[b]pyridine-3-carbonyl)-amino]-2,2-dimethyl-butyric acid,
(78) methyl 2-[(1-butyl-5,6-dimethyl-2-oxo-1,2-dihydropyridine-3-carbonyl)-amino]-3-methyl-butyrate,
(79) {[1-(4-fluorobenzyl)-5,6-dimethyl-2-oxo-1,2-dihydropyridine-3-carbonyl]-amino}-phenylacetic acid,
(80) benzyl-(2-{2-[(1-cyclohexylmethyl-2-oxo-1,2,5,6,7,8,9,10-octahydro-cycloocta[b]pyridine-3-carbonyl)-amino]-2-methyl-propionyloxy}-ethyl)-dimethyl-ammonium,
(81) 1-cyclohexylmethyl-2-oxo-1,2,5,6,7,8,9,10-octahydro-cycloocta[b]pyridine-3-carboxylic acid (2-benzenesulfonylhydrazino-1,1-dimethyl-2-oxo-ethyl)-amide,
(82) 1-cyclohexylmethyl-2-oxo-1,2,5,6,7,8,9,10-octahydro-cycloocta[b]pyridine-3-carboxylic acid {1,1-dimethyl-2-oxo-2-[N'-(pyridine-3-carbonyl)-hydrazino]-ethyl}-amide,
(83) 3,3-dimethyl-2-{[2-oxo-1-(tetrahydrofuran-2-ylmethyl)-1,2,5,6,7,8,9,10-octahydro-cycloocta[b]pyridine-3-carbonyl]-amino}-butyric acid,

(84) methyl [(1-butyl-6-ethyl-5-methyl-2-oxo-1,2-dihydro-pyridine-3-carbonyl)-amino]-phenyl acetate,
(85) methyl {[1-(3-methanesulfonylpropyl)-2-oxo-1,2,5,6,7,8,9,10-octahydro-cycloocta[b]pyridine-3-carbonyl]-amino}-phenyl acetate,
(86) [(1-cyclohexylmethyl-2-oxo-1,2,5,6,7,8,9,10-octahydro-cycloocta[b]pyridine-3-carbonyl)-amino]-acetic acid 2-morpholine-4-yl-ethyl ester
(87) {[1-(3-cyano-propyl)-2-oxo-1,2,5,6,7,8,9,10-octahydro-cycloocta[b]pyridine-3-carbonyl]-amino}-phenylacetic acid,
(88) dibutyl-(2-{2-[(1-cyclohexylmethyl-2-oxo-1,2,5,6,7,8,9,10-octahydro-cycloocta[b]pyridine-3-carbonyl)-amino]-2-methyl-propionyloxy}-ethyl)-methyl-ammonium iodide,
(89) 1-cyclohexylmethyl-2-oxo-1,2,5,6,7,8,9,10-octahydro-cycloocta[b]pyridine-3-carboxykic acid [2-(4-isobutyryl-piperazine-1-yl)-1,1-dimethyl-2-oxo-ethyl]-amide,
(90) 4,4,4-trifluoro-3-{[1-(4-fluoro-benzyl)-2-oxo-1,2,5,6,7,8,9,10-octahydro-cycloocta[b]pyridine-3-carbonyl]-amino}-butyric acid,
(91) 2-[(1-cyclohexylmethyl-2-oxo-1,2,5,6,7,8,9,10-octahydro-cycloocta[b]pyridine-3-carbonyl)-amino]-4,4-dimethyl-valeric acid,
(92) 1-cyclohexylmethyl-2-oxo-1,2,5,6,7,8,9,10-octahydro-cycloocta[b]pyridine-3-carboxylic acid (2-methanesulfonyl 1,1-dimethyl-2-oxo-ethyl)-amide,
(93) methyl 2-[(1-butyl-2-oxo-1,5,7,8-tetrahydro-2H-pyrano[4,3-b]pyridine-3-carbonyl)-amino]-3-methyl-butyrate,
(94) methyl {2-[(1-cyclohexylmethyl-2-oxo-1,2,5,6,7,8,9,10-octahydro-cycloocta[b]pyridine-3-carbonyl)-amino]-2-methyl-propionylamino}-acetate,
(95) 1-cyclohexylmethyl-2-oxo-1,2,5,6,7,8,9,10-octahydro-cycloocta[b]pyridine-3-carboxylic acid [1-methyl-1-(2-morpholine-4-yl-ethylcarbamoyl)-ethyl]-amide,
(96) 1-cyclohexylmethyl-2-oxo-1,2,5,6,7,8,9,10-octahydro-cycloocta[b]pyridine-3-carboxylic acid [1-(2-hydroxy-1,1-bis-hydroxymethyl-ethylcarbamoyl)-1-methyl-ethyl]-amide,
(97) 1-cyclohexylmethyl-2-oxo-1,2,5,6,7,8,9,10-octahydro-cycloocta[b]pyridine-3-carboxylic acid 1,1-dimethyl-2-oxo-2-[N'-isopropylcarbamoylhydrazino]-ethyl}-amide,
(98) {[6-ethyl-1-(4-fluorobenzyl)-5-methyl-2-oxo-1,2-dihydropyridine-3-carbonyl]-amino}-thiophene-2-yl-acetic acid,
(99) methyl [(1-furan-2-ylmethyl-2-oxo-1,2,5,6,7,8,9,10-octahydro-cycloocta[b]pyridine-3-carbonyl)-amino]-phenyl acetate,
(100) methyl benzofuran-2-yl-[(1-cyclohexylmethyl-2-oxo-1,2,5,6,7,8,9,10-octahydro-cycloocta[b]pyridine-3-carbonyl)-amino]-acetate,
(101) 2-[(1-cyclohexylmethyl-2-oxo-1,2,5,6,7,8,9,10-octahydro-cycloocta[b]pyridine-3-carbonyl)-amino]-2-methyl-propionic acid 2-carbazole-9-yl-ethyl ester,
(102) 1-cyclohexylmethyl-2-oxo-1,2,5,6,7,8,9,10-octahydro-cycloocta[b]pyridine-3-carboxylic acid [1,1-dimethyl-2-oxo-2-(3-propylcarbamoyl-piperidine-1-yl)-ethyl]-amide,
(103) 1-cyclohexylmethyl-2-oxo-1,2,5,6,7,8,9,10-octahydro-cycloocta[b]pyridine-3-carboxylic acid {1-[(imino-ureido-methyl)-carbamoyl]-1-methyl-ethyl}-amide,
(104) 1-cyclohexylmethyl-2-oxo-1,2,5,6,7,8,9,10-octahydro-cycloocta[b]pyridine-3-carboxylic acid {1-[bis-(2-hydroxy-ethyl)-carbamoyl]-1-methyl-ethyl}-amide,
(105) methyl 3-[(1-butyl-5-ethyl-2-oxo-6-propyl-1,2-dihydropyridine-3-carbonyl)-amino]-3-phenyl-propionate,
(106) methyl {[1-(2-cyano-ethyl)-2-oxo-1,2,5,6,7,8,9,10-octahydro-cycloocta[b]pyridine-3-carbonyl]-amino}-phenyl acetate,
(107) [(1-cyclohexylmethyl-2-oxo-1,2,5,6,7,8,9,10-octahydro-cycloocta[b]pyridine-3-carbonyl)-amino]-acetic acid 2-(2-oxo-pyrrolidine-1-yl)-ethyl ester,
(108) [(1-cyclohexylmethyl-2-oxo-1,2,5,6,7,8,9,10-octahydro-cycloocta[b]pyridine-3-carbonyl)-amino]-acetic acid 2-acetylamino-ethyl ester,
(109) (1-{2-[(1-cyclohexylmethyl-2-oxo-1,2,5,6,7,8,9,10-octahydro-cycloocta[b]pyridine-3-carbonyl)-amino]-2-methyl-propionyl}-piperidine-4-yl)-carbamic acid tert-butyl ester,
(110) 1-cyclohexylmethyl-2-oxo-1,2,5,6,7,8,9,10-octahydro-cycloocta[b]pyridine-3-carboxylic acid [2-(3-butyl-carbamoyl-piperidine-1-yl)-1,1-dimethyl-2-oxo-ethyl]-amide,
(111) [(1-cyclohexylmethyl-2-oxo-1,2,5,6,7,8,9,10-octahydro-cycloocta[b]pyridine-3-carbonyl)-amino]-naphthalene-1-yl-acetic acid,
(112) (4-{2-[(1-cyclohexylmethyl-2-oxo-1,2,5,6,7,8,9,10-octahydro-cycloocta[b]pyridine-3-carbonyl)-amino]-2-methyl-propionyloxy}-butyl)-trimethyl-ammonium iodide,
(113) 1-cyclohexylmethyl-2-oxo-1,2,5,6,7,8,9,10-octahydro-cycloocta[b]pyridine-3-carboxylic acid [1-(2-carbamoyl-ethylcarbamoyl)-1-methyl-ethyl]-amide,
(114) 1-cyclohexylmethyl-2-oxo-1,2,5,6,7,8,9,10-octahydro-cycloocta[b]pyridine-3-carboxylic acid [2-(4-methanesulfonylpiperadine-1-yl)-1,1-dimethyl-2-oxo-ethyl]-amide,
(115) methyl [(1-butyl-2-oxo-1,2,5,6,7,8,9,10-octahydro-cycloocta[b]pyridine-3-carbonyl)-amino]-acetate,
(116) methyl [(1-isobutyl-2-oxo-1,2,5,6,7,8,9,10-octahydro-cycloocta[b]pyridine-3-carbonyl)-amino]-phenyl acetate,
(117) [(1-cyclohexylmethyl-2-oxo-1,2,5,6,7,8,9,10-octahydro-cycloocta[b]pyridine-3-carbonyl)-amino]-(2-methoxy-phenyl)-acetic acid,
(118) ethyl 2-[(1-cyclohexylmethyl-2-oxo-1,2,5,6,7,8,9,10-octahydro-cycloocta[b]pyridine-3-carbonyl)-amino]-cyclopent-1-en-carboxylate,
(119) methyl 4-{[(1-cyclohexylmethyl-2-oxo-1,2,5,6,7,8,9,10-octahydro-cycloocta[b]pyridine-3-carbonyl)-amino]-methyl}-cyclohexanecarboxylate,
(120) 1-cyclohexylmethyl-2-oxo-1,2,5,6,7,8,9,10-octahydro-cycloocta[b]pyridine-3-carboxylic acid {1-methyl-1-[1-(propane-2-sulfonyl)-piperidine-4-ylcarbamoyl]-ethyl}-amide,
(121) 1-cyclohexylmethyl-2-oxo-1,2,5,6,7,8,9,10-octahydro-cycloocta[b]pyridine-3-carboxylic acid 1,1-dimethyl-2-oxo-2-[(pyridine-3-carbonyl)-amino]-ethyl}-amide,
(122) methyl {[2-oxo-1-(4-trifluoromethyl-benzyl)-1,2,5,6,7,8,9,10-octahydro-cycloocta[b]pyridine-3-carbonyl]-amino}-phenyl acetate,
(123) methyl 2-{[1-(1-ethyl-pyrrolidine-2-2-ylmethyl)-2-oxo-1,2,5,6,7,8,9,10-octahydro-cycloocta[b]pyridine-3-carbonyl]-amino}-3-methyl-butyrate,
(124) 2-[(1-cyclohexylmethyl-2-oxo-1,2,5,6,7,8,9,10-octahydro-cycloocta[b]pyridine-3-carbonyl)-amino]-2-methyl-propionic acid phenylcarbamoyloxy methyl ester,
(125) 1-cyclohexylmethyl-2-oxo-1,2,5,6,7,8,9,10-octahydro-cycloocta[b]pyridine-3-carboxylic acid (2-benzoylamino-1,1-dimethyl-2-oxo-ethyl)-amide,
(126) methyl [(1-butyl-4-hydroxy-2-oxo-1,2,5,6,7,8,9,10-octahydro-cycloocta[b]pyridine-3-carbonyl)-amino]-cyclohexyl-acetate, (127) methyl 2-[(5,6-dimethyl-2-oxo-1-pyridine-4-ylmethyl-1,2-dihydropyridine-3-carbonyl)-amino]-3-methyl-butyrate,
(128) 1-cyclohexylmethyl-2-oxo-1,2,5,6,7,8,9,10-octahydro-cycloocta[b]pyridine-3-carboxylic acid (2-isopropylsulfonylhydrazino-1,1-dimethyl-2-oxo-ethyl)-amide,
(129) methyl {[1-(4-methyl-benzyl)-2-oxo-1,2,5,6,7,8,9,10-octahydro-cycloocta[b]pyridine-3-carbonyl]-amino}-phenyl acetate,
(130) 1-cyclohexylmethyl-2-oxo-1,2,5,6,7,8,9,10-octahydro-cycloocta[b]pyridine-3-carboxylic acid [2-(3-carbamoyl-piperidine-1-yl)-1,1-dimethyl-2-oxo-ethyl]-amide,
(131) 1-cyclohexylmethyl-2-oxo-1,2,5,6,7,8,9,10-octahydro-cycloocta[b]pyridine-3-carboxylic acid (2-methanesulfonylhydrazino-1,1-dimethyl-2-oxo-ethyl)-amide,
(132) 1-cyclohexylmethyl-2-oxo-1,2,5,6,7,8,9,10-octahydro-cycloocta[b]pyridine-3-carboxylic acid[2-(4-acetylpiperazine-1-yl-1,1-dimethyl-2-oxo-ethyl)amide,
(133) methyl 2-[(1-butyl-5,6-dimethyl-2-oxo-1,2-dihydro-pyridine-3-carbonyl)-amino]-4-methyl-valerate,
(134) 1-cyclohexylmethyl-2-oxo-1,2,5,6,7,8,9,10-octahydro-cycloocta[b]pyridine-3-carboxylic acid (1-carbamoyl-1-methyl-ethyl)-amide,
(135) 1-cyclohexylmethyl-2-oxo-1,2,5,6,7,8,9,10-octahydro-cycloocta[b]pyridine-3-carboxylic acid 1,1-dimethyl-2-oxo-2-[N'-(thiophene-2-carbonyl)-hydrazino]-ethyl}-amide,
(136) methyl {[1-(3-acetylamino-propyl)-2-oxo-1,2,5,6,7,8,9,10-octahydro-cycloocta[b]pyridine-3-carbonyl]-amino}-phenyl acetate,
(137) methyl 4-[(1-cyclohexylmethyl-2-oxo-1,2,5,6,7,8,9,10-octahydro-cycloocta[b]pyridine-3-carbonyl)-amino]-benzoate,
(138) methyl 6-[(1-cyclohexylmethyl-2-oxo-1,2,5,6,7,8,9,10-octahydro-cycloocta[b]pyridine-3-carbonyl)-amino]-hexanoate,
(139) (2-{2-[(1-cyclohexylmethyl-2-oxo-1,2,5,6,7,8,9,10-octahydro-cycloocta[b]pyridine-3-carbonyl)-amino]-2-methyl-propionyloxy}-ethyl)-trimethyl-ammonium iodide,
(140) 1-cyclohexylmethyl-2-oxo-1,2,5,6,7,8,9,10-octahydro-cycloocta[b]pyridine-3-carboxylic acid {1-[2-(4-hydroxy-phenyl)-ethylcarbamoyl]-1-methyl-ethyl}-amide,
(141) methyl 2-[(1-butyl-5,6-dimethyl-2-oxo-1,2-dihydropyridine-3-carbonyl)-amino]-2-methyl-propionate,
(142) 1-[(1-cyclohexylmethyl-2-oxo-1,2,5,6,7,8,9,10-octahydro-cycloocta[b]pyridine-3-carbonyl)-amino]-cyclohexanecarboxylic acid,
(143) methyl [(1-cyclohexylmethyl-2-oxo-1,2,5,6,7,8,9,10-octahydro-cycloocta[b]pyridine-3-carbonyl)-amino]-naphthalene-1-yl-acetate,
(144) 1-cyclohexylmethyl-2-oxo-1,2,5,6,7,8,9,10-octahydro-cycloocta[b]pyridine-3-carboxylic acid {1-[2-(3,4-dihydroxy-phenyl)-ethylcarbamoyl]-1-methyl-ethyl}-amide,
(145) methyl 2-[(1-cyclohexylmethyl-5,6-dimethyl-2-oxo-1,2-dihydropyridine-3-carbonyl)-amino]-propionate,
(146) 1-cyclohexylmethyl-2-oxo-1,2,5,6,7,8,9,10-octahydro-cycloocta[b]pyridine-3-carboxylic acid {1,1-dimethyl-2-oxo-2-[(pyridine-4-carbonyl)-amino]-ethyl}-amide,
(147) {1-[(1-cyclohexylmethyl-2-oxo-1,2,5,6,7,8,9,10-octahydro-cycloocta[b]pyridine-3-carbonyl)-amino]-cyclohexyl}-acetic acid,
(148) ethyl 1-{2-[(1-cyclohexylmethyl-2-oxo-1,2,5,6,7,8,9,10-octahydro-cycloocta[b]pyridine-3-carbonyl)-amino]-2-methyl-propionyl}-piperizine-4-carboxylate,
(149) [(1-butyl-2-oxo-1,2,5,6,7,8,9,10-octahydro-cycloocta[b]pyridine-3-carbonyl)-amino]-thiophene-3-yl-acetic acid,
(150) 1-cyclohexylmethyl-2-oxo-1,2,5,6,7,8,9,10-octahydro-cycloocta[b]pyridine-3-carboxylic acid [1-(carbamoylmethyl-carbamoyl)-1-methyl-ethyl]-amide,
(151) 1-cyclohexylmethyl-2-oxo-1,2,5,6,7,8,9,10-octahydro-cycloocta[b]pyridine-3-carboxylic acid {1,1-dimethyl-2-oxo-2-[4-(propane-2-sulfonyl)-piperazine-1-yl]-ethyl}-amide,
(152) 1-cyclohexylmethyl-2-oxo-1,2,5,6,7,8,9,10-octahydro-cycloocta[b]pyridine-3-carboxylic acid (1-methyl-1-thioacetylcarbamoyl-ethyl)-amide,
(153) (2-{2-[(1-cyclohexylmethyl-2-oxo-1,2,5,6,7,8,9,10-octahydro-cycloocta[b]pyridine-3-carbonyl)-amino]-2-methyl-propionyloxy}-ethyl)-triethyl-ammonium iodide,
(154) 2-[(1-cyclohexylmethyl-2-oxo-1,2,5,6,7,8,9,10-octahydro-cycloocta[b]pyridine-3-carbonyl)-amino]-cyclohexanecarboxylic acid,
(155) 2-{[2-oxo-1-(tetrahydrofuran-2-yl-methyl)-1,2,5,6,7,8,9,10-octahydro-cycloocta[b]pyridine-3-carbonyl]-amino}-cyclohexanecarboxylic acid,
(156) [(1-cyclohexylmethyl-2-oxo-1,2,5,6,7,8,9,10-octahydro-cycloocta[b]pyridine-3-carbonyl)-amino]-thiophene-3-yl-acetic acid,
(157) 1-cyclohexylmethyl-2-oxo-1,2,5,6,7,8,9,10-octahydro-cycloocta[b]pyridine-3-carboxylic acid [1-(4-carbamoyl-phenylcarbamoyl)-1-methyl-ethyl]-amide,
(158) methyl [(1-butyl-5,6-dimethyl-2-oxo-1,2-dihydropyridine-3-carbonyl)-amino]-phenyl acetate,
(159) [(1-cyclohexylmethyl-2-oxo-1,2,5,6,7,8,9,10-octahydro-cycloocta[b]pyridine-3-carbonyl)-amino]-acetic acid 2-tert-butoxycarbonyamino-ethyl ester,
(160) methyl [(1-butyl-2-oxo-1,2,5,6,7,8,9,10-octahydro-cycloocta[b]pyridine-3-carbonyl)-amino]-(4-hydroxy-phenyl)-acetate,
(161) methyl benzo[b]thiophene-2-yl-[(1-cyclohexylmethyl-2-oxo-1,2,5,6,7,8,9,10-octahydro-cycloocta[b]pyridine-3-carbonyl)-amino]-acetate,
(162) methyl 2-[(1-butyl-5,6-dimethyl-2-oxo-1,2-dihydropyridine-3-carbonyl)-amino]-3-(4-hydroxy-phenyl)-propionate,
(163) methyl 3-[(1-butyl-4-hydroxy-2-oxo-1,2,5,6,7,8,9,10-octahydro-cycloocta[b]pyridine-3-carbonyl)-amino]-3-phenyl-propionate,
(164) [(1-cyclohexylmethyl-2-oxo-1,2,5,6,7,8,9,10-octahydro-cycloocta[b]pyridine-3-carbonyl)-amino]-acetic acid 2-methylsulfanyl-ethyl ester,
(165) [(1-cyclohexylmethyl-2-oxo-1,2,5,6,7,8,9,10-octahydro-cycloocta[b]pyridine-3-carbonyl)-amino]-acetic acid 2-pyrrolidine-1-yl-ethyl ester,
(166) 4-{2-[(1-cyclohexylmethyl-2-oxo-1,2,5,6,7,8,9,10-octahydro-cycloocta[b]pyridine-3-carbonyl)-amino]-2-methyl-propionyl}-piperazine-1-carboxylic acid tert-butyl ester,
(167) 1-cyclohexylmethyl-2-oxo-1,2,5,6,7,8,9,10-octahydro-cycloocta[b]pyridine-3-carboxylic acid [2-(4-hydrazinocarbonyl-piperidine-1-yl)-1,1-dimethyl-2-oxo-ethyl]-amide,
(168) methyl 2-[(1-cyclohexylmethyl-5,6-dimethyl-2-oxo-1,2-dihydropyridine-3-carbonyl)-amino]-3-(1H-indole-2-yl)-propionate,
(169) 1-cyclohexylmethyl-2-oxo-1,2,5,6,7,8,9,10-octahydro-cycloocta[b]pyridine-3-carboxylic acid [1-(cyanomethyl-carbamoyl)-1-methyl-ethyl]-amide,
(170) methyl 2-[(1-butyl-5,6-dimethyl-2-oxo-1,2-dihydropyridine-3-carbonyl)-amino]-cyclohexanecarboxylate, (171) {[1-(4-chloro-benzyl)-2-oxo-1,2,5,6,7,8,9,10-octahydro-cycloocta[b]pyridine-3-carbonyl]-amino}-phenylacetic acid,
(172) (3-{2-[(1-cyclohexylmethyl-2-oxo-1,2,5,6,7,8,9,10-octahydro-cycloocta[b]pyridine-3-carbonyl)-amino]-2-methyl-propionyloxy}-propyl)-trimethyl-ammonium iodide,
(173) [(1-butyl-2-oxo-1,2,5,6,7,8,9,10-octahydro-cycloocta[b]pyridine-3-carbonyl)-amino]-phenylacetic acid,
(174) butyl-(2-{2-[(1-cyclohexylmethyl-2-oxo-1,2,5,6,7,8,9,10-octahydro-cycloocta[b]pyridine-3-carbonyl)-amino]-2-methyl-propionyloxy}-ethyl)-dimethyl-ammonium,
(175) 1-cyclohexylmethyl-2-oxo-1,2,5,6,7,8,9,10-octahydro-cycloocta[b]pyridine-3-carboxylic acid [2-(4-methanesulfonylamino-piperidine-1-yl)-1,1-dimethyl-2-oxo-ethyl]-amide,
(176)
(177) methyl 2-[(1-cyclohexylmethyl-5,6-dimethyl-2-oxo-1,2-dihydropyridine-3-carbonyl)-amino]-4-methylsulfanyl-butyrate,
(178) 1-cyclohexylmethyl-2-oxo-1,2,5,6,7,8,9,10-octahydro-cycloocta[b]pyridine-3-carboxylic acid [1,1-dimethyl-2-(4-methyl-piperazine-1-yl)-2-oxo-ethyl]-amide,
(179) 1-cyclohexylmethyl-2-oxo-1,2,5,6,7,8,9,10-octahydro-cycloocta[b]pyridine-3-carboxylic acid (1-methyl-1-phenylcarbamoyl-ethyl)-amide,
(180) 1-cyclohexylmethyl-2-oxo-1,2,5,6,7,8,9,10-octahydro-cycloocta[b]pyridine-3-carboxylic acid {2-[4-(3-isopropyl-ureido)-piperidine-1-yl]-1,1-dimethyl-2-oxo-ethyl}-amide,
(181) 1-cyclohexylmethyl-2-oxo-1,2,5,6,7,8,9,10-octahydro-cycloocta[b]pyridine-3-carboxylic acid {1,1-dimethyl-2-oxo-2-[4-(piperidine-1-carbonyl)-piperidine-1-yl]-ethyl}-amide,
(182) 2-[(1-butyl-5,6-dimethyl-2-oxo-1,2-dihydropyridine-3-carbonyl)-amino]-3-phenyl-propionic acid
(183) dimethyl 2-[(1-cyclohexylmethyl-5,6-dimethyl-2-oxo-1,2-dihydropyridine-3-carbonyl)-amino]-succinate,
(184) [(1-cyclohexylmethyl-2-oxo-1,2,5,6,7,8,9,10-octahydro-cycloocta[b]pyridine-3-carbonyl)-amino]-(4-fluoro-phenyl)-acetic acid,
(185) 1-butyl-2-oxo-1,2,5,6,7,8,9,10-octahydro-cycloocta[b]pyridine-3-carboxylic acid {[(2-hydroxy-ethyl)-methyl-carbamoyl]-phenyl-methyl}-amide,
(186) 1-cyclohexylmethyl-2-oxo-1,2,5,6,7,8,9,10-octahydro-cycloocta[b]pyridine-3-carboxylic acid [1-(4-methanesulfonylamino-phenylcarbamoyl)-1-methyl-ethyl]-amide,
(187) methyl 2-[(1-butyl-2-oxo-1,2,5,6,7,8-hexahydroquinoline-3-carbonyl)-amino]-3-methyl-butyrate,
(188) methyl {[1-(3-cyano-propyl)-2-oxo-1,2,5,6,7,8,9,10-octahydro-cycloocta[b]pyridine-3-carbonyl]-amino}-phenyl acetate,
(189) methyl 2-methyl-2-{[2-oxo-1-(2-piperidine-1-yl-ethyl)-1,2,5,6,7,8,9,10-octahydro-cycloocta[b]pyridine-3-carbonyl]-amino}-propionate,
(190) ethyl 2-[(1-butyl-2-oxo-1,2,5,6,7,8-hexahydroquinoline-3-carbonyl)-amino]-cyclohexanecarboxylate,
(191) methyl 2-methyl-2-{[2-oxo-1-(2-oxo-[1,3]dioxolan-4-ylmethy)-1,2,5,6,7,8,9,10-octahydro-cycloocta[b]pyridine-3-carbonyl]-amino}-propionate,
(192) [(1-benzyl-2-oxo-1,2,5,6,7,8,9,10-octahydro-cycloocta[b]pyridine-3-carbonyl)-amino]-phenylacetic acid,
(193) 1-cyclohexylmethyl-2-oxo-1,2,5,6,7,8,9,10-octahydro-cycloocta[b]pyridine-3-carboxylic acid (1,1-dimethyl-2-{4-[methyl-(propane-2-sulfonyl)-amino]-piperidine-1-yl}-2-oxo-ethyl)-amide,
(194) 3-[(1-cyclohexylmethyl-2-oxo-1,2,5,6,7,8,9,10-octahydro-cycloocta[b]pyridine-3-carbonyl)-amino]-5-methyl-hexanoic acid,
(195) methyl 2-{[1-(1-ethyl-pyrrolidine-2-2-ylmethyl)-2-oxo-1,2,5,6,7,8,9,10-octahydro-cycloocta[b]pyridine-3-carbonyl]-amino}-4,4-dimethyl-valerate,
(196) 1-cyclohexylmethyl-2-oxo-1,2,5,6,7,8,9,10-octahydro-cycloocta[b]pyridine-3-carboxylic acid [1-(2-hydroxy-1-hydroxymethyl-ethylcarbamoyl)-1-methyl-ethyl]-amide,
(197) 1-cyclohexylmethyl-2-oxo-1,2,5,6,7,8,9,10-octahydro-cycloocta[b]pyridine-3-carboxylic acid [2-(N'-benzoyl-hydrazino)-1,1-dimethyl-2-oxo-ethyl]-amide,
(198) {[1-(3-methyl-butyl)-2-oxo-1,2,5,6,7,8,9,10-octahydro-cycloocta[b]pyridine-3-carbonyl]-amino}-phenylacetic acid,
(199) 2-[(1-cyclohexylmethyl-2-oxo-1,2,5,6,7,8,9,10-octahydro-cycloocta[b]pyridine-3-carbonyl)-amino]-2-methyl-propionyloxy-valeric acid methyl ester,
(200) 1-cyclohexylmethyl-2-oxo-1,2,5,6,7,8,9,10-octahydrocycloocta[b]pyridine-3-carboxylic acid [2-(4-carbamoyl-piperidine-1-yl)-1,1-dimethyl-2-oxo-ethyl]-amide,
(201) 1-cyclohexylmethyl-2-oxo-1,2,5,6,7,8,9,10-octahydro-cycloocta[b]pyridine-3-carboxylic acid {1-[2-(4-hydroxy-3-methoxy-phenyl)-ethylcarbamoyl]-1-methyl-ethyl}-amide,
(202) 1-cyclohexylmethyl-2-oxo-1,2,5,6,7,8,9,10-octahydro-cycloocta[b]pyridine-3-carboxylic acid [1-(2,3-dihydroxy-propylcarbamoyl)-1-methyl-ethyl]-amide,
(203) methyl {2-[(1-cyclohexylmethyl-2-oxo-1,2,5,6,7,8,9,10-octahydro-cycloocta[b]pyridine-3-carbonyl)-amino]-ethoxy}-acetate,
(204) 1-cyclohexylmethyl-2-oxo-1,2,5,6,7,8,9,10-octahydro-cycloocta[b]pyridine-3-carboxylic acid (1-hydrazinocarbonyl-1-methyl-ethyl)-amide,
(205) 1-cyclohexylmethyl-2-oxo-1,2,5,6,7,8,9,10-octahydro-cycloocta[b]pyridine-3-carboxylic acid {1,1-dimethyl-2-oxo-2-[4-(propane-2-sulfonylamino)-piperidine-1-yl]-ethyl}-amide,
(206) 1-cyclohexylmethyl-2-oxo-1,2,5,6,7,8,9,10-octahydro-cycloocta[b]pyridine-3-carboxylic acid (1-benzylcarbamoyl-1-methyl-ethyl)-amide,
(207) methyl 2-[(1-butyl-2-oxo-1,2,5,6,7,8-hexahydroquinoline-3-carbonyl)-amino]-2-methyl-propionate,
(208) 1-cyclohexylmethyl-2-oxo-1,2,5,6,7,8,9,10-octahydro-cycloocta[b]pyridine-3-carboxylic acid {1,1-dimethyl-2-[4-(2-methyl-propane-2-sulfonyamino)-piperidine-1-yl]-2-oxo-ethyl}-amide,
(209) methyl 3-[(1-cyclohexylmethyl-2-oxo-1,2,5,6,7,8-hexahydroquinoline-3-carbonyl)-amino]-3-phenyl-propionate,
(210) ethyl 2-{[1-(3-acetylamino-propyl)-2-oxo-1,2,5,6,7,8,9,10-octahydro-cycloocta[b]pyridine-3-carbonyl]-amino}-cyclohexanecarboxylate,
(211) 2-[(1-cyclohexylmethyl-2-oxo-1,2,5,6,7,8,9,10-octahydro-cycloocta[b]pyridine-3-carbonyl)-amino]-2-methyl-propionic acid 1-diethylcarbamoyloxy-ethyl ester,
(212) 1-cyclohexylmethyl-2-oxo-1,2,5,6,7,8,9,10-octahydro-cycloocta[b]pyridine-3-carboxylic acid [1-(5-carbamoyl-pyridine-2-ylcarbamoyl)-1-methyl-ethyl]-amide,
(213) 1-cyclohexylmethyl-2-oxo-1,2,5,6,7,8,9,10-octahydro-cycloocta[b]pyridine-3-carboxylic acid [1-(2-acetylamino-ethylcarbamoyl)-1-methyl-ethyl]-amide, (214) 1-cyclohexylmethyl-2-oxo-1,2,5,6,7,8,9,10-octahydro-cycloocta[b]pyridine-3-carboxylic acid [2-(4-isopropylcarbamoyl-piperazine-1-yl)-1,1-dimethyl-2-oxoethyl]-amide,
(215) 1-cyclohexylmethyl-2-oxo-1,2,5,6,7,8,9,10-octahydro-cycloocta[b]pyridine-3-carboxylic acid [1-(2-hydroxy-ethylcarbamoyl)-1-methyl-ethyl]-amide,
(216) methyl [(1-cyclohexylmethyl-2-oxo-1,2,5,6,7,8,9,10-octahydro-cycloocta[b]pyridine-3-carbonyl)-amino]-(2-methoxy-phenyl)-acetate,
(217) methyl 1-(1-cyclohexylmethyl-2-oxo-1,2,5,6,7,8,9,10-octahydro-cycloocta[b]pyridine-3-carbonyl)-pyrrolidine-2-carboxylate,
(218) methyl 1-[(1-butyl-5,6-dimethyl-2-oxo-1,2-dihydropyridine-3-carbonyl)-amino]-cyclohexanecarboxylate,
(219) methyl ({2-[(1-cyclohexylmethyl-2-oxo-1,2,5,6,7,8,9,10-octahydro-cycloocta[b]pyridine-3-carbonyl)-amino]-2-methyl-propionyl}-methyl-amino)-acetate,
(220) {2-[(1-cyclohexylmethyl-2-oxo-1,2,5,6,7,8,9,10-octahydro-cycloocta[b]pyridine-3-carbonyl)-amino]-thiazole-4-yl}-acetic acid ethyl ester,
(221) ethyl 3-[(1-cyclohexylmethyl-2-oxo-1,2,5,6,7,8,9,10-octahydro-cycloocta[b]pyridine-3-carbonyl)-amino]-propionate,
(222) {[1-(3-methyl-butyl)-2-oxo-1,2,5,6,7,8,9,10-octahydro-cycloocta[b]pyridine-3-carbonyl]-amino}-thiophene-2-yl-acetic acid,
(223) [(1-butyl-2-oxo-1,2,5,6,7,8,9,10,11,12-decahydrocyclodeca[b]pyridine-3-carbonyl)-amino]-phenylacetic acid,
(224) methyl [(1-cyclohexylmethyl-2-oxo-1,2,5,6,7,8,9,10-octahydro-cycloocta[b]pyridine-3-carbonyl)-amino]-acetate,
(225) methyl 4-[(1-cyclohexylmethyl-2-oxo-1,2,5,6,7,8,9,10-octahydro-cycloocta[b]pyridine-3-carbonyl)-amino]-cyclohexanecarboxylate,
(226) methyl [(1-butyl-2-oxo-1,2,5,6,7,8,9,10-octahydro-cycloocta[b]pyridine-3-carbonyl)-amino]-phenyl acetate,
(227) methyl [(1-butyl-4-hydroxy-2-oxo-1,2,5,6,7,8,9,10-octahydro-cycloocta[b]pyridine-3-carbonyl)-amino]-phenyl acetate,
(228) [(1-cyclohexylmethyl-2-oxo-1,2,5,6,7,8,9,10-octahydro-cycloocta[b]pyridine-3-carbonyl)-amino]-furan-2-yl-acetic acid,
(229) {2-[(1-cyclohexylmethyl-2-oxo-1,2,5,6,7,8,9,10-octahydro-cycloocta[b]pyridine-3-carbonyl)-amino]-thiazole-4-yl}-oxo-acetic acid ethyl ester,
(230) 2-[(1-cyclohexylmethyl-2-oxo-1,2,5,6,7,8,9,10-octahydro-cycloocta[b]pyridine-3-carbonyl)-amino]-4-methyl-thiazole-5-carboxylic acid ethyl ester,
(231) dimethyl 2-[(1-butyl-2-oxo-1,2,5,6,7,8,9,10-octahydro-cycloocta[b]pyridine-3-carbonyl)-amino]-succinate,
(232) methyl {[1-(4-cyano-butyl)-2-oxo-1,2,5,6,7,8,9,10-octahydro-cycloocta[b]pyridine-3-carbonyl]-amino}-phenyl acetate,
(233) methyl 2-[(1-butyl-5,6-dimethyl-2-oxo-1,2-dihydropyridine-3-carbonyl)-amino]-3-phenyl acetate,
(234) methyl 2-[(1-cyclohexylmethyl-5,6-dimethyl-2-oxo-1,2-dihydropyridine-3-carbonyl)-amino]-4-methylsulfanyl-butyrate,
(235) methyl 3-methyl-2-{[2-oxo-1-(2-piperidine-1-yl-ethyl)-1,2,5,6,7,8,9,10-octahydro-cycloocta[b]pyridine-3-carbonyl]-amino}-butyrate,
(236) ethyl 2-{[2-oxo-1-(tetrahydrofuran-2-ylmethyl)-1,2,5,6,7,8,9,10-octahydro-cycloocta[b]pyridine-3-carbonyl]-amino}-cyclohexanecarboxylate,
(237) ethyl 2-[(1-cyclohexylmethyl-2-oxo-1,2,5,6,7,8-hexahydroquinoline-3-carbonyl)-amino]-cyclohexane carboxylate,
(238) ethyl 3-[(1-cyclohexylmethyl-2-oxo-1,2,5,6,7,8,9,10-octahydro-cycloocta[b]pyridine-3-carbonyl)-amino]-benzoate,
(239) methyl 2-methyl-2-{[2-oxo-1-(tetrahydrofuran-2-ylmethyl)-1,2,5,6,7,8,9,10-octahydro-cycloocta[b]pyridine-3-carbonyl]-amino}-propionate,
(240) methyl 5-[(1-cyclohexylmethyl-2-oxo-1,2,5,6,7,8,9,10-octahydro-cycloocta[b]pyridine-3-carbonyl)-amino]-valerate,
(241) methyl 2-[(1-cyclohexylmethyl-2-oxo-1,5,7,8-tetrahydro-2H-thiopyrano[4,3-b]pyridine-3-carbonyl)-amino]-3-methyl-butyrate,
(242) 2-[(1-butyl-5-ethyl-2-oxo-6-propyl-1,2-dihydropyridine-3-carbonyl)-amino]-3,3-dimethyl-butyric acid 2-hydroxy-1-hydroxymethyl-ethyl ester,
(243) 2-[(1-cyclohexylmethyl-2-oxo-1,2,5,6,7,8,9,10-octahydro-cycloocta[b]pyridine-3-carbonyl)-amino]-2-methyl-propionic acid diethylcarbamoyloxymethyl ester,
(244) 1-cyclohexylmethyl-2-oxo-1,2,5,6,7,8,9,10-octahydro-cycloocta[b]pyridine-3-carboxylic acid [1-(6-hydroxy-hexylcarbamoyl)-1-methyl-ethyl]-amide,
(245) methyl [(1-cyclohexylmethyl-2-oxo-2,5,6,7,8,9-hexahydroquinoline-1H-cyclohepta[b]pyridine-3-carbonyl)-amino]-phenyl acetate,
(246) methyl 2-[(1-cyclohexylmethyl-5-ethyl-2-oxo-6-propyl-1,2-dihydropyridine-3-carbonyl)-amino]-3-phenyl propionate,
(247) 1-cyclohexylmethyl-6-ethyl-5-methyl-2-oxo-1,2-dihydropyridine-3-carboxylic acid {1-[bis-(2-hydroxyethyl)-carbamoyl]-2,2-dimethyl-propyl}-amide,
(248) methyl 2-[(1-allyl-2-oxo-1,2,5,6,7,8,9,10-octahydrocycloocta[b]pyridine-3-carbonyl)-amino]-2-methyl-propionate,
(249) ethyl 2-[(1-butyl-5-ethyl-2-oxo-6-propyl-1,2-dihydropyridine-3-carbonyl)-amino]-cyclohexanecarboxylate,
(250) methyl 3-[(1-cyclohexylmethyl-2-oxo-1,2,5,6,7,8,9,10-octahydro-cycloocta[b]pyridine-3-carbonyl)-amino]-propionate,
(251) [(1-cyclohexylmethyl-2-oxo-1,2,5,6,7,8,9,10-octahydro-cycloocta[b]pyridine-3-carbonyl)-amino]-acetic acid 2,2,2-trifluoro-ethyl ester,
(252) 1-butyl-2-oxo-1,2,5,6,7,8,9,10-octahydro-cycloocta[b]pyridine-3-carboxylic acid {(2-[(2-hydroxy-ethyl)-methyl-carbamoyl]-cyclohexyl)-amide,
(253) 2-[(1-cyclohexylmethyl-2-oxo-1,2,5,6,7,8,9,10-octahydro-cycloocta[b]pyridine-3-carbonyl)-amino]-2-methyl-propionic acid 2-dibutylamino-ethyl ester,
(254) 1-cyclohexylmethyl-2-oxo-1,2,5,6,7,8,9,10-octahydro-cycloocta[b]pyridine-3-carboxylic acid {1-[2-(3,4-bis-benzyloxy-phenyl)-ethylcarbamoyl]-1-methyl-ethyl}-amide,
(255) methyl [(1-butyl-2-oxo-1,2,5,6,7,8-hexahydroquinoline-3-carbonyl)-amino]-phenyl acetate,
(256) methyl 2-[(1,6-dibutyl-2-oxo-5-propyl-1,2-dihydropyridine-3-carbonyl)-amino]-3-methyl-butyrate,
(257) methyl {[1-(4-cyano-benzyl)-2-oxo-1,2,5,6,7,8,9,10-octahydro-cycloocta[b]pyridine-3-carbonyl]-amino}-phenyl acetate,
(258) 2-[(1-butyl-2-oxo-1,2,5,6,7,8,9,10-octahydro-cycloocta[b]pyridine-3-carbonyl)-amino]-3-methyl-butyric acid 2-hydroxy-1-hydroxymethyl-ethyl ester,
(259) {[1-(3-cyano-propyl)-2-oxo-1,2,5,6,7,8,9,10-octahydro-cycloocta[b]pyridine-3-carbonyl]-amino}-phenylacetic acid, (260) 1-cyclohexylmethyl-2-oxo-1,2,5,6,7,8,9,10-octahydro-cycloocta[b]pyridine-3-carboxylic acid [1-(5-hydroxy-pentylcarbamoyl)-1-methyl-ethyl]-amide, (261) (S)-[(1-cyclohexylmethyl-2-oxo-1,2,5,6,7,8,9,10-octahydro-cycloocta[b]pyridine-3-carbonyl)-amino]-thiophene-2-yl-acetic acid, (262) methyl 2-[(1-cyclohexylmethyl-2-oxo-1,2,5,6,7,8,9,10-octahydro-cycloocta[b]pyridine-3-carbonyl)-amino]-methyl benzoate, (263) 4-[(1-cyclohexylmethyl-2-oxo-1,2,5,6,7,8,9,10-octahydro-cycloocta[b]pyridine-3-carbonyl)-amino]-butyrate, (264) 1-cyclohexylmethyl-6-ethyl-5-methyl-2-oxo-1,2-dihydropyridine-3-carboxylicacid [1-(2-hydroxy-1-hydroxymethyl-ethylcarbamoyl)-2,2-dimethyl-propyl]-amide, (265) {[1-(4-fluorobenzyl)-2-oxo-1,2,5,6,7,8,9,10-octahydro-cycloocta[b]pyridine-3-carbonyl]-amino}-furan-2-yl-acetic acid, (266) 1-cyclohexylmethyl-2-oxo-1,2,5,6,7,8,9,10-octahydro-cycloocta[b]pyridine-3-carboxylic acid [2-(4-hydroxy-piperidine-1-yl)-1,1-dimethyl-2-oxo-ethyl]-amide, (267) 2-[(1-cyclohexylmethyl-2-oxo-1,2,5,6,7,8,9,10-octahydro-cycloocta[b]pyridine-3-carbonyl)-amino]-2-methyl-propionic acid 2-diethylamino-ethyl ester, (268) 1-cyclohexylmethyl-2-oxo-1,2,5,6,7,8,9,10-octahydro-cycloocta[b]pyridine-3-carboxylic acid [1,1-dimethyl-2-(4-methylcarbamoyl-piperidine-1-yl)-2-oxo-ethyl]-amide, (269) methyl 2-[(1-cyclohexylmethyl-5,6-dimethyl-2-oxo-1,2-dihydropyridine-3-carbonyl)-amino]-3-(4-hydroxyphenyl)-propionate, (270) methyl 2-[(1-butyl-4-hydroxy-2-oxo-1,2,5,6,7,8-hexahydroquinoline-3-carbonyl)-amino]-3-methyl-butyrate, (271) [(1-cyclohexylmethyl-2-oxo-1,2,5,6,7,8,9,10-octahydro-cycloocta[b]pyridine-3-carbonyl)-amino]-phenylacetic acid, (272) methyl 2-[(1-butyl-2-oxo-1,2,5,6,7,8-hexahydroquinoline-3-carbonyl)-amino]-3-methyl-butyrate, (273) methyl 2-[(1-[1,3]dioxane-2-ylmethyl-2-oxo-1,2,5,6,7,8,9,10-octahydro-cycloocta[b]pyridine-3-carbonyl)-amino]-3-methyl-butyrate, (274) methyl [(1-butyl-2-oxo-1,2,5,6,7,8,9,10,11,12-decahydrocyclodeca[b]pyridine-3-carbonyl)-amino]-phenyl acetate, (275) methyl [(1-cyclohexylmethyl-2-oxo-1,2,5,6,7,8,9,10-octahydro-cycloocta[b]pyridine-3-carbonyl)-amino]-(4-hydroxy-phenyl)-acetate, (276) methyl 2-{[1-(3-methanesulfonylamino-propyl)-2-oxo-1,2,5,6,7,8,9,10-octahydro-cycloocta[b]pyridine-3-carbonyl]-amino}-2-methyl-propionate, (277) methyl 1-[(1,6-dibutyl-2-oxo-5-propyl-1,2-dihidoropyridine-3-carbonyl)-amino]-cyclohexanecarboxylate, (278) {[1-(4-fluorobenzyl)-2-oxo-1,2,5,6,7,8,9,10-octahydro-cycloocta[b]pyridine-3-carbonyl]-amino}-phenylacetic acid, (279) [(1-cyclohexylmethyl-2-oxo-1,2,5,6,7,8,9,10-octahydro-cycloocta[b]pyridine-3-carbonyl)-amino]-thiophene-2-yl-acetic acid, (280) 1-cyclohexylmethyl-2-oxo-1,2,5,6,7,8,9,10-octahydro-cycloocta[b]pyridine-3-carboxylic acid [1-(3-hydroxy-propylcarbamoyl)-1-methyl-ethyl]-amide, (281) methyl [(1-cyclohexylmethyl-2-oxo-1,2,5,6,7,8,9,10-octahydro-cycloocta[b]pyridine-3-carbonyl)-amino]-(4-methoxyphenyl)-acetate, (282) 1-cyclohexylmethyl-2-oxo-1,2,5,6,7,8,9,10-octahydro-cycloocta[b]pyridine-3-carboxylic acid {2-[4-(2-hydroxy-ethylcarbamoyl)-piperidine-1-yl]-1,1-dimethyl-2-oxo-ethyl}-amide, (283) methyl 2-[(1-butyl-5,6-dimethyl-2-oxo-1,2-dihydropyridine-3-carbonyl)-amino]-3-methyl-valerate, (284) methyl 2-[(1-cyclohexylmethyl-5-methoxy-6-methyl-2-oxo-1,2-dihydropyridine-3-carbonyl)-amino]-3-methyl-butyrate, (285) methyl 2-[(1-[1,3]dioxolan-2-ylmethyl-2-oxo-1,2,5,6,7,8,9,10-octahydro-cycloocta[b]pyridine-3-carbonyl)-amino]-3-methyl-butyrate, (286) 2-[(1-butyl-2-oxo-2,5,6,7-tetrahydro-1H-[1]pyridine-3-carbonyl)-amino]-3-methyl-butyric acid methyl ester, (287) methyl {[1-(4-fluorobenzyl)-5,6-dimethyl-2-oxo-1,2-dihydro pyridine-3-carbonyl]-amino}-phenyl acetate, (288) methyl 1-[(1-butyl-2-oxo-1,2,5,6,7,8-hexahydroquinoline-3-carbonyl)-amino]-cyclohexanecarboxylate, (289) 2-[(1-cyclohexylmethyl-2-oxo-1,2,5,6,7,8,9,10-octahydro-cycloocta[b]pyridine-3-carbonyl)-amino]-2-methyl-propionic acid 2-dimethylamino-ethyl ester, (290) 2-[(1-cyclohexylmethyl-2-oxo-1,2,5,6,7,8,9,10-octahydro-cycloocta[b]pyridine-3-carbonyl)-amino]-2-methyl-propionic acid butylcarbamoyloxymethyl ester, (291) 2-[(1-cyclohexylmethyl-2-oxo-1,2,5,6,7,8,9,10-octahydro-cycloocta[b]pyridine-3-carbonyl)-amino]-2-methyl-propionic acid 4-dimethylamino-butyl ester, (292) methyl 2-[(1-benzo[1,3]dioxol-5-ylmethyl-2-oxo-1,2,5,6,7,8,9,10-octahydro-cycloocta[b]pyridine-3-carbonyl)-amino]-3-methyl-butyrate, (293) 1-cyclohexylmethyl-2-oxo-1,2,5,6,7,8,9,10-octahydro-cycloocta[b]pyridine-3-carboxylic acid [1-(1-methanesulfonylpiperidine-4-ylcarbamoyl)-1-methyl-ethyl]-amide, (294) 1-cyclohexylmethyl-2-oxo-1,2,5,6,7,8,9,10-octahydro-cycloocta[b]pyridine-3-carboxylic acid [1-(1-benzenesulfonyl-piperidine-4-ylcarbamoyl)-1-methyl-ethyl]-amide, (295) 1-cyclohexylmethyl-2-oxo-1,2,5,6,7,8,9,10-octahydro-cycloocta[b]pyridine-3-carboxylic acid {1-[(2,3-dihydroxy-propyl)-methyl-carbamoyl]-1-methyl-ethyl}-amide, (296) methyl 2-[(1-cyclohexylmethyl-2-oxo-1,2,5,6,7,8-hexahydroquinoline-3-carbonyl)-amino]-3-methyl-butyrate, (297) 2-[(1-cyclohexylmethyl-2-oxo-1,2,5,6,7,8,9,10-octahydro-cycloocta[b]pyridine-3-carbonyl)-amino]-2-methyl-propionic acid 1-cyclohexyloxycarbonyloxy-ethyl ester, (298) piperidine-1-carboxylic acid 2-[(1-cyclohexylmethyl-2-oxo-1,2,5,6,7,8,9,10-octahydro-cycloocta[b]pyridine-3-carbonyl)-amino]-2-methyl-propionyloxymethyl ester, (299) 1-cyclohexylmethyl-6-ethyl-5-methyl-2-oxo-1,2-dihydropyridine-3-carboxylic acid [1-(2-hydroxy-ethylcarbamoyl)-2,2-dimethyl-propyl]-amide, (300) methyl 2-[(1-cyclohexylmethyl-2-oxo-1,2,5,6,7,8,9,10-octahydro-cycloocta[b]pyridine-3-carbonyl)-amino]-3-thiazole-4-yl-propionate, (301) 1-cyclohexylmethyl-2-oxo-1,2,5,6,7,8,9,10-octahydro-cycloocta[b]pyridine-3-carboxylic acid [1-(3-hydroxy-2,2-dimethyl-propylcarbamoyl)-1-methyl-ethyl]-amide, (302) methyl {[1-(4-chlorobenzyl)-2-oxo-1,2,5,6,7,8,9,10-octahydro-cycloocta[b]pyridine-3-carbonyl]-amino}-phenyl acetate, (303) methyl 3-methyl-2-{[2-oxo-1-(2-piperidine-1-yl-ethyl)-1,2,5,6,7,8,9,10-octahydro-cycloocta[b]pyridine-3-carbonyl]-amino}-butyrate,
(304) methyl (4-chloro-phenyl)-[(1-cyclohexylmethyl-2-oxo-1,2,5,6,7,8,9,10-octahydro-cycloocta[b]pyridine-3-carbonyl)-amino]-acetate,
(305) methyl {[1-(4-chlorobenzyl)-5,6-dimethyl-2-oxo-1,2-dihydropyridine-3-carbonyl]-amino}-phenyl acetate,
(306) methyl 2-{[1-(3-methanesulfonylpropyl)-2-oxo-1,2,5,6,7,8,9,10-octahydro-cycloocta[b]pyridine-3-carbonyl]-amino}-3-methyl-butyrate,
(307) methyl 2-[(1,6-dibutyl-2-oxo-5-propyl-1,2-dihydropyridine-3-carbonyl)-amino]-2-methyl-propionate,
(308) ethyl 2-{[1-(4-cyano-benzyl)-2-oxo-1,2,5,6,7,8,9,10-octahydro-cycloocta[b]pyridine-3-carbonyl]-amino}-cyclohexanecarboxylate,
(309) {[1-(4-fluorobenzyl)-2-oxo-1,2,5,6,7,8,9,10-octahydro-cycloocta[b]pyridine-3-carbonyl]-amino}-thiophen-2-yl-acetic acid,
(310) 1-cyclohexylmethyl-2-oxo-1,2,5,6,7,8,9,10-octahydro-cycloocta[b]pyridine-3-carboxylic acid [1-(4-hydroxy-butylcarbamoyl)-1-methyl-ethyl]-amide,
(311) 1-butyl-2-oxo-1,2,5,6,7,8,9,10-octahydro-cycloocta[b]pyridine-3-carboxylic acid {1-[((2-hydroxy-ethyl)-methyl-carbamoyl]-2-methyl-propyl}-amide,
(312) 1-butyl-2-oxo-1,2,5,6,7,8,9,10-octahydro-cycloocta[b]pyridine-3-carboxylic acid {(–[(2-hydroxy-ethyl)-methyl-carbamoyl]-2,2-dimethyl-propyl)-amide,
(313) methyl 2-[(1-butyl-5,6-dimethyl-2-oxo-1,2-dihydropyridine-3-carbonyl)-amino]-4-methyl-valerate,
(314) methyl 2-{[5,6-dimethyl-1-(3-methyl-butyl)-2-oxo-1,2-dihydropyridine-3-carbonyl]-amino}-3-methyl-butyrate,
(315) methyl 2-{[1-(4-fluorobenzyl)-2-oxo-1,2,5,6,7,8,9,10-octahydro-cycloocta[b]pyridine-3-carbonyl]-amino}-2-methyl-propionate,
(316) 1-cyclohexylmethyl-6-ethyl-5-methyl-2-oxo-1,2-dihydropyridine-3-carboxylic acid {(–[(2-hydroxy-ethyl)-methyl-carbamoyl]-2-methyl-propyl}-amide,
(317) 2-[(1-cyclohexylmethyl-2-oxo-1,2,5,6,7,8,9,10-octahydro-cycloocta[b]pyridine-3-carbonyl)-amino]-2-methyl-propionic acid 1-butylcarbamoyloxy-ethyl ester,
(318) 1-cyclohexylmethyl-6-ethyl-5-methyl-2-oxo-1,2-dihydropyridine-3-carboxylic acid {1-[(2,3-dihydroxy-propyl)-methyl-carbamoyl]-2,2-dimethyl-propyl}-amide,
(319) 1-cyclohexylmethyl-2-oxo-1,2,5,6,7,8,9,10-octahydro-cycloocta[b]pyridine-3-carboxylic acid {1-[2-(2-hydroxy-ethoxy)-ethylcarbamoyl]-1-methyl-ethyl}-amide,
(320) 1-cyclohexylmethyl-2-oxo-1,2,5,6,7,8,9,10-octahydro-cycloocta[b]pyridine-3-carboxylic acid (2-acetylamino-1,1-dimethyl-2-oxo-ethyl)-amide,
(321) {2-[(1-cyclohexylmethyl-2-oxo-1,2,5,6,7,8,9,10-octahydro-cycloocta[b]pyridine-3-carbonyl)-amino]-thiazole-4-yl}-oxoacetic acid,
(322) 1-cyclohexylmethyl-2-oxo-1,2,5,6,7,8,9,10-octahydro-cycloocta[b]pyridine-3-carboxylic acid (4-carbamoylmethyl-thiazol-2-yl)-amide,
(323) methyl 2-[(1-cyclohexylmethyl-2-oxo-1,2,5,6,7,8,9,10-octahydro-cycloocta[b]pyridine-3-carbonyl)-amino]-succinate,
(324) methyl 2-[(1-cyclohexylmethyl-4-hydroxy-5,6-dimethyl-2-oxo-1,2-dihydropyridine-3-carbonyl)-amino]-3-methyl-butyrate,
(325) methyl 1-[(1-butyl-2-oxo-1,2,5,6,7,8,9,10-octahydro-cycloocta[b]pyridine-3-carbonyl)-amino]-cyclohexanecarboxylate,
(326) methyl 1-[(1-cyclohexylmethyl-2-oxo-1,2,5,6,7,8,9,10-octahydro-cycloocta[b]pyridine-3-carbonyl)-amino]-cyclopentanecarboxylate,
(327) methyl 2-[(1-cyclohexylmethyl-2-oxo-1,2,5,6,7,8,9,10-octahydro-cycloocta[b]pyridine-3-carbonyl)-amino]-4,4-dimethyl-valerate,
(328) methyl 2-[(1-cyclohexylmethyl-2-oxo-1,2,5,6,7,8,9,10-octahydro-cycloocta[b]pyridine-3-carbonyl)-amino]-3,3-dimethyl-butyrate,
(329) methyl 2-[(1-cyclohexylmethyl-5-ethyl-2-oxo-6-propyl-1,2-dihydropyridine-3-carbonyl)-amino]-3-methyl-butyrate,
(330) methyl 2-[(1-cyclohexylmethyl-6-ethyl-5-methyl-2-oxo-1,2-dihydropyridine-3-carbonyl)-amino]-3-methyl-butyrate,
(331) methyl 2-[(1-butyl-6-ethyl-5-methyl-2-oxo-1,2-dihydropyridine-3-carbonyl)-amino]-3-methyl-butyrate,
(332) methyl 1-[(1-butyl-6-ethyl-5-methyl-2-oxo-1,2-dihydro pyridine-3-carbonyl)-amino]-cyclohexanecarboxylate,
(333) methyl 1-[(1-cyclohexylmethyl-6-ethyl-5-methyl-2-oxo-1,2-dihidoropyridine-3-carbonyl)-amino]-cyclohexanecarboxylate,
(334) methyl 1-[(1-butyl-5-ethyl-2-oxo-6-propyl-1,2-dihydropyridine-3-carbonyl)-amino]-cyclohexanecarboxylate,
(335) methyl 1-[(1-cyclohexylmethyl-5-ethyl-2-oxo-6-propyl-1,2-dihydropyridine-3-carbonyl)-amino]-cyclohexanecarboxylate,
(336) methyl 1-[(1-cyclohexylmethyl-5,6-dimethyl-2-oxo-1,2-dihydropyridine-3-carbonyl)-amino]-cyclohexanecarboxylate,
(337) methyl 3-methyl-2-{[2-oxo-1-(tetrahydrofuran-2-ylmethyl)-1,2,5,6,7,8,9,10-octahydro-cycloocta[b]pyridine-3-carbonyl]-amino}-butyrate,
(338) methyl 1-{[2-oxo-1-(tetrahydrofuran-2-ylmethyl)-1,2,5,6,7,8,9,10-octahydro-cycloocta[b]pyridine-3-carbonyl]-amino}-cyclohexanecarboxylate,
(339) methyl 3,3-dimethyl-2-{[2-oxo-1-(tetrahydrofuran-2-ylmethyl)-1,2,5,6,7,8,9,10-octahydro-cycloocta[b]pyridine-3-carbonyl]-amino}-butyrate,
(340) methyl 2-[(1-cyclohexylmethyl-4-hydroxy-2-oxo-1,2,5,6,7,8,9,10-octahydro-cycloocta[b]pyridine-3-carbonyl)-amino]-3-methyl-butyrate,
(341) methyl 1-[(1-cyclohexylmethyl-4-hydroxy-2-oxo-1,2,5,6,7,8,9,10-octahydro-cycloocta[b]pyridine-3-carbonyl)-amino]-cyclohexanecarboxylate,
(342) ethyl 2-[(1-cyclohexylmethyl-4-hydroxy-2-oxo-1,2,5,6,7,8,9,10-octahydro-cycloocta[b]pyridine-3-carbonyl)-amino]-cyclohexanecarboxylate,
(343) methyl {[1-(3-methyl-butyl)-2-oxo-1,2,5,6,7,8,9,10-octahydro-cycloocta[b]pyridine-3-carbonyl]-amino}-phenyl acetate,
(344) methyl 2-{[1-(2-methoxy-ethyl)-2-oxo-1,2,5,6,7,8,9,10-octahydro-cycloocta[b]pyridine-3-carbonyl]-amino}-3-methyl-butyrate,
(345) methyl 2-[(1-butyl-2-oxo-2,5,6,7,8,9-hexahydroquinoline-1H-cyclohepta[b]pyridine-3-carbonyl)-amino]-3-methyl-butyrate,
(346) methyl 2-[(1-cyclohexylmethyl-2-oxo-1,2,5,6,7,8-hexahydroquinoline-3-carbonyl)-amino]-3-methyl-butyrate,
(347) methyl 2-[(1-butyl-2-oxo-1,2,5,6,7,8-hexahydroquinoline-3-carbonyl)-amino]-4-methyl-valerate,
(348) methyl 2-[(1-cyclohexylmethyl-2-oxo-1,2,5,6,7,8-hexahydroquinoline-3-carbonyl)-amino]-4-methyl-valerate, (349) ethyl 2-[(1-cyclohexylmethyl-2-oxo-1,2,5,6,7,8,9,10-octahydro-cycloocta[b]pyridine-3-carbonyl)-amino]-2-methyl-propionate,
(350) isopropyl 2-[(1-cyclohexylmethyl-2-oxo-1,2,5,6,7,8,9,10-octahydro-cycloocta[b]pyridine-3-carbonyl)-amino]-2-methyl-propionate,
(351) methyl 2-[(1-allyl-2-oxo-1,2,5,6,7,8,9,10-octahydro-cycloocta[b]pyridine-3-carbonyl)-amino]-3-methyl-butyrate,
(352) 2-[(1-cyclohexylmethyl-2-oxo-1,2,5,6,7,8,9,10-octahydro-cycloocta[b]pyridine-3-carbonyl)-amino]-2-methyl-propionic acid 2,2-dimethyl-[1,3]dioxolan-4-ylmethyl ester,
(353) 2-[(1-cyclohexylmethyl-2-oxo-1,2,5,6,7,8,9,10-octahydro-cycloocta[b]pyridine-3-carbonyl)-amino]-2-methyl-propionic acid 2-hydroxy-1-hydroxymethyl-ethyl ester,
(354) 2-[(1-cyclohexylmethyl-2-oxo-1,2,5,6,7,8,9,10-octahydro-cycloocta[b]pyridine-3-carbonyl)-amino]-2-methyl-propionic acid 2,3-dihydroxy-propyl ester,
(355) methyl 2-[(1-butyl-2-oxo-1,2,5,6,7,8-hexahydroquinoline-3-carbonyl)-amino]-3-phenyl-propionate,
(356) methyl 2-[(4-cyclohexylmethyl-3-oxo-3,4,5,6,7,8-hexahydro-naphthalene-2-carbonyl)-amino]-3-phenyl-propionate,
(357) methyl 2-[(1-butyl-2-oxo-1,2,5,6,7,8-hexahydroquinoline-3-carbonyl)-amino]-3-methyl-valerate,
(358) methyl 2-[(1-cyclohexylmethyl-2-oxo-1,2,5,6,7,8-hexahydroquinoline-3-carbonyl)-amino]-3-methyl-valerate,
(359) methoxymethyl 2-[(1-cyclohexylmethyl-2-oxo-1,2,5,6,7,8,9,10-octahydro-cycloocta[b]pyridine-3-carbonyl)-amino]-2-methyl-propionate,
(360) 1-cyclohexylmethyl-2-oxo-1,2,5,6,7,8,9,10-octahydro-cycloocta[b]pyridine-3-carboxylic acid (1-dimethylcarbamoyl-1-methyl-ethyl)-amide,
(361) methyl 2-[(1-cyclohexylmethyl-2-oxo-2,5,6,7,8,9-hexahydroquinoline-1H-cyclohepta[b]pyridine-3-carbonyl)-amino]-3-methyl-butyrate,
(362) methyl 1-[(1-butyl-2-oxo-2,5,6,7,8,9-hexahydroquinoline-1H-cyclohepta[b]pyridine-3-carbonyl)-amino]-cyclohexanecarboxylate,
(363) methyl 1-[(1-cyclohexylmethyl-2-oxo-2,5,6,7,8,9-hexahydroquinoline-1H-cyclohepta[b]pyridine-3-carbonyl)-amino]-cyclohexanecarboxylate,
(364) methyl 2-[(1-butyl-2-oxo-1,2,5,6,7,8,9,10,11,12-decahydrocyclodeca[b]pyridine-3-carbonyl)-amino]-3-methyl-butyrate,
(365) methyl [(1-cyclohexylmethyl-6-ethyl-5-methyl-2-oxo-1,2-dihydropyridine-3-carbonyl)-amino]-phenyl acetate,
(366) methyl [(1-cyclohexylmethyl-5-ethyl-2-oxo-6-propyl-1,2-dihydropyridine-3-carbonyl)-amino]-phenyl acetate,
(367) methyl 2-[(1-cyclohexylmethyl-2-oxo-1,2,5,6,7,8-hexahydroquinoline-3-carbonyl)-amino]-2-methyl-propionate,
(368) methyl [(1-cyclohexylmethyl-2-oxo-1,2,5,6,7,8-hexahydroquinoline-3-carbonyl)-amino]-phenyl acetate,
(369) methyl 2-[(1-butyl-2-oxo-1,2,5,6,7,8,9,10-octahydro-cycloocta[b]pyridine-3-carbonyl)-amino]-2-methyl-propionate,
(370) methyl 1-{[1-(4-fluorobenzyl)-5,6-dimethyl-2-oxo-1,2-dihydropyridine-3-carbonyl]-amino}-cyclohexanecarboxylate,
(371) methyl 2-{[6-ethyl-1-(4-fluorobenzyl)-5-methyl-2-oxo-1,2-dihydropyridine-3-carbonyl]-amino}-3-methyl-butyrate,
(372) methyl 2-{[5-ethyl-1-(4-fluorobenzyl)-2-oxo-6-propyl-1,2-dihydropyridine-3-carbonyl]-amino}-3-methyl-butyrate,
(373) phenyl 2-[(1-cyclohexylmethyl-2-oxo-1,2,5,6,7,8,9,10-octahydro-cycloocta[b]pyridine-3-carbonyl)-amino]-2-methyl-propionate,
(374) methyl 1-[(1-cyclohexylmethyl-2-oxo-1,2,5,6,7,8-hexahydroquinoline-3-carbonyl)-amino]-cyclohexanecarboxylate,
(375) methyl 1-[(1-butyl-4-hydroxy-2-oxo-1,2,5,6,7,8,9,10-octahydro-cycloocta[b]pyridine-3-carbonyl)-amino]-cyclohexanecarboxylate,
(376) ethyl 2-[(1-butyl-4-hydroxy-2-oxo-1,2,5,6,7,8,9,10-octahydro-cycloocta[b]pyridine-3-carbonyl)-amino]-cyclohexanecarboxylate,
(377) 1-cyclohexylmethyl-2-oxo-1,2,5,6,7,8,9,10-octahydro-cycloocta[b]pyridine-3-carboxylic acid {1-[(2-hydroxy-ethyl)-methyl-carbamoyl]-1-methyl-ethyl}-amide,
(378) ethyl 2-[(1-butyl-2-oxo-1,2,5,6,7,8,9,10-octahydro-cycloocta[b]pyridine-3-carbonyl)-amino]-cyclohexanecarboxylate,
(379) methyl 2-[(1-butyl-2-oxo-1,2,5,6,7,8,9,10-octahydro-cycloocta[b]pyridine-3-carbonyl)-amino]-3,3-dimethyl-butyrate,
(380) methyl 2-[(1-butyl-5-ethyl-2-oxo-6-propyl-1,2-dihydropyridine-3-carbonyl)-amino]-2-methyl-propionate,
(381) methyl 2-[(1-cyclohexylmethyl-5-ethyl-2-oxo-6-propyl-1,2-dihydropyridine-3-carbonyl)-amino]-2-methyl-propionate,
(382) 1-cyclohexylmethyl-2-oxo-1,2,5,6,7,8,9,10-octahydro-cycloocta[b]pyridine-3-carboxylic acid (2-oxo-tetrahydrofuran-3-yl)-amide,
(383) methyl 2-[(1-butyl-5-ethyl-2-oxo-6-propyl-1,2-dihydropyridine-3-carbonyl)-amino]-3,3-dimethyl-butyrate,
(384) methyl 2-[(1-cyclohexylmethyl-5-ethyl-2-oxo-6-propyl-1,2-dihydropyridine-3-carbonyl)-amino]-3,3-dimethyl-butyrate,
(385) methyl {[5-ethyl-1-(4-fluorobenzyl)-2-oxo-6-propyl-1,2-dihydropyridine-3-carbonyl]-amino}-phenylacetate,
(386) methyl {[6-ethyl-1-(4-fluorobenzyl)-5-methyl-2-oxo-1,2-dihydropyridine-3-carbonyl]-amino}-phenylacetate,
(387) S-methyl 2-[(1-cyclohexylmethyl-2-oxo-1,2,5,6,7,8,9,10-octahydro-cycloocta[b]pyridine-3-carbonyl)-amino]-2-methyl-thiopropionate,
(388) 2-[(1-cyclohexylmethyl-2-oxo-1,2,5,6,7,8,9,10-octahydro-cycloocta[b]pyridine-3-carbonyl)-amino]-2-methyl-propionic acid 5-methyl-2-oxo-[1,3]dioxol-4-ylmethyl ester,
(389) 2-[(1-cyclohexylmethyl-2-oxo-1,2,5,6,7,8,9,10-octahydro-cycloocta[b]pyridine-3-carbonyl)-amino]-2-methyl-propionic acid 2-oxo-[1,3]dioxolan-4-yl ester,
(390) methyl 2-[(1-butyl-5-ethyl-2-oxo-6-propel-1,2-dihydropyridine-3-carbonyl)-amino]-4-methyl-valerate,
(391) methyl 2-[(1-butyl-5-ethyl-2-oxo-6-propyl-1,2-dihydropyridine-3-carbonyl)-amino]-3-phenyl-propionate,
(392) methyl 2-{[1-(3-azide-propyl)-2-oxo-1,2,5,6,7,8,9,10-octahydro-cycloocta[b]pyridine-3-carbonyl]-amino}-2-methyl-propionate,
(393) 1-cyclohexylmethyl-2-oxo-1,2,5,6,7,8,9,10-octahydro-cycloocta[b]pyridine-3-carboxylic acid [1-(methoxymethyl-carbamoyl)-1-methyl-ethyl]-amide,
(394) methyl 2-[(1-cyclohexylmethyl-5,6-dimethyl-2-oxo-1,2-dihydropyridine-3-carbonyl)-amino]-3-phenyl-propionate,
(395) methyl 2-{[1-(2-cyano-ethyl)-2-oxo-1,2,5,6,7,8,9,10-octahydro-cycloocta[b]pyridine-3-carbonyl]-amino}-3-methyl-butyrate, (396) 2-[(1-cyclohexylmethyl-6-ethyl-5-methyl-2-oxo-1,2-dihydropyridine-3-carbonyl)-amino]-3,3-dimethyl-butyric acid 2-hydroxy-1-hydroxymethyl-ethyl ester,
(397) methyl [(1-cyclohexylmethyl-2-oxo-1,2,5,6,7,8,9,10-octahydro-cycloocta[b]pyridine-3-carbonyl)-amino]-thiophene-3-yl-acetate,
(398) methyl 2-{[1-(3-cyano-propyl)-2-oxo-1,2,5,6,7,8,9,10-octahydro-cycloocta[b]pyridine-3-carbonyl]-amino}-3-methyl-butyrate,
(399) methyl [(1-benzyl-2-oxo-1,2,5,6,7,8,9,10-octahydro-cycloocta[b]pyridine-3-carbonyl)-amino]-phenylacetate,
(400) methyl (R)-cyclohexyl-[(1-cyclohexylmethyl-2-oxo-1,2,5,6,7,8,9,10-octahydro-cycloocta[b]pyridine-3-carbonyl)-amino]-acetate,
(401) 1-cyclohexylmethyl-2-oxo-1,2,5,6,7,8,9,10-octahydro-cycloocta[b]pyridine-3-carboxylic acid [1-(1-isopropylcarbamoyl-piperidine-4-ylcarbamoyl)-1-methyl-ethyl]-amide,
(402) 2-[(1-butyl-2-oxo-1,2,5,6,7,8,9,10-octahydro-cycloocta[b]pyridine-3-carbonyl)-amino]-3,3-dimethyl-butyric acid 2-hydroxy-1-hydroxymethyl-ethyl ester,
(403) 2-[(1-cyclohexylmethyl-6-ethyl-5-methyl-2-oxo-1,2-dihydropyridine-3-carbonyl)-amino]-3-methyl-butyric acid 2-hydroxy-1-hydroxymethyl-ethyl ester,
(404) 2-[(1-cyclohexylmethyl-2-oxo-1,2,5,6,7,8,9,10-octahydro-cycloocta[b]pyridine-3-carbonyl)-amino]-2-methyl-propionic acid 1-isopropoxycarbonyloxy-ethyl ester,
(405) 2-[(1-cyclohexylmethyl-2-oxo-1,2,5,6,7,8,9,10-octahydro-cycloocta[b]pyridine-3-carbonyl)-amino]-2-methyl-propionic acid 3-dimethylamino-propyl ester,
(406) methyl (R)-2-[(1-cyclohexylmethyl-2-oxo-1,2,5,6,7,8,9,10-octahydro-cycloocta[b]pyridine-3-carbonyl)-amino]-propionate,
(407) 2-[(1-cyclohexylmethyl-2-oxo-1,2,5,6,7,8,9,10-octahydro-cycloocta[b]pyridine-3-carbonyl)-amino]-2-methyl-propionic acid 2-(2,5-dioxo-pyrrolidine-1-yl)-ethyl ester,
(408) methyl (R)-2-[(1-cyclohexylmethyl-2-oxo-1,2,5,6,7,8,9,10-octahydro-cycloocta[b]pyridine-3-carbonyl)-amino]-3-methyl-butyrate,
(409) methyl 2-[(1-cyclohexylmethyl-2-oxo-1,2,5,6,7,8,9,10-octahydro-cycloocta[b]pyridine-3-carbonyl)-amino]-2-methyl-propionate,
(410) methyl 2-[(1-cyclohexylmethyl-5,6-dimethyl-2-oxo-1,2-dihydropyridine-3-carbonyl)-amino]-3-methyl-valerate,
(411) methyl 2-[(1-butyl-5-ethyl-2-oxo-6-propyl-1,2-dihydropyridine-3-carbonyl)-amino]-3-methyl-butyrate,
(412) methyl 2-[(1-butyl-2-oxo-1,2,5,6,7,8,9,10-octahydro-cycloocta[b]pyridine-3-carbonyl)-amino]-3-phenyl-propionate,
(413) methyl 1-[(1-cyclohexylmethyl-2-oxo-1,2,5,6,7,8,9,10-octahydro-cycloocta[b]pyridine-3-carbonyl)-amino]-cyclopropanecarboxylate,
(414) [(1-cyclohexylmethyl-2-oxo-1,2,5,6,7,8,9,10-octahydro-cycloocta[b]pyridine-3-carbonyl)-amino]-acetic acid 2-fluoroethyl ester,
(415) 2-[(1-cyclohexylmethyl-2-oxo-1,2,5,6,7,8,9,10-octahydro-cycloocta[b]pyridine-3-carbonyl)-amino]-2-methyl-propionic acid 1-(ethoxycarbonyloxy)ethyl ester,
(416) methyl [(1-butyl-2-oxo-1,2,5,6,7,8,9,10-octahydro-cycloocta[b]pyridine-3-carbonyl)-amino]-thiophene-3-yl-acetate,
(417) methyl 2-{[1-(4-cyano-benzyl)-2-oxo-1,2,5,6,7,8,9,10-octahydro-cycloocta[b]pyridine-3-carbonyl]-amino}-3-methyl-butyrate,
(418) methyl {[1-(4-fluorobenzyl)-2-oxo-1,2,5,6,7,8,9,10-octahydro-cycloocta[b]pyridine-3-carbonyl]-amino}-phenyl acetate,
(419) methyl 2-{[1-(4-cyano-benzyl)-2-oxo-1,2,5,6,7,8,9,10-octahydro-cycloocta[b]pyridine-3-carbonyl]-amino}-2-methyl-propionate,
(420) 2-[(1-cyclohexylmethyl-2-oxo-1,2,5,6,7,8,9,10-octahydro-cycloocta[b]pyridine-3-carbonyl)-amino]-2-methyl-propionic acid isobutylcarbamoyloxymethyl ester,
(421) methyl 2-{[1-(4-cyano-butyl)-2-oxo-1,2,5,6,7,8,9,10-octahydro-cycloocta[b]pyridine-3-carbonyl]-amino}-3-methyl-butyrate,
(422) methyl 2-{[1-(4-methoxy-benzyl)-2-oxo-1,2,5,6,7,8,9,10-octahydro-cycloocta[b]pyridine-3-carbonyl]-amino}-3-methyl-butyrate,
(423) methyl (S)-2-[(1-cyclohexylmethyl-2-oxo-1,2,5,6,7,8,9,10-octahydro-cycloocta[b]pyridine-3-carbonyl)-amino]-3-methyl-butyrate,
(424) methyl 2-[(1-cyclohexylmethyl-5,6-dimethyl-2-oxo-1,2-dihydropyridine-3-carbonyl)-amino]-4-methyl-valerate,
(425) methyl 2-{[1-(4-fluorobenzyl)-5,6-dimethyl-2-oxo-1,2-dihydropyridine-3-carbonyl]-amino}-3-methyl-butyrate,
(426) methyl 2-[(1-cyclohexylmethyl-2-oxo-1,2,5,6,7,8,9,10-octahydro-cycloocta[b]pyridine-3-carbonyl)-amino]-3-phenyl-propionate,
(427) methyl 2-[(1-butyl-5-ethyl-2-oxo-6-propyl-1,2-dihydropyridine-3-carbonyl)-amino]-3-methyl-valerate,
(428) methyl 1-{[6-ethyl-1-(4-fluorobenzyl)-5-methyl-2-oxo-1,2-dihydropyridine-3-carbonyl]-amino}-cyclohexanecarboxylate,
(429) methyl 1-{[5-ethyl-1-(4-fluorobenzyl)-2-oxo-6-propyl-1,2-dihydropyridine-3-carbonyl]-amino}-cyclohexanecarboxylate,
(430) diethyl 2-[(1-cyclohexylmethyl-2-oxo-1,2,5,6,7,8,9,10-octahydro-cycloocta[b]pyridine-3-carbonyl)-amino]-malonate,
(431) methyl [(1-butyl-2-oxo-1,2,5,6,7,8,9,10-octahydro-cycloocta[b]pyridine-3-carbonyl)-amino]-thiophene-2-yl-acetate,
(432) [(1-butyl-2-oxo-1,2,5,6,7,8,9,10-octahydro-cycloocta[b]pyridine-3-carbonyl)-amino]-thiophen-2-yl-acetic acid,
(433) methyl 2-{[1-(4-fluorobenzyl)-2-oxo-1,2,5,6,7,8,9,10-octahydro-cycloocta[b]pyridine-3-carbonyl]-amino}-3-methyl-butyrate,
(434) methyl [(1-cyclohexylmethyl-2-oxo-1,2,5,6,7,8,9,10-octahydro-cycloocta[b]pyridine-3-carbonyl)-amino]-thiophen-2-yl-acetate,
(435) methyl 2-{[1-(4-fluorobenzyl)-2-oxo-1,2,5,6,7,8,9,10-octahydro-cycloocta[b]pyridine-3-carbonyl]-amino}-3,3-dimethyl-butyrate,
(436) methyl {[1-(4-fluorobenzyl)-2-oxo-1,2,5,6,7,8,9,10-octahydro-cycloocta[b]pyridine-3-carbonyl]-amino}-furan-2-yl-acetate,
(437) methyl [(1-cyclohexylmethyl-2-oxo-1,2,5,6,7,8,9,10-octahydro-cycloocta[b]pyridine-3-carbonyl)-amino]-(4-fluoro-phenyl)-acetate,
(438) methyl 3-methyl-2-{[2-oxo-1-(4-trifluoromethyl-benzyl)-1,2,5,6,7,8,9,10-octahydro-cycloocta[b]pyridine-3-carbonyl]-amino}-butyrate,
(439) methyl [(1-cyclohexylmethyl-2-oxo-1,2,5,6,7,8,9,10-octahydro-cycloocta[b]pyridine-3-carbonyl)-amino]-phenyl acetate, (440) methyl 3-methyl-2-{[1-(4-methyl-benzyl)-2-oxo-1,2,5,6,7,8,9,10-octahydro-cycloocta[b]pyridine-3-carbonyl]-amino}-butyrate,
(441) methyl 1-{[1-(4-fluorobenzyl)-2-oxo-1,2,5,6,7,8,9,10-octahydro-cycloocta[b]pyridine-3-carbonyl]-amino}-cyclohexanecarboxylate,
(442) methyl 2-[(1-cyclohexylmethyl-6-ethyl-5-methyl-2-oxo-1,2-dihydro-pyridine-3-carbonyl)-amino]-2-methyl-propionate,
(443) methyl 1-[(1-furan-2-ylmethyl-2-oxo-1,2,5,6,7,8,9,10-octahydro-cycloocta[b]pyridine-3-carbonyl)-amino]-cyclohexanecarboxylate,
(444) 1-cyclohexylmethyl-2-oxo-1,2,5,6,7,8,9,10-octahydro-cycloocta[b]pyridine-3-carboxylic acid [1,1-dimethyl-2-oxo-2-(4-propylcarbamoyl-piperidine-1-yl)-ethyl]-amide,
(445) methyl (S)-2-[(1-cyclohexylmethyl-2-oxo-1,2,5,6,7,8,9,10-octahydro-cycloocta[b]pyridine-3-carbonyl)-amino]-propionate,
(446) methyl (S)-cyclohexyl-1-[(1-cyclohexylmethyl-2-oxo-1,2,5,6,7,8,9,10-octahydro-cycloocta[b]pyridine-3-carbonyl)-amino]-acetate,
(447) methyl 1-[(1-cyclohexylmethyl-2-oxo-1,2,5,6,7,8,9,10-octahydro-cycloocta[b]pyridine-3-carbonyl)-amino]-cyclohexanecarboxylate,
(448) ethyl 2-[(1-cyclohexylmethyl-2-oxo-1,2,5,6,7,8,9,10-octahydro-cycloocta[b]pyridine-3-carbonyl)-amino]-cyclohexanecarboxylate,
(449) methyl 2-[(1-butyl-2-oxo-1,2,5,6,7,8,9,10-octahydro-cycloocta[b]pyridine-3-carbonyl)-amino]-3-methyl-butyrate,
(450) methyl 2-[(1-butyl-2-oxo-1,2,5,6,7,8,9,10-octahydro-cycloocta[b]pyridine-3-carbonyl)-amino]-3-methyl-butyrate,
(451) methyl 2-[(1-cyclohexylmethyl-5-ethyl-2-oxo-6-propyl-1,2-dihydropyridine-3-carbonyl)-amino]-4-methyl-valerate,
(452) methyl 2-[(1-cyclohexylmethyl-6-ethyl-5-methyl-2-oxo-1,2-dihydropyridine-3-carbonyl)-amino]-3,3-dimethyl-butyrate,
(453) methyl {[1-(4-fluorobenzyl)-2-oxo-1,2,5,6,7,8,9,10-octahydro-cycloocta[b]pyridine-3-carbonyl]-amino}-thiophene-2-yl-acetate,
(454) methyl [(1-cyclohexylmethyl-2-oxo-1,2,5,6,7,8,9,10-octahydro-cycloocta[b]pyridine-3-carbonyl)-amino]-furan-2-yl-acetate,
(455) methyl {[6-ethyl-1-(4-fluorobenzyl)-5-methyl-2-oxo-1,2-dihydropyridine-3-carbonyl]-amino}-thiophen-2-yl-acetate,
(456) methyl 2-[(1-benzyl-2-oxo-1,2,5,6,7,8,9,10-octahydro-cycloocta[b]pyridine-3-carbonyl)-amino]-3-methyl-butyrate,
(457) methyl {[1-(3-methyl-butyl)-2-oxo-1,2,5,6,7,8,9,10-octahydro-cycloocta[b]pyridine-3-carbonyl]-amino}-thiophen-2-yl-acetate,
(458) methyl 2-{[1-(4-chloro-benzyl)-2-oxo-1,2,5,6,7,8,9,10-octahydro-cycloocta[b]pyridine-3-carbonyl]-amino}-3-methyl-butyrate,
(459) 1-cyclohexylmethyl-2-oxo-1,2,5,6,7,8,9,10-octahydro-cycloocta[b]pyridine-3-carboxylic acid (4-carbamoyl-thiazol-2-yl)-amide,
(460) 1-cyclohexylmethyl-2-oxo-1,2,5,6,7,8,9,10-octahydro-cycloocta[b]pyridine-3-carboxylic acid (4-aminooxalyl-thiazole-2-yl)-amide,
(461) 1-cyclohexylmethyl-2-oxo-1,2,5,6,7,8,9,10-octahydro-cycloocta[b]pyridine-3-carboxylic acid [2-(4-benzenesulfonylamino-piperidine-1-yl)-1,1-dimethyl-2-oxo-ethyl]-amide,
(462) 1-{([(1-cyclohexylmethyl-2-oxo-1,2,5,6,7,8,9,10-octahydro-cycloocta[b]pyridine-3-carbonyl)-amino]-methyl}-cyclohexanecarboxylic acid,
(463) (S)-3-{[1-(4-fluorobenzyl)-2-oxo-1,2,5,6,7,8,9,10-octahydro-cycloocta[b]pyridine-3-carbonyl]-amino}-5-methyl-hexanoic acid,
(464) (1-{[1-(4-fluorobenzyl)-2-oxo-1,2,5,6,7,8,9,10-octahydro-cycloocta[b]pyridine-3-carbonyl]-amino}-cyclohexyl)-acetic acid,
(465) 1-cyclohexylmethyl-2-oxo-1,2,5,6,7,8,9,10-octahydro-cycloocta[b]pyridine-3-carboxylic acid {2-[3-(2-hydroxy-ethylcarbamoyl)-piperidine-1-yl]-1,1-dimethyl-2-oxo-ethyl}-amide,
(466) {5-[(1-cyclohexylmethyl-2-oxo-1,2,5,6,7,8,9,10-octahydro-cycloocta[b]pyridine-3-carbonyl)-amino]-thiophene-3-yl}-acetic acid,
(467) (1-{[(1-cyclohexylmethyl-2-oxo-1,2,5,6,7,8,9,10-octahydro-cycloocta[b]pyridine-3-carbonyl)-amino]-methyl}-cyclohexyl)-acetic acid,
(468) 4-[(1-cyclohexylmethyl-2-oxo-1,2,5,6,7,8,9,10-octahydro-cycloocta[b]pyridine-3-carbonyl)-amino]-4-methyl-valeric acid,
(469) 1-cyclohexylmethyl-2-oxo-1,2,5,6,7,8,9,10-octahydro-cycloocta[b]pyridine-3-carboxylic acid [1,1-dimethyl-2-oxo-2-(2-pyridine-4-yl-acetyl-1-amino)-ethyl]-amide,
(470) 1-cyclohexylmethyl-2-oxo-1,2,5,6,7,8,9,10-octahydro-cycloocta[b]pyridine-3-carboxylic acid [2-(2,2-dimethoxy-propionylamino)-1,1-dimethyl-2-oxo-ethyl]-amide,
(471) 1-cyclohexylmethyl-2-oxo-1,2,5,6,7,8,9,10-octahydro-cycloocta[b]pyridine-3-carboxylic acid [1,1-dimethyl-2-(2-morpholine-4-yl-acetylamino)-2-oxo-ethyl]-amide,
(471) {2-[(1-benzyl-2-oxo-1,2,5,6,7,8,9,10-octahydro-cycloocta[b]pyridine-3-carbonyl)-amino]-thiazole-4-yl}-acetic acid,
(472) 1-cyclohexylmethyl-2-oxo-1,2,5,6,7,8,9,10-octahydro-cycloocta[b]pyridine-3-carboxylic acid [1,1-dimethyl-2-oxo-2-(3-pentylcarbamoyl-piperidine-1-yl)-ethyl]-amide,
(473) 1-cyclohexylmethyl-2-2-oxo-1,2,5,6,7,8,9,10-octahydro-cycloocta[b]pyridine-3-carboxylic acid {1,1-dimethyl-2-[4-(morpholine-4-carbonyl)-piperidine-1-yl]-2-oxo-ethyl}-amide,

EFFECT OF INVENTION

In general, the compounds of the present invention have strong activity for both of the CB1 and CB2 receptors or either of them. In general, the strength of the activity can be indicated by the bonding activity (Ki value) to the receptor, the smaller the Ki value, the stronger the activity is (in vitro activity). Though the compounds of the present invention generally have the very wide range of bonding activity in the order of 0.1 nM to 5000 nM to both or either of the receptors, and the degrees of the selectivity to the both receptors (the ratio of Ki values to the CB1 and CB2 receptors) are also various, when applying the compound on the skin, the effect of restraining itching can be expected (in vivo activity) if the Ki value is about 50 nM or less. Consequently, a compound having a Ki value of 50 nM or less can be considered to be a preferable compound. As for the actual anti-pruritic activity of the compound of the present invention, when the compound to be inspected is dissolved in a solvent and applied on the skin with a compound 40/80 which causes itching, the effect can be confirmed by the density needed torestrain itching by 50% or more compared with the control group. It can be thought that the compound is the most preferable compound If itching can be restrained 50% or more significantly in the density of the active ingredient 3% or less.

Moreover, itching can be restrained also by the oral administration.

The compounds of the present invention have such features as low inhibition activity for enzyme (CYP), low central nerve side effects, excellent photostability, and the like.

BEST MODE FOR CARRYING OUT THE INVENTION

The compounds related to the present invention can be manufactured by the processes described below.

In the following descriptions, the following abbreviations will be used.

Me: methyl
Et: ethyl
n-Pr: n-propyl
i-Pr: isopropyl
n-Bu: n-butyl
Ac: acetyl
DBU: 1,8-diazabicyclo[5,4,0]undecene
DMF: dimethylformamide
DMSO: dimethylsulfoxide
HOBt: 1-hydroxybenzotriazole
Ms: methanesulfonyl
Diglyme: diethylene glycol dimethyl ether
Triglyme: triethylene glycol dimethyl ether
TFA: trifluoroacetic acid
TLC: thin-layer chromatography
THF: tetrahydrofuran
Ts: para-toluenesulfonyl
WSCD: 1-ethyl-3-(3-dimethylaminopropyl)carbodiimide hydrochlorides The compounds of the present invention can be synthesized through compounds (V) with a carboxyl group in the third position as key intermediates. These key intermediates are synthesized by either of the methods shown in the route 1 to 3, and $R^1$, $R^2$, $R^3$, and $R^4$ are introduced in the process of the method. Though $R^1$ to $R^4$ become directly partial structures in the compound of the present invention, it is also possible that chemically transformable functional groups are incorporated beforehand and they are properly transformed into necessary functional groups for the compound of the present invention. This example will be described later.

Route 1

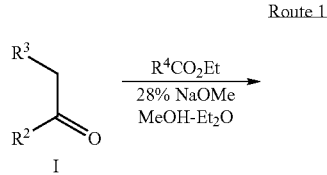

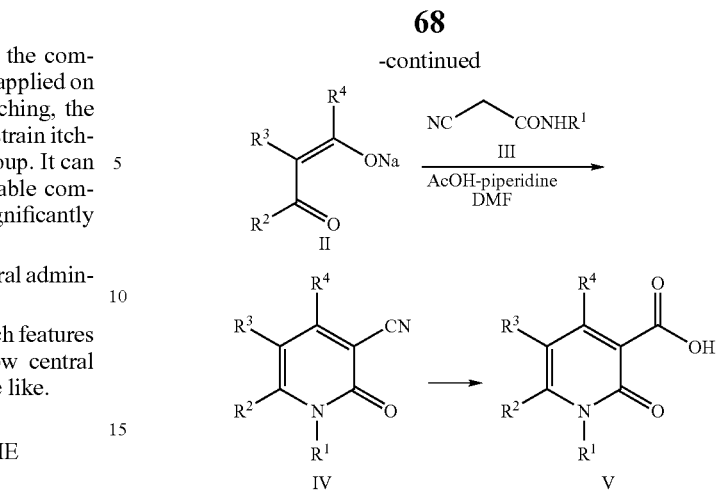

wherein $R^1$, $R^2$, $R^3$, and $R^4$ are as defined above.

Route 1: This method is suitable for synthesis of a compound in which $R^2$ is an alkyl, and $R^3$ is an alkyl or an alkoxy. Ketone (I) and formate ($R^4$=H) are dissolved in a solvent such as ether or the like and stirred together with a sodium methoxide methanol solution at temperatures from ice temperature to room temperature for 12 to 24 hours, then B-diketone can be obtained as sodium salt (II). When the compound (II) is suspended in DMF without being purified and refluxed together with acetic acid being excessive a little, the catalytic amount of piperidine and cyanoacetamide derivative (III) for from several to 24 hours, 3-cyanopyridone derivative (IV) is obtained. At this time, if a suitable functional group is previously introduced in $R^1$, it can be transformed into various kinds of functional groups in the later phase. When an isomer is formed, both or only the necessary isomer may be taken out by the silica gel chromatography or the recrystallization at the phase of compound (IV). When the nitrile group of IV is refluxed for several to 24 hours in the water containing alcohol together with sodium hydroxide or potassium hydroxide in 1 to several equivalent weights, the aimed 3-carboxylic acid (V) is obtained. The end point of the reaction is decided by the vanishment of the raw material with TLC or HPLC. V can generally be made to be a key intermediate with sufficient purity by the recrystallization.

Route 2

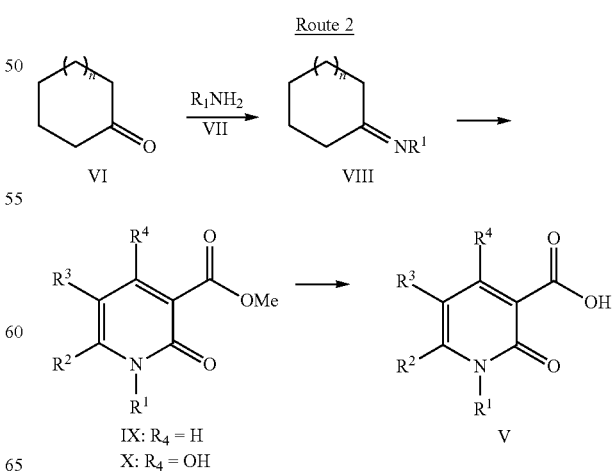

wherein $R^1$ and $R^4$ are as defined above; $R^2$ and $R^3$ taken together with the adjacent carbon atoms form a 5 to 10 membered cycloalkene which may contain one group selected from —O—, —S—, —SO—, and —SO$_2$— in the ring.

Route 2: This method is particularly suitable for synthesis of a compound in which $R^2$ and $R^3$ are bonded in cyclic. That is, when a cyclic ketone body (VI) is warmed together with primary amine (VII) in a high boiling point solvent such as toluene, diglyme, or triglyme for 3 to 24 hours at the reflux temperature of the solvent while being dehydrated with the use of a dehydrator of Dean Stark, animine (VIII) is obtained. When the boiling point of the compound (VII) is low, it is also possible that the compound (VI) and the compound (VII) are stirred at room temperature with the catalytic amount of an acid catalyst such as concentrated hydrochloric acid or concentrated sulfuric acid to be transformed into the corresponding compound (VIII). Moreover, even if the methylene group in the compound (VI) is replaced with an oxygen atom or a sulfur atom, the reaction progresses similarly. In addition, when a suitable functional group is introduced into $R^1$ beforehand, the group can be transformed into any one of various functional groups at an arbitrary phase. Methoxymethylene dimethyl malonate is added to the compound (VIII) and refluxed for 1 to 10 hours, a 3-methyl ester body (IX) in which $R^4$ is hydrogen is obtained. When trimethyl methanetricarboxylate is used instead of the malonic ester, 3-methyl ester (X) in which $R^4$ is the hydroxy group is obtained. In this case, the use of a high bp: solvent such as triglyme is preferable. Though it is preferable to refine the compound (IX) and the compound (X) by the silica gel chromatography or the recrystallization, generally, they are not refined, and the aimed key intermediate (V) can be induced by immediately adding the necessary amount of a water containing alcohol solvent such as methanol or ethanol, or a solvent of THF or the like when the compounds being insoluble in alcohol, and stirring with the slightly excessive amount or several equivalent weight of lithium hydroxide, sodium hydroxide, potassium hydroxide, or the like for 0.5 to several hours. The compound (V) synthesized by this method can generally be made to be a key intermediate with enough purity by the recrystallization.

wherein $R^1$, $R^2$, and $R^3$ are as defined above; R is a C1-C6 alkyl.

Route 3: When ketone (I or VI) and dimethylformamide dialkyl acetal are warmed at 100° C. to the reflux temperature of the solvent for 12 to 24 hours, ketoimine (XI) is obtained. As dimethylformamide dialkyl acetal, dimethylformamide dimethyl acetal, which is a commercial item easily obtainable, is generally used. When the compound (XI) is nor refined and is stirred with cyano acetic ester in a solvent such as methanol at room temperature, an ester body (XII) is precipitated as a hardly soluble solid. Compound (XII) is dissolved in DMF, THF, DMSO, or these compounds and is stirred with the slightly excessive amount of sodium hydride at room temperature to 60° C. for 0.5 to several hours. After that, when an alkylating agent ($R^1$—X) is added and stirred at room temperature to 50° C. for one to several hours, the compound (XIII) and compound (XIV) which are substituted for the first place or the second place are generally formed at the rate of 1:1. At this time, a suitable functional group can be introduced into $R^1$ beforehand. As X of an alkylating agent, chlorine, bromine, iodine, the toluenesulfonyloxy group, the methanesulfonyloxy group, and the like are preferable. The compound (XIV) can be easily removed by the silica gel chromatography or the recrystallization. Then, the compound (XIII) is hydrolyzed by the above-mentioned method, leading to a key intermediate (V).

The compound (V), which can be synthesized by the above-mentioned method, is a key intermediate which can be used as a raw material for synthesizing all of the compounds of the present invention, and the manufacturing method will be described more in detail by the referential examples. However, the manufacturing method of the compound (V) is not limited only to these three routes.

Next, as an example in which a suitable functional group is incorporated beforehand and transformed to the desired functional group at a suitable phase, the method of introducing the amino group into the end of $R^1$ will be described.

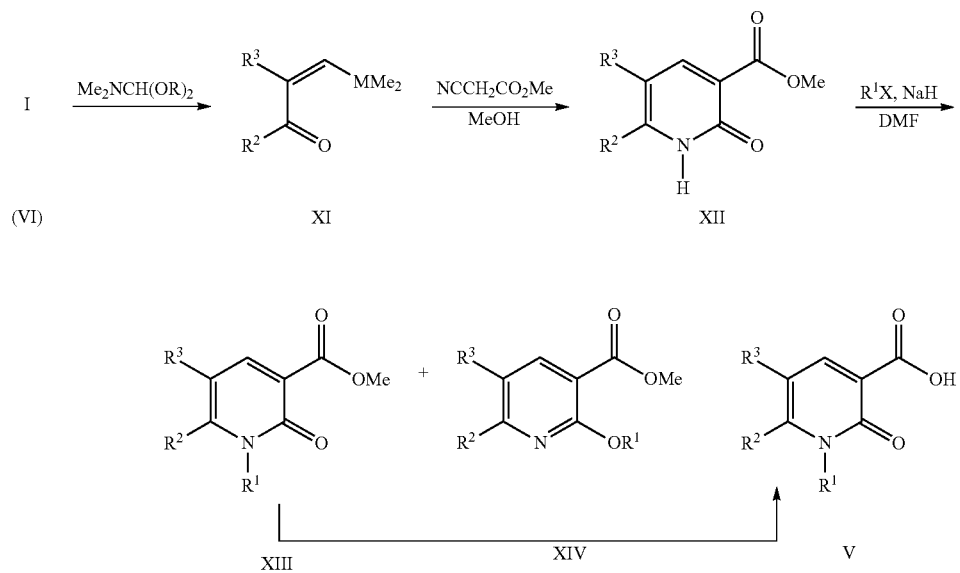

Route 3

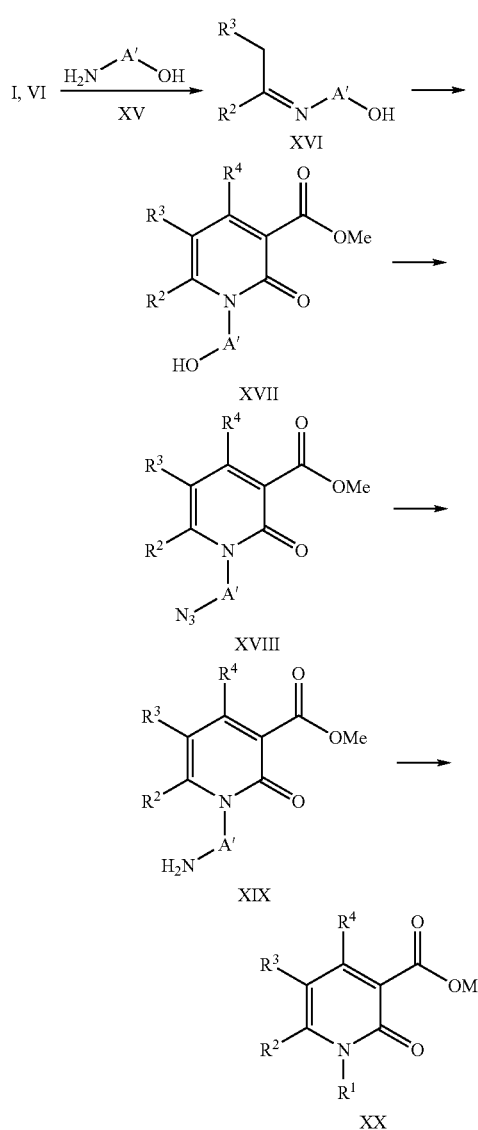

wherein $R^1$, $R^2$, $R^3$, and $R^4$ are as defined above; A' is a C1-C8 alkylene group optionally substituted with one to two substituents selected from the above-mentioned substituent group A.

The 3-ester (XVII) is obtained from a compound (I) or a compound (VI) and a compound (XV) by the method of route 1 or 2. The hydroxy group can be transformed to various functional groups. For example, when compound (XVII) is reacted in a solvent such as THF or methylene chloride with the chlorinated toluene sulfonate and chlorinated methane sulfonate in the presence of a tertiary base such as pyridine or triethyl amine at temperatures from ice temperature to room temperature, a tosylate body or a mesylate body which corresponds respectively is obtained. These substituents can easily receive the nucleophilic substitution reaction as a leaving group to be transformed into other functional groups. For example, when these substituents are reacted with sodium azide in a solvent such as DMF or DMSO at temperatures of 100° C. to the reflux temperature of the solvent, they can be transformed into azide (XVIII). The azide is easily reduced with catalytic reduction, or by triphenylphosphine and the like to form an amino (XIX). The compound (XIX) is further not only transformed easily into various functional groups such as secondary amine, tertiary amine, an amide, a sulfonamide, and a carbamate, which are widely used as partial structures in pharmaceuticals, but made to be new intermediates by introducing proper protecting groups. Though it does not needed to explain the methods of concretely transforming these functional groups for those skilled in the art, concrete methods have been given in, for example, Harrison, I., Harrison, S., Compendium of Organic Synthesis Vol I-II, Wiley-Interscience, NY (1971, 1977), Hegedus, L. S., Wade, L., Compendium of Organic Synthesis Vol III, John Wiley & Sons, NY (1977), Sandler, S. R., Karo, W., Organic Functional Group Preparations, 2nd Ed., Academic Press, NY (1983), Experimental chemistry course, 4th Ed., Organic synthesis I-V, Maruzen (1992), and others. Carboxylic acids (V), in which R1 is modified, can be obtained by hydrolyzing various compounds (XX) manufactured in such ways. As for other functional groups, the above-mentioned methods have only to be followed basically.

Next, the methods of transforming key intermediates (V) into 3-carbamoyl (XXII to XXV), which are features for the compounds of the present invention, will be described. It does not needed to explain the methods of transforming carboxylic acids into acid amide bodies for those skilled in the art. Concretely, though it is sufficient only to follow the methods described in the following documents, for example, Harrison, I., Harrison, S., Compendium of Organic Synthesis Vol I-II, Wiley-Interscience, NY (1971, 1977), Hegedus, L. S., Wade, L., Compendium of Organic Synthesis Vol III, John Wiley & Sons, NY (1977), Sandler, S. R., Karo, W., Organic Functional Group Preparations, 2nd Ed., Academic Press, NY (1983), Experimental chemistry course, 4th Ed., Organic synthesis I-V, Maruzen (1992), and others, acid amide bodies can be usually manufactured acid by the following methods.

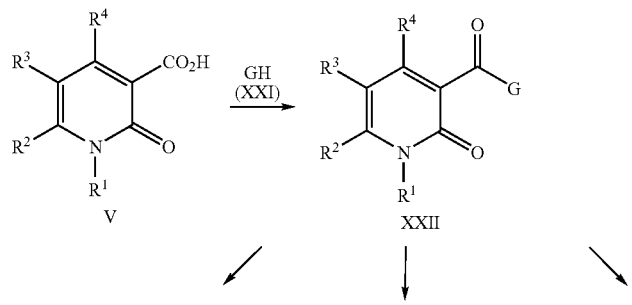

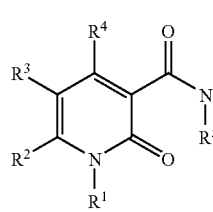

XXIII

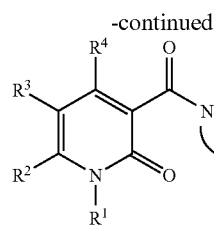

XXIV

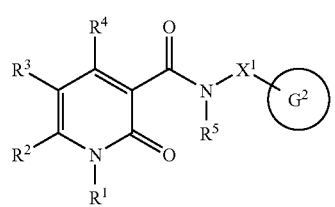

XXV wherein $R^1$, $R^2$, $R^3$, $R^4$, $R^5$, $X^1$, $X^2$, $X^3$, Y, Z, G, $G^1$, and $G^2$ are as defined above.

Carboxylic acid (V) is reacted with oxalyl chloride in a solvent such as dichloromethane or THF in the presence of the catalytic amount of DMF at room temperature and transformed into the acid chloride. Instead of using oxalyl chloride, carboxylic acid (V) can also be transformed into the acid chloride by refluxing it with thionyl chloride in a nonpolar solvent such as benzene or methylene chloride, or without using a solvent. When the acid chloride is not refined and reacted with an amine body (XXI) in a solvent such as methylene chloride or THF in the presence of a base such as triethyl amine or pyridine at temperatures from cooling with ice to room temperature for one to six hours, amide (XXII) is obtained. When the amino group of the compound (XXI) is a salt such as an inorganic acid, tertiary amine only has to be added simultaneously in the reaction mixture in the enough amount of neutralizing the salt. The compound (XXII) can also be manufactured directly from the compound (XXI) and the compound (V) in the presence of an activator such as, for example, WSCD-HOBt. When the progress of the reaction is late, the irradiation of the microwave is effective, and even such a reaction as does not progress under a usual condition ends within tens of minutes. The separation of a product difficult to be isolated can also be facilitated with the use of a reagent fixed to a polymer carrier.

Compounds (XXI) can be classified into compounds (XXIII), compounds (XXIV), and compounds (XV) according to the kinds of G. Furthermore, the part of —Y—Z can be transformed into various functional groups with the use of the definite method if necessary. For example, when —Y—Z is alkoxy in a compound (XXIII) or a compound (XXIV), after the alkoxy is transformed into acid halide with the use of a carboxylic acid XXVI obtained by the hydrolysis, the acid halide can be reacted with alcohols, mercaptans or amines to form compounds (XXIII) in which Y becomes an oxygen atom, a sulfur atom, and a nitrogen atom, respectively. In this case, the amidation method previously described can be applied.

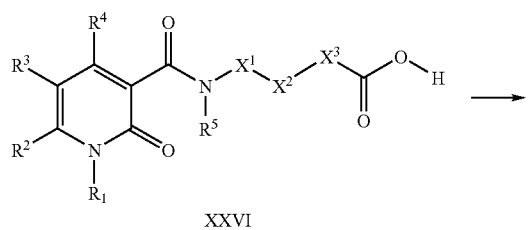

XXVI

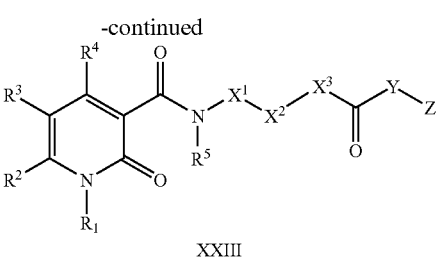

XXIII wherein $R^1$, $R^2$, $R^3$, $R^4$, $R^5$, $X^1$, $X^2$, $X^3$, Y, and Z are as defined above.

When the asymmetric center exists in the alpha place in the carbonyl and the racemization progresses in the process of the hydrolysis, a protecting group such as, for example, the benzhydryl group or the tertiary butyl group, which can receive easily the acid hydrolysis at room temperature, is introduced as Z and the hydrolysis may be carried out in a mild acid condition. The compounds of the present invention have a wide variety of structures, and the compounds (XXIII) are not only compounds of the present invention but also very useful as intermediates for manufacturing more complex derivatives and will be described in detail in examples.

Examples of manufacturing various compounds of the present invention using carboxylic acids (XXVI) include, for example, manufacturing amide bodies (XXVIII) by the reactions with compounds (XXVII) which have the amino group. In this time, for example, if a protected amino group exists in the terminal, after canceling the protection, another substituent can be newly introduced and the amino group can also be transformed easily into various functional groups widely used as partial structures in pharmaceuticals such as an amid body, a sulfonamide body, and a carbamate body.

In the present invention, not only a compound of the present invention, which has the cannabinoid receptor agonist action, but also the salt allowed in medicine manufacture or a solvate thereof can be used.

When an optical isomer, a stereoisomer, and a geometrical isomer exist in a compound of the present invention, all isomers are included.

As for salts allowed in medicine manufacture, basic salts include, for example, alkali metal salts such as sodium salt and potassium salt; alkaline-earth metal salts such as calcium salt and magnesium salt; ammonium salts; aliphatic amine salts such as trimethylamine salt, triethylamine salt, dicyclohexylamine salt, ethanolamine salt, diethanolamine salt, triethanolamine salt, and procaine salt; aralkylamine salts such as N,N-dibenzylethylenediamine; heterocycle aromatic amines such as pyridine salt, picoline salt, quinoline salt, and isoquinoline salt; quaternary ammonium salts such as tetramethylammonium salt, tetramethylammonium salt, benzyltrimethylammonium salts, benzyltriethylammonium salt, benzyltributylammonium salt, methyltrioctylammonium salt, and tetrabutylammonium salt; basic amino acid salts such as arginine salt and lysine salt: acid salts include, for example, inorganic acid salts such as hydrochlorides, sulfates, nitrates, phosphates, carbonates, hydrogencarbonates, and perchlorates; organic acid salts such as acetates, propionates, lactates, maleates, fumarates, tartrates, malates, citrates, and ascorbates; sulfonates such as methanesulfonates, isethionates, benzenesulfonates, and p-toluenesulfonates; amino acids such as aspartates, and glutamates.

The solvates mean solvates of the compound of the present invention or those of the salts allowed in medicine manufacture, and, for example, monosolvates, disolvates, monohydrates, dihydrates, and the like are enumerated.

The anti-pruritus agent concerned with the present invention can be used as a therapeutic agent for itching such as pruritus at the time of, allergic or nonallergic, for example, atopic dermatitis, hives, contact dermatitis, psoriasis vulgaris, senile xerosis, kidney dialysis, or hepatic failure. Further, suppressing itching is also useful for preventing the disease and the injury secondarily generated by the scratch action, the beating, and the like attendant upon itching.

The compounds of the present invention are excellent in stability, photostability and disposition, and can be used for other diseases, in which the toxicity such as the enzyme inhibition (CYP) and the central nerve side effects is low and the cannabinoid receptor agonist takes part, for the purpose of treatment or prevention. For example, the description in Nature, vol. 365, p. 61 to 65, (1993) indicates that the cannabinoid receptor agonist has anti-inflammatory activity and analgesic activity, the description in Journal of Cannabis Therapeutics, vol. 2, No. 1, p. 59 to 71 (2002) indicates that the cannabinoid receptor agonist has bronchodilatory activity, and the description in International Publication No. 03/035109, pamphlet indicates that the cannabimoid receptor agonist has anti-pruritic activity.

That is, the compounds of the present invention can be used as an anti-pruritus agent, an anti-inflammatory agent, an anti-allergic agent, an analgesic agent, pain therapy agents (annociceptivity pain therapeutic agent, a neuropathic pain therapeutic agent, a psychogenic pain therapeutic agent, an acute pain therapeutic agent, a chronic pain therapeutic agent, and the like), an immunodeficiency therapeutic agent, an immunosuppressive agent, an immunoregulatory agent, an autoimmune disease therapeutic agent, a chronic articular rheumatism therapeutic agent, an osteoarthritis therapeutic agent, a multiple sclerosis therapeutic agent, antiasthmatic agents (an inhibitor for inflammatory cellular infiltration in the respiratory tract, an inhibitor for hyperirritability in the respiratory tract, a bronchodilator, a mucus secretion retardant, and the like), a chronic obstructive pulmonary disease therapeutic agent, a pulmonary emphysema therapeutic agent, pulmonary fibrosis therapeutic agent, a cough suppressant, an allergic rhinitis therapeutic agent, dermatitis therapeutic agents (an atopic dermatitis therapeutic agent, a hives therapeutic agent, a contact dermatitis therapeutic agent, a psoriasis vulgaris therapeutic agent), an inflammatory bowel disease therapeutic agent, an arteriosclerosis therapeutic agent, a glaucoma therapeutic agent, an anorexia therapeutic agent, and the like.

In the treatment of the disease concerned with the present invention, the compounds of the present invention can be used together with or combining with other therapeutic agents. In the treatment of itching such as pruritus at the time of, allergic or nonallergic, for example, atopic dermatitis, hives, contact dermatitis, psoriasis vulgaris, senile xerosis, kidney dialysis, or hepatic failure, as anti-pruritus agents, the compounds of the present invention can also be used together with or combining with a corticosteroid receptor agonist, an immunosuppressive agent, a PDE IV inhibitory agent, an IgE antibody generation retardant, a histamine H1 receptor antagonist, a histamine H4 receptor antagonist, a chemokine receptor antagonist, a VLA-4 antagonist, a nonsteroidal anti-inflammatory agent, or a PPARgamma agonist.

Moreover, in the respiratory disease, the compounds of the present invention can also be used together with or combining with a corticosteroid receptor agonist, an immunosuppressive agent, a PDE IV inhibitory agent, an IgE antibody generation retardant, a histamine H1 receptor antagonist, a histamine H4 receptor antagonist, a chemokine receptor antagonist, a VLA-4 antagonist, a nonsteroidal anti-inflammatory agent, a PPARgamma agonist, a leukotriene receptor antagonist, a leukotriene synthesis inhibitor, a prostaglandin receptor antagonist, a thromboxane A2 receptor antagonist, a beta2 receptor antagonist, an anticholinergic drug, a mast cell isolation depressant, and a cough suppressant.

To use a compound of the present invention for treatment, the compound is made to be a drug product for usual oral or parenteral administration. The pharmaceutical composition containing a compound of the present invention can take the forms for oral and parenteral administration. That is, the composition can also be made to be oral administration drug products such as a tablet, a capsule, a granule, powdered medicine, and syrup, and parenteral administration drug products including solutions for injection such as intravenous injection, intramuscular injection, and hypodermic injection, or drug products for dermal administration such as suspension, an inhalant, eye-drops, nose drops, a suppository, a gel agent, an ointment, or a droplet distributed ointment.

These drug products can be manufactured using suitable carriers, vehicles, solvents, bases, and the like which are already known to those skilled in the art. For example, in case of a tablet, an active ingredient and an auxiliary ingredient are compressed or formed together. As an auxiliary ingredient, a vehicle which is allowed in the drug product, for example, a bonding agent (for instance, cornstarch and the like), fillers (for instance, lactose, microcrystalline cellulose, and the like), disintegrating agents (for instance, starch sodium glycolate and the like), or lubricants (for instance, magnesium stearate and the like) are used. The tablet may be properly coated. In case of liquid preparations such as syrup, a liquid medicine, and a suspension agent, for example, suspending agents (for instance, methyl cellulose and the like.), emulsifying agents (for instance, lecithin and the like), and preservative are used. In case of drug products for injection, they may be either in the form of solution, suspension, or oily or aqueous emulsion, and these may contain an emulsion stabilizer, a dispersant, or the like. When being used as an inhalant, the drug products are used as a liquid medicine which can adjust to an inhaler, and when also being used as eye-drops, these drug products are used as a liquid medicine or a suspending agent. When being used as a gel agent, an active ingredient, a solvent, and a gelling agent are stirred together to be peptized. When being used as a droplet distributed ointment, an active ingredient, a solvent, an ointment base, and the like are used.

Though the dosage of the compound of the present invention differs according to the administering form, the patient's symptom, age, weight, and the sex, or a medicine to be used together (in case of being), and the like, and finally is entrusted to the doctor's judgement, in case of the oral administration, the daily dosage is 0.01 to 100 mg per 1 kg in body weight, preferably 0.01 to 10 mg, and more preferably 0.1 to 10 mg, and in case of parenteral administration, the daily dosage is 0.001 to 100 mg per 1 kg in body weight, preferably 0.001 to 1 mg, and more preferably 0.01 to 1 mg. These daily dosages have only to be administered by being divided into one to four times.

To make the above-mentioned description more concretely, reference examples and examples are given as follows. However, the methods for synthesizing the compounds of the present invention should not be limited to the methods described here.

EXAMPLES

As 3-pyridone carboxylic acid, those obtained from the market or synthesized by the following synthesis methods were used.

Example 1

Synthesis of 1-cyclohexylmethyl-2-oxo-1,2,5,6,7,8,9,10-octahydro-cycloocta[b]pyridine-3-carboxylic acid (AA01)

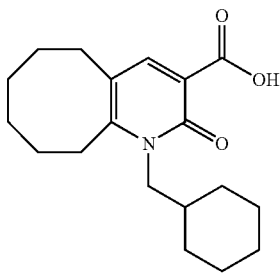

Under the nitrogen gas atmosphere, a solution of cyclooctanone (15 g, 118 mmol) and cyclohexylmethylamine (16.1 g, 142 mmol) in toluene (300 mL) was refluxed under azeotropic dehydration for 6 hours. After that, diethyl ethoxymethylenemalonate (24 mL, 142 mmol) was added, and the mixture was further refluxed for 2 hours. After the reaction mixture had been removed by distillation under reduced pressure, the residue was dissolved in the mixed solvent of THF (200 mL) and methanol (200 mL), then a 2M sodium hydroxide aqueous solution was added and the mixture was stirred for 2 hours at room temperature. The reaction mixture was removed by distillation under reduced pressure, water was added to the residue and the water layer was washed with diethyl ether one time. Then, after 2 M hydrochloric acid was added to the water layer to acidify it, the water layer was extracted with ethyl acetate. The organic layer was washed with water and then dried with anhydrous sodium sulfate. The solvent was removed by distillation under reduced pressure and a pale yellow solid (AA01, 21.5 g, 57%, mp: 162-163° C.) was obtained.

NMR: (DMSO-d6) 1.00-1.88 (m, 19H), 2.71 (t, 2H, J=5.7), 3.00 (t, 2H, J=5.7), 4.05 (d, 2H, J=6.3), 8.20 (s, 1H)

Example 2

Synthesis of 1-(4-fluorobenzyl)-2-oxo-1,2,5,6,7,8,9,10-octahydro-cycloocta[b]pyridine-carboxylic acid (AA02)

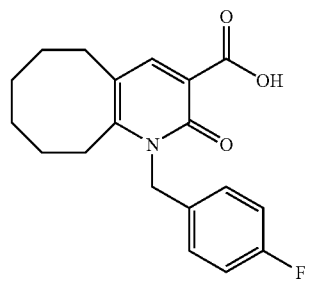

Under the nitrogen gas atmosphere, a solution of cyclooctanona (7.55 g, 59.8 mmol) and perfluorobenzylamine (8.20 g, 71.8 mmol) in toluene (100 mL) was refluxed under azeotropic dehydration for 6 hours. After that, diethyl ethoxymethylenemalonate (12.1 mL, 59.8 mmol) was added, and the mixture was further refluxed for 2 hours. After the reaction mixture had been removed by distillation under reduced pressure, THF (100 mL), methanol (100 mL), and a 2M sodium hydroxide aqueous solution were added to the residue in order, and the mixture was stirred for 2 hours at room temperature. The reaction mixture was removed by distillation under reduced pressure, water was added to the residue and was washed with diethyl ether one time. Then, 2 M hydrochloric acid was added to the water layer and was extracted with ethyl acetate. The organic layer was washed with water and then dried with anhydrous sodium sulfate. The solvent was removed by distillation under reduced pressure and a pale yellow solid (AA02, 9.8 g, 50%, mp: 170-172° C.) was obtained.

NMR: (CDCl3) 1.36-1.88 (m, 8H), 2.67 (t, 2H, J=6.0), 2.88 (t, 2H, J=6.0), 5.46 (s, 2H), 7.00-7.16 (m, 4H), 8.37 (s, 1H), 14.47 (br s, 1H)

Example 3

Synthesis of 1-butyl-5-ethyl-2-oxo-6-propyl-1,2-dihydro-pyridine-3-carboxylic acid (AA03)

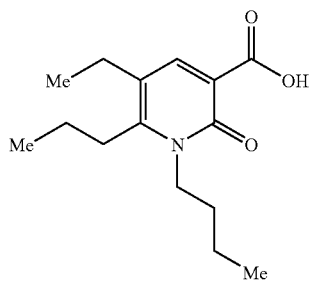

Under the nitrogen gas atmosphere, a solution of 4-heptanone (5.0 mM, 35.75 mmol), n-butylamine (4.25 mL, 4.29 mmol), and three drops of concentrated hydrochloric acid was stirred for 18.5 hours at room temperature. After that, water was added and the mixture was extracted with ethyl acetate. After the organic layer had been washed with water and then dried with anhydrous sodium sulfate, the solvent was removed by distillation under reduced pressure. The obtained oily matter was dissolved in 2-methoxyethyl ether (40 mL), and heated and stirred with dimethyl methoxymethylenemalonate (5.66 g, 32.5 mmol) at 120° C. for 3 hours. After the solvent had been removed by distillation under reduced pressure, the residue was refined with silica gel (100 g) column chromatography (ethyl acetate-hexane of 1:1 in mixing ratio and then that of 2:1), and a ark reddish-brown oily substance was obtained. The substance was dissolved in THF (20 mL) without purification, and a 1M lithium hydroxide aqueous solution (15.18 mL) and water (4.82 mL) were added, and then the mixture was stirred for 2 hours at room temperature. After that, the mixture was diluted with water and washed with diethyl ether. After 2M hydrochloric acid had been added to the water layer to acidify it, the water layer was extracted with ethyl acetate. The organic layer was washed with water and then dried with anhydrous sodium sulfate. The solvent was removed by distillation under reduced pressure and a pale yellow solid (AA03, 1.68 g, 18%) was obtained.

NMR: (CDCl3) 1.01 (t, 3H, J=7.5), 1.12 (t, 3H, J=7.5), 1.22 (t, 3H, J=7.5), 1.40-1.90 (m, 6H), 2.53 (q, 2H, J=7.5), 2.70 (m, 2H), 4.13 (t, 2H, J=7.5), 8.33 (s, 1H), 14.79 (br s, 1H)

Example 4

Synthesis of methyl 1-(4-cyanobenzyl)-2-oxo-1,2,5,6,7,8,9,10-octahydro-cycloocta[b]pyridine-3-carboxylate (AA04)

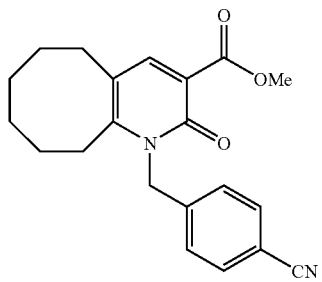

1) Synthesis of methyl 2-oxo-1,2,5,6,7,8,9,10-octahydro-cycloocta[b]pyridine-3-carboxylate Under the nitrogen gas atmosphere, a solution of cyclooctanone (15.87 mL, 120 mmol) and DMF dimethyl acetal was heated and stirred at 100° C. for 12 hours. After that, the solvent was removed by distillation under reduced pressure and a pale yellow oily matter (16.54 g) was obtained. This was dissolved in methanol (50 mL), and methyl cyanoacetate (8.87 mL, 100.37 mmol) was added and stirred at room temperature. The precipitated solid was separated by filtration and washed with diethyl ether, and the desired compound was obtained as a colorless solid (13.8 g, 49%, and mp: 220-224° C.).

NMR: (CDCl3) 1.58-1.88 (m, 8H), 2.59 (t, 2H, J=6.0), 2.82 (t, 2H, J=6.0), 3.90 (s, 3H), 8.04 (s, 1H), 12.39 (br, 1H)

2) Synthesis of methyl 1-(4-cyanobenzyl)-2-oxo-1,2,5,6,7,8,9,10-octahydro-cycloocta[b]pyridine-3-carboxylate (AA04)

Under the nitrogen gas atmosphere, methyl 2-oxo-1,2,5,6,7,8,9,10-octahydro-cycloocta[b]pyridine-3-carboxylate (300 mg, 1.27 mmol) was dissolved in DMF (5 mL), sodium hydride (61 mg, 1.53 mmol) was added, and the mixture was stirred at room temperature for 30 minutes. After that, 4-cyanobenzylamine (274.9 mg, 1.40 mmol) was added, and the mixture was further stirred at room temperature for 1 hour. Subsequently, water and 5% citric acid were added to the reaction mixture, and the obtained mixture was extracted with ethyl acetate. The organic layer was washed with water and then dried with anhydrous sodium sulfate. The solvent was removed by distillation under reduced pressure, and the residue was refined with silica gel (10 g) column chromatography (ethyl acetate-hexane of 1:1 in mixing ratio), and colorless solid of methyl 1-(4-cyanobenzyl)-2-oxo-1,2,5,6,7,8,9,10-octahydro-cycloocta[b]pyridine-3-carboxylate (AA04, 100 mg, 22%, mp: 72-75° C.) and colorless solid of methyl 2-(4-cyanophenoxy)-5,6,7,8,9,10-hexahydro-cycloocta[b]pyridine-3-carboxylate (123 mg, 28%, mp: 122-123° C.) were obtained.

AA04

NMR: CDCl3 1.38-1.93 (m, 8H), 2.61 (t, 2H, J=6.0), 2.75 (t, 2H, J=6.0), 3.90 (s, 3H), 5.44 (br, 2H), 7.23 (d, 2H, J=8.4), 7.60 (d, 2H, J=8.4), 8.01 (s, 1H))

methyl 2-(4-cyanophenoxy)-5,6,7,8,9,10-hexahydro-cycloocta[b]pyridine-3-carboxylate NMR: (CDCl3) 1.28-1.34 (m, 4H), 1.60-1.80 (m, 4H), 2.72 (t, 2H, J=6.3), 2.85 (t, 2H, J=6.3), 3.91 (s, 3H), 5.56 (s, 2H), 7.65 (s, 4H), 7.92 (s, 1H)

Example 5

Synthesis of methyl 1-(3-cyanopropyl)-2-oxo-1,2,5,6,7,8,9,10-octahydro-cycloocta[b]pyridine-3-carboxylate (AA05)

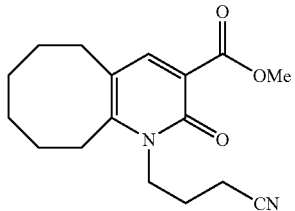

Under the nitrogen gas atmosphere, 2-oxo-1,2,5,6,7,8,9,10-octahydro-cycloocta[b]pyridine-3-methyl carboxylate (8 g, 34 mmol), which had been obtained in Example 4, was dissolved in DMF (160 mL), sodium hydride (1.63 g, 40.8 mmol) was added, and the mixture was stirred at 50° C. for 1 hour. After that, the mixture was returned to be at room temperature, and 4-bromobutyronitrile (3.71 mL, 37.4 mmol) was added and the mixture was stirred at 50° C. for 2 hours. After that, water and 5% citric acid were added, and the obtained mixture was extracted with ethyl acetate. After the organic layer had been washed with water and dried with anhydrous sodium sulfate, the solvent was removed by distillation under reduced pressure, and the residue was refined with silica gel (160 g) column chromatography (ethyl acetate-hexane of 3:7 in mixing ratio), and colorless oily matter (AA05, 3.71 g, 36%, mp: 82-84° C.) and a corresponding O-alkyl (39%) were obtained.

AA05

NMR: (CDCl3) 1.38-1.93 (m, 8H), 2.04-2.16 (m, 2H), 2.55 (t, 2H, J=5.7), 2.60 (t, 2H, J=6.0), 2.90 (t, 2H, J=6.0), 3.90 (s, 3H), 4.21 (t, 2H, J=6.0)), 8.01 (s, 1H)

Example 6

Synthesis of ethyl 1-benzyl-6-ethyl-5-methyl-2-oxo-1,2-dihydropyridine-3-carboxylate (AA06)

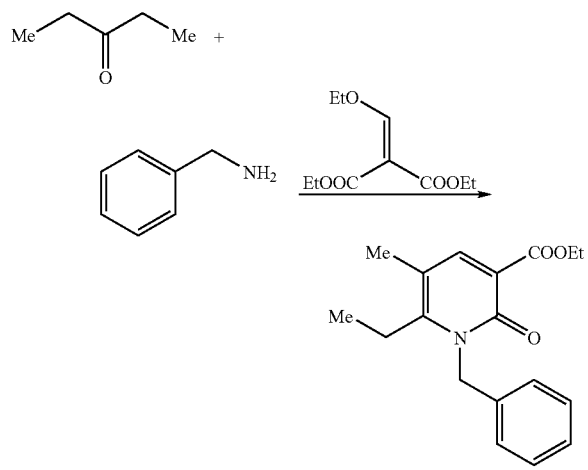

A toluene solution (50 mL) of 3-pentanone (5.00 g, 58.1 mmol) and benzylamine (6.23 g, 58.1 mmol) was heated and refluxed under azeotropic dehydration for 3 hours. After that, diethyl ethoxymethylenemalonate (12.56 g, 58.1 mmol) was added, and the mixture was further continued to be heated and refluxed for 5 hours. The solvent was removed by distillation under reduced pressure, and the residue was refined with silica gel (300 g) column chromatography (ethyl acetate-hexane of 1:5 in mixing ratio and then those of 1:3 and 2:1), and pale yellow oily matter (AA06, 1.92 g, 11.0%) was obtained.

NMR: (CDCl3) 1.12 (t, 3H, J=7.7), 1.38 (t, 3H, J=7.2), 2.15 (s, 3H), 2.64 (q, 2H, J=7.5), 4.36 (q, 2H, J=7.2), 5.43 (br, 2H), 7.11 (d, 2H, J=6.9), 7.20-7.32 (m, 3H), 8.04 (s, 1H)

Example 7

Synthesis of 1-benzyl-6-ethyl-5-methyl-2-oxo-1,2-dihydropyridine-3-carboxylic acid (AA07)

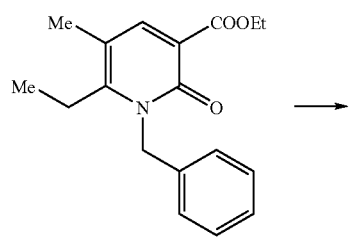

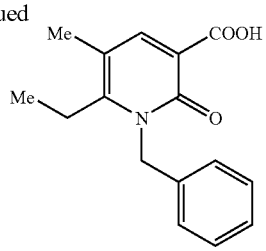

2M sodium hydroxide solution (7.9 mL, 15.8 mmol) was added to a methanol/THF (7.9 mL/7.9 mL) solution of ethyl 1-benzyl-6-ethyl-5-methyl-2-oxo-1,2-dihydropyridine-3-carboxylate (AA06, 1.92 g, 6.3 mmol), which had been obtained in Example 6, at room temperature and stirred at the same temperature for 2 hours. The reaction mixture was diluted with water (10 mL) and washed with ether (20 mL). 2M hydrochloric acid (8 mL, 16 mmol) was added to the water layer and the obtained mixture was extracted with ethyl acetate (20 mL) two times. The organic layer was washed with water (20 mL) two times and then dried with anhydrous sodium sulfate. The solvent was removed by distillation under reduced pressure, and yellow oily 1-benzyl-6-ethyl-5-methyl-2-oxo-1,2-dihydropyridine-3-carboxylic acid (AA07, 1.43 g) was obtained. The product was let alone for a night and was crystallized. The crystal was recrystallized from ethyl acetate and a white columnar crystal (AA07, 1.00 g, 58.5%) was obtained.

Mp: 113-114° C.

NMR: (CDCl3) 1.18 (t, 3H, J=7.7), 2.24 (s, 3H), 2.73 (q, 2H, J=7.5), 5.49 (br s, 2H), 7.09 (m, 2H), 7.29-7.38 (m, 3H), 8.38 (s, 1H), 14.53 (br s, 1H)

Example 8

Synthesis of ethyl 1-cyclohexylmethyl-2-oxo-1,5,7,8,tetrahydro-2H-thiopyrano[4,3-b]pyridine-3-carboxylate (AA08)

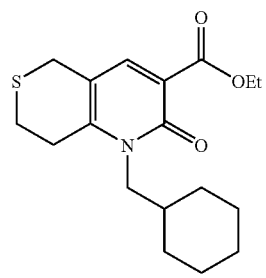

After a toluene (40 mL) solution of tetrahydrothiopyran-4-one (5.05 g, 43.5 mmol) and aminomethylcyclohexane (5.41 g, 47.8 mM) was heated and refluxed under azeotropic dehydration for 4 hours, diethyl ethoxymethylenemalonate (9.40 g, 43.5 mmol) was added, and the mixture was further continued to be heated and refluxed for 17 hours. The solvent was removed by distillation under reduced pressure, and the residue was refined with silica gel (160 g) column chromatography (ethyl acetate-toluene of 1:5 in mixing ratio and then that of 2:3), and red oily ethyl 1-cyclohexylmethyl-2-oxo-1,5,7,8,tetrahydro-2H-thiopyrano[4,3-b]pyridine-3-carboxylate (AA08, 8.17 g, 31.5%) was obtained.

NMR: (CDCl3) 1.00-1.25 (m, 5H), 1.38 (t, 3H, J=7.2), 1.60-1.96 (m, 6H), 2.90-3.03 (m, 4H), 3.62 (s, 2H), 3.93 (br, 2H), 4.36 (q, 2H, J=7.2), 7.89 (s, 1H)

Example 9

Synthesis of 1-cyclohexylmethyl-2-oxo-1,5,7,8,tetrahydro-2H-thiopyrano[4,3-b]pyridine-3-carboxylic acid (AA09)

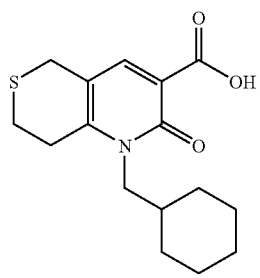

4M sodium hydroxide solution (15.2 mL, 60.8 mM) was added to a methanol (30 mL) solution of ethyl 1-cyclohexylmethyl-2-oxo-1,5,7,8,tetrahydro-2H-thiopyrano[4,3-b]pyridine-3-carboxylate (AA08, 8.16 g, 24.3 mmol), which had been obtained in Example 8, at room temperature, and the mixture was heated and refluxed for 30 minutes. The reaction mixture was diluted with water (100 mL) and washed with ether (100 mL). 5M hydrochloric acid (13 mL, 65 mmol) was added to the water layer, the precipitated crystal was separated by filtration and washed with water, and the brown crystal of 1-cyclohexylmethyl-2-oxo-1,5,7,8,tetrahydro-2H-thiopyrano[4,3-b]pyridine-3-carboxylic acid (6.78 g) was obtained. The crystal was recrystallized from ethanol-water to give light brown crystalline powder (AA09, 6.30 g, 84.3%).

Mp: 144-145° C.
NMR: (DMSO-d6) 0.99-1.25 (m, 5H), 1.46-1.87 (m, 6H), 2.97 (t, 2H, J=6.0), 3.15 (t, 2H, J=6.0). 3.78 (s, 2H), 4.07 (br, 2H), 8.24 (s, 1H), 14.84 (s, 1H)

Example 11

Synthesis of 1,5-dibutyl-6-methyl-2-oxo-1,2-dihydropyridine-3-carbonitrile (AA11)

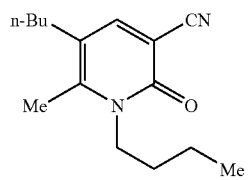

Under the nitrogen gas atmosphere, a mixture of 28% sodium methoxide methanol solution (39 mL, 202 mmol) and ether (260 mL) was cooled to 3° C. in an ice bath, and the mixture of 2-heptanone (22.84 g, 200 mmol) and ethyl formate (16.15 g, 218 mmol) was dropped in about 20 minutes. After that, being stirred at the same temperature for 30 minutes, then the mixture was returned to be at room temperature and was further stirred for 20 hours afterwards. The precipitated product was removed by filtration and washed enough with ether (about 620 g). The mother liquor and the washing layer were combined and concentrated to give a crude product of 29.34 g. This crude product was repeatedly washed with hexane and ether, and powdered yellow ocher sodium salt of 3-[1-hydroxymethylidyne]-heptan-2-one (11.33 g, 34.5%) was obtained.

This salt (2.13 g, 13 mmol) was suspended in DMF (10 mL), and n-butylcyanoacetamide (1.40 g, 10 mmol), acetic acid (0.75 mL, 13.1 mmol), piperidine (0.20 mL, 2.02 mmol) were added in order at room temperature, and the mixture was refluxed at 135° C. for 7 hours. After that, the reaction mixture was let alone at room temperature for 13 hours and then poured into ice water, and the obtained mixture was extracted with ethyl acetate two times. The organic layer was washed with diluted hydrochloric acid one time and with water two times, and then died with anhydrous magnesium sulfur. The solvent was removed by distillation under reduced pressure, and a red oily crude product of 2.03 g was obtained. This crude product was refined by the silica gel chromatography, and the desired 1,5-dibutyl-6-methyl-2-oxo-1,2-dihydropyridine-3-carbonitrile (AA11, 420 mg, 17.3%) and 1-butyl-2-oxo-6-pentyl-1,2-dihydropyridine-3-carbonitrile (230 mg, 9.4%) were obtained.

AA11
NMR:(CDCl3) 0.95 (t, 3H, J=6.9, 0.98 (t, 3H, J=6.9), 1.5-1.7 (m, 8H), 2.42 (s, 3H), ca 2.4 (m, 2H), 4.08 (2H, m), 7.57 (1H, s))

1-butyl-2-oxo-6-pentyl-1,2-dihydropyridine-3-carbonitrile

NMR: (CDCl3) 0.94 (t, 3H, J=6.8), 0.98 (t, 3H, J=7.2), 1.3-1.7 (m, 10H), 2.66 (m, 2H), 4.04 (m, 2H), 6.11 (ABd, 1H, J=7.5), 7.67 (ABd, 1H, J=7.5)) was obtained.

Example 12

Synthesis of 1,5-dibutyl-6-methyl-2-oxo-1,2-dihydropyridine-3-carboxylic acid (AA12)

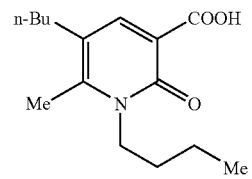

1,5-dibutyl-6-methyl-2-oxo-1,2-dihydropyridine-3-carbonitrile (AA11, 420 mg, 1.705 mmol), which had been obtained in Example 11, was dissolved in 80% aqueous ethanol solution and the solution was refluxed together with potassium hydroxide (770 mg, 13.7 mmol) for 22 hours. The solvent was removed by distillation under reduced pressure, water was added to the residue, and the obtained mixture was washed with ethyl acetate one time. The water layer was acidified by 2M hydrochloric acid (3 mL), and the precipitated solid was separated by filtration and was washed with water. Then the solid was air-dried, and an yellow ocher solid of 1,5-dibutyl-6-methyl-2-oxo-1,2-dihydropyridine-3-carboxylic acid (AA12, 352 mg, 78%, mp: 106-108° C.) was obtained.

NMR: (CDCl3) 0.95 (t, 3H, J=7.2), 1.01 (t, 3H, J=7.3), 1.3-1.8 (m, 8H), 2.49 (s, 3H), 2.51 (t, 2H, J=7.5), 4.17 (m, 2H), 8.29 (s, 1H)

Example 13

Synthesis of 1-butyl-6-methyl-2-oxo-5-pentyl-1,2-dihydropyridine-3-carboxylic acid (AA13)

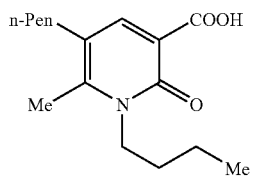

AA13 was synthesized from 2-octanone by the same method as that in Example 12.
Mp: 106-109° C.
NMR: (CDCl3) 0.93 (t, 3H, J=6.9), 1.01 (t, 3H, J=7.2), 1.3-1.8 (m, 10H), 2.49 (s, 3H), 2.50 (m, 2H), 4.17 (2, 2H), 8.29 (s, 1H), 14.77 (brs, 1H)

Example 14

Synthesis of 1-benzyl-5,6-dimethyl-2-oxo-1,2-dihydropyridine-3-carboxylic acid (AA14)

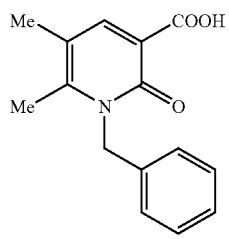

AA14 was synthesized from 2-butanone by the same method as that in Example 12.
Mp: 148-151° C.
NMR: 2.21 (s, 3H), 2.38 (s, 3H), 5.50 (s, 2H), 7.1-7.15 (m, 2H), 7.2-7.4 (m, 3H), 8.37 (s, 1H), 14.57 (brs, 1H)

Example 15

Synthesis of 1-butyl-6-ethyl-5-methyl-2-oxo-1,2-dihydropyridine-3-carboxylic acid (AA15)

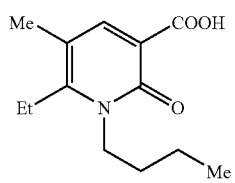

AA15 was synthesized from 2-pentanone by the same method as that in Example 12.
Mp: 121° C.
NMR: (CDCl3) 1.00 (t, 3H, J=7.2), 1.27 (t, 3H, J=7.6), 2.79 (m, 2H), 1.71 (m, 2H), 2.23 (s, 3H), 2.79 (q, 2H, J=7.6), 8.29 (s, 1H), 14.77 (brs, 1H)

Example 16

Synthesis of ethyl 1-cyclohextkmethyl-4-hydroxy-2-oxo-1,2,5,6,7,8,9,10-octahydro-cycloocta[b]pyridine-3-carboxylate (AA 16)

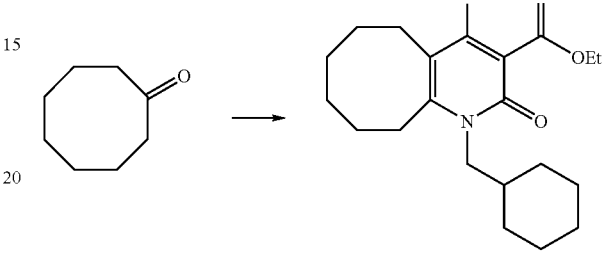

The toluene (30 mL) solution of cyclooctanone (4.23 g, 33.52 mmol) and aminomethylcyclohexane (4.36 mL, 33.52 mmol) was refluxed under azeotropic dehydration for 15 hours. After the reaction mixture had been let alone and cooled to room temperature, the mixture was concentrated under reduced pressure. The residue was distilled under reduced pressure and 5.90 g of colorless oily matter (80%, bp: 120-122° C.) was obtained.

This matter (1.15 g, 5.19 mmol) was stirred in triglyme (7 mL) together with triethylmethane tricarboxylic acid (0.88 mL, 4.15 mmol) at 135° C. for 36 hours. Diluted hydrochloric acid was added to the reaction mixture, and the mixture was extracted with toluene. The organic layer was washed with water and saturated saline, dried, and concentrated, and then the residue was refined with silica gel column chromatography (hexane-ethyl acetate (15-25%)), and obtained as a colorless solid (AA16, 667 mg, 45%).
NMR: (CDCl3) 0.89-1.98 (m, 22H), 2.60-2.96 (m, 4H), 4.20-4.35 (m, 2H), 4.45 (q, 2H, J=7.2), 13.71 (s, 1H).

Example 17

Synthesis of methyl 1-butyl-4-hydroxy-2-oxo-1,2,5,6,7,8,9,10-octahydro-cycloocta[b]pyridine-3-carboxylate (AA17)

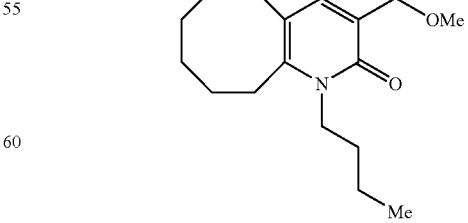

A concentrated hydrochloric acid was added to a mixture of cyclooctanone (3.84 g, 30.43 mmol) and butylamine (3.01 mL, 30.43 mmol) by two drops, and the mixture was stirred at room temperature for 15 hours. Diluted sodium carbonate aqueous solution and ethyl acetate were added in the reaction mixture to separate the mixture, and the organic layer was washed with water and saturated saline. After the organic layer had been dried, the solvent was removed by distillation and 4.72 g of colorless oily matter was obtained (86%). This imine (4.67 g, 25.76 mmol) was reacted as mentioned above together with trimethylmethane tricarboxylic acid (3.42 g, 18 mM) in trigrim (40 mL), and viscous yellow oily matter (AA17, 2.62 g, 47%) was obtained.

NMR: (CDCl3) 0.96 (t, 2H, J=7.2), 1.36-1.81 (m, 12H), 2.67 (m, 2H), 2.86 (t, 2H, J=6.0), 3.94-4.02 (m, 2H), 13.55 (s, 1H).

Example 18

Synthesis of ethyl 1-(3-hydroxypropyl)-2-oxo-1,2,5,6,7,8,9,10-octahydro-cycloocta[b]pyridine-3-carboxylate (AA18)

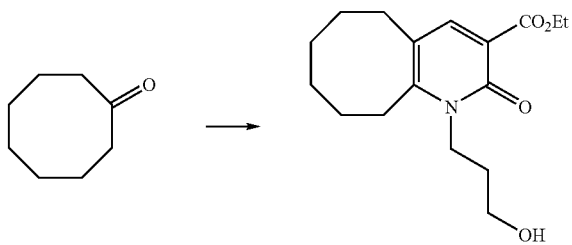

Cyclooctanone (10.00 g, 79.18 mmol) was dissolved in toluene (140 mL) and was refluxed together with 2-amino-1-propanol (6.10 mL, 79.75 mmol) under azeotropic dehydration for 14.5 hours. After that, diethyl ethoxymethylenemalonate (16.0 mL, 79.18 mmol) was added, and the solution was refluxed further for 5.5 hors. The solution was concentrated under reduced pressure until the amount of the solvent became about half, and the residue was eluted and refined with silica gel (192 g) column chromatography (ethyl acetate-hexane (1:1), ethyl acetate, ethyl acetate-methanol (4:1) in order), thus brown oily matter (AA18, 13.63 g, 56%) was obtained.

NMR: (CDCl3) 1.35-1.55 (m, 4H), 1.38 (t, 3H, J=7.2), 1.63-1.83 (m, 4H), 1.86-1.97 (m, 2H), 2.58-2.62 (m, 2H), 2.88-2.93 (m, 2H), 3.52-3.55 (m, 2H), 4.32 (brs, 2H), 4.37 (q, 2H, J=7.2), 7.95 (s, 1H)

Example 19

Synthesis of ethyl 1-(3-methanesulfonylpropyl)-2-oxo-1,2,5,6,7,8,9,10-octahydro-cycloocta[b]pyridine-3-carboxylate (AA19)

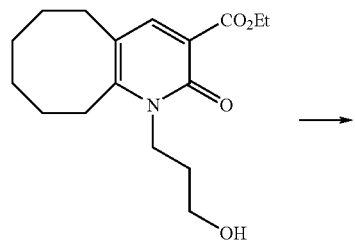

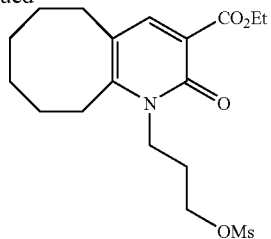

Ethyl 1-(3-hydroxypropyl)-2-oxo-1,2,5,6,7,8,9,10-octahydro-cycloocta[b]pyridine-3-carboxylate (AA18, 13.63 g, 44.34 mmol), which had been obtained in Example 15, was dissolved in anhydrous THF (105 mL), and triethylamine (9.28 mL, 66.53 mmol) and methanesulfonyl chloride (4.12 mL, 53.23 mmol) were added while stirring and cooling the solution with ice, and further the mixture was stirred for 45 minutes. After the reaction mixture had been acidified by being poured into diluted aqueous hydrochloric acid solution, the location liquid was extracted with ethyl acetate. The organic layer was washed with water, a saturated sodium bicarbonate aqueous solution, and water, and then dried with anhydrous magnesium sulfate. The solvent was removed by distillation under reduced pressure, and the residue was eluted and refined with silica gel (176 g) column chromatography (ethyl acetate, and then ethyl acetate-methanol (9:1) in order), and light orange color oily matter (AA19, 7.85 g, 46%) was obtained.

NMR: (CDCl3) 1.35-1.58 (m, 7H), 1.62-1.84 (m, 4H), 2.14-2.26 (m, 2H), 2.58-2.62 (m, 2H), 2.86-2.90 (m, 2H), 3.06 (s, 3H), 4.20-4.29 (m, 2H), 4.32-4.44 (m, 4H), 7.96 (s, 1H)

Example 20

Synthesis of ethyl 1-(3-azidepropyl)-2-oxo-1,2,5,6,7,8,9,10-octahydro-cycloocta[b]pyridine-3-carboxylate (AA20)

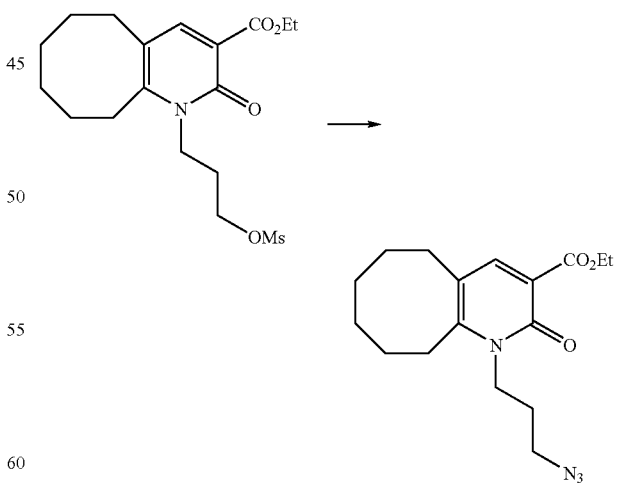

Ethyl 1-(3-methanesulfonylpropyl)-2-oxo-1,2,5,6,7,8,9,10-octahydro-cycloocta[b]pyridine-3-carboxylate (AA19, 7.85 g, 20.36 mmol), which had been obtained in Example 19, was dissolved in anhydrous DMF (60 mL), and sodium azide (2.13 g, 32.76 mmol) was added to the solution while cooling the solution with ice and the mixture was further stirred for 40 minutes. After that, the mixture was returned to be at room temperature and further stirred for 16 hours. The reaction mixture was poured into water and extracted with ethyl acetate. The organic layer was washed with water, and dried with anhydrous magnesium sulfate. Then, the solvent was removed by distillation and yellow oily matter (AA20, 6.74 g, 99.5%) was obtained.

NMR: (CDCl$_3$) 1.35-1.55 (m, 4H), 1.39 (t, 3H, J=7.2), 1.62-1.83 (m, 4H), 1.93-2.04 (m, 2H), 2.57-2.61 (m, 2H), 2.87-2.91 (m, 2H), 3.46 (t, 2H, J=6.3), 4.13-4.21 (m, 2H), 4.37 (q, 2H, J=7.2), 7.96 (s, 1H);

IR (chloroform): 2100, 1728, 1693, 1650, 1591, 1543, 1482, 1453, 1439, 1414, 1380, 1363, 1351, 1319

Example 21

Synthesis of ethyl 1-(3-methanesulfonylaminopropyl)-2-oxo-1,2,5,6,7,8,9,10-octahydro-cycloocta[b]pyridine-3-carboxylate (AA21)

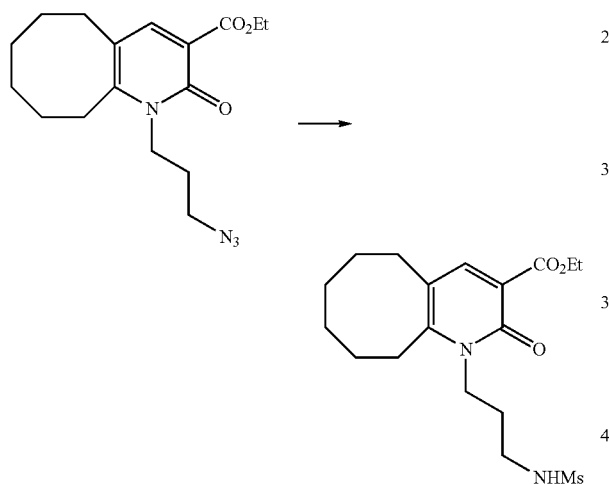

Ethyl 1-(3-azidepropyl)-2-oxo-1,2,5,6,7,8,9,10-octahydro-cycloocta[b]pyridine-3-carboxylate (AA20, 3.25 g, 9.78 mmol), which had been obtained in Example 20, was dissolved in anhydrous THF (33 mL), and water (16 mL) and then triphenylphosphine (3.08 g, 11.73 mmol) were added and the mixture was refluxed for 1 hour and 30 minutes. The reaction mixture was acidified by adding diluted aqueous hydrochloric acid solution and then washed with ethyl ether. The water layer was removed by distillation, and a pale yellow solid was obtained. The solid was suspended in anhydrous THF (50 mL), and triethylamine (4.10 mL, 29.40 mmol) and methanesulfonyl chloride (1.67 mL, 21.58 mmol) were added while stirring and cooling the solution with ice, and the mixture was stirred for 50 minutes. After that, the mixture was returned to be at room temperature and further stirred for 2 hours. After the reaction mixture had been poured into diluted aqueous hydrochloric acid solution to acidify the mixture, the mixture was extracted with ethyl acetate. The organic layer was washed with water and saturated sodium bicarbonate water, and then dried with anhydrous magnesium sulfate. The solvent was removed by distillation under reduced pressure, and the residue was eluted and refined with silica gel (42 g) column chromatography (ethyl acetate, and then ethyl acetate-methanol (17:3) in order), and a pale yellow residue (1.90 g) was obtained. This residue was recrystallized with the use of ethyl acetate-hexane, and a colorless prism-like crystal (AA21, 1.69 g, 45%) was obtained.

Mp: 138-139° C.

NMR: (CDCl$_3$) 1.35-1.54 (m, 4H), 1.38 (s, 3H), 1.62-1.82 (m, 4H), 1.92-2.03 (m, 2H), 2.57-2.61 (m, 2H), 2.84-2.91 (m, 2H), 2.96 (s, 3H), 3.08-3.16 (m, 2H), 4.21-4.30 (m, 2H), 4.35 (q, 2H, J=7.2), 5.84 (brs, 1H), 7.93 (s, 1H);

IR (chloroform): 3235, 1727, 1695, 1646, 1589, 1543, 1481, 1453, 1440, 1411, 1363, 1328;

Elemental analysis (C$_{18}$H$_{28}$N$_2$O$_5$S)

Calculated (%): C, 56.23; H, 7.34; N, 7.29; S, 8.34.

Analytical (%): C, 56.11; H, 7.28; N, 7.28; S, 8.07.

Example 22

Synthesis of 1-(3-methanesulfonylaminopropyl)-2-oxo-1,2,5,6,7,8,9,10-octahydro-cycloocta[b]pyridine-3-carboxylic acid (AA22)

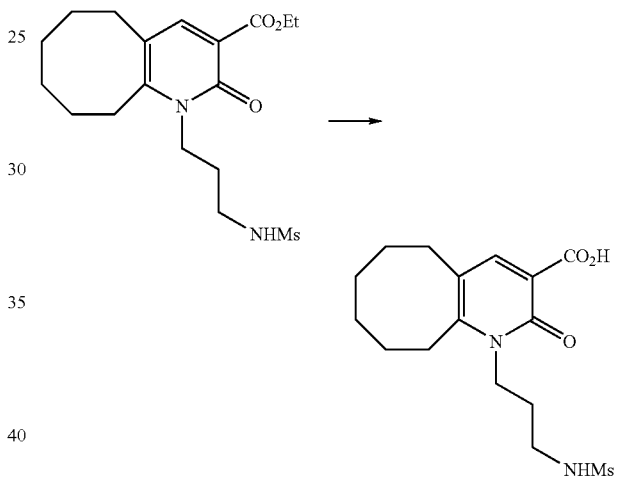

Ethyl 1-(3-methanesulfonylaminopropyl)-2-oxo-1,2,5,6,7,8,9,10-octahydro-cycloocta[b]pyridine-3-carboxylate. (AA21, 1.66 g, 4.33 mmol), which had been obtained in Example 21, was dissolved in methanol (17 mL), and 4M sodium hydroxide aqueous solution (4.32 mL, 17.40 mmol) was added and the mixture was warmed at 50° C. for 5 hours. The reaction mixture was poured into water. After the water layer had been washed with ethyl ether, the layer was acidified with 2M aqueous hydrochloric acid solution and extracted with ethyl acetate. The organic layer was washed with water and then dried with anhydrous magnesium sulfate, and a colorless needle crystal (AA22, 1.52 g, 98%) was obtained.

Mp: 197-198° C.

NMR: (DMSO-d6) 1.28-1.49 (m, 4H), 1.55-1.67 (m, 2H), 1.69-1.92 (m, 4H), 2.68-2.76 (m, 2H), 2.92 (s, 3H), 2.97-3.14 (m, 4H), 4.14-4.24 (m, 2H), 7.16 (t, 1H, J=6.0), 8.21 (s, 1H), 14.90 (s, 1H);

IR (nujol): 3203, 2675, 1701, 1622, 1551, 1463, 1442, 1415, 1374, 1316;

Elemental analysis (C$_{16}$H$_{24}$N$_2$O$_5$S)

Calculated (%): C, 53.91H, 6.79; N, 7.86; S, 9.00.

Analytical (%): C, 53.87; H, 6.67; N, 7.89; S, 8.90.

Example 23

Synthesis of ethyl 1-(3-acetylaminopropyl)-2-oxo-1,2,5,6,7,8,9,10-octahydro-cycloocta[b]pyridine-3-carboxylate (AA23)

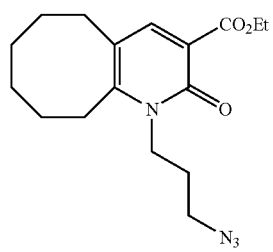

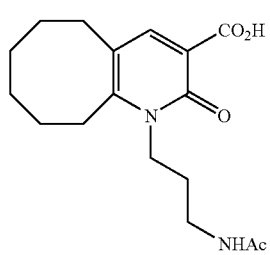

Ethyl 1-(3-azidepropyl)-2-oxo-1,2,5,6,7,8,9,10-octahydro-cycloocta[b]pyridine-3-carboxylate (AA20, 1.73 g, 5.21 mmol), which had been obtained in Example 20, was dissolved in THF (17 mL), and water (8.5 mL) and then triphenylphosphine (1.64 g, 6.25 mmol) were added and the mixture was refluxed for 90 minutes. The reaction mixture was poured into water and washed with ethyl ether. The water layer was concentrated under reduced pressure and a yellow oily amine body (1.58 g) was obtained. This amine body was dissolved in anhydrous THF (15 mL), and pyridine (0.83 mL, 10.26 mmol) and methyl chlorocarbonate were added while stirring and cooling the solution with ice, and the mixture was stirred for 50 minutes. After that, the mixture was further stirred at room temperature for two hours and 20 minutes. After the reaction mixture had been poured into diluted aqueous hydrochloric acid solution to acidify the mixture, the mixture was extracted with ethyl acetate. The organic layer was washed with water and saturated sodium bicarbonate water, and then dried with anhydrous magnesium sulfate. The solvent was removed by distillation under reduced pressure, and the residue was eluted and refined with silica gel (66 g) column chromatography (ethyl acetate, and then ethyl acetate-methanol (4:1) in order), and a pale yellow solid (AA23, 643 mg) was obtained. This solid was recrystallized with ethyl acetate-hexane, and a pale yellow needle crystal (AA23, 568 mg, 30%) was obtained.

Mp: 103-104° C.

NMR: (CDCl$_3$) 1.36-1.54 (m, 4H), 1.38 (t, 3H, J=7.2), 1.62-1.82 (m, 4H), 1.83-1.94 (m, 2H), 2.56-2.60 (m, 2H), 2.84-2.88 (m, 2H), 3.16-3.27 (m, 2H), 3.66 (s, 3H), 4.12-4.23 (m, 2H), 4.36 (q, 2H, J=7.2), 5.64 (brs, 1H), 7.93 (s, 1H)

Example 24

Synthesis of 1-(3-acetylaminopropyl)-2-oxo-1,2,5,6,7,8,9,10-octahydro-cycloocta[b]pyridine-3-carboxylic acid (AA24)

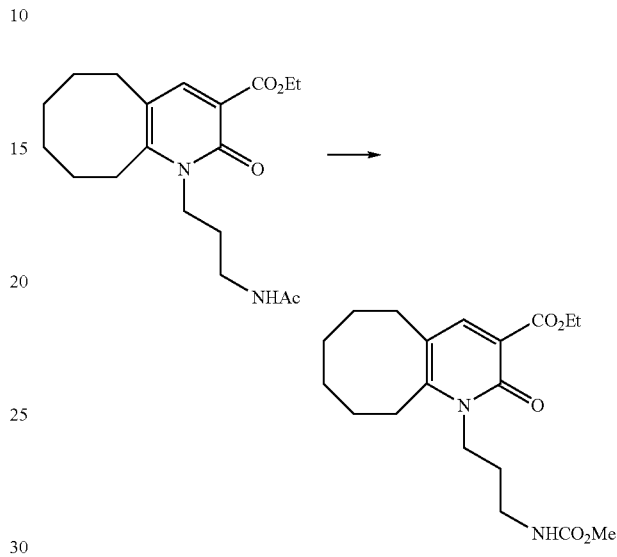

Ethyl 1-(3-acetylaminopropyl)-2-oxo-1,2,5,6,7,8,9,10-octahydro-cycloocta[b]pyridine-3-carboxylate (AA23, 560 mg, 1.54 mmol), which had been obtained in Example 23, was dissolved in methanol (6 mL), and 4M aqueous sodium hydroxide solution (1.15 mL, 4.63 mmol) was added and the mixture was stirred at room temperature for one hour and 50 minutes. The reaction mixture was poured into water and washed with ethyl ether. The water layer was acidified with 2M aqueous hydrochloric acid solution and extracted with ethyl acetate. After the organic layer had been washed with water and dried with anhydrous magnesium sulfate, the solvent was removed by distillation and colorless oily matter (AA24, 544 mg) was obtained. This oily matter was recrystallized with the use of ethyl acetate-hexane, and a colorless needle crystal (AA24, 502 mg, 97%) was obtained.

Mp: 148-149° C.

NMR: (CDCl$_3$) 1.35-1.56 (m, 4H), 1.60-1.86 (m, 4H), 1.88-2.01 (m, 2H), 2.65-2.69 (m, 2H), 2.93-2.97 (m, 2H), 3.24 (q, 2H, J=6.3), 3.69 (s, 3H), 4.20-4.30 (m, 2H), 5.44 (brs, 1H), 8.30 (s, 1H), 14.54 (s, 1H);

IR (chloroform): 3451, 2693, 1721, 1626, 1567, 1544, 1513, 1464, 1412, 1381, 1364, 1333, 1316;

Elemental analysis ($C_{17}H_{24}N_2O_5$)

Calculated (%): C, 60.70; H, 7.19; N, 8.33.

Analytical (%): C, 60.52; H, 7.11; N, 8.32.

The following 3-pyridone carboxylic acids (AA25 to AA41) were synthesized by the use of a similar method to the above-mentioned one. The structural formulas and the data of NMR were described in Table 1 to 3.

TABLE 1

| Comp. No. | Structure | ¹H-NMR(DMSO-d$_6$/TMS) δ |
| --- | --- | --- |
| AA25 | 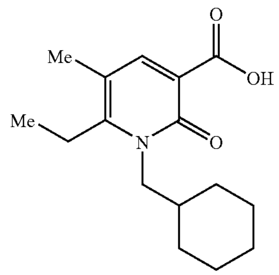 | 1.00-1.30 (m, 5H), 1.22 (t, 3H, J=7.5), 1.55-1.90 (m, 6H), 2.24 (s, 3H), 2.82 (q, 2H, J=7.2), 3.90-4.20 (m, 2H), 8.29 (s, 1H) |
| AA26 | 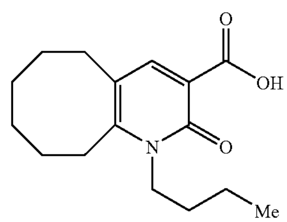 | 1.00 (t, 3H, J=7.5), 1.35-1.55 (m, 6H), 1.60-1.86 (m, 6H), 2.63-2.71 (m, 2H), 2.90-2.99 (m, 2H), 3.99-4.21 (m, 2H), 8.27 (s, 1H), 14.78 (br s, 1H) |
| AA27 | 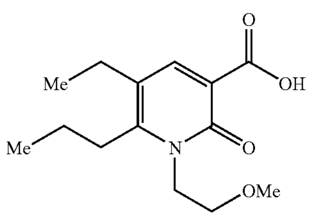 | 1.10 (t, 3H, J=7.5), 1.20-1.28 (m, 4H), 1.52-1.64 (m, 2H), 2.51-2.59 (q, 2H, J=7.5), 2.84-2.90 (m, 2H), 3.30 (s, 3H), 3.72 (t, 2H, J=5.1), 4.36 (t, 2H, J=5.1), 8.36 (s, 1H) |
| AA28 | 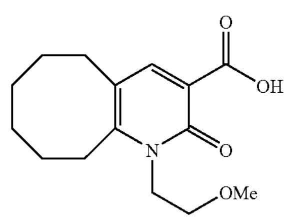 | 1.32-1.54 (m, 4H), 1.66 (m, 4H), 2.67 (t, 2H, J=6.0), 3.11 (t, 2H, J=6.0), 3.30 (s, 3H), 3.72 (t, 2H, J=5.4), 4.40 (t, 2H, J=5.4), 8.30 (s, 1H), 14.64 (br, 1H) |
| AA29 | 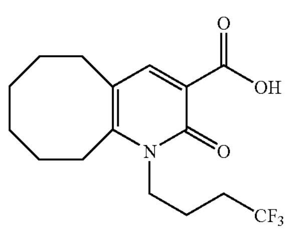 | 1.35-1.90 (m, 8H), 1.90-2.10 (m, 2H), 2.15-2.40 (m, 2H), 2.60-2.75 (m, 2H), 2.85-3.00 (m, 2H), 4.15-4.30 (m, 2H), 8.30 (s, 1H) |
| AA30 | 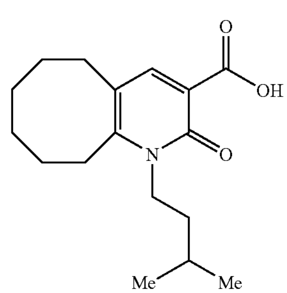 | 1.02 (d, 6H, J=6.6), 1.40-1.85 (m, 12H), 2.67 (m, 2H), 2.93 (m, 2H), 4.16 (m, 2H), 8.27 (s, 1H) |

TABLE 1-continued

| Comp. No. | Structure | ¹H-NMR(DMSO-d₆/TMS) δ |
|---|---|---|
| AA31 | (cycloocta-fused pyridinone with 3-CO₂Et and N-isopentyl) | 0.98 (d, 6H, J=6.6), 1.39 (t, 3H, J=6.3), 1.43-1.80 (m, 11H), 2.58 (m, 2H), 2.85 (m, 2H), 4.09 (m, 2H), 4.37 (d, 2H, J=6.6), 7.93 (s, 1H) |

TABLE 2

| Comp. No. | Structure | ¹H-NMR(DMSO-d₆/TMS) δ |
|---|---|---|
| AA32 | 5-Me, 6-Et, 3-CO₂H, N-isopentyl pyridinone | 1.02 (d, 6H, J=6.6), 1.28 (t, 3H, J=7.5), 1.56-1.66 (m, 2H), 1.78 (m, 1H), 2.23 (s, 3H), 2.79 (q, 2H, J=7.5), 4.10-4.21 (m, 2H), 8.28(s, 1H) |
| AA33 | 5-Me, 6-Et, 3-CO₂Et, N-isopentyl pyridinone | 0.99 (d, 6H, J=6.6), 1.22 (t, 3H, J=7.5), 1.38 (t, 3H, J=7.5), 1.54-1.79 (m, 3H), 2.14 (s, 3H), 2.70 (q, 2H, J=7.5), 4.09 (m, 2H), 4.36 (q, 2H, J=7.5), 4.36 (d, 2H, J=7.5), 7.95 (s, 1H) |
| AA34 | 5-Me, 6-Et, 3-CO₂H, N-(3,4-difluorobenzyl) pyridinone | CDCl3 1.21 (t, 3H, J=7.7), 2.25 (s, 3H), 2.73(q, 2H, J=7.4), 5.42 (br s, 2H), 6.86 (m, 1H), 6.96 (ddd, 1H, J=10.8, 7.4 and 2.3), 7.15 (dt, 1H, J=9.9 and 8.3), 8.39 (s, 1H), 14.31 (br s, 1H) |
| AA35 | cycloocta-fused 3-CO₂H, N-(3,4-difluorobenzyl) pyridinone | 1.37-1.55 (m, 4H), 1.65-1.80 (m, 4H), 2.64-2.72 (m, 2H), 2.82-2.91 (m, 2H), 5.42 (s, 2H), 6.85 (m, 1H), 6.95 (m, 1H), 7.15 (m, 1H), 8.38(s, 1H), 14.34 (br s, 1H) |

TABLE 2-continued

| Comp. No. | Structure | ¹H-NMR(DMSO-d₆/TMS) δ |
|---|---|---|
| AA36 | 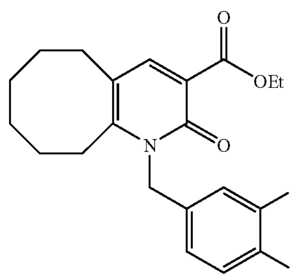 | 1.39 (t, 3H, J=7.2), 1.35-1.54 (m, 4H), 1.63-1.75 (m, 4H), 2.55-2.65 (m, 2H), 2.73-2.82(m, 2H), 4.37 (q, 2H, J=7.2), 5.35 (s, 2H), 6.86 (m, 1H), 6.95 (m, 1H), 7.09 (m, 1H), 8.03 (s, 1H) |
| AA37 | 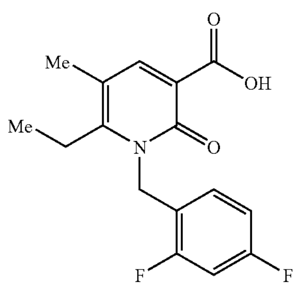 | CDCl3 1.21 (t, 3H, J=7.7), 2.25 (s, 3H), 2.72 (q, 2H, J=7.6), 5.46 (br s, 2H), 6.81-6.96 (m, 3H), 8.39 (s, 1H), 14.35 (br s, 1H) |
| AA38 | 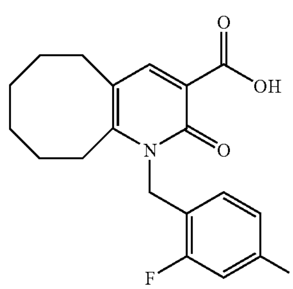 | 1.36-1.55 (m, 4H), 1.66-1.81 (m, 4H), 2.64-2.72 (m, 2H), 2.82-2.89 (m, 2H), 5.46 (s, 2H), 6.79-6.96 (m, 3H), 8.38 (s, 1H), 14.38 (br s, 1H) |

TABLE 3

| Comp. No. | Structure | ¹H-NMR(DMSO-d₆/TMS) δ |
|---|---|---|
| AA39 | 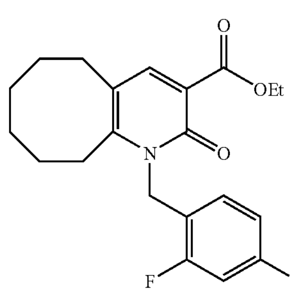 | 1.39 (t, 3H, J=7.2), 1.35-1.53 (m, 4H), 1.63-1.75 (m, 4H), 2.56-2.63 (m, 2H), 2.71-2.80 (m, 2H), 4.38 (q, 2H, J=7.2), 5.40 (s, 2H), 6.72-6.87 (m, 2H), 6.95 (m, 1H), 8.02 (s, 1H) |

TABLE 3-continued

| Comp. No. | Structure | $^1$H-NMR(DMSO-$d_6$/TMS) δ |
|---|---|---|
| AA40 | (4-methyl-5-ethyl-... 1-(4-fluorobenzyl) pyridinone carboxylic acid structure) | DMSO-d6 1.05 (t, 3H, J=7.5), 2.24 (s, 3H), 2.75 (q, 2H, J=7.5), 5.48 (s, 2H), 7.15-7.25 (m, 4H), 8.32 (s, 1H), (s, 1H), 14.68 (s, 1H) |
| AA41 | (4-methyl-5-ethyl-... 1-(4-chlorobenzyl) pyridinone carboxylic acid structure) | CDCl3 1.20 (t, 3H, J=7.7), 2.24 (s, 3H), 2.72 (q, 2H, J=7.7), 5.44 (br s, 2H), 7.05 (d, 2H, J=8.7), 7.33 (d, 2H, J=8.4), 8.38 (s, 1H), 14.39 (br s, 1H) |

As amine derivatives, those obtained from the market or synthesized by the following synthesis methods were used.

Example 25

Synthesis of N-α-(2-benzo[b]thienyl)glycine methyl ester hydrochloride (BB01)

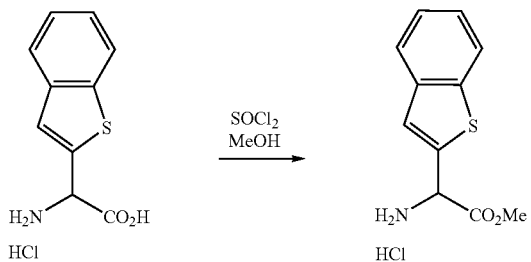

According to the method described in Tetrahedron, Vol. 53, No. 48, pp. 16463-16470, 1997, N-α-(2-benzo[b]thienyl)glycine hydrochloride (2.694 g, 9.17 mmol) was suspended in methanol (27 mL), and thionyl chloride (2.02 mL, 27.69 mmol) was dropped in 5 minutes while stirring and cooling the suspension with ice. After that, the mixture was stirred at room temperature for 63 hours. The solvent was removed by distillation under reduced pressure, and the residue was washed with acetone and a colorless crystal (BB01, 2.546 g, 89%) was obtained.

Mp: 196-198° C.

NMR: (DMSO-d6) 3.78 (s, 3H), 5.79 (s, 1H), 7.38-7.46 (m, 2H), 7.68 (s, 1H), 7.92 (m, 1H), 8.01 (m, 1H), 9.36 (brs, 3H)

Example 26

Synthesis of N-α-(4-biphenyl)glycine methyl ester hydrochloride (BB02)

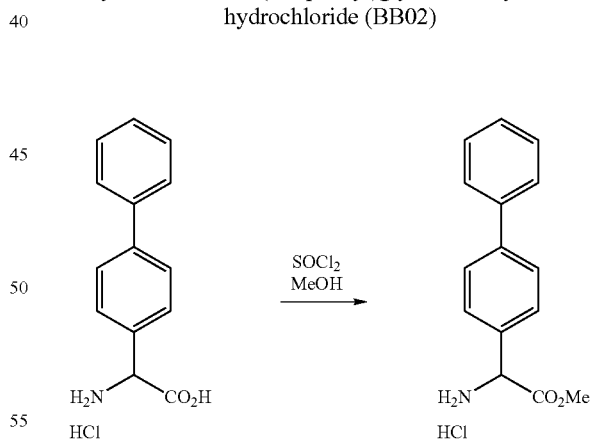

According to the method described in Tetrahedron, Vol, 53, No. 48, pp. 16463-16470, 1997, N-α-(4-biphenyl)glycine hydrochloride (2.148 g, 9.17 mmol) was suspended in methanol (24 mL), and thionyl chloride (1.67 mL, 22.90 mmol) was dropped in 5 minutes while cooling the suspension with ice. After that, the mixture was stirred at room temperature for 20 hours, and a colorless crystal (BB02, 1.760 g, 69%) was obtained.

Mp: 224-225° C.

NMR: (DMSO-d6) 3.74 (s, 3H), 5.35 (s, 1H), 7.40 (m, 1H), 7.46-7.61 (m, 2H), 7.58-7.61 (m, 2H), 7.68-7.71 (m, 2H), 7.75-7.78 (m, 2H), 9.08 (brs, 3H)

Example 27

Synthesis of ethyl 4-amino-3-trifluoromethyl-phenoxy-acetate (BB03)

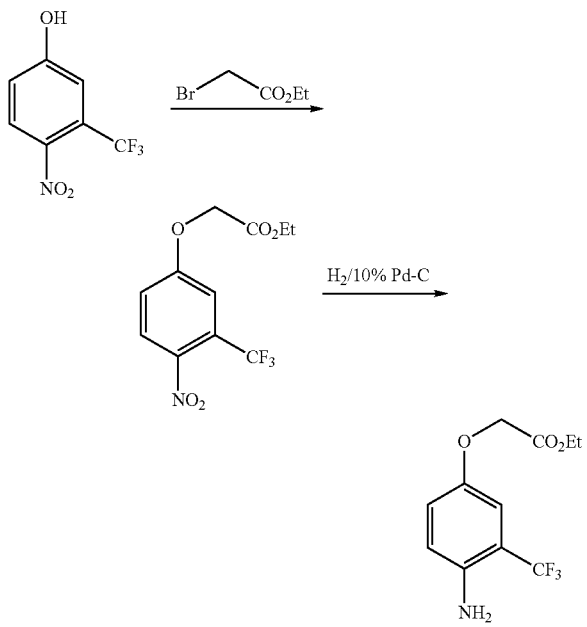

1) Synthesis of ethyl 4-nitro-3-trifluoromethyl-phenoxy-acetate

Ethyl bromoacetate (1.2 g, 10.9 mmol) was added in the suspension of 4-nitro-3-trifluoromethyl phenol (2.0 g, 9.66 mmol) and potassium carbonate (2.0 g, 14.5 mmol) in acetone, and the mixture was attired at room temperature for 6 hours. After the reaction mixture had been poured in ice water and acidified with 2N hydrochloric acid, the mixture was extracted with ethyl acetate. The organic layer was washed with 5% sodium hydrogencarbonate aqueous solution and then with water, and dried with anhydrous sodium sulfate. The solvent was removed by distillation under reduced pressure, and 4-nitro-3-trifluoromethyl-phenoxy-ethyl acetate (3.24 g (theoretical amount: 2.83 g),-100%) was obtained as a yellow solid and was used in the next reaction without purification.

NMR: (CDCl$_3$) 1.32 (t, 3H, J=7.2), 4.30 (q, 2H, J=7.2), 4.75 (s, 2H), 7.10 (dd, 1H, J=2.7, 9.0), 7.33 (d, 1H, J=2.4), 8.01 (d, 1H, 9.0)

2) Synthesis of ethyl 4-amino-3-trifluoromethyl-phenoxy-acetate

In the ethyl acetate (30 mL) solution of 4-nitro-3-trifluoromethyl-phenoxyethyl acetate (3.24 g (theoretical amount: 2.83 g, 9.66 mmol) which had been obtained in 1), 10% palladium carbon (0.3 g) was added and hydrogen was added. After the catalyst had been separated by filtration, the solvent was removed by distillation under reduced pressure and crude 4-amino-3-trifluoromethyl-phenoxyethyl acetate (BB03, 3.08 g (theoretical amount: 2.54 g)–100%) was obtained as oily matter.

NMR: (CDCl$_3$) 1.30 (t, 3H, J=7.2), 4.27 (q, 2H, J=7.2), 4.56 (s, 2H), 6.76 (d, 1H, J=8.7), 6.96 (dd, 1H, J=3.0, 9.0), 7.01 (d, 1H, J=2.7)

Experimental Example 28

Synthesis of methyl 4-amino-tetrahydro-pyran-4-carboxylate monohydrochloride (BB04)

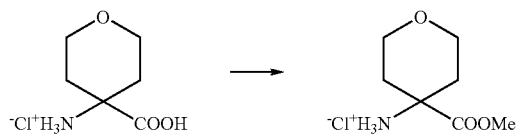

Thionyl chloride (4.02 mL, 55.1 mmol) was added in the dehydrated methanol (100 mL) solution of 4-amino-4-carboxytetrahydro-pyran monohydrochloride (5.00 g, 27.5 mmol) in an ice bath, and the mixture was heated and refluxed for 2.5 hours. The solvent was removed by distillation under reduced pressure, and the obtained crude product was washed with ethyl acetate and then dried under reduced pressure to give a colorless solid (BB04, 5.06 g).

NMR: (DMSO) 1.84-1.93 (m, 2H), 2.02-2.09 (m, 2H), 3.57-3.69 (m, 2H), 3.79 (s, 3H), 3.80-3.88 (m, 2H), 8.89 (brs, 3H)

Experimental Example 29

Synthesis of ethyl 3-(4-amino-tetrahydro-pyran-4-yl)-propionate monohydrochloride (BB05)

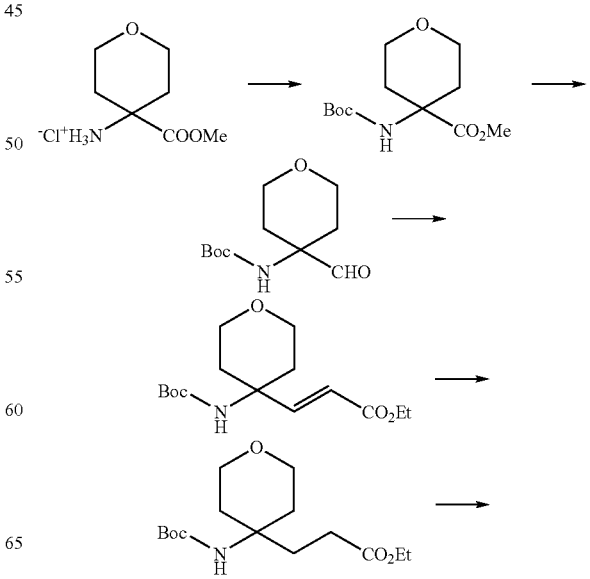

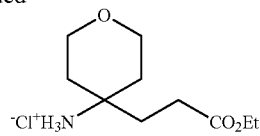

1) Synthesis of ethyl 4-t-butoxycarbonylamino-tetrahydro-pyran-4-carboxylate Triethylamine (5.41 mL, 38.8 mM) and di-t-butyl dicarbonate (7.13 mL, 31.0 mmol) were dropped in order in the dehydrated 1,4-dioxane (50 mL) solution of methyl 4-amino-tetrahydro-pyran-4-carboxylate monohydrochloride (5.06 g, 25.8 mmol) in an ice bath. After the reaction mixture had been stirred at room temperature for 6 hours, di-t-butyl dicarbonate (2.97 mL, 12.9 mmol) was added in the reaction mixture in the ice bath and the mixture was further stirred at room temperature for a night. After the reaction mixture had been poured into 2N hydrochloric acid aqueous solution (12 mL), the mixture was extracted with ethyl acetate. The organic layer was washed with water, saturated aqueous sodium hydrogencarbonate solution, and saturated saline in order, and then dried with anhydrous magnesium sulfate. The solvent was removed by distillation under reduced pressure, and the residue was refined with silica gel column chromatography (the ethyl acetate-hexane solution of 3:7 to 1:0 in mixing ratio) to give colorless oily matter (5.24 g).

NMR: (CDCl3) 1.44 (s, 9H), 1.86-1.90 (m, 2H), 2.14-2.24 (m, 2H), 3.64-3.72 (m, 2H), 3.75 (s, 3H), 3.78-3.84 (m, 2H), 4.78 (brs, 1H)

2) Synthesis of t-butyl (4-formyl-tetrahydro-pyran-4-yl)-carbamate

The toluene solution of diisobutylaluminum hydride (72.3 mL, 73.0 mmol) was dropped in the dehydrated toluene (50 mL) solution of methyl 4-t-butoxycarbonylamino-tetrahydro-pyran-4-carboxylate (4.74 g, 18.3 mmol) which had been obtained in 1) at −78° C. for 1 hour. After the reaction mixture had been stirred at the same temperature for 20 minutes, saturated aqueous ammonium chloride solution (20 mL) was dropped in 10 minutes and the mixture was stirred at room temperature for 15 minutes. Then, methanol (3 mL) was added and the mixture was further stirred at room temperature for 20 minutes. The precipitated insoluble matter was removed by filtration with Celite, and the filtrate was extracted with ethyl acetate. The organic layer was washed with water and saturated saline in order, and then dried with anhydrous magnesium sulfate. The crude product was refined with silica gel column chromatography (the ethyl acetate-hexane solution of 3:7 to 1:0 in mixing ratio) to give the desired product of colorless oily matter (2.00 g) and N-t-butyl-(4-hydroxymethyl-tetrahydro-pyran-4-yl)-carbamate (1.32 g).

NMR: (CDCl3) 1.45 (s, 9H), 1.70-1.75 (m, 2H), 1.99-2.08 (m, 2H), 3.64-3.72 (m, 2H), 3.78-3.87 (m, 2H), 4.88 (brs, 1H), 9.48 (s, 1H)

3) Synthesis of ethyl 3-(4-t-butoxycarbonylamino-tetrahydro-pyran-4-yl)-acrylate In the dehydrated THF (50 mL) solution of N-t-butyl-(4-formyl-tetrahydro-pyran-4-yl)-carbamate (2.0 g, 8.7 mmol) which had been obtained in 2), (carboethoxymethylene)triphenylphosphorane (3.19 g, 9.2 mmol) was added at room temperature. The reaction mixture was heated and refluxed Under the nitrogen gas atmosphere for 6.5 hours, and (carboethoxymethylene)triphenylphosphorane (3.19 g, 9.2 mmol) was added and the reaction mixture was further heated and refluxed for 17 hours. After the solvent was removed by distillation under reduced pressure, the residue was refined with silica gel column chromatography (the ethyl acetate-hexane solution of 3:7 to 1:0 in mixing ratio) to give colorless oily matter (2.71 g).

NMR: (CDCl3) 1.29 (t, 3H, J=7.2 Hz), 1.44 (s, 9H), 1.82-1.91 (m, 2H), 1.97-2.01 (m, 2H), 3.65-3.83 (m, 4H), 4.20 (q, 2H, J=7.2 Hz), 4.57 (s, 1H), 5.89 (d, 1H, J=15.9 Hz), 6.94 (d, 1H, J=15.9 Hz)

4) Synthesis of ethyl 3-(4-t-butoxycarbonylamino-tetrahydro-pyran-4-yl)-propionate In the ethyl acetate (30 mL) and methanol (12 mL) mixed solution of ethyl 3-(4-t-butoxycarbonylamino-tetrahydro-pyran-4-yl)-acrylate which had been obtained in 3), 5% palladium carbon catalyst was added at room temperature. The reaction mixture was stirred under the hydrogen gas stream at room temperature for 75 minutes. The palladium catalyst was removed by filtration with Celite, and the filtrate was concentrated and dried up to give colorless oily matter (2.69 g).

NMR: (CDCl3) 1.26 (t, 3H, J=7.2 Hz), 1.44 (s, 9H), 1.61-1.67 (m, 2H), 1.91-1.95 (m, 2H), 2.05-2.11 (m, 2H), 2.28-2.33 (m, 2H), 3.57-3.79 (m, 4H), 4.13 (q, 2H, J=7.2 Hz), 4.29 (brs, 1H)

5) Synthesis of ethyl 3-(4-amino-tetrahydro-pyran-4-yl)-propionate monohydrochloride (BB05)

4N hydrochloric acid-ethyl acetate solution (12.9 mL, 51.6 mmol) was added in a ethyl acetate (40 mL) solution of ethyl 3-(4-t-butoxycarbonylamino-tetrahydro-pyran-4-yl)-propionate (2.59 g, 8.6 mmol), which had been obtained in 4), in an ice bath. The reaction mixture was stirred at room temperature for 4 hours, and 4N hydrochloric acid-ethyl acetate solution (4.3 mL, 17.2 mmol) was added and the reaction mixture was further stirred at room temperature for 1 hour. The formed solid was filtered to give a colorless solid (BB05, 1.28 g).

NMR: (DMSO) 1.20 (t, 3H, J=7.2 Hz), 1.67-1.69 (m, 4H), 1.96-2.02 (m, 2H), 2.44-2.47 (m, 2H), 3.49-3.57 (m, 2H), 3.69-3.76 (m, 2H), 4.08 (q, 2H, J=7.2 Hz), 8.16 (brs, 3H)

Experimental Example 30

Synthesis of methyl 1-amino-4,4-dimethyl-cyclohexanecarboxylate monohydrochloride (BB06)

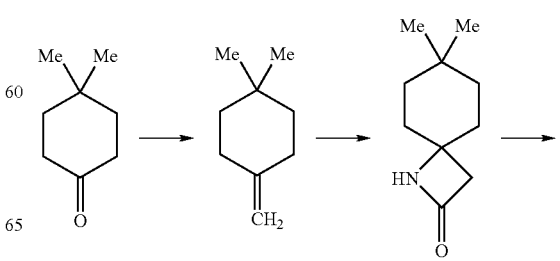

-continued

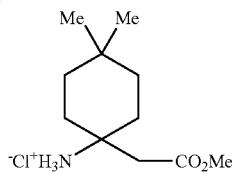

1) Synthesis of 1,1-dimethyl-4-methylene-cyclohexane

Methyltriphenylphosphonium bromide (2.97 g, 8.3 mmol) was added in the dehydrated DMSO (8 mL) solution of sodium hydride (0.35 g, 8.7 mmol) in an ice bath. The reaction mixture was stirred at room temperature for 10 minutes, and the dehydrated DMSO solution (1.5 mL) of 4,4-dimethyl-cyclohexanone (1.0 g, 7.9 mmol) was added slowly in an ice bath. The reaction mixture was stirred at room temperature for 18 hours and poured into ice water. The organic layer was extracted with diethyl ether, and then the layer was washed with water and dried with anhydrous magnesium sulfate, and removed by filtration. The filtrate was concentrated until becoming about half in volume. The formed insoluble matter was removed by filtration, then the filtrate was removed by distillation under reduced pressure, and colorless oily matter (0.91 g) was obtained.

NMR: (CDCl3) 0.94 (s, 6H), 1.35 (t, 4H, J=6.6 Hz), 2.15 (t, 4H, J=6.9 Hz), 4.58 (s, 21H)

2) Synthesis of 7,7-dimethyl-1-aza-spiro[3.5]nonan-2-one

Chlorosulfonyl isocyanic acid (0.67 mL, 7.7 mmol) was dropped into the dehydrated diethyl ether (11 mL) solution of 1,1-dimethyl-4-methylene-cyclohexane (0.91 g, 7.4 mmol), which had been obtained in 1), in an ice bath. The reaction mixture was stirred at room temperature for 1 hour, and chlorosulfonyl isocyanic acid (0.67 mL, 7.7 mmol) was added in the reaction required in the ice bath and further stirred at room temperature for 1 hour. After chlorosulfonyl isocyanic acid (0.32 mL, 3.7 mmol) had been added in the reaction mixture in the ice bath and further stirred at room temperature for 2 hours, the aqueous solution (4.5 mL) containing sodium thiosulfate pentahydrate (4.56 g, 18.4 mmol) and 10% potassium hydroxide solution was added alternately in the reaction mixture in the ice bath and the pH was adjusted to be about 10, and then the reaction mixture was stirred for 2 hours. The insoluble matter was removed by filtration, and the filtrate was extracted with chloroform. Then the organic layer was washed with water and dried with anhydrous magnesium sulfate. The solvent was removed by distillation under reduced pressure and a colorless solid (0.75 g) was obtained.

NMR: (DMSO) 0.89 (s, 6H), 1.18-1.38 (m, 4H), 1.55-1.61 (m, 4H), 2.50-2.52 (m, 2H), 8.19 (brs, 1H)

3) Synthesis of methyl 1-amino-4,4-dimethyl-cyclohexanecarboxylate monohydrochloride Concentrated hydrochloric acid (0.55 mL) was added in the methanol (14 mL) solution of 7,7-dimethyl-1-aza-spiro [3.5]nonan-2-one (0.75 g, 4.5 mmol) which had been obtained in 2) at room temperature. After the reaction mixture had been heated and refluxed for 9 hours, the solvent was removed by distillation under reduced pressure and a colorless solid (BB06, 1.05 g) was obtained.

NMR: (DMSO) 0.89 (s, 3H), 0.91 (s, 3H), 1.24-1.40 (m, 6H), 1.65-1.73 (m, 2H), 2.75 (s, 2H), 3.66 (s, 3H), 8.07 (brs, 3H)

Example 31

Synthesis' of methyl 1-amino-4,4-difluorocyclohexanecarboxylate (BB07) and methyl 1-amino-4-fluoro-3-cyclohexenecarboxylate (BB08)

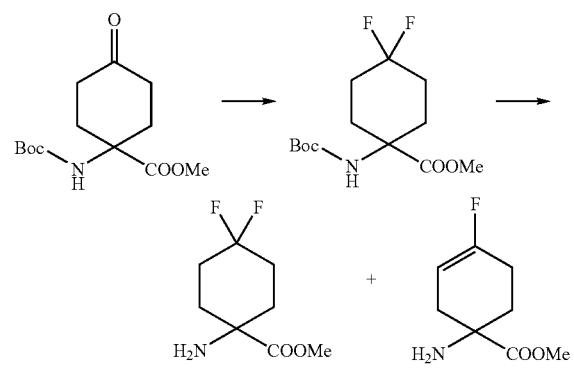

1) Synthesis' of methyl 1-tert-butoxycarbonylamino-4,4-difluorocyclohexanecarboxylate Methyl 1-tert-butoxycarbonylamino-4-oxocyclohexanecarboxylate (1.24 g, 4.39 mmol) was dissolved in dichloromethane (13 mL), and DAST ((dimethylamino)sulfur trifluoride) (7.0 mL, 52.65 mmol) was added slowly and then the mixture was stirred at room temperature for 2 days. The reaction mixture was dropped slowly into ice water (80 mL) while stirring, and then the mixture was stirred at 0° C. for 1 hour. Dichloromethane (110 mL) was added, the organic layer was washed with water, and the water layer was extracted with dichloromethane (100 mL). The united organic layer was dried with sodium sulfate and then removed by distillation under reduced pressure. The organic layer was refined with silica gel column chromatography to give a mixture containing the desired matter (556 mg).

$^1$H NMR: (DMSO-d6): 1.36 (s, 9H), 1.8-2.1 (m, 8H), 3.59 (s, 3H), 7.4 (brs, 1H). $^{19}$F NMR: (DMSO-d6): −99.9 (d, 1F, J=229),-91.4 (d, 1F, J=236).

2) Synthesis of methyl 1-amino-4,4-difluorocyclohexanecarboxylate (BB07) and methyl 1-amino-4-fluoro-3-cyclohexenecarboxylate (BB08)

Methyl 1-tert-butoxycarbonylamino-4,4-difluorocyclohexanecarboxylate which had been obtained in 1) was dissolved in methanol (2.5 mL), and 10% hydrochloric acid-methanol (3.38 g, 9.27 mmol) was added and the mixture was stirred for 3 days. The reaction mixture was removed by distillation. The proper quantity of diethyl ether was added in the reaction mixture to crystallize it, and the crystal (421 mg) was isolated. The crystal was dissolved in chloroform, and the solution was alkalinized by adding saturated sodium hydrogencarbonate aqueous solution and then extracted with chloroform (30 mL×2). The organic layer was removed by distillation under reduced pressure and refined with silica gel column chromatography to give methyl 1-amino-4,4-difluorocyclohexanecarboxylate (BB07, 191 mg) and methyl 1-amino-4-fluoro-3-cyclohexenecarboxylate (BB08, 55 mg).

methyl 1-amino-4,4-difluorocyclohexanecarboxylate (BB07)

¹H NMR: (CDCl3): 1.69-2.29 (m, 10H), 3.74 (s, 3H).

methyl 1-amino-4-fluoro-3-cyclohexenecarboxylate (BB08)

¹H NMR: (CDCl3): 1.8-2.7 (m, 6H), 1.97 (brs, 2H), 3.75 (s, 3H), 5.1-5.2 (m, 1H).

Experimental Example 32

Synthesis of methyl 1-amino-4-fluoro-cyclohexanecarboxylate (BB09)

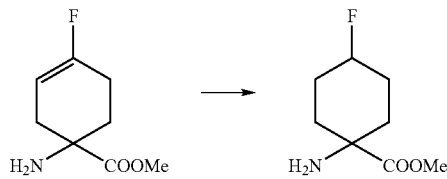

Methyl 1-amino-4-fluoro-3-cyclohexenecarboxylate (52 mg) was dissolved in the mixed solvents of methanol (2 mL) and ethyl acetate (2 mL), and 10% palladium-carbon (35 mg) was added and hydrogen gas was introduced for 14 hours. The insoluble matter was filtered and the solvent was removed by distillation under reduced pressure, and a mixture of the desired matter (BB09, 38 mg) was obtained.
¹H NMR: (CDCl₃): 1.4-2.3 (m, 10H), 3.72 (s, 3H), 4.6-4.9 (m, 1H).

Experimental Example 33

Synthesis of methyl 1-amino-4,4-difluorocyclohexanecarbozylate monohydrochloride (BB10)

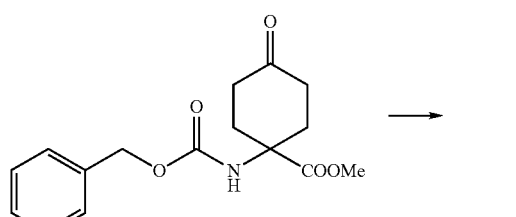

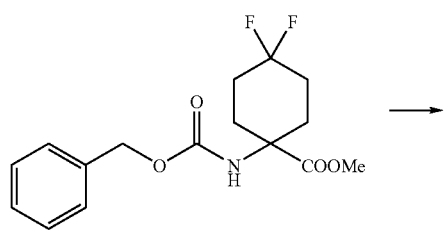

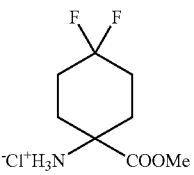

1) Synthesis of methyl 1-benzyloxycarbonylamino-4,4-difluorocyclohexanecarboxylate Methyl 1-benzyloxycarbonylamino-4-oxocyclohexanecarbonate (1.03 g, 3.37 mmol) was dissolved in dichloromethane (10 mL), and DAST ((dimethylamino)sulfur trifluoride) (4.45 mL, 33.67 mmol) was added slowly in the solution at room temperature, then the mixture was stirred at room temperature for 25 hours. The reaction mixture was dropped slowly into ice water (40 mL) while stirring and the mixture was stirred at 0° C. for 15 minutes. Then, dichloromethane (30 mL) was added, and the organic layer was washed with water (25 mL×2) and the water layer was extracted with dichloromethane (30 mL). The united organic layer was dried with sodium sulfate and then removed by distillation under reduced pressure. The organic layer was refined with silica gel column chromatography to give a mixture containing the desired compound (718 mg).
¹H NMR: (CDCl₃): 1.8-2.7 (m, 8H), 3.70 (brs, 3H), 4.97-5.16 (m, 3H), 7.29-7.39 (m, 5H).

2) Synthesis of methyl 1-amino-4,4-difluorocyclohexanecarboxylate hydrochloride

Methyl 1-benzyloxycarbonylamino-4,4-difluorocyclohexanecarboxylate which had been obtained in 1) was dissolved in the mixed solvents of ethyl acetate (50 mL) and methanol (25 mL), and 4N hydrochloric acid-ethyl acetate (1.03 mL) was added. Here, 10% palladium-carbon (120 mg) was added and hydrogen gas (4.5 to 5 in atmospheric pressure) was introduced, and the mixture was stirred at room temperature for 2 days. After the insoluble matter had been removed by filtration, the filtrate was removed by distillation under reduced pressure and a crystal containing the desired compound (BB10, 467 mg) was obtained.
¹H NMR: (DMSO-d6): 1.8-2.3 (m, 8H), 3.79 (s, 3H), 8.92 (brs, 3H). ¹⁹F NMR (DMSO-d6): −97.3 (d, 1F, J=235), −95.3 (d, 1F, J=235).

Example 34

Synthesis of ethyl 2-amino-4-fluoro-4-methyl-valerate (BB11)

Ethyl 2-(benzhydridene-amino)-4-fluoro-4-methyl-valerate (apparently 6.0 g) was dissolved in ethanol (60 mL), and 10% palladium-carbon (2.0 g) was added and hydrogen gas was introduced at room temperature, then the mixture was stirred for 14 hours. After the insoluble matter had been filtered, the solvent was removed by distillation under reduced pressure, methyl-tert-butyl ether (40 mL) and sulfuric acid (1.53 g) dissolved in water (40 mL) were added in the residue while cooling it with ice, and the mixture was stirred for 10 minutes. The organic layer was removed, and the water layer was washed with methyl-tert-butyl ether (30 mL×2). After potassium carbonate (4.14 g, 30.0 mmol) was added in the water layer while cooling it with ice and its pH was made to be 10, the water layer was extracted with the mixture of isopropyl acetate and dichloromethane of 4:1 in mixing ratio (40 mL×4). After the organic layer was dried with magnesium sulfate, the solvent was removed by distillation under reduced pressure and an oily mixture of the desired matter (BB11, 1.08 g) was obtained.

$^1$H NMR: (CDCl$_3$) 1.27 (t, 3H, J=6.9), 1.40 (d, 3H, J=3.0), 1.47 (d, 3H, J=3.0), 1.86 (brs, 2H), 1.8-2.2 (m, 2H), 3.69 (dd, 1H, J=5.1, 7.8), 4.19 (q, 2H, J=7.2).

Example 35

Synthesis of ethyl 4-amino-6-fluoro-6-methyl-valerate hydrochloride (BB12)

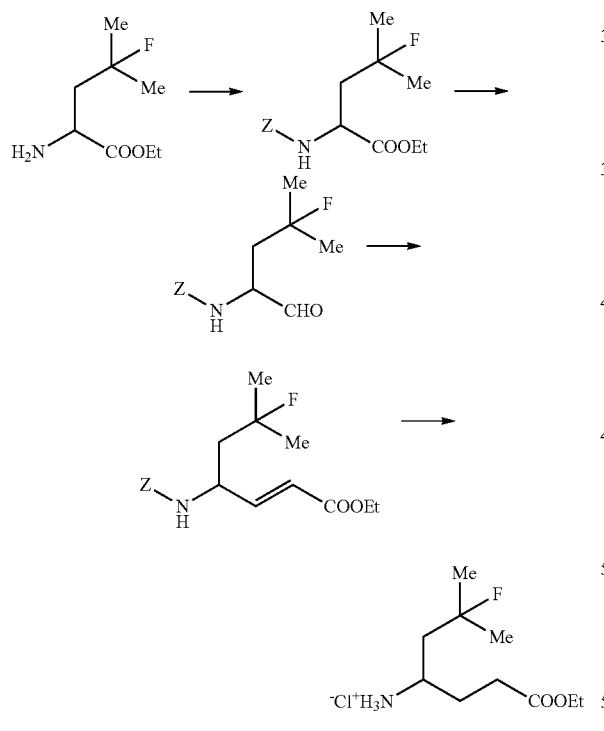

1) Synthesis of ethyl 2-benzyloxycarbonylamino-4-fluoro-4-methyl-valerate 2-amino-4-fluoro-4-methyl-ethyl valerate (apparently 0.60 g) was dissolved in tetrahydrofuran (8 mL), and pyridine (0.6 mL, 7.45 mmol) was added. Z-chloride (0.53 mL, 3.72 mM) was further added while cooling with ice, and the mixture was stirred at room temperature for 4.5 hours. Cold water (8 mL) was added in the mixture while cooling it with ice and the pH was adjusted to be 2 by adding 2N aqueous hydrochloric acid solution. The mixture was extracted with ethyl acetate (50 mL×2), and the organic layer was washed using in the order of water (15 mL), saturated aqueous sodium hydrogencarbonate solution (15 mL), and water (15 mL). The organic layer was dried with sodium sulfate and then separated by distillation under reduced pressure and refined with silica gel column chromatography. After that, the eluted solvent was removed by distillation under reduced pressure and the desired oily compound (730 mg) was obtained.

$^1$H NMR: (CDCl$_3$): 1.27 (t, 3H, J=7.2), 1.42 (d, 6H, J=21.6), 1.95-2.22 (m, 2H), 4.20 (q, 2H, J=6.6), 4.47 (dt, 1H, J=4.8, 12.6), 5.12 (s, 2H), 5.42 (d, 1H, J=5.7), 7.3-7.4 (m, 5H).

2) Synthesis of ethyl (E)-4-benzyloxycarbonylamino-6-fluoro-6-methyl-2-valerate

Ethyl 2-benzyloxycarbonylamino-4-fluoro-4-methyl-valerate (1.16 g, 3.73 mmol) which had been obtained in 1) was dissolved in toluene (15.8 mL), and 1.01 M diisobutylaluminumhydride-toluene solution (7.38 mL) was dropped into the solution at −78° C. At the same temperature, the solution was stirred for 1 hour, and saturated aqueous ammonium chloride solution (3 mL) and methanol (1 mL) were dropped into. The temperature of the reaction mixture was raised to room temperature, and water was added and then the reaction mixture was extracted with ethyl acetate (100 mL×2). The organic layer was washed with water (30 mL) and saturated saline (50 mL). The organic layer was dried with sodium sulfate and then removed by distillation under reduced pressure to give an oily mixture (1.15 g). To the oily mixture, tetrahydrofuran (13.8 mL) was added and carbetoxymethylenetriphenylphosphorane (1.04 g, 2.98 mmol) was added, and the mixture was heated and refluxed for two hours. The solvent was removed by distillation under reduced pressure, the residual mixture was refined with silica gel column chromatography, and then the eluted solvent was removed by distillation under reduced pressure and the desired oily compound (599 mg) was obtained.

$^1$H NMR: (CDCl$_3$): 1.29 (t, 3H, J=6.9), 1.41 (d, 6H, J=21.3), 1.8-2.0 (m, 2H), 4.19 (q, 2H, J=7.2), 4.57 (br, 1H), 5.11 (s, 2H), 5.95 (d, 1H, J=15.6), 6.87 (dd, 1H, J=5.1, 15.6), 7.3-7.4 (m, 5H).

3) Synthesis of ethyl 4-amino-6-fluoro-6-methyl-valerate hydrochloride (BB12)

Ethyl (E)-4-benzyloxycarbonylamino-6-fluoro-6-methyl-2-valerate (590 mg, 1.75 mmol) which had been obtained in 2) was dissolved in ethyl acetate (7.1 mL), and 4 N hydrochloric acid-ethyl acetate (0.87 ml, 3.50 mL) and ethanol (3.5 mL) were added. Further, 10% palladium-carbon (100 mg) was added and hydrogen gas was introduced for 3 hours. After the insoluble matter had been filtered, the solvents were removed by distillation under reduced pressure and the desired crystal (BB12, 454 mg) was obtained.

$^1$H NMR (DMSO-d6): 1.19 (t, 3H, J=6.9), 1.37 (d, 6H, J=21.6), 1.8-2.0 (m, 4H), 2.5-3.3 (m, 3H), 4.07 (q, 2H, J=7.2), 7.97 (brs, 3H).

Example 36

Synthesis of (1-amino-cyclohexylmethoxy)-acetic acid hydrochloride (BB13)

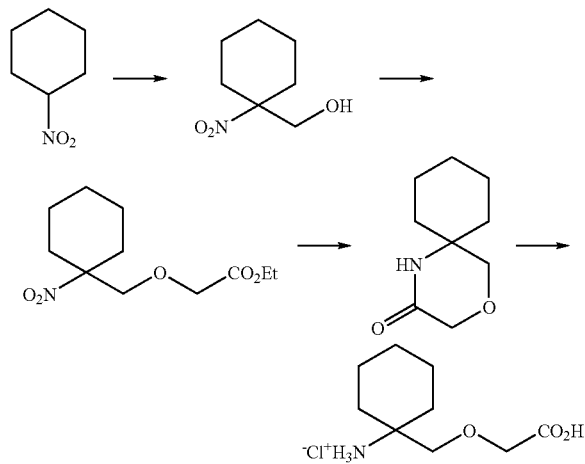

1) Synthesis of (1-nitro-cyclohexyl)-methanol

A ethanol (5 mL) solution of nitrocyclohexane (5.00 g, 38.7 mmol) and sodium hydroxide (12.5 g, 0.3 mmol) was heated to 55° C., 35% formalin solution (3.0 mL, 35 mmol) was added, and the mixture was heated and stirred at the same temperature for 1.5 hours. The reaction mixture was diluted with water, 2M hydrochloric acid (0.5 mL, 1 mmol) was added, and the mixture was extracted with ethyl acetate (15 mL) two times. The organic layer was washed with 5% sodium bicarbonate aqueous solution (10 mL) and water (20 mL), and then dried with anhydrous sodium sulfate. The solvents were removed by distillation under reduced pressure, the residue was refined with silica gel column chromatography (Highflash 3L, manufactured by Yamazen Corporation, the mixture of hexane and ethyl acetate of 3:1 in mixing ratio), and colorless oily (1-nitro-cyclohexyl)-methanol (6.96 g) was obtained.

NMR: (d$_6$-DMSO) 1.20-1.72 (m, 8H), 2.17-2.25 (m, 2H), 3.65 (d, 2H, J=4.5), 5.33 (t, 2H, J=5.1)

2) Synthesis of ethyl (1-nitro-cyclohexylmethoxy)-acetate

Under the nitrogen gas atmosphere, NaH (2.32 g, 58 mmol) was added in the DMF (70 mL) solution of (1-nitro-cyclohexyl)-methanol (6.96 g, 35 mmol) which had been obtained in 1) while cooling the solution with ice, and the mixture was stirred for 20 minutes while making the temperature rise naturally. Bromoethyl acetate (9.96 g, 58.0 mmol) was dropped, and the mixture was stirred at room temperature over-night. The reaction mixture was diluted with water (200 mL), 2M hydrochloric acid (20 mL, 40 mmol) was added, and the mixture was extracted with ethyl acetate (50 mL) two times. The organic layer was washed with 5% sodium bicarbonate aqueous solution (20 mL) and water (50 mL), and then dried with anhydrous sodium sulfate. The solvents were removed by distillation under reduced pressure, the residue was refined with silica gel column chromatography (Highflash 4L, manufactured by Yamazen Corporation, the mixture of hexane and ethyl acetate of 5:1 in mixing ratio), and pale yellow oily ethyl (1-nitro-cyclohexylmethoxy)-acetate (5.47 g, 57%) was obtained.

NMR: (d$_6$-DMSO) 1.19 (t, 3H, J=7.2), 1.30-1.65 (m, 6H), 1.80 (m, 2H), 2.20 (dd, 2H, J=14.4 and 5.7), 3.83 (s, 2H), 4.11 (q, 2H, J=7.2), 4.11 (s, 2H)

3) Synthesis of 4-oxa-1-aza-spiro[5.5]-undecan-2-one

Under the nitrogen gas atmosphere, ammonium formate (5.75 g, 91.1 mmol) and 10% Pd-carbon (4.5 mg) was added in the methanol (90 mL) solution of (1-nitro-cyclohexylmethoxy)-ethyl acetate (4.5 g, 18.2 mmol) which had been obtained in 2), and the mixture was heated and stirred at 50° C. over-night. After that, the mixture was filtered with Celite, the filtrate was concentrated under reduced pressure, the residue was refined with silica gel column chromatography (Highflash 3L, manufactured by Yamazen Corporation, and the mixtures of hexane and ethyl acetate of 5:1, 1:1, and 1:2 in mixing ratio), and an orange-colored crystal of 4-oxa-1-aza-spiro[5.5]-undecan-2-one (1.67 g, 54%) was obtained.

NMR: (d$_6$-DMSO) 1.20-1.50 (m, 6H), 1.58 (d, 4H, J=9.9), 3.57 (s, 2H), 3.92 (s, 2H), 8.04 (s, 1H)

4) Synthesis of (1-amino-cyclohexylmethoxy)-acetic acid hydrochloride

In 4-oxa-1-aza-spiro[5.5]-undecan-2-one (1.67 g, 9.9 mmol) which had been obtained in 3), 6N hydrochloric acid (30 mL, 180 mmol) was added, and the mixture was heated and stirred at 100° C. for 1.5 hours. The solvent was removed by distillation under reduced pressure, toluene (100 mL) was added in the remainder, and the azeotropic dehydration operation was conducted two times under reduced pressure to give a pale yellow crystal. Further toluene (50 ml) was added to the crystal and the azeotropic dehydration operation was conducted, and then washing the crystal with ether, the white crystal of (1-amino-cyclohexylmethoxy)-acetic acid hydrochloride (BB13, 1.91 g, 87%) was obtained.

NMR: (d$_6$-DMSO) 1.20-1.80 (m, 10H), 3.61 (s, 2H), 4.12 (s, 2H), 7.96 (s, 3H), 12.77 (br s, 1H)

Example 37

Synthesis of 2-{4-[(1-cyclohexylmethyl-2-oxo-1,2,5,6,7,8,9,10-octahydro-cycloocta[b]pyridine-3-carbonyl)-amino]-3-trifluoromethyl-phenyl}acetic acid (XI-088)

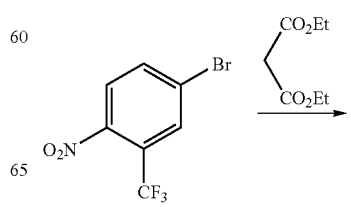

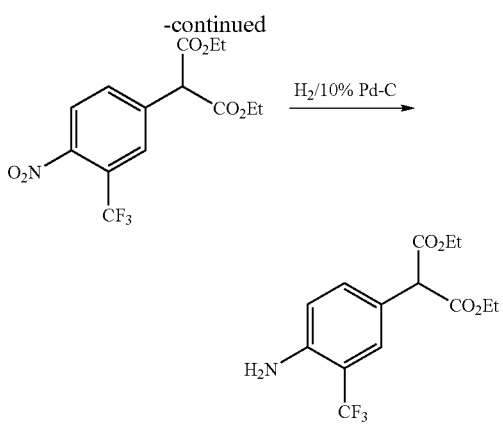

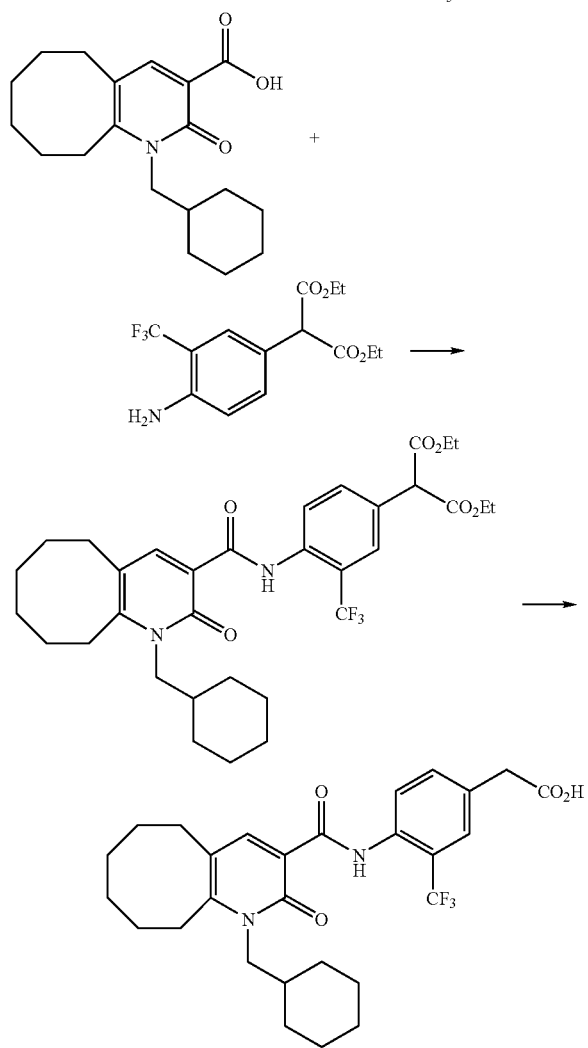

1) Synthesis of diethyl 2-(4-nitro-3-trifluoromethyl-phenyl)-malonate

Sodium hydride (60% oiliness) (0.33 g, 8.25 mmol) was added in the dimethylformamide (20 mL) solution of diethyl malonate (1.23 mL, 8.14 mmol) while cooling the solution with ice, and the mixture was directly stirred for 4 hours. 5-bromo-2-nitrobenzotrifluoride (2.0 g, 7.41 mmol) was added in the reaction mixture while cooling it with ice, and the temperature was raised to room temperature and then the mixture was further heated and stirred at 70° C. for 3 hours. After the reaction solution was poured into ice water and acidified with 2N hydrochloric acid, the solution was extracted with ethyl acetate. After the organic layer had been washed with 5% sodium hydrogencarbonate aqueous solution and then with water and dried over anhydrous sodium sulfate, the solvents were concentrated under reduced pressure. The residue was subjected to silica gel column chromatograph (45 g) and was eluted with the mixture of ethyl acetate and n-hexane of 1:5 in mixing ratio. The eluted liquid was concentrated under reduced pressure and yellow oily diethyl 2-(4-nitro-3-trifluoromethyl-phenyl)-malonate (1.1 g, 42%) was obtained.

NMR: ($CDCl_3$) 1.29 (t, 6H, J=7.2), 4.25 (q, 2H, J=6.9), 4.27 (q, 2H, J=7.2), 4.75 (s, 1H), 7.80-7.92 (m, 3H)

2) Synthesis of diethyl 2-(4-amino-3-trifluoromethyl-phenyl)-malonate

10% palladium carbon (0.1 g) was added in the ethyl acetate (20 mL) solution of diethyl 2-(4-nitro-3-trifluoromethyl-phenyl)-malonate (1.1 g, 3.15 mmol) which had been obtained in 1), and the solution was hydrogenated. After the catalyst was removed by filtration, the solvent was concentrated under reduced pressure and yellow oily diethyl 2-(4-amino-3-trifluoromethyl-phenyl)-malonate (1.38 g (the content of 0.39%), 68%) was obtained, and the product was used in the next reaction without purification.

NMR: ($CDCl_3$) 1.20-1.35 (m, 6H), 4.10-4.30 (m, 4H), 6.77 (d, 1H, J=8.4), 7.34-7.46 (m, 2H)

3) Synthesis of diethyl 2-{4-[(1-cyclohexylmethyl-2-oxo-1,2,5,6,7,8,9,10-octahydro-cycloocta[b]pyridine-3-carbonyl)-amino]-3-trifluoromethyl-phenyl}-malonate An acid chloride solution was adjusted in such away that 1-cyclohexylmethyl-2-oxo-1,2,5,6,7,8,9,10-octahydro-cycloocta[b]pyridine-3-carboxylic acid (0.25 g, 0.79 mmol) which had been obtained in 3) was dissolved in tetrahydrofuran (3 mL), and oxalyl chloride (0.076 mL, 0.87 mmol) and a drop (with a capillary pipet) of dimethylhormamide were added and stirred at room temperature for 30 minutes. In the tetrahydrofuran (3 mL) solution of 2-(4-amino-3-trifluoromethyl-phenyl)diethyl malonate (1.38 g (the content is 0.39%), 1.69 mmol), triethylamine (0.33 mL, 2.37 mmol), and then the acid chloride solution adjusted as mentioned above were added and stirred at room temperature for six hours. After the reaction mixture had been poured into ice water and acidified with 2N hydrochloric acid, the mixture was extracted with ethyl acetate. After the organic layer had been washed with 5% sodium hydrogencarbonate aqueous solution and then with water and dried over anhydrous sodium sulfate, the solvents were concentrated under reduced pressure. The residue was subjected to silica gel (30 g) column chromatography (the mixture of ethyl acetate and n-hexane of 1:5 in mixing ratio). The eluted liquid was concentrated under reduced pressure and yellow oily diethyl 2-{4-[(1-cyclohexylmethyl-2-oxo-1,2,5,6,7,8,9,10-octahydro-cycloocta[b]pyridine-3-carbonyl)-amino]-3-trifluoromethyl-phenyl}-malonate (0.29 g, 59%) was obtained.

Mp: 160 to 162° C.

NMR: ($CDCl_3$) 1.27 (t, 6H, J=7.2), 1.05-1.90 (m, 19H), 2.62-2.72 (m, 2H), 2.88-2.97 (m, 2H), 3.90-4.20 (m, 2H), 4.15-4.30 (m, 4H), 4.62 (s, 1H), 7.60 (dd, 1H, J=1.8, 8.4), 7.68 (d, 1H, J=1.8), 8.35 (s, 1H), 8.41 (d, 1H, J=8.4), 12.53 (s, 1H)

4) Synthesis of 2-{4-[(1-cyclohexylmethyl-2-oxo-1,2,5,6,7,8,9,10-octahydro-cycloocta[b]pyridine-3-carbonyl)-amino]-3-trifluoromethyl-phenyl}acetic acid (XI-088)

Diethyl 2-{4-[(1-cyclohexylmethyl-2-oxo-1,2,5,6,7,8,9,10-octahydro-cycloocta[b]pyridine-3-carbonyl)-amino]-3-trifluoromethyl-phenyl}-malonate (0.29 g, 0.47 mmol) which had been obtained in 3) was dissolved in tetrahydrofuran-methanol (1:1) (3.8 mL), and 1N sodium hydroxide aqueous solution (1.9 mL, 1.90 mmol) was added at room temperature and the mixture was stirred for 25 hours. The mixture was further stirred at 80° C. for 9 hours. after that, the reaction mixture was poured into ice water and acidified with 2N hydrochloric acid, then the mixture was extracted with ethyl acetate. The organic layer was washed with water and then dried over anhydrous sodium sulfate, and the solvents were concentrated under reduced pressure. The residue was subjected to silica gel (12 g) column chromatography (the mixture of chloroform, methanol, and water of 32:9:1 in mixing ratio). After the eluted liquid was concentrated under reduced pressure and recrystallized from acetone-water (1:10), a white needle crystal of 2-{4-[(1-cyclohexylmethyl-2-oxo-1,2,5,6,7,8,9,10-octahydro-cycloocta[b]pyridine-3-carbonyl)-amino]-3-trifluoromethyl-phenyl}acetic acid (XI-088, 0.09 g, 37%) was obtained.

NMR: (DMSO-$d_6$) 1.05-1.84 (m, 19H), 2.63-2.77 (m, 2H), 2.90-3.05 (m, 2H), 3.69 (s, 2H), 3.90-4.20 (m, 2H), 7.56 (d, 1H, J=9.0), 7.63 (m, 1H), 8.20 (d, 1H, J=8.7), 8.27 (s, 1H)

Example 38

Synthesis of methyl [(1-cyclohexylmethyl-2-oxo-1,2,5,6,7,8,9,10-octahydro-cycloocta[b]pyridine-3-carbonyl)-amino]-acetate (I-081)

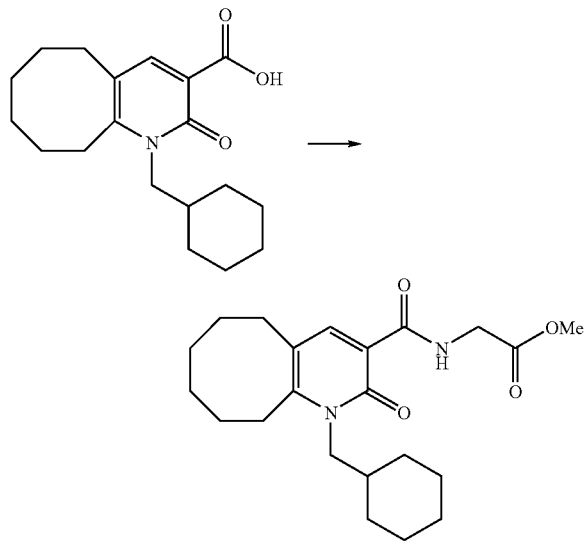

1-Cyclohexylmethyl-2-oxo-1,2,5,6,7,8,9,10-octahydro-cycloocta[b]pyridine-3-carboxylic acid (AA01, 0.20 g, 0.63 mmol) which had been obtained in Example 1 was dissolved in anhydrous dichloromethane (2.0 mL), and oxalyl chloride (82 µL, 0.95 mmol) and a drop of DMF were added while cooling the solution with ice. After the temperature had been raised to room temperature and the solution stirred for 1 hour, the solvent was removed by distillation under reduced pressure. The residue was dissolved in THF (2.0 mL) and glycine methyl ester hydrochloride (0.119 g, 0.948 mmol) and triethylamine (0.263 mL, 1.89 mmol) were added. After the mixture was stirred at room temperature for 1 hour, water was added and the mixture was extracted with ethyl acetate while cooling the mixture with ice. The organic layer was washed with saturated saline and then dried over anhydrous magnesium sulfate. The solvents were removed by distillation under reduced pressure, and the residue was refined with silica gel column chromatography and a pale red color crystal of I-081 (195 mg, 80%) was obtained.

Example 39

Synthesis of [(1-cyclohexylmethyl-2-oxo-1,2,5,6,7,8,9,10-octahydro-cycloocta[b]pyridine-3-carbonyl)-amino]-acetic acid (I-355)

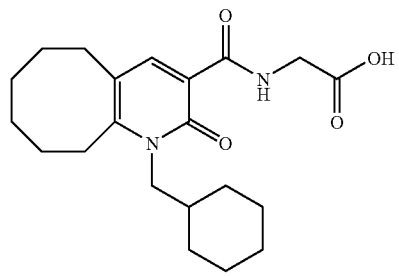

Methyl [(1-cyclohexylmethyl-2-oxo-1,2,5,6,7,8,9,10-octahydro-cycloocta[b]pyridine-3-carbonyl)-amino]-acetate (I-081, 0.12 g, 0.309 mmol) which had been obtained in Example 38 was dissolved in the mixed solvent of methanol (1.0 mL) and THF (1.0 mL), and 2M sodium hydroxide aqueous solution (0.46 mL) was added. After stirring for 1 hour, the solution was neutralized with 2M hydrochloric acid and extracted with ethyl acetate. The organic layer was washed with saturated aqueous sodium hydrogencarbonate solution and saturated saline and then dried over anhydrous sodium sulfate. The solvents were removed by distillation under reduced pressure, and a colorless crystal of I-355 (120 mg, 100%) was obtained.

IR (KBr): 2926, 2852, 1739, 1657, 1536.

Example 40

Synthesis of methyl [(1-cyclohexylmethyl-2-oxo-1,2,5,6,7,8,9,10-octahydro-cyclooct[b]pyridine-3-carbonyl)-amino]-butyrate (III-005)

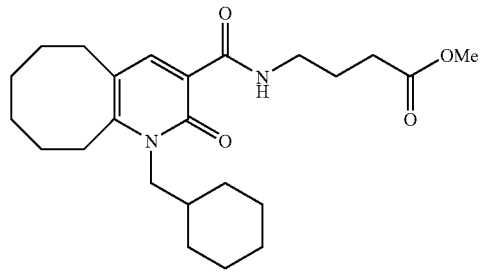

Under the nitrogen gas atmosphere, 1-cyclohexylmethyl-2-oxo-1,2,5,6,7,8,9,10-octahydro-cycloocta[b]pyridine-3-carboxylic acid (AA01, 0.15 g, 0.47 mM) which had been obtained in Example 1 was dissolved in dichloromethane (1.5 mL), and oxalyl chloride (62 mL, 0.71 mmol) and a drop of DMF were added while cooling the solution with ice, and then the mixture was stirred at room temperature. After 1 hour, the solvent was removed by distillation under reduced pressure, dichloromethane (5 mL) was added in the residue, then methyl 3-aminobutyrate hydrochloride (87.2 mg, 0.568 mmol) and PS-DIEA (manufactured by Argonoto Corporation, 0.31 g, 1.19 mmol) were added. After two days' stirring, MP-isocyanate and PS-carbonate were added. After that, the stirring was conducted for three hours, and then the reaction mixture was filtered and the solvent was removed by distillation under reduced pressure. And, the residue was refined with a flash tube to give a colorless crystal of III-005 (0.1496 g, 76%).

Example 41

Synthesis of [(1-cyclohexylmethyl-2-oxo-1,2,5,6,7,8,9,10-octahydro-cycloocta[b]pyridine-3-carbonyl)-amino]-butyric acid (III-013)

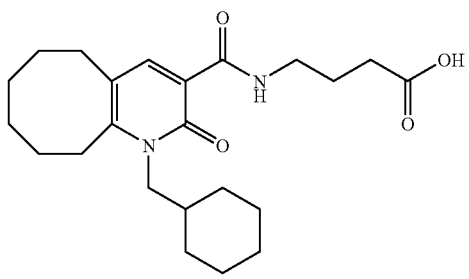

Methyl [(1-cyclohexylmethyl-2-oxo-1,2,5,6,7,8,9,10-octahydro-cyclooct[b]pyridine-3-carbonyl)-amino]-butyrate (III-005, 56.5 mg, 0.136 mmol) which had been obtained in Example 40 was dissolved in methanol (1.5 mL), and 2M aqueous sodium hydroxide solution (0.27 mL, 0.54 mmol) was added and the solution was stirred at room temperature. After 2.5 hours, 2M hydrochloric acid was added to acidify the solution. and the solution was extracted with ethyl acetate. The organic layer was dried over anhydrous sodium sulfate, and the solvent was removed by distillation under reduced pressure and a colorless amorphous III-013 (51.9 mg, 95%) was obtained.

Example 42

Synthesis of [(1-cyclohexylmethyl-2-oxo-1,2,5,6,7,8,9,10-octahydro-cycloocta[b]pyridine-3-carbonyl)-amino]-acetic acid fluoromethyl ester (I-311)

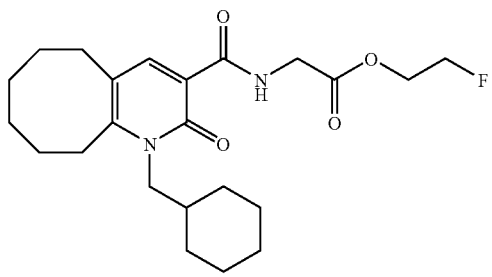

[(1-Cyclohexylmethyl-2-oxo-1,2,5,6,7,8,9,10-octahydro-cycloocta[b]pyridine-3-carbonyl)-amino]-acetic acid (I-355, 0.15 g, 0.40 mmol) which had been obtained in Example 39 was dissolved in 1,1,2-trichloroethane, and fluoroethanol (47 µL, 0.80 mmol) and concentrated sulfuric acid (20 µL, 0.40 mmol) were added Under the nitrogen gas atmosphere and the mixture was heated to 80° C. After 22 hours, the reaction mixture was poured into saturated aqueous sodium hydrogencarbonate solution and extracted with ethyl acetate. After the organic layer had been washed with brine, the solvent was removed by distillation under reduced pressure, and the residue was refined with silica gel column chromatography, and a colorless crystal of I-311 (101 mg, 60%) was obtained.

IR (KBr): 3235, 2925, 2855, 1763, 1665, 1618, 1580, 1529, 1446, 1212.

Example 43

Synthesis of [(1-cyclohexylmethyl-2-oxo-1,2,5,6,7,8,9,10-octahydro-cycloocta[b]pyridine-3-carbonyl)-amino]-acetic acid trifluoromethy ester (I-312)

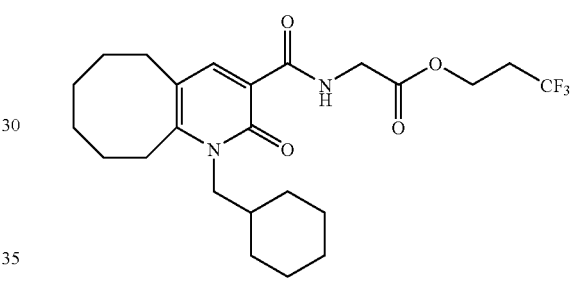

Under the nitrogen gas atmosphere, 60% sodium hydride which had been washed with hexane (3.05 g, 76.3 mmol) was suspended in diethyl ether (60 mL), and trifluoroethanol (5.56 mL, 76.3 mmol) was added and stirred for 10 minutes while cooling the suspension with ice. After that, triphenylphodphine (10.0 g, 38.1 mmol) was added, and the suspension was further stirred for 5 minutes. Then, bromine (1.95 mL, 38.1 mmol) was added slowly, and the suspension was stirred for 1.5 hours. Subsequently, the insoluble matter was removed by filtration with a glass filter, and the solvent was removed by distillation under reduced pressure. The addition of dichloromethane (30 mL) in the residue made 1.27M ditrifluoromethoxytriphenylphosphate solution. 1-cyclohexylmethyl-2-oxo-1,2,5,6,7,8,9,10-octahydro-cycloocta[b]pyridine-3-carboxylic acid (I-355, 0.10 g, 0.267 mmol) which had been obtained in Example 38 was dissolved in dichloromethane (1 mL), and the above-mentioned ditrifluoromethoxytriphenylphosphate (0.25 mL, 0.32 mmol) was added and the mixture was stirred at room temperature. After 1.5 hours, further the same amount of ditrifluoromethoxytriphenylphosphate was added. After stirring for 18 hours, the solvent in the reaction mixture was removed by distillation under reduced pressure, the residue was refined with column chromatography, and a colorless amorphous I-312 (45.4 mg, 37%) was obtained.

Example 44

Synthesis' of methyl 2-[(1-cyclohexylmethyl-2-oxo-1,2,5,6,7,8,9,10-octahydro-cycloocta[b]pyridine-3-carbonyl]-amino]-2-methyl-propionate (I-084)

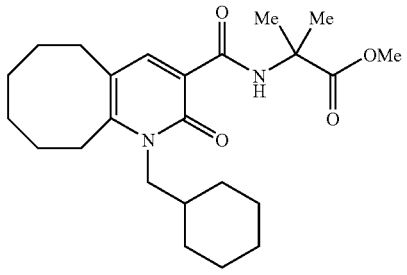

Under the nitrogen gas atmosphere, 1-cyclohexylmethyl-2-oxo-1,2,5,6,7,8,9,10-octahydro-cycloocta[b]pyridine-3-carboxylic acid (AA01, 500 mg, 1.57 mmol) which had been obtained in Example 1 was dissolved in methylene chloride (5 mL), and oxalyl chloride (164.9 µL, 1.89 mmol) and DMF (three drops) were added and the mixture was stirred at room temperature for 1 hour. After that, dimethylglycine methyl ester hydrochloride (290.3 mg, 1.89 mmol) and triethylamine (658.5 µL, 4.72 mmol) were added and the mixture was further stirred for 2 hours. Subsequently, water was added, and the mixture was acidified with hydrochloric acid and then extracted with ethyl acetate. The organic layer was washed with water and then dried over anhydrous sodium sulfate. The solvents were removed by distillation under reduced pressure and a pale yellow solid of I-084 (607 mg, 93%, mp: 177 to 178° C.) was obtained.

NMR: (CDCl3) 1.00-1.95 (m, 25H), 2.61 (t, 2H, J=5.7), 2.92 (t, 2H, J=5.7), 3.76 (s, 3H), 4.00 (br, 2H), 8.27 (s, 1H), 10.30 (s, 1H)

Example 45

Synthesis' of 2-[(1-cyclohexylmethyl-2-oxo-1,2,5,6,7,8,9,10-octahydro-cycloocta[b]pyridine-3-carbonyl)-amino]-2-methyl-propionic acid (I-358)

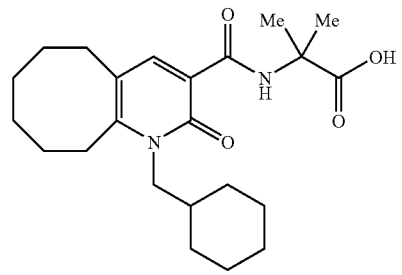

Methyl 2-[(1-cyclohexylmethyl-2-oxo-1,2,5,6,7,8,9,10-octahydro-cycloocta[b]pyridine-3-carbonyl)-amino]-2-methyl-propionate (I-084, 597 mg, 1.43 mmol) which had been obtained in Example 44 was dissolved in the mixed solvent of THF (6 mL) and methanol (6 mL), and the solution was stirred together with 2M sodium hydroxide aqueous solution (1.79 mL, 3.58 mmol) at 60° C. for 1 hour. After the concentration of the mixture, the water layer was washed with diethyl ether and acidified with hydrochloric acid and then extracted with ethyl acetate. The organic layer was washed with water and then dried over anhydrous sodium sulfate. The solvents were removed by distillation under reduced pressure and a colorless solid of I-358 (446 mg, 77%, mp: 260-263° C.) was obtained.

Example 46

Synthesis of 2-[(1-cyclohexylmethyl-2-oxo-1,2,5,6,7,8,9,10-octahydro[b]pyridine-3-carbonyl)-amino]-2-methyl-propionate 2-dimethylamino ethyl ester (I-325)

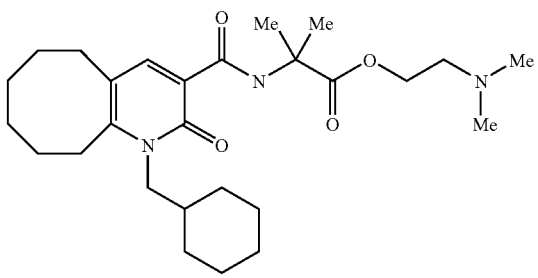

Under the nitrogen gas atmosphere, 2-[(1-cyclohexylmethyl-2-oxo-1,2,5,6,7,8,9,10-octahydro-cycloocta[b]pyridine-3-carbonyl)-amino]-2-methyl-propionic acid (I-358, 600 mg, 1.49 mmol) which had been obtained in Example 45 was dissolved in DMF (12 mL), and the solution was stirred together with WSCD (325 mg, 1.79 mmol) and HOBt (40.2 mg, 0.298 mmol) at 80° C. for 30 minutes. After that, N,N-dimethylaminoethanol (300 µL, 2.98 mmol) was added and the mixture was heated and stirred at 80° C. for 7 hours. Subsequently, water was added and the mixture was extracted with ethyl acetate, and then the organic layer was washed with water and dried over anhydrous sodium sulfate. The solvents were removed by distillation under reduced pressure, and the residue was refined with silica gel (5 g) column chromatography (the mixture of chloroform-methanol of 9:1 in mixing ratio), and thus a colorless solid of I-325 (629 mg, 76%, mp: 101-103° C.) was obtained.

Example 47

Synthesis of (2-{2-[(1-cyclohexylmethyl-2-oxo-1,2,5,6,7,8,9,10-octahydro-cycloocta[b]pyridine-3-carbonyl)-amino]-2-methyl-propionyloxy}-ethyl)-trimethylammonium iodide (I-326)

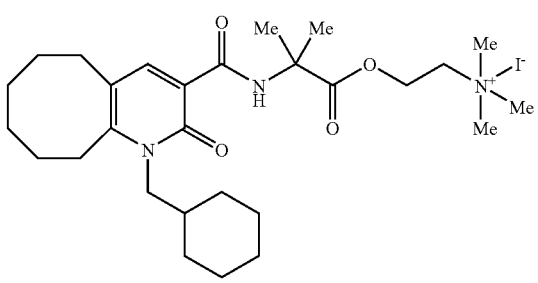

In an acetonitrile (10 mL) solution of cyclohexylmethyl-2-oxo-1,2,5,6,7,8,9,10-octahydro[b]pyridine-3-carbonyl]-amino]-2-methyl-propionic acid 2-dimethylamino ethyl ester (I-325, 200 mg, 0.422 mmol) which had been obtained in Example 46, methyl iodide (262 µL) was added, and the mixture was heated and stirred at 85° C. for 1 hour in a sealed tube. After that, the solvent was removed by distillation under reduced pressure, and a pale yellow oily I-326 (244 mg, 94%) was obtained.

Example 48

Synthesis of 1-cyclohexyl-2-oxo-1,2,5,6,7,8,9,10-octahydro-cycloocta[b]pyridine-3-carboxylic acid (2-methanesulfonylamino-1,1-dimethyl-2-oxo-ethyl)-amide (I-003)

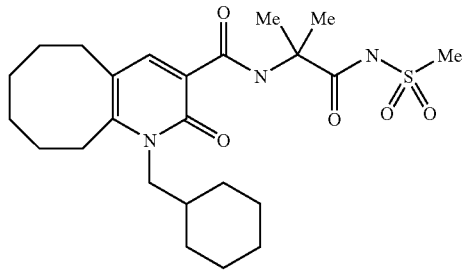

Under the nitrogen gas atmosphere, in a methylene chloride (4 mL) solution of 2-[(1-cyclohexylmethyl-2-oxo-1,2,5,6,7,8,9,10-octahydro-cycloocta[b]pyridine-3-carbonyl)-amino]-2-methyl-propionic acid (I-358, 402 mg, 1.00 mmol) which had been obtained in Example 45, oxalyl chloride (104.7 µL, 1.20 mmol) and DMF (three drops) were added, and the mixture was stirred at room temperature for 1 hour. After that, methansulfonamide (114 mg, 1.20 mmol) and DBU (448 µL, 3.0 mmol) were added and the mixture was stirred at room temperature for 7 hours. Water was added in the reaction mixture, and the mixture was acidified with hydrochloric acid and then extracted with ethyl acetate. The organic layer was washed with saturated sodium hydrogencarbonate aqueous solution and water, and then dried over anhydrous sodium sulfate. After the solvents had been removed by distillation under reduced pressure, the residue was refined with silica gel (10 g) column chromatography (the mixture of ethyl acetate-hexane of 1:1 in mixing ratio), and a colorless solid of I-003 (381 mg, 79%, mp: 186-187° C.) was obtained.

Example 49

Synthesis of 1-cyclohexylmethyl-2-oxo-1,2,5,6,7,8,9,10-octahydro-cycloocta[b]pyridine-3-carboxylic acid (1-benzylcarbamoyl-1-methyl ethyl)-amide (I-005)

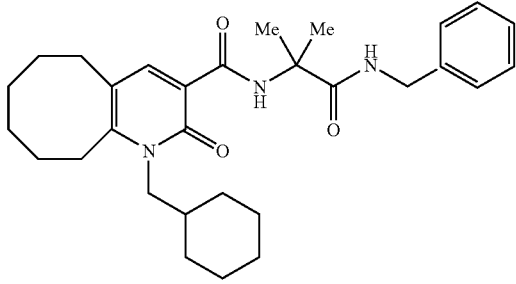

Under the nitrogen gas atmosphere, in a methylene chloride (3 mL) solution of 2-[(1-cyclohexylmethyl-2-oxo-1,2,5,6,7,8,9,10-octahydro-cycloocta[b]pyridine-3-carbonyl)-amino]-2-methyl-propionic acid (I-358, 150 mg, 0.373 mmol) which had been obtained in Example 45, oxalyl chloride (39 µL, 0.447 mmol) and DMF (one drop) were added, and the mixture was stirred at room temperature for 1 hour. After that, benzylamine (203 mL, 1.86 mmol) was added and the mixture was further stirred at room temperature for 5 hours. Water was added in the reaction mixture, and then the mixture was acidified with hydrochloric acid and extracted with ethyl acetate. The organic layer was washed with saturated aqueous sodium hydrogencarbonate solution and water, and then dried over anhydrous sodium sulfate. The solvents were removed by distillation under reduced pressure, and the residue was refined with silica gel (5 g) column chromatography (the mixture of ethyl acetate-hexane of 3:1 in mixing ratio), thus a colorless solid of I-005 (158 mg, 86%, mp: 132-134° C.) was obtained.

Example 50

Synthesis of 1-cyclohexylmethyl-2-oxo-1,2,5,6,7,8,9,10-octahydro-cycloocta[b]pyridine-3-carboxylic acid [1-(methoxymethylcarbamoyl)-1-methyl-ethyl]-amide (I-024)

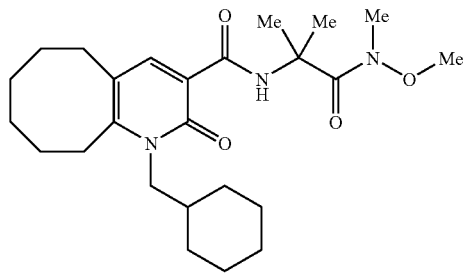

Under the nitrogen gas atmosphere, in a methylene chloride (3 mL) solution of 2-[(1-cyclohexylmethyl-2-oxo-1,2,5,6,7,8,9,10-octahydro-cycloocta[b]pyridine-3-carbonyl)-amino]-2-methyl-propionic acid (I-358, 150 mg, 0.373 mmol) which had been obtained in Example 45, oxalyl chloride (39 µL, 0.447 mmol) and DMF (one drop) were added, and the mixture was stirred at room temperature for 1 hour. Next, N,O-dimethylhydroxyamine hydrochloride (40 mg, 0.409 mmol) and triethylamine (208 µL, 1.49 mmol) were added and the mixture was stirred at room temperature for 3 hours. After that, water was added in the mixture, and the mixture was acidified with hydrochloric acid and then extracted with ethyl acetate. The organic layer was washed with saturated sodium hydrogencarbonate aqueous solution and water, and then dried over anhydrous sodium sulfate. After the solvents had been removed by distillation under reduced pressure, the residue was refined with silica gel (5 g) column chromatography (ethyl acetate), and a colorless solid of I-024 (110 mg, 65%, mp: 166 to 168° C.) was obtained.

Example 51

Synthesis of methyl 2-[(1-butyl-5-ethyl-2-oxo-6-propyl-1,2-dihydro-pyridine-3-carbonyl)-amino]-2,3-dimethyl-butyrate (I-211)

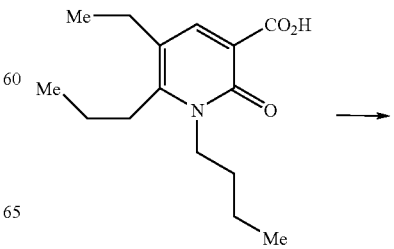

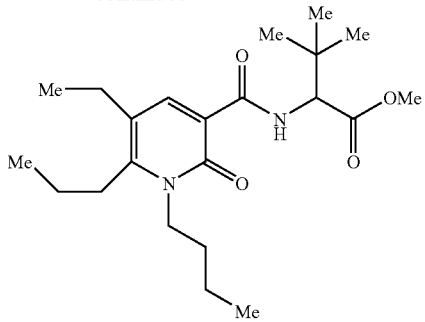

In an anhydrous THF (4 mL) solution of 1-butyl-5-ethyl-2-oxo-6-propyl-1,2-dihydropyridine-3-carboxylic acid (AA03, 425 mg, 1.60 mmol) which had been obtained in Example 3, oxalyl chloride (147 μL, 1.69 mmol) and DMF (8 μL) were added, and the mixture was stirred at room temperature for 1 hour. Next, triethylamine (0.89 mL, 6.38 mmol) and the above-mentioned acid chloride solution were sequentially added in an anhydrous DMF (4 mL) solution of L-tert-leucine methyl ester hydrochloride (349 mg, 1.92 mmol) while stirring and cooling the solution with ice. After that, the mixed solution was stirred at room temperature for 90 minutes. The reaction mixture was acidified by pouring into diluted hydrochloric acid, and then extracted with ethyl acetate. The organic layer was washed with water, saturated sodium bicarbonate aqueous solution, and water, and then dried over anhydrous magnesium sulfate. The solvents were removed by distillation under reduced pressure, and the residue was eluted and refined with silica gel (52 g) column chromatography (ethyl acetate-hexane (2:1)) to give a pale yellow oily I-211 (572 mg, 92%).

IR (CHCl3): 3236, 1738, 1666, 1617, 1578, 1528, 1465, 1437, 1404, 1371, 1323; $[\alpha]_D^{22}$+28.7±0.7° (c=1.014, MeOH);

Elemental analysis: $(C_{22}H_{36}N_2O_4 \cdot 0.1MeOH)$
Calculated (%): C, 67.07; H, 9.27; N, 7.08.
Analytical (%): C, 66.99; H, 9.27; N, 7.21.

Example 52

Synthesis of 2-[(1-butyl-5-ethyl-2-oxo-6-propyl-1,2-dihydro-pyridine-3-carbonyl)-amino]-2,3-dimethyl-butyric acid (I-438)

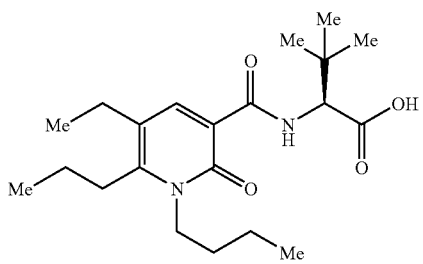

Methyl 2-[(1-butyl-5-ethyl-2-oxo-6-propyl-1,2-dihydro-pyridine-3-carbonyl)-amino]-2,3-dimethyl-butyrate (I-211, 313 mg, 0.797 mmol) which had been obtained in Example 51 was dissolved in methanol (8 mL), and the solution was stirred together with 4M sodium hydroxide aqueous solution (0.8 mL) at 50° C. for 25 hours. The reaction mixture was poured into water, and the water layer was washed with ethyl ether. The water layer was acidified with 2M hydrochloric acid aqueous solution and extracted with ethyl acetate. The organic layer was washed with water and dried over anhydrous magnesium sulfate, and then the solvent was removed by distillation and colorless solid matter (331 mg) was obtained. This solid matter was recrystallized with ethyl acetate-hexane, and a colorless prism-like crystal of I-438 (271 mg, 88%) was obtained.

Mp: 140-141° C.

IR (nujol): 2607, 1727, 1657, 1577, 1533, 1467, 1406, 1374, 1334; $[\alpha]_D^{22}$+31.2±0.7° (c=1.007, MeOH);

Elemental analysis: $(C_{21}H_{34}N_2O_4 \cdot 0.2H_2O)$
Calculated (%): C, 66.15; H, 9.11; N, 7.28.
Analytical (%): C, 66.17; H, 9.12; N, 7.40.

Example 53

Synthesis of ethyl 2-[(1-butyl-5-ethyl-2-oxo-6-propyl-1,2-dihydropyridine-3-carbonyl)-amino]-cyclohexanecarboxylate (II-029)

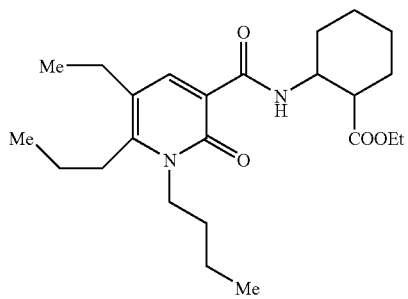

In the anhydrous THF (4 mL) solution of 1-butyl-5-ethyl-2-oxo-6-propyl-1,2-dihydropyridine-3-carboxylic acid (AA03, 451 mg, 1.70 mmol) which had been obtained in Example 3, oxalyl chloride (156 μL, 1.79 mmol) and DMF (8 μL) were added, and the mixture was stirred at room temperature for 1 hour. Next, triethylamine (0.95 mL, 6.81 mmol) and then the above-mentioned acid chloride solution were added in the anhydrous DMF (4 mL) solution of 2-amino-1-ethyl cyclohexanecarboxylate hydrochloride (424 mg, 2.04 mmol) while stirring and cooling the solution with ice. After that, the mixed solution was stirred at room temperature for 90 minutes. The reaction mixture was acidified by pouring into diluted hydrochloric acid, and then extracted with ethyl acetate. The organic layer was washed with water, saturated sodium bicarbonate aqueous solution, and water, and then dried over anhydrous magnesium sulfate. The solvents were removed by distillation under reduced pressure, and the residue was eluted and refined with silica gel (57 g) column chromatography (ethyl acetate-hexane (2:1)) to give a pale yellow oily II-029 (694 mg, 96%).

IR (CHCl3): 3252, 1724, 1664, 1615, 1578, 1529, 1464, 1406, 1378, 1312;

Elemental analysis: $(C_{24}H_{32}N_2O_4 \cdot 0.2MeOH)$
Calculated: C, 68.39; H, 9.20; N, 6.59.
Analytical: C, 68.32; H, 9.39; N, 6.79.

Example 54

Synthesis of 2-[(1-butyl-5-ethyl-2-oxo-6-propyl-1,2-dihydropyridine-3-carbonyl)-amino]-cyclohexanecarboxylic acid (II-056)

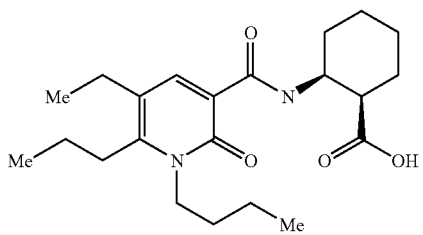

In the methanol (9 mL) solution of 2-[(1-butyl-5-ethyl-2-oxo-6-propyl-1,2-dihydropyridine-3-carbonyl)-amino]-ethyl cyclohexanecarboxylate (II-029, 368 mg, 0.88 mmol) which had been obtained in Example 53, 4M sodium hydroxide aqueous solution (0.66 mL, 2.66 mmol) was added, and the mixture was stirred at 50° C. for 25.5 hours. The reaction mixture was poured into water and washed with ethyl ether. The water layer was acidified with 2M hydrochloric acid aqueous solution and extracted with ethyl acetate. The organic layer was washed with water and dried over anhydrous magnesium sulfate, and then the solvent was removed by distillation and a colorless foam-like substance (359 mg) was obtained. This substance was recrystallized with ethyl acetate-hexane, and a colorless columnar crystal of II-056 (296 mg, 86%) was obtained.

Mp: 167-169° C.
IR (nujol): 3190, 3060, 1724, 1656, 1599, 1582, 1538, 1482, 1462, 1409, 1377, 1348, 1319;
Elemental analysis: ($C_{22}H_{34}N_2O_4$)
Calculated: C, 67.66; H, 8.78; N, 7.17.
Analytical: C, 67.61; H, 8.76; N, 7.32.

Example 55

Synthesis of methyl 1-{[(3-methanesulfonylaminopropyl)-2-oxo-1,2,5,6,7,8,9,10-octahydro-cycloocta[b]pyridine-3-carbonyl]-amino}-methyl-propionate (I-240)

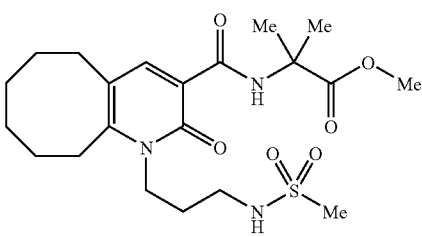

In the anhydrous THF (4 mL) solution of 1-(3-methanesulfonylaminopropyl)-2-oxo-1,2,5,6,7,8,9,10-octahydro-cycloocta[b]pyridine-3-carboxylic acid (AA22, 425 mg, 1.19 mmol) which had been obtained in Example 22, oxalyl chloride (109 μL, 1.25 mmol) and DMF (6 μL) were added, and the mixture was stirred at room temperature for 1 hour. Next, triethylamine (0.67 mL, 4.80 mmol) and the above-mentioned acid chloride solution were sequentially added in the anhydrous DMF (4 mL) solution of dimethylglycine methyl ester hydrochloride (220 mg, 1.43 mmol) while stirring and cooling the solution with ice, and the mixture was stirred at room temperature for 16 hours. The reaction mixture was acidified by pouring into diluted hydrochloric acid, and then extracted with ethyl acetate. The organic layer was washed with water, saturated sodium bicarbonate water, and water, and then dried over anhydrous magnesium sulfate. The solvents were removed by distillation under reduced pressure, and the residue was eluted and refined with silica gel (48 g) column chromatography (ethyl acetate-hexane (1:1) and then ethyl acetate) to give a colorless foam-like substance (544 mg). This substance was recrystallized with ethyl acetate-methanol-hexane, and a colorless columnar crystal of I-240 (499 mg, 92%, mp: 156-157° C.) was obtained.

NMR: (CDCl₃) 1.32-1.54 (m, 4H), 1.60-1.84 (m, 4H), 1.62 (s, 6H), 1.95-2.06 (m, 2H), 2.60-2.64 (m, 2H), 2.88-2.92 (m, 2H), 2.97 (s, 3H), 3.06-3.18 (m, 2H), 3.76 (s, 3H), 4.24-4.36 (m, 2H), 5.74 (t, 1H, J=6.0), 8.30 (s, 1H), 10.17 (s, 1H);
IR (chloroform): 3257, 1738, 1667, 1619, 1577, 1529, 1484, 1458, 1439, 1408, 1384, 1363, 1329;
Elemental analysis: ($C_{21}H_{33}N_3O_6S$)
Calculated: C, 55.36; H, 7.30; N, 9.22; S, 7.04.
Analytical: C, 55.25; H, 7.39; N, 9.14; S, 6.98.

Example 56

Synthesis of 1-{[(3-methanesulfonylaminopropyl)-2-oxo-1,2,5,6,7,8,9,10-octahydro-cycloocta[b]pyridine-3-carbonyl]-amino}-methyl-propionic acid (I-506)

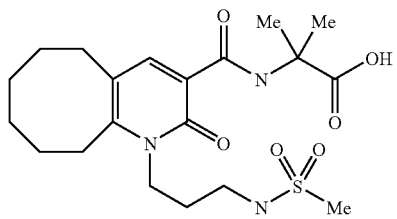

In a methanol (7 mL) solution of methyl 1-{[(3-methanesulfonylamino-propyl)-2-oxo-1,2,5,6,7,8,9,10-octahydro-cycloocta[b]pyridine-3-carbonyl]-amino}-methyl-propionate (I-240, 269 mg, 0.59 mmol) which had been obtained in Example 55, 4M sodium hydroxide aqueous solution (0.45 mL, 1.81 mmol) was added, and the mixture was stirred at 50° C. for 17 hours. After that, the reaction mixture was poured into water and washed with ethyl ether. The water layer was acidified with 2M hydrochloric acid aqueous solution and extracted with ethyl acetate. The organic layer was washed with water and dried over anhydrous magnesium sulfate, and a colorless foam-like substance (282 mg) was obtained. This substance was recrystallized with ethyl acetate-hexane, and a colorless prism-like crystal of I-506 (226 mg, 87%, mp: 183-184° C.) was obtained.

NMR: (DMSO-d₆) 1.25-1.88 (m, 10H), 1.48 (s, 6H), 2.60-2.70 (m, 2H), 2.90-3.01 (m, 2H), 2.93 (s, 3H), 3.03-3.12 (m, 2H), 4.07-4.18 (m, 2H), 7.15 (t, 1H, J=6.0), 8.09 (s, 1H), 10.22 (s, 1H), 12.40 (brs, 1H);
IR (nujol): 3171, 3029, 1736, 1657, 1581, 1537, 1485, 1460, 1413, 1377, 1364, 1334, 1318;
Elemental analysis: ($C_{20}H_{31}N_3O_6S$)
Calculated: C, 54.40; H, 7.08; N, 9.52; S, 7.26.
Analytical: C, 54.37; H, 7.02; N, 9.29; S, 7.16.

Example 57

Synthesis of methyl 1-{[(3-acetylamino-propyl)-2-oxo-1,2,5,6,7,8,9,10-octahydro-cycloocta[b]pyridine-3-carbonyl]-amino}-methyl-propionate (I-251)

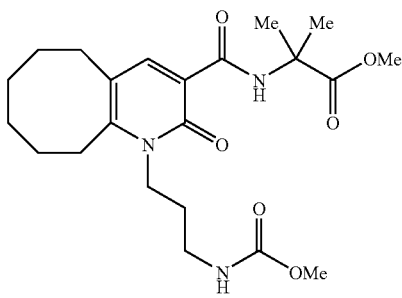

1-(3-Acetylaminopropyl)-2-oxo-1,2,5,6,7,8,9,10-octahydro-cycloocta[b]pyridine-3-carboxylic acid (AA23, 240 mg, 0.71 mmol) which had been obtained in Example 23 was dissolved in anhydrous THF (3 mL), oxalyl chloride (65 μL, 0.75 mmol) and DMF (5 μL) were added, and the mixture was stirred at room temperature for 1 hour. Dimethylglycine methyl ester hydrochloride (131 mg, 0.85 mmol) was dissolved in anhydrous DMF (3 mL), and triethylamine (0.40 mL, 2.87 mmol) and then the above-mentioned acid chloride solution were added while stirring and cooling the solution with ice. After that, the mixture was stirred at room temperature for 1 hour. The reaction mixture was acidified by pouring into diluted hydrochloric acid, and then extracted with ethyl acetate. The organic layer was washed with water, saturated sodium bicarbonate aqueous solution, and water, and then dried over anhydrous magnesium sulfate. The solvents were removed by distillation under reduced pressure, and the residue was sequentially eluted and refined with silica gel (46 g) column chromatography (ethyl acetate-hexane (2:1) and ethyl acetate) to give a colorless foam-like substance (296 mg). This substance was recrystallized with ethyl acetate-methanol-hexane, and a colorless mineral phosphate-like crystal of I-251 (273 mg, 88%, mp: 135-136° C.) was obtained.

NMR: (CDCl$_3$) 1.32-1.53 (m, 4H), 1.60-1.80 (m, 4H), 1.63 (s, 6H), 1.1.97 (m, 2H), 2.59-2.63 (m, 2H), 2.86-2.90 (m, 2H), 3.18-3.29 (m, 2H), 3.69 (s, 3H), 3.76 (s, 3H), 4.15-4.27 (m, 2H), 5.50 (m, 1H), 8.28 (s, 1H), 10.24 (s, 1H);

IR (chloroform): 3453, 3256, 1723, 1667, 1619, 1577, 1528, 1484, 1439, 1409, 1384, 1364, 1333;

Elemental analysis: ($C_{22}H_{33}N_3O_6$)

Calculated: C, 60.67; H, 7.64; N, 9.65.

Analytical: C, 60.49; H, 7.60; N, 9.59

Example 58

Synthesis of 1-{[(3-acethyamino-propyl)-2-oxo-1,2,5,6,7,8,9,10-octahydro-cycloocta[b]pyridine-3-carbonyl]-amino}-methyl-propionic acid (I-518)

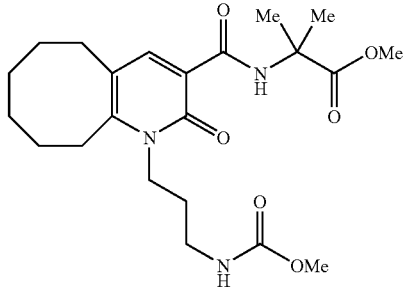

Methyl 1-{[(3-acetylamino-propyl)-2-oxo-1,2,5,6,7,8,9,10-octahydro-cycloocta[b]pyridine-3-carbonyl]-amino}-methyl-propionate (AA24, 153 mg, 0.35 mmol) which had been obtained in Example 24 was dissolved in methanol (3 mL), 4M sodium hydroxide aqueous solution (0.26 mL, 1.05 mmol) was added, and the mixture was stirred at 50° C. for 5 hours. After standing to cool, the reaction mixture was poured into water, and the water layer was washed with ethyl ether. The water layer was acidified with 2M aqueous hydrochloric acid solution, and then extracted with ethyl acetate. The organic layer was washed with water and dried over anhydrous magnesium sulfate, and then the solvent was removed by distillation and a colorless oily I-518 (148 mg, 96%) was obtained.

NMR: (DMSO-d$_6$) 1.24-1.82 (m, 10H), 1.48 (s, 6H), 2.60-2.68 (m, 2H), 2.86-2.96 (m, 2H), 3.05-3.16 (m, 2H), 3.53 (s, 3H), 4.00-4.14 (m, 2H), 7.27 (m, 1H), 8.08 (s, 1H), 10.21 (s, 1H), 12.42 (brs, 1H);

IR (KBr): 3391, 1726, 1665, 1620, 1577, 1530, 1456, 1409, 1382, 1362, 1315;

Elemental analysis: ($C_{21}H_{31}N_3O_6$·0.1AcOEt·0.4H$_2$O)

Calculated: C, 58.75; H, 7.51; N, 9.60.

Analytical: C, 58.81; H, 7.35; N, 9.59.

Example 59

The synthesis of 2-[(1-cyclohexylmethyl-2-oxo-1,2,5,6,7,8,9,10-octahydro-cycloocta[b]pyridine-3-carbonyl)-amino]-2-methyl-propionic acid 5-methyl-2-oxo-[1,3]-dioxol-4-ylmethyl ester (-308)

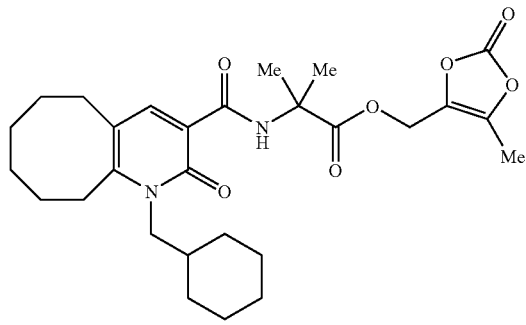

2-[(1-Cyclohexylmethyl-2-oxo-1,2,5,6,7,8,9,10-octahydro-cycloocta[b]pyridine-3-carbonyl)-amino]-2-methylpropionic acid (I-358, 250 mg, 0.621 mmol) which had been obtained in Example 45, 4-bromomethyl-5-methyl-[1,3]dioxol-2-on (180 mg, 0.933 mmol), and potassium bicarbonate (150 mg, 1.50 mmol) were suspended in DMF (2.5 mL), and the suspension was stirred at room temperature for 15 hours. After that, 5% citric acid aqueous solution was added, and the suspension was extracted with ethyl acetate. The organic layer was washed with water and saturated saline, and dried over sodium sulfate, and then the solvents were removed by distillation. The residue was refined with silica gel column chromatography (hexane-ethyl acetate (30-34%)), and I-308 was obtained as colorless foam-like matter (318 mg, 99%).

Example 60

Synthesis of 2-[(1-cyclohexylmethyl-2-oxo-1,2,5,6,7,8,9,10-octahydro-cycloocta[b]pyridine-3-carbonyl)-amino]-2-methyl-propionic acid trans-2-phenyl-[1,3]dioxane-5-yl ester (I-302)

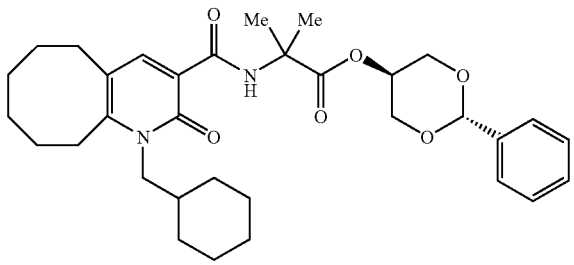

2-[(1-Cyclohexylmethyl-2-oxo-1,2,5,6,7,8,9,10-octahydro-cycloocta[b]pyridine-3-carbonyl)-amino]-2-methyl-propionic acid (I-358, 200 mg, 0.497 mmol) which had been obtained in Example 45 was transformed to the acid chloride using oxalyl chloride-DMF by the usual way, and then pyridine (1 mL) and trans-2-phenyl-[1,3]dioxan-5-ol (180 mg, 1.00 mmol) were added, and the mixture was reacted at room temperature for one hour, subsequently at 50° C. for 1 hour. After that, diluted hydrochloric acid was added in the reaction mixture, and then the mixture was extracted with ethyl acetate. The organic layer was washed with water, saturated sodium bicarbonate water, and saturated saline in order, and then dried. After that, the solvent was removed by distillation, and the residue was refined with silica gel column chromatography (hexane-ethyl acetate (40 to 50%)), and further recrystallized from methanol, resulting in obtaining I-302 as a colorless needle crystal (57 mg, 20%, mp: 166-168° C.).

Example 61

Synthesis of 2-[(1-cyclohexylmethyl-2-oxo-1,2,5,6,7,8,9,10-octahydro-cycloocta[b]pyridine-3-carbonyl)-amino]-2-methyl-propionic acid 2-hydroxy-1-hydroxymethyl-ethyl ester (I-303)

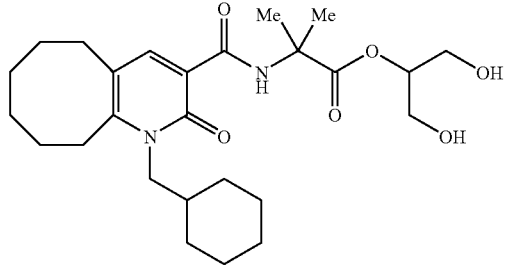

2-[(1-Cyclohexylmethyl-2-oxo-1,2,5,6,7,8,9,10-octahydro-cycloocta[b]pyridine-3-carbonyl)-amino]-2-methyl-propionic acid trans-2-phenyl-[1,3]dioxane-5-yl ester (I-302, 255 mg, 0.451 mmol) which had been obtained in Example 60 was dissolved in the mixture of methanol (1 mL), THF (2 mL), and 2M hydrochloric acid (1 mL), and the solution was stirred at room temperature for 3 hours. The solution was diluted with water and extracted with ethyl acetate. The organic layer was washed with water and dried, and then the solvents were removed by distillation. The residue was refined with silica gel column chromatography (hexane-ethyl acetate (35-80%)), and further recrystallized from hexane, and I-303 was obtained as a colorless crystal (85 mg, 40%, mp: 123-125° C.).

Example 62

Synthesis of 2-[(1-cyclohexylmethyl-2-oxo-1,2,5,6,7,8,9,10-octahydro-cycloocta[b]pyridine-3-carbonyl)-amino]-2-methyl-propionic acid 2-oxo-[1,3]dioxolan-4-yl ester (I-309)

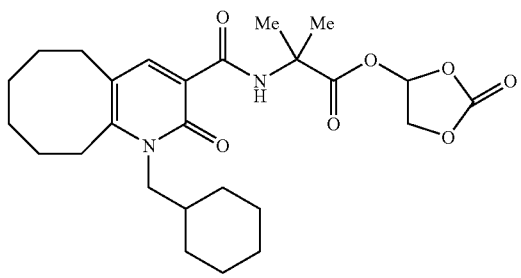

2-[(1-Cyclohexylmethyl-2-oxo-1,2,5,6,7,8,9,10-octahydro-cycloocta[b]pyridine-3-carbonyl)-amino]-2-methyl-propionic acid (I-358, 250 mg, 0.621 mmol) which had been obtained in Example 45, 4-chloro-[1,3]dioxolan-2-one (84 μL, 0.93 mmol), potassium bicarbonate (186 mg, 1.86 mmol), and a small quantity of potassium iodide were suspended in DMF (2.5 mL), and the suspension was stirred at room temperature for 15 hours. After that, 5% citric acid aqueous solution was added, and the suspension was extracted with ethyl acetate. The organic layer was washed with water and saturated saline, and dried over sodium sulfate, and then the solvents were removed by distillation. The residue was refined with silica gel column chromatography (hexane-ethyl acetate (30%)), and I-309 was obtained as colorless foam-like matter (96 mg, 31%).

Example 63

Synthesis of 2-[(1-cyclohexylmethyl-2-oxo-1,2,5,6,7,8,9,10-octahydro-cycloocta[b]pyridine-3-carbonyl)-amino]-2-methyl-thiopropionic acid S-methyl ester (I-001)

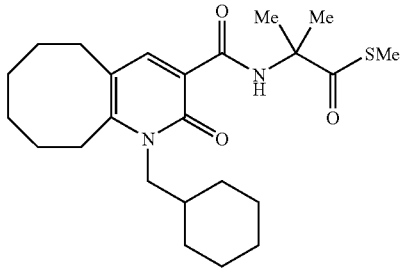

2-[(1-Cyclohexylmethyl-2-oxo-1,2,5,6,7,8,9,10-octahydro-cycloocta[b]pyridine-3-carbonyl)-amino]-2-methyl-propionic acid (I-358, 250 mg, 0.621 mmol) which had been obtained in Example 45 was made to be the acid chloride by the oxalyl chloride-DMF method according to the usual way, and then the acid chloride was dissolved in DMF (2 mL). After that, sodium thiomethoxide (92 mg, 1.24 mmol) was added, and the mixture was reacted for 30 minutes while cooling with ice, and further for 2 hours at room temperature. After that, the same treatment as described above was conducted, and then the residue was refined with silica gel column chromatography (hexane-ethyl acetate (25%)), and I-001 was obtained as a colorless crystal (140 mg, 52%, mp: 196-198° C.).

Example 64

Synthesis of 1-cyclohexylmethyl-2-oxo-1,2,5,6,7,8,9,10-octahydro-cycloocta[b]pyridine-3-carboxylic acid {1-[(2-hydroxyethyl)-methyl-carbamoyl]-1-methyl-ethyl}-amide (I-019)

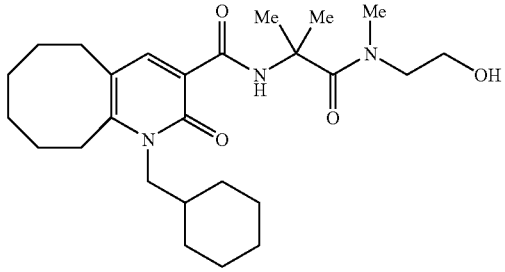

2-[(1-Cyclohexylmethyl-2-oxo-1,2,5,6,7,8,9,10-octahydro-cycloocta[b]pyridine-3-carbonyl)-amino]-2-methyl-propionic acid (I-358, 250 mg, 0.621 mmol) which had been obtained in Example 45, N-methyl ethanolamine (60 µL, 0.745 mmol), WSCD (143 mg, 0.683 mmol), and a small quantity of HOBt were reacted in DMF (2.5 mL) at room temperature for 18 hours. After that, the same treatment as described above was conducted, and then the residue was refined with silica gel column chromatography (ethyl acetate), and I-019 was obtained as a colorless solid (171 mg, 60%, mp: 195-196° C.).

Example 65

Synthesis of 1-cyclohexylmethyl-2-oxo-1,2,5,6,7,8,9,10-octahydro-cycloocta[b]pyridine-3-carboxylic acid (2-oxo-tetrahydrofuran-3-yl)-amide (I-072)

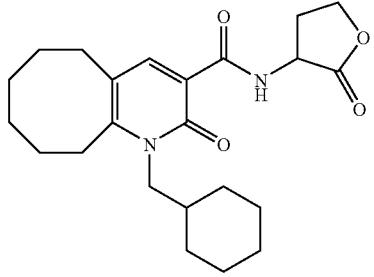

1-Cyclohexylmethyl-2-oxo-1,2,5,6,7,8,9,10-octahydro-cycloocta[b]pyridine-3-carboxylic acid (AA01, 250 mg, 0.788 mmol) which had been obtained in Example 1 was made to be the acid chloride according to the conventional method, and the acid chloride was dissolved in THF. Then, the solution was dropped into the DMF (2 mL) mixed liquid of 3-amino-dihydro-furan-2-one hydrobromide (187 mg, 1.03 mmol) and triethylamine (0.38 mL, 2.36 mmol) while cooling with ice. After that, the mixture was stirred at the same temperature for 30 minutes, and further stirred continuously at room temperature for 3 hours. The mixture was subjected to the same after-treatment as described above, and then refined with silica gel column chromatography (hexane-ethyl acetate (40 to 60%)), and I-072 was obtained as a colorless solid (242 mg, 77%, mp: 136-140° C.).

Example 66

Synthesis of 1-[(1-cyclohexylmethyl-4-hydroxy-2-oxo-1,2,5,6,7,8,9,10-octahydro-cycloocta[b]pyridine-3-carbonyl)-amino]-cyclohexanecarboxylic acid methyl ester (I-149)

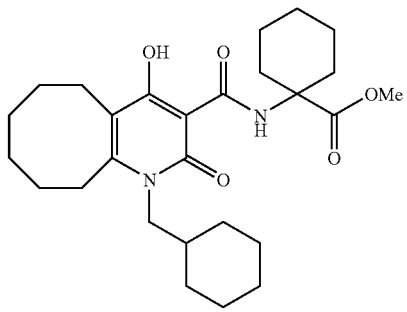

A toluene (4 mL) solution of ethyl 1-cyclohexylmethyl-4-hydroxy-2-oxo-1,2,5,6,7,8,9,10-octahydro-cycloocta[b]pyridine-3-carboxylate (AA16, 250 mg, 0.692 mmol) which had been obtained in Example 16, 1-amino-methyl cyclohexanecarboxylate hydrochloride (174 mg, 0.90 mmol), and triethylamine (125 µL, 0.90 mmol) was refluxed for 20 hours. After the reaction mixture had been cooled to room temperature, the insoluble matter was removed by filtration, and the filtrate was concentrated. Then the residue was refined with silica gel column chromatography (hexane-ethyl acetate (10 to 15%)), and I-149 was obtained as colorless foam-like matter (223 mg, 68%).

Example 67

Synthesis of ethyl 2-[(1-cyclohexylmethyl-4-hydroxy-2-oxo-1,2,5,6,7,8,9,10-octahydro-cycloocta[b]pyridine-3-carbonyl)-amino]-cyclohexanecarboxylate (II-023)

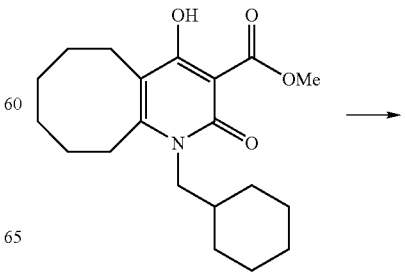

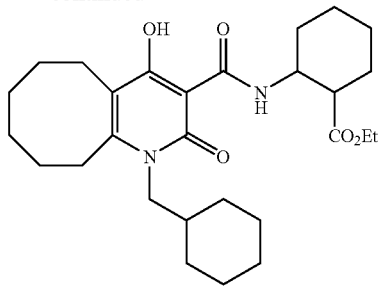

II-023 was synthesized by the quite similar method to that in Example 66.

Example 68

Synthesis of 1-butyl-4-hydroxy-2-oxo-1,2,5,6,7,8,9,10-octahydro-cyclohepta[b]pyridine-3-carboxylic acid (2-oxo-azepane-3-yl)-amide (I-071)

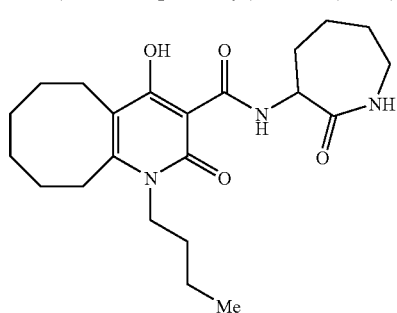

I-071 was synthesized by the quite similar method to that in Example 66.

Example 69

Synthesis of 1-cyclohexylmethyl-2-oxo-1,2,5,6,7,8,9,10-octahydro-cycloocta[b]pyridine-3-carboxylic acid (1-hydrazinocarbonyl-1-methyl-ethyl)-amide (I-050)

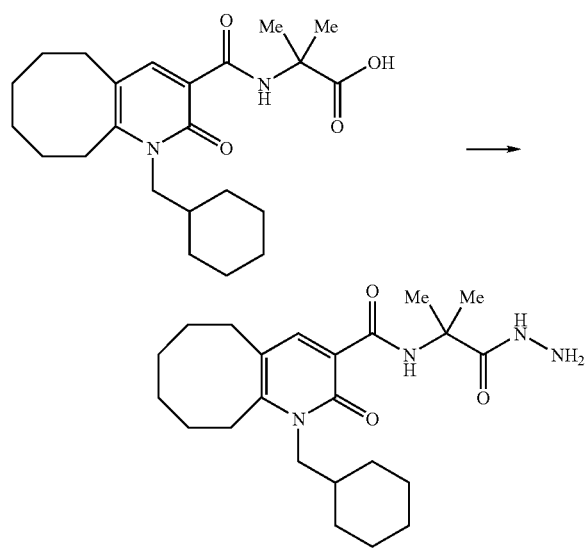

2-[(1-Cyclohexylmethyl-2-oxo-1,2,5,6,7,8,9,10-octahydro-cycloocta[b]pyridine-3-carbonyl)-amino]-2-methyl-propionic acid (I-358, 403 mg, 1.00 mmol) which had been obtained in Example 45 was suspended in anhydrous DMF (4 mL), and stirred together with WSCD (422 mg, 2.20 mmol), HOBt (27 mg, 0.20 mmol), and hydrazine monohydrate (58 μL, 1.20 mmol) at room temperature for 2 hours. The reaction mixture was poured into water and extracted with ethyl acetate. The organic layer was washed with water, saturated sodium bicarbonate aqueous solution, and water, and dried over anhydrous magnesium sulfate, and then the solvent was removed by distillation under reduced pressure. The residue was recrystallized with ethyl acetate-methanol-hexane and a colorless needle crystal of I-050 (339 mg, 81%, mp: 177-180° C.) was obtained.

IR (nujol): 3343, 3216, 3177, 1665, 1605, 1579, 1526, 1455, 1410, 1377, 1360, 1333;

Elemental analysis: ($C_{23}H_{36}N_4O_3$)

Calculated: C, 66.32; H, 8.71; N, 13.45.

Analytical: C, 66.11; H, 8.78; N, 13.20.

Example 70

Synthesis of 1-cyclohexylmethyl-2-oxo-1,2,5,6,7,8,9,10-octahydro-cycloocta[b]pyridine-3-carboxylic acid (1-methylsulfonylhydrazinocarbonyl-1-methyl-ethyl)-amide (I-052)

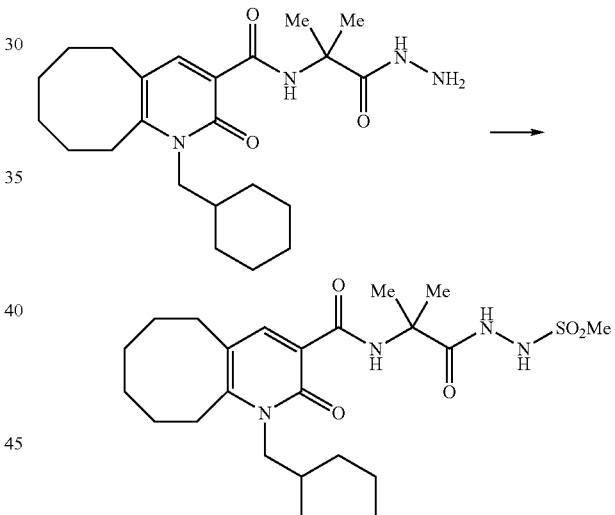

1-Cyclohexylmethyl-2-oxo-1,2,5,6,7,8,9,10-octahydro-cycloocta[b]pyridine-3-carboxylic acid (1-hydrazinocarbonyl-1-methyl-ethyl)-amide (I-050, 24 g, 2.98 mmol) which had been obtained in Example 69 was suspended in anhydrous THF (13 mL), and pyridine (0.48 mL, 5.94 mmol) and methanesulfonyl chloride (0.35 mL, 4.52 mmol) was added while stirring and cooling the suspension with ice. After that, the mixture was stirred at room temperature for 2 hours and 30 minutes. The reaction mixture was acidified by pouring into diluted hydrochloric acid, and then extracted with ethyl acetate. The organic layer was washed with water, saturated sodium bicarbonate aqueous solution, and water, and then dried over anhydrous magnesium sulfate. The solvents were removed by distillation under reduced pressure, and the residue was eluted and refined with silica gel (61 g) column chromatography (ethyl acetate-hexane (1:1) and then ethyl acetate) to give a colorless crystal of I-052 (1.57 g). This was

Example 71

Synthesis of 1-cyclohexylmethyl-2-oxo-1,2,5,6,7,8,9,10-octahydro-cycloocta[b]pyridine-3-carboxylic acid [1,1-dimethyl-2-(4-methyl-piperazine-1-yl)-2-oxo-ethyl]-amide (I-047)

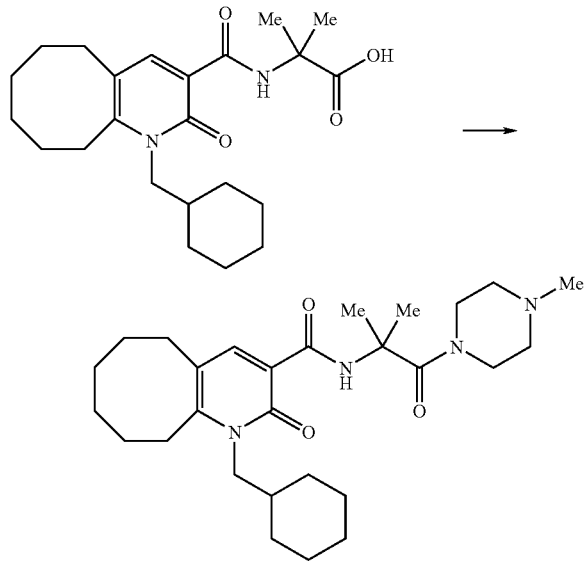

2-[(1-Cyclohexylmethyl-2-oxo-1,2,5,6,7,8,9,10-octahydro-cycloocta[b]pyridine-3-carbonyl)-amino]-2-methyl-propionic acid (I-358, 350 mg, 0.87 mmol) which had been obtained in Example 45 was suspended in anhydrous DMF (5 mL), and WSCD (200 mg, 1.04 mmol), HOBt (24 mg, 0.18 mmol), and N-methyl piperazine (116 mL, 1.05 mmol) were added and the mixture was stirred at room temperature for 2 hours. The reaction mixture was poured into water and extracted with ethyl acetate. The organic layer was washed with water, saturated sodium bicarbonate water, and water, and then dried over anhydrous magnesium sulfate. The solvents were removed by distillation under reduced pressure, and the residue was recrystallized with ethyl acetate-methanol-hexane and a colorless needle crystal of I-047 (313 mg, 74%, mp: 183-184° C.) was obtained.

IR (nujol): 3179, 2791, 2761, 2745, 1668, 1639, 1621, 1581, 1548, 1519, 1459, 1442, 1419, 1378, 1360, 1335, 1317;

Elemental analysis: ($C_{28}H_{44}N_4O_3$)

Calculated: C, 69.39; H, 9.15; N, 11.56.

Analytical: C, 69.27; H, 9.10; N, 11.53.

Example 72

Synthesis of methyl 2-[(1-cyclohexylmethyl-2,6-dioxo-1,2,5,6,7,8, hexahydro-6-thiopyrano[4,3-b]pyridine-3-carbonyl]-amino)-3-methyl-butyrate (I-258)

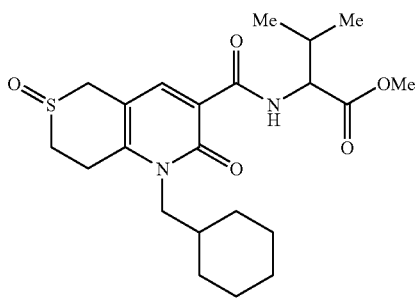

1-Cyclohexylmethyl-2-oxo-1,5,7,8,tetrahydro-2H-thiopyrano[4,3-b]pyridine-3-carboxylic acid (AA09) which had been obtained in Example 9 was dissolved in a chloroform (7 mL) solution of methyl 2-[(1-cyclohexylmethyl-2-oxo-1,5,7,8,tetrahydro-6-thiopyrano[4,3-b]pyridine-3-carbonyl)-amino]-3-methyl-butyrate (I-256, 350 mg, 0.832 mmol) which had been synthesized by the method similar to that in Example 37, and then methchlorobenzoic acid (215 mg, 1.25 mmol) was added while cooling the solution with ice, and the mixture was stirred at the same temperature for 12 minutes. The reaction mixture was washed with saturated aqueous sodium hydrogencarbonate solution and water, and then the organic layer was dried over anhydrous magnesium sulfate. The solvent was removed by distillation under reduced pressure, and the residue was refined with silica gel (42 g) column chromatography (chloroform-methanol of 50:1 and then that of 25:1), and colorless oily matter (330 mg) was obtained. This oily matter was recrystallized from ethyl acetate-methanol to give the white crystalline powder of I-258 (247 mg, 68.0%, mp: 216-218° C.).

IR (nujol): 3226 (NH), 1736, 1663, 1530 (C=O)

Example 73

Synthesis of methyl 2-[(1-cyclohexylmethyl-2,6,6-trioxo-1,2,5,6,7,8,hexahydro-6-thiopyrano[4,3-b]pyridine-3-carbonyl]-amino)-3-methyl-butyrate (I-257)

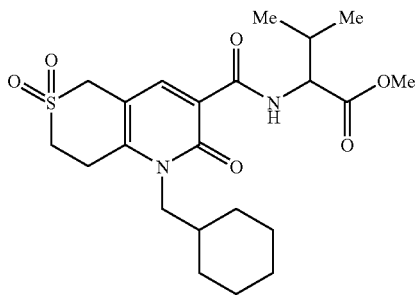

1-Cyclohexylmethyl-2-oxo-1,5,7,8,tetrahydro-2H-thiopyrano[4,3-b]pyridine-3-carboxylic acid (AA09) which had been obtained in Example 9 was dissolved in the chloroform (7 mL) solution of 2-[(1-cyclohexylmethyl-2-oxo-1,5,7,8,tetrahydro-6-thiopyrano[4,3-b]pyridine-3-carbonyl)-amino]-3-methyl-methyl butyrate (I-256, 350 mg, 0.832 mmol) which had been synthesized using a method similar to that of Example 37, and then methchlorobenzoic acid (442 mg, 2.56 mmol) was added while cooling the solution with ice, and the mixture was stirred at the same temperature for 10 minutes. After that, the temperature was raised to room temperature, and the mixture was further stirred for 3 hours. The reaction mixture was washed with saturated sodium hydrogencarbonate aqueous solution and water, and then the organic layer was dried over anhydrous magnesium sulfate. The solvent was removed by distillation under reduced pressure, and a white solid of I-257 (428 mg) was obtained. This solid was recrystallized from ethyl acetate-hexane, and white crystalline powder (297 mg, 78.8%, mp: 242-245° C.) was obtained.

IR (nujol): 3235 (NH), 1741, 1662, 1532 (C=O)

Example 74

Synthesis of methyl [(6-ethyl-1-(4-fluoro-benzyl)-5-methyl-2-oxo-1,2-dihydropyridine-3-carbonyl)-amino]-thiophene-2-yl-acetate (I-273)

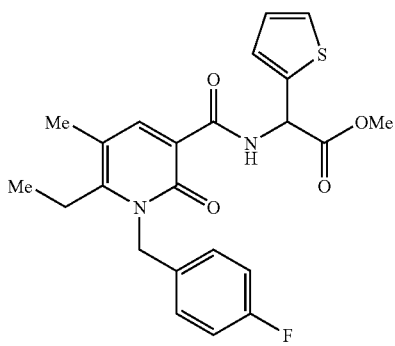

In an anhydrous THF (3 mL) solution of 6-ethyl-1-(4-fluorobenzyl)-5-methyl-2-oxo-1,2-dihydropyridine-3-carboxylic acid (289 mg, 1.00 mmol), oxalyl chloride (0.10 mL, 1.15 mmol) and DMF (10 μL) were added at room temperature, and the mixture was stirred for 15 minutes. This THF solution was dropped in the anhydrous DMF (3 mL) solution of N-α-(2-thienyl)glycine methyl ester hydrochloride (208 mg, 1.00 mmol), which had been synthesized using a method similar to that of Example 25, and triethylamine (0.56 mL, 4.00 mmol), while cooling the solution with ice. After that, the mixture was heated to room temperature, and further stirred for four hours. Water and 2M hydrochloric acid (2 mL) were added in the reaction mixture, and the mixture was extracted with ethyl acetate. The organic layer was washed with water two times, and dried over anhydrous magnesium sulfate. The solvents were removed by distillation under reduced pressure, and a yellow solid was obtained. This solid was recrystallized from ethyl acetate-hexane, and the straw-color crystalline powder of I-273 (365 mg, 82.5%, mp: 182-184° C.) was obtained.

IR (nujol): 3151 (NH), 1748, 1668, 1510 (C=O)

Example 75

Synthesis of (−)-[(1-cyclohexylmethyl-2-oxo-1,2,5,6,7,8,9,10-octahydro-cycloocta[b]pyridine-3-carbonyl)-amino]-phenylacetic acid (I-195)

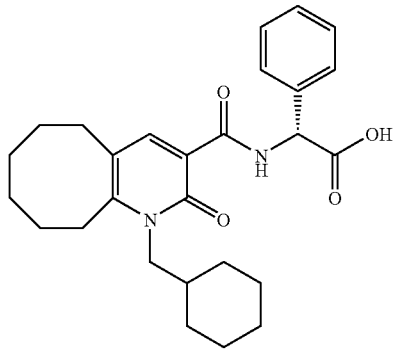

In an anhydrous THF (3 mL) solution of 1-cyclohexylmethyl-2-oxo-1,2,5,6,7,8,9,10-octahydro-cycloocta[b]pyridine-3-carboxylic acid (AA01, 317 mg, 1.00 mmol) which had been obtained in Example 1, oxalyl chloride (0.10 mL, 1.15 mmol) and DMF (10 μL) were added at room temperature, and the mixture was stirred for 15 minutes. This THF solution was dropped into the anhydrous DMF (3 mL) solution of (−)-α-phenylglycine benzohydrile ester para-toluene sulfonate (514 mg, 1.05 mmol) and triethylamine (0.56 mL, 4.00 mmol), while cooling the solution with ice. After that, the mixture was stirred at the same temperature for 50 minutes and was acidified by adding ice water and then 2M hydrochloride acid (2 mL). After that, the mixture was extracted with ethyl acetate (15 mL). The organic layer was washed with water two times, and dried over anhydrous magnesium sulfate. The solvents were removed by distillation under reduced pressure, and a colorless solid ester body (629 mg) was obtained. This ester body was recrystallized from ethyl acetate-hexane, and white crystalline powder (439 mg, 71.2%) was obtained.

Mp: 178-180° C.
IR (nujol): 3196(NH), 1745, 1667, 1532 (C=O);
NMR: (CDCl$_3$) 0.98-1.92 (m, 19H), 2.60 (t, 2H, J=6.0), 2.90 (t, 2H, J=6.3). 4.01 (br, 2H), 5.90 (d, 1H, J=6.19), 6.87 (s, 1H), 6.97-7.46 (m, 15H), 8.24 (s, 1H), 11.04 (d, 1H, J=6.9);
[α]$_D$ −5.2±0.50 (22° C., C=1.002, CDCl$_3$)

Successively, trifluoroacetic acid (0.4 mL) was added in the dichloromethane (4 mL) solution of the ester (391 mg, 0.634 mM) and anisole (0.8 mL) while cooling the solution with ice, and the mixture was stirred at the same temperature for one hour and 30 minutes. After that, the mixture was heated to room temperature and stirred for 4 hours and 30 minutes, and then the solvent was removed by distillation under reduced pressure. Hexane was added to the residue to solidify it, and then the solid was washed with hexane and white powder (255 mg) was obtained. This powder was recrystallized from ethyl acetate-hexane, and white crystalline powder (I-195, 218 mg, 76.2%, optical purity is 100% ee) was obtained.

Mp: 208-211° C.;
Optical purity measurement conditions: HPLC column; CHIRALCEL OD (Daicel), 4.6φ×250, Moving bed; acetonitrile (0.1% TFA)-water (0.1% TFA)=60:40, Flow rate; 1 ml/min., Detection; UV 254 nm, Retention time; 11.6 minutes;

IR (nujol): 3254 (NH), 1742, 1671, 1518 (C=O);
NMR: (DMSO-d6) 1.00-1.84 (m, 19H), 2.64 (brt, 2H), 2.95 (brt, 2H). 4.00 (br, 2H), 5.48 (d, 1H, J=6.9), 7.31-7.44 (m, 5H), 8.10 (s, 1H), 10.71 (d, 1H, J=6.9), 13.07 (br, 1H);
[α]$_D$ −5.4±0.5° (22° C., C=1.006, CH$_3$OH)

Structures and NMR spectrum data of the compounds synthesized by the methods described above will be shown in the following Tables 4 to 287.

TABLE 4

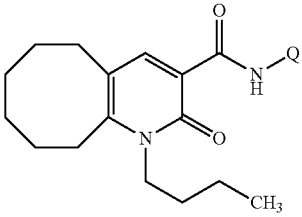

| Comp. No. | Q | ¹H-NMR(CDCl₃/TMS) δ |
|---|---|---|
| I-027 | 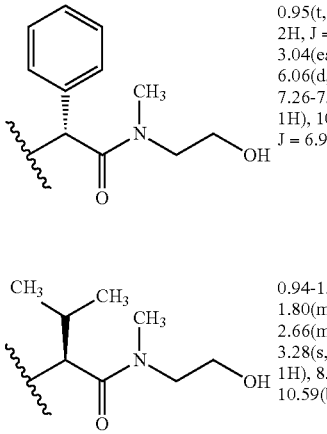 | 0.95(t, 3H, J = 6.9), 1.30-1.80(m, 12H), 2.60(t, 2H, J = 6.0), 2.86(t-like, 2H), 3.02 and 3.04(each s, total 3H), 3.07-4.17(m, 6H), 6.06(d, J = 6.9) and 6.19(d, total 1H, J = 5.4), 7.26-7.02(m, 5H), 8.22 and 8.25(each s, total 1H), 10.82(d, J = 5.4), and 11.09(d, total 1H, J = 6.9) |
| I-028 | 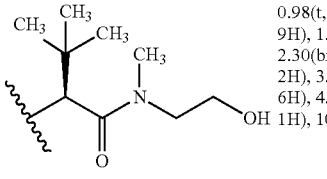 | 0.94-1.16(m, 9H), 1.32-1.52(m, 6H), 1.60-1.80(m, 6H), 2.22(m, 1H), 2.39(br, 1H), 2.56-2.66(m, 2H), 2.85-2.89(m, 2H), 3.01 and 3.28(s, total 3H), 3.22-4.20(m, 6H), 4.82(m, 1H), 8.21 and 8.22(s, total 1H), 10.51 and 10.59(brd, total 1H) |
| I-029 | 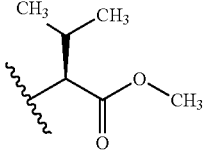 | 0.98(t, 3H, J = 7.5), 1.38 and 1.15(s, total 9H), 1.32-1.54(m, 6H), 1.58-1.80(m, 6H), 2.30(br, 1H), 2.56-2.64(m, 2H), 2.85-2.89(m, 2H), 3.00 and 3.31(s, total 3H), 3.10-4.30(m, 6H), 4.91(m, 1H), 8.21 and 8.22(s, total 1H), 10.69 and 10.83(brd, total 1H) |
| I-111 | 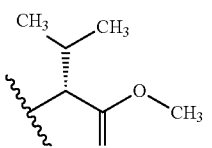 | 0.97(t, 3H, J = 7.5), 1.03(d, 3H, J = 6.9), 1.04(d, 3H, J = 6.9), 1.36-1.80(m, 12H), 2.28(m, 1H), 2.62(brt, 2H), 2.89(brt, 2H), 3.75(s, 3H), 4.12(brm, 2H), 4.67(dd, 1H, J = 5.4 and 8.1), 8.27(s, 1H), 10.46(d, 1H, J = 8.1) |
| I-112 | 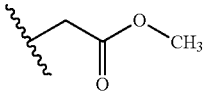 | 0.97(t, 3H, J = 7.5), 1.03(d, 3H, J = 6.9), 1.04(d, 3H, J = 6.9), 1.36-1.80(m, 12H), 2.28(m, 1H), 2.62(brt, 2H), 2.89(brt, 2H), 3.75(s, 3H), 4.12(brm, 2H), 4.67(dd, 1H, J = 5.4 and 8.1), 8.27(s, 1H), 10.46(d, 1H, J = 8.1) |
| I-113 |  | 0.99(t, 3H, J = 7.2), 1.34-1.82(m, 12H), 2.63(brt, 2H), 2.89(brt, 2H), 3.76(s, 3H), 4.11(brt, 2H), 4.22(d, 2H, J = 5.7), 8.28(s, 1H), 10.41(brt, 1H) |

TABLE 5
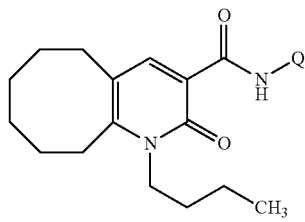
| Comp. No. | Q | ¹H-NMR(CDCl₃/TMS) δ |
|---|---|---|
| I-114 | 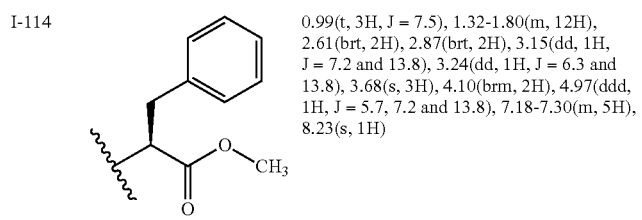 | 0.99(t, 3H, J = 7.5), 1.32-1.80(m, 12H), 2.61(brt, 2H), 2.87(brt, 2H), 3.15(dd, 1H, J = 7.2 and 13.8), 3.24(dd, 1H, J = 6.3 and 13.8), 3.68(s, 3H), 4.10(brm, 2H), 4.97(ddd, 1H, J = 5.7, 7.2 and 13.8), 7.18-7.30(m, 5H), 8.23(s, 1H) |
| I-119 | 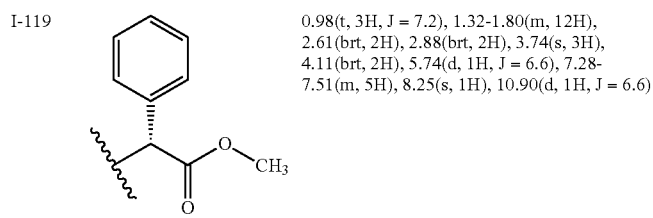 | 0.98(t, 3H, J = 7.2), 1.32-1.80(m, 12H), 2.61(brt, 2H), 2.88(brt, 2H), 3.74(s, 3H), 4.11(brt, 2H), 5.74(d, 1H, J = 6.6), 7.28-7.51(m, 5H), 8.25(s, 1H), 10.90(d, 1H, J = 6.6) |
| I-124 | 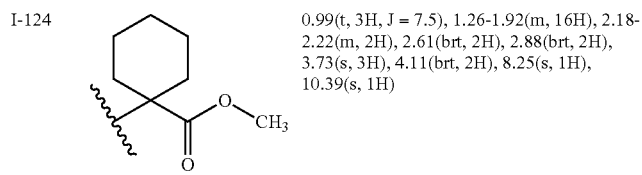 | 0.99(t, 3H, J = 7.5), 1.26-1.92(m, 16H), 2.18-2.22(m, 2H), 2.61(brt, 2H), 2.88(brt, 2H), 3.73(s, 3H), 4.11(brt, 2H), 8.25(s, 1H), 10.39(s, 1H) |
| I-192 | 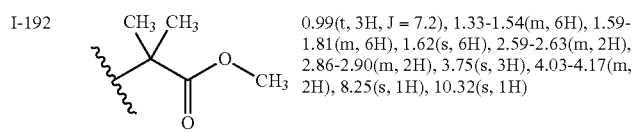 | 0.99(t, 3H, J = 7.2), 1.33-1.54(m, 6H), 1.59-1.81(m, 6H), 1.62(s, 6H), 2.59-2.63(m, 2H), 2.86-2.90(m, 2H), 3.75(s, 3H), 4.03-4.17(m, 2H), 8.25(s, 1H), 10.32(s, 1H) |
| I-203 | 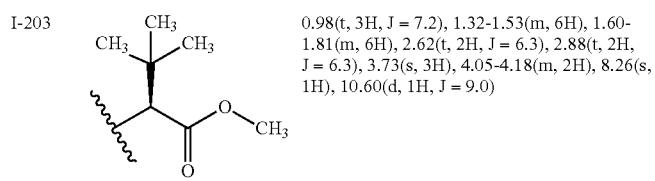 | 0.98(t, 3H, J = 7.2), 1.32-1.53(m, 6H), 1.60-1.81(m, 6H), 2.62(t, 2H, J = 6.3), 2.88(t, 2H, J = 6.3), 3.73(s, 3H), 4.05-4.18(m, 2H), 8.26(s, 1H), 10.60(d, 1H, J = 9.0) |
| I-204 | 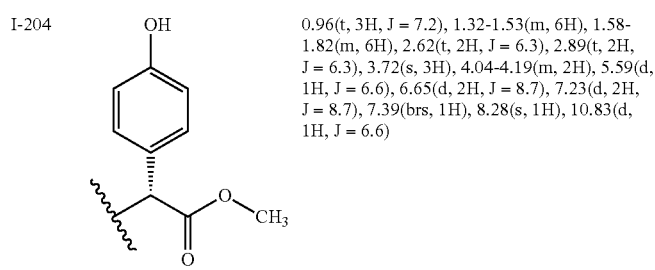 | 0.96(t, 3H, J = 7.2), 1.32-1.53(m, 6H), 1.58-1.82(m, 6H), 2.62(t, 2H, J = 6.3), 2.89(t, 2H, J = 6.3), 3.72(s, 3H), 4.04-4.19(m, 2H), 5.59(d, 1H, J = 6.6), 6.65(d, 2H, J = 8.7), 7.23(d, 2H, J = 8.7), 7.39(brs, 1H), 8.28(s, 1H), 10.83(d, 1H, J = 6.6) |

TABLE 6

| Comp. No. | Q | ¹H-NMR(CDCl₃/TMS) δ |
|---|---|---|
| I-243 | (2-thienyl, -CH(CO₂CH₃)-) | 0.97(t, 3H, J = 7.2), 1.32-1.80(m, 12H), 2.61(brt, 2H), 2.88(brt, 2H), 3.80(s, 3H), 4.11(brt, 2H), 6.02(d, 1H, J = 6.9), 6.97(dd, 1H, J = 3.6 and 5.1), 7.16(m, 1H), 7.26(dd, 1H, J = 1.2 and 5.1), 8.27(s, 1H), 10.89(d, 1H, J = 6.9) |
| I-248 | (3-thienyl, -CH(CO₂CH₃)-) | 0.98(t, 3H, J = 7.2), 1.32-1.81(m, 12H), 2.62(brt, 2H), 2.88(brt, 2H), 3.77(s, 3H), 4.10(br, 2H), 5.87(d, 1H, J = 6.9), 7.20(dd, 1H, J = 1.5 and 5.1), 7.31(dd, 1H, J = 3.0 and 5.1), 7.38(ddd, 1H, J = 1.5, 3.0 and 5.1), 8.27(s, 1H), 10.83(d, 1H, J = 6.9) |
| I-319 | (tert-Bu, -CH-C(O)O-CH(CH₂OH)CH₂OH) | 0.99(t, 3H, J = 7.2), 1.08-1.20(m, 9H), 1.32-1.54(m, 6H), 1.60-1.82(m, 6H), 2.61-2.65(m, 2H), 2.87-2.91(m, 2H), 3.76-4.24(m, 6H), 4.36(d, 1H, J = 6.6), 5.00(m, 1H), 8.24(s, 1H), 10.77(d, 1H, J = 6.6) |
| I-323 | (iPr, -CH-C(O)O-CH(CH₂OH)CH₂OH) | 0.99(t, 3H, J = 7.5), 1.10(dd, 6H, J = 5.1 and 6.9), 1.34-1.54(m, 6H), 1.60-1.83(m, 6H), 2.28(m, 1H), 2.60-2.66(m, 2H), 2.85-2.94(m, 2H), 3.76-4.22(m, 6H), 4.43(t, 1H, J = 6.3), 4.99(m, 1H), 8.24(s, 1H), 10.62(d, 1H, J = 6.3) |
| I-363 | (iPr, -CH-COOH) | DMSO-d6 0.93(d, 6H, J = 7.2), 0.94(t, 3H, J = 7.2), 1.26-1.78(m, 12H), 2.17(m, 1H), 2.65(brt, 2H), 2.93(brt, 2H), 4.08(brm, 2H), 4.40(dd, 1H, J = 4.8 and 8.4), 8.11(s, 1H), 10.29(d, 1H, J = 8.4), 12.76(brs, 1H) |
| I-364 | (iPr, -CH-COOH) | DMSO-d6 0.93(d, 6H, J = 7.2), 0.94(t, 3H, J = 7.2), 1.25-1.80(m, 12H), 2.17(m, 1H), 2.65(brt, 2H), 2.93(brt, 2H), 4.08(brm, 2H), 4.40(dd, 1H, J = 4.5 and 8.4), 8.11(s, 1H), 10.29(d, 1H, J = 8.4), 12.75(brs, 1H) |
| I-386 | (-CH₂-COOH) | DMSO-d6 0.93(t, 3H, J = 7.2), 1.26-1.78(m, 12H), 2.65(brt, 2H), 2.93(brt, 2H), 4.02(d, 2H, J = 5.7), 4.08(brt, 2H), 8.11(s, 1H), 10.11(t, 1H, J = 5.4), 12.67(brs, 1H) |

TABLE 7

| Comp. No. | Q | ¹H-NMR(CDCl₃/TMS) δ |
|---|---|---|
| I-392 | (S)-phenyl-CH-COOH group | DMSO-d6 0.93(t, 3H, J = 7.2), 1.22-1.78 (m, 12H), 2.64(brt, 2H), 2.92(brt, 2H), 4.07 (brt, 2H), 5.49(d, 1H, J = 6.9), 7.31-7.41(m, 5H), 8.09(s, 1H), 10.74(d, 1H, J = 6.9), 13.07(brs, 1H) |
| I-397 | 1-(cyclohexyl)-COOH group | DMSO-d6 0.94(t, 3H, J = 7.5), 1.17-1.78 (m, 16H), 1.99-2.06(m, 2H), 2.64(brt, 2H), 2.93(brt, 2H), 4.08(brt, 2H), 8.07(s, 1H), 12.19(s, 1H) |
| I-463 | C(CH₃)₂COOH group | DMSO-d6 0.93(t, 3H, J = 7.2), 1.25-1.78 (m, 12H), 1.48(s, 6H), 2.58-2.68(m, 2H), 2.87-2.97(m, 2H), 3.75(s, 3H), 4.00-4.13 (m, 2H), 8.07(s, 1H), 10.23(s, 1H), 12.41 (brs, 1H) |
| I-475 | CH(C(CH₃)₃)COOH group | DMSO-d6 0.91(t, 3H, J = 7.2), 1.00(s, 9H), 1.26-1.48(m, 6H), 1.52-1.66(m, 4H), 1.67-1.79(m, 2H), 2.60-2.69(m, 2H), 2.88-2.97 (m, 2H), 3.98-4.18(m, 2H), 4.26(d, 1H, J = 8.4), 8.11(s, 1H), 10.42(d, 1H, J = 8.4), 12.64(brs, 1H) |
| I-476 | (4-hydroxyphenyl)-CH-COOH group | DMSO-d6 0.92(t, 3H, J = 7.5), 1.22-1.47 (m, 6H), 1.50-1.64(m, 4H), 1.66-1.78(m, 2H), 2.59-2.68(m, 2H), 2.87-2.97(m, 2H), 3.98-4.12(m, 2H), 5.34(d, 1H, J = 6.9), 6.77 (d, 2H, J = 8.7), 7.20(d, 2H, J = 8.7), 8.09(s, 1H), 9.53(s, 1H), 10.57 (d, 1H, J = 6.9), 12.87(brs, 1H) |
| I-509 | (thiophen-2-yl)-CH-COOH group | DMSO-d6 0.93(t, 3H, J = 7.2), 1.26-1.78 (m, 12H), 2.65(brt, 2H), 2.93(brt, 2H), 4.07 (brt, 2H), 5.76(d, 1H, J = 7.2), 7.03(dd, 1H, J = 3.6 and 5.1), 7.13(m, 1H), 7.51(dd, 1H, J = 1.5 and 5.1), 8.12(s, 1H), 10.73(d, 1H, J = 7.2), 13.32(br, 1H) |

TABLE 8

| Comp. No. | Q | ¹H-NMR(CDCl₃/TMS) δ |
|---|---|---|
| I-515 | (thiophen-3-yl)-CH-COOH group | DMSO-d6 0.93(t, 3H, J = 7.2), 1.20-1.80(m, 12H), 2.65(brt, 2H), 2.93(brt, 2H), 4.07(br, 2H), 5.59(d, 1H, J = 6.9), 7.13(dd, 1H, J = 1.2 and 3.0), 7.50(m, 1H), 7.58(dd, 1H, J = 3.0 and 5.1), 8.12(s, 1H), 10.63(d, 1H, J = 6.9), 13.06(br, 1H) |

TABLE 8-continued

| Comp. No. | Q | ¹H-NMR(CDCl₃/TMS) δ |
|---|---|---|
| II-001 | | 0.99(t, 3H, J = 7.2), 1.26-2.04(m, 20H), 2.62(t-like, 2H), 2.75-2.89(m, 4H), 3.29(s, 3H), 3.51-4.18(m, 5H), 4.88(brm, 1H), 8.17(s, 1H), 10.82(brd, 1H) |
| II-010 | | 0.98(t, 3H, J = 7.5), 1.32-1.54(m, 6H), 1.61-1.81(m, 6H), 2.60-2.64(m, 2H), 2.86-2.90(m, 2H), 2.93-3.08(m, 2H), 3.71(s, 3H), 3.77(s, 3H), 4.02-4.18(m, 2H), 5.10(m, 1H), 8.26(s, 1H), 10.71(d, 1H, J = 8.1) |
| II-026 | | 0.98(t, 3H, J = 7.2), 1.23(t, 3H, J = 7.2), 1.32-1.82(m, 18H), 1.89-2.08(m, 2H), 2.62(t, 2H, J = 6.3), 2.79(quint, 1H, J = 3.9), 2.87(t, 2H, J = 6.3), 4.03-4.23(m, 4H), 4.54(m, 1H), 8.25(s, 1H), 10.44(d, 1H, J = 8.7) |
| II-052 | | DMSO-d6 0.93(t, 3H, J = 7.2), 1.16-1.95(m, 19H), 2.57-2.68(m, 2H), 2.86-2.95(m, 2H), 3.92-4.06(m, 2H), 4.03(q, 2H, J = 7.2), 4.42(m, 1H), 8.09(s, 1H), 10.25(d, 1H, J = 9.0), 12.10(brs, 1H) |
| II-055 | | DMSO-d6 0.93(t, 3H, J = 7.5), 1.24-1.48(m, 6H), 1.51-1.66(m, 4H), 1.67-1.78(m, 2H), 2.59-2.97(m, 6H), 3.96-4.14(m, 2H), 4.79(m, 1H), 8.11(s, 1H), 10.37(d, 1H, J = 8.1), 12.30-13.04(m, 2H) |

TABLE 9

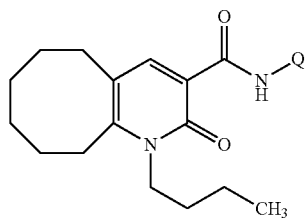

| Comp. No. | Q | ¹H-NMR(CDCl₃/TMS) δ |
|---|---|---|
| III-004 | (5-methoxycarbonyl-thiophen-2-yl) | 0.94(t, 3H, J = 7.2), 1.18-1.82(m, 12H), 2.71(brt, 2H), 2.98(brt, 2H), 3.79(s, 3H), 4.14(brt, 2H), 7.02(d, 1H, J = 4.2), 7.63(d, J = 4.2, 1H), 8.25(s, 1H), 13.20(s, 1H) |
| III-012 | (5-carboxy-thiophen-2-yl) | DMSO-d6 0.94(t, 3H, J = 7.2), 1.28-1.81(m, 12H), 2.71(brt, 2H), 2.98(brt, 2H), 4.13(brt, 2H), 6.98(d, 1H, J = 4.2), 7.55(d, J = 4.2, 1H), 8.26(s, 1H), 12.65(brs, 1H), 13.16(s, 1H) |
| IV-028 | (2-carboxymethyl-thiazol-4-yl) | DMSO-d6 0.95(t, 3H, J = 7.5), 1.20-1.85(m, 12H), 2.65-2.75(m, 2H), 2.91-3.03(m, 2H), 3.61(s, 2H), 4.05-4.20(m, 2H), 7.02(s, 1H), 8.27(s, 1H), 12.00-12.90(br, 1H), 13.47(s, 1H) |
| X-110 | 4,4,4-trifluoro-3-(carboxymethyl) | DMSO-d6 0.91(t, 3H, J = 7.2), 1.24-1.78(m, 12H), 2.60-2.94(m, 6H), 4.04(m, 2H), 5.14(brs, 1H), 8.14(s, 1H), 10.40(d, 1H, J = 9.6) |
| X-123 | (2-carboxy-cyclohex-1-en-1-yl) | DMSO-d6 0.93(t, 3H, J = 6.9), 1.20-1.82(m, 16H), 2.20-2.38(br, 2H), 2.56-2.70(br, 2H), 2.70-2.98(m, 4H), 3.95-4.20(m, 2H), 8.08(s, 1H), 12.22(br, 1H), 12.58(s, 1H) |
| X-125 | (5-carboxymethyl-1,2,4-thiadiazol-3-yl) | DMSO-d6 0.95(t, 3H, J = 7.5), 1.30-1.82(m, 12H), 2.73(t, 2H, J = 6.3), 3.00(t, 2H, J = 6.3), 3.82(s, 2H), 4.16(t, 2H, J = 7.2), 8.32(s, 1H), 13.84(s, 1H) |
| X-128 | 3,3-diethyl-(carboxymethyl) | DMSO-d6 0.80(t, 6H, J = 7.2), 0.93(t, 3H, J = 7.2), 1.24-1.96(m, 16H), 2.63(br, 2H), 2.77(s, 2H), 2.91(br, 2H), 4.04(br, 2H), 8.08(s, 1H), 9.84(s, 1H), 11.96(s, 1H) |

TABLE 10

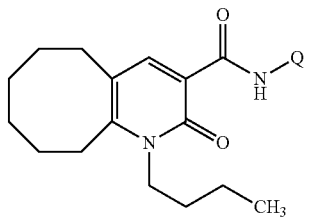

| Comp. No. | Q | ¹H-NMR(CDCl₃/TMS) δ |
|---|---|---|
| X-131 | (tetrahydropyran-4-yl with COOH at 4-position, attached via CH₂) | DMSO-d6 0.96(t, 3H, J = 7.2 Hz), 1.30-1.79(m, 12H), 1.95-2.02(m, 4H), 2.65(br-s, 2H), 2.92(br-s, 2H), 3.51(t, 2H, J = 9.0 Hz), 3.75(t, 2H, J = 9.0 Hz), 4.09(br-s, 2H), 8.08(s, 1H), 10.5(s, 1H), 12.5(br-s, 1H) |
| X-138 | (4-methyl-3-substituted pentyl with CH₂COOH) | DMSO-d6 0.85-0.89(m, 6H), 0.93(t, 3H, J = 7.2), 1.26-1.77(m, 15H), 2.44(t, 2H, J = 5.7), 2.64(br, 2H), 2.91(t, 2H, J = 6.0), 4.04(br, 2H), 4.34(br, 1H), 8.10(s, 1H), 9.86(d, 1H, J = 8.7), 12.16(s, 1H) |
| X-139 | (3-benzoyl with CH₂COOH) | DMSO-d6 0.93(t, 3H, J = 7.5 Hz), 1.30-1.79(m, 12H), 1.95-2.02(m, 4H), 2.63-2.73(m, 4H), 2.90-3.01(m, 4H), 4.03(br-s, 2H), 5.79(s, 1H), 7.50-7.64(m, 3H), 8.00(d, 2H, J = 7.2 Hz), 10.5(d, 1H, J = 9.0 Hz), 12.44(br-s, 1H) |
| X-157 | (1-(carboxymethyl)cyclohexyl attached to cyclohexyl) | DMSO-d6 0.93(t, 3H, J = 7.2), 1.12-1.76(m, 20H), 2.21(brd, 2H, J = 7.2), 2.64(br, 2H), 2.78(s, 2H), 2.91(br, 2H), 4.04(br, 2H), 8.08(s, 1H), 9.96(s, 1H), 11.96(br, 1H) |
| X-202 | (4-methyl-3-substituted pentyl with CH₂CH₂COOH) | DMSO-d6 0.86(t, 6H, J = 6.3), 0.93(t, 3H, J = 7.2), 1.22-1.86(m, 17H), 2.20(t, 2H, J = 7.2), 2.56-2.68(m, 2H), 2.86-2.96(m, 2H), 3.96-4.12(m, 3H), 8.10(s, 1H), 9.68(d, 1H, J = 9.0), 11.99(brs, 1H) |
| X-205 | (6-(2-carboxyvinyl)pyridin-3-yl type) | DMSO-d6 0.95(t, 3H, J = 7.2), 1.28-1.82(m, 12H), 2.66-2.75(m, 2H), 2.93-3.03(m, 2H), 4.06-4.22(m, 2H), 6.58(d, 1H, J = 16.2), 7.59(d, 1H, J = 16.2), 8.22(dd, 1H, J = 2.1 and 8.7), 8.28(s, 1H), 8.30(d, 1H, J = 8.7), 8.62(d, 1H, J = 2.1), 12.42(brs, 1H), 12.82(s, 1H) |

TABLE 11
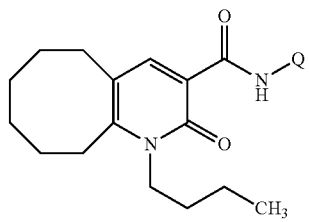
| Comp. No. | Q | ¹H-NMR(CDCl₃/TMS) δ |
|---|---|---|
| X-225 | 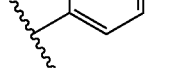 | DMSO-d6 0.95(t, 3H, J = 7.2), 1.27-1.50(m, 6H), 1.56-1.82(m, 6H), 2.65-2.75(m, 2H), 2.91-3.02(m, 2H), 4.04-4.22(m, 2H), 6.45(d, 1H, J = 15.9), 7.55(d, 1H, J = 15.9), 7.68(d, 2H, J = 8.7), 7.76(d, 2H, J = 8.7), 8.26(s, 1H), 12.31(brs, 1H), 12.46(s, 1H) |
| X-232 | 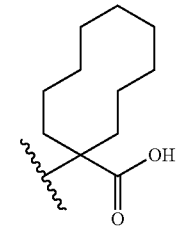 | DMSO-d6 0.93(t, 3H, J = 7.5), 1.25-1.94(m, 28H), 2.05-2.20(m, 2H), 2.57-2.68(m, 2H), 2.78-2.98(m, 2H), 3.96-4.16(m, 2H), 8.08(s, 1H), 10.05(s, 1H), 12.18(br, 1H) |
| X-235 | 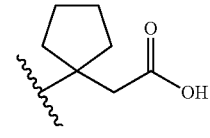 | DMSO-d6 0.93(t, 3H, J = 7.5), 1.25-1.84(m, 18H), 2.00-2.15(m, 2H), 2.56-2.68(m, 2H), 2.82-2.98(m, 4H), 3.96-4.14(m, 2H), 8.08(s, 1H), 9.95(s, 1H), 11.97(br, 1H) |
| XI-004 | 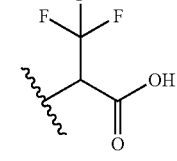 | DMSO-d6 0.94(t, 3H, J = 7.2), 1.22-1.50(m, 6H), 1.52-1.81(m, 6H), 2.61-2.71(m, 2H), 2.89-2.99(m, 2H), 3.96-4.20(m, 2H), 5.44(m, 1H), 8.17(s, 1H), 10.84(d, 1H, J = 8.4), 14.33(br, 1H) |
| XI-013 | 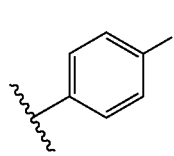 | DMSO-d6 0.94(t, 3H, J = 7.2), 1.27-1.82(m, 12H), 2.64-2.74(m, 2H), 2.91-3.01(m, 2H), 4.05-4.18(m, 2H), 4.65(s, 2H), 6.90(d, 2H, J = 9.0), 7.61(d, 2H, J = 9.0), 8.23(s, 1H), 12.13(s, 1H), 12.98(brs, 1H) |
| XI-130 | 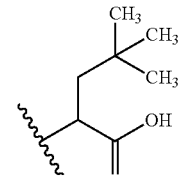 | DMSO-d6 0.93(s, 9H), 0.94(t, 3H, J = 5.4), 1.25-1.48(m, 6H), 1.58(m, 5H), 1.73(m, 3H), 2.64(m, 2H), 2.92(m, 2H), 4.06(m, 2H), 4.49(m, 1H), 8.11(s, 1H), 10.17(d, 1H, J = 6.3) |

TABLE 12
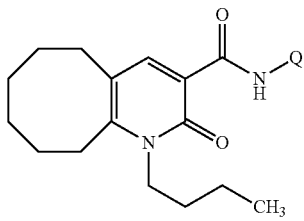
| Comp. No. | Q | $^1$H-NMR(CDCl$_3$/TMS) δ |
|---|---|---|
| XI-131 | 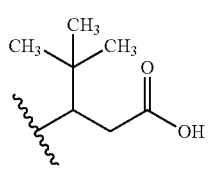 | DMSO-d6 0.89(s, 9H), 0.93(t, 3H, J = 5.4), 1.25-1.48(m, 6H), 1.58(m, 5H), 1.72(m, 2H), 2.17(m, 1H), 2.64(m, 2H), 2.91(m, 2H), 4.06(m, 2H), 4.27(m, 1H), 8.10(s, 1H), 9.99(d, 1H, J = 7.2) |
| XI-148 | 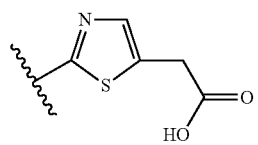 | DMSO-d6 0.95(t, 3H, J = 7.2), 1.24-1.84(m, 12H), 2.65-2.77(m, 2H), 2.90-3.05(m, 2H), 3.82(s, 2H), 4.05-4.20(m, 2H), 7.31(s, 1H), 8.28(s, 1H), 12.66(br s, 1H), 13.39(s, 1H) |
| XI-153 | 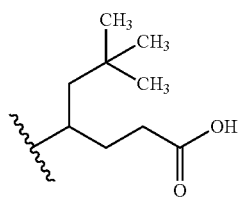 | DMSO-d6 0.87(s, 9H), 0.92(t, 3H, J = 7.2), 1.26-1.82(m, 16H), 2.18(t, 2H, J = 7.5), 2.59-2.68(m, 2H), 2.86-2.93(m, 2H), 3.98-4.16(m, 3H), 8.10(s, 1H), 9.77(d, 1H, J = 9.0), 11.99(brs, 1H) |
| XI-166 | 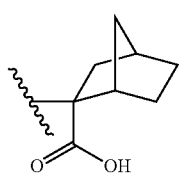 | DMSO-d6 0.94(t, 3H, J = 7.2), 1.10-2.0(m, 20H), 2.20-3.00(m, 6H), 3.95-4.20(m, 2H), 8.05(s, 1H), 10.44(s, 1H) |
| XI-185 | 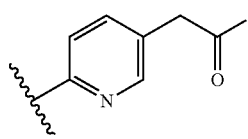 | DMSO-d6 0.95(t, 3H, J = 7.2), 1.26-1.84(m, 12H), 2.65-2.78(m, 2H), 2.90-3.03(m, 2H), 3.60(s, 2H), 4.06-4.20(m, 2H), 7.72(dd, 1H, J = 2.1, 8.7), 8.19-8.24(m, 2H), 8.27(s, 1H), 12.47(br s, 1H), 12.61(s, 1H) |
| XI-188 | 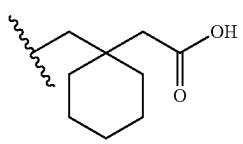 | DMSO-d6 0.93(t, 3H, J = 7.2), 1.3-1.6(m, 22H), 1.72(br, 2H), 2.20(s, 2H), 2.65(t, 2H, J = 4.8), 2.92(t, 2H, J = 5.7), 4.05(br, 1H), 8.11(s, 1H), 10.03(t, 1H, J = 6.3) |
| XI-195 | 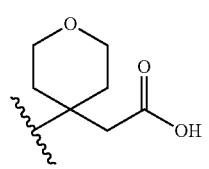 | DMSO-d6 0.93(t, 3H, J = 7.5), 1.20-2.30(m, 16H), 2.55-3.00(m, 4H), 2.84(s, 2H), 3.50(t, 2H, J = 11.1), 3.60-4.20(m, 4H), 8.10(s, 1H), 10.13(s, 1H) |

TABLE 13

| Comp. No. | Q | $^1$H-NMR(CDCl$_3$/TMS) δ |
|---|---|---|
| XI-223 | cyclobutyl-CH$_2$-COOH (1,1-disubstituted cyclobutane with CH$_2$COOH) | DMSO-d6 0.93(t, J = 7.5, 3H), 1.24-1.48(m, 6H), 1.48-1.64(m, 4H), 1.64-1.92(m, 4H), 2.16-2.30(m, 4H), 2.58-2.68(m, 2H), 2.88(s, 2H), 2.84-2.96(m, 2H), 4.04(t, 2H, J = 7.5), 8.06(s, 1H), 10.10(s, 1H), 12.02(br, 1H) |
| XI-230 | 4-(CH$_2$CH$_2$COOH)-tetrahydropyran-4-yl | DMSO-d6 0.93(t, 3H, J = 7.2), 1.26-1.80(m, 14H), 2.00-2.20(m, 6H), 2.60-2.68(m, 2H), 2.88-2.97(m, 2H), 3.40-3.54(m, 2H), 3.63-3.74(m, 2H), 4.00-4.12(m, 2H), 8.09(s, 1H), 10.00(s, 1H), 12.04(brs, 1H) |
| XI-242 | 4,4-difluoro-1-carboxycyclohexyl | DMSO-d6 0.94(t, 3H, J = 7.4), 1.3-2.3(m, 20H), 2.65(brt, 2H), 2.94(brt, 2H), 4.09(brt, 2H), 8.08(s, 1H), 10.42(s, 1H) |
| XI-289 | 2-(2-carboxyvinyl)pyrimidin-5-yl | DMSO-d6 0.95(t, 3H, J = 7.5), 1.25-1.85(m, 12H), 2.65-2.75(m, 2H), 2.92-3.02(m, 2H), 4.06-4.20(m, 2H), 6.73(d, 1H, J = 16.5), 7.57(d, 1H, J = 16.2), 8.25(s, 1H), 9.03(s, 2H), 13.05(s, 1H) |

TABLE 14

| Comp. No. | Q | $^1$H-NMR(CDCl$_3$/TMS) δ |
|---|---|---|
| I-151 | (R)-α-(methoxycarbonyl)benzyl | 0.99 (d, 3H, J = 6.3), 1.00 (d, 3H, J = 6.3), 1.32-1.84 (m, 11H), 2.60 (t, 2H, J = 6.0), 2.87 (t, 2H, J = 6.0), 3.74 (s, 3H), 4.05-4.20 (m, 2H), 5.74 (d, 1H, J = 6.9), 7.24-7.56 (m, 5H), 8.25 (s, 1H), 10.90 (d, 1H, J = 6.3) |

TABLE 14-continued
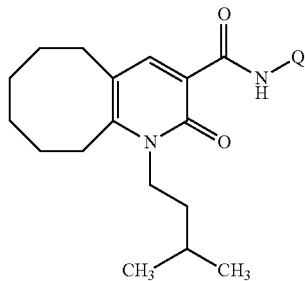
| Comp. No. | Q | $^1$H-NMR(CDCl$_3$/TMS) δ |
|---|---|---|
| I-286 | 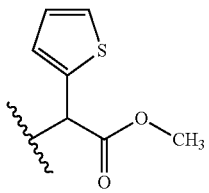 | 0.99 (d, 3H, J = 6.3), 1.00 (d, 3H, J = 6.3), 1.32-1.83 (m, 11H), 2.62 (t-like, 2H), 2.88 (t-like, 2H), 3.80 (s, 3H), 4.13 (br, 2H), 6.02 (d, 1H, J = 6.6), 6.97 (dd, 1H, J = 3.3 and 4.8), 7.16 (m, 1H), 7.26 (dd, 1H, J = 1.2 and 4.8), 8.27 (s, 1H), 10.89 (d, 1H, J = 6.6) |
| I-424 | 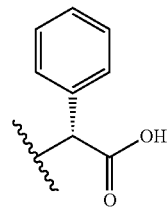 | DMSO-d6 0.96 (d, 6H, J = 6.6), 1.25-1.80 (m, 11H), 2.58-2.70 (m, 2H), 2.85-2.96 (m, 2H), 3.98-4.15 (m, 2H), 5.49 (d, 1H, J = 6.9), 7.30-7.44 (m, 5H), 8.09 (s, 1H), 10.71 (d, 1H, J = 6.9), 13.07 (br, 1H) |
| I-551 | 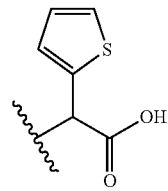 | DMSO-d6 0.96 (d, 6H, J = 6.3), 1.22-1.80 (m, 11H), 2.65 (brt, 2H), 2.91 (brt, 2H), 4.08(br, 2H), 5.77 (dd, 1H, J = 0.6 and 7.2), 7.03 (dd, 1H, J = 3.6 and 5.1), 7.13 (m, 1H), 7.51 (dd, 1H, J = 1.2 and 5.1), 8.12 (s, 1H), 10.71 (d, 1H, J = 7.2), 13.30 (br, 1H) |
| XI-109 | 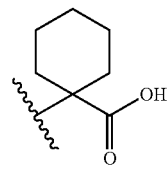 | 1.01 (d, 6H, J = 6.6), 1.3-1.7 (m, 18H), 1.96 (dt, 2H, J = 3.9, 14.4), 2.33 (d, 2H, J = 13.8), 2.65 (dd, 2H, J = 5.7, 5.7), 2.91 (dd, 2H, J = 6.3, 6.3), 4.1-4.3 (br, 2H), 8.27 (s, 1H), 10.75 (s, 1H) |
| XI-118 | 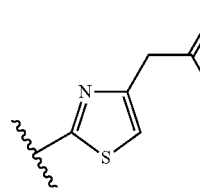 | DMSO-d6 0.98 (d, 6H, J = 6.6), 1.35 (br, 2H), 1.45 (br, 2H), 1.5-1.8 (m, 8H), 2.71 (brt, 2H), 2.97 (brt, 2H), 4.16 (br, 2H), 7.02 (s, 1H), 8.27 (s, 1H), 13.47 (s, 1H) |

TABLE 15
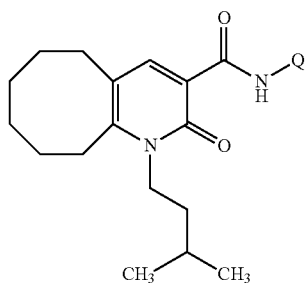
| Comp. No. | Q | $^1$H-NMR(CDCl$_3$/TMS) δ |
|---|---|---|
| XI-181 | 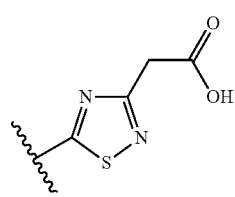 | DMSO-d6 0.98 (d, 6H, J = 6.6), 1.26-1.86 (m, 11H), 2.65-2.80 (m, 2H), 2.90-3.05 (m, 2H), 3.81 (s, 2H), 4.10-4.25 (m, 2H), 8.32 (s, 1H), 12.65 (br s, 1H), 13.84 (s, 1H) |
| XI-182 | 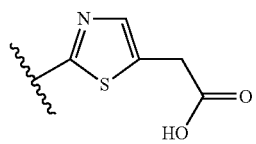 | DMSO-d6 0.98 (d, 6H, J = 6.6), 1.26-1.84 (m, 11H), 2.65-2.77 (m, 2H), 2.90-3.03 (m, 2H), 3.82 (s, 2H), 4.10-4.25 (m, 2H), 7.31 (s, 1H), 8.24 (s, 1H), 12.63 (br s, 1H), 13.39 (s, 1H) |
| XI-186 | 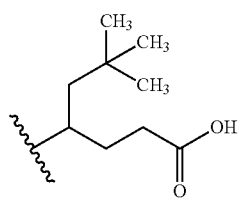 | DMSO-d6 0.87 (s, 9H), 0.95 (d, 6H, J = 6.6), 1.26-1.82 (m, 15H), 2.18 (t, 2H, J = 7.5), 2.58-2.68 (m, 2H), 2.85-2.94 (m, 2H), 4.00-4.16 (m, 3H), 8.10 (s, 1H), 9.75 (d, 1H, J = 9.0), 11.99 (brs, 1H) |
| XI-192 | 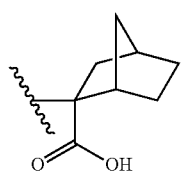 | DMSO-d6 0.95 (s, 3H), 0.97 (s, 3H), 1.10-1.80 (m, 19H), 2.15-3.00 (m, 6H), 4.00-4.20 (m, 2H), 8.05 (s, 1H), 10.43 (s, 1H) |
| XI-198 | 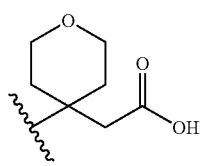 | DMSO-d6 0.95 (s, 3H), 0.97 (s, 3H), 1.25-2.30 (m, 13H), 2.55-3.00 (m, 4H), 2.85 (s, 2H), 3.50 (t, 2H, J = 11.4), 3.65-4.20 (m, 4H), 8.09 (s, 1H), 10.11 (s, 1H) |
| XI-201 | 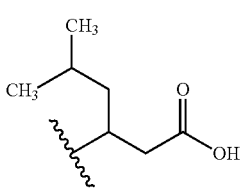 | DMSO-d6 0.87 (dd, 6H, J = 6.3 and 3.3), 0.95 (d, 6H, J = 6.6), 1.28-1.80 (m, 14H), 2.44 (dd, 2H, J = 6.2 and 5.0), 2.64 (t, 2H, J = 5.7), 2.89 (t, 2H, J = 5.9), 4.05 (br s, 2H), 4.34 (m, 1H), 8.10 (s, 1H), 9.83 (d, 1H, J = 8.7), 12.16 (br s, 1H) |

TABLE 16

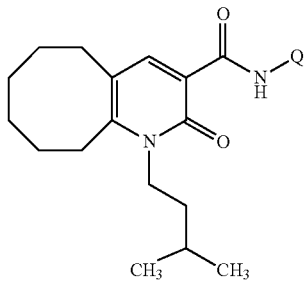

| Comp. No. | Q | ¹H-NMR(CDCl₃/TMS) δ |
|---|---|---|
| XI-202 | ![structure with CH₃, CH₃, CH₃ groups and COOH] | DMSO-d6 0.89 (s, 9H), 0.96 (d, 6H, J = 6.3), 1.26-1.89 (m, 11H), 2.16 (dd, 1H, J = 14.7 and 10.2), 2.58 (dd, 1H, J = 14.7 and 3.9), 2.64(t, 2H, J = 5.4), 2.90 (t, 2H, J = 5.7), 4.07 (dd, 2H, J = 10.2 and 6.0), 4.27 (td, 1H, J = 9.8 and 3.7), 8.09(s, 1H), 9.96 (d, 1H, J = 9.6), 12.06 (br s, 1H) |
| XI-207 | ![cyclohexyl with CH₂COOH] | DMSO-d6 0.95 (d, 6H, J = 6.6), 1.26-1.79(m, 21H), 2.19 (s, 2H), 2.64 (t, 2H, J = 5.1), 2.90 (t, 2H, J = 5.9), 3.40 (d, 2H, J = 6.3), 4.08 (br s, 2H), 8.11 (s, 1H), 10.01 (t, 1H, J = 6.2), 12.28 (br s, 1H) |
| XI-228 | ![CF₃ group with COOH] | DMSO-d6 0.95 (d, 6H, J = 6.6), 1.25-1.79 (m, 11H), 2.62-2.74 (m, 3H), 2.84-2.94 (m, 3H), 4.05-4.18 (br, 2H), 5.16 (m, 1H), 8.16 (s, 1H), 10.40 (d, 1H, J = 9.0), 12.64 (br, 1H) |
| XI-235 | ![cyclohexyl with CH₂COOH] | DMSO-d6 0.96 (d, 6H, J = 7.0), 1.15-1.64 (m, 16H), 1.65-1.79 (m, 3H), 2.15-2.26 (m, 2H), 2.60-2.67 (m, 2H), 2.79 (s, 2H), 2.86-2.92 (m, 2H), 3.98-4.15 (m, 2H), 8.08 (s, 1H), 9.94 (s, 1H), 11.9 (s, 1H) |
| XI-236 | ![cyclopentyl with CH₂COOH] | DMSO-d6 0.96 (d, 6H, J = 7.0), 1.27-1.35 (m, 2H), 1.37-1.81 (m, 13H), 2.02-2.12 (m, 2H), 2.58-2.66 (m, 2H), 2.81-2.93 (m, 4H), 3.96-4.15 (m, 2H), 8.02 (s, 1H), 9.97 (s, 1H), 11.9(s, 1H) |
| XI-237 | ![cyclobutyl with CH₂COOH] | DMSO-d6 0.96 (d, 6H, J = 7.0), 1.27-1.35 (m, 2H), 1.37-1.53 (m, 4H), 1.53-1.63 (m, 2H), 1.66-1.78 (m, 3H), 1.80-1.90 (m, 2H), 2.15-2.29 (m, 4H), 2.59-2.66 (m, 2H), 2.85-2.92 (m, 4H), 4.02-4.09 (m, 2H), 8.10 (s, 1H), 10.1 (s, 1H), 12.0 (s, 1H) |

TABLE 17

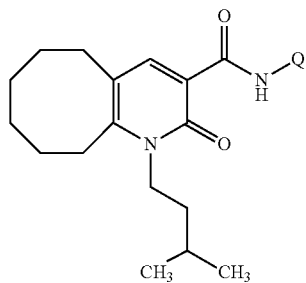

| Comp. No. | Q | ¹H-NMR(CDCl₃/TMS) δ |
|---|---|---|
| XI-247 | pyridyl-CH₂-C(=O)-OH (attached via 2-position of pyridine, substituent at 5-position) | DMSO-d6 0.98 (d, 6H, J = 6.6), 1.26-1.84 (m, 11H), 2.65-2.75 (m, 2H), 2.90-3.00 (m, 2H), 3.60 (s, 2H), 4.08-4.20 (m, 2H), 7.72 (dd, 1H, J = 2.4, 8.4), 8.13-8.26 (m, 2H), 8.26 (s, 1H), 12.61 (s, 1H) |
| XI-261 | -CH(CH₂C(CH₃)₃)C(=O)OH | 0.99 (s, 9H), 1.01 (d, 6H, J = 7.5), 1.40-1.80 (m, 12H), 2.14-2.20 (m, 1H), 2.65 (t, 2H, J = 5.7), 2.89-2.92 (m, 2H), 4.13 (m, 2H), 4.53-4.59 (m, 1H), 8.29 (s, 1H), 10.61 (d, 1H, J = 6.0) |
| XI-263 | -CH(CH₂CH(CH₃)₂)CH₂CH₂C(=O)OH | 0.89 (d, 3H, J = 6.6), 0.93 (t, 3H, J = 6.6), 1.02 (d, 6H, J = 6.6), 1.33-1.80 (m, 15H), 1.94-2.05 (m, 1H), 2.32-2.47 (m, 2H), 2.66 (t, 2H, J = 6.0), 2.88-2.93 (m, 2H), 4.06 (m, 1H), 4.19 (m, 2H), 8.36 (s, 1H), 10.28 (s, 1H) |

TABLE 18

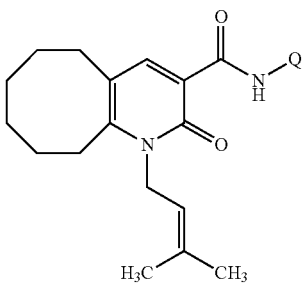

| Comp. No. | Q | ¹H-NMR(CDCl₃/TMS) δ |
|---|---|---|
| XI-105 | 2-thiazolyl-CH₂-C(=O)-OH (attached at 2-position, CH₂COOH at 4-position) | DMSO-d6 1.30-1.90 (m, 8H), 1.71 (s, 3H), 1.81 (s, 3H), 2.65-2.77 (m, 2H), 2.87-3.00 (m, 2H), 3.62 (s, 2H), 4.82 (d, 2H, J = 5.7), 5.11 (m, 1H), 7.02 (s, 1H), 8.29 (s, 1H), 12.40 (br s, 1H), 13.40 (s, 1H) |

TABLE 18-continued
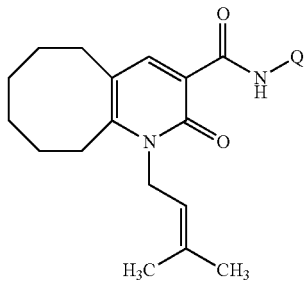
| Comp. No. | Q | ¹H-NMR(CDCl₃/TMS) δ |
|---|---|---|
| XI-114 | 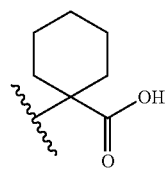 | DMSO-d6 1.37 (m, 6H), 1.55-1.75 (m, 10H), 1.70 (s, 3H), 1.77 (s, 3H), 2.00-2.07 (m, 2H), 2.64 (m, 2H), 2.88 (m, 2H), 4.76 (m, 2H), 5.06 (m, 1H), 8.08 (s, 1H), 12.20 (s, 1H) |
TABLE 19
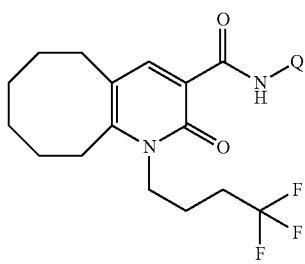
| Comp. No. | Q | ¹H-NMR(CDCl₃/TMS) δ |
|---|---|---|
| X-36 | 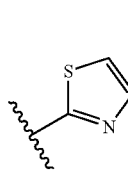 | DMSO-d6 1.28-1.95 (m, 10H), 2.39-2.56 (m, 2H), 2.71 (br, 2H), 2.99 (br, 2H), 3.61 (s, 2H), 4.22 (t, 2H, J = 7.5), 7.02 (s, 1H), 8.29 (s, 1H), 13.39 (s, 1H) |
| X-54 | 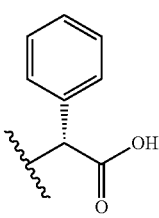 | DMSO-d6 1.30-1.86 (m, 10H), 2.39-2.56 (m, 2H), 2.65 (br, 2H), 2.94 (t, 2H, J = 6.0), 5.49 (d, 1H, J = 6.9), 7.32-7.41 (m, 5H), 8.11 (s, 1H), 10.69 (d, 1H, J = 6.9) |
| X-55 | 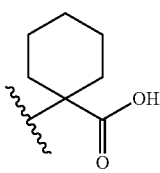 | DMSO-d6 1.20-2.08 (m, 20H), 2.40-2.57 (m, 2H), 2.65 (br, 2H), 2.94 (br, 2H), 4.16 (t, 2H, J = 7.5), 8.08 (s, 1H), 10.21 (s, 1H), 12.23 (br, 1H) |

TABLE 19-continued
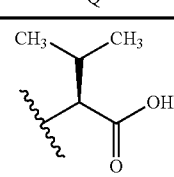
| Comp. No. | Q | ¹H-NMR(CDCl₃/TMS) δ |
|---|---|---|
| X-102 | 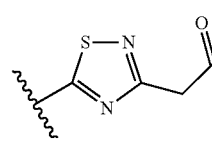 | DMSO-d6 0.92 (d, 6H, J = 6.6), 1.25-1.88 (m, 10H), 2.17 (m, 1H), 2.40-2.57 (m, 2H), 2.66 (br, 2H), 2.94 (br, 2H), 4.16 (br, 2H), 4.39 (dd, 1H, J = 4.5 and 8.4), 8.13 (s, 1H), 10.23 (d, 1H, J = 8.4), 12.80 (br, 1H) |
| X-103 | 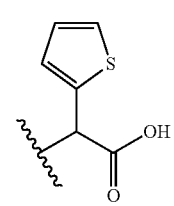 | DMSO-d6 1.28-1.95 (m, 10H), 2.40-2.57 (m, 2H), 2.73 (br, 2H), 3.01 (t, 2H, J = 5.4), 3.81 (s, 2H), 4.24 (t, 2H, J = 7.8), 8.34 (s, 1H), 13.75 (s, 1H) |
| X-106 | 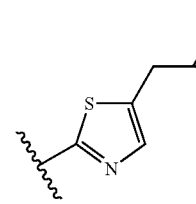 | DMSO-d6 1.30-1.90 (m, 10H), 2.38-2.55 (m, 2H), 2.66 (t, 2H, J = 6.3), 2.95 (t, 2H, J = 6.3), 4.15 (t, 2H, J = 7.5), 5.76 (d, 1H, J = 6.9), 7.02 (dd, 1H, J = 3.6 and 5.1), 7.12 (d, 1H, 3.0), 7.50 (dd, 1H, J = 1.2 and 5.1), 8.13 (s, 1H), 10.67 (d, 1H, J = 6.9), 13.32 (br, 1H) |
| X-115 | 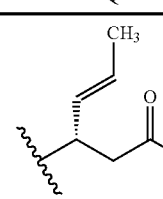 | DMSO-d6 1.28-1.94 (m, 10H), 2.40-2.55 (m, 2H), 2.72 (br, 2H), 2.99 (br, 2H), 3.81 (s, 2H), 4.22 (t, 2H, J = 6.9), 7.31 (s, 1H), 8.29 (s, 1H), 13.32 (s, 1H) |
TABLE 20
| Comp. No. | Q | ¹H-NMR(CDCl₃/TMS) δ |
|---|---|---|
| X-116 |  | DMSO-d6 1.28-1.88 (n, 13H), 2.40-2.55 (m, 4H), 2.65 (br, 2H), 2.93 (br, 2H), 4.13 (br, 2H), 4.77 (br, 1H), 5.55-5.60 (m, 2H), 8.12 (s, 1H), 9.99 (d, 1H, J = 8.4) |

TABLE 20-continued
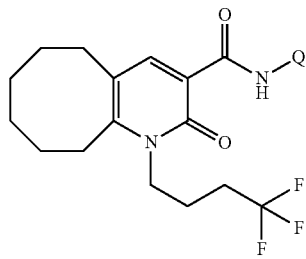
| Comp. No. | Q | $^1$H-NMR(CDCl$_3$/TMS) δ |
|---|---|---|
| X-117 | 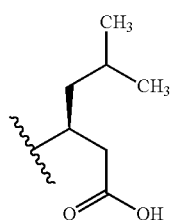 | DMSO-d6 0.87 (m, 6H), 1.24-1.84 (m, 13H), 2.37-2.48 (m, 4H), 2.65 (br, 2H), 2.92 (br, 2H), 4.11 (br, 2H), 4.33 (br, 1H), 8.12 (s, 1H), 9.81 (d, 1H, J = 8.7) |
| X-129 | 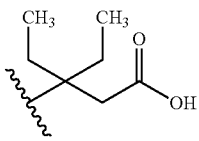 | DMSO-d6 0.81 (t, 6H, 7.2), 1.26-1.94 (m, 14H), 2.39-2.55 (m, 2H), 2.64 (br, 2H), 2.77 (s, 2H), 2.92 (br, 2H), 4.13 (t, 2H, J = 7.8), 8.11 (s, 1H), 9.78 (s, 1H), 11.97 (s, 1H) |
| X-155 | 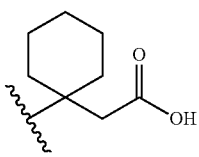 | DMSO-d6 1.15-1.88 (m, 18H), 2.22 (d, 2H, J = 8.7), 2.42-2.52 (m, 2H), 2.64 (br, 2H), 2.78 (s, 2H), 2.93 (br, 2H), 4.14 (t, 2H, J = 7.8), 8.11 (s, 1H), 9.91 (s, 1H), 11.82 (br, 1H) |
| X-158 | 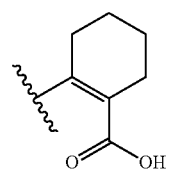 | DMSO-d6 1.28-1.86 (m, 14H), 2.23 (br, 2H), 2.37-2.48 (m, 2H), 2.64 (br, 2H), 2.80 (br, 2H), 2.93 (br, 2H), 4.12 (t, 2H, J = 7.5), 8.10 (s, 1H), 12.26 (br, 1H), 12.56 (s, 1H) |
| X-169 | 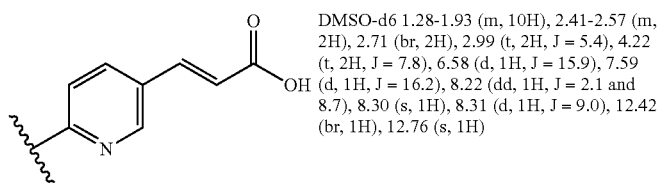 | DMSO-d6 1.28-1.93 (m, 10H), 2.41-2.57 (m, 2H), 2.71 (br, 2H), 2.99 (t, 2H, J = 5.4), 4.22 (t, 2H, J = 7.8), 6.58 (d, 1H, J = 15.9), 7.59 (d, 1H, J = 16.2), 8.22 (dd, 1H, J = 2.1 and 8.7), 8.30 (s, 1H), 8.31 (d, 1H, J = 9.0), 12.42 (br, 1H), 12.76 (s, 1H) |

TABLE 21

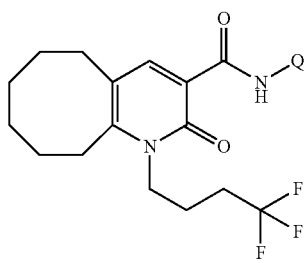

| Comp. No. | Q | ¹H-NMR(CDCl₃/TMS) δ |
|---|---|---|
| X-170 | (pyridine with propanoic acid) | DMSO-d6 1.28-1.93 (m, 10H), 2.41-2.53 (m, 2H), 2.56 (t, 2H, J = 7.5), 2.70 (br, 2H), 2.80 (t, 2H, J = 7.5), 2.98 (br, 2H), 4.21 (t, 2H, J = 7.2), 7.70 (dd, 1H, J = 2.4 and 8.4), 8.19 (d, 1H, J = 8.4), 8.20 (s, 1H), 8.28 (s, 1H), 12.18 (br, 1H), 12.50 (s, 1H) |
| X-199 | (thiazole-cyclopentane carboxylic acid) | DMSO-d6 1.10-1.8 (10H, m), 2.71 (brs, 2H), 2.99 (brs, 2H), 3..34 (brs, 2H), 4.22 (brs, 2H), 7.01 (s, 1H), 8.28 (s, 1H), 12.24 (s, 1H), 13.36 (s, 1H) |
| XI-140 | (tert-butyl substituted carboxylic acid) | DMSO-d6 0.93 (s, 9H), 1.32 (m, 2H), 1.43 (m, 2H), 1.58 (m, 3H), 1.78 (m, 5H), 2.45 (m, 2H), 2.65 (m, 2H), 2.94 (m, 2H), 4.16 (m, 2H), 4.49 (m, 1H), 8.13 (s, 1H), 10.11 (d, 1H, J = 6.0) |
| XI-141 | (tert-butyl substituted carboxylic acid) | DMSO-d6 0.89 (s, 9H), 1.32 (m, 2H), 1.44 (m, 2H), 1.60 (m, 2H), 1.71 (m, 2H), 1.82 (m, 2H), 2.18 (m, 1H), 2.47 (m, 2H), 2.62 (m, 3H), 2.93 (m, 2H), 4.14 (m, 2H), 4.28 (m, 1H), 8.12 (s, 1H), 9.93 (d, 1H, J = 7.2) |
| XI-161 | (isobutyl substituted carboxylic acid) | DMSO-d6 0.86 (dd, 6H, J = 6.3 and 5.7), 1.27-1.84 (m, 15H), 2.20 (t, 2H, J = 7.7), 2.46 (m, 2H), 2.65 (t, 2H, J = 5.7), 2.92 (t, 2H, J = 5.9), 4.03-4.15 (m, 3H), 8.12 (s, 1H), 9.62 (d, 1H, J = 9.0), 12.03 (br s, 1H) |
| XI-170 | (norbornane carboxylic acid) | DMSO-d6 1.0-2.0 (m, 20H), 2.20-3.05 (m, 8H), 4.00-4.25 (m, 2H), 8.07 (s, 1H), 10.38 (t, 1H, J = 5.7) |
| XI-176 | (CF₃ substituted carboxylic acid) | DMSO-d6 1.26-1.49 (m, 4H), 1.52-1.89 (m, 5H), 2.38-2.54 (m, 3H), 2.62-2.76 (m, 3H), 2.82-3.00 (m, 3H), 4.11-4.17 (m, 2H), 5.16 (m, 1H), 8.18 (s, 1H), 10.38 (d, 1H, J = 9.0), 12.66 (br, 1H) |

TABLE 22

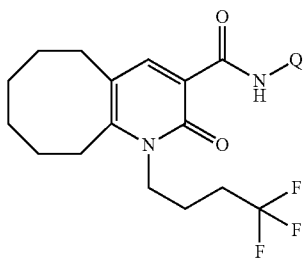

| Comp. No. | Q | $^1$H-NMR(CDCl$_3$/TMS) δ |
|---|---|---|
| XI-178 | [structure: CH$_2$CH(CH$_2$C(CH$_3$)$_3$)CH$_2$CH$_2$COOH] | DMSO-d6 0.87 (s, 9H), 1.22-1.90 (m, 14H), 2.18 (t, 2H, J = 7.5), 2.35-2.52 (m, 2H), 2.60-2.69 (m, 2H), 2.88-2.97 (m, 2H), 4.02-4.24 (m, 3H), 8.12 (s, 1H), 9.71 (d, 1H, J = 9.0), 11.99 (brs, 1H) |
| XI-217 | [structure: 1,1-disubstituted cyclopentane with CH$_2$COOH] | 1.40 (m, 2H), 1.50 (m, 2H), 1.69-2.03 (m, 12H), 2.19-2.34 (m, 4H), 2.63-2.66 (m, 2H), 2.87-2.91 (m, 2H), 3.06 (s, 2H), 4.16-4.21 (m, 2H), 8.31 (s, 1H), 10.41 (s, 1H) |
| XI-226 | [structure: 1,1-disubstituted cyclobutane with CH$_2$COOH] | DMSO-d6 1.22-1.46 (m, 4H), 1.52-1.94 (m, 8H), 2.22 (t, 3H, J = 7.5), 2.36-2.52 (m, 2H), 2.60-2.68 (m, 2H), 2.88 (s, 3H), 2.86-2.98 (m, 2H), 4.12 (t, 2H, J = 7.5), 8.09 (s, 1H), 10.05 (s, 1H), 12.01 (br, 1H) |
| XI-244 | [structure: CH$_2$-cyclohexane-1,1-bis(CH$_2$COOH)] | DMSO-d6 1.22-1.89 (m, 20H), 2.20 (s, 2H), 2.46 (m, 2H), 2.65 (br s 2H), 2.95 (t, 2HhHH, J = 5.1), 3.40 (d, 2H, J = 6.3), 4.15 (t, 2H, J = 8.4), 8.14 (s, 1H), 9.98 (t, 1H, J = 6.3), 12.18 (br s, 1H) |
| XI-253 | [structure: pyridinyl-CH$_2$COOH] | DMSO-d6 1.24-1.96 (m, 10H), 2.50-2.60 (m, 2H), 2.64-2.76 (m, 2H), 2.92-3.04 (m, 2H), 3.60 (s, 2H), 4.15-4.30 (m, 2H), 7.72 (dd, 1H, J = 2.1, 8.4), 8.19-8.25 (m, 2H), 8.28 (s, 1H), 12.45 (br s, 1H), 12.54 (s, 1H) |
| XI-260 | [structure: 1,1-disubstituted cyclohexane with CH$_2$CH$_2$COOH] | 1.27-1.77 (m, 18H), 1.96-2.04 (m, 2H), 2.18-2.38 (m, 6H), 2.61-2.70 (m, 2H), 2.86-2.94 (m, 2H), 4.15-4.24 (m, 2H), 8.31 (s, 1H), 9.94 (s, 1H) |
| XI-266 | [structure: 4,4-dimethylcyclohexane-1-CH$_2$COOH] | DMSO-d6 0.85 (s, 3H), 0.90 (s, 3H), 1.14-1.25 (m, 8H), 1.25-1.90 (m, 8H), 2.05-2.17 (m, 2H), 2.38-2.50 (m, 3H), 2.64 (m, 1H), 2.81 (s, 2H), 2.88-3.00 (m, 2H), 4.08-4.15 (m, 2H), 8.10 (s, 1H), 9.90 (s, 1H), 11.90 (br, 1H) |

TABLE 23

| Comp. No. | Q | ¹H-NMR(CDCl₃/TMS) δ |
|---|---|---|
| XI-283 | (tetrahydropyran-4-yl)-CH₂-COOH | DMSO-d6 1.22-2.00 (m, 12H), 2.10-2.75 (m, 6H), 2.85 (s, 2H), 2.90-3.00 (m, 2H), 3.50 (t, 2H, J = 11), 3.64-3.80 (m, 2H), 4.05-4.22 (m, 2H), 8.11 (s, 1H), 10.07 (s, 1H) |
| XI-287 | 4,4-dimethylcyclohexyl-1-COOH | DMSO-d6 0.89 (s, 9H), 0.91 (s, 3H), 1.20-2.00 (m, 18H), 2.40-3.00 (m, 6H), 4.10-4.22 (m, 2H), 8.08 (s, 1H), 10.23 (s, 1H) |
| XI-291 | 2-(pyrimidin-2-yl)-CH=CH-COOH (pyrimidin-5-yl acrylic acid) | DMSO-d6 1.28-1.98 (m, 10H), 2.40-2.60 (m, 2H), 2.65-2.77 (m, 2H), 2.93-3.05 (m, 2H), 4.14-4.30 (m, 2H), 6.73 (d, 1H, J = 16.2), 7.57 (d, 1H, J = 16.2), 8.27 (s, 1H), 9.03 (s, 2H), 12.30 (br s, 1H), 12.98 (s, 1H) |

TABLE 24

| Comp. No. | Q | ¹H-NMR(CDCl₃/TMS) δ |
|---|---|---|
| I-152 | CH(CH₃)₂ substituted CH-COOCH₃ | 1.03 (d, 6H, J = 6.9), 1.31-1.79 (m, 10H), 2.29 (m, 1H), 2.62-2.66 (m, 2H), 3.02-3.06 (m, 2H), 3.03 (s, 3H), 3.74 (s, 3H), 4.36 (t, 2H, J = 5.7), 4.69 (dd, 1H, J = 5.4 and 7.8), 8.29 (s, 1H), 10.38 (d, 1H, J = 6.3) |

TABLE 24-continued
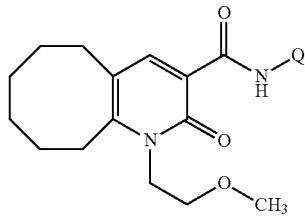
| Comp. No. | Q | ¹H-NMR(CDCl₃/TMS) δ |
|---|---|---|
| I-153 | (R)-phenyl-CH(-)-C(O)OCH₃ | 1.30-1.78 (m, 8H), 2.62 (t, 2H, J = 6.0), 3.03 (t, 2H, J = 6.0), 3.29 (s, 3H), 3.68 (t, 2H, J = 5.4), 3.74 (s, 3H), 4.34 (t, 2H, J = 5.4), 5.74 (d, 1H, J = 6.6), 7.30-7.41 (m, 3H), 7.47-7.52 (m, 2H), 8.28 (s, 1H), 10.84 (d, 1H, J = 6.6) |
| I-425 | (CH₃)₂CH-CH(-)-C(O)OH | DMSO-d6 0.92 (d, 6H, J = 6.6), 1.23-1.77 (m, 8H), 2.15 (m, 1H), 2.62-2.70 (m, 2H), 2.94-3.06 (m, 2H), 3.23 (s, 3H), 3.62 (t, 2H, J = 5.4), 4.22-4.35 (m, 2H), 4.39 (dd, 1H, J = 4.5 and 8.4), 8.13 (s, 1H), 10.22 (d, 1H, J = 8.4), 12.74 (br, 1H) |
| I-426 | (R)-phenyl-CH(-)-C(O)OH | DMSO-d6 1.20-1.78 (m, 8H), 2.40-2.64 (m, 2H), 2.98-3.05 (m, 2H), 3.22 (s, 3H), 3.61 (t, 2H, J = 5.7), 4.29 (t, 2H, J = 5.4), 5.48 (d, 1H, J = 6.9), 7.30-7.45 (m, 5H), 8.11 (s, 1H), 10.68 (d, 1H, J = 6.9), 13.06 (br, 1H) |
| XI-035 | 1-(cyclopentyl)-CH₂-C(O)OH | DMSO-d6 1.24-1.50 (m, 4H), 1.52-1.84 (m, 12H), 2.04-2.17 (m, 2H), 2.60-2.68 (m, 2H), 2.95-3.05 (m, 2H), 3.23 (s, 3H), 3.59 (t, 2H, J = 7.6), 4.23 (t, 2H, J = 7.6), 8.10 (s, 1H), 9.85 (s, 1H), 12.00 (br, 1H) |
| XI-039 | thiazol-2-yl-CH₂-C(O)OH | DMSO-d6 1.24-1.80 (m, 8H), 2.67-2.77 (m, 2H), 3.02-3.13 (m, 2H), 3.24 (s, 3H), 3.62 (s, 2H), 3.67 (t, 1H, J = 5.1), 4.36 (t, 1H, J = 5.1), 7.02 (s, 1H), 8.30 (s, 1H), 12.41 (br s, 1H), 13.37 (s, 1H) |

TABLE 25

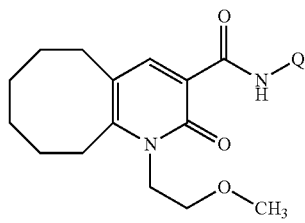

| Comp. No. | Q | $^1$H-NMR(CDCl$_3$/TMS) δ |
|---|---|---|
| XI-047 | 1-carboxycyclohexyl | DMSO-d6 1.15-1.80 (m, 16H), 1.98-2.10 (m, 2H), 2.60-2.70 (m, 2H), 2.95-3.10 (m, 2H), 3.24 (s, 3H), 3.63 (t, 2H, J = 5.4), 4.30 (t, 2H, J = 5.4), 8.09 (s, 1H), 10.22 (s, 1H), 12.20 (br s, 1H) |
| XI-123 | 1-(carboxymethyl)cyclohexyl | DMSO-d6 1.11-1.78 (m, 16H), 2.14-2.28 (m, 2H), 2.62-2.68 (m, 2H), 2.78 (s, 2H), 2.94-3.08 (m, 2H), 3.23 (s, 3H), 3.61 (t, 2H, J = 5.4), 4.27 (t, 2H, J = 5.4), 8.10 (s, 1H), 9.89 (s, 1H), 11.81 (br, 1H) |
| XI-138 | 4,4-dimethyl-1-carboxypentyl (neopentyl α-carboxy) | DMSO-d6 0.93 (s, 9H), 1.30 (m, 2H), 1.42 (m, 2H), 1.57 (m, 3H), 1.73 (m, 3H), 2.65 (m, 2H), 3.01 (m, 2H), 3.23 (s, 3H), 3.61 (m, 2H), 4.28 (m, 2H), 4.48 (m, 1H), 8.13 (s, 1H), 10.10 (d, 1H, J = 6.0) |
| XI-139 | 3-tert-butyl-4-carboxybutyl | DMSO-d6 0.90 (s, 9H), 1.30 (m, 2H), 1.43 (m, 2H), 1.59 (m, 2H), 1.70 (m, 2H), 2.16 (m, 1H), 2.62 (m, 3H), 3.01 (m, 2H), 3.24 (s, 3H), 3.61 (m, 2H), 4.28 (m, 3H), 8.12 (s, 1H), 9.93 (d, 1H, J = 7.2) |
| XI-150 | 5-(carboxymethyl)-1,2,4-thiadiazol-3-yl | DMSO-d6 1.20-1.84 (m, 8H), 2.65-2.80 (m, 2H), 3.02-3.15 (m, 2H), 3.24 (s, 3H), 3.68 (t, 1H, J = 5.1), 3.81 (s, 2H), 4.38 (d, 2H, J = 5.1), 8.34 (s, 1H), 12.69 (br s, 1H), 13.78 (s, 1H) |
| XI-158 | 2-(carboxymethyl)thiazol-5-yl | DMSO-d6 1.24-1.82 (m, 8H), 2.65-2.80 (m, 2H), 3.02-3.15 (m, 2H), 3.24 (s, 3H), 3.67 (t, 2H, J = 5.4), 3.82 (s, 2H), 4.30-4.45 (m, 2H), 7.31 (s, 1H), 8.30 (s, 1H), 12.65 (br s, 1H), 13.30 (s, 1H) |
| XI-160 | 6-methyl-4-(carboxypropyl)heptyl | DMSO-d6 0.86 (t, 6H, J = 6.0), 1.14-1.80 (m, 13H), 2.21 (t, 2H, J = 7.7), 2.65 (t, 2H, J = 5.7), 3.01 (t, 2H, J = 6.2), 3.23 (s, 3H), 3.60 (t, 2H, J = 5.7), 4.04 (m, 1H), 4.27 (t, 2H, J = 5.4), 8.12 (s, 1H), 9.51 (d, 1H, J = 9.0), 12.00 (br s, 1H) |

TABLE 26

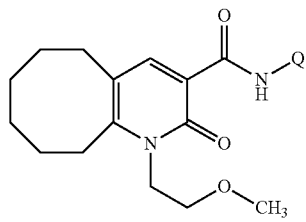

| Comp. No. | Q | $^1$H-NMR(CDCl$_3$/TMS) δ |
|---|---|---|
| XI-169 | (norbornyl-COOH) | DMSO-d6 1.10-1.18 (m, 16H), 2.20-3.10 (m, 6H), 3.24 (s, 3H), 3.63 (t, 2H, J = 5.4), 4.20-4.40 (m, 2H), 8.08 (s, 1H), 10.39 (s, 1H) |
| XI-173 | CF$_3$-CH(CH$_2$COOH)- | DMSO-d6 1.22-1.52 (m, 4H), 1.52-1.78 (m, 4H), 2.62-2.72 (m, 4H), 2.85 (dd, 1H, J = 4.8 and 16.5), 2.98-3.07 (m, 2H), 3.23 (s, 3H), 3.61 (t, 2H, J = 5.4), 4.29 (t, 2H, J = 5.4), 5.18 (m, 1H), 8.18 (s, 1H), 10.37 (d, 1H, |
| XI-177 | (CH$_3$)$_3$C-CH$_2$-CH(CH$_2$CH$_2$COOH)- | DMSO-d6 0.88 (s, 9H), 1.23-1.82 (m, 12H), 2.19 (t, 2H, J = 7.5), 2.60-2.69 (m, 2H), 2.95-3.04 (m, 2H), 3.22 (s, 3H), 3.60 (t, 2H, J = 5.4), 4.10 (m, 1H), 4.27 (t, 2H, J = 5.4), 8.12 (s, 1H), 9.85 (d, 1H, J = 9.0), 12.00 (brs, 1H) |
| XI-199 | (CH$_3$)$_2$CH-CH$_2$-CH(CH$_2$COOH)- | DMSO-d6 0.87 (dd, 6H, J = 6.3 and 3.3), 1.24-1.73 (m, 11H), 2.44 (t, 2H, J = 6.6), 2.64 (t, 2H, J = 5.4), 3.00 (t, 2H, J = 5.9), 3.23 (s, 3H), 3.59 (t, 2H, J = 5.3), 4.26 (t, 2H, J = 5.3), 4.33 (m, 1H), 8.12 (s, 1H), 9.80 (d, 1H, J = 8.7), 12.18 (br s, 1H) |
| XI-224 | cyclobutyl-CH$_2$COOH | DMSO-d6 1.24-1.49 (m, 6H), 1.49-1.76 (m, 4H), 1.76-1.95 (m, 2H), 2.16-2.30 (m, 4H), 2.59-2.76 (m, 2H), 2.88 (s, 2H), 2.94-3.06 (m, 2H), 3.23 (s, 3H), 3.60 (t, 2H, J = 5.4), 8.09 (s, 1H), 10.03 (s, 1H), 12.02 (br, 1H) |
| XI-243 | cyclohexyl(CH$_2$-)(CH$_2$COOH) | DMSO-d6 1.26-1.80 (m, 18H), 2.25 (s, 2H), 2.72 (t, 2H, J = 5.4), 3.09 (t 2H, J = 6.5), 3.31 (s, 3H), 3.49 (d, 2H, J = 6.3), 3.70 (t, 2H, J = 5.4), 4.39 (t, 2H, J = 5.6), 8.34 (s, 1H), 10.23 (t, 1H, J = 6.0), 12.49 (br s, 1H) |
| XI-252 | pyridinyl-CH$_2$COOH | DMSO-d6 1.24-1.80 (m, 8H), 2.65-2.75 (m, 2H), 3.00-3.10 (m, 2H), 3.60 (s, 2H), 3.67 (t, 1H, J = 5.1), 4.30-4.40 (m, 2H), 7.72 (dd, 1H, J = 2.1, 8.7), 8.19-8.26 (m, 2H), 8.29 (s, 1H), 12.40 (br s, 1H), 12.52 (s, 1H) |

TABLE 27

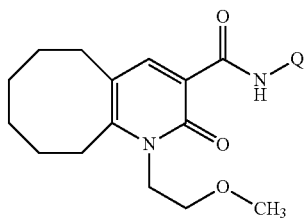

| Comp. No. | Q | $^1$H-NMR(CDCl$_3$/TMS) δ |
|---|---|---|
| XI-267 | cyclohexyl with 4,4-dimethyl and CH$_2$COOH | DMSO-d6 0.86 (s, 3H), 0.90 (s, 3H), 1.15-1.52 (m, 8H), 1.53-1.78 (m, 6H), 2.02-2.18 (m, 2H), 2.60-2.71 (m, 2H), 2.81 (s, 2H), 2.92-3.16 (m, 2H), 3.23 (s, 3H), 3.61 (t, 2H, J = 7.5), 4.27 (t, 2H, J = 5.4), 8.10 (s, 1H), 9.89 (s, 1H), 11.95 (br, 1H) |
| XI-279 | pyridin-2-yl acrylic acid | DMSO-d6 1.25-1.80 (m, 8H), 2.67-2.77 (m, 2H), 3.00-3.12 (m, 2H), 3.25 (s, 3H), 3.67 (t, 1H, J = 5.1), 4.30-4.40 (m, 2H), 6.58 (d, 1H, J = 16.2), 7.59 (d, 1H, J = 15.9), 8.22 (dd, 1H, J = 2.1, 8.7), 8.31 (d, 1H, J = 8.7), 8.31 (s, 1H), 8.62 (d, 1H, J = 1.8), 12.44 (br s, 1H), 12.73 (s, 1H) |
| XI-290 | pyrimidin-2-yl acrylic acid | DMSO-d6 1.25-1.80 (m, 8H), 2.65-2.77 (m, 2H), 3.00-3.10 (m, 2H), 3.25 (s, 3H), 3.67 (t, 1H, J = 5.1), 4.30-4.40 (m, 2H), 6.73 (d, 1H, J = 16.5), 7.57 (d, 1H, J = 16.2), 8.27 (s, 1H), 9.03 (s, 2H), 12.96 (s, 1H) |
| XI-297 | cyclohexyl-CH$_2$CH$_2$COOH | 1.34-1.71 (m, 3H, J = 6.6), 2.19-2.41 (m, 6H), 2.63-2.67 (m, 2H), 3.02-3.07 (m, 2H), 3.33 (s, 3H), 3.71 (t, 2H, J = 5.1), 4.36 (t, 2H, J = 5.4), 8.34 (s, 1H), 10.01 (1H, s) |
| XI-305 | 4,4-dimethylcyclohexyl-COOH | 0.93 (s, 3H), 0.96 (s, 3H), 1.36-1.80 (m, 12H), 2.05-2.24 (m, 2H), 2.66 (m, 2H), 3.08 (m, 2H), 3.30 (s, 3H), 3.70 (2H, t, J = 5.1), 4.37 (t, 2H, J = 5.1), 8.31 (s, 1H), 10.67 (s, 1H) |

TABLE 28

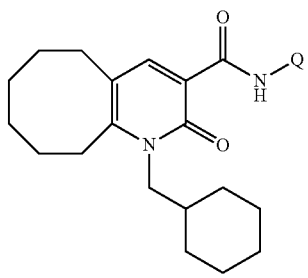

| Comp. No. | Q | ¹H-NMR(CDCl₃/TMS) δ |
|---|---|---|
| I-001 | CH₃ CH₃, C(=O)-S-CH₃ | 1.02-1.96 (m, 19H), 1.65 (s, 6H), 2.73 (s, 3H), 2.61 (t, 2H, J = 6.0), 2.92 (t, 2H, J = 6.3), 4.00 (br, 2H), 8.29 (s, 1H), 10.45 (s, 1H) |
| I-002 | CH₃ CH₃, C(=O)-NH₂ | 1.00-1.98 (m, 25H), 2.63 (t, 2H, J = 5.7), 2.92 (t, 2H, J = 5.7), 4.03 (br, 2H), 5.23 (br, 1H), 6.97 (br, 1H), 8.28 (s, 1H), 10.38 (br, 1H) |
| I-003 | CH₃ CH₃, C(=O)-NH-S(=O)₂-CH₃ | 1.00-1.98 (m, 26H), 2.65 (t, 2H, J = 6.0), 2.95 (t, 2H, J = 6.0), 3.29 (s, 3H), 4.09 (br, 2H), 8.27 (s, 1H), 10.56 (d, 1H, J = 5.7) |
| I-005 | CH₃ CH₃, C(=O)-NH-CH₂-Ph | 1.00-1.90 (m, 26H), 2.62 (t, 2H, J = 5.7), 2.92 (t, 2H, J = 6.3), 3.98 (br, 2H), 4.48 (d, 2H, J = 6.0), 7.18-7.40 (m, 5H), 8.26 (s, 1H), 10.35 (br s, 1H) |
| I-006 | CH₃ CH₃, C(=O)-NH-Ph | 1.00-1.90 (m, 26H), 2.65 (t, 2H, J = 6.0), 2.93 (t, 2H, J = 6.0), 4.00 (br, 2H), 7.03 (m, 1H), 7.24-7.30 (m, 2H), 7.56-7.62 (m, 2H), 8.31 (s, 1H), 10.53 (br s, 1H) |
| I-007 | CH₃ CH₃, C(=O)-NH-CH₃ | 1.00-1.90 (m, 25H), 2.63 (t, 2H, J = 6.0), 2.80 (d, 3H, J = 4.5), 2.92 (t, 2H, J = 6.0), 4.00 (br, 2H), 7.09 (br s, 1H), 8.27 (s, 1H), 10.35 (br s, 1H) |
| I-008 | CH₃ CH₃, C(=O)-N(CH₃)₂ | 1.00-1.90 (m, 25H), 2.63 (t, 2H, J = 6.0), 2.92 (t, 2H, J = 6.0), 3.03 (s, 6H), 4.02 (br, 2H), 8.29 (s, 1H), 10.29 (br s, 1H) |
| I-009 | CH₃ CH₃, C(=O)-NH-CH₂-C(=O)-O-CH₃ | 1.02-1.90 (m, 19H), 1.66 (s, 6H), 2.63 (t, 2H, J = 6.0), 2.93 (t, 2H, J = 6.3), 3.73 (s, 3H), 4.02 (br, 2H), 4.06 (d, 2H, J = 5.4), 7.52 (brt, 1H), 8.28 (s, 1H), 10.40 (s, 1H) |
| I-010 | CH₃ CH₃, C(=O)-NH-CH₂CH₂-OH | 1.00-1.96 (m, 18H), 1.62 (s, 6H), 2.63 (t, 2H, J = 6.0), 2.93 (t, 2H, J = 6.3), 3.37 (q, 2H, J = 6.0), 3.73 (t, 2H, J = 5.4), 3.98 (br, 2H), 6.76 (brt, 1H), 8.25 (s, 1H), 10.49 (s, 1H) |

TABLE 29

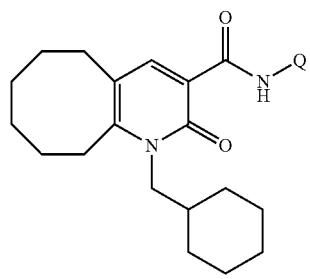

| Comp. No. | Q | ¹H-NMR(CDCl₃/TMS) δ |
|---|---|---|
| I-011 | ![structure with CH₃ CH₃, NH, C(=O), OH] | 1.02-1.90(m, 19H), 1.63(s, 6H), 2.64(t, 2H, J = 5.7), 2.95(t, 2H, J = 6.0), 4.00(br, 2H), 4.09(d, 2H, J = 5.7), 7.06(t, 1H, J = 6.0), 8.26(s, 1H), 10.59(s, 1H) |
| I-012 | ![structure with CH₃ CH₃, NH, N(CH₃)₂] | 1.00-2.00(m, 19H), 1.63(s, 6H), 2.19(s, 6H), 2.42(t, 2H, J = 6.3), 2.63(t, 2H, J = 6.0), 2.92(t, 2H, J = 6.3), 3.34(q, 2H, J = 6.3), 4.00(br, 2H), 7.08(brt, 1H), 8.26(s, 1H), 10.30(s, 1H) |
| I-013 | ![structure with CH₃ CH₃, NH, two OH] | 1.02-1.97(m, 19H), 1.63(s, 6H), 2.62(t, 2H, J = 6.0), 2.93(t, 2H, J = 6.3), 3.75(m, 1H), 3.86(dd, 2H, J = 3.3, 11.7), 3.98(dd, 1H, J = 3.3, 11.7), 6.83(d, 1H, J = 7.2), 8.20(s, 1H), 10.59(s, 1H) |
| I-014 | ![structure with CH₃ CH₃, NH, OH, OH] | 1.03-1.93(m, 19H), 1.62(s, 6H), 2.63(t, 2H, J = 6.0), 2,94(t, 2H, J = 6.3), 3.30-3.50(m, 2H), 3.54-3.69(m, 2H), 3.80-4.17(m, 3H), 6.90(brt, 1H), 8.24(s, 1H), 10.50(s, 1H) |
| I-015 | ![structure with CH₃ CH₃, NH, morpholine] | 1.03-1.91(m, 19H), 1.63(s, 6H), 2.41(brs, 4H), 2.48(t, 2H, J = 6.0), 2.63(t, 2H, J = 6.0), 2.93(t, 2H, J = 6.3), 3.34(q, 2H, J = 6.0), 3.53(brt, 4H), 4.03(br, 2H), 7.19(brt, 1H), 8.26(s, 1H), 10.32(s, 1H) |
| I-016 | ![structure with CH₃ CH₃, NH, three OH] | 1.01-1.92(m, 19H), 1.65(s, 6H), 2.62(t, 2H, J = 6.0), 2.93(t, 2H, J = 6.3), 3.75(s, 6H), 4.00(br, 2H), 4.40(br, 3H), 7.28(s, 1H9, 8.16(s, 1H), 10.68(s, 1H) |
| I-017 | ![structure with CH₃ CH₃, CH₃, N, OH, OH] | 1.02-1.89(m, 19H), 1.63(s, 6H), 2.63(t, 2H, J = 6.0), 2.93(t, 2H, J = 6.3), 3.12(s, 3H), 3.34-3.70(m, 4H), 4.01(br, 2H), 4.07-4.16(m, 2H), 8.27(s, 1H), 10.48(s, 1H) |
| I-018 | ![structure with CH₃ CH₃, N, two OH] | 1.03-1.88(m, 19H), 1.65(s, 6H), 2.63(t, 2H, J = 6.0), 2.93(t, 2H, J = 6.3), 3.62(br, 4H), 3.62-4.20(m, 4H), 8.22(s, 1H), 10.51(s, 1H) |

TABLE 30

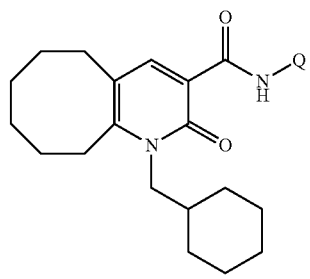

| Comp. No. | Q | ¹H-NMR(CDCl₃/TMS) δ |
|---|---|---|
| I-019 | CH₃ CH₃ CH₃ with N-CH₂CH₂OH, C=O | 1.02-1.90(m, 19H), 1.66(s, 6H), 2.62(t, 2H, J = 6.0), 2.92(t, 2H, J = 6.3), 3.17(br, 2H), 3.71(br, 2H), 4.09(br, 2H), 8.28(s, 1H), 10.34(s, 1H) |
| I-020 | CH₃ CH₃ CH₃ with N-CH₂C(=O)OCH₃, C=O | 1.02-1.89(m, 19H), 1.63(s, 6H), 2.63(t, 2H, J = 6.0), 2.93(t, 2H, J = 6.3), 3.09(s, 3H), 3.53(t, 2H, J = 4.5), 3.82(t, 2H, J = 4.8), 4.01(br, 2H), 8.27(s, 1H), 10.47(s, 1H) |
| I-021 | CH₃ CH₃ with NH-morpholine, C=O | 1.03-1.97(m, 19H), 1.64(s, 6H), 2.65(t, 2H, J = 6.0), 2.88-2.98(m, 6H), 3.81(t, 4H, J = 4.8), 4.05(br, 2H), 8.26(s, 1H), 8.33(s, 1H), 10.34(s, 1H) |
| I-022 | CH₃ CH₃ CH₃ with N-CH₂COOH, C=O | 1.02-1.90(m, 19H), 1.66(s, 6H), 2.65(t, 2H, J = 6.0), 2.95(t, 2H, J = 6.3), 3.13(s, 3H), 4.00(br, 2H), 4.24(s, 2H), 8.28(s, 1H), 10.76(s, 1H) |
| I-023 | with NH-CH₂CH₂OH, C=O | 1.07-1.83(m, 19H), 2.65(t, 2H, J = 6.9), 2.94(t, 2H, J = 6.3), 3.41-3.43(m, 2H), 3.70-3.74(m, 2H), 3.91-4.20(m, 4H), 8.30(s, 1H), 10.52(s, 1H) |
| I-024 | CH₃ CH₃ CH₃ with N-OCH₃, C=O | 1.00-1.94(m, 25H), 2.62(t, 2H, J = 6.0), 2.91(t, 2H, J = 6.0), 3.19(s, 3H), 3.51(s, 3H), 4.02(br, 2H), 8.30(s, 1H), 10.34(br s, 1H) |
| I-025 | CH₃ CH₃ with NH-CH₂CH₂CH₂OH, C=O | 1.00-1.92(m, 21H), 1.65(s, 6H), 2.64(t, 2H, J = 6.0), 2.94(t-like, 2H), 3.43(q-like, 3H), 3.63(t-like, 2H), 4.00(br, 2H), 7.23(br, 1H), 8.28(s, 1H), 10.39(brs, 1H) |
| I-026 | CH₃ CH₃ with NH-(CH₂)₄OH, C=O | 1.02-1.94(m, 23H), 1.64(s, 6H), 2.64(t-like, 2H), 2.93(t, 2H, J = 6.3), 3.29-3.31(m, 2H), 3.63-3.67(m, 2H), 3.99(br, 2H), 7.15(br, 1H), 8.26(s, 1H), 10.34(brs, 1H) |

TABLE 31

| Comp. No. | Q | $^1$H-NMR(CDCl$_3$/TMS) δ |
|---|---|---|
| I-031 | | 0.87(d, 1H, J = 10.2), 0.94(s, 3H), 1.18(s, 3H), 1.01-2.31(m, 25H), 1.57(s, 3H), 1.64(s, 3H), 2.55-3.01(m, 6H), 3.61(m, 1H), 3.78(m, 1H), 4.00(br, 2H), 4.11(m, 1H), 6.53(brd, 1H, J = 8.4), 8.22(s, 1H), 10.46(brs, 1H) |
| I-032 | | 1.00-1.94(m, 25H), 2.64(t, 2H, J = 6.0), 2.75(t, 2H, J = 7.2), 2.91(t, 2H, J = 6.0), 3.44(q, 2H, J = 6.6), 3.98(br, 2H), 6.69(d, 2H, J = 8.4), 7.02(d, 2H, J = 8.4), 7.08(m, 1H), 8.26(s, 1H), 10.31(br s, 1H) |
| I-033 | | 1.00-1.94(m, 25H), 2.64(t, 2H, J = 6.0), 2.75(t, 2H, J = 7.2), 2.91(t, 2H, J = 6.0), 3.44(q, 2H, J = 6.6), 3.74(s, 3H), 3.98(br, 2H), 6.69(d, 2H, J = 8.4), 7.05-7.15(m, 3H), 8.26(s, 1H), 10.29(br s, 1H) |
| I-036 | | 1.02-1.94(m, 19H), 1.63(s, 6H), 2.38-2.47(m, 4H), 2.51(t, 2H, J = 5.4), 2.61-2.65(m, 2H), 2.77(br, 1H), 2.90-2.95(m, 2H), 3.58(t, 2H, J = 5.4), 3.66-3.80(m, 4H), 3.86-4.20(br, 2H), 8.26(s, 1H), 10.26(s, 1H) |
| I-037 | | 1.02-1.94(m, 19H), 1.58(s, 6H), 1.83(s, 3H), 2.60-2.73(m, 2H), 2.88-3.01(m, 2H), 3.50-3.78(m, 4H), 3.85-4.36(m, 11H), 8.19(s, 1H), 10.45(s, 1H) |
| I-040 | | 1.01-1.92(m, 23H), 1.63(s, 6H), 2.17(brs, 2H), 2.64(t-like, 2H), 2.93(t-like, 2H), 13.27(q-like, 2H), 3.62(t, 2H, J = 6.0), 4.00(br, 2H), 7.08(brt, 1H), 8.26(s, 1H), 10.35(brs, 1H) |
| I-041 | | 1.01-1.92(m, 27H), 1.64(s, 6H), 2.64(t-like, 2H), 2.93(t-like, 2H), 3.26(q-like, 2H), 3.62(t, 2H, J = 6.3), 3.99(br, 2H), 7.18(brt, 1H), 8.28(s, 1H), 10.34(brs, 1H) |
| I-042 | | 1.00-1.91(m, 19H), 1.65(s, 61-), 2.65(t-like, 2H), 2.93(t-like, 2H), 3.45(q-like, 2H), 3.56-3.61(m, 4H), 3.68-3.70(m, 2H), 3.99(br, 2H), 7.81(brt, 1H), 8.28(s, 1H), 10.48(brs, 1H) |

TABLE 32

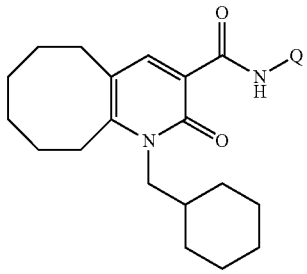

| Comp. No. | Q | $^1$H-NMR(CDCl$_3$/TMS) δ |
|---|---|---|
| I-043 | ![structure: C(CH3)2-C(=O)-NH-CH2CH2-N+(CH3)3] | 1.00-2.08(m, 19H), 1.62(s, 6H), 2.64(t-like, 2H), 2.93(t-like, 2H), 3.47(s, 9H), 3.84(brs, 4H), 4.00(br, 2H), 7.71(brt, 1H), 8.15(s, 1H), 10.39(s, 1H) |
| I-044 | ![structure: C(CH3)2-C(=O)-NH-CH2-C(CH3)2-CH2OH] | 0.86(s, 6H), 1.01-1.92(m, 19H), 1.65(s, 6H), 2.64(t-like, 2H), 2.94(t-like, 2H), 3.09(d, 2H, J = 6.6), 3.17(s, 2H), 3.99(br, 2H), 7.55(brt, 1H), 8.27(s, 1H), 10.37(brs, 1H) |
| I-045 | ![structure: C(CH3)2-C(=O)-N(piperidine-4-OH)] | 1.02-1.90(m, 24H), 1.63(S, 6H), 2.61-2.65(m, 2H), 2.90-2.94(m, 2H), 3.14-3.30(m, 2H), 3.70-4.30(br, 2H), 3.80(m, 1H), 4.12-4.36(m, 2H), 8.26(s, 1H), 10.30(s, 1H) |
| I-046 | ![structure: C(CH3)2-C(=O)-NH-tetrazole] | 1.02-1.93(m, 19H), 1.74(s, 6H), 2.62-2.66(m, 2H), 2.93-2.97(m, 2H), 3.75-4.18(br, 2H), 8.27(s, 1H), 10.68(s, 1H), 11.29(s, 1H), 13.29(brs, 1H) |
| I-047 | ![structure: C(CH3)2-C(=O)-N(piperazine-N-CH3)] | 1.02-2.00(m, 19H), 1.64(s, 6H), 2.24(s, 3H), 2.28-2.38(m, 4H), 2.61-2.65(m, 2H), 2.90-2.94(m, 2H), 3.66-3.78(m, 4H), 3.80-4.20(br, 2H), 8.26(s, 1H), 10.25(s, 1H) |
| I-048 | ![structure: C(CH3)2-C(=O)-N(piperidine-4-NHSO2-C(CH3)3)] | 1.02-1.94(m, 19H), 1.59(s, 6H), 2.64-2.68(m, 2H), 2.94-2.98(m, 2H), 3.50-3.66(m, 4H), 3.60(s, 6H), 3.86-4.16(br, 2H), 4.04-4.14(m, 4H), 8.18(s, 1H), 10.46(s, 1H) |
| I-049 | ![structure: C(CH3)2-C(=O)-N(piperazine-N+(CH3)2)] | 1.02-1.94(m, 19H), 1.59(s, 6H), 2.64-2.68(m, 2H), 2.94-2.98(m, 2H), 3.50-3.66(m, 4H), 3.60(s, 6H), 3.86-4.16(br, 2H), 4.04-4.14(m, 4H), 8.18(s, 1H), 10.46(s, 1H) |

TABLE 32-continued

[Structure: 1-(cyclohexylmethyl)-2-oxo-1,2,5,6,7,8,9,10-octahydrocycloocta[b]pyridine-3-carboxamide core with N-Q substituent]

| Comp. No. | Q | $^1$H-NMR(CDCl$_3$/TMS) δ |
|---|---|---|
| I-050 | [CH$_3$ CH$_3$ C(C(=O)NHNH$_2$)] | 1.00-1.92(m, 19H), 1.65(s, 6H), 2.45-2.90(br, 2H), 2.62-2.71(m, 2H), 2.91-2.95(m, 2H), 3.75-4.25(br, 2H), 8.25(br, 1H), 8.26(s, 1H), 10.38(s, 1H) |

TABLE 33

[Structure: 1-(cyclohexylmethyl)-2-oxo-1,2,5,6,7,8,9,10-octahydrocycloocta[b]pyridine-3-carboxamide core with N-Q substituent]

| Comp. No. | Q | $^1$H-NMR(CDCl$_3$/TMS) δ |
|---|---|---|
| I-051 | [CH$_3$ CH$_3$ C(C(=O)NHNHC(=O)NHCH(CH$_3$)$_2$)] | 1.02-1.94(m, 19H), 1.22(d, 6H, J = 6.0), 1.62(s, 6H), 2.62-2.66(m, 2H), 2.93-2.97(m, 2H), 3.80-4.15(br, 2H), 3.97(m, 1H), 5.91(brs, 1H), 6.46(d, 1H, J = 7.8), 7.79(s, 1H), 8.23(s, 1H), 10.52(s, 1H) |
| I-052 | [CH$_3$ CH$_3$ C(C(=O)NHNHS(=O)$_2$CH$_3$)] | 1.02-1.94(m, 19H), 1.65(s, 6H), 2.62-2.66(m, 2H), 2.92-2.96(m, 2H), 3.06(s, 3H), 3.75-4.18(br, 2H), 6.93(d, 1H, J = 5.4), 8.24(s, 1H), 8.86(d, 1H, J = 5.4), 10.46(s, 1H) |
| I-053 | [CH$_3$ CH$_3$ C(C(=O)-piperidin-4-yl-C(=O)NH$_2$)] | 1.02-1.90(m, 19H), 1.62(S, 6H), 2.33(m, 1H), 2.61-2.65(m, 2H), 2.76-2.96(m, 4H), 2.90-2.94(m, 2H), 3.75-4.25(br, 2H), 4.45-4.65(m, 4H), 5.35(brs, 1H), 5.64(brs, 1H), 8.24(s, 1H), 10.31(s, 1H) |
| I-054 | [CH$_3$ CH$_3$ C(C(=O)NHCH$_2$C(=O)NH$_2$)] | 1.02-1.95(m, 19H), 1.62(s, 6H), 2.63-2.67(m, 2H), 2.93-2.97(m, 2H), 3.75-4.15(br, 2H), 3.95(d, 2H, J = 6.6), 5.37(brs, 1H), 6.65(t, 1H, J = 6.6), 7.66(brs, 1H), 8.20(s, 1H), 10.55(s, 1H) |

TABLE 33-continued
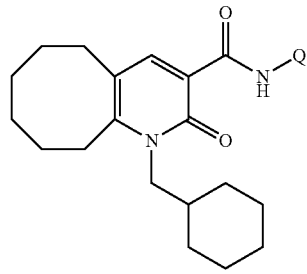
| Comp. No. | Q | $^1$H-NMR(CDCl$_3$/TMS) δ |
|---|---|---|
| I-055 | 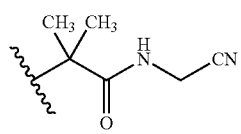 | 1.01-1.92(m, 19H), 1.65(s, 6H), 2.63-2.67(m, 2H), 2.92-2.96(m, 2H), 3.80-4.20(br, 2H), 4.17(d, 2H, J = 6.0), 8.25(s, 1H), 8.30(t, 1H, J = 6.0), 10.50(s, 1H) |
| I-056 | 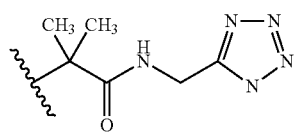 | 1.01-1.94(m, 19H), 1.66(s, 6H), 2.66-2.70(m, 2H), 2.93-2.98(m, 2H), 3.80-4.20(br, 2H), 4.86(d, 2H, J = 6.0), 6.74(t, 1H, J = 6.0), 8.33(s, 1H), 10.86(s, 1H) |
| I-057 | 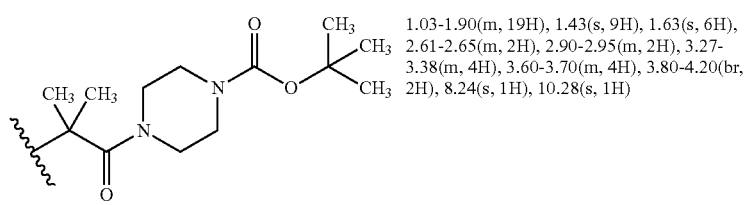 | 1.03-1.90(m, 19H), 1.43(s, 9H), 1.63(s, 6H), 2.61-2.65(m, 2H), 2.90-2.95(m, 2H), 3.27-3.38(m, 4H), 3.60-3.70(m, 4H), 3.80-4.20(br, 2H), 8.24(s, 1H), 10.28(s, 1H) |
TABLE 34
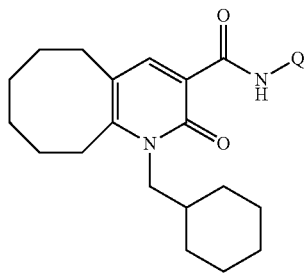
| Comp. No. | Q | $^1$H-NMR(CDCl$_3$/TMS) δ |
|---|---|---|
| I-058 | 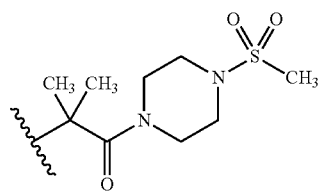 | 1.02-1.90(m, 19H), 1.62(S, 6H), 2.61-2.65(m, 2H), 2.69(s, 3H), 2.92-2.96(m, 2H), 3.04-3.17(m, 4H), 3.75-3.87(m, 4H), 3.80-4.20(br, 2H), 8.23(s, 1H), 10.28(s, 1H) |

TABLE 34-continued

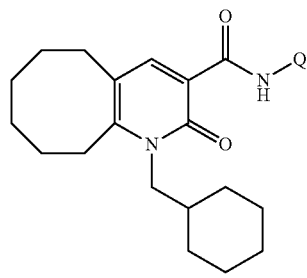

| Comp. No. | Q | $^1$H-NMR(CDCl$_3$/TMS) δ |
|---|---|---|
| I-059 | (piperazine sulfonyl isopropyl, dimethyl acyl) | 1.02-1.90(m, 19H), 1.28(d, 6H, J = 6.9), 1.62(S, 6H), 2.61-2.65(m, 2H), 2.91-2.95(m, 2H), 3.14(m, 1H), 3.20-3.30(m, 4H), 3.68-3.82(m, 4H), 3.80-4.20(br, 2H), 8.24(s, 1H), 10.27(s, 1H) |
| I-060 | (dimethyl, N-N-sulfonyl isopropyl) | 1.02-1.94(m, 19H), 1.46(d, 6H, J = 6.6), 1.64(s, 6H), 2.62-2.66(m, 2H), 2.92-2.96(m, 2H), 3.41(m, 1H), 3.80-4.20(br, 2H), 6.85(d, 1H, J = 5.4), 8.24(s, 1H), 8.95(d, 1H, J = 5.4), 10.44(s, 1H) |
| I-061 | (dimethyl, N-N-sulfonyl phenyl) | DMSO-d6 1.01-1.86(m, 19H), 1.31(s, 6H), 2.60-2.70(m, 2H), 2.89-3.01(m, 2H), 3.80-4.16(br, 2H), 7.47-7.65(m, 3H), 7.78-7.84(m, 2H), 8.05(s, 1H), 9.67(s, 1H), 10.00(s, 1H), 10.12(s, 1H) |
| I-062 | (dimethyl, N-sulfonyl phenyl) | 1.00-1.90(m, 25H), 2.67(t, 2H, J = 6.0), 2.95(t, 2H, J = 6.0), 4.01(br, 2H), 7.47-7.66(m, 3H), 8.06-8.11(m, 2H), 8.32(s, 1H), 10.59(br, 1H), 11.68(br, 1H) |
| I-072 | (tetrahydrofuranone) | 1.02-1.92(m, 19H), 2.41(m, 1H), 2.64(t, 2H, J = 6.0), 2.74(m, 1H), 2.93(t, 2H, J = 6.3), 4.01(br, 2H), 4.31(ddd, 1H, J = 6.6 and 9.3 and 10.5), 4.52(dt, 1H, J = 1.8 and 9.0), 4.73(ddd, 1H, J = 7.2 and 9.0 and 11.1), 8.28(s, 1H), 10.54(d, 1H, J = 7.2) |
| I-081 | (methyl ester) | 1.12-1.87(m, 19H), 2.64(t, 2H, J = 5.7), 2.92(t, 2H, J = 6.6), 3.77(s, 3H), 4.08(m, 2H), 4.22(d, 2H, J = 5.7), 8.29(s, 1H), 10.40(t, 1H, J = 5.7) |

TABLE 35

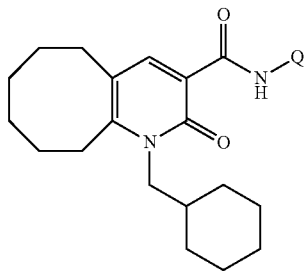

| Comp. No. | Q | ¹H-NMR(CDCl₃/TMS) δ |
|---|---|---|
| I-082 | CH₃-CH(CH₃)-CH(-)-C(=O)-O-CH₃ | 1.02(d, 3H, J = 6.9), 1.04(d, 3H, J = 6.9), 1.11-1.84(m, 19H), 2.30 (m, 1H), 2.63(t, 2H, J = 5.7), 2.91(t, 2H, J = 6.6), 3.75(s, 3H), 4.12(m, 2H), 4.66(dd, 1H, J = 5,4, 2.7), 8.27(s, 1H), 10.45(d, 1H, J = 8.1) |
| I-083 | CH₃-CH(CH₃)-CH(-)-C(=O)-O-CH₃ | 1.02(d, 3H, J = 6.9), 1.04(d, 3H, J = 6.9), 1.11-1.84(m, 19H), 2.30 (m, 1H), 2.63(t, 2H, J = 5.7), 2.91(t, 2H, J = 6.6), 3.75(s, 3H), 4.12(m, 2H), 4.66(dd, 1H, J = 5,4, 2.7), 8.27(s, 1H), 10.45(d, 1H, J = 8.1) |
| I-084 | (CH₃)₂C(-)-C(=O)-O-CH₃ | 1.05-1.83(m, 19H), 1.62(s, 6H), 2.62(t, 2H, J = 5.7), 2.91 (t, 2H, J = 6.0), 3.76(s, 3H), 3.90-4.16(m, 2H), 8.26(s, 1H), 10.31(s, 1H) |
| I-104 | cyclohexyl-C(-)-C(=O)-O-CH₃ | 1.11-2.22(m, 29H), 2.61(t, 2H, J = 6.0), 2.91(t, 2H, J = 6.6), 3.98-4.16 (m, 2H), 8.25(s, 1H), 10.40(s, 1H) |

TABLE 35-continued

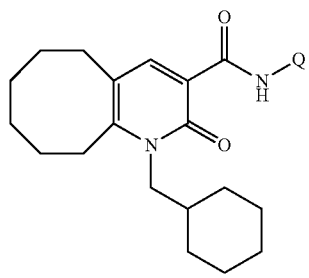

| Comp. No. | Q | ¹H-NMR(CDCl₃/TMS) δ |
|---|---|---|
| I-105 | benzyl-CH(-)-C(=O)-O-CH₃ | 1.15-1.69(m, 19H), 2.62(t, 2H, J = 6.0), 2.90(t, 2H, J = 6.3), 3.16-3.23 (m, 2H), 3.93-4.14(m, 2H), 4.96 (m, 1H), 7.20-7.27(m, 5H), 8.23(s, 1H), 10.50(d, 1H, J = 7.5) |
| I-130 | cyclopentyl-C(-)-C(=O)-O-CH₃ | 1.09-2.32(m, 27H), 2.61(t, 2H, J = 6.0), 2.91(t, 2H, J = 6.0), 3.74(s, 3H), 3.98-4.16(m, 2H), 8.26(s, 1H), 10.31(s, 1H) |
| I-131 | (CH₃)₃C-CH₂-CH(-)-C(=O)-O-CH₃ | 0.93-2.05(m, 31H), 0.99(s, 9H), 2.62(t, 2H, J = 6.3), 2.91(t, 2H, J = 6.0), 3.73(s, 3H), 3.91-4.13 (m, 2H), 4.76(m, 1H), 8.27(s, 1H), 10.28(d, 1H, J = 7.8) |

TABLE 36

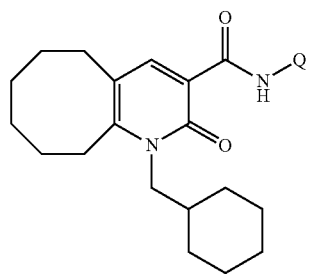

| Comp. No. | Q | ¹H-NMR(CDCl₃/TMS) δ |
|---|---|---|
| I-132 | (CH₃)₃C-CH(-)-C(=O)-O-CH₃ | 1.01-1.72(m, 19H), 1.09(s, 9H), 2.62(t, 2H, J = 6.0), 2.91(t, 2H, J = 6.3), 3.74(s, 3H), 3.92-4.16(m, 2H), 4.54(d, 1H, J = 8.1), 8.26(s, 1H), 10.61(d, 1H, J = 7.8) |

TABLE 36-continued

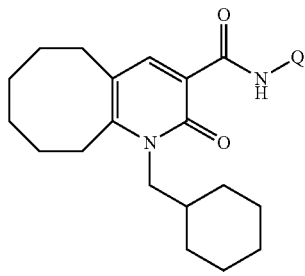

| Comp. No. | Q | ¹H-NMR(CDCl₃/TMS) δ |
|---|---|---|
| I-146 | [structure: CH(CH₃)C(=O)OCH₃] | 1.01-1.93(m, 22H), 2.63(t, 2H, J = 6.0), 2.96(t, 2H, J = 6.0), 3.78(s, 3H), 4.00(br, 2H), 4.74(m, 1H), 8.28(s, 1H), 10.36(br, 1H) |
| I-157 | [structure: CH(cyclohexyl)C(=O)OCH₃] | 1.01-1.93(m, 30H), 2.63(t, 2H, J = 6.0), 2.96(t, 2H, J = 6.0), 3.74(s, 3H), 4.05(br, 2H), 4.66(m, 1H), 8.27(s, 1H), 10.42(br, 1H) |
| I-159 | [structure: CH(cyclohexyl)C(=O)OCH₃] | 1.01-1.93(m, 30H), 2.63(t, 2H, J = 6.0), 2.96(t, 2H, J = 6.0), 3.74(s, 3H), 4.05(br, 2H), 4.66(m, 1H), 8.27(s, 1H), 10.42(br, 1H) |
| I-184 | [structure: CH(2-thienyl)COOH] | DMSO-d6 1.00-1.84(m, 19H), 2.66(brm, 2H), 2.96(brm, 2H), 3.99(br, 2H), 5.75(d, 1H, J = 6.6), 7.03(dd, 1H, J = 3.6 and 5.1), 7.13(m, 1H), 7.51(dd, 1H, J = 1.5 and 5.1), 8.13(s, 1H), 10.70(d, 1H, J = 6.6), 13.30(br, 1H) |
| I-185 | [structure: C(CH₃)₂C(=O)N-piperidine-4-COOH] | DMSO-d6 1.00-1.82(m, 23H), 1.46(s, 6H), 2.38(m, 1H), 2.60-2.69(m, 2H), 2.72-3.00(m, 4H), 3.85-4.10(br, 2H), 4.13-4.25(m, 2H), 8.07(s, 1H), 10.28(s, 1H), 12.16(brs, 1H) |
| I-190 | [structure: CH(CH₃)COOH] | DMSO-d6 1.01-1.93(m, 22H), 2.65(br, 2H), 2.95(br, 2H), 4.00(br, 2H), 4.41(m, 1H), 8.11(s, 1H), 10.19(d, 1H, J = 7.2), 12.78(br, 1H) |

TABLE 37

[Structure: cycloocta-fused pyridinone with N-CH2-cyclohexyl and C(=O)NH-Q substituent]

| Comp. No. | Q | ¹H-NMR(CDCl₃/TMS) δ |
|---|---|---|
| I-191 | cyclohexyl-CH(—)-C(=O)OH | DMSO-d6 1.01-1.93(m, 30H), 2.65(br, 2H), 2.96(br, 2H), 3.97(br, 2H), 4.38(m, 1H), 8.12(s, 1H), 10.24(d, 1H, J = 8.4), 12.72(br, 1H) |
| I-195 | cyclohexyl-CH(—)-C(=O)OH (stereo) | DMSO-d6 1.01-1.93(m, 30H), 2.65(br, 2H), 2.96(br, 2H), 3.97(br, 2H), 4.38(m, 1H), 8.12(s, 1H), 10.24(d, 1H, J = 8.4), 12.72(br, 1H) |
| I-209 | 4-HO-C₆H₄-CH(—)-C(=O)OCH₃ | 1.00-1.90(m, 19H), 2.63(t, 2H, J = 6.0), 2.93(t, 2H, J = 6.3), 3.73(s, 3H), 4.06(br, 2H), 5.60(d, 1H, J = 6.6), 6.67(d, 2H, J = 8.4), 7.25(d, 2H, J = 8.4), 8.28(s, 1H), 10.81(d, 1H, J = 6.6) |

TABLE 37-continued

| Comp. No. | Q | ¹H-NMR(CDCl₃/TMS) δ |
|---|---|---|
| I-210 | 4-Cl-C₆H₄-CH(—)-C(=O)OCH₃ | 1.00-1.92(m, 19H), 2.59(t, 2H, J = 6.0), 2.92(t, 2H, J = 6.3), 3.75(s, 3H), 4.02(br, 2H), 5.72(d, 1H, J = 6.6), 7.31-7.45(m, 4H), 8.28(s, 1H), 10.96(d, 1H, J = 6.0) |
| I-235 | 1-(methoxycarbonyl)cyclopropyl | 1.17-1.72(m, 23H), 2.61-2.65(m, 2H), 2.90-2.94(m, 2H), 3.69(s, 3H), 3.81-4.08(m, 2H), 8.31(s, 1H), 10.34(s, 1H) |
| I-244 | CH₃-CH(—)-C(=O)OH | DMSO-d6 1.01-1.93(m, 22H), 2.65(br, 2H), 2.95(br, 2H), 4.00(br, 2H), 4.41(m, 1H), 8.11(s, 1H), 10.19(d, 1H, J = 7.2), 12.78(br, 1H) |

TABLE 38

[Structure: cycloocta-fused pyridinone with N-CH2-cyclohexyl and C(=O)NH-Q]

| Comp. No. | Q | ¹H-NMR(CDCl₃/TMS) δ |
|---|---|---|
| I-259 | 2-thienyl-CH(—)-C(=O)OCH₃ | 1.00-1.92(m, 19H), 2.62(t, 2H, J = 6.0), 2.92(t, 2H, J = 6.3), 3.80(s, 3H), 4.00(br, 2H), 6.02(d, 1H, J = 6.9), 6.98(dd, 1H, J = 3.6 and 5.1), 7.16(m, 1H), 7.26(dd, 1H, J = 1.2 and 5.1), 8.28(s, 1H), 10.88(d, 1H, J = 6.9) |

TABLE 38-continued

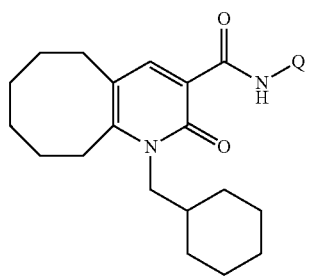

| Comp. No. | Q | $^1$H-NMR(CDCl$_3$/TMS) δ |
|---|---|---|
| I-260 | (3-thienyl-CH(CO$_2$CH$_3$)-) | 1.00-1.94(m, 19H), 2.62(t, 2H, J = 6.0), 2.92(t, 2H, J = 6.3), 3.77(s, 3H), 4.00(br, 2H), 5.87(d, 1H, J = 6.9), 7.02(dd, 1H, J = 1.2 and 5.1), 7.29(dd, 1H, J = 3.0 and 5.1), 7.38(m, 1H), 8.28(s, 1H), 10.82(d, 1H, J = 6.9) |
| I-264 | (2-furyl-CH(CO$_2$CH$_3$)-) | 1.00-1.94(m, 19H), 2.62(t, 2H, J = 6.0), 2.92(t, 2H, J = 6.6), 3.79(s, 3H), 4.00(br, 2H), 5.94(d, 1H, J = 7.2), 6.35(dd, 1H, J = 1.8 and 3.3), 6.43(m, 1H), 7.40(dd, 1H, J = 0.9 and 1.8), 8.28(s, 1H), 10.82(d, 1H, J = 7.2) |
| I-265 | (dioxolane-methyl ester group) | 1.09-1.89(m, 19H), 1.35(s, 3H), 1.48(s, 3H), 2.63(t, 2H, J = 5.7), 2.92(t, 2H, J = 6.3), 3.78(s, 3H), 3.95-4.12(m, 4H), 4.33-4.40(m, 2H), 4.55(m, 1H), 5.19(d, 1H, 7.5), 8.29(s, 1H), 10.45(t, 1H, J = 5.4) |
| I-268 | (pivaloyl-piperidinyl-sulfonamide group) | 1.02-1.97(m, 23H), 1.33(d, 6H, J = 6.9), 1.61(s, 6H), 2.62-2.66(m, 2H), 2.80-3.00(m, 4H), 3.07(m, 1H), 3.41(m, 1H), 3.80-4.20(br, 2H), 4.00(d, 1H, J = 9.0), 4.40-4.56(m, 2H), 8.24(s, 1H), 10.31(s, 1H) |
| I-269 | (thiazol-4-yl-CH$_2$-CH(CO$_2$CH$_3$)-) | 1.00-1.96(m, 19H), 2.62(brt, 2H), 2.90(brt, 2H), 3.44(dd, 1H, J = 7.2 and 14.7), 3.52(dd, 1H, J = 5.4 and 14.7), 3.74(s, 3H), 3.98(br, 2H), 5.12(td, 1H, J = 5.7 and 7.2), 7.15(d, 1H, J = 2.1), 8.24(s, 1H), 8.75(d, 1H, J = 2.1), 10.53(d, 1H, J = 7.2) |

TABLE 39

| Comp. No. | Q | ¹H-NMR(CDCl₃/TMS) δ |
|---|---|---|
| I-274 | 1-naphthyl-CH(COOCH₃)- | 0.95-1.88(m, 19H), 2.61(t-like, 2H), 2.89(t-like, 2H), 3.74(s, 3H), 3.95 (br, 2H), 6.56(d, 1H, J = 7.2), 7.45-7.64(m, 5H), 7.85(t, 2H, J = 8.4), 8.29(s, 1H), 8.31(d, 1H, J = 8.4), 10.93(d, 1H, J = 7.2) |
| I-275 | 4-MeO-C₆H₄-CH(COOCH₃)- | 0.98-1.93(m, 19H), 2.59-2.63(m, 2H), 2.89-2.93(m, 2H), 3.74(s, 3H), 3.79(s, 3H), 3.80-4.20(br, 2H), 5.66(d, 1H, J = 6.3), 6.89 (d, 2H, J = 9.0), 7.42(d, 2H, J = 9.0), 8.26(s, 1H), 10.81(d, 1H, J = 6.3) |
| I-276 | 4-F-C₆H₄-CH(COOCH₃)- | 1.00-1.94(m, 19H), 2.60-2.63(m, 2H), 2.89-2.94(m, 2H), 3.75(s, 3H), 3.80-4.20(br, 2H), 5.72(d, 1H, J = 6.3), 7.05(t, 2H, J = 8.7), 7.47(dd, 2H, J = 5.1 and 8.7), 8.25(s, 1H), 10.92(d, 1H, J = 6.3) |

TABLE 39-continued

| Comp. No. | Q | ¹H-NMR(CDCl₃/TMS) δ |
|---|---|---|
| I-277 | 2-MeO-C₆H₄-CH(COOCH₃)- | 0.98-1.90(m, 19H), 2.60(t, 2H, J = 6.0), 2.89(t, 2H, J = 6.3), 3.72(s, 3H), 3.89(s, 3H), 3.98(br, 2H), 6.07(d, 1H, J = 7.5), 6.91(d-like, 1H), 6.95(td, 1H, J = 7.5 and 0.9), 7.28(m, 1H), 7.44(dd, 1H, J = 7.5 and 1.8), 8.27(s, 1H), 10.82(d, 1H, J = 7.5) |
| I-284 | benzothiophen-2-yl-CH(COOCH₃)- | 1.00-1.94(m, 19H), 2.61-2.65(m, 2H), 2.90-2.94(m, 2H), 3.82(s, 3H), 3.86-4.22(br, 2H), 6.10(d, 1H, J = 6.9), 7.26-7.36(m, 2H), 7.39(s, 1H), 7.70-7.81(m, 2H), 8.28(s, 1H), 11.02(d, 1H, J = 6.9) |

TABLE 40

| Comp. No. | Q | ¹H-NMR(CDCl₃/TMS) δ |
|---|---|---|
| I-291 | (R)-Ph-CH(COOCH₃)- | 0.99-1.92(m, 19H), 2.61(t-like, 2H), 2.91(t-like, 2H), 3.74(s, 3H), 4.00(br, 2H), 5.74(d, 1H, J = 6.6), 7.27-7.52(m, 5H), 8.26(s, 1H), 10.89(d, 1H, J = 6.6) |

TABLE 40-continued

| Comp. No. | Q | ¹H-NMR(CDCl₃/TMS) δ |
|---|---|---|
| I-296 | (4-phenylphenyl)-CH(CO₂CH₃)- | 1.00-1.94(m, 19H), 2.60-2.64(m, 2H), 2.90-2.94(m, 2H), 3.78(s, 3H), 3.80-4.20(br, 2H), 5.79(d, 1H, J = 6.6), 7.34(m, 1H), 7.40-7.47(m, 2H), 7.54-7.62(m, 6H), 8.27(s, 1H), 10.95(d, 1H, J = 6.6) |
| I-297 | (benzofuran-2-yl)-CH(CO₂CH₃)- | 1.00-1.95(m, 19H), 2.61-2.65(m, 2H), 2.90-2.94(m, 2H), 3.81(s, 3H), 3.82-4.18(br, 2H), 6.09(d, 1H, J = 7.5), 6.82(s, 1H), 7.17-7.31(m, 2H), 7.46-7.56(m, 2H), 8.28(s, 1H), 10.99(d, 1H, J = 7.5) |
| I-300 | -C(CH₃)₂C(O)OCH₂CH₃ | 1.00-1.90(m, 22H), 2.61(t, 2H, J = 6.0), 2.91(t, 2H, J = 6.0), 3.95(br, 2H), 4.22(q, 2H, J = 6.9), 8.27(s, 1H), 10.30(s, 1H) |
| I-301 | -C(CH₃)₂C(O)OCH(CH₃)₂ | 1.03-1.95(m, 25H), 2.61(t, 2H, J = 6.0), 2.91(t, 2H, J = 6.3), 4.00(br, 2H), 5.09(m, 1H), 8.26(s, 1H), 10.31(s, 1H) |
| I-302 | -C(CH₃)₂C(O)O-(2-phenyl-1,3-dioxan-5-yl) | 1.00-1.96(m, 20H), 1.59(s, 3H), 1.70(s, 3H), 2.59(t, 2H, J = 6.0), 2.91(t, 2H, J = 6.6), 3.97(br, 2H), 4.15(d, 2H, J = 12.0), 4.32(d, 2H, J = 12.0), 4.78(t, 1H, J = 1.5), 5.52(s, 1H), 7.30-7.47(m, 5H), 8.24(s, 1H), 10.31(s, 1H) |

TABLE 41

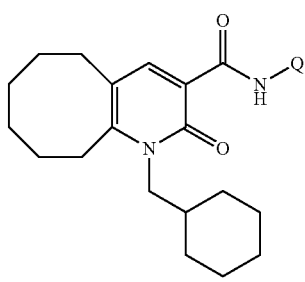

| Comp. No. | Q | $^1$H-NMR(CDCl$_3$/TMS) δ |
|---|---|---|
| I-303 | ![Q structure with dioxolane] | 1.04-1.96(m, 31H), 2.61(t, 2H, J = 6.0), 2.92(t, 2H, J = 6.3), 3.78-4.34(m, 7H), 8.24(s, 1H), 10.29(s, 1H) |
| I-304 | ![Q structure with diol] | 1.10-1.90(m, 25H), 2.62(t, 2H, J = 6.0), 2.93(t, 2H, J = 6.0), 3.76(dd, 2H, J = 5.7 and 12.6), 3.91(dd, 2H, J = 3.3 and 12.6), 3.98(br, 2H), 4.98(m, 1H), 8.21(s, 1H), 10.56(s, 1H) |
| I-305 | ![Q structure with diol] | 1.05-1.90(m, 25H), 2.63(t, 2H, J = 6.0), 2.93(t, 2H, J = 6.3), 3.56(dd, 2H, J = 5.4 and 11.4), 3.66(dd, 2H, J = 4.2 and 11.4), 3.80-4.10(m, 3H), 4.27-4.32(m, 2H), 8.23(s, 1H), 10.56(s, 1H) |
| I-306 | ![Q structure with methoxymethyl] | 1.04-1.90(m, 19H), 1.61(s, 3H), 1.65(s, 3H), 2.61(t, 2H, J = 6.0), 2.92(t, 2H, J = 6.3), 3.47(s, 3H), 4.00(br, 2H), 5.32(s, 2H), 8.25(s, 1H) |
| I-307 | ![Q structure with phenyl] | 1.02-1.96(m, 19H), 1.75(s, 6H), 2.63(t, 2H, J = 6.0), 2.92(t, 2H, J = 6.3), 4.00(br, 2H), 7.14-7.36(m, 5H), 8.30(s, 1H), 10.37(s, 1H) |
| I-308 | ![Q structure with dioxolone] | 1.01-1.96(m, 19H), 1.59(s, 6H), 2.19(s, 3H), 2.62(t, 2H, J = 6.0), 2.92(t, 2H, J = 6.3), 4.00(br, 2H), 4.89(s, 2H), 8.21(s, 1H), 10.28(s, 1H) |
| I-309 | ![Q structure with carbonate] | 1.02-1.96(m, 19H), 1.61(s, 6H), 2.62(t, 2H, J = 6.0), 2.93(t, 2H, J = 6.3), 4.02(br, 2H), 4.49(dd, 1H, J = 2.1 and 10.2), 4.60(dd, 1H, J = 5.4 and 10.4), 6.73(dd, 1H, J = 2.1 and 5.4), 8.19(s, 1H), 10.34(s, 1H) |

TABLE 42

| Comp. No. | Q | ¹H-NMR(CDCl₃/TMS) δ |
|---|---|---|
| I-310 | diethyl malonate group | 1.10-1.87(m, 19H), 1.31(t, 6H, J = 6.9), 2.62(t, 2H, J = 5.7), 2.91(t, 2H, J = 6.3), 3.92-4.18(m, 2H), 4.19-4.34(m, 4H), 5.36(d, 1H, J = 6.6), 8.25(s, 1H), 10.95(d, 1H, J = 6.3) |
| I-311 | 2-fluoroethyl ester | 1.06-1.71(m, 19H), 2.64(t, 2H, J = 6.0), 2.92(t, 2H, J = 5.7), 3.94-4.18(m, 2H), 4.26(d, 2H, J = 5.7), 4.38-4.69(m, 4H), 8.29(s, 1H), 10.43(t, 1H, J = 2.4) |
| I-312 | 2,2,2-trifluoroethyl ester | 1.06-2.05(m, 19H), 2.64(t, 2H, J = 6.3), 2.93(t, 2H, J = 6.3), 3.91-4.18(m, 2H), 4.30(d, 2H, J = 5.7), 4.54(q, 2H, J = 8.4), 8.29(s, 1H), 10.46(t, 1H, J = 5.1) |
| I-313 | 2-(methylthio)ethyl ester | 1.16-1.71(m, 19H), 2.15(s, 3H), 2.64(t, 2H, J = 6.0), 2.75(t, 2H, J = 6.9), 2.92(t, 2H, J = 6.0), 3.84-4.13(m, 2H), 4.22(d, 2H, J = 5.7), 4.34(t, 2H, J = 6.9), 8.29(s, 1H), 10.41(t, 1H, J = 5.1) |
| I-314 | 2-(pyrrolidin-1-yl)ethyl ester | 1.02-1.88(m, 21H), 2.60-2.78(m, 6H), 2.79(t, 2H, J = 6.0), 2.92(t, 2H, J = 6.0), 3.79-4.12(m, 2H), 4.19-4.34(m, 4H), 8.28(s, 1H), 10.39(t, 1H, J = 5.4) |
| I-315 | 2-morpholinoethyl ester | 1.10-1.75(m, 19H), 2.52(t, 2H, J = 4.8), 2.61-2.68(m, 4H), 2.92(t, 2H, J = 6.9), 3.68-3.77(m, 4H), 3.82-4.12(m, 2H), 4.22(d, 2H, J = 5.4), 4.31(t, 2H, J = 6.0), 8.29(s, 1H), 10.43(t, 1H, J = 5.4) |
| I-316 | 2-(2-oxopyrrolidin-1-yl)ethyl ester | 1.03-1.85(m, 19H), 1.96-2.07(m, 2H), 2.38(t, 2H, J = 8.1), 2.64(t, 2H, J = 6.0), 2.92(t, 2H, J = 6.9), 3.43-3.58(m, 4H), 3.82(m, 2H), 4.20(d, 2H, J = 5.4), 4.31(t, 2H, J = 5.7), 8.28(s, 1H), 10.41(t, 1H, J = 5.7) |
| I-317 | 2-(Boc-amino)ethyl ester | 1.07-1.83(m, 19H), 1.45(s, 9H), 2.64(t, 2H, J = 5.7), 2.93(t, 2H, J = 6.3), 3.41-3.44(m, 2H), 3.81-4.25(m, 4H), 5.17(br, 1H), 8.29(s, 1H), 10.47(t, 1H, J = 5.4) |

TABLE 43

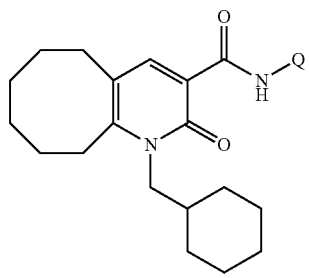

| Comp. No. | Q | $^1$H-NMR(CDCl$_3$/TMS) δ |
|---|---|---|
| I-318 | CH$_3$ CH$_3$ ~~~C(=O)−O−CH(CH$_3$)−O−C(=O)−O−CH$_3$ (with gem-dimethyl) | 1.02-2.00(m, 31H), 2.61(t, 2H, J = 6.0), 2.91(t, 3H, J = 6.0), 4.04(br, 2H), 4.17-4.30(m, 2H), 6.80(q, 1H, J = 5.4), 8.24(s, 1H), 10.25(br, 1H) |
| I-320 | ~~~CH$_2$C(=O)−O−CH$_2$CH$_2$−NH−C(=O)−CH$_3$ | 1.06-1.80(m, 19H), 2.01(s, 3H), 2.65(t, 2H, J = 6.0), 2.94(t, 2H, J = 6.0), 3.56(dd, 2H, J = 5.7, 10.8), 3.97-4.18(m, 2H), 4.17(d, 2H, J = 5.4), 4.27(m, 2H), 6.55(br, 1H), 8.27(s, 1H), 10.49(t, 1H, J = 5.4) |
| I-322 | ~~~CH$_2$C(=O)−O−CH$_2$CH$_2$−(2-pyridyl) | 1.06-1.86(m, 19H), 2.64(t, 2H, J = 5.7), 2.92(t, 2H, J = 5.7) 3.15(t, 2H, J = 6.9), 3.95-4.09(m, 2H), 4.17(d, 2H, J = 5.7), 4.56(t, 2H, J = 6.6), 7.13-7.22(m, 2H), 7.47(m, 1H), 8.28(s, 1H), 8.55(d, 1H, J = 5.1), 10.38(t, 1H, J = 5.4) |
| I-324 | ~~~CH$_2$C(=O)−O−CH$_2$−O−C(=O)−C(CH$_3$)$_3$ | 1.06-1.72(m, 19H), 1.22(s, 9H), 2.64(t, 2H, J = 6.3), 2.92(t, 2H, J = 6.3), 3.98-4.15(m, 2H), 4.25(d, 2H J = 5.7), 5.82(s, 2H), 8.28(s, 1H), 10.42(t, 1H, J = 4.8) |
| I-325 | CH$_3$ CH$_3$ ~~~C(CH$_3$)$_2$C(=O)−O−CH$_2$CH$_2$−N(CH$_3$)$_2$ | 1.00-1.94(m, 26H), 2.28(s, 6H), 2.55-2.70(m, 2H), 2.85-2.97(m, 2H), 3.98(br, 2H), 4.29(t, 2H, J = 5.4), 8.25(s, 1H), 10.32(br s, 1H) |
| I-326 | CH$_3$ CH$_3$ ~~~C(CH$_3$)$_2$C(=O)−O−CH$_2$CH$_2$−N$^+$(CH$_3$)$_3$ I$^-$ | 1.00-1.94(m, 25H), 2.55-2.70(m, 2H), 2.87-2.99(m, 2H), 3.52(s, 9H), 4.05(br, 2H), 4.05-4.08(m, 2H), 4.58-4.70(m, 2H), 8.11(s, 1H), 10.41(br s, 1H) |
| I-328 | CH$_3$ CH$_3$ ~~~C(CH$_3$)$_2$C(=O)−O−CH(CH$_3$)−O−C(=O)−O−CH(CH$_3$)$_2$ | 1.06-1.86(m, 19H), 1.31(d, 6H, J = 6.3), 1.62(s, 6H), 2.61(t, 2H, J = 6.0), 2.91(t, 2H, J = 6.0), 3.81-4.11(m, 2H), 4.89(m, 1H), 6.81(q, 1H, J = 5.1), 8.24(s, 1H), 10.26(s, 1H) |

TABLE 44

| Comp. No. | Q | $^1$H-NMR(CDCl$_3$/TMS) δ |
|---|---|---|
| I-329 | CH$_3$, CH$_3$, O, O, O, CH$_3$, cyclohexyl | 0.88-1.94(m, 29H), 1.54(d, 3H, J = 6.0), 1.72(s, 6H), 2.63(t, 2H, J = 6.0), 2.92(t, 2H, J = 6.3), 3.75-4.23(m, 2H), 4.66(m, 1H), 6.83(q, 1H, J = 5.1), 8.24(s, 1H), 10.25(s, 1H) |
| I-331 | CH$_3$, CH$_3$, O, O, O, CH$_3$ | 0.94(t, 3H, J = 6.9), 1.06-1.85(m, 23H), 1.61(s, 6H), 2.35(t, 2H, J = 7.8), 2.61(t, 2H, J = 6.0), 2.91(t, 2H, J = 6.3), 3.95-4.14(m, 2H), 5.81(s, 2H), 8.22(s, 1H), 10.27(s, 1H) |
| I-332 | CH$_3$, CH$_3$, O, O, O, N-piperidine | 0.96-1.87(m, 29H), 1.62(s, 6H), 2.61(t, 2H, J = 5.7), 2.92(t, 2H, J = 6.0), 3.41-3.45(m, 4H), 3.83-4.16(m, 2H), 5.84(s, 2H), 8.23(s, 1H), 10.27(s, 1H) |
| I-333 | CH$_3$, CH$_3$, O, O, O, N(CH$_2$CH$_3$)$_2$ | 1.02-1.89(m, 25H), 1.62(s, 6H), 2.61(t, 2H, J = 5.7), 2.94(t, 2H, J = 6.6), 3.22-3.34(m, 4H), 3.87-4.14(m, 2H), 5.85(s, 2H), 8.23(s, 1H), 10.28(s, 1H) |
| I-334 | CH$_3$, CH$_3$, O, O, NH, O, n-butyl | 0.91(t, 3H, J = 7.5), 1.09-1.73(m, 23H), 1.61(s, 6H), 2.61(t, 2H, J = 5.1), 2.92(t, 2H, J = 5.1), 3.15-3.22(m, 2H), 3.79-4.18(m, 2H), 4.91(m, 1H), 8.23(s, 1H), 10.28(s, 1H) |
| I-335 | CH$_2$, CH$_3$, O, O, NH, O, CH(CH$_3$)$_2$ | 0.90(d, 6H, J = 6.6), 1.01-1.86(m, 20H), 1.61(s, 6H), 2.63(t, 2H, J = 6.0), 2.92(t, 2H, J = 6.3), 3.97-4.09(m, 2H), 4.98(t, 1H, J = 6.0), 5.79(s, 2H), 8.22(s, 1H), 10.27(s, 1H) |
| I-336 | CH$_3$, CH$_3$, O, O, O, CH$_3$, N(CH$_2$CH$_3$)$_2$ | 1.11-1.85(m, 25H), 1.52(d, 3H, J = 5.4), 1.63(s, 6H), 2.61(t, 2H, J = 6.0), 2.91(t, 2H, J = 6.6), 3.21-3.28(m, 4H), 3.81-4.18(m, 2H), 6.87(q, 1H, J = 5.4), 8.25(s, 1H), 10.27(s, 1H) |
| I-337 | CH$_3$, CH$_3$, O, O, O, CH$_3$, NH, n-butyl | 0.90(t, 3H, J = 7.2), 1.09-1.92(m, 23H), 1.62(s, 6H), 2.61(t, 2H, J = 5.7), 2.91(t, 2H, J = 6.3), 3.15-3.19(m, 2H), 3.72-4.13(m, 2H), 4.78(m, 1H), 6.83(q, 1H, J = 5.7), 8.24(s, 1H), 10.26(s, 1H) |

TABLE 45
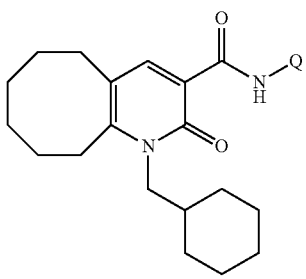
| Comp. No. | Q | ¹H-NMR(CDCl₃/TMS) δ |
|---|---|---|
| I-338 | 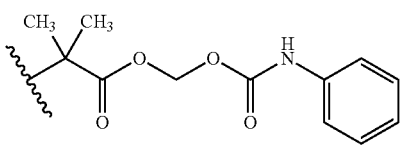 | 0.88-1.74(m, 19H), 1.63(s, 6H), 2.39(t, 2H, J = 5.7), 2.87(t, 2H, J = 6.3), 3.95-4.15(m, 2H), 5.86(s, 2H), 6.83(s, 1H), 7.02-7.40(m, 5H), 8.09(s, 1H), 10.33(s, 1H) |
| I-339 | 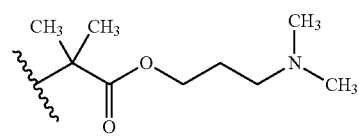 | 1.00-1.94(m, 26H), 2.21(s, 6H), 2.36(t, 2H, J = 7.8), 2.60(t, 2H, J = 6.0), 2.91(t, 2H, J = 6.0), 3.98(br, 2H), 4.20(t, 2H, J = 5.4), 8.25(s, 1H), 10.29(br s, 1H) |
| I-340 | 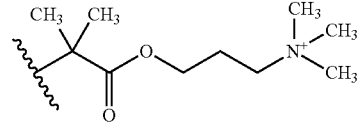 | 1.00-1.94(m, 25H), 2.18-2.30(m, 2H), 2.63(t, 2H, J = 6.0), 2.94(t, 2H, J = 6.0), 3.45(s, 9H), 3.70-3.80(m, 2H), 4.00(br, 2H), 4.35-4.40(m, 2H), 8.01(s, 1H), 10.41(br s, 1H) |
| I-341 | 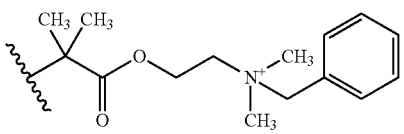 | 1.00-1.94(m, 25H), 2.55-2.70(m, 2H), 2.87-2.99(m, 2H), 3.34(s, 6H), 4.00(br, 2H), 4.05-4.08(m, 2H), 4.58-4.70(m, 2H), 5.06(s, 2H), 7.40-7.52(m, 3H), 7.66-7.70(m, 2H), 8.08(s, 1H), 10.41(br s, 1H) |
| I-342 | 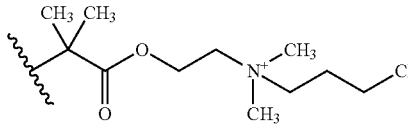 | 1.00-1.94(m, 32H), 2.58-2.70(m, 2H), 2.87-2.99(m, 2H), 3.49(s, 6H), 3.67-3.73(m, 2H), 3.78-4.20(m, 4H), 4.60-4.70(m, 2H), 8.11(s, 1H), 10.41(br s, 1H) |
| I-343 | 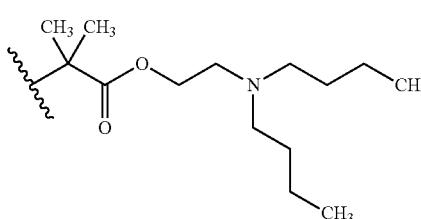 | 0.88(t, 6H, J = 7.2), 1.00-1.94(m, 33H), 2.38-2.50(m, 4H), 2.55-2.70(m, 2H), 2.72-2.80(m, 2H), 2.88-2.97(m, 2H), 3.98(br, 2H), 4.22(t, 2H, J = 5.4), 8.25(s, 1H), 10.30(br s, 1H) |
| I-344 | 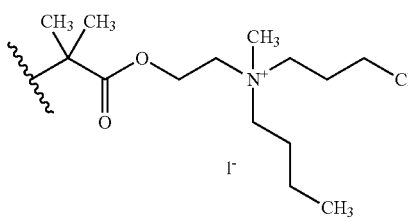 | 1.00(t, 6H, J = 7.2), 1.00-1.94(m, 33H), 2.58-2.68(m, 2H), 2.89-3.00(m, 2H), 3.35(s, 3H), 3.47-3.70(m, 4H), 3.80-4.12(m, 4H), 4.60-4.69(m, 2H), 8.11(s, 1H), 10.38(br s, 1H) |

TABLE 46

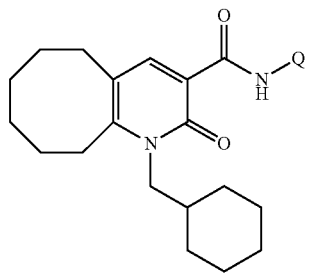

| Comp. No. | Q | ¹H-NMR(CDCl₃/TMS) δ |
|---|---|---|
| I-345 | CH₃ CH₃ group with ester-O-(CH₂)₄-N(CH₃)₂ | 1.00-1.94(m, 29H), 2.21(s, 6H), 2.29(t, 2H, J = 7.2), 2.61(t, 2H, J = 6.0), 2.91(t, 2H, J = 6.0), 3.98(br, 2H), 4.17(q, 2H, J = 6.3), 8.25(s, 1H), 10.29(br s, 1H) |
| I-346 | CH₃ CH₃ group with ester-O-(CH₂)₄-N⁺(CH₃)₃ | 1.00-1.94(m, 29H), 2.64(t, 2H, J = 6.0), 2.93(t, 2H, J = 6.0), 3.43(s, 9H), 3.64-3.76(m, 2H), 3.96(br, 2H), 4.27(t, 2H, J = 6.3), 8.05(s, 1H), 10.36(br s, 1H) |
| I-355 | -CH₂-C(O)OH | DMSO-d6 1.11-1.67(m, 19H), 2.66(t, 2H, J = 6.0), 2.95(t, 2H, J = 6.0), 4.00(m, 2H), 4.03(m, 2H), 8.12(s, 1H), 10.10(t 1H, J = 5.4), 12.67(s, 1H) |
| I-356 | CH(iPr)C(O)OH | DMSO-d6 0.92(d, 3H, J = 6.9), 1.03(d, 3H, J = 6.0), 1.03-2.51(m, 19H), 2.16(m, 1H), 2.66(t, 2H, J = 5.7), 2.96(t, 2H, J = 6.0), 4.03(m, 2H), 4.39(m, 1H), 8.12(s, 1H), 10.28(d, 1H, J = 8.1), 12.76(s, 1H) |
| I-357 | CH(iPr)C(O)OH (stereoisomer) | DMSO-d6 0.92(d, 3H, J = 6.9), 1.03(d, 3H, J = 6.0), 1.03-2.51(m, 19H), 2.16(m, 1H), 2.66(t, 2H, J = 5.7), 2.96(t, 2H, J = 6.0), 4.03(m, 2H), 4.39(m, 1H), 8.12(s, 1H), 10.28(d, 1H, J = 8.1), 12.76(s, 1H) |
| I-358 | C(CH₃)₂C(O)OH | DMSO-d6 1.11-1.83(m, 19H), 1.48(s, 6H), 2.66(t, 2H, J = 4.8), 2.95(t, 2H, J = 6.0), 3.97-4.07(m, 2H), 8.09(s, 1H), 10.22(s, 1H), 12.42(s, 1H) |
| I-379 | 1-carboxycyclohexyl | DMSO-d6 1.13-2.05(m, 29H), 2.65(t, 2H, J = 5.1), 2.96(t, 2H, J = 6.0), 3.98-4.11(m, 2H), 8.08(s, 1H), 10.27(s, 1H), 12.18(s, 1H) |

TABLE 47
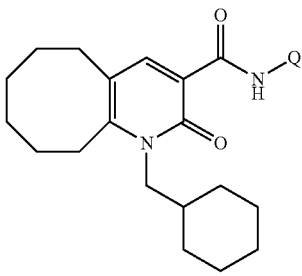
| Comp. No. | Q | $^1$H-NMR(CDCl$_3$/TMS) δ |
|---|---|---|
| I-380 | 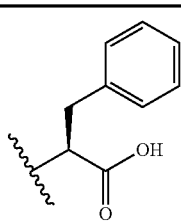 | DMSO-d6 1.13-1.75(m, 19H), 2.62-3.18(m, 6H), 3.96-4.06(m, 2H), 4.70(m, 1H), 7.18-7.27(m, 5H), 8.08(s, 1H), 10.25(d, 1H, J = 7.8), 12.88(s, 1H) |
| I-402 | 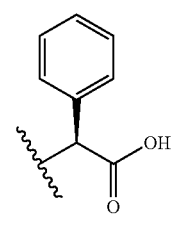 | 1.04-1.82(m, 19H), 2.60-2.69(m, 2H), 2.89-3.00(m, 2H), 3.98-4.13(m, 2H), 5.71(d, 1H, J = 6.3), 7.25-7.54(m, 5H), 8.27(s, 1H), 11.00(d, 1H, J = 6.0) |
| I-403 | 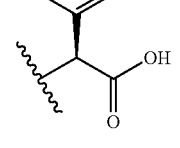 | 1.06-1.86(m, 23H), 2.11-2.19(m, 2H), 2.44-2.66(m, 2H), 2.65(t, 2H, J = 6.0), 2.95(t, 2H, J = 5.7), 3.95-4.14(m, 2H), 8.29(s, 1H), 10.80(s, 1H) |
| I-404 | 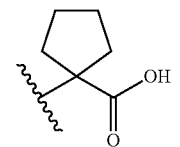 | 0.98(s, 9H), 1.06-1.80(m, 20H), 2.15(dd, 1H, J = 3.6, 14.7), 2.65(t, 2H, J = 5.7), 2.93(t, 2H, J = 6.0), 3.92-4.16(m, 2H), 4.53(m, 1H), 8.28(s, 1H), 10.63(d, 1H, J = 6.3) |
| I-405 | 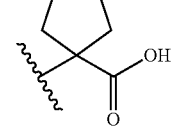 | 1.06-1.93(m, 19H), 1.15(s, 9H), 2.64(t, 2H, J = 6.0), 2.92(t, 2H, J = 6.6), 4.02-4.16(m, 2H), 4.47(d, 2H, J = 7.8), 8.28(s, 1H), 10.76(d, 1H, J = 7.8) |
| I-419 | 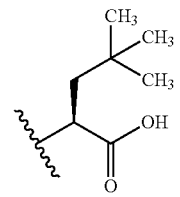 | 1.01-1.93(m, 25H), 2.64(t, 2H, J = 6.0), 2.77(t, 2H, J = 8.01), 2.93(t, 2H, J = 6.0), 2.99(s, 3H), 3.42-3.55(m, 2H), 3.83(s, 3H), 3.86(s, 3H), 4.00(br, 2H), 6.74-6.75(m, 3H), 8.26(s, 1H), 10.32(br, 1H) |
| I-421 | 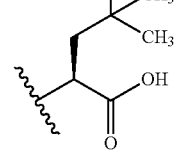 | 1.01-1.93(m, 25H), 2.64(t, 2H, J = 6.0), 2.77(t, 2H, J = 8.01), 2.93(t, 2H, J = 6.0), 3.42-3.55(m, 2H), 3.86(S, 3H), 4.00(br, 2H), 5.43(br, 1H), 6.63-6.74(m, 3H), 7.13(br, 1H), 8.24(s, 1H), 10.30(br, 1H) |

TABLE 48

[Structure: cycloocta-fused pyridinone with N-cyclohexylmethyl substituent and 3-carboxamide C(=O)NH-Q]

| Comp. No. | Q | ¹H-NMR(CDCl₃/TMS) δ |
|---|---|---|
| I-430 | [2,2-dimethyl-propanoyl-NH-(1-methanesulfonyl-piperidin-4-yl)] | 1.01-1.91(m, 21H), 1.62(s, 6H), 1.96-2.07(m, 2H), 2.62-2.66(m, 2H), 2.77(s, 3H), 2.82-2.98(m, 4H), 3.58-3.69(m, 2H), 3.80-4.20(br, 3H), 7.42(d, 1H, J = 7.5), 8.24(s, 1H), 10.34(s, 1H) |
| I-432 | [2,2-dimethyl-propanoyl-NH-NH-C(=O)-CH₃] | 1.01-1.93(m, 19H), 1.67(s, 6H), 2.03(s, 3H), 2.61-2.65(m, 2H), 2.91-2.95(m, 2H), 3.75-4.20(br, 2H), 8.27(s, 1H), 8.28(brs, 1H), 9.58(d, 1H, J = 6.6), 10.46(brs, 1H) |
| I-454 | [2,2-dimethyl-propanoyl-NH-NH-C(=O)-NH₂] | 1.02-1.94(m, 19H), 1.62(s, 6H), 2.63-2.67(m, 2H), 2.93-2.97(m, 2H), 3.75-4.20(br, 2H), 5.40-6.20(br, 2H), 6.18(brs, 1H), 7.99(brs, 1H), 8.22(s, 1H), 10.58(s, 1H) |
| I-455 | [2,2-dimethyl-propanoyl-NH-C(=O)-phenyl] | 1.01-1.93(m, 25H), 2.66(t, 2H, J = 6.0), 2.96(t, 2H, J = 6.0), 4.00(br, 2H), 7.42-7.60(m, 3H), 8.02(d, 2H, J = 7.2), 8.03(s, 1H), 10.67(br, 1H), 11.69(br, 1H) |
| I-456 | [2,2-dimethyl-propanoyl-NH-C(=O)-phenyl] | 1.01-1.93(m, 25H), 2.49(s, 3H), 2.66(s, 2H, J = 6.0), 2.96(t, 2H, J = 6.0), 4.00(br, 2H), 8.26(s, 1H), 9.16(d, 1H, J = 2.1), 10.45(br, 1H) |
| I-461 | [2,2-dimethyl-propanoyl-(piperazin-1-yl)-C(=O)-CH(CH₃)₂] | 1.02-1.90(m, 19H), 1.09(d, 6H, J = 6.6), 1.63(s, 6H), 2.61-2.65(m, 2H), 2.72(m, 1H), 2.91-2.96(m, 2H), 3.37-3.54(m, 4H), 3.60-3.77(m, 4H), 3.80-4.20(br, 2H), 8.23(s, 1H), 10.32(s, 1H) |
| I-462 | [2,2-dimethyl-propanoyl-O-CH₂CH₂-(9H-carbazol-9-yl)] | 1.01-1.93(m, 25H), 2.66(t, 2H, J = 6.0), 2.96(t, 2H, J = 6.0), 4.00(br, 2H), 4.49-4.64(m, 4H), 7.18-7.28(m, 2H), 7.40-7.52(m, 4H), 8.06(d, 2H, J = 7.8), 8.24(s, 1H), 10.27(br, 1H) |

TABLE 49
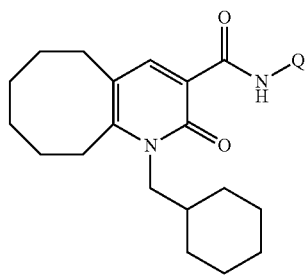
| Comp. No. | Q | ¹H-NMR(CDCl₃/TMS) δ |
|---|---|---|
| I-465 | (CH₃)₂C(C(=O)O-CH₂CH₂-N⁺(CH₂CH₃)₃) I⁻ | 1.01-1.93(m, 34H), 2.66(t, 2H, J = 6.0), 2.96(t, 2H, J = 6.0), 3.44-3.60(m, 6H), 3.87(t, 2H, J = 5.1), 4.00(br, 2H), 4.59(t, 2H, J = 5.1), 8.13(s, 1H), 10.39(br, 1H) |
| I-481 | 4-HO-C₆H₄-CH(COOH)- | 1.03-1.92(m, 19H), 2.59-3.00(m, 4H), 3.75(s, 3H), 4.06(br, 2H), 5.56(s, 1H), 6.80(d, 2H, J = 8.4), 7.34(d, 2H, J = 8.4), 8.23(s, 1H) |
| I-482 | 4-Cl-C₆H₄-CH(COOH)- | 1.00-1.90(m, 19H), 2.62(t, 2H, J = 6.0), 2.92(t, 2H, J = 6.3), 3.40(br, 2H), 5.69(d, 1H, J = 6.3), 7.32-7.49(m, 4H), 8.25(s, 1H), 11.03(d, 1H, J = 6.3) |
| I-501 | 1-carboxycyclopropyl | 1.05-1.73(m, 23H), 2.63-2.69(m, 2H), 2.91-2.96(m, 2H), 4.00-4.18(m, 2H), 8.32(s, 1H), 10.61(s, 1H) |
| I-510 | (CH₃)₂C(C(=O)NH-NH-C(=O)-C₆H₅)- | 1.02-1.96(m, 19H), 1.68(s, 6H), 2.61-2.65(m, 2H), 2.91-2.95(m, 2H), 3.80-4.20(br, 2H), 7.40-7.56(m, 3H), 7.78-7.85(m, 2H), 8.31(s, 1H), 8.83(d, 1H, J = 5.7), 10.03(d, 1H, J = 5.7), 10.53(s, 1H) |
| I-525 | 2-thienyl-CH(COOH)- | DMSO-d6 1.00-1.84(m, 19H), 2.66(brm, 2H), 2.96(brm, 2H), 3.99(br, 2H), 5.75(d, 1H, J = 6.6), 7.03(dd, 1H, J = 3.6 and 5.1), 7.13(m, 1H), 7.51(dd, 1H, J = 1.5 and 5.1), 8.13(s, 1H), 10.70(d, 1H, J = 6.6), 13.30(br, 1H) |

TABLE 50

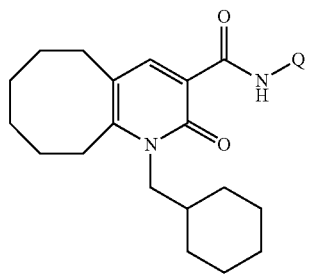

| Comp. No. | Q | ¹H-NMR(CDCl₃/TMS) δ |
|---|---|---|
| I-526 | thiophen-3-yl-CH(COOH)- | DMSO-d6 1.00-1.84(m, 19H), 2.65(brm, 2H), 2.96(brm, 2H), 4.00(br, 2H), 5.58(d, 1H, J = 6.9), 7.12(dd, 1H, J = 1.2 and 5.1), 7.51(m, 1H), 7.58(dd, 1H, J = 3.0 and 5.1), 8.13(s, 1H), 10.60(d, 1H, J = 6.9), 13.07(br, 1H) |
| I-530 | furan-2-yl-CH(COOH)- | DMSO-d6 1.00-1.85(m, 19H), 2.62(brm, 2H), 2.96(brm, 2H), 3.99(br, 2H), 5.65(d, 1H, J = 7.5), 6.45-6.48(m, 2H), 7.68(dd, 1H, J = 0.9 and 1.8), 8.13(s, 1H), 10.64(d, 1H, J = 7.2), 13.27(br, 1H) |
| I-533 | (CH₃)₂C(CH₃)-C(O)NH-C₆H₄-NHSO₂CH₃ | 1.02-1.92(m, 19H), 1.73(s, 6H), 2.64-2.68(m, 2H), 2.90-2.96(m, 2H), 2.94(s, 3H), 3.75-4.25(br, 2H), 6.58(s, 1H), 7.16(d, 2H, J = 8.7), 7.56(d, 2H, J = 8.7), 8.31(s, 1H), 9.98(s, 1H), 10.56(s, 1H) |
| I-534 | thiazol-4-yl-CH₂-CH(COOH)- | DMSO-d6 1.00-1.80(m, 19H), 2.64(brt, 2H), 2.93(brt, 2H), 3.22-3.33(m, 2H), 3.99(br, 2H), 4.81(m, 1H), 7.38(d, 1H, J = 1.8), 8.08(s, 1H), 9.01(d, 1H, J = 1.8), 10.21(d, 1H, J = 7.8), 12.83(br, 1H) |
| I-539 | naphthalen-1-yl-CH(COOH)- | DMSO-d6 0.96-1.80(m, 19H), 2.63(brt, 2H), 2.93(brt, 2H), 3.94(br, 2H), 6.27(d, 1H, J = 7.2), 7.53-7.64(m, 4H), 7.92-8.01(m, 2H), 8.12(s, 1H), 8.21(d, 1H, J = 8.4), 10.82(d, 1H, J = 7.2), 13.16(br, 1H) |
| I-540 | 4-MeO-C₆H₄-CH(COOH)- | DMSO-d6 1.00-1.84(m, 19H), 2.66-2.70(m, 2H), 2.90-3.00(m, 2H), 3.75(s, 3H), 3.80-4.15(br, 2H), 5.37(d, 1H, J = 6.6), 6.96(d, 2H, J = 9.0), 7.32(d, 2H, J = 9.0), 8.10(s, 1H), 10.61(d, 1H, J=6.6), 12.94(brs, 1H) |

TABLE 51

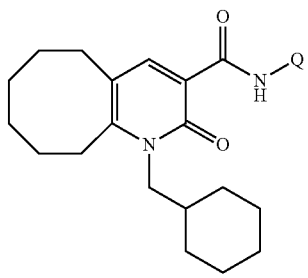

| Comp. No. | Q | ¹H-NMR(CDCl₃/TMS) δ |
|---|---|---|
| I-541 | 4-fluorophenyl-CH(COOH)- | DMSO-d6 1.00-1.84(m, 19H), 2.60-2.70(m, 2H), 2.90-3.02(m, 2H), 3.85-4.20(br, 2H), 5.50(d, 1H, J = 6.9), 7.23(t, 2H, J = 9.0), 7.44(dd, 2H, J = 5.4 and 9.0), 8.10(s, 1H), 10.72(d, 1H, J = 6.9), 13.19(brs, 1H) |
| I-542 | 2-methoxyphenyl-CH(COOH)- | DMSO-d6 0.98-1.82(m, 19H), 2.60(brt, 2H), 2.94(brt, 2H), 3.82(s, 3H), 3.97(br, 2H), 5.77(d, 1H, J = 7.8), 6.96(td, 1H, J = 7.5 and 0.9), 7.06(d, 1H, J = 7.5), 7.27-7.35(m, 2H), 8.10(s, 1H), 10.55(d, 1H, J = 7.8), 12.72(br, 1H) |
| I-549 | benzothiophen-2-yl-CH(COOH)- | DMSO-d6 1.00-1.86(m, 19H), 2.60-2.71(m, 2H), 2.90-3.02(m, 2H), 3.85-4.15(br, 2H), 5.87(d, 1H, J = 6.9), 7.32-7.42(m, 2H), 7.47(s, 1H), 7.84(m, 1H), 7.93(m, 1H), 8.13(s, 1H), 10.85(d, 1H, J = 6.9), 13.52(brs, 1H) |
| I-556 | -C(CH₃)₂C(O)NHNHC(O)-pyridin-3-yl | 1.02-2.10(m, 19H), 1.71(s, 6H), 2.61-2.65(m, 2H), 2.91-2.95(m, 2H), 3.80-4.20(br, 2H), 7.34(brs, 1H), 8.21(d, 1H, J = 7.8), 8.29(s, 1H), 8.75(brs, 1H), 9.09(bes, 1H), 9.33(brs, 1H), 10.05(s, 1H), 10.56(s, 1H) |
| I-561 | biphenyl-4-yl-CH(COOH)- | DMSO-d6 1.00-1.86(m, 19H), 2.59-2.70(m, 2H), 2.89-3.02(m, 2H), 3.80-4.20(br, 2H), 5.53(d, 1H, J = 6.9), 7.34-7.53(m, 5H), 7.64-7.74(m, 4H), 8.11(s, 1H), 10.77(d, 1H, J = 6.9), 13.15(brs, 1H) |
| I-562 | benzofuran-2-yl-CH(COOH)- | DMSO-d6 1.00-1.86(m, 19H), 2.60-2.70(m, 2H), 2.90-3.01(m, 2H), 3.85-4.05(br, 2H), 5.86(d, 1H, J = 7.2), 6.95(s, 1H), 7.23-7.36(m, 2H), 7.57-7.67(m, 2H), 8.13(s, 1H), 10.80(d, 1H, J = 7.2), 13.48(br, 1H) |

TABLE 52

| Comp. No. | Q | $^1$H-NMR(CDCl$_3$/TMS) δ |
|---|---|---|
| I-565 | (CH$_3$)$_2$C(C(=O)NHCH$_2$CH$_2$-3,4-dimethoxyphenyl)- | 1.01-1.93(m, 25H), 2.64(t, 2H, J = 6.0), 2.77(t, 2H, J = 8.01), 2.93(t, 2H, J = 6.0), 3.42-3.55(m, 2H), 3.83(s, 3H), 3.86(s, 3H), 4.00(br, 2H), 6.74-6.75(m, 3H), 7.19(br, 1H), 8.26(s, 1H), 10.32(br, 1H) |
| I-566 | (CH$_3$)$_2$C(C(=O)NHCH$_2$CH$_2$-3,4-methylenedioxyphenyl)- | 1.01-1.93(m, 25H), 2.64(t, 2H, J = 6.0), 2.77(t, 2H, J = 8.01), 2.93(t, 2H, J = 6.0), 3.42-3.55(m, 2H), 4.00(br, 2H), 5.87(s, 2H), 6.62(s, 2H), 6.69(s, 1H), 7.11(br, 1H), 8.27(s, 1H), 10.30(br, 1H) |
| I-567 | (CH$_3$)$_2$C(C(=O)NHCH$_2$CH$_2$-3,4-dibenzyloxyphenyl)- | 1.01-1.93(m, 25H), 2.64(t, 2H, J = 6.0), 2.77(t, 2H, J = 8.01), 2.93(t, 2H, J = 6.0), 3.42-3.55(m, 2H), 4.00(br, 2H), 5.08(s, 2H), 5.13(s, 2H), 6.68-6.84(m, 3H), 7.12(t, 1H, J = 5.4), 7.24-7.48(m, 10H), 8.25(s, 1H), 10.31(br, 1H) |
| I-568 | (CH$_3$)$_2$C(C(=O)NH-piperidin-4-yl-N-isopropylsulfonyl)- | 1.01-1.90(m, 21H), 1.32(d, 6H, J = 6.6), 1.62(s, 6H), 1.92-2.03(m, 2H), 2.63-2.66(m, 2H), 2.92-2.96(m, 2H), 2.98-3.10(m, 2H), 3.16(m, 1H), 3.66-3.78(m, 2H), 3.83-4.15(m, 3H), 7.34(d, 1H, J = 7.5), 8.25(s, 1H), 10.33(s, 1H) |
| I-569 | (CH$_3$)$_2$C(C(=O)NHNHC(=O)-thiophen-2-yl)- | 1.02-1.95(m, 19H), 1.68(s, 6H), 2.61-2.65(m, 2H), 2.91-2.95(m, 2H), 3.80-4.40(br, 2H), 7.08(dd, 1H, J = 3.6 and 4.8), 7.50(dd, 1H, J = 0.9 and 4.8), 7.61(d, 1H, J = 3.6), 8.30(s, 1H), 8.69(brs, 1H), 9.86(brs, 1H), 10.52(s, 1H) |
| I-570 | (CH$_3$)$_2$C(C(=O)-piperidin-1-yl-4-NHBoc)- | 1.01-1.92(m, 24H), 1.41(s, 9H), 1.62(s, 6H), 2.62-2.66(m, 2H), 2.83-3.03(m, 4H), 3.58(m, 1H), 3.75-4.20(br, 2H), 4.32-4.52(m, 2H), 8.25(s, 1H), 10.28(s, 1H) |
| I-571 | (CH$_3$)$_2$C(C(=O)NHC(=O)CH$_3$)- | CDCl3 1.01-1.93(m, 25H), 2.66(t, 2H, J = 6.0), 2.96(t, 2H, J = 6.0), 4.00(br, 2H), 7.44(m, 1H), 8.33(s, 1H), 8.36(t, 1H, J = 2.1), 8.77(dd, 1H, J = 2.1 and 3.6), 9.23(d, 1H, J = 2.1), 10.74(br, 1H), 11.96(br, 1H) |

TABLE 53

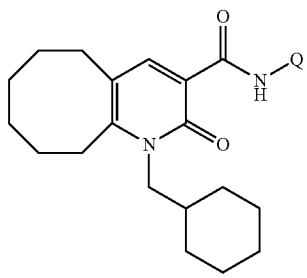

| Comp. No. | Q | $^1$H-NMR(CDCl$_3$/TMS) δ |
|---|---|---|
| I-572 | *(structure: dimethyl group, piperidine N-acyl, 4-methanesulfonamido piperidine)* | 1.02-1.98(m, 23H), 1.61(s, 6H), 2.62-2.66(m, 2H), 2.86-3.02(m, 4H), 2.94(s, 3H), 3.45(m, 1H), 3.70-4.20(br, 2H), 4.38(d, 1H, J = 7.5), 4.40-4.56(m, 2H), 8.24(s, 1H), 10.31(s, 1H) |
| I-574 | *(structure: 2,2-dimethyl, ester, 2-(diethylamino)ethyl)* | 1.01-1.93(m, 35H), 2.66(t, 2H, J = 6.0), 2.79(br, 2H), 2.96(t, 2H, J = 6.0), 4.00(br, 2H), 4.26(br, 2H), 8.24(s, 1H), 10.27(br, 1H) |
| I-575 | *(structure: dimethyl group, piperidine N-acyl, 4-[N-methyl-(1-methylethyl)sulfonamido]piperidine)* | 0.99-1.90(m, 23H), 1.30(d, 6H, J = 6.9), 1.63(s, 6H), 2.60-2.64(m, 2H), 2.66-2.98(br, 2H), 2.67(s, 3H), 2.91-2.95(m, 2H), 3.10(m, 1H), 3.76(m, 1H), 3.80-4.20(br, 2H), 4.45-4.80(br, 2H), 8.24(s, 1H), 10.29(s, 1H) |
| I-576 | *(structure: 2,2-dimethyl, amide, 4-carbamoylphenyl)* | 1.02-1.90(m, 19H), 1.74(s, 6H), 2.64-2.68(m, 2H), 2.92-2.96(m, 2H), 3.70-4.20(br, 2H), 5.30-6.30(br, 2H), 7.68(d, 2H, J = 9.0), 7.77(d, 2H, J = 9.0), 8.31(s, 1H), 10.45(s, 1H), 10.60(s, 1H) |
| I-577 | *(structure: 2,2-dimethyl, amide, 5-carbamoyl-2-pyridyl)* | 1.02-1.96(m, 19H), 1.72(s, 6H), 2.53-2.68(m, 2H), 2.85-2.98(m, 2H), 3.70-4.20(br, 2H), 5.50-6.40(br, 2H), 8.11(dd, 1H, J = 2.1 and 8.7), 8.30(s, 1H), 8.37(d, 1H, J = 8.7), 8.74(brs, 1H), 9.78(s, 1H), 10.56(s, 1H) |
| I-578 | *(structure: dimethyl, piperidine N-acyl, 4-(ethoxycarbonyl)piperidine methyl ester)* | 1.02-1.90(m, 23H), 1.22(t, 3H, J = 7.2), 1.63(s, 6H), 2.43(m, 1H), 2.61-2.65(m, 2H), 2.90-2.94(m, 2H), 2.95-3.08(m, 2H), 3.80-4.15(br, 2H), 4.09(q, 2H, J = 7.2), 4.30-4.43(m, 2H), 8.26(s, 1H), 10.30(s, 1H) |

TABLE 53-continued

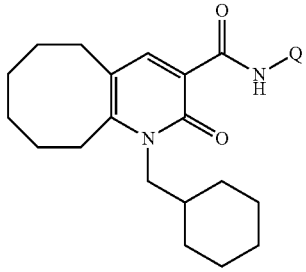

| Comp. No. | Q | ¹H-NMR(CDCl₃/TMS) δ |
|---|---|---|
| I-579 | (piperazine with acetyl and gem-dimethyl acyl linker) | 1.03-1.90(m, 19H), 1.63(s, 6H), 2.06(s, 3H), 2.61-2.65(m, 2H), 2.91-2.95(m, 2H), 3.34-3.52(m, 4H), 3.62-3.76(m, 4H), 3.80-4.20(br, 2H), 8.23(s, 1H), 10.30(s, 1H) |

TABLE 54

| Comp. No. | Q | ¹H-NMR(CDCl₃/TMS) δ |
|---|---|---|
| I-580 | (3-carbamoylpiperidine with gem-dimethyl acyl linker) | 1.02-1.88(m, 23H), 1.61(s, 6H), 2.04(m, 1H), 2.46(m, 1H), 2.62-2.66(m, 2H), 2.91-2.95(m, 2H), 3.40-4.30(m, 5H), 5.34(brs, 1H), 6.82(br, 1H), 8.23(s, 1H), 10.30(s, 1H) |
| I-581 | (piperidine-4-carboxamide N-propyl with gem-dimethyl acyl linker) | 0.88(t, 3H, J = 7.2), 1.02-1.88(m, 25H), 1.63(s, 6H), 2.25(m, 1H), 2.60-2.64(m, 2H), 2.72-2.80(m, 2H), 2.90-2.94(m, 2H), 3.17(q, 2H, J = 7.2), 3.75-4.20(br, 2H), 4.46-4.64(m, 2H), 5.58(m, 1H), 8.24(s, 1H), 10.33(s, 1H) |
| I-582 | (N-(3,4-dihydroxyphenethyl)amide with gem-dimethyl linker) | 1.01-1.93(m, 25H), 2.60-2.74(m, 4H), 2.96(t, 2H, J = 6.0), 3.38-3.47(q, 2H, J = 6.0), 4.00(br, 2H), 5.77(br, 1H), 6.55(d, 1H, J = 8.4), 6.69-6.83(m, 3H), 8.23(s, 1H), 10.33(br, 1H) |

TABLE 54-continued

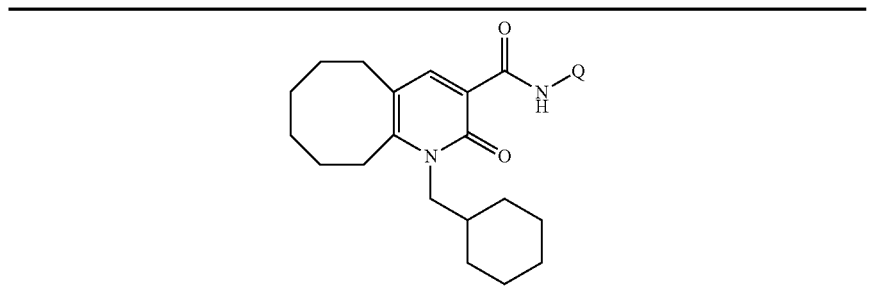

| Comp. No. | Q | $^1$H-NMR(CDCl$_3$/TMS) δ |
|---|---|---|
| I-583 | CH$_3$ CH$_3$, with NH, C=O, piperidine-N-SO$_2$-phenyl | 1.02-1.91(m, 21H), 1.56(s, 6H), 1.92-2.03(m, 2H), 2.37-2.48(m, 2H), 2.63-2.67(m, 2H), 2.92-2.96(m, 2H), 3.60-3.76(m, 3H), 3.80-4.20(br, 2H), 7.21(d, 1H, J = 8.1), 7.49-7.63(m, 3H), 7.73-7.78(m, 2H), 8.23(s, 1H), 10.28(s, 1H) |
| I-584 | CH$_3$ CH$_3$, with NH, C=O, C(=S)-phenyl | 1.01-1.93(m, 25H), 2.65(t, 2H, J = 6.0), 2.96(t, 2H, J = 6.0), 4.00(br, 2H), 7.32-7.40(m, 3H), 7.44-7.50(m, 2H), 8.30(s, 1H), 10.62(br, 1H), 11.68(br, 1H) |
| I-585 | CH$_3$ CH$_3$, with NH, C=O, C(=S)-pyridyl | 1.01-1.93(m, 25H), 2.65(t, 2H, J = 6.0), 2.96(t, 2H, J = 6.0), 4.00(br, 2H), 7.37(m, 1H), 8.10(d, 1H, J = 6.9), 8.31(s, 1H), 8.66(dd, 1H, J = 2.1 and 4.8), 8.92(d, 1H, J = 2.4), 10.66(br, 1H), 11.76(br, 1H) |
| I-586 | CH$_3$ CH$_3$, with NH, C=O, C(=S)-NH$_2$ | 1.01-1.93(m, 25H), 2.65(t, 2H, J = 6.0), 2.96(t, 2H, J = 6.0), 3.00(s, 3H), 4.00(br, 2H), 8.30(s, 1H), 10.50(br, 1H), 10.92(br, 1H) |

TABLE 55

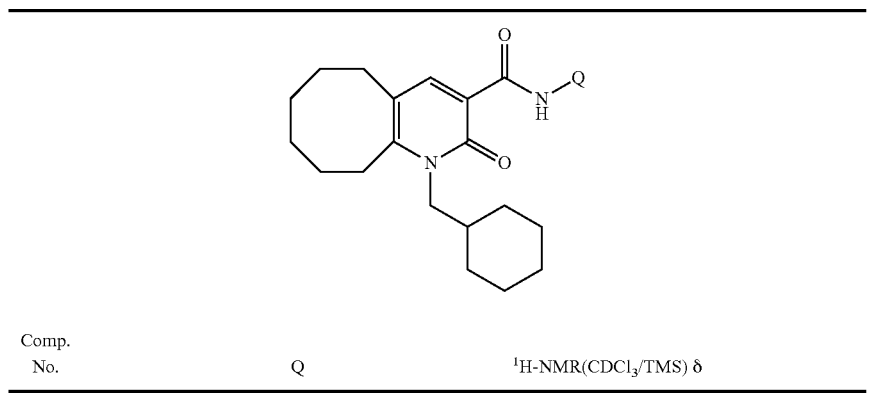

| Comp. No. | Q | $^1$H-NMR(CDCl$_3$/TMS) δ |
|---|---|---|
| I-587 | CH$_3$, CH(CO-OCH$_3$) | 1.01-1.93(m, 22H), 2.63(t, 2H, J = 6.0), 2.96(t, 2H, J = 6.0), 3.78(s, 3H), 4.00(br, 2H), 4.74(m, 1H), 8.28(s, 1H), 10.36(br, 1H) |

TABLE 55-continued

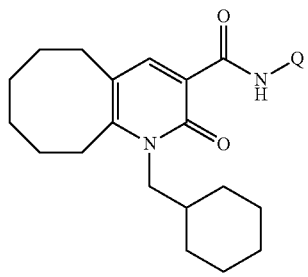

| Comp. No. | Q | $^1$H-NMR(CDCl$_3$/TMS) δ |
|---|---|---|
| I-588 | [structure: C(CH₃)₂-C(O)-NH-CH₂CH₂-C(O)-NH₂] | 1.02-1.96(m, 19H), 1.60(s, 6H), 2.46-2.50(m, 2H), 2.61-2.65(m, 2H), 2.92-2.96(m, 2H), 3.51-3.57(m, 2H), 3.80-4.20(br, 2H), 5.34(brs, 1H), 6.71(brs, 1H), 6.87(m, 1H), 8.18(s, 1H), 10.39(s, 1H) |
| I-589 | [structure: C(CH₃)₂-C(O)-NH-CH₂CH₂-NH-C(O)CH₃] | 1.03-1.96(m, 19H), 1.61(s, 6H), 1.95(s, 3H), 2.61-2.65(m, 2H), 2.93-2.97(m, 2H), 3.32-3.48(m, 4H), 3.80-4.20(br, 2H), 6.59(t, 1H, J = 5.7), 6.89(m, 1H), 8.23(s, 1H), 10.46(s, 1H) |
| I-590 | [structure: C(CH₃)₂-C(O)-NH-CH₂-C(O)-NHCH₃] | 1.02-1.94(m, 19H), 1.62(s, 6H), 2.63-2.67(m, 2H), 2.82(d, 3H, J = 4.8), 2.93-2.97(m, 2H), 3.80-4.20(br, 2H), 3.96(d, 2H, J = 6.6), 6.56(t, 1H, J = 6.6), 7.58(m, 1H), 8.21(s, 1H), 10.54(s, 1H) |
| I-592 | [structure: C(CH₃)₂-C(O)-N-piperidine-3-C(O)OCH₂CH₃] | 1.02-1.90(m, 22H), 1.20(t, 3H, J = 7.2), 1.63(s, 6H), 2.01(m, 1H), 2.43(m, 1H), 2.61-2.65(m, 2H), 2.72-2.96(m, 2H), 2.90-2.94(m, 2H), 3.75-4.20(br, 2H), 4.07(q, 2H, J = 7.2), 4.44(m, 1H), 4.73(m, 1H), 8.26(s, 1H), 10.32(s, 1H) |
| I-593 | [structure: C(CH₃)₂-C(O)-N-piperidine-3-COOH] | DMSO-d6 1.00-1.92(m, 23H), 1.47(s, 6H), 2.12(m, 1H), 2.58-2.83(m, 4H), 2.88-3.00(m, 2H), 3.75-4.30(m, 3H), 4.43(m, 1H), 8.08(s, 1H), 10.35(s, 1H), 12.23(br, 1H) |
| I-594 | [structure: C(CH₃)₂-C(O)-N-piperidine-3-C(O)NHCH₂CH₃] | 0.91(t, 3H, J = 7.5), 1.02-1.88(m, 26H), 1.63(s, 6H), 2.04(brs, 1H), 2.37(brs, 1H), 2.61-2.65(m, 2H), 2.90-2.95(m, 2H), 3.12-3.26(m, 2H), 3.40-4.25(m, 4H), 6.62(brs, 1H), 8.23(s, 1H), 10.29(s, 1H) |

TABLE 56

[Structure: cycloocta-fused pyridinone core with 1-(cyclohexylmethyl) substituent and 3-carboxamide N–Q group]

| Comp. No. | Q | $^1$H-NMR(CDCl$_3$/TMS) δ |
|---|---|---|
| I-595 | [2,2-dimethyl-3-(3-(N-ethylcarbamoyl)piperidin-1-yl)-3-oxopropyl] | 1.02-1.88(m, 27H), 1.63(s, 6H), 2.04(brs, 1H), 2.37(brs, 1H), 2.61-2.65(m, 2H), 2.90-2.94(m, 2H), 3.20-3.34(m, 2H), 3.40-4.25(m, 4H), 6.64(brs, 1H), 8.23(s, 1H), 10.29(s, 1H) |
| I-596 | [2,2-dimethyl-3-(2-(ethylsulfonyl)hydrazinyl)-3-oxopropyl] | 1.02-1.94(m, 19H), 1.45(t, 3H, J = 7.5), 1.64(s, 6H), 2.62-2.66(m, 2H), 2.92-2.96(m, 2H), 3.18(q, 2H, J = 7.5), 3.80-4.20(br, 2H), 6.92(d, 1H, J = 5.4), 8.24(s, 1H), 8.90(d, 1H, J = 5.4), 10.45(s, 1H) |
| I-597 | [3-((2-(2,4,5-trihydroxyphenyl)ethyl)amino)-2,2-dimethyl-3-oxopropyl] | 1.01-1.93(m, 25H), 2.60-2.74(m, 4H), 2.96(m, 2H), 3.30-3.47(m, 2H), 4.00(br, 2H), 5.30(s, 1H), 6.39(s, 1H), 6.52(s, 1H), 7.19(br, 1H), 8.28(s, 1H), 10.28(br, 1H) |
| I-598 | [2-(2,5-dioxopyrrolidin-1-yl)ethyl 2,2-dimethylpropanoate] | 1.01-1.93(m, 25H), 2.61(t, 2H, J = 6.0), 2.70(br, 4H), 2.91(t, 2H, J = 6.0), 3.81(t, 2H, J = 5.4), 3.98(br, 2H), 4.37(t, 2H, J = 5.4), 8.22(s, 1H), 10.23(br, 1H) |
| I-599 | [3-(4-(3-isopropylureido)piperidin-1-yl)-2,2-dimethyl-3-oxopropyl] | 1.01-1.93(m, 25H), 1.11(d, 6H, J = 6.3), 1.61(s, 6H), 2.61-2.65(m, 2H), 2.88-3.08(m, 4H), 3.68-3.86(m, 2H), 3.80-4.20(br, 2H), 4.28-4.50(m, 2H), 8.21(s, 1H), 10.35(s, 1H) |
| I-600 | [N-(1-(isopropylcarbamoyl)piperidin-4-yl)-2,2-dimethylpropanamide] | 1.02-1.98(m, 23H), 1.14(d, 6H, J = 6.3), 1.62(s, 6H), 2.62-2.66(m, 2H), 2.89-3.01(m, 4H), 3.71-3.82(m, 2H), 3.80-4.20(br, 2H), 3.84-4.00(m, 2H), 4.23(m, 1H), 7.22(d, 1H, J = 8.1), 8.25(s, 1H), 10.32(s, 1H) |
| I-601 | [2,2-dimethyl-3-oxo-3-(4-(piperidine-1-carbonyl)piperidin-1-yl)propyl] | 1.02-1.90(m, 28H), 1.63(s, 6H), 2.57-2.68(m, 4H), 2.80-2.98(m, 4H), 3.33-3.56(m, 4H), 3.80-4.20(br, 2H), 4.46-4.62(m, 2H), 8.27(s, 1H), 10.30(s, 1H) |

TABLE 57

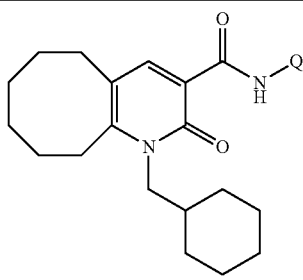

| Comp. No. | Q | ¹H-NMR(CDCl₃/TMS) δ |
|---|---|---|
| I-602 | (piperidine-1-yl with CMe₂ linker and 4-C(O)NHCH₃) | 1.02-1.90(m, 24H), 1.62(s, 6H), 2.26(m, 1H), 2.61-2.64(m, 2H), 2.77(d, 3H, J = 4.8), 2.83(m, 1H), 2.90-2.94(m, 2H), 3.75-4.20(br, 2H), 4.46-4.64(m, 2H), 5.61(m, 1H), 8.24(s, 1H), 10.32(s, 1H) |
| I-603 | (CMe₂-C(O)-NH-C(=NH)-NH-C(O)-NH₂) | DMSO-d6 1.02-1.86(m, 19H), 1.51(s, 6H), 2.58-2.68(m, 2H), 2.90-3.00(m, 2H), 3.84-4.12(br, 2H), 6.85-7.10(br, 2H), 8.07(s, 1H), 8.71(brs, 1H), 9.22(brs, 1H), 9.46(brs, 1H), 10.42(s, 1H) |
| I-604 | (piperazine with CMe₂-C(O) and C(O)NH-iPr) | 1.02-1.90(m, 19H), 1.12(d, 6H, J = 6.3), 1.62(s, 6H), 2.61-2.65(m, 2H), 2.90-2.95(m, 2H), 3.21-3.32(m, 4H), 3.64-3.76(m, 4H), 3.85-4.22(m, 4H), 8.23(s, 1H), 10.31(s, 1H) |
| I-605 | (piperidine with CMe₂-C(O) and 4-C(O)NHNH₂) | 1.02-1.90(m, 23H), 1.62(s, 6H), 2.20-2.56(m, 3H), 2.62-2.65(m, 2H), 2.75-2.98(m, 4H), 3.75-4.20(br, 2H), 4.44-4.64(m, 2H), 8.25(s, 1H), 10.35(s, 1H) |
| I-606 | (piperidine with CMe₂-C(O) and 4-C(O)NH-NH-SO₂CH₃) | 1.02-1.90(m, 23H), 1.61(s, 6H), 2.51(m, 1H), 2.60-2.69(m, 2H), 2.78-3.00(m, 4H), 2.92(s, 3H), 3.80-4.20(br, 2H), 4.44-4.64(m, 2H), 7.14(d, 1H, J = 4.5), 8.25(s, 1H), 8.87(d, 1H, J = 4.5), 10.41(s, 1H) |
| I-607 | (piperidine with CMe₂-C(O) and 4-C(O)NH-CH₂CH₂OH) | 1.02-1.86(m, 23H), 1.62(s, 6H), 1.96(brs, 1H), 2.34(m, 1H), 2.61-2.65(m, 2H), 2.74-2.98(m, 4H), 3.38(q, 2H, J = 4.8), 3.68(t, 2H, J = 4.8), 3.80-4.20(br, 2H), 4.46-4.64(m, 2H), 6.46(m, 1H), 8.22(s, 1H), 10.39(s, 1H) |
| I-608 | (piperidine with CMe₂-C(O) and 3-C(O)NH-n-Bu) | 0.92(t, 3H, J = 7.2), 1.02-1.88(m, 28H), 1.63(s, 6H), 2.01(brs, 1H), 2.36(brs, 1H), 2.61-2.65(m, 2H), 2.90-2.94(m, 2H), 3.14-3.28(m, 2H), 3.38-4.25(m, 4H), 6.60(br, 1H), 8.23(s, 1H), 10.29(s, 1H) |

TABLE 58

| Comp. No. | Q | $^1$H-NMR(CDCl$_3$/TMS) δ |
|---|---|---|
| I-609 | | 1.01-1.93(m, 25H), 2.61(t, 2H, J = 6.0), 2.93(t, 2H, J = 6.0), 4.03(br, 2H), 7.41(m, 1H), 7.84(m, 1H), 8.24(s, 1H), 8.25(m, 1H), 8.37(m, 1H), 10.41(br, 1H), 11.57(br, 1H) |
| I-610 | | 1.01-1.93(m, 25H), 2.61(t, 2H, J = 6.0), 2.93(t, 2H, J = 6.0), 4.03(br, 2H), 7.92(br, 2H), 8.30(br, 1H), 8.82(br, 2H), 10.74(br, 1H), 12.01(br, 1H) |
| I-611 | | 1.02-1.93(m, 19H), 1.62(s, 6H), 2.63-2.67(m, 2H), 2.93-2.97(m, 2H), 3.80-4.20(br, 2H), 5.51(s, 2H), 8.21(s, 1H), 10.13(s, 1H), 10.56(s, 1H) |
| I-612 | | 1.02-1.96(m, 24H), 1.61(s, 6H), 2.55(m, 1H), 2.62-2.66(m, 2H), 2.80-3.02(m, 3H), 3.23(s, 3H), 3.80-4.20(br, 2H), 4.43-4.62(m, 2H), 8.23(s, 1H), 9.57(brs, 1H), 10.46(s, 1H) |
| I-613 | | 1.02-1.90(m, 24H), 1.58(s, 6H), 2.62-2.66(m, 2H), 2.88(m, 1H), 2.91-2.95(m, 2H), 3.28(m, 1H), 3.75-4.15(br, 2H), 4.24-4.42(m, 2H), 4.64(d, 1H, J = 8.1), 7.45-7.60(m, 3H), 7.81-7.87(m, 2H), 8.24(s, 1H), 10.28(s, 1H) |
| I-614 | | 1.00-1.90(m, 24H), 1.57(s, 6H), 2.56-2.72(m, 3H), 2.80-3.10(m, 3H), 3.75-4.20(br, 2H), 4.36-4.60(m, 2H), 6.06(brs, 2H), 8.26(s, 1H), 10.51(s, 1H), 10.56(s, 1H) |
| I-615 | | 1.02-1.88(m, 23H), 1.59(s, 6H), 2.24(brs, 1H), 2.56(brs, 1H), 2.62-2.66(m, 2H), 2.86-2.98(m, 2H), 3.02-3.32(m, 2H), 3.60-4.40(m, 7H), 4.64(brs, 1H), 7.54(brs, 1H), 8.15(s, 1H), 10.39(brs, 1H) |

TABLE 59

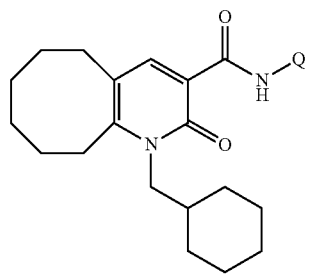

| Comp. No. | Q | $^1$H-NMR(CDCl$_3$/TMS) δ |
|---|---|---|
| I-616 | ![structure: CH3,CH3 dimethyl group attached to N-piperidine with C(=O)NH-n-Pentyl] | 0.89(t, 3H, J = 6.9), 1.02-1.88(m, 30H), 1.60(s, 6H), 2.01(brs, 1H), 2.36(brs, 1H), 2.61-2.65(m, 2H), 2.90-2.94(m, 2H), 3.14-3.28(m, 2H), 3.40-4.20(m, 4H), 6.60(brs, 1H), 8.23(s, 1H), 10.29(s, 1H) |
| I-617 | ![structure: dimethyl group, piperidine-C(=O)-morpholine] | 1.02-1.88(m, 22H), 1.66(s, 6H), 2.53-2.67(m, 4H), 2.80-2.98(m, 4H), 3.40-3.50(m, 2H), 3.54-3.69(m, 6H), 3.75-4.20(br, 2H), 4.46-4.62(m, 2H), 8.26(s, 1H), 10.29(s, 1H) |
| I-618 | ![structure: CH3,CH3 dimethyl, NH-C(=O)-CH2-4-pyridyl] | 1.01-1.93(m, 25H), 2.65(t, 2H, J = 6.0), 2.95(t, 2H, J = 6.0), 4.00(br, 2H), 4.25(s, 2H), 7.31(d, 2H, J = 4.5), 8.24(s, 1H), 8.56(d, 2H, J = 4.5), 9.44(br, 1H), 10.49(br, 1H) |
| I-619 | ![structure: CH3,CH3 dimethyl, NH-C(=O)-C(OCH3)2CH3] | 1.01-1.93(m, 25H), 2.65(t, 2H, J = 6.0), 2.95(t, 2H, J = 6.0), 3.18(s, 6H), 4.02(br, 2H), 8.26(s, 1H), 10.38(br, 1H), 10.55(br, 1H) |
| I-620 | ![structure: CH3,CH3 dimethyl, NH-C(=O)-CH2-morpholine] | 1.01-1.93(m, 25H), 2.42-2.59(br, 4H), 2.63(t, 2H, J = 6.0), 2.95(t, 2H, J = 6.0), 3.23-3.47(br, 2H), 3.48-3.60(br, 4H), 4.00(br, 2H), 8.26(s, 1H), 10.14(br, 1H), 10.44(br, 1H) |
| II-002 | ![structure: CH(CO2CH3)CH2CO2CH3] | 1.09-1.92(m, 19H), 2.63(t, 2H, J = 6.0), 2.91(t, 2H, J = 6.3), 3.00(dd, 2H, J = 2.1, 5.1), 3.71(s, 3H), 3.78(s, 3H), 4.02(m, 2H), 5.09(m, 1H), 8.26(s, 1H), 10.70(d, 1H, J = 7.8) |
| II-006 | ![structure: 2-(methoxycarbonyl)phenyl] | 1.17-1.72(m, 19H), 2.67(t, 2H, J = 5.7), 2.94(t, 2H, J = 7.5), 3.99(s, 3H), 4.05-4.16(m, 2H), 7.12(dd, 1H, J = 7.2, 8.7), 7.54(dd, 1H, J = 6.9, 8.7), 8.01(d, 1H, J = 7.2), 8.35(s, 1H), 8.62(d, 1H, J = 6.9), 12.98(s, 1H) |

TABLE 60

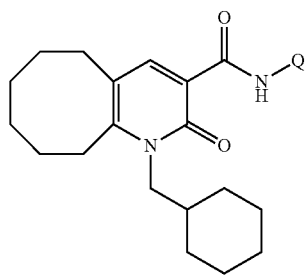

| Comp. No. | Q | ¹H-NMR(CDCl₃/TMS) δ |
|---|---|---|
| II-014 | ![structure: -CH(CH2CH2C(O)OCH3)-] | 1.6-1.88(m, 19H), 2.61-2.69(m, 4H), 2.89-2.99(m, 2H), 3.67-3.77(m, 2H), 3.71(s, 3H), 3.94-4.07(m, 2H), 8.29(s, 1H), 10.16(s, 1H) |
| II-015 | ![structure: -CH(CH2CH2C(O)OCH2CH3)-] | 1.05-1.83(m, 19H), 1.27(t, 3H, J = 5.7), 2.61-2.67(m, 4H), 2.91(t, 2H, J = 6.3), 3.71(q, 2H, J = 6.6), 3.81-3.99(m, 2H), 4.16(q, 2H, J = 7.2), 8.28(s, 1H), 10.17(br, 1H) |
| II-016 | ![structure: cyclohexyl with -C(O)OCH2CH3] | 1.00-2.05(m, 28H), 2.62(t, 2H, J = 5.7), 2.80 (m, 1H), 3.89(t, 2H, J = 6.3), 3.77-4.09(m, 2H), 4.06-4.17(m, 2H), 4.53(m, 1H), 8.25(1H, s), 10.43(d, 1H, J = 8.7) |
| II-017 | ![structure: cyclopentene with -C(O)OCH2CH3] | 1.15-1.92(m, 19H), 1.33(t, 3H, J = 7.2), 2.46-2.65(m, 6H), 2.92(t, 2H, J = 5.7), 3.31(t, 2H, J = 7.5), 4.11-4.20(m, 2H), 4.32(q, 2H, J = 7.2), 8.25(1H, s), 12.94(s, 1H) |
| II-034 | ![structure: -CH(CH2COOH)COOH] | DMOS-d6 1.12-1.91(m, 19H), 2.65(t, 2H, J = 5.4), 2.71-2.95(m, 2H), 3.33(t, 2H, J = 6.0), 3.92-4.06(m, 2H), 4.76(m, 1H), 8.13(s, 1H), 12.21-12.91(m, 2H) |
| II-035 | ![structure: -CH(CH2CH2COOH)-] | 1.05-1.83(m, 19H), 2.64(t, 2H, J = 5.7), 2.72(t, 2H, J = 6.3), 2.92(t, 2H, J = 6.0), 3.68-3.74(m, 2H), 3.78-4.17(m, 2H), 8.31(s, 1H), 10.27(t, 1H, J = 5.7) |
| II-038 | ![structure: cyclopentene with -COOH] | DMSO-d6 1.12-1.83(m, 21H), 2.43(t, 2H, J = 6.9), 2.65(t, 2H, J = 6.3), 2.95(t, 2H, J = 6.0), 3.16(t, 2H, J = 7.2), 3.99-4.04(m, 2H), 8.14(s, 1H), 12.10(s, 1H), 12.75(s, 1H) |

TABLE 61

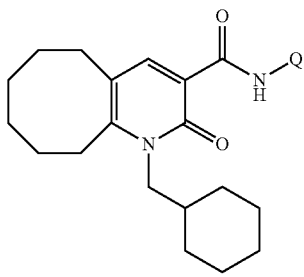

| Comp. No. | Q | ¹H-NMR(CDCl₃/TMS) δ |
|---|---|---|
| II-039 | (2-carboxycyclohexyl) | DMSO-d6 1.13-1.81(m, 25H), 2.62-2.66(m, 3H), 2.91-2.95(m, 2H), 3.95-4.05(m, 2H), 4.41(m, 1H), 8.10(s, 1H), 10.23(d, 1H, J = 8.7), 12.14(s, 1H) |
| II-042 | (2-carboxyphenyl) | 1.17-1.73(m, 19H), 2.66(t, 2H, J = 5.1), 2.94(t, 2H, J = 6.6), 3.94-4.22(m, 2H), 7.13(dd, 1H, J = 7.2, 8.1), 7.58(dd, 1H, J = 8.4, 7.2), 8.09(d, 1H, J = 8.1), 8.37(s, 1H), 8.73(d, 1H, J = 8.4), 13.15(s, 1H) |
| II-064 | (2-carboxythiophen-3-yl) | DMSO-d6 1.00-1.95(m, 19H), 2.60-2.65(m, 2H), 2.90-3.00(m, 2H), 3.90-4.15(br, 2H), 7.81(d, 1H, J = 5.4), 8.20(d, 1H, J = 5.7), 8.23 (s, 1H), 13.02(s, 1H) |
| II-065 | (3-carboxy-4,5,6,7-tetrahydrobenzothiophen-2-yl) | 1.04-1.96(m, 23H), 2.60-2.74(m, 4H), 2.85-3.00(m, 4H), 3.90-4.30(br, 2H), 8.35(s, 1H), 14.11(s, 1H) |
| II-066 | (2-carboxy-4-methylthiophen-3-yl) | DMSO-d6 1.02-1.90(m, 19H), 2.08(d, 3H, J = 0.9), 2.63-2.75(m, 2H), 2.92-3.03(m, 2H), 3.90-4.15(br, 2H), 7.48(s, 1H), 8.21(s, 1H), 12.01(s, 1H) |
| II-068 | (1-phenyl-2-carboxyethyl) | DMSO-d6 1.00-1.84(m, 19H), 2.64(brt, 2H), 2.77-2.97(m, 4H), 3.98(br, 2H), 5.40(q-like, 1H), 7.23-7.40(m, 5H), 8.11(s, 1H), 10.42(d, 1H, J = 8.1), 12.26(br, 1H) |

TABLE 62

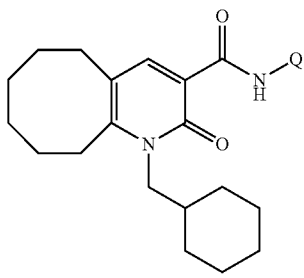

| Comp. No. | Q | ¹H-NMR(CDCl₃/TMS) δ |
|---|---|---|
| II-069 | ![structure: CH(CH3)2-CH2-CH(*)-CH2-COOH] | 0.94(t, 6H, J = 6.3), 1.06-1.73(m, 18H), 2.63-2.72(m, 4H), 2.91-2.95(m, 2H), 4.00(br, 2H), 4.37(m, 1H), 8.29(s, 1H), 10.43(d, 1H, J = 7.8) |
| II-070 | ![structure: CH2-C(CH3)2-COOH] | 1.08-1.71(m, 24H), 2.64(t, 2H, J = 6.0), 2.91(t, 2H, J = 6.0), 3.65(d, 2H, J = 6.0), 4.11(br, 2H), 8.31(s, 1H), 10.29(t 1H, J = 6.0) |
| II-071 | ![structure: benzyl-CH(*)-CH2-COOH] | 1.07-1.73(m, 19H), 2.62(t, 3H, J = 6.0), 2.70(d, 2H, J = 6.0), 2.92(t, 2H, J = 6.0), 3.03(d, 2H, J = 6.0), 4.17(2H, br), 4.61-4.67(m, 1H), 7.16-7.28(m, 5H), 8.26(s, 1H), 10.47(d, 1H, J = 6.0) |
| II-072 | ![structure: 1-phenylpyrazole-4-COOH] | 1.00-1.86(m, 19H), 2.57-2.67(m, 2H), 2.88-2.98(m, 2H), 3.80-4.20(br, 2H), 7.33-7.47(m, 3H), 7.52-7.58(m, 2H), 8.13(s, 1H), 8.25(s, 1H), 12.79(s, 1H) |
| II-073 | ![structure: 1-(CH2COOH)cyclohexyl] | 1.04-1.88(m, 26H), 2.15-2.17(m, 2H), 2.64(t, 3H, J = 6.0), 2.93(t, 2H, J = 6.0), 2.98(s, 1H), 4.00(br, 2H), 8.28(s, 1H), 10.77(s, 1H) |
| II-074 | ![structure: cyclohexyl-CH(*)-CH2-COOH] | 1.08-1.88(m, 30H), 2.60-2.79(m, 4H), 2.93(t, 2H, J = 6.9), 3.77-4.12(m, 3H), 8.29(s, 1H), 10.60(d, 1H, J = 6.0) |

TABLE 63

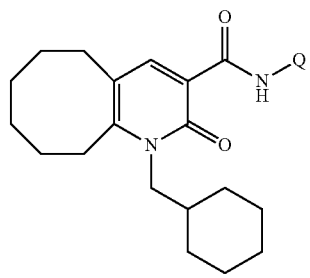

| Comp. No. | Q | $^1$H-NMR(CDCl$_3$/TMS) δ |
|---|---|---|
| II-075 | ![CH3-CH=CH-CH(-)-CH2-COOH] | 1.06-1.84(m, 21H), 2.62-2.99(m, 6H), 4.00(bs(, 2H), 4.88-4.95(m, 1H), 5.57-5.81(m, 2H), 8.30(s, 1H), 10.39(d, 1H, J = 7.5) |
| II-076 | ![CF3-CH(-)-CH2-COOH] | 1.05-1.85(m, 19H), 2.64(t, 2H, J = 5.4), 2.74-2.95(m, 6H), 4.00(br, 2H), 5.35(m, 1H), 8.32(s, 1H), 10.61(d, 1H, J = 9.6) |
| II-077 | ![cyclohexyl-C(COOH)-CH2-] | 1.09-2.17(m, 25H), 2.62(t, 2H, J = 6.0), 2.91(t, 2H, J = 6.0), 3.65(m, 2H), 4.00(br, 2H), 8.28(s, 1H), 10.21(t, 1H, J = 6.0) |
| II-081 | ![C(CH3)2-CH2CH2-COOH] | 1.02-1.83(m, 25H), 2.09-2.27(m, 2H), 2.39-2.43(m, 2H), 2.62(t, 2H, J = 6.3), 2.91(t, 2H, J = 6.3), 3.97(br, 2H), 8.28(s, 1H), 10.00(s, 1H) |
| II-082 | ![CH(CH3)-CH2-COOH] | DMSO-d6 1.00-1.84(m, 19H), 1.20(d, 3H, J = 6.6), 2.41(dd, 1H, J = 6.9 and 15.6), 2.55(dd, 1H, J = 5.7 and 15.6), 2.64(brt, 2H), 2.94(brt, 2H), 3.96(br, 2H), 4.27(m, 1H), 8.11(s, 1H), 9.90(d, 1H, J = 8.7), 12.25(br, 1H) |
| III-001 | ![-CH2CH2-O-C(=O)-NH-Ph] | 1.06-1.86(m, 19H), 2.65(t, 2H, J = 6.0), 2.92(t, 2H, J = 6.3), 3.73-4.35(m, 6H), 6.91(s, 1H), 7.05(t, 1H, J = 7.2), 7.27-7.38(m, 5H), 8.32(s, 1H), 10.20(d, 1H, J = 5.7) |
| III-005 | ![-CH2CH2CH2-C(=O)-OCH3] | 1.09-1.88(m, 19H), 1.93-1.98(m, 2H), 2.42(t, 2H, J = 7.5), 2.62-2.66(m, 2H), 2.89-2.96(m, 2H), 3.44-3.48(m, 2H), 3.67(s, 3H), 3.85-4.12(m, 2H), 8.29(d, 1H, J = 4.2), 10.00(s, 1H) |

TABLE 64

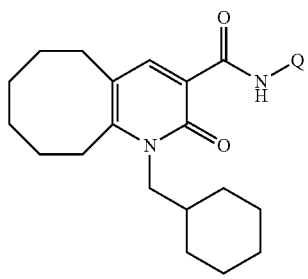

| Comp. No. | Q | ¹H-NMR(CDCl₃/TMS) δ |
|---|---|---|
| III-008 | 3-(ethoxycarbonyl via -CH₂CH₃ ester)phenyl | 1.18-1.74(m, 19H), 1.41(t, 3H, J = 7.2), 2.68(t, 2H, J = 6.3), 2.96(t, 2H, J = 6.6), 3.95-4.18(m, 2H), 4.38(q, 2H, J = 7.2), 7.42(dd, 1H, J = 7.8, 8.1), 7.78(d, 1H, J = 7.8), 8.12(d, 1H, J = 8.1), 8.30(s, 1H), 8.41(s, 1H), 12.32(s, 1H) |
| III-011 | 3-carboxyphenyl | 1.15-1.75(m, 19H), 2.69(t, 2H, J = 5.7), 2.97(t, 2H, J = 6.6), 3.84-4.15(m, 2H), 7.46(dd, 1H, J = 5.7, 4.8), 7.84(d, 1H, J = 5.7), 8.24(d, 1H, J = 4.8), 8.34(s, 1H), 8.42(s, 1H), 12.37(s, 1H) |
| III-013 | 3-carboxypropyl | 1.07-1.85(m, 19H), 1.90-2.05(m, 2H), 2.43(t, 2H, J = 6.3), 2.68(t, 2H, J = 6.0), 2.94(t, 2H, J = 5.7), 3.52-3.56(m, 2H), 3.82-4.08(m, 2H), 8.32(s, 1H), 10.39(s, 1H) |
| III-014 | 5-carboxyfuran-2-yl | DMSO-d6 1.00-1.90(m, 19H), 2.65-2.77(m, 2H), 2.93-3.05(m, 2H), 4.06(br, 2H), 6.49(d, 1H, J = 3.6), 7.25(d, 1H, J = 3.6), 8.26(s, 1H), 12.84(br, 1H), 13.20(s, 1H) |
| III-015 | 4-methyl-5-carboxythiazol-2-yl | 1.02-1.90(m, 19H), 2.63-2.73(m, 2H), 2.69(s, 3H), 2.92-3.00(m, 2H), 3.90-4.20(br, 2H), 8.36(s, 1H), 13.66(s, 1H) |
| III-016 | 4-methyl-5-(ethoxycarbonyl)thiazol-2-yl | 1.04-1.90(m, 19H), 1.36(t, 3H, J = 7.2), 2.62-2.73(m, 2H), 2.67(s, 3H), 2.90-3.00(br, 2H), 4.31(q, 2H, J = 7.2), 8.34(s, 1H), 13.60(s, 1H) |
| III-017 | 4-carboxy-4,4-dimethylbutyl | 1.06-2.05(m, 27H), 2.64(t, 2H, J = 6.3), 2.91(t, 2H, J = 6.3), 3.44-3.51(m, 2H), 4.00(br, 2H), 8.30(s, 1H), 9.97(m 1H) |

TABLE 65
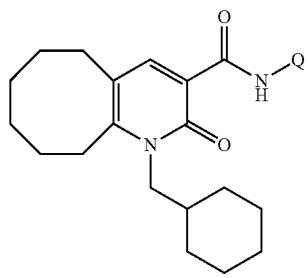
| Comp. No. | Q | ¹H-NMR(CDCl₃/TMS) δ |
|---|---|---|
| III-018 | 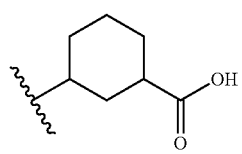 | 1.05-2.09(m, 27H), 2.37(d, 2H, J = 12.3), 2.50(t, 2H, J = 12.3), 2.64(t, 2H, J = 5.1), 2.92(t, 2H, J = 5.1), 3.95-3.99(m, 2H), 8.32(s, 1H), 10.21(t, 1H, J = 7.6) |
| III-019 | 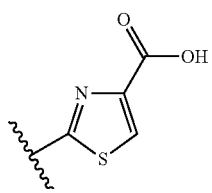 | 1.04-1.94(m, 19H), 2.63-2.74(m, 2H), 2.91-3.02(m, 2H), 3.90-4.20(br, 2H), 7.94(s, 1H), 8.36(s, 1H), 13.66(s, 1H) |
| III-020 | 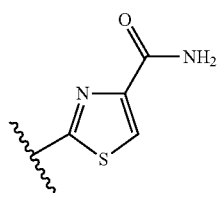 | 1.04-1.94(m, 19H), 2.63-2.74(m, 2H), 2.92-3.03(m, 2H), 3.90-4.25(br, 2H), 5.61(br, 1H), 7.15(br, 1H), 7.82(s, 1H), 8.38(s, 1H), 13.50(s, 1H) |
| III-021 | 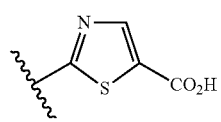 | DMSO-d6 1.00-1.95(m, 19H), 2.64-2.80(m, 2H), 2.94-3.08(m, 2H), 3.94-4.20(br, 2H), 8.09(s, 1H), 8.33(s, 1H), 12.80-13.50(br, 1H), 13.75(s, 1H) |
| III-022 | 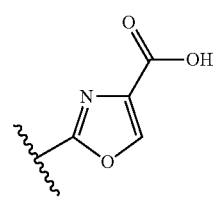 | DMSO-d6 1.15-1.90(m, 19H), 2.63-2.80(m, 2H), 2.93-3.08(m, 2H), 3.95-4.15(br, 2H), 8.27(s, 1H), 8.54(s, 1H), 13.29(s, 1H) |
| III-023 | 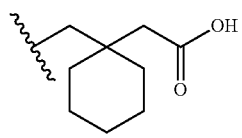 | |
| IV-002 | 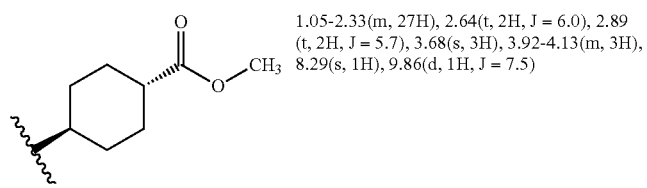 | 1.05-2.33(m, 27H), 2.64(t, 2H, J = 6.0), 2.89(t, 2H, J = 5.7), 3.68(s, 3H), 3.92-4.13(m, 3H), 8.29(s, 1H), 9.86(d, 1H, J = 7.5) |

TABLE 66
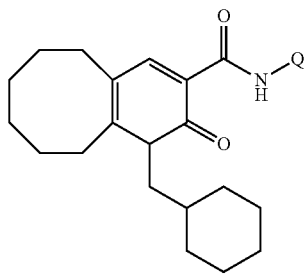
| Comp. No. | Q | $^1$H-NMR(CDCl$_3$/TMS) δ |
|---|---|---|
| IV-003 | | 1.14-1.74(m, 19H), 2.68(t, 2H, J = 5.7), 2.95(t, 2H, J = 5.4), 3.90(s, 3H), 3.95-4.18(m, 2H), 7.85(d, 2H, J = 5.7), 8.02(d, 2H, J = 6.6), 8.39(s, 1H), 12.48(s, 1H) |
| IV-008 | | 1.09-1.85(m, 23H), 2.36(t, 2H, J = 7.2), 2.62-2.66(m, 2H), 2.88-2.96(m, 2H), 3.43-3.63(m, 2H), 3.66(s, 3H), 3.89-3.98(m, 2H), 8.30(s, 1H), 9.96(s, 1H) |
| IV-009 | | 1.15-1.71(m, 19H), 2.64(t, 2H, J = 6.3), 2.91(t, 2H, J = 6.6), 3.66(s, 3H), 3.66-3.71(m, 4H), 3.82-4.14(m, 2H), 4.67(s, 2H), 8.31(s, 1H), 10.21(s, 1H) |
| IV-010 | ![](N-benzyl-N-methoxycarbonylmethyl-aminopropyl) | 1.17-1.73(m, 19H), 2.64(t, 2H, J = 6.0), 2.91-2.95(m, 4H), 3.42-3.57(m, 4H), 3.68(s, 3H), 3.90(s, 2H), 3.91-4.18(m, 2H), 7.23-7.43(m, 5H), 8.28(s, 1H), 10.10(s, 1H) |
| IV-011 | ![](N-methoxycarbonylmethyl-aminopropyl) | 1.06-1.87(m, 20H), 2.64(t, 2H, J = 5.7), 2.87-2.94(m, 4H), 3.49(s, 2H), 3.56-3.60(m, 2H), 3.73(s, 3H), 3.82-4.18(m, 2H), 8.30(s, 1H), 10.10(m, 1H) |
| IV-012 | | 1.09-2.19(m, 28H), 2.62-2.65(m, 2H), 2.91(t, 2H, J = 6.3), 3.89-4.00(m, 2H), 8.30(s, 1H), 9.90(d, 1H, J = 4.8) |
| IV-013 | | 1.09-1.86(m, 19H), 2.69(t, 2H, J = 5.4), 2.96(t, 2H, J = 6.0), 3.84-4.21(m, 2H), 7.88(d, 2H, J = 8.7), 8.09(d, 2H, J = 9.0), 8.40(s, 1H), 12.54(s, 1H) |

TABLE 67

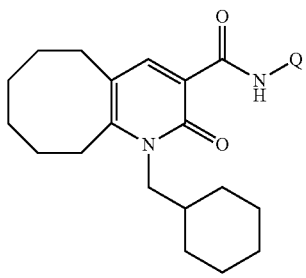

| Comp. No. | Q | ¹H-NMR(CDCl₃/TMS) δ |
|---|---|---|
| IV-018 | ![structure: -(CH₂)₄-COOH] | 1.05-1.80(m, 23H), 2.41(t, 2H, J = 7.2), 2.64(t, 2H, J = 5.7), 2.92(t, 2H, J = 6.6), 3.43-3.47(m, 2H), 3.81-4.12(m, 2H), 8.31(s, 1H), 10.04(s, 1H) |
| IV-019 | ![structure: -(CH₂)₃-N(CH₂Ph)-CH₂COOH] | 1.11-1.73(m, 19H), 2.65-3.04(m, 6H), 3.65(m, 4H), 4.03-4.14(m, 4H), 7.25-7.40(m, 5H), 8.31(s, 1H) |
| IV-020 | ![structure: -(CH₂)₃-NH-CH₂COOH] | 0.88-1.70(m, 19H), 2.60-2.69(m, 2H), 2.88-3.10(m, 2H), 3.33-4.16(m, 10H), 8.27(s, 1H), 10.35(m, 1H) |
| IV-021 | ![structure: thiazole-C(O)-C(O)OEt] | 1.04-1.90(m, 19H), 1.44(t, 3H, J = 7.2), 2.64-2.73(m, 2H), 2.92-3.01(m, 2H), 3.95-4.15(br, 2H), 4.46(q, 2H, J = 7.2), 8.27(s, 1H), 8.35(s, 1H), 13.57(s, 1H) |
| IV-022 | ![structure: thiazole-C(O)-COOH] | 1.04-1.90(m, 19H), 2.60-2.74(m, 2H), 2.94-3.02(m, 2H), 3.90-4.20(br, 2H), 8.36(s, 1H), 8.55(d, 1H, J = 0.9), 13.89(s, 1H) |
| IV-023 | ![structure: thiazole-CH₂-COOH] | 1.04-1.92(m, 19H), 2.65-2.73(m, 2H), 2.93-3.02(m, 2H), 3.79(s, 2H), 3.95-4.15(br, 2H), 6.71(s, 1H), 8.36(s, 1H), 13.63(s, 1H) |
| IV-024 | ![structure: thiazole-CH₂-COOEt] | DMSO-d6 1.04-1.90(m, 19H), 1.20(t, 3H, J = 7.2), 2.65-2.77(m, 2H), 2.95-3.07(m, 2H), 3.07(s, 2H), 3.92-4.16(br, 2H), 4.10(q, 2H, J = 7.2), 7.05(s, 1H), 8.29(s, 1H), 13.48(s, 1H) |

TABLE 68
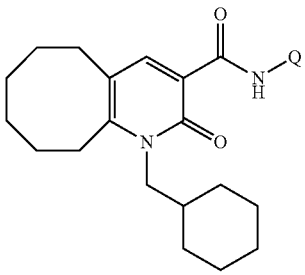
| Comp. No. | Q | $^1$H-NMR(CDCl$_3$/TMS) δ |
|---|---|---|
| IV-025 | 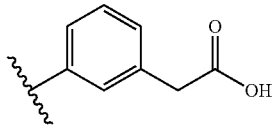 | DMSO-d6 1.03-1.89(m, 19H), 2.70(brt, 2H), 2.99(brt, 2H), 3.58(s, 2H), 4.05(br, 2H), 6.99(d, 1H, J = 7.8), 7.29(t, 1H, J = 7.8), 7.52(s, 1H), 7.69(d, 1H, J = 7.8), 8.25(s, 1H), 12.30(s, 1H), 12.34(br, 1H) |
| IV-026 | 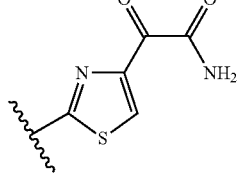 | 1.00-1.90(m, 19H), 2.62-2.73(m, 2H), 2.90-3.00(m, 2H), 3.90-4.20(br, 2H), 5.68(br, 1H), 7.46(br, 1H), 8.35(s, 1H), 8.91(s, 1H), 13.64(s, 1H) |
| IV-027 | 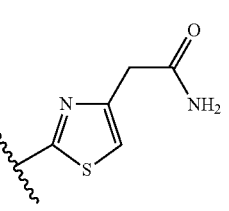 | DMSO-d6 1.05-1.90(m, 19H), 2.66-2.77(m, 2H), 2.93-3.05(m, 2H), 3.44(s, 2H), 3.95-4.20(br, 2H), 6.96(br, 2H), 7.39(s, 1H), 8.29(s, 1H), 13.47(s, 1H) |
| IV-029 | 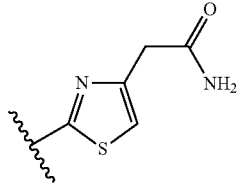 | DMSO-d6 1.04-1.88(m, 19H), 2.70(brt, 2H), 2.99(brt, 2H), 3.49(s, 2H), 4.05(br, 2H), 6.78-6.79(m, 2H), 8.23(s, 1H), 12.88(s, 1H) |
| V-001 | 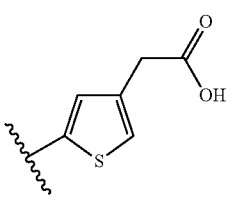 | 1.01-2.05(m, 17H), 2.26(m, 1H), 2.64(t, 2H, J = 6.0), 2.92(t, 2H, J = 6.3), 3.30(m, 2H), 3.65(s, 3H), 3.97-4.13(m, 2H), 8.30(s, 1H), 10.01(t, 1H, J = 5.4) |
| V-005 | 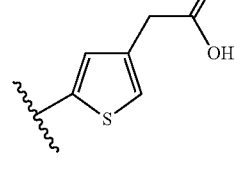 | 1.16-1.71(m, 19H), 1.09(s, 9H), 2.62(t, 2H, J = 6.0), 2.91(t, 2H, J = 6.3), 3.74(s, 3H), 3.92-4.16(m, 2H), 4.54(d, 1H, J = 8.1), 8.26(s, 1H), 10.61(d, 1H, J = 7.8) |
| V-006 | 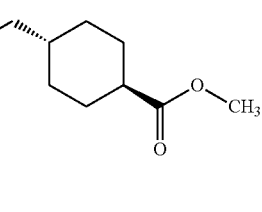 | 1.09-1.72(m, 25H), 2.31(t, 2H, J = 7.5), 2.61-2.66(m, 2H), 2.89-2.94(m, 2H), 3.66(s, 3H), 3.88-4.18(m, 2H), 8.30(s, 1H), 9.94(m, 1H) |

TABLE 68-continued
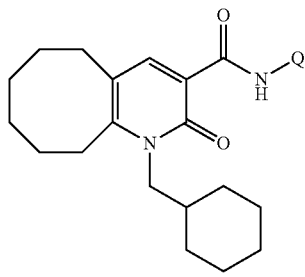
| Comp. No. | Q | $^1$H-NMR(CDCl$_3$/TMS) δ |
|---|---|---|
| V-007 | 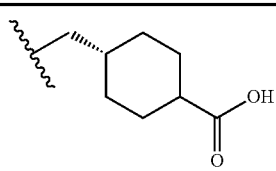 | 1.03-2.07(m, 28H), 2.29(m, 1H), 2.64(t, 2H, J = 6.3), 2.91(t, 2H, J = 5.7), 3.31(m, 2H), 3.91-4.09(m, 2H), 8.31(s, 1H), 10.03(t, 1H, J = 5.7) |
TABLE 69
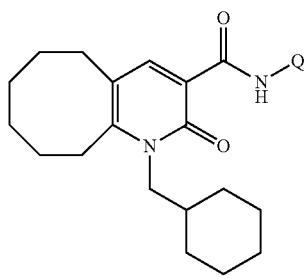
| Comp. No. | Q | $^1$H-NMR(CDCl$_3$/TMS) δ |
|---|---|---|
| V-011 | 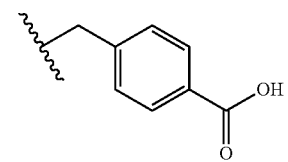 | 1.05-1.82(m, 19H), 2.66(t, 2H, J = 5.7), 2.93(t, 2H, J = 5.7), 3.85-4.18(m, 2H), 4.71(d 2H, J = 5.7), 7.44(d, 2H, J = 8.1), 8.01(d, 2H, J = 8.1), 8.35(s, 1H), 10.46(d, 1H, J = 6.0)HH |
| V-012 | 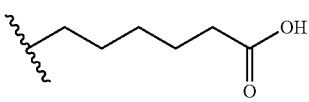 | 1.09-1.79(m, 23H), 2.37(t, 2H, J = 7.8), 2.62-2.66(m, 2H), 2.89-2.91(m, 2H), 3.43(dd, 2H, J = 6.9, 13.2), 3.86-4.14(m, 2H), 8.31(s, 1H), 9.97(s, 1H) |
| V-013 | 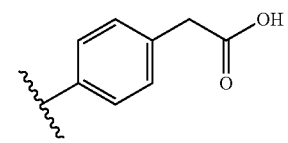 | DMSO-d6 1.04-1.90(m, 19H), 2.70(brt, 2H), 2.99(brt, 2H), 3.54(s, 2H), 4.05(br, 2H), 7.23(d, 2H, J = 8.4), 7.64(d, 2H, J = 8.4), 8.25(s, 1H), 12.24(s, 1H), 12.29(br, 1H) |
| X-1 | 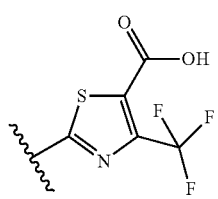 | DMSO-d6 1.00-1.90(m, 19H), 2.65-2.80(m, 2H), 2.95-3.10(m, 2H), 3.95-4.20(br, 2H), 8.34(s, 1H), 13.96(s, 1H) |

TABLE 69-continued

| Comp. No. | Q | ¹H-NMR(CDCl₃/TMS) δ |
|---|---|---|
| X-2 | (thiazole-CONH-CH₂-COOH, attached at 2-position of thiazole) | DMSO-d6 1.00-1.90(m, 19H), 2.65-2.80(m, 2H), 2.95-3.10(m, 2H), 3.89(d, 2H, J = 6.0), 3.95-4.18(br, 2H), 7.87(s, 1H), 8.33(s, 1H), 8.66(t, 1H, J = 6.0), 12.20-13.00(br, 1H), 13.70(s, 1H) |
| X-3 | (thiazole-CONH-CH₂CH₂-COOH, attached at 2-position of thiazole) | DMSO-d6 1.00-1.90(m, 19H), 2.65-2.80(m, 2H), 2.95-3.07(m, 2H), 3.40-3.55(m, 2H), 3.95-4.25(br, 2H), 7.83(s, 1H), 8.32(s, 1H), 8.44(t, 1H, J = 6.0), 11.80-12.80(br, 1H), 13.62(s, 1H) |
| X-4 | (thiazole-CONH-CH₂-COOH, attached at 5-position of thiazole) | DMSO-d6 1.02-1.90(m, 19H), 2.65-2.80(m, 2H), 2.94-3.09(m, 2H), 3.91(d, 2H, J = 6.0), 3.95-4.18(br, 2H), 8.15(s, 1H), 8.32(s, 1H), 8.91(t, 1H, J = 6.0), 12.40-13.00(br, 1H), 13.68(s, 1H) |

TABLE 70

| Comp. No. | Q | ¹H-NMR(CDCl₃/TMS) δ |
|---|---|---|
| X-5 | -C(CH₃)₂-C(O)-NH-CH₂-C(O)-NH-NH-S(O)₂-CH₃ | 1.02-1.94(m, 19H), 1.61(s, 6H), 2.64-2.68(m, 21H), 2.92-2.67(m, 2H), 2.97(s, 3H), 3.80-4.15(br, 2H), 4.09(d, 2H, J = 6.6), 6.61(t, 1H, J = 6.6), 6.86(d, 1H, J = 5.1), 8.41(s, 1H), 10.33(d, J = 5.1, 1H), 10.67(s, 1H) |
| X-6 | -C(CH₃)₂-C(O)-NH-CH₂-C(O)-piperidine | 1.01-1.96(m, 25H), 1.65(s, 6H), 2.59-2.63(m, 2H), 2.89-2.94(m, 2H), 3.31-3.35(m, 2H), 3.52-3.55(m, 2H), 3.80-4.15(br, 2H), 4.08(d, 2H, J = 3.6), 7.37(m, 1H), 8.26(s, 1H), 10.37(s, 1H) |

TABLE 70-continued
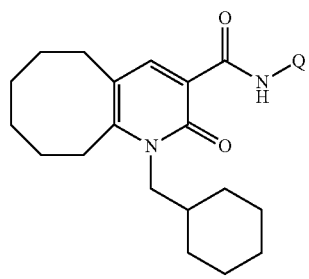
| Comp. No. | Q | $^1$H-NMR(CDCl$_3$/TMS) δ |
|---|---|---|
| X-7 | 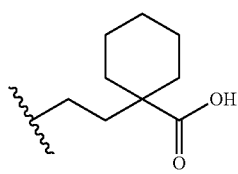 | 1.06-2.20(m, 31H), 2.64(t, 2H, J = 6.0), 2.91(t, 2H, J = 6.0), 3.47(td, 2H, J = 6.0 and 16.2), 3.98(br, 2H), 8.30(s, 1H), 9.92(t, 1H, J = 6.0) |
| X-8 | 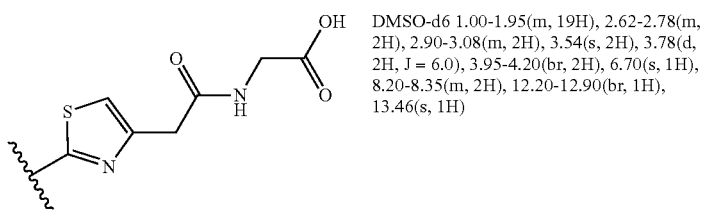 | DMSO-d6 1.00-1.95(m, 19H), 2.62-2.78(m, 2H), 2.90-3.08(m, 2H), 3.54(s, 2H), 3.78(d, 2H, J = 6.0), 3.95-4.20(br, 2H), 6.70(s, 1H), 8.20-8.35(m, 2H), 12.20-12.90(br, 1H), 13.46(s, 1H) |
| X-9 | 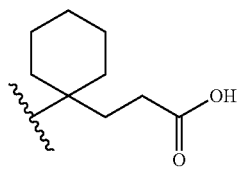 | 1.07-1.83(m, 27H), 2.08-2.29(m, 4H), 2.35-2.41(m, 2H), 2.62(t, 2H, J = 5.4), 2.91(t, 2H, J = 5.4), 4.00(br, 2H), 8.28(s, 1H), 10.07(s, 1H) |
| X-11 | 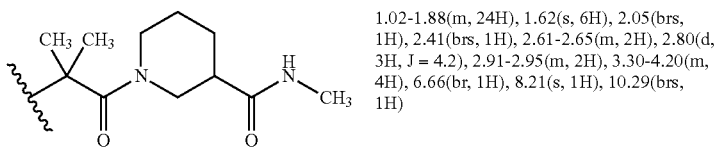 | 1.02-1.88(m, 24H), 1.62(s, 6H), 2.05(brs, 1H), 2.41(brs, 1H), 2.61-2.65(m, 2H), 2.80(d, 3H, J = 4.2), 2.91-2.95(m, 2H), 3.30-4.20(m, 4H), 6.66(br, 1H), 8.21(s, 1H), 10.29(brs, 1H) |
| X-12 | 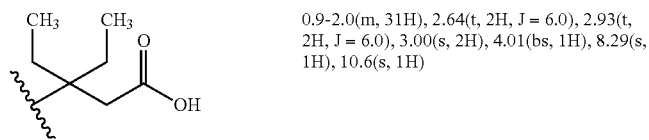 | 0.9-2.0(m, 31H), 2.64(t, 2H, J = 6.0), 2.93(t, 2H, J = 6.0), 3.00(s, 2H), 4.01(bs, 1H), 8.29(s, 1H), 10.6(s, 1H) |
| X-13 | 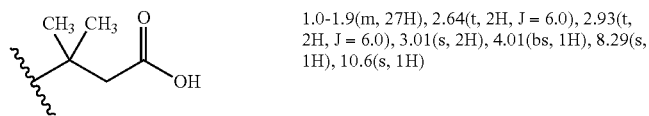 | 1.0-1.9(m, 27H), 2.64(t, 2H, J = 6.0), 2.93(t, 2H, J = 6.0), 3.01(s, 2H), 4.01(bs, 1H), 8.29(s, 1H), 10.6(s, 1H) |

TABLE 71

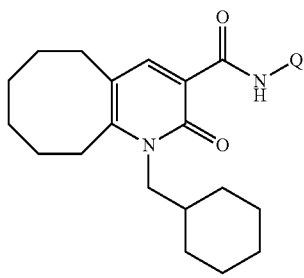

| Comp. No. | Q | $^1$H-NMR(CDCl$_3$/TMS) δ |
|---|---|---|
| X-14 | isoxazole-CH$_2$-COOH | DMSO-d6 1.02-1.86(m, 19H), 2.71(t-like, 2H), 3.00(t-like, 2H), 3.93(s, 2H), 4.05(br, 2H), 6.94(s, 1H), 8.27(s, 1H), 12.78(s, 1H), 12.88(br, 1H) |
| X-15 | -C(CH$_3$)$_2$-C(O)-NH-C(O)-CH(OEt)$_2$ | CDCl3 1.01-1.94(m, 31H), 2.64(t, 2H, J = 6.0), 2.96(t, 2H, J = 6.0), 3.51(m, 4H), 4.00(br, 2H), 4.84(s, 1H), 8.28(s, 1H), 10.24(br, 1H), 10.42(br, 1H) |
| X-16 | -C(CH$_3$)$_2$-C(O)-NH-C(O)-C≡CH | CDCl3 1.01-1.93(m, 25H), 2.64(t, 2H, J = 6.0), 2.94(t, 2H, J = 6.0), 3.29(s, 1H), 4.00(br, 2H), 8.28(s, 1H), 10.45(br, 1H), 10.53(br, 1H) |
| X-17 | -C(CH$_3$)$_2$-C(O)-NH-C(O)-C$_6$H$_4$-N(CH$_3$)$_2$ | CDCl3 1.01-1.90(m, 25H), 2.65(t, 2H, J = 6.0), 2.94(t, 2H, J = 6.0), 3.02(s, 6H), 4.00(br, 2H), 6.91(br, 1H), 7.26-7.44(m, 3H), 8.28(s, 1H), 10.64(br, 1H), 11.59(br, 1H) |
| X-18 | -C(CH$_3$)$_2$-C(O)-NH-C(O)-C$_6$H$_4$-N$^+$(CH$_3$)$_3$ I$^-$ | CDCl3 1.01-1.90(m, 25H), 2.74(t, 2H, J = 6.0), 2.94(t, 2H, J = 6.0), 3.81-4.14(m, 11H), 7.79(t, 1H, J = 8.1), 8.16(d, 1H, J = 8.1), 8.19(s, 1H), 8.28(dd, 1H, J = 2.4 and 8.1) 8.52(m, 1H), 10.82(br, 1H), 11.08(br, 1H) |
| X-19 | -C(CH$_3$)$_2$-C(O)-N(piperidine)-NH-C(O)-NH-CH(CH$_3$)$_2$ | 1.02-1.88(m, 24H), 1.19(dd, 6H, J = 3.9 and 6.6), 1.60(s, 6H), 2.55-2.75(m, 3H), 2.85-3.03(m, 3H), 3.65-4.04(m, 4H), 4.29(m, 1H), 4.69(m, 1H), 5.88(m, 1H), 8.17(s, 1H), 10.59(s, 1H) |
| X-20 | -C(CH$_3$)$_2$-C(O)-N(piperidine)-NH-SO$_2$CH$_3$ | 1.02-1.92(m, 23H), 1.59(s, 6H), 2.56-2.80(m, 3H), 2.84-3.04(m, 3H), 3.09(s, 3H), 3.60-4.45(br, 2H), 3.72(m, 1H), 4.31(m, 1H), 4.72(m, 1H), 6.55(m, 1H), 8.41(s, 1H), 10.53(s, 1H) |
| X-21 | thiadiazole-CH$_2$-COOH | DMSO-d6 1.0-1.8(m, 19H), 2.72(br-s, 2H), 3.01(br-s, 2H), 3.81(s, 2H), 4.07(br-s, 2H), 8.33(s, 1H), 12.6(br-s, 1H), 13.8(br-s, 1H) |

TABLE 72

| Comp. No. | Q | ¹H-NMR(CDCl₃/TMS) δ |
|---|---|---|
| X-23 | (2-hydroxy-carboxylic acid butyl group) | 1.0-1.9(m, 21H), 2.65(t, 2H, J = 6.0), 2.94(t, 2H, J = 6.0), 3.70-3.81(m, 1H), 3.86-4.16(m, 3H), 4.38(t, 1H, J = 3.3), 8.27(s, 1H), 10.7(s, 1H) |
| X-25 | (2-cyano-2-methylpropyl) | CDCl3 1.01-1.94(m, 31H), 2.64(t, 2H, J = 6.0), 2.93(t, 2H, J = 6.0), 4.00(br, 2H), 8.32(s, 1H), 10.35(br, 1H) |
| X-27 | (thiazolyl-propenoic acid) | DMSO-d6 1.0-1.8(m, 22H), 2.20-2.28(m, 2H), 2.72(br-s, 2H), 3.01(br-s, 2H), 4.03(br-s, 2H), 6.90(t, 1H, J = 7.2 Hz), 8.28(s, 1H), 13.4(br-s, 1H) |
| X-28 | (pent-2-ynoic acid) | 1.00-1.90(m, 21H), 2.66(t, 2H, J = 6.0), 2.93(t, 2H, J = 6.0), 4.01(bs, 1H), 4.33(d, 2H, J = 5.4), 8.30(s, 1H), 10.3(t, 1H, J = 5.4) |
| X-29 | (isopropyl urea piperidine amide) | 1.02-1.93(m, 24H), 1.14(dd, 6H, J = 6.6 and 9.0), 1.62(s, 6H), 2.61-2.65(m, 2H), 2.91-2.95(m, 2H), 3.08(dd, 1H, J = 7.5 and 13.5), 3.22(m, 1H), 3.42-3.60(m, 2H), 3.70-4.20(m, 3H), 4.81(br, 1H), 7.26(m, 1H), 8.24(s, 1H), 10.34(s, 1H) |
| X-30 | (methylsulfonyl piperidine amide) | 1.02-1.94(m, 22H), 1.64(s, 6H), 2.62-2.66(m, 2H), 2.78(s, 3H), 2.91-2.95(m, 2H), 3.07(dd, 1H, J = 6.9 and 12.0), 3.14-3.23(m, 2H), 3.39(dd, 1H, J = 3.3 and 12.0), 3.75-4.20(m, 4H), 7.63(d, 1H, J = 8.1), 8.25(s, 1H), 10.36(s, 1H) |
| X-31 | (propionyl piperidine amide) | 1.01-1.91(m, 24H), 1.10(t, 3H, J = 7.5), 1.62(s, 6H), 2.14(q, 2H, J = 7.5), 2.61-2.65(m, 2H), 2.82-3.02(m, 3H), 3.75-4.20(br, 2H), 3.93(m, 1H), 4.36-4.58(m, 2H), 5.38(d, 1H, J = 7.8), 8.24(s, 1H), 10.30(s, 1H) |

TABLE 73
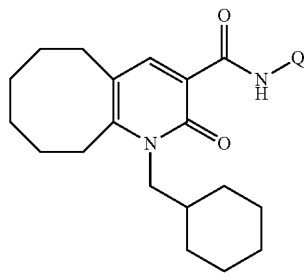
| Comp. No. | Q | $^1$H-NMR(CDCl$_3$/TMS) δ |
|---|---|---|
| X-32 | 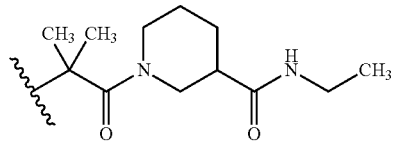 | 1.02-1.86(m, 23H), 1.20(t, 3H, J = 7.5), 1.60(s, 6H), 2.30-2.50(m, 2H), 2.56-2.66(m, 2H), 2.71(m, 1H), 2.85-3.04(m, 3H), 3.60-4.45(m, 2H), 4.16(m, 1H), 4.34(m, 1H), 4.69(m, 1H), 7.18(m, 1H), 8.20(s, 1H), 10.48(s, 1H) |
| X-33 | 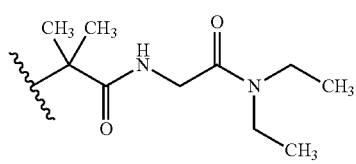 | 1.02-1.96(m, 19H), 1.11(t, 3H, J = 7.2), 1.19(t, 3H, J = 7.2), 1.66(s, 6H), 2.59-2.63(m, 2H), 2.90-2.94(m, 2H), 3.27(q, 2H, J = 7.2), 3.38(q, 2H, J = 7.2), 3.80-4.15(br, 2H), 4.09(d, 2H, J = 3.6), 7.34(m, 1H), 8.27(s, 1H), 10.37(s, 1H) |
| X-34 | 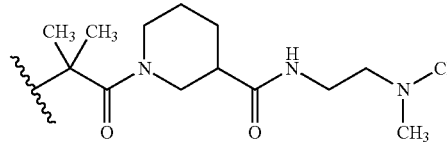 | 1.02-1.98(m, 24H), 1.61(s, 6H), 2.39(s, 6H), 2.52-2.72(m, 4H), 2.90-2.94(m, 2H), 3.24-3.60(m, 4H), 3.74-4.30(m, 4H), 6.89(brs, 1H), 8.24(s, 1H), 10.31(s, 1H) |
| X-37 | 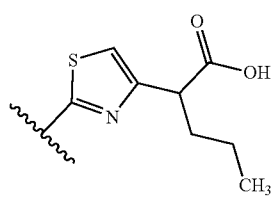 | DMSO-d6 0.91(t, 3H, J = 7.2 Hz), 1.0-1.96(m, 26H), 2.71(br-s, 2H), 3.01(br-s, 2H), 3.63(t, 1H, J = 7.5 Hz), 4.03(br-s, 2H), 7.0(s, 1H), 8.28(s, 1H), 12.3(br-s, 1H), 13.5(br-s, 1H) |
| X-38 | 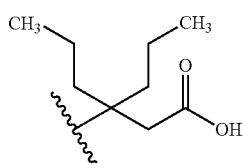 | 0.94(t, 6H, J = 7.2), 1.05-1.88(m, 25H), 2.64(t, 2H, J = 6.0), 2.93(t, 2H, J = 6.0), 3.00(s, 2H), 4.01(bs, 1H), 8.28(s, 1H), 10.7(t, 1H, J = 5.4) |
| X-39 | 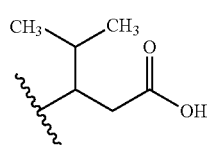 | 1.00-1.90(m, 27H), 1.94-2.07(m, 1H), 2.58-2.79(m, 4H), 2.93(t, 2H, J = 6.0), 3.90-4.18(m, 2H), 8.30(s, 1H), 10.6(bs, 1H) |
| X-40 | 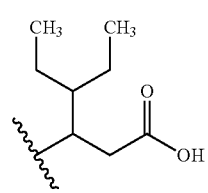 | 0.85-1.86(m, 32H), 2.60-2.74(m, 4H), 2.93(t, 2H, J = 6H), 4.00(bs, 1H), 4.30-4.39(m, 1H), 8.30(s, 1H), 10.6(d, 1H, J = 7.5) |

TABLE 74

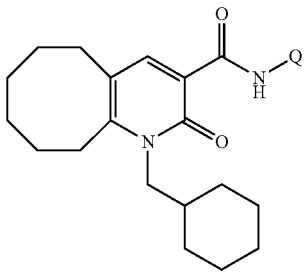

| Comp. No. | Q | $^1$H-NMR(CDCl$_3$/TMS) δ |
|---|---|---|
| X-41 | [structure: CH$_2$CH(CF$_3$)CH$_2$COOH branch] | DMSO-d6 1.02-1.80(m, 21H), 2.65(t, 2H, J = 6), 2.93(t, 2H, J = 6H), 3.66-3.85(m, 3H), 4.00(bs, 1H), 8.12(s, 1H), 10.2(bs, 1H) |
| X-42 | [structure: CH(CH$_3$)CH$_2$OCH$_2$COOH] | 1.00-1.90(m, 24H), 2.65(t, 2H, J = 6.0), 2.93(t, 2H, J = 6.0), 3.59(dd, 1H, J = 9.9 and 4.8), 3.70(dd, 1H, J = 9.9 and 6.9), 4.00(bs, 1H), 4.14-4.25(m, 2H), 4.37-4.52(m, 1H), 8.3l(s, 1H), 10.2(d, 1H, J = 7.8) |
| X-43 | [structure: C(CH$_3$)$_2$C(O)-piperidine-2-COOH] | DMSO-d6 0.92-1.80(m, 24H), 1.48(s, 6H), 2.04(m, 1H), 2.55-2.75(m, 2H), 2.88-2.99(m, 2H), 3.07(m, 1H), 3.70-4.44(m, 3H), 5.07(m, 1H), 8.08(s, 1H), 10.33(s, 1H), 12.62(brs, 1H) |
| X-44 | [structure: C(CH$_3$)$_2$C(O)-piperidine-2-C(O)NHEt] | 1.02-1.92(m, 24H), 1.14(t, 3H, J = 7.5), 1.62(s, 6H), 2.53(m, 1H), 2.59-2.68(m, 2H), 2.77(m, 1H), 2.92-2.96(m, 2H), 3.12-3.44(m, 2H), 3.75-4.20(br, 2H), 4.31(m, 1H), 5.48(m, 1H), 7.65(m, 1H), 8.22(s, 1H), 10.51(s, 1H) |
| X-46 | [structure: thiophene-CH$_2$COOH] | DMSO-d6 1.03-1.90(m, 19H), 2.70(t-like, 2H), 2.99(t-like, 2H), 3.71(s, 2H), 4.05(br, 2H), 6.70(d, 1H, J = 3.9), 6.73(d, 1H, J = 3.9), 8.23(s, 1H), 12,45(brs, 1H), 12,83(s, 1H) |
| X-47 | [structure: thiophene-CH=CH-COOH] | DMSO-d6 1.04-1.90(m, 19H), 2.71(t-like, 2H), 3.00(t-like, 2H), 3.71(s, 2H), 4.05(br, 2H), 5.99(d, 1H, J = 15.6), 6.98(d, 2H, J = 3.9), 7.33(d, 1H, J = 3.9), 7.67(d, 1H, J = 15.6), 8.25(s, 1H), 12,15(brs, 1H), 13.14(s, 1H) |

TABLE 74-continued

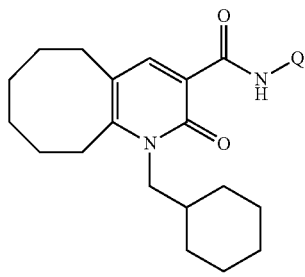

| Comp. No. | Q | $^1$H-NMR(CDCl$_3$/TMS) δ |
|---|---|---|
| X-49 | (thiophene with -CH$_2$CH$_2$COOH) | DMSO-d6 1.02-1.88(m, 19H), 2.56(t, 2H, J = 7.2), 2.70(t-like, 2H), 2.94(t, 2H, J = 7.2), 2.99(t-like, 2H), 4.04(br, 2H), 6.62(d, 1H, J = 3.9), 6.70(d, 1H, J = 3.9), 8.22(s, 1H), 12,23(br, 1H), 12,80(s, 1H) |

TABLE 75

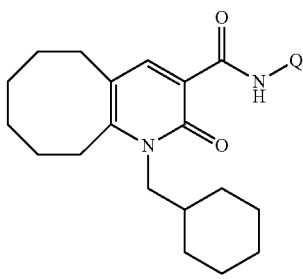

| Comp. No. | Q | $^1$H-NMR(CDCl$_3$/TMS) δ |
|---|---|---|
| X-51 | (isopropyl-CH-CH$_2$-O-CH$_2$-COOH) | 0.95-1.88(m, 27H), 1.90-2.02(m, 1H), 2.67(t, 2H, J = 6.0), 2.94(t, 2H, J = 6.0), 3.65(dd, 1H, J = 9.9 and 3.9), 3.79(t, 1H, J = 9.9), 4.06-4.23 (m, 4H), 8.36(s, 1H), 10.5(s, 1H) |
| X-52 | (gem-dimethyl-C(O)-piperidine-C(O)NH-CH$_2$-C(O)NH$_2$) | 1.00-1.90(m, 23H), 1.59(s, 6H), 2.10(m, 1H), 2.54-2.68(m, 3H), 2.91-2.95(m, 2H), 3.56-3.38(m, 2H), 3.80-4.30(br, 2H), 4.03(d, 2H, J = 5.1), 4.47(br, 1H), 5.51(brs, 1H), 7.09(brs, 1H), 7.61(brs, 1H), 8.14(s, 1H), 10.39(s, 1H) |
| X-53 | (gem-dimethyl-C(O)-piperidine-C(O)NH-CH$_2$CH$_2$-NHC(O)CH$_3$) | 1.02-1.92(m, 22H), 1.60(s, 6H), 2.03(s, 3H), 2.27(m, 1H), 2.55(brs, 1H), 2.62-2.66(m, 2H), 2.86-2.97(m, 2H), 2.99-3.20(m, 2H), 3.25-3.45(m, 2H), 3.46-3.68(m, 2H), 3.70-4.20(br, 2H), 4.32(m, 1H), 4.64(m, 1H), 7.31-7.52(m, 2H), 8.12(s, 1H), 10.39(s, 1H) |

TABLE 75-continued

| Comp. No. | Q | ¹H-NMR(CDCl₃/TMS) δ |
|---|---|---|
| X-56 | benzyl-S-CH₂-CH(—)-COOH | DMSO-d6 1.01-1.92(m, 19H), 2.60-2.78(br, 2H), 2.89(d, 2H,J = 2.4), 2.94-3.10(br, 2H), 3.78(s, 2H), 4.00(br, 2H), 4.73(q, 1H,J = 5.1 and 12.9), 7.20-7.32(m, 5H), 8.14(s, 1H), 10.46(d, 1H, J = 7.8), 13.12(br, 1H) |
| X-57 | CH₃-S-CH₂-CH(—)-COOH | DMS0-d6 1.01-1.92(m, 19H), 2.08(s, 3H), 2.60-2.77(m, 2H), 2.94-3.10(m, 4H), 4.00(br, 2H), 4.69(q, 1H,J = 5.1), 8.12(s, 1H), 10.37(d, 1H, J = 7.5), 13.01(br, 1H) |
| X-58 | (CH₃)C(—)=CH-COOH | DMSO-d6 0.81-1.82(m, 19H), 1.72(s, 3H), 2.50-2.70(m, 2H), 2.81-3.00(m, 2H), 4.02(br, 2H), 4.86(s, 1H), 8.11(br, 1H), 13.00(br, 1H) |
| X-59 | (CF₃)C(—)=CH-COOH | DMS0-d6 0.81-1.82(m, 19H), 2.62-2.75(m, 2H), 2.91-3.04(m, 2H), 4.04(br, 2H), 6.25(s, 1H), 8.18(s, 1H), 12.42(br, 1H) |

TABLE 76

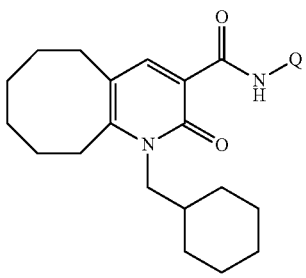

| Comp. No. | Q | $^1$H-NMR(CDCl$_3$/TMS) δ |
|---|---|---|
| X-60 | (3-(thiophen-2-yl)propanoic acid, attached via C3) | DMSO-d6 0.80-1.82(m, 19H), 2.57-2.80(m, 2H), 2.80-3.04(m, 4H), 3.97(br, 2H), 5.66(q, 1H, J = 6.9 and 14.7), 6.97(m, 1H), 7.05(d, 1H, J = 3.3), 7.39(m, 1H), 8.14(s, 1H), 10.42(d, 1H, J = 8.4) |
| X-61 | (3-(furan-2-yl)propanoic acid, attached via C3) | DMSO-d6 0.80-1.82(m, 19H), 2.57-2.80(m, 2H), 2.80-2.90(m, 2H), 2.90-3.00(m, 2H), 3.97(br, 2H), 5.49(q, 1H, J = 6.9 and 14.7), 6.29(m, 1H), 7.60(m, 1H), 7.67(m, 1H), 8.14(s, 1H), 10.29(d, 1H, J = 8.4), 12.50(br, 1H) |
| X-62 | (4,5,6,7-tetrahydrobenzothiazole-4-carboxylic acid, attached via C2) | DMSO-d6 1.0-2.1(m, 23H), 2.69-2.70(m, 4H), 2.98(brs, 2H), 3.57(t, 1H, J = 6.9 Hz), 4.07(br-s, 2H), 8.26(s, 1H), 13.8(br-s, 1H) |
| X-64 | (3-(thiazol-4-yl)propanoic acid, attached via C2 of thiazole) | DMSO-d6 1.04-1.88(m, 19H), 2.60(t, 2H, J = 7.5), 2.71(t-like, 2H), 2.84(t, 2H, J = 7.5), 3.00(t-like, 2H), 4.07(brd, 2H), 6.86(s, 1H), 8.28(s, 1H), 12.15(br, 1H), 13.43(s, 1H) |
| X-65 | (3-(thiazol-4-yl)acrylic acid, attached via C2 of thiazole) | DMSO-d6 1.05-1.90(m, 19H), 2.72(t-like, 2H), 3.01(t-like, 2H), 4.08(brd, 2H), 6.46(d, 1H, J = 16.6), 7.49(d, 1H, J = 15.6), 7.68(s, 1H), 8.30(s, 1H), 12.39(br, 1H), 13.59(s, 1H) |
| X-66 | (3-propyl, carboxymethyl branch) | 0.94(t, 3H, J = 7.2), 1.05-1.88(m, 25H), 2.60-2.82(m, 4H), 2.93(t, 2H, J = 6.0), 4.00(bs, 1H), 4.31(bs, 1H), 8.33(s, 1H), 10.4(s, 1H) |
| X-67 | (3-butyl, carboxymethyl branch) | 0.90(t, 3H, J = 6.9), 1.00-1.90(m, 27H), 2.60-2.80(m, 4H), 2.93(t, 2H, J = 6.0), 4.00(bs, 1H), 4.25-4.37(m, 1H), 8.33(s, 1H), 10.4(s, 1H) |

TABLE 77

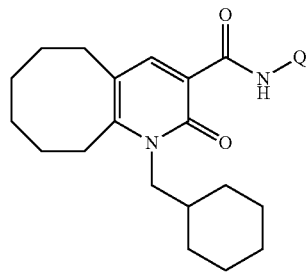

| Comp. No. | Q | $^1$H-NMR(CDCl$_3$/TMS) δ |
|---|---|---|
| X-68 | benzylsulfinyl-CH$_2$-CH(COOH)- (wavy bond) | DMSO-d6 1.01-1.92(m, 19H), 2.60-2.78(br, 2H), 2.94-3.00(br, 2H), 3.69(d, 2H, J = 2.4), 4.00(br, 2H), 4.50(s, 2H), 4.97(q, 1H, J = 5.1 and 12.9), 7.36(s, 5H), 8.14(s, 1H), 10.48(d, 1H, J = 7.8), 13.12(br, 1H) |
| X-69 | benzylsulfinyl-CH$_2$-CH(COOH)- (wavy bond) | DMSO-d6 1.01-1.92(m, 19H), 2.60-2.78(br, 2H), 2.94-3.05(br, 2H), 3.20-2.38(m, 2H), 3.80-4.20(m, 4H), 4.45(m, 1H), 4.97-5.30(m, 1H), 7.20-7.48(m, 5H), 8.32(m, 1H), 11.02(m, 1H) |
| X-70 | (CH$_3$)$_2$C-C(O)-piperidinyl-C(O)-piperidinyl | 1.02 1.88(m, 31H), 1.65(s, 6H), 2.61-2.65(m, 2H), 2.89-2.93(m, 2H), 3.34-3.56(m, 4H), 3.67(m, 1H), 3.75-4.25(br, 2H), 4.29(m, 1H), 5.47(m, 1H), 8.25(s, 1H), 10.33(s, 1H) |
| X-71 | (CH$_3$)$_2$C-C(O)-NH-piperidinyl-N-C(O)-NH-Ph | 1.00-1.90(m, 23H), 1.64(s, 6H), 2.14-2.38(m, 2H), 2.84-2.89(m, 2H), 3.07(m, 1H), 3.34(dd, 1H, J = 2.4 and 13.5), 3.58-3.79(m, 2H), 3.75-4.20(br, 2H), 4.15(m, 1H), 6.96(t, 1H, J = 7.5), 7.11(d, 1H, J = 8.1), 7.21-7.29(m, 2H), 7.54(d, 2H, J = 7.5), 7.62(s, 1H), 8.06(s, 1H), 10.42(s, 1H) |
| X-72 | CH$_2$=C(COOH)- | DMS0-d6 1.00-1.93(m, 19H), 2.60-2.74(br, 2H), 2.92-3.05(br, 2H), 4.00(br, 2H), 5.56(m, 1H), 5.71(s, 1H), 6.23(s, 1H), 8.15(s, 1H), 12.03(br, 1H) |

TABLE 77-continued
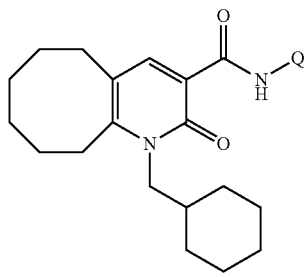
| Comp. No. | Q | ¹H-NMR(CDCl₃/TMS) δ |
|---|---|---|
| X-73 | 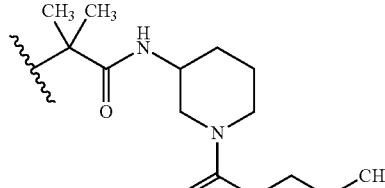 | DMSO-d6 0.81-1.82(m, 19H), 2.62-2.75(m, 2H), 2.91-3.04(m, 2H), 4.04(br, 2H), 6.25(s, 1H), 8.18(s, 1H), 12.42(br, 1H) |
TABLE 78
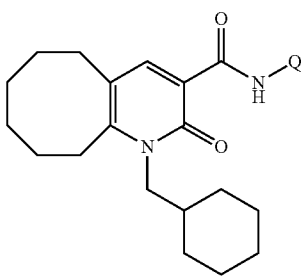
| Comp. No. | Q | ¹H-NMR(CDCl₃/TMS) δ |
|---|---|---|
| X-74 | 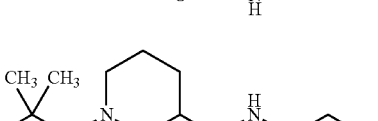 | 0.90(t, 3H, J = 7.5), 1.02-1.94(m, 25H), 1.62(s, 6H), 2.61-2.65(m, 2H), 2.91-2.95(m, 2H), 3.05-3.33(m, 4H), 3.42-3.55(m, 2H), 3.80-4.20(br, 2H), 3.90(m, 1H), 5.10(br, 1H), 7.23 (d, 1H, J = 7.5), 8.22(s, 1H), 10.34(s, 1H) |
| X-75 | 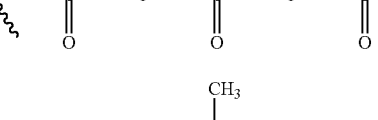 | 1.02-1.88(m, 21H), 1.61(s, 6H), 1.94-2.16(m, 3H), 2.36-2.60(m, 3H), 2.63-2.67(m, 2H), 2.91-2.95(m, 2H), 3.36-3.70(m, 4H), 3.75-4.25 (br, 3H), 5.66(brs, 1H), 6.75-7.22(m, 2H), 8.20 (s, 1H), 10.35(s, 1H) |
| X-76 |  | 0.96(s, 9H), 1.00-1.82(m, 23H), 2.60-2.82(m, 4H), 2.92(t, 2H, J = 6.0), 4.00(bs, 1H), 4.46 (bs, 1H), 8.34(s, 1H), 10.4(s, 1H) |

TABLE 78-continued

| Comp. No. | Q | ¹H-NMR(CDCl₃/TMS) δ |
|---|---|---|
| X-77 | [structure: 3,3-dimethylbutyl with CH₃ groups and CH₂COOH] | 1.06(s, 9H), 1.00-1.82(m, 21H), 2.51(dd, 1H, J = 16.0 and 6.3), 2.65(t, 2H, J = 6), 2.83(dd, 1H, J = 16.0 and 3.6), 2.93(t, 2H, J = 6.9), 3.90-4.10(m, 2H), 8.31(s, 1H), 10.8(s, 1H) |
| X-78 | [structure: CH(COOH)CH₂NHSO₂CH(CH₃)₂] | 1.00-1.86(m, 27H), 2.65(t, 2H, J = 6.0), 2.93(t, 2H, J = 6.0), 3.17-3.30(m, 1H), 3.57-4.15(m, 3H), 4.30-4.40(m, 1H), 5.82(d, 1H, J = 7.2), 8.30(s, 1H), 10.6(t, 1H, J = 6.0) |
| X-79 | [structure: 5-methylthiophen-2-yl-CH(COOH)] | DMSO-d6 1.00-1.84(m, 19H), 2.41(d, 3H, J = 0.9), 2.65(t-like, 2H), 2.95(t-like, 2H), 3.98(brd, 2H), 5.64(d, 1H, J = 6.9), 6.69(m, 1H), 6.90(d, 1H, J = 3.3), 8.12(s, 1H), 10.61(d, 1H, J = 6.9), 13.21(br, 1H) |
| X-80 | [structure: 5-chlorothiophen-2-yl-CH(COOH)] | DMSO-d6 1.00-1.86(m, 19H), 2.65(t-like, 2H), 2.96(t-like, 2H), 4.00(brd, 2H), 5.70(dd, 1H, J = 0.6 and 6.9), 6.97(dd, 1H, J = 0.6 and 3.9), 7.02(d, 1H, J = 3.9), 8.12(s, 1H), 10.73(d, 1H, J = 6.9), 13.49(br, 1H) |

TABLE 79

[Structure: core scaffold with Q substituent]

| Comp. No. | Q | ¹H-NMR(CDCl₃/TMS) δ |
|---|---|---|
| X-81 | [pyridine-carboxylic acid] | DMSO-d6 1.00-1.82(m, 19H), 2.72(br, 2H), 3.00(br, 2H), 4.07(br, 2H), 8.28-8.38(m, 3H), 8.84(m, 1H), 12.96(s, 1H), 13.23(br, 1H) |
| X-82 | [neopentyl urea glycine] | DMSO-d6 1.00-1.93(m, 25H), 2.58-2.72(br, 2H), 2.90-3.02(br, 2H), 3.38(d, 2H, J = 6.0), 3.69(d, 2H, J = 6.0), 4.02(br, 2H), 6.15(t, 2H, J = 6.0), 8.12(s, 1H), 9.82(s, 1H), 12.45(br, 1H) |
| X-83 | [neopentyl urea benzoic acid] | DMSO-d6 1.00-1.93(m, 25H), 2.58-2.72(br, 2H), 2.90-3.02(br, 2H), 3.49(d, 2H, J = 6.0), 4.02(br, 2H), 6.24(t, 1H, J = 6.0), 7.31(t, 1H, J = 7.8), 7.46(dd, 1H, J = 1.2 and 7.8), 7.55(dd, 1H, J = 1.2 and 8.1), 8.03(s, 1H), 8.14(s, 1H), 8.72(s, 1H), 9.92(s, 1H), 12.79(br, 1H) |
| X-84 | [2-methylpropanoic acid] | DMSO-d6 1.00-1.93(m, 22H), 2.48-2.72(m, 3H), 2.90-3.02(br, 2H), 3.36-3.48(m, 2H), 4.03(br, 2H), 8.11(s, 1H), 9.99(t, 1H, J = 5.7), 12.40(br, 1H) |
| X-86 | [thiazole dimethyl acetic acid] | DMSO-d6 1.0-1.8(m, 19H), 1.47(s, 6H), 2.72(br-s, 2H), 3.01(brs, 2H), 4.07(br-s, 2H), 6.99(s, 1H), 8.29(s, 1H), 12.2(br-s, 1H), 13.4(br-s, 1H) |
| X-88 | [tetrahydropyran acetic acid] | 1.00-1.96(m, 23H), 2.29(d, 2H, J = 13.5), 2.63(t, 2H, J = 6.0), 2.93(t, 2H, J = 6.0), 3.03(s, 2H), 3.67-3.88(m, 4H), 4.00(bs, 1H), 8.25(s, 1H), 10.6(s, 1H) |
| X-90 | [thiazole acetic acid] | DMSO-d6 1.03-1.88(m, 19H), 2.72(t-like, 2H), 3.00(t-like, 2H), 3.82(d, 2H, J = 0.6), 4.07(brd, 2H), 7.31(t, 1H, J = 0.6), 8.29(s, 1H), 12.62(br, 1H), 13.39(s, 1H) |

TABLE 79-continued
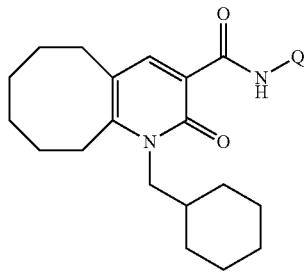
| Comp. No. | Q | ¹H-NMR(CDCl₃/TMS) δ |
|---|---|---|
| X-91 | 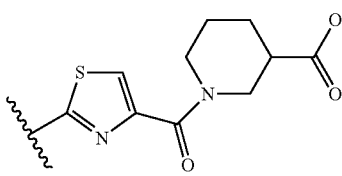 | 1.02-1.96(m, 23H), 2.12(br, 1H), 2.65-2.75 (brm, 3H), 2.96(br, 2H), 3.24(br, 1H), 3.00-4.80(brm, 4H), 7.55(s, 1H), 8.37(s, 1H), 13.41(brs, 1H) |
TABLE 80
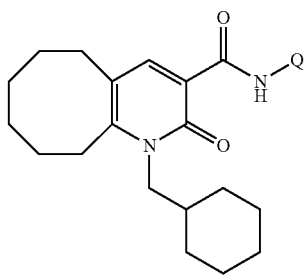
| Comp. No. | Q | ¹H-NMR(CDCl₃/TMS) δ |
|---|---|---|
| X-92 | 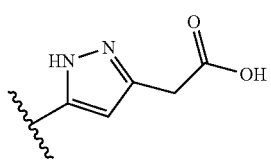 | DMSO-d6 1.00-1.80(m, 19H), 2.69(br, 2H), 2.97(br, 2H), 3.61(s, 2H), 4.04(br, 2H), 6,53(s, 1H), 8.23(s, 1H), 12.30(s, 1H), 12.39(br, 1H) |
| X-93 | 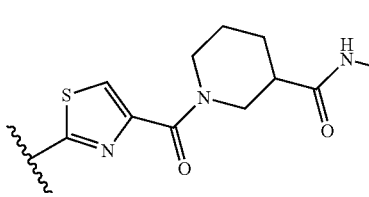 | 0.88(br, 3H), 1.04-4.20(brm, H), 2.69(t, 2H, J = 6.3), 2.97(t, 2H, J = 6.0), 6.50-7.20 (brm, 1H), 7.57(brs, 1H), 8.37(s, 1H), 13.36-13.68(brm, 1H) |
| X-95 | 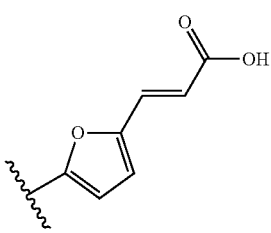 | DMSO-d6 1.04-1.90(m, 19H), 2.71(t-like, 2H), 3.00(t-like, 2H), 4.06(brd, 2H), 6.03(d, 1H, J = 15.6), 6.51(d, 1H, J = 3.6), 6.97(d, 1H, J = 3.6), 7.32(d, 1H, J = 15.6), 8.25(s, 1H), 12.19(br, 1H), 13.10(s, 1H) |

TABLE 80-continued
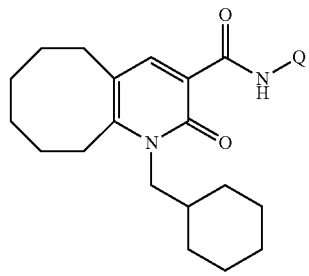
| Comp. No. | Q | $^1$H-NMR(CDCl$_3$/TMS) δ |
|---|---|---|
| X-97 | 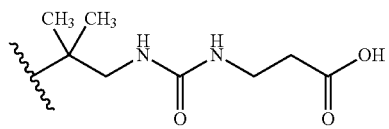 | DMSO-d6 1.00-1.93(m, 25H), 2.32(t, 2H, J = 6.6), 2.58-2.72(br, 2H), 2.90-3.02(br, 2H), 3.18(q, 2H, J = 6.0), 3.35(m, 2H), 3.97(br, 2H), 5.98(t, 2H, J = 6.0), 8.11(s, 1H), 9.80(s, 1H), 12.15(br, 1H) |
| X-98 | 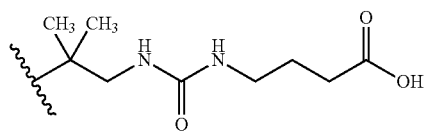 | DMSO-d6 1.00-1.93(m, 27H), 2.17(t, 2H, J = 7.5), 2.58-2.72(br, 2H), 2.90-3.02(m, 4H), 3.35(m, 2H), 3.98(br, 2H), 5.82(t, 1H, J = 6.0), 5.94(t, 1H, J = 6.0), 8.11(s, 1H), 9.82(s, 1H), 12.10(br, 1H) |
| X-99 | 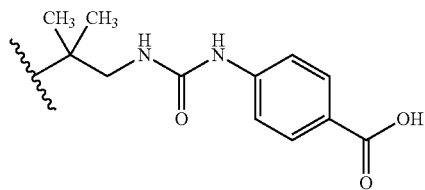 | DMSO-d6 1.00 1.93(m, 25H), 2.58-2.72(br, 2H), 2.90-3.02(br, 2H), 3.35(m, 2H), 3.98(br, 2H), 7.52(br, 1H), 7.80(d, 2H, J = 8.7), 8.09(d, 2H, J = 8.7), 8.20(br, 1H), 8.90(s, 1H), 10.62(br, 1H), 12.63(br, 1H) |
| X-104 | 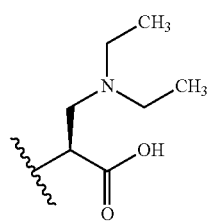 | DMSO-d6 1.06-1.84(m, 25H), 2.64(bs, 2H), 2.83-3.06(m, 6H), 3.17-3.26(m, 2H), 4.00(bs, 1H), 4.28-4.37(m, 1H), 8.10(s, 1H), 10.2(d, 1H, J = 5.4) two protons overlap with water |

TABLE 81

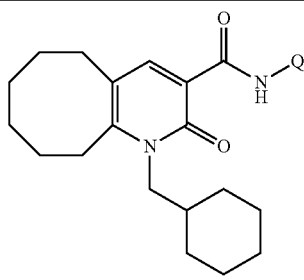

| Comp. No. | Q | ¹H-NMR(CDCl₃/TMS) δ |
|---|---|---|
| X-105 | pyridine-CH=CH-COOH substituent | DMSO-d6 1.08-1.86(m, 19H), 2.71(br, 2H), 3.00(br, 2H), 4.06(br, 2H), 6.59(d, 1H, J = 16.2), 7.59(d, 1H, J = 15.9), 8.21(dd, 1H, J = 2.1 and 9.0), 8.29(s, 1H), 8.31(d, 1H, J = 9.0), 8.61(d, 1H, J = 2.1), 12.82(s, 1H) |
| X-108 | 3-(2,2-dimethylpropyl)quinazoline-2,4-dione substituent | DMSO-d6 1.00-1.93(m, 25H), 2.58-2.72(br, 2H), 2.90-3.02(br, 2H), 3.35(m, 2H), 3.98(br, 2H), 4.37(s, 2H), 7.16(t, 2H, J = 7.5), 7.65(td, 1H, J = 1.5 and 7.5), 7.86(dd, 1H, J = 1.5 and 8.1), 8.08(s, 1H), 9.90(s, 1H), 11.37(br, 1H) |
| X-114 | 4-methylthiazol-2-yl | 1.00-1.90(m, 19H), 2.38(s, 3H), 2.60-2.70(m, 2H), 2.90-3.00(m, 2H), 3.90-4.20(br, 2H), 6.53(s, 1H), 8.34(s, 1H), 13.50(s, 1H) |
| X-119 | 4-(1-carboxycyclopentyl)thiazol-2-yl | DMSO-d6 1.0-1.8(m, 23H), 1.99-2.08(m, 2H), 2.24-2.29(m, 2H), 2.70(br-s, 2H), 2.98(br-s, 2H), 4.04(br-s, 2H), 6.99(s, 1H), 8.26(s, 1H), 13.4(br-s, 1H) |
| X-126 | 2-carboxycyclohex-1-enyl | DMSO-d6 1.00-1.82(m, 23H), 2.20-2.36(br, 2H), 2.54-2.70(br, 2H), 2.76-2.84(br, 2H), 2.84-3.00(br, 2H), 4.00(br, 2H), 8.09(s, 1H), 12.24(br, 1H), 12.60(s, 1H) |
| X-127 | pyridine-CH₂CH₂-COOH substituent | DMSO-d6 1.08-1.84(m, 19H), 2.56(t, 2H, J = 7.5), 2.70(t, 2H, J = 5.4), 2.80(t, 2H, J = 7.5), 2.98(br, 2H), 4.04(br, 2H), 7.70(dd, 1H, J = 2.4 and 8.4), 8.18(d, 1H, J = 8.7), 8.20(d, 1H, J = 2.4), 8.27(s, 1H), 12.22(br, 1H), 12.57(s, 1H) |
| X-130 | 4-oxo-4-phenyl-3-ylbutanoic acid substituent | DMSO-d6 1.0-1.8(m, 19H), 2.62-2.74(m, 3H), 2.93-3.02(m, 3H), 4.04(br-s, 2H), 5.72(q, 1H, J = 7.5 Hz), 7.49-7.63(m, 3H), 7.99(d, 1H, J = 7.5 Hz), 8.10(s, 1H), 10.49(d, 1H, J = 8.4Hz), 12.42(br-s, 1H) |

TABLE 82

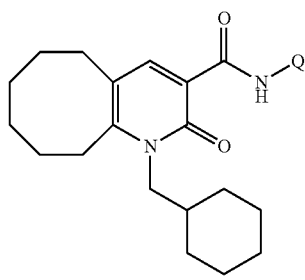

| Comp. No. | Q | $^1$H-NMR(CDCl$_3$/TMS) δ |
|---|---|---|
| X-134 | (2-substituted-4-phenylthiazol-5-yl)acetic acid | DMSO-d6 1.04-1.90(m, 19H), 2.68-2.78(m, 2H), 2.95-3.07(m, 2H), 3.88(s, 2H), 3.98-4.15(br, 2H), 7.35-7.51(m, 3H), 7.59-7.65(m, 2H), 8.31(s, 1H), 12.79(brs, 1H), 13.51(s, 1H) |
| X-137 | 2-propylbutanoic acid | DMSO-d6 0.79(t, 3H, J = 7.2), 0.98-1.72(m, 23H), 2.55(t, 2H, J = 5.7), 2.85(br, 2H), 3.90 (br, 2H), 4.34(m, 1H), 8.01(s, 1H), 10.10(d, 1H, J = 7.8) |
| X-148 | 2-isobutyl-3-methylbutanoic acid | DMSO-d6 0.90(dd, 6H, J = 6.0 and 10.5), 1.02-1.86(m, 22H), 2.60-2.69(m, 2H), 2.90-3.00(m, 2H), 3.80-4.15(br, 2H), 4.46(m, 1H), 8.12(s, 1H), 10.15(d, 1H, J = 7.8), 12.73(brs, 1H) |
| X-151 | (2-substituted-5-carboxythiazol-4-yl)acetic acid | DMSO-d6 1.00-1.90(m, 19H), 2.65-2.78(m, 2H), 2.93-3.07(m, 2H), 3.98(s, 2H), 4.00-4.20(br, 2H), 8.32(s, 1H), 12.20-13.40(m, 2H), 13.74(s, 1H) |
| X-154 | 4-isobutyl-hexanoic acid derivative | DMSO-d6 0.82-0.92(m, 6H), 1.02-1.86(m, 24H), 2.20(t, 2H, J = 7.2), 2.59-2.69(m, 2H), 2.89-2.99(m, 2H), 3.80-4.12(m, 3H), 8.11(s, 1H), 9.69(d, 1H, J = 9.0), 12.03(brs, 1H) |
| X-156 | 2-carbamoyl-succinic acid derivative | DMSO-d6 1.04-1.82(m, 19H), 2.64-2.67(m, 4H), 2.95(br, 2H), 3.96(br, 2H), 4.71(m, 1H), 7.13(s, 1H), 7.46(s, 1H), 8.11(s, 1H), 10.23(d, 1H, J = 8.1) |

TABLE 82-continued

[Structure: cyclooctane-fused pyridinone with cyclohexylmethyl N-substituent and C(=O)-NH-Q amide]

| Comp. No. | Q | $^1$H-NMR(CDCl$_3$/TMS) δ |
|---|---|---|
| X-159 | [5-chloro-thiazol-2-yl with 4-CH$_2$COOH] | DMSO-d6 1.05-1.90(m, 19H), 2.65-2.80(m, 2H), 2.90-3.07(m, 2H), 3.61(s, 2H), 3.95-4.15(br, 2H), 8.29(s, 1H), 12.20-13.00(br, 1H), 13.62(s, 1H) |

TABLE 83

[Structure: cyclooctane-fused pyridinone with cyclohexylmethyl N-substituent and C(=O)-NH-Q amide]

| Comp No. | Q | $^1$H-NMR(CDCl$_3$/TMS) δ |
|---|---|---|
| X-160 | [5-bromo-thiazol-2-yl with 4-CH$_2$COOH] | DMSO-d6 1.00-1.90(m, 19H), 2.65-2.77(m, 2H), 2.93-3.07(m, 2H), 3.61(s, 2H), 3.95-4.15(br, 2H), 8.29(s, 1H), 12.20-13.00(br, 1H), 13.64(s, 1H) |
| X-166 | [1-(4-(methoxycarbonyl)phenyl)-1-hydroxyethyl linker] | 1.00-1.89(m, 19H), 2.67(t, 2H, J = 6.0 Hz), 2.93 (t, 2H, J = 6.0 Hz), 3.69(m, 2H), 3.91(s,3H), 3.91-4.02(br-s, 2H), 5.04(t, 1H, J = 6.0 Hz), 7.49 (d, 2H, J = 8.1 Hz), 8.01(d, 2H, J = 8.1 Hz), 8.36 (br-s, 1H), 10.46(br-s, 1H) |
| X-167 | [1-(4-carboxyphenyl)-1-hydroxyethyl linker] | DMSO-d6 1.0-1.8(m, 19H), 2.62(brs, 2H), 2.92 (br-s, 2H), 3.56(m, 1H), 4.00(br-s, 2H), 4.77 (br-s, 1H), 5.75(br-s, 1H), 7.48(d, 2H, J = 8.1 Hz), 7.87(d, 2H, J = 8.1 Hz), 8.08(s, 1H), 10.1 (br-s, 1H) |

TABLE 83-continued
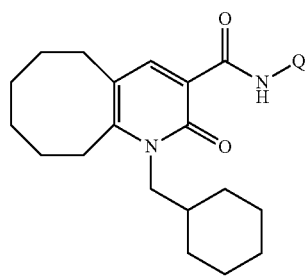
| Comp No. | Q | $^1$H-NMR(CDCl$_3$/TMS) δ |
|---|---|---|
| X-177 | (5-phenyl-thiazol-2-yl)-CH$_2$COOH group | DMSO-d6 1.04-1.90(m, 19H), 2.65-2.80(m, 2H), 2.95-3.05(m, 2H), 3.61(s, 2H), 4.00-4.20(br, 2H), 7.30-7.55(m, 5H), 8.30(s, 1H), 13.54(s, 1H) |
| X-181 | (pyrimidin-2-yl)-CH=CH-COOH group | DMSO-d6 1.08-1.86(m, 19H), 2.72(t, 2H, J = 5.2), 3.00(br, 2H), 4.05(br, 2H), 6.74(d, 1H, J = 15.9), 7.57(d, 1H, J = 16.2), 8.26(s, 1H), 9.03 (s, 2H), 12.45(br, 1H), 13.05(s, 1H) |
| X-182 | CH(COOH)(CH$_2$)$_3$CH$_3$ | DMSO-d6 0.86(t, 3H, J = 6.9), 1.06-1.86(m, 25H), 2.65(t, 2H, J = 5.7), 2.95(br, 2H), 3.99(br, 2H), 4.43(m, 1H), 8.11(s, 1H), 10.21(d, 1H, J = 7.5), 12.78(br, 1H) |
| X-183 | (pyrimidin-2-yl)-CH$_2$CH$_2$-COOH group | DMSO-d6 1.08-1.86(m, 19 H), 2.61(t, 2H, J = 7.5), 2.71(br, 2H), 2.79(t, 2H, J = 7.5), 2.99(br, 2H), 4.05(br, 2H), 8.24(s, 1H), 8.58(s, 2H), 12.27(br, 1H), 12.78(s, 1H) |

TABLE 84

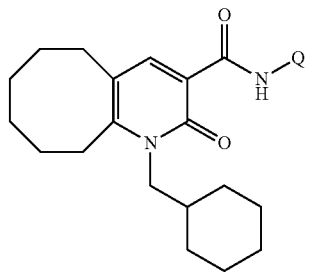

| Comp. No. | Q | ¹H-NMR(CDCl₃/TMS) δ |
|---|---|---|
| X-189 | thiazole with ≡CH and CH₂COOH substituents | DMSO-d6 1.10-1.90(m, 19H), 2.60-2.80(m, 2H), 2.90-3.10(m, 2H), 3.67(s, 2H), 3.95-4.20(br, 2H), 4.74(s, 1H), 8.30(s, 1H), 12.58 (brs, 1H), 13.7l(s, 1H) |
| X-191 | thiazole with CH₂C(O)CH₃ and thiophene substituents | DMSO-d6 1.02-1.90(m, 19H), 2.66-2.78(m, 2H), 2.95-3.07(m, 2H), 3.73(s, 2H), 3.95-4.20(br, 2H), 7.16(dd, 1H, J = 3.6 and 5.1), 7.24(dd, 1H, J = 1.2 and 3.6), 7.64(dd, 1H, J = 0.9 and 5.1), 8.29(s, 1H), 12.56(br s, 1H), 13.58(s. 1H) |
| X-192 | thiazole with ethyl ester substituent | 1.10-1.8(m, 22H), 2.65(t, 2H), 2.93(t, 2H), 4.00(brs, 2H), 4.42(q, 2H, J = 7.2), 4.97(d, 2H, J = 6.0), 8.10(s, 1H), 8.33(s, 1H), 10.69(t, 1H, J = 6.0 Hz) |
| X-195 | thiazole with CH₂COOH and 4-CF₃-phenyl substituents | DMSO-d6 1.04-1.90(m, 19H), 2.67-2.79(m, 2H), 2.96-3.08(m, 2H), 3.69(s, 2H), 3.95-4.20(br, 2H), 7.73(d, 2H, J = 8.1), 7.84(d, 2H, J = 8.4), 8.30(s, 1H), 12.64(br s, 1H), 13.62(s, 1H) |
| X-200 | thiazole with carboxylic acid | DMSO-d6 1.10-1.8(19H, m), 2.66(brs, 2H), 2.96(brs, 2H), 3..33(brs, 2H), 4.00(brs, 2H), 4.81(d, 2H, J = 6.3), 8.17(s, 1H), 8.33(s, 1H), 10.53(t, 1H, J = 6.0), 12.98(brs, 1H) |
| X-201 | CH₂C(O)-phenyl-COOCH₃ | DMSO-d6 1.11-1.7(19H, m), 2.62(brs, 2H), 2.92(brs, 2H), 3.61(s, 3H), 4.97(d, 2H, J = 6.0), 7.48(d, 2H, J = 8.1), 7.87(d, 2H, J = 8.4), 8.08(s, 1H), 10.09(t, 1H, J = 6.0) |

TABLE 84-continued

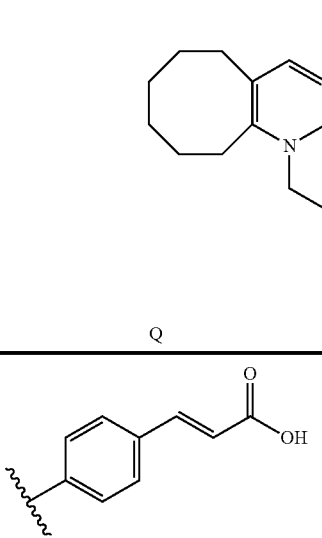

| Comp. No. | Q | $^1$H-NMR(CDCl$_3$/TMS) δ |
|---|---|---|
| X-212 | ![structure: 4-(carboxyvinyl)phenyl] | DMSO-d6 1.04-1.89(m, 19H), 2.66-2.76(m, 2H), 2.95-3.04(m, 2H), 3.95-4.20(br, 2H), 6.44(d, 1H, J = 16.2), 7.55(d, 1H, J = 16.2), 7.68(d, 2H, J = 8.7), 7.76(d, 2H, J = 8.7), 8.27(s, 1H), 12.25(br, 1H), 12.44(s, 1H) |

TABLE 85

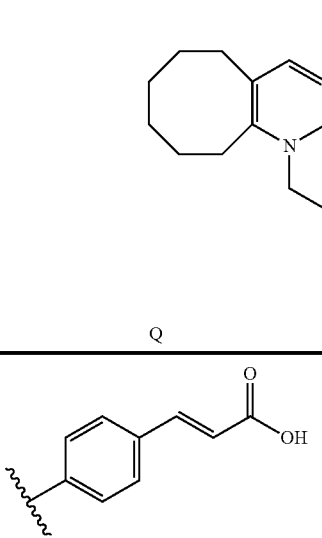

| Comp. No. | Q | $^1$H-NMR(CDCl$_3$/TMS) δ |
|---|---|---|
| X-220 | ![structure: 4-(carboxymethoxy)phenyl] | DMSO-d6 1.02-1.90(m, 19H), 2.64-2.75(m, 2H), 2.93-3.03(m, 2H), 3.90-4.20(br, 2H), 4.65(s, 2H), 6.90(d, 2H, J = 9.0), 7.61(d, 2H, J = 9.0), 8.24(s, 1H), 12.12(s, 1H), 12.98(brs, 1H) |
| X-228 | ![structure: 5-methyl-thiazol-4-yl-acetic acid] | DMSO-d6 1.00-1.90(m, 19H), 2.29(s, 3H), 2.65-2.77(m, 2H), 2.92-3.05(m, 2H), 3.55(s, 2H), 3.95-4.15(br, 2H), 8.27(s, 1H), 12.36(br s, 1H), 13.35(s, 1H) |
| X-229 | ![structure: 2-(trifluoromethyl)propanoic acid] | DMSO-d6 1.02-1.86(m, 19H), 2.62-2.75(m, 2H), 2.92-3.05(m, 2H), 3.85-4.15(br, 2H), 5.43(m, 1H), 8.18(s, 1H), 10.83(d, 1H, J = 9.0), 14.22(brs, 1H) |

TABLE 85-continued
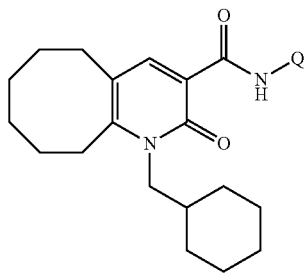
| Comp. No. | Q | $^1$H-NMR(CDCl$_3$/TMS) δ |
|---|---|---|
| X-240 | 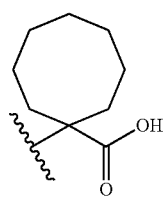 | DMSO-d6 1.02-1.86(m, 29H), 1.93-2.17(m, 4H), 2.58-2.68(m, 2H), 2.90-3.01(m, 2H), 3.85-4.15(br, 2H), 8.06(s, 1H), 10.13(s, 1H), 12.19(brs, 1H) |
| XI-002 | 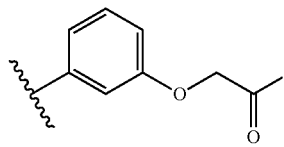 | DMSO-d6 1.02-1.90(m, 19H), 2.64-2.75(m, 2H), 2.93-3.05(m, 2H), 3.85-4.20(br, 2H), 4.68(s, 2H), 6.65(m, 1H), 7.14-7.29(m, 2H), 7.45(m, 1H), 8.26(s, 1H), 12.26(s, 1H), 13.01(brs, 1H) |
| XI-010 | 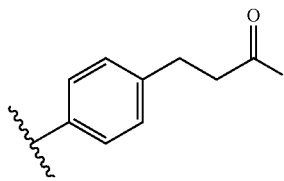 | DMS0-d6 1.02-1.90(m, 19H), 2.52(t, 2H, J = 7.5), 2.65-2.74(m, 2H), 2.80(t, 2H, J = 7.5), 2.94-3.03(m, 2H), 3.85-4.20(br, 2H), 7.20(d, 2H, J = 8.4), 7.60(d, 2H, J = 8.4), 8.25(s, 1H), 12.11(brs, 1H), 12.20(s, 1H) |
| XI-020 | 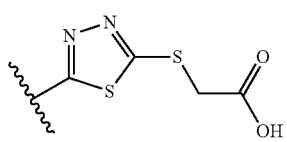 | DMSO-d6 1.04-1.90(m, 19H), 2.67-2.78(m, 2H), 2.97-3.08(m, 2H), 4.00-4.20(m, 2H), 4.13(s, 2H), 8.30(s, 1H), 13.00(br s, 1H), 13.82(s, 1H) |

TABLE 86

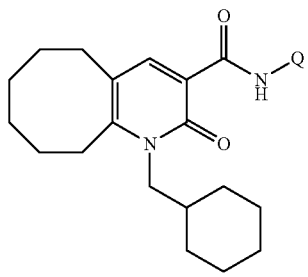

| Comp. No. | Q | ¹H-NMR(CDCl₃/TMS) δ |
|---|---|---|
| XI-021 | (5-pyridyl-2-oxy)CH₂COOH | DMSO-d6 1.02 1.92(m, 19H), 2.65-2.75(m, 2H), 2.93-3.05(m, 2H), 3.90-4.20(br, 2H), 4.80(s, 2H), 6.91(d, 1H, J = 8.7), 8.06(dd, 1H, J = 2.7 and 8.7), 8.26(s, 1H), 8.44(d, 1H, J = 2.7), 12.11(s, 1H), 12.82(brs, 1H) |
| XI-032 | 1-carboxy-cyclodecyl | DMSO-d6 1.00-1.96(m, 35H), 2.04-2.20(m, 2H), 2.58-2.70(m, 2H), 2.89-3.00(m, 2H), 3.97(br, 2H), 8.07(s, 1H), 10.03(s, 1H), 12.21(br, 1H) |
| XI-036 | (1-cyclopentyl)CH₂COOH | DMSO-d6 1.00-1.84(m, 25H), 2.04-2.17(m, 2H), 2.60-2.68(m, 2H), 2.87(s, 2H), 2.95-3.05(m, 2H), 3.95(br, 2H), 8.09(s, 1H), 9.90(s, 1H), 11.92(br, 1H) |
| XI-040 | (1-cyclobutyl)CH₂COOH | 1.00-2.08(m, 23H), 2.23-2.45(m, 4H), 2.60-2.68(m, 2H), 2.90-2.97(m, 2H), 3.09(s, 2H), 4.01(br, 2H), 8.28(s, 1H), 10.77(s, 1H) |
| XI-043 | CH(CH₂OCH₃)COOH | DMSO-d6 1.00-1.97(m, 20H), 2.64-2.67(m, 2H), 2.92-3.02(m, 2H), 3.27(s, 3H), 3.61(dd, 1H, J = 3.9 and 9.9), 3.77(dd, 1H, J = 3.9 and 9.9), 4.00(br, 2H), 4.61(m, 1H), 8.13(s, 1H), 10.31(d, 1H, J = 7.8) |
| XI-045 | (6-pyridyl-3-yl)CH₂COOH | DMSO-d6 1.03-1.88(m, 19H), 2.65-2.75(m, 2H), 2.93-3.04(m, 2H), 3.60(s, 2H), 3.94-4.15(br, 2H), 7.72(dd, 1H, J = 1.8 and 8.7), 8.18-8.24(m, 2H), 8.28(s, 1H), 12.45(brs, 1H), 12.61(s, 1H) |
| XI-050 | CH(CH₂OCH₃)CH₂CH₂COOH | DMSO-d6 1.01-1.92(m, 21H), 2.20-2.28(m, 2H), 2.18-2.26(m, 2H), 2.60-2.69(m, 2H), 2.90-2.99(m, 2H), 3.27(s, 3H), 3.30-3.45(m, 2H), 3.84-4.15(br, 2H), 4.12(m, 1H), 8.12(s, 1H), 9.86(d, 1H, J = 8.7), 12.07(brs, 1H) |

TABLE 87

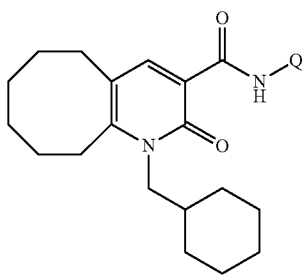

| Comp. No. | Q | ¹H-NMR(CDCl₃/TMS) δ |
|---|---|---|
| XI-051 | (4-carboxy-tetrahydropyran-4-yl)methyl | DMSO-d6 1.00-1.96(m, 25H), 2.60-2.68(m, 2H), 2.88-3.02(m, 2H), 3.46-3.48(m, 2H), 3.69-3.78(m, 2H), 3.97(br, 2H), 8.11(s, 1H), 10.06(t, 1H, J = 5.7), 12.57(br, 1H) |
| XI-056 | 2-cyano-1-carboxyethyl | DMSO-d6 1.02-1.88(m, 19H), 2.61-2.71(m, 2H), 2.91-3.02(m, 2H), 3.06-3.22(m, 2H), 3.85-4.15(br, 2H), 4.78(q, 1H, J = 6.0), 8.14(s, 1H), 10.51(d, 1H, J = 7.2), 13.32(brs, 1H) |
| XI-059 | (5-carboxymethyl-indol-1-yl)methyl | DMSO-d6 1.14-1.90(m, 19H), 2.65-2.80(m, 2H), 2.95-3.05(m, 2H), 3.90-4.20(m, 2H), 4.99(s, 2H), 6.43(d, 1H, 3.0), 7.29(dd, 1H, J = 2.1, 8.7), 7.33(d, 1H, J = 3.0), 7.35(d, 1H, J = 8.7), 8.06(s, 1H), 8.26(s, 1H), 12.19(s, 1H), 12.94(br s, 1H) |
| XI-071 | (4-carboxymethyl-imidazol-1-yl)methyl | DMSO-d6 1.04 1.90(m, 19H), 2.60-2.75(m, 2H), 2.90-3.05(m, 2H), 3.90-4.18(m, 2H), 4.85(s, 2H), 7.36(d, 1H, J = 1.5), 7.46(d, 1H, J = 1.2), 8.20(s, 1H), 12.13(s, 1H), 13.05(br s, 1H) |
| XI-074 | (5-carboxymethyl-1,3,4-thiadiazol-2-yl) | DMSO-d6 1.10-1.89(m, 19H), 2.73(br s, 2H), 3.02(br s, 2H), 4.08(br s, 2H), 4.13(s, 2H), 8.32(s, 1H), 13.07(br s, 1H), 13.75(s, 1H) |
| XI-076 | 4-(2,2-dimethylpropyl)-4-carboxybutyl | DMSO-d6 0.87(s, 9H), 1.00-1.82(m, 23H), 2.18(t, 2H, J = 7.5), 2.60-2.68(m, 2H), 2.87-2.98(m, 2H), 3.80-4.15(br, 2H), 4.08(m, 1H), 8.11(s, 1H), 9.79(d, 1H, J = 9.0), 12.01(brs, 1H) |

TABLE 88

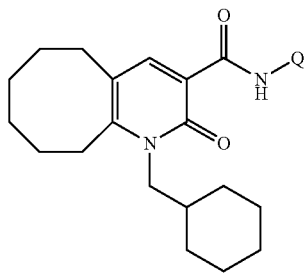

| Comp. No. | Q | ¹H-NMR(CDCl₃/TMS) δ |
|---|---|---|
| XI-080 | cyclopentane with CO₂H | DMSO-d6 1.00-1.86(m, 19H), 2.59(d, 2H, J = 15.9), 2.60-2.68(m, 2H),, 2.90-3.00(m, 2H), 3.02(d, 2H, J = 15.9), 3.80-4.10(br, 2H), 5.68(s, 2H), 8.08(s, 1H), 10.31(s, 1H), 12.42(brs, 1H) |
| XI-084 | isobutyl-CH(CO₂H)- | DMSO-d6 0.85(d, 6H, J = 6.6), 1.00- 1.8(m, 24H), 2.60-2.70(m, 2H), 2.95-3.05(m, 2H), 3.85-4.10(br, 2H), 4.43(dd, 1H, J = 7.2 and 12.9), 8.11(s, 1H), 10.22(d, 1H, J = 7.8), 12.81(brs, 1H) |
| XI-086 | 2-(carboxymethyl)phenyl | DMSO-d6 1.04-1.84(m, 19H), 2.63-2.75(m, 2H), 2.90-3.05(m, 2H), 3.67(s, 2H), 3.95-4.20(m, 2H), 7.09(m, 1H), 7.23-7.32(m, 1H), 8.06(d, 1H, J = 8.1), 8.24(s, 1H), 12.08(s, 1H), 12.37(br s, 1H) |
| XI-088 | 4-(carboxymethyl)-2-CF₃-phenyl | DMSO-d6 1.05-1.84(m, 19H), 2.63-2.77(m, 2H), 2.90-3.05(m, 2H), 3.69(s, 2H), 3.90-4.20(m, 2H), 7.56(d, 1H, J = 9.0), 7.63(m, 1H), 8.20(d, 1H, J = 8.7), 8.27(s, 1H), 12.47(s, 1H) |
| XI-090 | N-(carboxymethyl)pyrrol-3-yl | DMSO-d6 1.06-1.90(m, 19H), 2.60-2.75(m, 2H), 2.90-3.05(m, 2H), 3.90-4.20(m, 2H), 4.68(s, 2H), 6.06(m, 1H), 6.23(m, 1H), 7.23(m, 1H),8.18(s, 1H), 11.81(8, 1H), 12.80(br s, 1H) |
| XI-092 | 4-(carboxymethoxy)-2-CF₃-phenyl | DMSO-d6 1.05-1.90(m, 19H), 2.67 2.75(m, 2H), 2.92-3.04(m, 2H), 3.90-4.20(m, 2H), 4.80(s, 2H), 7.21(d, 1H, J = 3.0), 7.26(dd, 1H, J = 2.4, 9.0), 8.06(d, 1H, J = 9.0), 8.25(s, 1H), 12.27(s, 1H), 13.10(br, 1H) |

TABLE 89

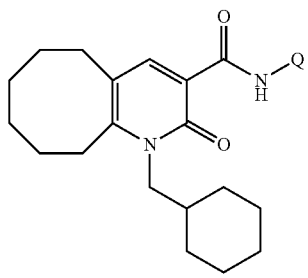

| Comp. No. | Q | $^1$H-NMR(CDCl$_3$/TMS) δ |
|---|---|---|
| XI-093 | (4-(carboxymethoxy)-3-fluorophenyl) | DMSO-d6 1.05-1.90(m, 19H), 2.63-2.76(m, 2H), 2.90-3.05(m, 2H), 3.90-4.20(m, 2H), 4.70(s, 2H), 6.79(m, 1H), 6.97(dd, 1H, J = 3.0, 12.9), 8.25(s, 1H), 8.28(m, 1H), 12.30(s, 1H), 13.06(br s, 1H) |
| XI-097 | (4-(carboxymethyl)-3-fluorophenyl) | DMSO-d6 1.13-1.81(m, 18H), 2.09(s, 1H), 2.51(br s, 2H), 2.99(br s, 2H), 3.58(s, 2H), 4.08(br s, 2H), 7.28-7.32(m, 2H), 7.78(d, 1H, J = 12.9), 8.26(s, 1H), 12.37(br s, 2H) |
| XI-101 | (4-(carboxymethyl)-2-trifluoromethylphenyl) | DMSO-d6 1.00-1.94(m, 19H), 2.65-2.75(m, 2H), 2.92-3.05(m, 2H), 3.74(s, 2H), 3.90-4.20(m, 2H), 7.47(d, 1H, J = 8.4), 7.79(dd, 1H, J = 1.8, 8.1), 8.24(d, 1H, J = 1.8), 8.27(s, 1H), 12.46(s, 1H) |
| XI-102 | (4-methyl-5-(carboxymethyl)thiazol-2-yl) | DMSO-d6 1.00-1.90(m, 19H), 2.18(s, 3H), 2.65-2.78(m, 2H), 2.95-3.05(m, 2H), 3.71(s, 2H), 3.95-4.20(m, 2H), 8.27(s, 1H), 12.60(br s, 1H), 13.35(s, 1H) |
| XI-108 | (3-fluoro-3-methyl-2-carboxybutyl) | 1.1-1.6(m, 18H), 1.44(dd, 6H, J = 10.8, 21.0), 2.26(ddd, 1H, J = 9.3, 24.6, 27.9), 2.49(ddd, 2H, J = 4.2, 15.3, 21.6), 2.65(t, 2H, J = 5.4), 2.93(t, 2H, J = 6.3), 3.7-4.3(br, 2H), 4.74(ddd, 1H, J = 4.2, 6.0, 9.3), 8.28(s, 1H), 10.77(d, 1H, J = 5.1) |
| XI-110 | (4,4-dimethyl-1-(carboxymethyl)cyclohexyl) | DMSO-d6 0.83(s, 3H), 0.89(s, 3H), 1.00-1.78(m, 25H), 2.04-2.14(m, 2H), 2.60-2.68(q, 2H, J = 7.5), 2.81(s, 2H), 2.78-2.84(m, 2H), 4.00(br, 2H), 8.08(s, 1H), 9.98(s, 1H) |

TABLE 90

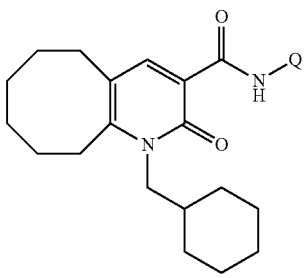

| Comp. No. | Q | $^1$H-NMR(CDCl$_3$/TMS) δ |
|---|---|---|
| XI-117 | 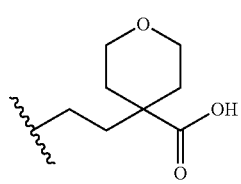 | DMSO-d6 1.0-2.0(m, 27H), 2.50-4.15(m, 10H), 8.10(s, 1H), 9.83(t, 1H, J = 5.7) |
| XI-120 | 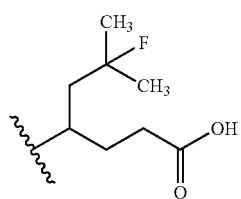 | DMSO-d6 1.0-1.8(m, 20H), 1.31(dd, 6H, J = 5.7, 21.6), 1.85(dd, 2H, J = 6.3, 20.4), 2.20(t, 2H, J = 8.1), 2.64 (brt, 2H), 2.94(brt, 2H), 3.97(br, 2H), 4.17(br, 2H9, 8.11(s, 1H), 9.82 (d, 1H, = 8.7) |
| XI-129 | 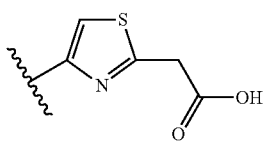 | DMSO-d6 1.02-1.90(m, 19H), 2.65-2.78(m, 2H), 2.90-3.0(m, 2H), 4.03(s, 2H), 3.90-4.20(m, 2H), 7.61(s, 1H), 8.26(s, 1H), 12.79(s, 1H), 12.86(br s, 1H) |

TABLE 91

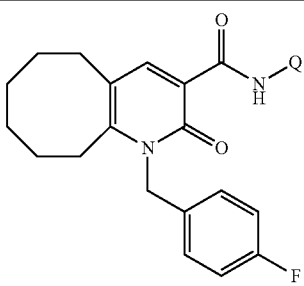

| Comp. No. | Q | $^1$H-NMR(CDCl$_3$/TMS) δ |
|---|---|---|
| I-253 | 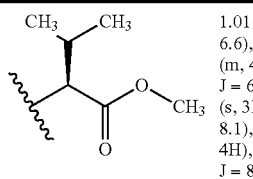 | 1.01(d, 3H, J = 6.6), 1.02(d, 3H, J = 6.6), 1.34-1.56(m, 4H), 1.58-1.78 (m, 4H), 2.27(m, 1H), 2.62(t, 2H, J = 6.0), 2.78(t, 2H, J = 6.0), 3.75 (s, 3H), 4.66(dd, 1H, J = 5.1 and 8.1), 5.44(br, 2H), 6.98-7.10(m, 4H), 8.37(s, 1H), 10.32(d, 1H, J = 8.1) |

TABLE 91-continued

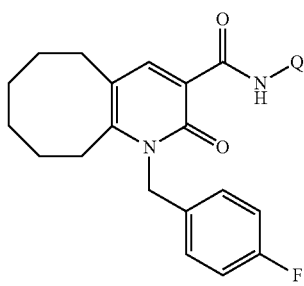

| Comp. No. | Q | $^1$H-NMR(CDCl$_3$/TMS) δ |
|---|---|---|
| I-254 | 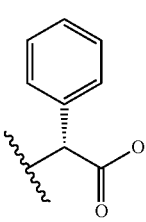 | 1.34-1.54(m, 4H), 1.54-1.80(m, 4H), 2.61(t, 2H, J = 6.0), 2.78(t, 2H, J = 6.0), 3.75(s, 3H), 5.42(br, 2H), 5.72(d, 1H, J = 6.6), 6.92-7.12(m, 4H), 7.26-7.40(m, 3H), 7.48(d, 2H, J = 6.6), 8.36(s, 1H), 10.75(d, 1H, J = 6.9) |
| I-255 | 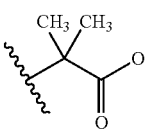 | 1.34-1.54(m, 4H), 1.61(s, 6H), 1.62-1.78(m, 4H), 2.62(t, 2H, J = 6.0), 2.78(t, 2H, J = 6.0), 3.75(s, 3H), 5.42(br, 2H), 6.94-7.10(m, 4H), 8.37(s, 1H), 10.20(br s, 1H) |
| I-262 | 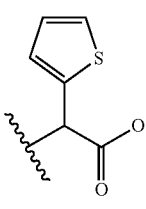 | 1.32-1.75(m, 8H), 2.63(brt, 2H), 2.79(brt, 2H), 3.79(s, 3H), 5.43(br, 2H), 6.00(d, 1H, J = 6.3), 6.95-7.08 (m, 5H), 7.15(m, 1H), 7.25(dd, 1H, J = 0.9 and 3.6), 8.37(s, 1H), 10.73 (d, 1H, J = 6.3) |
| I-263 | 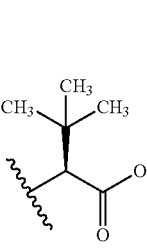 | 1.08(s, 9H), 1.32-1.74(m, 8H), 2.62(brt, 2H), 2.77(brt, 2H), 3.74(s, 3H), 4.54(d, 1H, J = 8.1), 5.45(br, 2H), 6.98-7.10(m, 4H), 8.36(s, 1H), 10.47(d, 1H, J = 8.1) |
| I-270 | 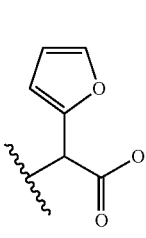 | 1.33-1.76(m, 8H), 2.63(brt, 2H), 2.79(brt, 2H), 3.79(s, 3H), 5.43(br, 2H), 5.92(d, 1H, J = 7.2), 6.33(dd, 1H, J = 1.8 and 3.3), 6.41(d, 1H, J = 3.3), 6.98-7.09(m, 4H), 7.38(d, 1H, J = 1.8), 8.37(s, 1H), 10.68(d, 1H, J = 7.2) |

TABLE 92

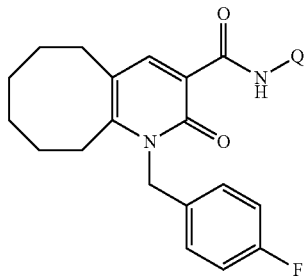

| Comp. No. | Q | ¹H-NMR(CDCl₃/TMS) δ |
|---|---|---|
| I-299 | cyclohexyl-C(=O)OCH₃ | 1.22-1.74(m, 14H), 1.82-1.92(m, 2H), 2.13-2.24(brm, 2H), 2.61(t, 2H, J = 6.0), 2.78(t, 2H, J = 6.3), 3.74(s, 3H), 5.43(br, 2H), 6.99-7.09(m, 4H), 8.35(s, 1H), 10.26 (brs, 1H) |
| I-522 | CH₃ CH₃ C(CH₃)₂CH(COOH) | DMSO-d6 1.34-1.50(m, 4H), 1.47 (s, 6H), 1.50-1.70(m, 4H), 2.66(t, 2H, J = 6.0), 2.83(t, 2H, J = 6.0), 5.42(br, 2H), 7.11-7.24(m, 4H), 8.18(s, 1H), 10.14(br s, 1H), 12.44 (br, 1H) |
| I-528 | thiophen-2-yl-CH-COOH | DMSO-d6 1.24-1.68(m, 8H), 2.67 (brm, 2H), 2.83(brm, 2H), 5.43 (brs, 2H), 5.76(d, 1H, J = 7.2), 7.01 (dd, 1H, J = 3.6 and 5.1), 7.10-7.21 (m, 5H), 7.49(dd, 1H, J = 1.2 and 5.1), 8.22(s, 1H), 10.62(d, 1H, J = 7.2), 13.32(br, 1H) |
| I-529 | CH₃ CH₃ CH₃ (tBu)CH-COOH | DMSO-d6 0.98(s, 9H), 1.22-1.70 (m, 8H), 2.67(brm, 2H), 2.82(brm, 2H), 4.26(d, 1H, J = 8.4), 5.44(brm, 2H), 7.12-7.22(m, 4H), 8.22(s, 1H), 10.32(d, 1H, J = 8.4), 12.69(br, 1H) |

TABLE 92-continued

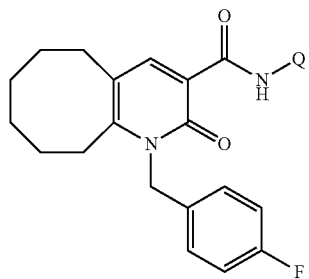

| Comp. No. | Q | ¹H-NMR(CDCl₃/TMS) δ |
|---|---|---|
| I-535 | furan-2-yl-CH-COOH | DMSO-d6 1.22-1.68(m, 8H), 2.67 (brt, 2H), 2.84(brt, 2H), 5.42(brs, 2H), 5.67(d, 1H, J = 7.5), 6.45 (d-like, 2H), 7.11-7.21(m, 4H), 7.64(t-like, 1H), 8.23(s, 1H), 10.56 (d, 1H, J = 7.5), 13.28(br, 1H) |
| I-564 | cyclohexyl-COOH | DMSO-d6 1.15-1.18(m, 16H), 1.96-2.08(brm, 2H), 2.66(brt, 2H), 2.83(brt, 2H), 5.44(brs, 2H), 7.11-7.22(m, 4H), 8.18(s, 1H), 10.16(s, 1H), 12.20(br, 1H) |
| II-067 | CF₃-CH-CH₂-COOH | 1.42-1.46(m, 4H), 1.69(bs, 4H), 2.65-2.74(m, 6H), 5.33-5.39(m, 3H), 6.99-7.26(m, 4H), 8.41(s, 1H), 10.47(d, 1H, J = 9.6) |

TABLE 93

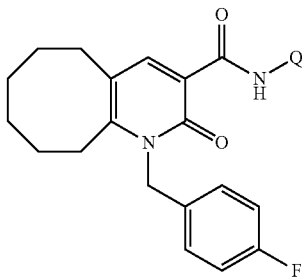

| Comp. No. | Q | ¹H-NMR(CDCl₃/TMS) δ |
|---|---|---|
| II-078 | (CH₃)₂CH-CH-CH₂-COOH | 0.92(d, 6H, J = 6.6), 1.24-1.78(m, 8H), 2.59-2.82(m, 6H), 4.40(m, 1H), 5.41(br, 2H), 7.02-7.04(m, 4H), 8.39(s, 1H), 10.19 (d, 1H, J = 6.6) |

TABLE 93-continued

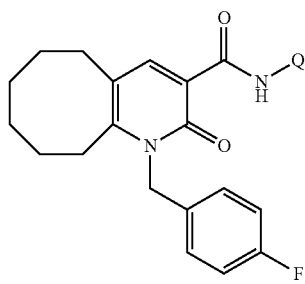

| Comp. No. | Q | $^1$H-NMR(CDCl$_3$/TMS) δ |
|---|---|---|
| II-079 | (CH$_3$-CH=CH-CH(-)-CH$_2$-COOH) | 1.4-1.45(m, 4H), 1.67-1.69(m, 7H), 2.63-2.83(m, 6H), 4.93(m, 1H), 5.41(br, 2H), 5.58(dd, 1H, J = 4.8, 15.3), 7.01-7.05(m, 4H), 8.39(s, 1H), 10.25 (d, 1H, J = 7.8) |
| II-080 | (1-cyclohexyl-CH$_2$-COOH) | 1.32-1.71(m, 16H), 2.17-2.19(m, 2H), 2.63-2.67(m, 2H), 2.78-2.82(m, 2H), 5.44(br, 2H), 7.02-7.09(m, 4H), 8.38(s, 1H), 10.51(s, 1H) |
| X-10 | (bis-cyclohexyl linker with CH$_2$COOH) | 1.24-1.71(m, 18H), 2.33(s, 2H), 2.67(t, 2H, J = 6.0), 2.84(t, 2H, J = 6.0), 3.43(d, 2H, J = 6.9), 5.43(br, 2H), 7.03-7.05(m, 4H), 8.42(s, 1H), 10.53(t, 1H, J = 6.9) |
| X-85 | (thiazol-4-yl-CH$_2$-COOH) | DMSO-d6 1.20-1.50(m, 4H), 1.50-1.74(m, 4H), 2.65-2.80(m, 2H), 2.83-2.97(m, 2H), 3.60(s, 2H), 5.49(br s, 2H), 7.03(s, 1H), 7.10-7.30(m, 4H), 8.38(s, 1H), 12.20-12.50(br, 1H), 13.31(s, 1H) |
| X-87 | (1,2,4-thiadiazol-3-yl-CH$_2$-COOH) | DMSO-d6 1.30-1.43(m, 4H), 1.62-1.63(m, 4H), 2.73(br-s, 2H), 2.92(br-s, 2H), 3.80(s, 2H), 5.50(br-s, 2H), 7.13-7.30(m, 4H), 8.41(s, 1H), 12.6(br-s, 1H), 13.66(br-s, 1H) |
| X-89 | (dipropyl quaternary C with CH$_2$COOH) | 0.92(t, 6H, J = 7.2), 1.20-1.91(m, 18H), 2.64(t, 2H, J = 6.0), 2.80(t, 2H, J = 6.0), 3.01(s, 2H), 5.42(bs, 1H), 6.98-7.06(m, 4H), 8.37(s, 1H), 10.4(s, 1H) |
| X-96 | (thiazol-5-yl-CH$_2$-COOH) | DMSO-d6 1.26-1.72(m, 8H), 2.73(t-like, 2H), 2.90(t-like, 2H), 3.82(d, 2H, J = 0.6), 5.49(brs, 2H), 7.14-7.24(m, 4H), 7.30(t, 1H, J = 0.6), 8.38(s, 1H), 12.63(br, 1H), 13.24(s, 1H) |

TABLE 94

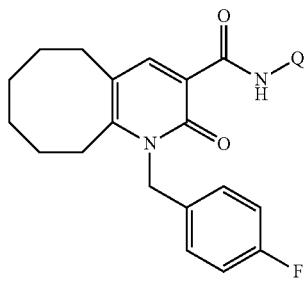

| Comp. No. | Q | ¹H-NMR(CDCl₃/TMS) δ |
|---|---|---|
| X-100 | tetrahydropyran-4-yl-CH₂-COOH | 1.36-1.76(m, 10H), 1.82-1.94(m, 2H), 2.27(d, 2H, J = 14), 2.64(t, 2H, J = 6.0), 2.80(t, 2H, J = 6.0), 3.05(s, 2H), 3.68-3.86(m, 4H), 5.42(bs, 1H), 6.98-7.06(m, 4H), 8.36(s, 1H), 10.5(s, 1H) |
| X-101 | CH₃(CH₂)₃CH(—)CH₂COOH | 0.89(t, 3H, J = 7.2), 1.32-1.76(m, 16H), 2.60-2.84(m, 6H), 4.22-4.36(m, 1H), 5.44(bs, 1H), 6.98-7.06(m, 4H), 8.40(s, 1H), 10.3(d, 1H, J = 7.5) |
| X-120 | 2-(1-carboxycyclopentyl)thiazol-2-yl | DMSO-d6 1.28-1.49(m, 4H), 1.60-1.71(m, 8H), 2.01-2.07(m, 2H), 2.21-2.27(m, 2H), 2.71(br-s, 2H), 2.90(br-s, 2H), 5.47(br-s, 2H), 6.99-7.21(m, 5H), 8.36(s, 1H), 13.25(s, 1H) |
| X-122 | 2-carboxycyclohex-1-en-1-yl | DMSO-d6 1.00-1.75(m, 12H), 2.20-2.38(br, 2H), 2.56-2.70(br, 2H), 2.70-2.98(m, 4H), 5.40(br, 2H), 7.10-7.29(m, 4H), 8.19(s, 1H), 12.23(br, 1H), 12.58(s, 1H) |
| X-149 | 2-carboxycyclopent-1-en-1-yl | DMSO-d6 1.22-1.46(m, 4H), 1.54-1.70(m, 4H), 1.80(t, 2H, J = 7.5), 2.42(t, 2H, J = 8.1), 2.62-2.70(br, 2H), 2.76-2.90(br, 2H), 3.18(t, 2H, J = 7.8), 5.42(br, 2H), 7.16(d, 4H, J = 7.5), 8.25(s, 1H), 12.10(br, 1H), 12.72(s, 1H) |
| X-168 | 6-(2-carboxyvinyl)pyridin-3-yl | DMSO-d6 1.28-1.70 (m, 8H), 2.73 (br, 2H), 2.90 (br, 2H), 5.49 (br, 2H), 6.58 (d, 1H, J = 16.2), 7.15-7.22 (m, 4H), 7.59 (d, 1H, J = 15.9), 8.23(dd, 1H, J = 2.1 and 8.7), 8.32 (d, 1H, J = 8.7), 8.39 (s, 1H), 8.60 (d, 1H, J = 2.1), 12.43 (s, 1H), 12.68 (s, 1H) |
| X-171 | 6-(2-carboxyethyl)pyridin-3-yl | DMSO-d6 1.26-1.66 (m, 8H), 2.56 (t, 2H, J = 7.5), 2.72 (br, 2H), 2.80 (t, 2H, J = 7.5), 2.89 (br, 2H), 5.48 (br, 2H), 7.15-7.21 (m, 4H), 7.71 (dd, 1H, J = 2.1 and 8.7), 8.37 (s, 1H), 12.18 (s, 1H), 12.43 (s, 1H) |

TABLE 95

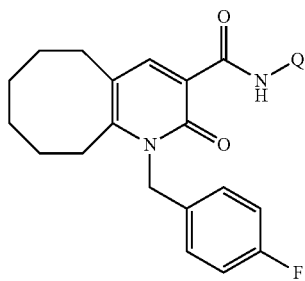

| Comp. No. | Q | ¹H-NMR(CDCl₃/TMS) δ |
|---|---|---|
| X-194 | CH₃ group with chain and CH(COOH) | DMSO-d6 0.85 (t, 3H, J = 6.6), 1.20-1.83 (m, 14H), 2.67 (br, 2H), 2.83 (br, 2H), 4.44 (m, 1H), 5.43 (brs, 2H), 7.10-7.21 (m, 4H), 8.21 (s, 1H), 10.12 (d, 1H, J = 7.5), 12.79 (br, 1H) |
| X-217 | C(Et)₂CH₂COOH | DMSO-d6 0.57(t, 6H, J = 7.2), 1.04-1.70(m, 12H), 2.40-2.62(m, 6H), 5.19(s, 2H), 6.86-6.99(m, 4H), 7.97(s, 1H), 9.51(s, 1H), 11.78(brs, 1H) |
| X-219 | CH(iBu)CH₂CH₂COOH | DMSO-d6 0.86(dd, 6H, J = 2.4 and 6.6), 1.22-1.68(m, 12H), 1.78(m, 1H), 2.20(t, 2H, J = 7.5), 2.62-2.71(m, 2H), 2.77-2.87(m, 2H), 4.05(m, 1H), 5.41(brs, 2H), 7.09-7.23(m, 4H), 8.21(s, 1H), 9.56(d, 1H, J = 8.7), 12.03(brs, 1H) |
| X-226 | 4-(CH=CHCOOH)phenyl | DMSO-d6 1.26-1.47(m, 4H), 1.54-1.70(m, 4H), 2.67-2.77(m, 2H), 2.82-2.93(m, 2H), 5.49(brs, 2H), 6.44(d, 1H, J = 15.9), 7.16-7.21(m, 4H), 7.54(d, 1H, J = 15.9), 7.67(d, 2H, J = 8.7), 7.74(d, 2H, J = 8.7), 8.36(s, 1H), 12.28(brs, 1H), 12.32(s, 1H) |
| XI-012 | 4-(CH₂CH₂COOH)phenyl | DMSO-d6 1.26-1.48(m, 4H), 1.55-1.70(m, 4H), 2.52(t, 2H, J = 7.5), 2.66-2.75(m, 2H), 2.79(t, 2H, J = 7.5), 2.83-2.92(m, 2H), 5.48(brs, 2H), 7.16-7.20(m, 4H), 7.19(d, 2H, J = 8.4), 7.59(d, 2H, J = 8.4), 8.34(s, 1H), 12.07(s, 1H), 12.12(brs, 1H) |
| XI-034 | 1-carboxycyclodecyl | DMSO-d6 1.20-1.68(m, 22H), 1.78-1.94(m, 2H), 2.04-2.20(m, 2H), 2.60-2.74(m, 2H), 2.78-2.88(m, 2H), 5.42(s, 2H), 7.10-7.22(m, 4H), 8.17(s, 1H), 9.92(s, 1H), 12.23(br, 1H) |

TABLE 95-continued
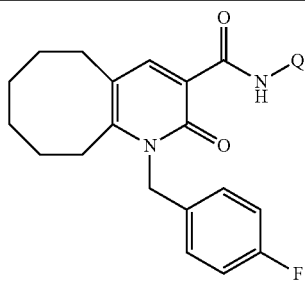
| Comp. No. | Q | ¹H-NMR(CDCl₃/TMS) δ |
|---|---|---|
| XI-125 | (pyrimidine-CH=CH-COOH group) | DMSO-d6 1.32(m, 2H), 1.42(m, 2H), 1.63(m, 4H), 2.73(m, 2H), 2.89(m, 2H), 5.48(s, 2H), 6.73(d, 1H, J = 16.2), 7.14-7.21(m, 4H), 7.56(d, 1H, J = 16.2), 8.36(s, 1H), 9.02(s, 2H), 12.89(s, 1H) |
TABLE 96
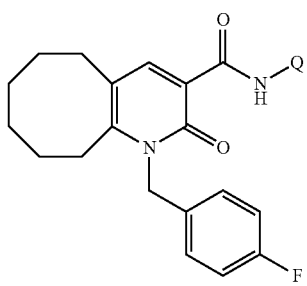
| Comp. No. | Q | ¹H-NMR(CDCl₃/TMS) δ |
|---|---|---|
| XI-136 | (CH₃)₃C-CH₂-CH(COOH)- | DMSO-d6 0.92(s, 9H), 1.30(m, 2H), 1.40(m, 2H), 1.58(m, 5H), 1.77(m, 1H), 2.66(m, 2H), 2.83(m, 2H), 4.48(m, 1H), 5.43(m, 2H), 7.15(m, 4H), 8.22(s, 1H), 10.05(d, 1H, J = 6.0) |
| XI-137 | (CH₃)₃C-CH(CH₂COOH)- | DMSO-d6 0.88(s, 9H), 1.30(m, 2H), 1.40(m, 2H), 1.60(m, 4H), 2.16(m, 1H), 2.57(m, 1H), 2.66(m, 2H), 2.82(m, 2H), 4.28(m, 1H), 5.42(m, 2H), 7.16(m, 4H), 8.21(s, 1H), 9.88(d, 1H, J = 7.2) |
| XI-156 | (CH₃)₃C-CH₂-CH(CH₂CH₂COOH)- | DMSO-d6 0.87(s, 9H), 1.22-1.82(m, 12H), 2.19(t, 2H, J = 7.5), 2.60-2.70(m, 2H), 2.76-2.87(m, 2H), 4.09(m, 1H), 5.41(brs, 2H), 7.08-7.21(m, 4H), 8.21(s, 1H), 9.66(d, 1H, J = 9.0), 11.97(brs, 1H) |

TABLE 96-continued
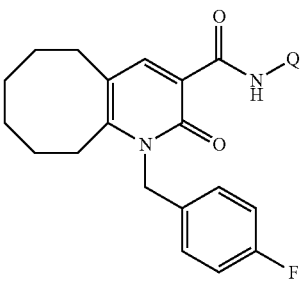
| Comp. No. | Q | ¹H-NMR(CDCl₃/TMS) δ |
|---|---|---|
| XI-168 | 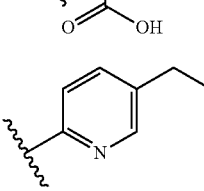 | DMSO-d6 1.10-1.18(m, 16H), 2.20-2.95(m, 6H), 5.30-5.60(m, 2H), 7.10-7.25(m, 4H), 8.16(s, 1H), 10.32(s, 1H) |
| XI-211 | 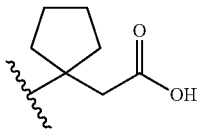 | DMSO-d6 1.25-1.50(m, 4H), 1.57-1.70(m, 4H), 2.67-2.77(m, 2H), 2.85-2.95(m, 2H), 3.60(s, 2H), 5.48(s, 2H), 7.12-7.26(m, 4H), 7.72(dd, 1H, J = 2.4, 8.4), 8.19(d, 1H, J = 2.1), 8.23(d, 1H, J = 8.4), 8.38(s, 1H), 12.47(s, 1H) |
| XI-215 | 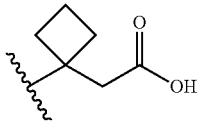 | 1.44(m, 2H), 1.69-1.88(m, 10H), 2.18-2.22(m, 2H), 2.63-2.67(m, 2H), 2.78-2.83(m, 2H), 5.41(s, 2H), 7.02-7.05(m, 4H), 8.39(s, 1H), 10.49(s, 1H) |
| XI-225 | 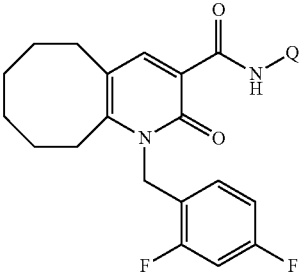 | DMSO-d6 1.22-1.46(m, 4H), 1.52-1.68(m, 4H), 1.77-1.92(m, 2H), 2.22(t, 3H, J = 7.5), 2.59-2.71(m, 2H), 2.76-2.87(m, 2H), 2.88(s, 3H), 5.40(br, 2H), 7.08-7.22(m, 4H), 8.18(s, 1H), 9.99(s, 1H), 12.02(br, 1H) |
TABLE 97
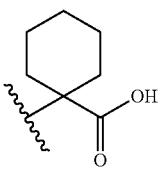
| Comp. No. | Q | ¹H-NMR(CDCl₃/TMS) δ |
|---|---|---|
| XI-008 | | DMSO-d6 1.28-1.50(m, 4H), 1.57-1.73(m, 4H), 2.70-2.80(m, 2H), 2.87-2.99(m, 2H), 3.60(s, 2H), 5.45(s, 2H), 6.88-7.10(m, 3H), 7.34(m, 1H), 8.39(s, 1H), 12.38(br s, 1H), 13.21(s, 1H) |
TABLE 97-continued
| Comp. No. | Q | ¹H-NMR(CDCl₃/TMS) δ |
|---|---|---|
| XI-018 | | DMSO-d6 1.10-1.80(m, 16H), 1.94-2.10(m, 2H), 2.63-2.74(m, 2H), 2.78-2.88(m, 2H), 5.40(s, 2H), 6.78(m, 1H), 7.03(m, 1H), 7.34(m, 1H), 8.19(s, 1H), 10.06(s, 1H), 12.23(br s, 1H) |

TABLE 98

[Structure: cyclooctane-fused pyridinone with N-(3,4-difluorobenzyl) group and C(=O)NH-Q carboxamide]

| Comp. No. | Q | ¹H-NMR(CDCl₃/TMS) δ |
|---|---|---|
| X-112 | [thiazol-4-yl-CH₂-COOH group, attached at 2-position] | DMSO-d6 1.27-1.49(m, 4H), 1.55-1.72(m, 4H), 2.67-2.80(m, 2H), 2.85-2.97(m, 2H), 3.60(s, 2H), 5.48(br s, 2H), 6.96-7.04(m, 1H), 7.03(s, 1H), 7.30-7.46(m, 2H), 8.38(s, 1H), 12.39(br s, 1H), 13.26(s, 1H) |
| XI-017 | [1-carboxycyclohexyl] | DMSO-d6 1.14-1.78(m, 16H), 1.96-2.08(m, 2H), 2.60-2.75(m, 2H), 2.75-2.90(m, 2H), 5.43(s, 2H), 6.86(m, 1H), 7.28(m, 1H), 7.40(m, 1H), 8.18(s, 1H), 10.12(s, 1H), 12.23(br s, 1H) |
| XI-124 | [1-(carboxymethyl)cyclohexyl] | DMSO-d6 1.10-1.68(m, 16H), 2.14-2.28(m, 2H), 2.62-2.68(m, 2H), 2.72-2.88(m, 4H), 5.41(br, 2H), 6.84-6.90(m, 1H), 7.19-7.29(m, 1H), 7.34-7.47(m, 1H), 8.20(s, 1H), 9.80(s, 1H), 11.83(br, 1H) |
| XI-127 | [1,2,4-thiadiazol-3-yl-CH₂-COOH] | DMSO-d6 1.25-1.48(m, 4H), 1.55-1.73(m, 4H), 2.68-2.80(m, 2H), 2.85-2.97(m, 2H), 3.81(s, 2H), 5.49(s, 2H), 7.02(m, 1H), 7.30-7.48(m, 2H), 8.42(s, 1H), 12.66(br s, 1H), 13.61(s, 1H) |
| XI-128 | [thiazol-5-yl-CH₂-COOH attached at 2-position] | DMSO-d6 1.20-1.50(m, 4H), 1.54-1.74(m, 4H), 2.67-2.80(m, 2H), 2.83-2.97(m, 2H), 3.82(s, 2H), 5.48(s, 2H), 6.98(m, 1H), 7.28-7.50(m, 2H), 7.30(s, 1H), 8.38(s, 1H), 12.65(br s, 1H), 13.19(s, 1H) |
| XI-144 | [CH(COOH)CH₂C(CH₃)₃] | DMSO-d6 0.92(s, 9H), 1.31(m, 2H), 1.41(m, 2H), 1.59(m, 5H), 1.76(m, 1H), 2.67(m, 2H), 2.84(m, 2H), 4.49(m, 1H), 5.42(m, 2H), 6.87(m, 1H), 7.24(m, 1H), 7.40(m, 1H), 8.22(s, 1H), 10.20(d, 1H, J = 6.0) |
| XI-145 | [CH(CH₂COOH)C(CH₃)₃-like chain] | DMSO-d6 0.88(s, 9H), 1.31(m, 2H), 1.41(m, 2H), 1.60(m, 4H), 2.16(m, 1H), 2.58(m, 1H), 2.67(m, 2H), 2.82(m, 2H), 4.29(m, 1H), 5.42(m, 2H), 6.88(m, 1H), 7.24(m, 1H), 7.40(m, 1H), 8.22(s, 1H), 9.85(d, 1H, J = 7.2) |

TABLE 99
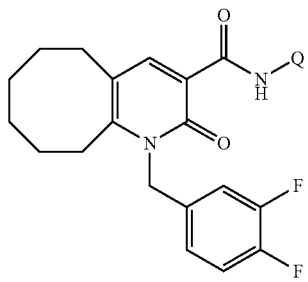
| Comp. No. | Q | ¹H-NMR(CDCl₃/TMS) δ |
|---|---|---|
| XI-147 | 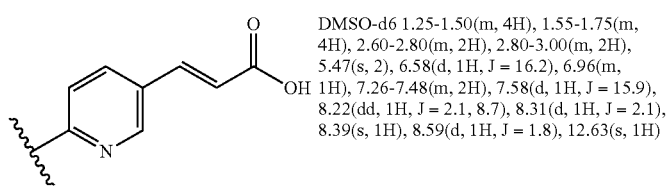 | DMSO-d6 1.25-1.50(m, 4H), 1.55-1.75(m, 4H), 2.60-2.80(m, 2H), 2.80-3.00(m, 2H), 5.47(s, 2), 6.58(d, 1H, J = 16.2), 6.96(m, 1H), 7.26-7.48(m, 2H), 7.58(d, 1H, J = 15.9), 8.22(dd, 1H, J = 2.1, 8.7), 8.31(d, 1H, J = 2.1), 8.39(s, 1H), 8.59(d, 1H, J = 1.8), 12.63(s, 1H) |
| XI-159 | 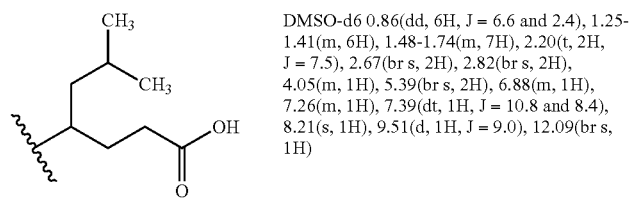 | DMSO-d6 0.86(dd, 6H, J = 6.6 and 2.4), 1.25-1.41(m, 6H), 1.48-1.74(m, 7H), 2.20(t, 2H, J = 7.5), 2.67(br s, 2H), 2.82(br s, 2H), 4.05(m, 1H), 5.39(br s, 2H), 6.88(m, 1H), 7.26(m, 1H), 7.39(dt, 1H, J = 10.8 and 8.4), 8.21(s, 1H), 9.51(d, 1H, J = 9.0), 12.09(br s, 1H) |
| XI-172 | 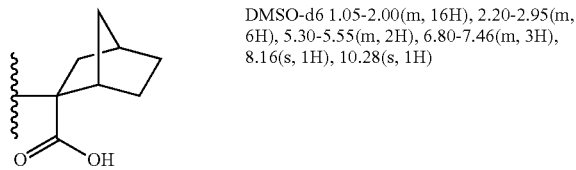 | DMSO-d6 1.05-2.00(m, 16H), 2.20-2.95(m, 6H), 5.30-5.55(m, 2H), 6.80-7.46(m, 3H), 8.16(s, 1H), 10.28(s, 1H) |
| XI-175 | 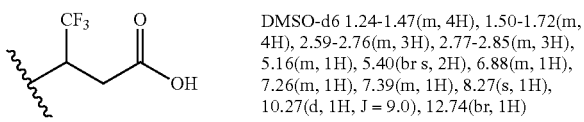 | DMSO-d6 1.24-1.47(m, 4H), 1.50-1.72(m, 4H), 2.59-2.76(m, 3H), 2.77-2.85(m, 3H), 5.16(m, 1H), 5.40(br s, 2H), 6.88(m, 1H), 7.26(m, 1H), 7.39(m, 1H), 8.27(s, 1H), 10.27(d, 1H, J = 9.0), 12.74(br, 1H) |
| XI-180 | 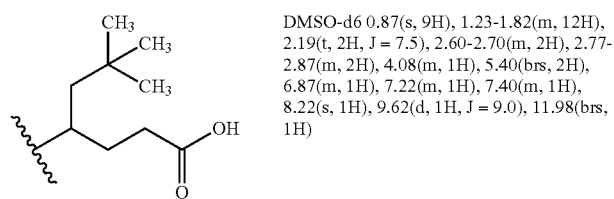 | DMSO-d6 0.87(s, 9H), 1.23-1.82(m, 12H), 2.19(t, 2H, J = 7.5), 2.60-2.70(m, 2H), 2.77-2.87(m, 2H), 4.08(m, 1H), 5.40(brs, 2H), 6.87(m, 1H), 7.22(m, 1H), 7.40(m, 1H), 8.22(s, 1H), 9.62(d, 1H, J = 9.0), 11.98(brs, 1H) |
| XI-200 | 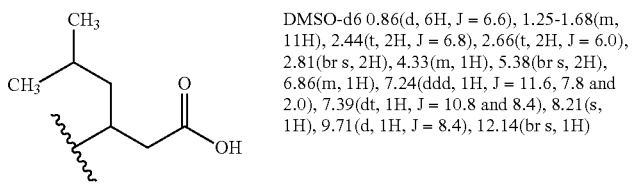 | DMSO-d6 0.86(d, 6H, J = 6.6), 1.25-1.68(m, 11H), 2.44(t, 2H, J = 6.8), 2.66(t, 2H, J = 6.0), 2.81(br s, 2H), 4.33(m, 1H), 5.38(br s, 2H), 6.86(m, 1H), 7.24(ddd, 1H, J = 11.6, 7.8 and 2.0), 7.39(dt, 1H, J = 10.8 and 8.4), 8.21(s, 1H), 9.71(d, 1H, J = 8.4), 12.14(br s, 1H) |

TABLE 100
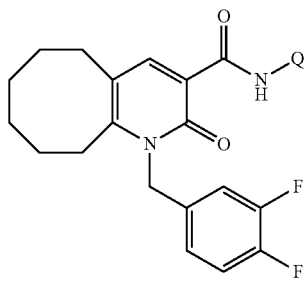
| Comp. No. | Q | $^1$H-NMR(CDCl$_3$/TMS) δ |
|---|---|---|
| XI-206 | 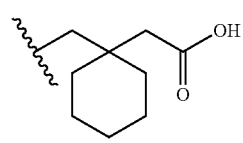 | DMSO-d6 1.26-1.68(m, 18H), 2.17(s, 2H), 2.67(br s, 2H), 2.81(br s, 2H), 3.40(d, 2H, J = 6.3), 5.41(br s, 2H), 6.86(m, 1H), 7.25(ddd, 1H, J = 11.9, 7.7 and 2.3), 7.39(dt, 1H, J = 10.8 and 8.4), 8.23(s, 1H), 9.89(t, 1H, J = 6.0), 12.06(br s, 1H) |
| XI-213 | 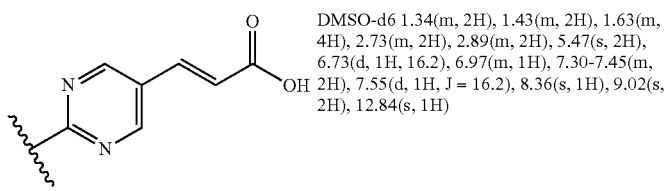 | DMSO-d6 1.34(m, 2H), 1.43(m, 2H), 1.63(m, 4H), 2.73(m, 2H), 2.89(m, 2H), 5.47(s, 2H), 6.73(d, 1H, 16.2), 6.97(m, 1H), 7.30-7.45(m, 2H), 7.55(d, 1H, J = 16.2), 8.36(s, 1H), 9.02(s, 2H), 12.84(s, 1H) |
| XI-214 | 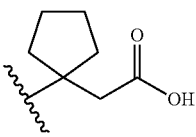 | 1.45(m, 2H), 1.69-1.90(m, 10H), 2.17-2.22(m, 2H), 2.64-2.68(m, 2H), 2.77-2.81(m, 2H), 5.40(s, 2H), 6.80(m, 1H), 6.87-6.93(m, 1H), 7.09-7.18(m, 1H), 8.39(s, 1H), 10.37(s, 1H) |
| XI-222 | 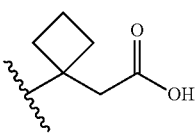 | DMSO-d6 1.23-1.52(m, 4H), 1.52-1.68(m, 4H), 1.78-1.92(m, 2H), 2.21(t, 4H, J = 7.8), 2.62-2.71(m, 2H), 2.76-2.86(m, 2H), 2.88(s, 2H), 5.39(br, 2H), 6.87(m, 1H), 7.25(m, 1H), 7.39(m, 1H), 8.18(s, 1H), 9.95(s, 1H), 11.86(br, 1H) |
| XI-249 | 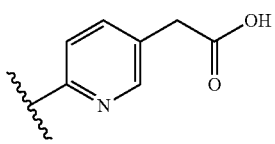 | DMSO-d6 1.26-1.50(m, 4H), 1.55-1.73(m, 4H), 2.66-2.78(m, 2H), 2.83-2.95(m, 2H), 3.60(s, 2H), 5.46(s, 2H), 6.96(m, 1H), 7.26-7.48(m, 2H), 7.72(dd, 1H, J = 2.4, 8.4), 8.19(d, 1H, J = 2.4), 8.23(d, 1H, J = 8.4), 8.37(s, 1H), 12.43(s, 1H), 12.44(br s, 1H) |
| XI-285 | 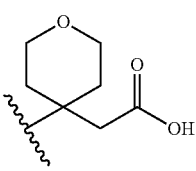 | DMSO-d6 1.20-2.20(m, 12H), 2.60-2.95(m, 4H), 2,86(s, 2H), 3.48(t, 2H, J = 10.5), 3.60-3.75(m, 2H), 5.30-5.55(m, 2H), 6.82-7.48(m, 2H), 8.20(s, 1H), 9.98(s, 1H) |

TABLE 101

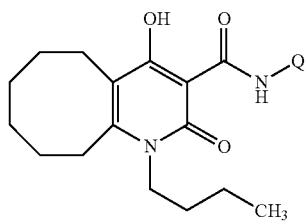

| Comp. No. | Q | ¹H-NMR(CDCl₃/TMS) δ |
|---|---|---|
| I-004 | (benzyl-CH-C(O)-NH-CH₂-COOH) | 0.98(t, 3H, J = 7.2), 1.36-1.81(m, 12H), 2.64(br, 2H), 2.85(t, 2H, J = 6.0), 3.15(dd, 1H, J = 8.7 and 13.8), 3.30(dd, 1H, J = 5.7 and 13.8), 3.89(dd, 1H, J = 4.2 and 18.3), 3.94(br, 2H), 4.25(dd, 1H, J = 6.3 and 15.3), 4.80(m, 1H), 6.91(brt, 1H), 7.20-7.37(m, 5H), 10.79(d, 1H, J = 7.5), 15.38(s, 1H) |
| I-071 | (azepan-2-one-3-yl) | 0.95(t, 3H, J = 7.2), 1.37-2.20(m, 18H), 2.65(br, 2H), 2.85(t, 2H, J = 6.0), 3.20-3.42(m, 2H), 3.90-4.20(m, 2H), 4.73(dd, 1H, J = 6.6 and 10.8), 6.02(brt, 1H), 11.18(d, 1H, J = 7.2), 15.77(s, 1H) |
| I-150 | (Ph-CH-COOCH₃) | 0.96(t, 3H, J = 7.2), 1.37-1.81(m, 12H), 2.65(br, 2H), 2.85(t, 2H, J = 6.0), 3.75(s, 3H), 4.00(br, 2H), 5.68(d, 1H, J = 6.9), 7.30-7.70(m, 5H), 11.37(d, 1H, J = 6.3), 15.42(s, 1H) |
| I-202 | (cyclohexyl-C-COOCH₃) | 0.98(t, 3H, J = 7.2), 1.23-2.12(m, 22H), 2.65(br, 2H), 2.86(t, 2H, J = 6.0), 3.72(s, 3H), 3.99(br, 2H), 10.86(s, 1H), 15.63(s, 1H) |
| I-423 | (Ph-CH-COOH) | 0.97(t, 3H, J = 7.2), 1.18-1.80(m, 12H), 2.64(br, 2H), 2.86(t, 2H, J = 6.0), 4.00(br, 2H), 5.64(d, 1H, J = 6.9), 7.26-7.53(m, 5), 11.37(d, 1H, J = 6.9), 15.59(s, 1H) |
| I-438 | (cyclohexyl-CH-COOCH₃) | 0.97(t, 3H, J = 7.2), 1.08-2.00(m, 22H), 2.66(br, 2H), 2.88(t, 2H, J = 6.0), 3.75(s, 3H), 3.99(br, 2H), 4.59(dd, 1H, J = 5.7 and 8.1), 10.89(d, 1H, J = 8.1), 15.69(s, 1H) |

TABLE 102
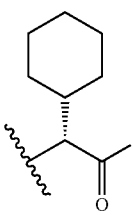
| Comp. No. | Q | ¹H-NMR(CDCl₃/TMS) δ |
|---|---|---|
| I-443 | 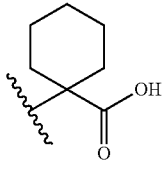 | 0.97(t, 3H, J = 7.2), 1.08-2.05(m, 22H), 2.66(br, 2H), 2.86(t, 2H, J = 6.0), 4.01(br, 2H), 4.60(dd, 1H, J = 5.7 and 8.4), 10.90(d, 1H, J = 8.1), 15.55(s, 1H) |
| I-474 | 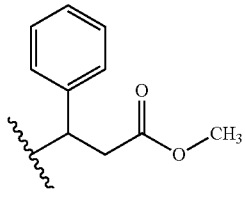 | 0.97(t, 3H, J = 7.2), 1.23-1.80(m, 18H), 1.88-1.96(m, 2H), 2.23-2.32(m, 2H), 2.66(br, 2H), 2.87(t, 2H, J = 6.0), 3.99(br, 2H), 11.03(s, 1H), 15.02(s, 1H) |
| II-009 | 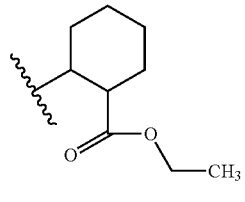 | 0.97(t, 3H, J = 7.2), 1.39-1.80(m, 12H), 2.65(br, 2H), 2.83-2.92(m, 3H), 3.01(dd, 1H, J = 7.2, 15.3), 3.64(s, 3H), 3.98(br, 2H), 5.60(q, 1H, J = 7.8), 7.25-7.42(m, 5H), 11.12(d, 1H, J = 8.1), 15.80(s, 1H) |
| II-025 | 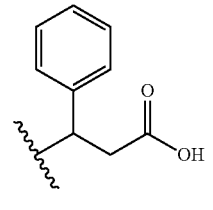 | 0.94(t, 3H, J = 7.2), 1.23(t, 3H, J = 7.2), 1.31-2.05(m, 21H), 2.64(br, 2H), 2.76(m, 1H), 2.84(t, 2H, J = 6.6), 3.98(br, 2H), 4.10-4.19(m, 2H), 4.51(m, 1H), 10.91(d, 1H, J = 8.7), 16.17(s, 1H) |
| II-050 | 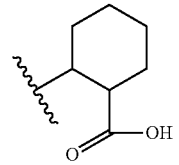 | 0.96(t, 3H, J = 7.2), 1.29-1.80(m, 12H), 2.65(br, 2H), 2.85(t, 2H, J = 6.0), 2.92(dd, 1H, J = 6.6 and 9.6), 3.08(dd, 1H, J = 7.5 and 16.2), 5.59(q, 1H, J = 7.8), 7.22-7.48(m, 5H), 11.07(d, 1H, J = 7.8), 15.75(s, 1H) |
| II-051 |  | 0.93(t, 3H, J = 7.2), 1.31-2.08(m, 21H), 2.64(br, 2H), 2.76(m, 1H), 2.84(t, 2H, J = 6.6), 3.85-4.10(m, 2H), 4.50(m, 1H), 10.91(d, 1H, J = 8.7), 16.04(s, 1H) |

TABLE 103
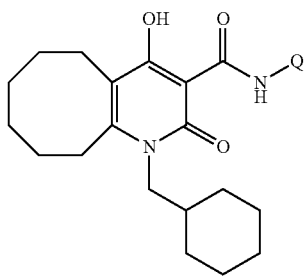
| Comp. No. | Q | ¹H-NMR(CDCl₃/TMS) δ |
|---|---|---|
| I-145 | (CH₃)₂CH-CH(-)-C(=O)OCH₃ | 1.00-1.80(m, 25H), 2.30(m, 1H), 2.65(brs, 2H), 2.89(t, 2H, J = 6.3), 3.76(s, 3H), 4.57(dd, 1H, J = 5.1 and 8.1), 10.94(d, 1H, J = 8.1), 15.71(s, 1H) |
| I-149 | 1-(methoxycarbonyl)cyclohexyl | 1.08-2.21(m, 29H), 2.65(m, 2H), 2.894, 2H, J = 6.3), 3.73(s, 3H), 3.7-4.1(br, 2H), 10.88(s, 1H), 15.67(s, 1H) |
| I-418 | (CH₃)₂CH-CH(-)-C(=O)OH | DMSO-d6 0.93-1.81(m, 25H), 2.20(m, 1H), 2.60(m, 1H), 2.95(m, 2H), 4.38(dd, 1H, J = 4.5 and 8.1), 10.84(d, 1H, J = 8.1), 15.96(s, 1H) |
| I-422 | 1-carboxycyclohexyl | 1.03-2.30(m, 29H), 2.50-2.90(br, 2H), 2.90(t, 2H, J = 6.0), 3.7-4.2(br, 2H), 11.08(s, 1H), 15.00(s, 1H) |
| II-023 | 2-(ethoxycarbonyl)cyclohexyl | 1.05-2.08(m, 35H), 2.45-2.80(m, 5H), 4.14(q, 2H, J = 7.2), 4.50(m, 1H), 10.92(d, 1H, J = 8.7), 16.22(s, 1H) |
| II-048 | 2-carboxycyclohexyl | 1.02-2.10(m, 27H), 2.3-3.2(m, 5H), 3.7-4.3(br, 2H), 4.98(m, 1H), 10.93(d, 1H, J = 9.0), 16.07(s, 1H) |

TABLE 104

[Structure: pyridinone with CH3, CH3 (ethyl), C(=O)NH-Q substituent, N-butyl chain]

| Comp. No. | Q | $^1$H-NMR(CDCl$_3$/TMS) δ |
|---|---|---|
| I-135 | [isopropyl-CH with CH(CO-OCH3) group] | 0.98-1.08(m, 8H), 1.22(t, 3H, 6.6), 1.40-1.52(m, 2H), 1.65-1.78(m, 3H), 2.18(s, 3H), 2.28(m, 1H), 2.74(q, 2H, J = 7.2), 3.74(s, 3H), 4.02-4.18(m, 2H), 4.64(dd, 1H, J = 4.8 and 8.7), 8.28(s, 1H), 10.42(d, 1H, J = 7.8) |
| I-136 | [cyclohexyl with CO-OCH3] | 0.99(t, 3H, J = 7.2), 1.22(t, 3H, 7.5), 1.40-1.94(m, 10H), 2.15-2.24(m, 5H), 2.28(m, 1H), 2.73(q, 2H, J = 7.8), 3.71(s, 3H), 4.05-4.16(m, 2H), 8.26(s, 1H), 10.35(br, 1H) |
| I-156 | [phenyl-CH with CO-OCH3] | 0.98(t, 3H, J = 7.2), 1.21(t, 3H, J = 7.2), 1.38-1.55(m, 2H), 1.58-1.80(m, 3H), 2.16(s, 3H), 2.72(q, 2H, J = 7.5), 4.00-4.20(m, 2H), 5.73(d, 1H, J = 7.2), 7.20-7.40(m, 3H), 7.45-7.52(m, 2H), 8.27(s, 1H), 10.87(d, 1H, J = 7.5) |
| I-408 | [isopropyl-CH with CH(COOH)] | DMSO-d6 0.90-1.00 (m, 9H), 1.16(t, 4H, 7.8), 1.35-1.47(m, 2H), 1.53-1.66(m, 2H), 2.17(s, 3H), 2.76(q, 2H, J = 7.5), 3.95-4.20(m, 2H), 4.40(dd, 1H, J = 4.8 and 8.7), 8.13(s, 1H), 10.27(d, 1H, J = 8.4), 12.90(br, 1H) |
| I-409 | [cyclohexyl with COOH] | DMSO-d6 0.94(t, 3H, J = 7.5), 1.16(t, 3H, 7.5), 1.40-1.78(m, 12H), 1.97-2.10(m, 2H), 2.17(s, 3H), 2.76(q, 2H, J = 7.2), 4.02-4.13(m, 2H), 8.08(s, 1H), 10.26(br, 1H), 12.14(br, 1H) |

TABLE 104-continued

| Comp. No. | Q | $^1$H-NMR(CDCl$_3$/TMS) δ |
|---|---|---|
| I-429 | [phenyl-CH with COOH] | |
| X-206 | [thiazol-2-yl-CH2-COOH] | DMSO-d6 0.95(t, 3H, J = 7.5), 1.19(t, 3H, J = 7.5), 1.34-1.50(m, 2H), 1.56-1.72(m, 2H), 2.23(s, 3H), 2.82(q, 2H, J = 7.5), 3.61(s, 2H), 4.10-4.20(m, 2H), 7.02(s, 1H), 8.29(s, 1H), 2.38(br s, 1H), 13.47(s, 1H) |

TABLE 105

[Structure: pyridinone with CH3, CH3 (ethyl), C(=O)NH-Q substituent, N-isopentyl chain]

| Comp. No. | Q | $^1$H-NMR(CDCl$_3$/TMS) δ |
|---|---|---|
| XI-106 | [thiazol-2-yl-CH2-COOH] | DMSO-d6 0.98(d, 6H), 1.21(t, 3H, J = 7.5), 1.48-1.62(m, 2H), 1.75(m, 1H), 2.23(s, 3H), 2.80(q, 2H, J = 7.2), 3.61(s, 2H), 3.80-4.21(m, 2H), 7.02(s, 1H), 8.29(s, 1H), 12.40(br s, 1H), 13.46(s, 1H) |
| XI-113 | [cyclohexyl with COOH] | DMSO-d6 0.97(d, 6H, J = 6.6), 1.18(s, 3H, J = 7.5), 1.26-1.78(m, 8H), 2.16(s, 3H), 2.75(q, 2H, J = 7.5), 4.09(m, 2H), 8.09(s, 1H), 10.24(s, 3H) |

TABLE 106

[Structure: 5-methyl-6-ethyl-1-(cyclohexylmethyl)-2-oxo-1,2-dihydropyridine-3-carboxamide with N-H-Q]

| Comp. No. | Q | ¹H-NMR (CDCl₃/TMS) δ |
|---|---|---|
| I-030 | [CH(iPr)-C(=O)-N(CH₃)-CH₂CH₂OH] | 0.98-1.30(m, 14H), 1.54-2.30(m, 8H), 2.15 and 2.17(s, total 3H), 2.75(q, 2H, J = 7.5), 3.00 and 3.28(s, total 3H), 3.24-4.18(m, 6H), 4.79(m, 1H), 8.23 and 8.24(s, total 1H), 10.46 and 10.55(brd, total 1H) |
| I-034 | [CH(tBu)-C(=O)-NH-CH₂CH₂OH] | 1.00-1.30(m, 8H), 1.14(s, 9H), 1.53-1.90(m, 6H), 2.09(br, 1H), 2.18(s, 3H), 2.76(q, 2H, J = 7.5), 3.40(q, 2H, J = 5.4), 3.62-3.78(m, 2H), 3.80-4.20(br, 2H), 4.19(d, 1H, J = 6.9), 6.54(m, 1H), 8.25(s, 1H), 10.71(d, 1H, J = 6.9) |
| I-035 | [CH(tBu)-C(=O)-N(CH₃)-CH₂-CH(OH)-CH₂OH] | 1.00-1.40(m, 18H), 1.52-1.92(m, 6H), 2.14-2.17(m, 3H), 2.33(br, 1H), 2.76(q, 2H, J = 7.5), 2.98-4.23(m, 7H), 3.33(s, 3H), 4.98(m, 1H), 8.24(m 1H), 10.66 and 10.88(m, total 1H) |
| I-038 | [CH(tBu)-C(=O)-NH-CH(CH₂OH)₂] | 1.01-1.30(m, 5H), 1.15(s, 9H), 1.16(t, 3H, J = 7.5), 1.54-1.92 (m, 6H), 2.18(s, 3H), 2.77(q, 2H, J = 7.5), 3.70-4.20(br, 2H), 3.77-3.94(m, 5H), 4.13(d, 1H, J = 6.0), 6.89(m, 1H), 8.22(s, 1H), 10.83(d, 1H, J = 6.0) |
| I-039 | [CH(tBu)-C(=O)-N(CH₂CH₂OH)₂] | 1.00-1.30(m, 5H), 1.14(t, 3H, J = 7.5), 1.17(s, 9H), 1.52-1.90(m, 6H), 2.16 (s, 3H), 2.75(q, 2H, J = 7.5), 3.26-3.50(m, 2H), 3.66-4.00(m, 5H), 3.80-4.20 (m, 2H), 4.20(m, 1H), 4.85(d, 1H, J = 6.6), 8.22(s, 1H), 10.86(d, 1H, J = 6.6) |

TABLE 106-continued

[Same core structure]

| Comp. No. | Q | ¹H-NMR (CDCl₃/TMS) δ |
|---|---|---|
| I-129 | [C(CH₃)₂-C(=O)-O-CH₃] | 1.00-1.31(m, 5H), 1.15(t, 3H, J = 7.5), 1.57-1.96(m, 6H), 1.61(s, 6H), 2.17 (s, 3H), 2.76(q, 2H, J = 7.5), 3.74(s, 3H), 3.80-4.20(br, 2H), 8.27 (s, 1H), 10.26(s, 1H) |
| I-134 | [CH(CH₃)-C(=O)-O-CH₃] | 0.94-1.28(m, 14H), 1.57-1.94(m, 6H), 2.18(s, 3H), 2.27(m, 1H), 2.73(q, 2H, 7.2), 3.74(s, 3H), 3.98(br, 2H), 4.62(dd, 1H, J = 4.8 and 8.1), 8.28(s, 1H), 10.42 (d, 1H, J = 7.8) |
| I-137 | [1-(cyclohexyl)-C(=O)-O-CH₃] | 0.99-1.47(m, 9H), 1.48-1.95(m, 13H), 2.14-2.26(m, 5H), 2.75(q, 2H, J = 7.5), 3.72(s, 3H), 4.02(br, 2H), 8.27(s, 1H), 10.35(br, 1H) |

TABLE 107

[Same core structure]

| Comp. No. | Q | ¹H-NMR(CDCl₃/TMS) δ |
|---|---|---|
| I-180 | [CH(Ph)-C(=O)-O-CH₃] | 0.99-1.35(m, 9H), 1.52-1.96(m, 5H), 2.17(s, 3H), 2.75 (q, 2H, J = 7.5), 3.74(s, 3H), 4.01(br, 2H), 5.73(d, 1H, J = 6.9), 7.29-7.39(m, 3H), 7.47-7.53(m, 2H), 8.27(s, 1H), 10.86(d, 1H, J = 8.4) |

TABLE 107-continued

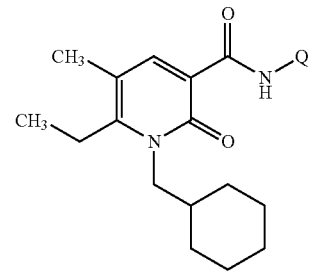

| Comp. No. | Q | $^1$H-NMR(CDCl$_3$/TMS) δ |
|---|---|---|
| I-182 | CH$_3$, CH$_3$ substituted acetic acid (dimethyl, -COOH) | DMSO-d6 1.00-1.22(m, 5H), 1.10(t, 3H, J = 7.5), 1.44-1.85(m, 6H), 1.47(s, 6H), 2.17(s, 3H), 2.78(q, 2H, J = 7.5), 3.80-4.10(br, 2H), 8.10(s, 1H), 10.20(s, 1H), 12.41(brs, 1H) |
| I-252 | CH$_3$, CH$_3$, CH$_3$ (t-butyl) substituted -COOCH$_3$ | 1.00-1.30(m, 5H), 1.08(s, 9H), 1.15(s, 3H), 1.55-1.83(m, 6H), 2.17(s, 3H), 2.76(q, 2H, J = 7.5), 3.73(s, 3H), 3.75-4.30(br, 2H), 4.54(d, 1H, J = 8.1), 8.27(S, 1H), 10.57(d, 1H, J = 8.1) |
| I-321 | CH$_3$, CH$_3$, CH$_3$ (t-butyl) substituted glyceryl ester | 1.02-1.30(m, 5H), 1.14(s, 9H), 1.17(t, 3H, J = 7.5), 1.55-1.88(m, 6H), 2.19(s, 3H), 2.77(q, 2H, J = 7.5), 3.60-4.30(br, 2H), 3.76-3.95(m, 4H), 4.34(d, 1H, J = 6.0), 4.99(m, 1H), 8.25(s, 1H), 10.74(d, 1H, J = 6.0) |
| I-327 | CH$_3$, CH$_3$ (isopropyl) substituted glyceryl ester | 1.02-1.30(m, 11H), 1.17(t, 3H, J = 7.5), 1.66-1.88(m, 6H), 2.19(s, 3H), 2.30(m, 1H), 2.97(q, 2H, J = 7.5), 3.76-4.18(m, 6H), 4.41(t, 1H, J = 6.0), 4.99(m, 1H), 8.26(s, 1H), 10.60(d, 1H, J = 6.0) |
| I-407 | CH$_3$, CH$_3$ (isopropyl) substituted -COOH | DMSO-d6 0.91(d, 6H, 6.9), 1.04-1.30(m, 8H), 1.47-1.87(m, 6H), 2.10-2.21(m, 4H), 2.70-2.88(m, 2H), 4.02(br, 2H), 4.40(dd, 1H, J = 4.5 and 7.5), 8.14(s, 1H), 10.25(d, 1H, J = 8.4) |
| I-410 | cyclohexyl-COOH | DMSO-d6 1.03-1.47(m, 9H), 1.47-1.85(m, 13H), 1.95-2.10(m, 2H), 2.17(s, 3H), 2.79(q, 2H, J = 7.5), 4.02(br, 2H), 8.09(s, 1H), 10.24(br, 1H), 12.13(br, 1H) |

TABLE 108

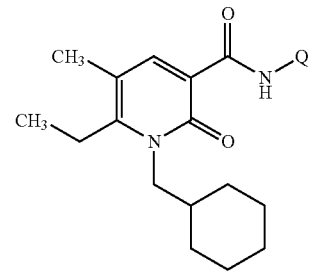

| Comp. No. | Q | $^1$H-NMR(CDCl$_3$/TMS) δ |
|---|---|---|
| I-519 | CH$_3$, CH$_3$, CH$_3$ (t-butyl) substituted -COOH | DMSO-d6 0.90-1.23 (m, 5H), 0.98(s, 9H), 1.11(t, 3H, J = 7.5), 1.46-1.85(m, 6H), 2.18(s, 3H), 2.79(q, 2H, J = 7.5), 3.80-4.20(br, 2H), 4.26(d, 1H, J = 8.7), 8.14(s, 1H), 10.40(d, 1H, J = 8.7), 12.65(brs, 1H) |
| I-573 | CH$_3$, CH$_3$ substituted -C(O)NHNHSO$_2$CH$_3$ | 1.02-1.33(m, 5H), 1.17(t, 3H, J = 7.5), 1.57-1.94(m, 6H), 1.64(s, 6H), 2.20(s, 3H), 2.79(q, 2H, J = 7.5), 3.07(s, 3H), 3.80-4.20(br, 2H), 6.94(d, 1H, J = 5.7), 8.26(s, 1H), 8.85(d, 1H, J = 5.7), 10.43(s, 1H) |
| X-22 | isoxazol-3-yl-CH$_2$-COOH (5-substituted) | DMSO-d6 1.04-1.86 (m, 14H), 2.23(s, 3H), 2.83(q, 2H, J = 7.5), 3.92(s, 2H), 4.05(br, 2H), 6.94(s, 1H), 8.28(s, 1H), 12,77(s, 1H), 12,87(br, 1H) |
| X-24 | thiazol-2-yl-CH$_2$-COOH (4-substituted) | DMSO-d6 1.05-1.25 (m, 8H), 1.45-1.90 (m, 6H), 2.24(s, 3H), 2.83(q, 2H, J = 7.8), 3.62(s, 2H), 3.95-4.20(br, 2H), 7.02(s, 1H), 8.31(s, 1H), 12.40(s, 1H), 13.48(s, 1H) |
| X-48 | thiophen-2-yl-CH$_2$-COOH (5-substituted) | DMSO-d6 1.03-1.88(m, 14H), 2.22(s, 3H), 2.82(q, 2H, J = 7.5), 3.71(s, 2H), 4.05(br, 2H), 6.68(d, 1H, J = 3.9), 6.72(d, 1H, J = 3.9), 8.25(s, 1H), 12,45(brs, 1H), 12,83(s, 1H) |
| X-109 | CF$_3$-CH-CH$_2$-COOH | DMSO-d6 1.00-1.20(m, 7H), 1.40-1.80(m, 7H), 2.16(s, 3H), 2.62-2.88(m, 4H), 3.97(brs, 2H), 5.10(brs, 1H), 8.17(s, 1H), 10.40(d, 1H, J = 9.6) |

| Comp. No. | Q | ¹H-NMR(CDCl₃/TMS) δ |
|---|---|---|
| X-132 | 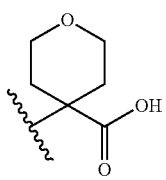 | DMSO-d6 1.16(t, 3H, J = 7.5 Hz), 1.51-18.9 (m, 11H), 2.16(s, 3H), 2.76-2.80(m, 2H), 3.43-3.51(m, 2H), 3.73-3.77(m, 2H), 3.99(br-s, 2H), 8.09 (s, 1H), 10.40(s, 1H), 12.43(br-s, 1H) |

TABLE 109

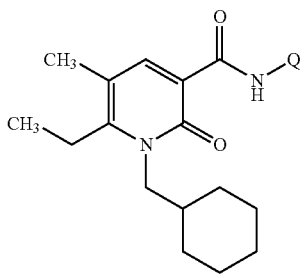

| Comp. No. | Q | ¹H-NMR(CDCl₃/TMS) δ |
|---|---|---|
| X-133 | | DMSO-d6 1.16(t, 3H, J = 7.5 Hz), 1.51-18.9 (m, 11H), 2.24(s, 3H), 2.85(q, 2H, J = 7.5 Hz), 3.81(s, 2H), 4.08(br-s, 2H), 8.34(s, 1H), 12.65(br-s, 1H), 13.84(s, 1H) |
| X-144 | | DMSO-d6 1.00-1.25(m, 8H), 1.40-1.82(m, 10H), 2.16(s, 3H), 2.22-2.36(br, 2H), 2.64-2.84(br, 4H), 3.97(br, 2H), 8.11(s, 1H), 12.11(br, 1H), 12.58(s, 1H) |
| X-162 | | DMSO-d6 1.02-1.82(m, 19H), 1.10(t, 3H, J = 7.5), 2.13-2.26(m, 2H), 2.17(s, 3H), 2.77(q, 2H, J = 7.5), 2.78 (s, 2H), 3.85-4.10(br, 2H), 8.11(s, 1H), 9.92(s, 1H), 11.88(brs, 1H) |
| X-173 | | DMSO-d6 0.90(dd, 6H, J = 5.4 and 10.8), 1.02-1.22(m, 5H), 1.10(t, 3H, J = 7.5), 1.46-1.84(m, 9H), 2.18(s, 3H), 2.79 (q, 2H, J = 7.5), 3.80-4.20(br, 2H), 4.46(m, 1H), 8.14(s, 1H), 10.14 (d, 1H, J = 8.1), 12.73(brs, 1H) |
| X-179 | | DMSO-d6 0.86(t, 6H, J = 6.3), 1.01-1.85(m, 16H), 1.10(t, 3H, J = 7.5), 2.17(s, 3H), 2.20(t, 2H, J = 7.5), 2.78(q, 2H, J = 7.5), 3.80-4.22(m, 3H), 8.13(s, 1H), 9.65 (d, 1H, J = 9.0), 12.02(brs, 1H) |

TABLE 109-continued

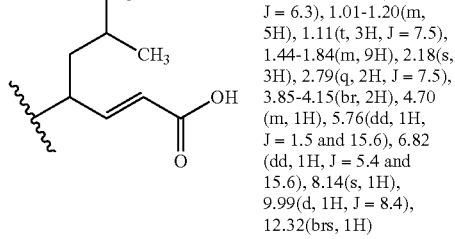

| Comp. No. | Q | ¹H-NMR(CDCl₃/TMS) δ |
|---|---|---|
| X-184 | | DMSO-d6 0.89(t, 6H, J = 6.3), 1.01-1.20(m, 5H), 1.11(t, 3H, J = 7.5), 1.44-1.84(m, 9H), 2.18(s, 3H), 2.79(q, 2H, J = 7.5), 3.85-4.15(br, 2H), 4.70 (m, 1H), 5.76(dd, 1H, J = 1.5 and 15.6), 6.82 (dd, 1H, J = 5.4 and 15.6), 8.14(s, 1H), 9.99(d, 1H, J = 8.4), 12.32(brs, 1H) |
| X-203 | | DMSO-d6 0.86(d, 3H, J = 6.3), 0.87(d, 3H, J = 6.3), 1.00-1.24(m, 5H), 1.10(t, 3H, J = 7.5), 1.33(m, 1H), 1.45-1.82 (m, 8H), 2.17(s, 3H), 2.36-2.52(m, 2H), 2.77 (q, 2H, J = 7.5), 3.70-4.10 (br, 2H), 4.32(m, 1H), 8.13(s, 1H), 9.83(d, 1H, J = 8.7), 12.11(brs, 1H) |

TABLE 110

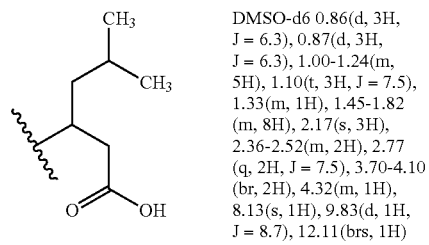

| Comp. No. | Q | ¹H-NMR (CDCl₃/TMS) δ |
|---|---|---|
| X-213 | | DMSO-d6 1.02-1.24 (m, 4H), 1.14(t, 3H, J = 7.5), 1.48-1.90(m, 7H), 2.23(s, 3H), 2.83(q, 2H, J = 7.5), 3.90-4.20(br, 2H), 6.45(d, 1H, J = 15.9), 7.55(d, 1H, J = 15.9), 7.68(d, 2H, J = 8.7), 7.76(d, 2H, J = 8.7), 8.29(s, 1H), 12.29 (brs, 1H), 12.45(s, 1H) |

TABLE 110-continued

[Structure: pyridinone with CH3, CH3 (ethyl shown as CH3-CH2), C(=O)NH-Q, N-CH2-cyclohexyl, 2-oxo]

| Comp. No. | Q | ¹H-NMR (CDCl₃/TMS) δ |
|---|---|---|
| X-218 | [structure: C(CH3)(Et)(Et)CH2COOH type with two ethyl groups on quaternary C bearing CH2COOH] | DMSO-d6 0.57(t, 6H, J = 7.2), 0.80-0.98(m, 8H), 1.24-1.72(m, 10H), 1.94(s, 3H), 2.48-2.60(m, 4H), 3.73(brs, 2H), 7.88(s, 1H), 9.58(s, 1H), 11.76(brs, 1H) |
| X-221 | [structure: 4-(OCH2COOH)phenyl] | DMSO-d6 1.04-1.27 (m, 5H), 1.13(t, 3H, J = 7.2), 1.48-1.88 (m, 6H), 2.22(s, 3H), 2.82(q, 2H, J = 7.2), 3.90-4.20(br 2H), 4.65(s, 2H), 6.90 (d, 2H, J = 9.0), 7.61(d, 2H, J = 9.0), 8.26(s, 1H), 12.12(s, 1H), 12.99(brs, 1H) |
| XI-003 | [structure: 3-(OCH2COOH)phenyl] | DMSO-d6 1.04-1.27 (m, 5H), 1.13(t, 3H, J = 7.2), 1.48-1.88 (m, 6H), 2.22(s, 3H), 2.82(q, 2H, J = 7.2), 3.90-4.15 (br, 2H), 4.68 (s, 2H), 6.65(m, 1H), 7.14-7.29(m, 2H), 7.45(m, 1H), 8.28(s, 1H), 12.26(s, 1H), 13.01(brs, 1H) |
| XI-011 | [structure: 4-(CH2CH2COOH)phenyl] | DMSO-d6 1.04-1.25 (m, 5H), 1.13(t, 3H, J = 7.5), 1.48-1.88 (m, 6H), 2.22(s, 3H), 2.47-2.56(m, 2H), 2.75-2.87(m, 4H), 3.90-4.20(br, 2H), 7.20(d, 2H, J = 8.4), 7.60(d, 2H, J = 8.4), 8.27(s, 1H), 12.11(brs, 1H), 12.19(s, 1H) |
| XI-033 | [structure: spiro-cyclohexyl with COOH on the quaternary carbon] | DMSO-d6 1.00-1.24 (m, 7H), 1.30-2.20 (m, 23H), 2.16(s, 3H), 2.58-2.70(m, 2H), 2.76(m, 2H), 3.97(br, 2H), 8.08(s, 1H), 10.00 (s, 1H), 12.19(br, 1H) |
| XI-126 | [structure: 2-pyrimidinyl-5-CH=CH-COOH] | DMSO-d6 1.14(t, 3H, J = 7.5), 1.15(m, 5H), 1.57-1.79(m, 6H), 2.83 (t, 3H, J = 7.5), 4.06 (s, 2H), 6.73(d, 1H, J = 16.2), 7.56(d, 1H, 16.2), 8.29(s, 1H), 9.02(s, 2H), 13.04(s, 1H) |

TABLE 111

[Structure: pyridinone with CH3, CH2CH3, C(=O)NH-Q, N-CH2-cyclohexyl, 2-oxo]

| Comp. No. | Q | ¹H-NMR(CDCl₃/TMS) δ |
|---|---|---|
| XI-134 | [structure: CH(COOH)CH2C(CH3)3, neopentyl on α-C of acid] | DMSO-d6 0.92(s, 9H), 1.11(m, 8H), 1.43-1.81 (m, 8H), 2.17(s, 3H), 2.78(m, 2H), 4.01(m, 2H), 4.49(m, 1H), 8.13 (s, 1H), 10.16(d, 1H, J = 5.7) |
| XI-135 | [structure: CH(CH2C(CH3)3)CH2COOH] | DMSO-d6 0.88(s, 9H), 1.10(m, 8H), 1.43-1.80 (m, 6H), 2.15(m, 1H), 2.17(s, 3H), 2.57(m, 1H), 2.77(m, 2H), 3.99(m, 2H), 4.26(m, 1H), 8.11 (s, 1H), 9.96(d, 1H, J = 9.6) |
| XI-155 | [structure: CH(CH2C(CH3)3)CH2CH2COOH] | DMSO-d6 0.86(s, 9H), 1.00-1.18(m, 8H), 1.38-1.82(m, 10H), 2.17(s, 3H), 2.18(t, 2H, J = 7.5), 2.71-2.83(m, 2H), 3.80-4.16(m, 3H), 8.13(s, 1H), 9.76(d, 1H, J = 9.3), 11.98(brs, 1H) |

TABLE 111-continued

| Comp. No. | Q | $^1$H-NMR(CDCl$_3$/TMS) δ |
|---|---|---|
| XI-157 | (thiazole-acetic acid group) | DMSO-d6 1.04-1.30(m, 8H), 1.48-1.90(m, 6H), 2.24(s, 3H), 2.84(q, 2H, J = 7.8), 3.82(s, 2H), 3.90-4.20(m, 2H), 7.31 (s, 1H), 8.31(s, 1H), 12.63(br s, 1H), 13.39(s, 1H) |
| XI-190 | (cyclohexyl-acetic acid group with ethyl) | DMSO-d6 1.11(t, 3H, J = 7.5), 1.03-1.80(m, 20H), 2.17(s, 3H), 2.14-2.24(br, 2H), 2.77(q, 2H, J = 7.5), 3.40(d, 2H, J = 5.7), 4.00(br, 2H), 8.11(s, 1H), 10.01(t, 1H, J = 6.0) |
| XI-191 | (norbornyl-carboxylic acid group) | DMSO-d6 1.00-1.85(m, 20H), 1.10(t, 3H, J = 7.8), 2.17(s, 2H), 2.10-2.70(m, 2H), 2.79(q, 2H, J = 7.2), 3.80-4.20(m, 2H), 8.08(s, 1H), 10.04(s, 1H) |
| XI-194 | (tetrahydropyran-acetic acid group) | DMSO-d6 1.00-1.82(m, 12H), 1.11(t, 3H, J = 7.5), 2.10-2.30(m, 2H), 2.17 (s, 2H), 2.78(q, 2H, J = 7.5), 2.84(s, 2H), 3.20-4.20(m, 6H), 8.11(s, 1H), 10.10(s, 1H) |

TABLE 112

| Comp. No. | Q | $^1$H-NMR (CDCl$_3$/TMS) δ |
|---|---|---|
| XI-216 | (cyclopentyl-acetic acid) | 1.17(t, 3H, J = 7.5), 1.06-1.26(m, 4H), 1.58-1.88(m, 11H), 2.17(m, 2H), 2.20(s, 3H), 2.78(q, 2H, J = 7.5), 3.04(s, 2H), 4.00(s, 2H), 8.31(s, 1H), 10.67(s, 1H) |
| XI-220 | (cyclobutyl-acetic acid) | DMSO-d6 1.07-1.24(m, 8H), 1.46-1.92(m, 8H), 2.16(s, 3H), 2.17-2.30 (m, 4H), 2.74-2.84(q, 2H, J = 7.5), 2.87(s, 2H), 3.96(br, 2H), 8.09(s, 1H), 10.06(s, 1H), 12.01(br, 1H) |
| XI-231 | (tetrahydropyran-propanoic acid) | DMSO-d6 1.00-1.22(m, 5H), 1.10(t, 3H, J = 7.5), 1.46-1.82 (m, 8H), 2.00-2.18(m, 6H), 2.17 (s, 3H), 2.78(q, 2H, J = 7.5), 3.40-3.52(m, 2H), 3.62-3.74(m, 2H), 3.85-4.15(br, 2H), 8.11(s, 1H), 9.97(s, 1H), 12.08(brs, 1H) |
| XI-246 | (pyridyl-acetic acid) | DMSO-d6 1.05-1.25(m, 8H), 1.47-1.77(m, 6H), 2.23(s, 3H), 2.82(q, 2H, J = 6.9), 3.60(s, 2H), 3.90-4.20(m, 2H), 7.72(dd, 1H, J = 2.4, 8.7), 8.19-8.25(m, 2H), 8.30(s, 1H), 12.49(br s, 1H), 12.61(s, 1H) |
| XI-280 | (pyridyl-acrylic acid) | DMSO-d6 1.04-1.26(m, 8H), 1.50-1.90(m, 6H), 2.23(s, 3H), 2.83(q, 2H, J = 7.5), 3.95-4.20 (m, 2H), 6.58(d, 1H, J = 16.2), 7.59(d, 1H, J = 15.9), 8.22(dd, 1H, J = 2.2, 8.4), 8.30(d, 1H, J = 8.1), 8.31(s, 1H), 8.61(d, 1H, J = 2.1), 12.36 (br s, 1H), 12.82(s, 1H) |

TABLE 113

Structure (parent for Q substituent): 5-methyl-6-ethyl-1-(4-fluorobenzyl)-2-oxo-1,2-dihydropyridine-3-carboxamide with N–H–Q.

| Comp. No. | Q | ¹H-NMR (CDCl₃/TMS) δ |
|---|---|---|
| X-26 | 5-(carboxymethyl)-1,2,4-thiadiazol-3-yl | DMSO-d6 1.06(t, 3H, J = 7.5 Hz), 2.24(s, 3H), 2.75(q, 2H, J = 7.5 Hz), 3.79(s, 2H), 5.49(br-s, 2H), 7.13-7.28(m, 4H), 8.42(s, 1H), 13.65(s, 1H) |
| X-45 | 2-(1-carboxybutyl)thiazol-4-yl | DMSO-d6 0.85(t, 3H, J = 7.2 Hz), 1.05(t, 3H, J = 7.2 Hz), 1.18-1.25(m, 2H), 1.70-1.95(m, 2H), 2.22(s, 3H), 2.31(m, 2H), 3.60(t, 1H, J = 7.8 Hz), 5.47(br-s, 2H), 6.98(s, 1H), 7.13-7.28(m, 4H), 8.37(s, 1H), 13.28(br-s, 1H) |
| X-63 | 4-carboxy-4,5,6,7-tetrahydrobenzothiazol-2-yl | DMSO-d6 1.05(t, 3H, J = 7.2 Hz), 1.63-2.05(m, 4H), 2.22(s, 3H), 2.69-2.76(m, 4H), 3.55(t, 1H, J = 6.0 Hz), 5.45-5.48(m, 2H), 7.12-7.24(m, 4H), 8.36(s, 1H), 13.19(s, 1H) |
| X-121 | 4-carboxytetrahydropyran-4-yl | DMSO-d6 1.04(t, 3H, J = 7.5 Hz), 2.17(s, 3H), 2.66(q, 2H, J = 7.5 Hz), 3.43-3.51(m, 2H), 3.71-3.76(m, 2H), 5.44(br-s, 2H), 7.17(d, 4H, J = 8.1 Hz), 8.19(s, 1H), 10.31(s, 1H), 12.50(br-s, 1H) |
| X-124 | 2-carboxycyclohex-1-en-1-yl | DMSO-d6 1.04(t, 3H, J = 7.5), 1.50-1.67(m, 4H), 2.17(s, 3H), 2.20-2.36(br, 2H), 2.60-2.76(br, 2H), 2.76-2.84(br, 2H), 5.40(br, 2H), 7.18(d, 4H, J = 7.5), 8.20(s, 1H), 12.22(br, 1H), 12.56(s, 1H) |

TABLE 113-continued

| Comp. No. | Q | ¹H-NMR (CDCl₃/TMS) δ |
|---|---|---|
| X-135 | 6-[(E)-2-carboxyvinyl]pyridin-3-yl (via pyridine N-linked) | DMSO-d6 1.07(t, 3H, J = 7.2), 2.24(s, 3H), 2.74(q, 2H, J = 7.2), 5.48(s, 2H), 6.63(d, 1H, J = 16.2), 7.15-7.26(m, 4H), 7.59(d, 1H, J = 16.2), 8.22(dd, 1H, J = 2.1 and 8.7), 8.31(d, 1H, J = 8.7), 8.40(s, 1H), 8.60(d, 1H, J = 1.8), 12.42(br, 1H), 12.68(s, 1H) |
| X-136 | 6-(2-carboxyethyl)pyridin-3-yl | DMSO-d6 1.07(t, 3H, J = 7.2), 2.23(s, 3H), 2.55(t, 2H, J = 7.5), 2.71-2.82(m, 4H), 5.47(s, 2H), 7.15-7.25(m, 4H), 7.71(d, 1H, J = 9.0), 8.16-8.20(m, 2H), 8.38(s, 1H), 12.25(br, 1H), 12.43(s, 1H) |

TABLE 114

Structure (parent for Q substituent): 5-methyl-6-ethyl-1-(4-fluorobenzyl)-2-oxo-1,2-dihydropyridine-3-carboxamide with N–H–Q.

| Comp. No. | Q | ¹H-NMR(CDCl₃/TMS) δ |
|---|---|---|
| X-150 | 2-carboxycyclopent-1-en-1-yl | DMSO-d6 1.04(t, 3H, J = 7.5), 1.72-1.90(m, 2H), 2.18(s, 3H), 1.80(t, 2H, J = 7.5), 2.42(t, 2H, J = 8.1), 2.62-2.76(br, 2H), 3.18(t, 2H, J = 7.8), 5.42(br, 2H), 7.17(d, 4H, J = 7.5), 8.27(s, 1H), 12.10(br, 1H), 12.72(s, 1H) |

TABLE 114-continued

| Comp. No. | Q | ¹H-NMR(CDCl₃/TMS) δ |
|---|---|---|
| X-163 | cyclohexyl-CH₂-COOH | DMSO-d6 1.04(t, 3H, J = 7.5), 1.10-1.58(m, 8H), 2.14-2.25(m, 2H), 2.18(s, 3H), 2.65(q, 2H, J = 7.5), 2.79(s, 2H), 5.42(brs, 2H), 7.10-7.23(m, 4H), 8.21(s, 1H), 9.82(s, 1H), 11.88(brs, 1H) |
| X-164 | CH₃CH₂CH₂CH(COOH)- | DMSO-d6 0.87(t, 3H, J = 7.5), 1.05(t, 3H, J = 7.5), 1.25-1.37(m, 2H), 1.60-1.82(m, 2H), 2.19(s, 3H), 2.67(q, 2H, J = 7.5), 4.44(m, 1H), 5.41(br, 2H), 7.14-7.22(m, 4H), 8.23(s, 1H), 10.10(d, 1H, J = 7.8) |
| X-165 | 2-thiazolyl-CH₂-COOH | DMSO-d6 1.06(t, 3H, J = 7.5), 2.24(s, 3H), 2.73(q, 2H, J = 7.8), 3.81(s, 2H), 5.48(br, 2H), 7.14-7.25(m, 4H), 7.29(s, 1H), 8.39(s, 1H), 13.24(s, 1H) |
| X-172 | (CH₃)₂CHCH₂CH(COOH)- | DMSO-d6 0.85-0.94(m, 6H), 1.05(t, 3H, J = 7.5), 1.54-1.70(m, 3H), 2.19(s, 3H), 2.58-2.75(m, 2H), 4.47(m, 1H), 5.29-5.55(m, 2H), 7.11-7.23(m, 4H), 8.23(s, 1H), 10.05(d, 1H, J = 7.8), 12.74(brs, 1H) |
| X-180 | (CH₃)₂CHCH₂CH(CH₂CH₂COOH)- | DMSO-d6 0.85(dd, 6H, J = 3.3 and 6.6), 1.04(t, 3H, J = 7.5), 1.22-1.45(m, 2H), 1.48-1.64(m, 2H), 1.77(m, 1H), 2.18(s, 3H), 2.20(t, 2H, J = 7.5), 2.66(q, 2H, J = 7.5), 4.05(m, 1H), 5.41(brs, 2H), 7.11-7.22(m, 4H), 8.23(s, 1H), 9.54(d, 1H, J = 9.0), 12.02(brs, 1H) |

TABLE 115

| Comp. No. | Q | ¹H-NMR(CDCl₃/TMS) δ |
|---|---|---|
| X-185 | (CH₃)₂CHCH₂CH(CH=CHCOOH)- | DMSO-d6 0.88(dd, 6H, J = 3.6 and 6.3), 1.05(t, 3H, J = 7.5), 1.43-1.53(m, 2H), 1.61(m, 1H), 2.19(s, 3H), 2.67(q, 2H, J = 7.5), 4.71(m, 1H), 5.306-5.45(m, 2H), 5.76(dd, 1H, J = 1.5 and 15.6), 6.81(dd, 1H, J = 5.7 and 15.6), 7.12-7.23(m, 4H), 8.24(s, 1H), 9.88(d, 1H, J = 8.1), 12.33(brs, 1H) |
| X-187 | 2-thiazolyl-C(cyclopentyl)-COOCH₃ | 1.20(t, 3H, J = 7.5 Hz), 1.68-1.74(m, 4H), 2.14-2.23(m, 2H), 2.25(s, 3H), 2.32-2.44(m, 2H), 2.73(q, 2H, J = 7.5 Hz), 3.67(s, 3H), 5.46(br-s, 2H), 6.69(s, 1H), 7.00-7.18(m, 4H), 8.46(s, 1H), 13.06(s, 1H) |
| X-188 | 2-thiazolyl-C(cyclopentyl)-COOH | DMSO-d6 1.06(t, 3H, J = 7.5 Hz), 1.60-1.73(m, 4H), 1.90-2.10(m, 2H), 2.22(s, 3H), 2.23-2.29(m, 2H), 2.75(q, 2H, J = 7.5 Hz), 5.48(br-s, 2H), 7.00(s, 1H), 7.13-7.27(m, 4H), 8.37(s, 1H), 12.21(br-s, 1H), 13.26(s, 1H) |
| X-193 | CH₃CH₂CH₂CH₂CH₂CH(COOH)- | DMSO-d6 0.84(t, 3H, J = 6.6), 1.05(t, 3H, J = 7.2), 1.27(br, 4H), 1.60-1.90(brm, 2H), 2.19(s, 3H), 2.60-2.78(brm, 2H), 4.44(m, 1H), 5.30-5.50(m, 2H), 7.10-7.21(m, 4H), 8.23(s, 1H), 10.11(d, 1H, J = 7.8), 12.78(br, 1H) |
| X-197 | cyclohexyl-C(CH₂-)-CH₂COOH | DMSO-d6 1.04(t, 3H, J = 7.5), 1.22-1.58(m, 10H), 2.17(s, 2H), 2.18(s, 3H), 2.65(q, 2H, J = 7.5), 3.40(d, 2H, J = 6.3), 5.43(brs, 2H), 7.11-7.21(m, 4H), 8.25(s, 1H), 9.94(t, 1H, J = 5.7), 12.15(brs, 1H) |

TABLE 115-continued

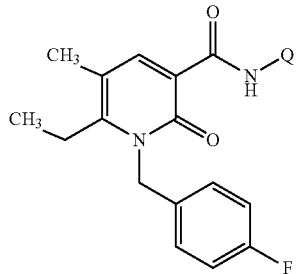

| Comp. No. | Q | $^1$H-NMR(CDCl$_3$/TMS) δ |
|---|---|---|
| X-204 | 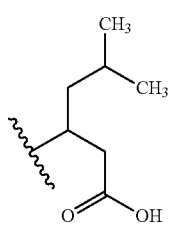 | DMSO-d6 0.86(d, 6H, J = 6.3), 1.04(t, 3H, J = 7.5), 1.33(m, 1H), 1.46-1.66(m, 2H), 2.18 (s, 3H), 2.36-2.53(m, 2H), 2.66(q, 2H, J = 7.5), 4.34(m, 1H), 5.28-5.54 (m, 2H), 7.10-7.23(m, 4H), 8.23(s, 1H), 9.76(d, 1H, J = 8.7), 12.14(brs, 1H) |

TABLE 116

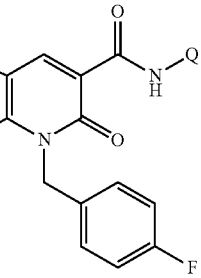

| Comp. No. | Q | $^1$H-NMR (CDCl$_3$/TMS) δ |
|---|---|---|
| X-214 | 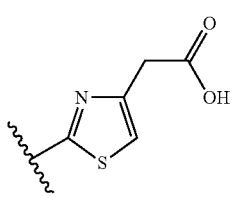 | DMSO-d6 1.07(t, 3H, J = 7.5), 2.34(s, 3H), 2.71(q, 2H, J = 7.5), 5.49(brs, 2H), 6.44(d, 1H, J = 15.9), 7.14-7.24(m, 4H), 7.55(d, 1H, J = 15.9), 7.67(d, 2H, J = 9.0), 7.75(d, 2H, J = 9.0), 8.38(s, 1H), 12.29 (brs, 1H), 12.33(s, 1H) |
| X-216 | 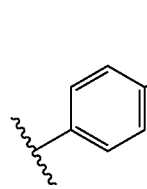 | DMSO-d6 0.77(t, 6H, J = 6.9), 1.02(t, 3H, J = 7.5), 1.67-1.90(m, 4H), 2.16(s 3H), 2.62 (m, 2H), 2.74(s, 2H), 5.38(s, 2H), 7.12-7.20 (m, 4H), 8.19(s, 1H), 9.69(s, 1H), 11.80(brs, 1H) |

TABLE 116-continued

| Comp. No. | Q | $^1$H-NMR (CDCl$_3$/TMS) δ |
|---|---|---|
| X-222 | 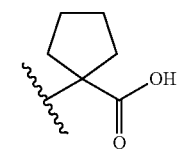 | DMSO-d6 1.07(t, 3H, J = 7.5), 2.24(s, 3H), 2.75(q, 2H, J = 7.5), 3.60(s, 2H), 5.49(s, 2H), 7.02(s, 1H), 7.15-7.30(m, 4H), 8.39(s, 1H), 12.40(br s, 1H), 13.31(s, 1H) |
| X-224 | 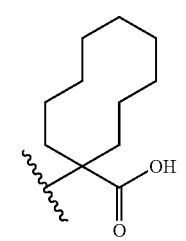 | DMSO-d6 1.04(t, 3H, J = 7.5), 1.60-1.78(m, 4H), 1.81-1.96(m, 2H), 2.06-2.24(m, 5H), 2.60-2.78(m, 2H), 5.42(br, 2H), 7.10-7.24(m, 4H), 8.19(s, 1H), 10.10(s, 1H), 12.32(br, 1H) |
| X-231 | 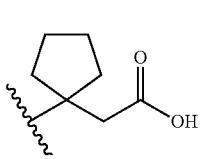 | DMSO-d6 1.05(t, 3H, J = 7.5), 1.32-1.64(m, 14H), 1.79-1.96(m, 2H), 2.04-2.24(m, 5H), 2.60-2.78(m, 2H), 5.42(br, 2H), 7.10-7.24(m, 4H), 8.18(s, 1H), 9.91(s, 1H), 12.21(br, 1H) |
| X-234 | 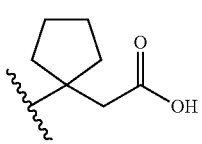 | DMSO-d6 1.04(t, 3H, J = 7.5), 1.54-1.84(m, 6H), 2.00-2.15(m, 2H), 2.18(s, 3H), 2.56-2.72(m, 2H), 2.87(s, 2H), 5.40(br, 2H), 7.08-7.24 (m, 4H), 8.20(s, 1H), 9.82(s, 1H), 11.93(br, 1H) |
| X-238 | 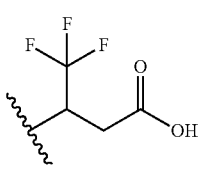 | DMSO-d6 1.05(t, 3H, J = 7.2), 2.20(s, 3H), 2.60-2.75(m, 3H), 2.86(dd, 1H, J = 5.1 and 17.1), 5.17(m, 1H), 5.42(br s, 2H), 7.10-7.25(m, 4H), 10.31(d, 1H, J = 9.3), 12.68(br s, 1H) |

TABLE 117

Structure: 3-carboxamide-N-Q, 5-methyl, 6-ethyl, 1-(4-fluorobenzyl)-2-oxo-1,2-dihydropyridine

| Comp. No. | Q | $^1$H-NMR (CDCl$_3$/TMS) δ |
|---|---|---|
| X-239 | cycloheptyl with -COOH | DMSO-d6 1.05(t, 3H, J = 7.5), 1.37-1.63(m, 10H), 1.90-2.14(m, 4H), 2.18(s, 3H), 2.66(q, 2H, J = 7.5), 5.42(brs, 2H), 7.11-7.24(m, 4H), 8.17(s, 1H), 10.02(s, 1H), 12.19(brs, 1H) |
| XI-014 | 4-(carboxymethoxy)phenyl | DMSO-d6 1.06(t, 3H, J = 7.5), 2.23(s, 3H), 2.70(q, 2H, J = 7.5), 4.65(s, 2H), 5.48(brs, 2H), 6.90(d, 2H, J = 9.0), 7.14-7.22(m, 4H), 7.61(d, 2H, J = 9.0), 8.36(s, 1H), 12.00(s, 1H), 12.98(brs, 1H) |
| XI-022 | 5-(carboxymethoxy)pyridin-2-yl | DMSO-d6 1.07(t, 3H, J = 7.5), 2.23(s, 3H), 2.71(q, 2H, J = 7.5), 4.79(s, 2H), 5.48(brs, 2H), 6.90(d, 1H, J = 9.0), 7.14-7.23(m, 4H), 8.07(dd, 1H, J = 2.7 and 9.0), 8.37(s, 1H), 8.43(d, 1H, J = 2.7), 12.00(s, 1H), 12.81(brs, 1H) |
| XI-023 | 5-(carboxymethylthio)-1,3,4-thiadiazol-2-yl | DMSO-d6 1.07(t, 3H, J = 7.5), 2.25(s, 3H), 2.76(q, 2H, J = 7.8), 4.12(s, 2H), 5.50(s, 2H), 7.14-7.29(m, 4H), 8.41(s, 1H), 13.06(br s, 1H), 13.65(s, 1H) |
| XI-031 | cyclohexylidene acetic acid | DMSO-d6 1.05(t, 3H, J = 7.2), 1.54(br, 6H), 2.15-2.25(m, 7H), 2.68(q, 2H, J = 7.5), 5.45(s, 2H), 7.14-7.24(m, 4H), 8.24(s, 1H), 11.14(s, 1H), 12.41(br s, 1H) |
| XI-041 | 1-(carboxymethyl)cyclobutyl | 1.16(t, 3H, J = 7.5), 1.86-2.18(m, 2H), 2.21(s, 3H), 2.34-2.39(m, 4H), 2.60-2.78(q, 2H, J = 7.5), 3.08(s, 2H), 5.41(s, 2H), 7.00-7.10(m, 4H), 8.38(s, 1H), 10.52(s, 1H) |

TABLE 117-continued

| Comp. No. | Q | $^1$H-NMR (CDCl$_3$/TMS) δ |
|---|---|---|
| XI-044 | 2-methoxymethyl-carboxy-ethyl | DMSO-d6 1.07(t, 3H, J = 7.5), 2.19(s, 3H), 2.60-2.67(m, 2H), 3.25(s, 3H), 3.61(dd, 1H, J = 3.9 and 9.9), 3.77(dd, 1H, J = 3.9 and 9.9), 4.62(m, 1H), 5.42(br, 2H), 7.12-7.22(m, 4H), 8.24(s, 1H), 10.22(d, 1H, J = 7.8) |

TABLE 118

Structure: same pyridone core

| Comp. No. | Q | $^1$H-NMR(CDCl$_3$/TMS) δ |
|---|---|---|
| XI-046 | 6-(carboxymethyl)pyridin-3-yl | DMSO-d6 1.07(t, 3H, J = 7.5), 2.24(s, 3H), 2.73(q, 2H, J = 7.5), 3.60(s, 2H), 5.48(brs, 2H), 7.13-7.26(m, 4H), 7.72(dd, 1H, J = 2.1 and 8.4), 8.19(d, 1H, J = 2.1), 8.22(d, 1H, J = 8.4), 8.39(s, 1H), 12.40(brs, 1H), 12.47(s, 1H) |
| XI-048 | 4-(methoxymethyl)-carboxybutyl | DMSO-d6 1.04(t, 3H, J = 7.5), 1.57-1.92(m, 2H), 2.19(s, 3H), 2.18-2.26(m, 2H), 2.66(q, 2H, J = 7.2), 3.25(s, 3H), 3.30-3.45(m, 2H), 4.11(m, 1H), 5.41(brs, 2H), 7.12-7.21(m, 4H), 8.23(s, 1H), 9.75(d, 1H, J = 8.7), 12.05(brs, 1H) |

TABLE 118-continued

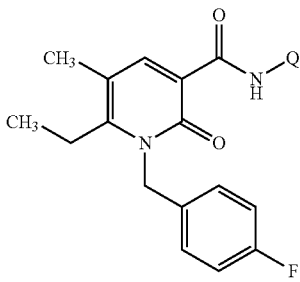

| Comp. No. | Q | ¹H-NMR(CDCl₃/TMS) δ |
|---|---|---|
| XI-052 | 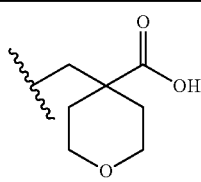 | DMSO-d6 1.04(t, 3H, J = 7.5), 1.40-1.49(m, 2H), 1.85-1.91(m, 2H), 2.18(s, 3H), 2.62-2.70 (m, 2H), 3.33-3.41(m, 2H), 3.52(d, 2H, J = 6.3), 3.70-3.74(m, 2H), 5.41 (s, 2H), 7.11-7.20(m, 4H), 8.23(s, 1H), 9.96(t, 1H, J = 6.3), 12.61(br, 1H) |
| XI-057 | 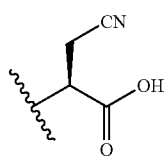 | DMSO-d6 1.06(t, 3H, J = 7.5), 2.20(s, 3H), 2.69(q, 2H, J = 7.5), 3.06-3.23(m, 2H), 4.79(q, 1H, J = 6.0), 5.32-5.54(m, 2H), 7.13-7.23(m, 4H), 8.26(s, 1H), 10.41(d, 1H, J = 7.2), 13.47(brs, 1H) |

TABLE 118-continued

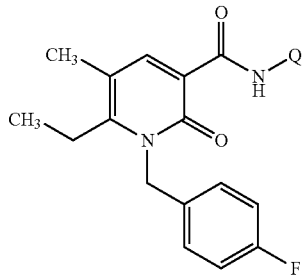

| Comp. No. | Q | ¹H-NMR(CDCl₃/TMS) δ |
|---|---|---|
| XI-058 | 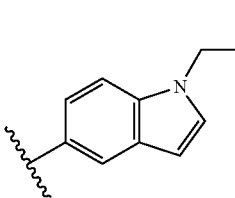 | DMSO-d6 1.07(t, 3H, J = 7.5), 2.24(s, 3H), 2.71(q, 2H, J = 7.2), 4.99(s, 2H), 5.49(s, 2H), 6.42(d, 1H, J = 3.0), 7.13-7.38 (m, 7H), 8.07(d, 1H, J = 1.8), 8.38(s, 1H), 12.06(s, 1H), 12.94(br s, 1H) |
| XI-070 | 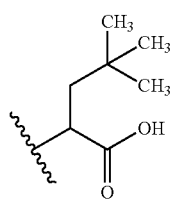 | DMSO-d6 0.91(s, 9H), 1.05(t, 3H, J = 7.5), 1.54(dd, 1H, J = 9.0 and 14.1), 1.76(dd, 1H, J = 3.0 and 14.1), 2.19 (s, 3H), 2.67-2.76(m, 2H), 4.49(m, 1H), 5.28-5.56(m, 2H), 7.11-7.23(m, 4H), 8.23(s, 1H), 10.04 (d, 1H, J = 8.1), 12.65(brs, 1H) |

TABLE 119

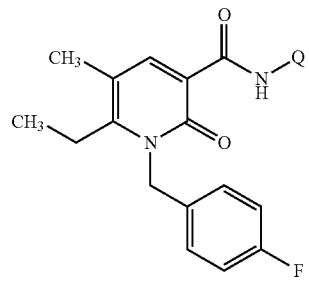

| Comp. No. | Q | ¹H-NMR(CDCl₃/TMS) δ |
|---|---|---|
| XI-072 | 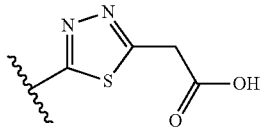 | DMSO-d6 1.07(t, 3H, J = 7.5), 2.25(s, 3H), 2.76(q, 2H, J = 7.5), 4.14(s, 2H), 5.51(br s, 2H), 7.15-7.28(m, 4H), 8.43(s, 1H), 13.00(br s, 1H), 13.58(s, 1H) |
| XI-075 | 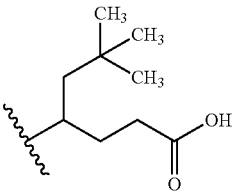 | DMSO-d6 0.86(s, 9H), 1.04(t, 3H, J = 7.2), 1.33-1.45(m, 2H), 1.50-1.81(m, 2H), 2.13-2.22(m, 2H), 2.18(s, 3H), 2.66(q, 2H, J = 7.2), 4.10(m, 1H), 5.41(brs, 2H), 7.10-7.22(m, 4H), 8.23(s, 1H), 9.64(d, 1H, J = 9.0), 11.99(brs, 1H) |

TABLE 119-continued
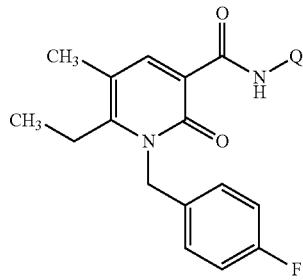
| Comp. No. | Q | ¹H-NMR(CDCl₃/TMS) δ |
|---|---|---|
| XI-077 | 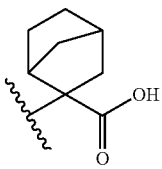 | DMSO-d6 1.06(t, 3H, J = 7.5), 2.22(s, 3H), 2.71(q, 2H, J = 7.5), 4.85(s, 2H), 5.47(s, 2H), 7.13-7.25(m, 4H), 7.37(d, 1H, J = 1.5), 7.45(d, 1H, J = 1.5), 8.32(s, 1H), 12.01(s, 1H), 13.10(br s, 1H) |
| XI-079 | 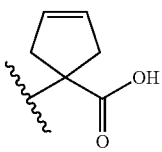 | DMSO-d6 1.05(t, 3H, J = 6.6), 1.08-1.84(m, 10H), 2.22(m, 1H), 2.44(m, 1H), 2.60-2.78(m, 3H), 5.43(br s, 2H), 7.10-7.22(m, 4H), 8.17(s, 1H), 10.30(s, 1H), 12.13(br, 1H) |
| XI-081 | | DMSO-d6 1.04(t, 3H, J = 7.5), 2.18(s, 3H), 2.58(d, 2H, J = 15.6), 2.67(q, 2H, J = 7.5), 3.01(d, 2H, J = 15.6), 5.41(brs, 2H), 5.66(s, 2H), 7.10-7.22(m, 4H), 8.20(s, 1H), 10.21(s, 1H), 12.45(brs, 1H) |
| XI-083 | 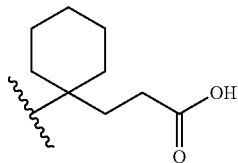 | DMSO-d6 1.04(t, 3H, J = 7.5), 1.04-1.60(m, 7H), 1.99-2.22(m, 6H), 2.18(s, 3H), 2.58-2.73(m, 3H), 5.43(s, 2H), 7.12-7.22(m, 4H), 8.22(s, 1H), 9.71(s, 1H), 11.95(br, 1H) |
| XI-085 | 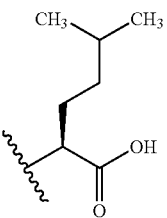 | DMSO-d6 0.83(d, 6H, J = 6.6), 1.05(t, 3H, J = 7.5), 1.10-1.28(m, 2H), 1.51(m, 1H), 1.61-1.88(m, 2H), 2.19(s, 3H), 2.59-2.75(m, 2H), 4.44(m, 1H), 5.30-5.55(m, 2H), 7.11-7.22(m, 4H), 8.23(s, 1H), 10.12(d, 1H, J = 7.5), 12.78(brs, 1H) |

TABLE 120

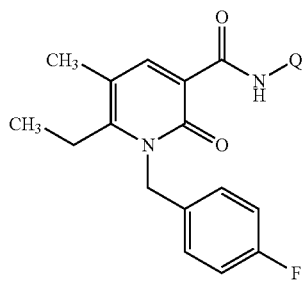

| Comp. No. | Q | $^1$H-NMR(CDCl$_3$/TMS) δ |
|---|---|---|
| XI-087 | (2-carboxymethyl-phenyl) | DMSO-d6 1.06(t, 3H, J = 7.5), 2.22(s, 3H), 2.70(q, 2H, J = 7.8), 3.65(s, 2H), 5.48(s, 2H), 7.06-7.33(m, 7H), 8.07(d, 1H, J = 8.1), 8.36(s, 1H), 11.95(s, 1H), 12.40(br s, 1H) |
| XI-089 | (4-carboxymethyl-2-fluoro-phenyl) | DMSO-d6 1.07(t, 3H, J = 7.4), 2.24(s, 3H), 2.71(q, 2H, J = 7.5), 3.57(s, 2H), 5.49(br s, 2H), 7.09(d, 1H, J = 8.7), 7.17-7.23(m, 5H), 8.38(s, 1H), 8.39(t, 1H, J = 8.4), 12.37(br s, 2H) |
| XI-091 | (4-(carboxymethoxy)-2-trifluoromethyl-phenyl) | DMSO-d6 1.07(t, 3H, J = 7.5), 2.22(s, 3H), 2.70(q, 2H, J = 7.5), 4.80(s, 2H), 5.48(s, 2H), 7.16-7.23(m, 5H), 7.26(dd, 1H, J = 3.0, 9.0), 8.08(d, 1H, J = 9.0), 8.37(s, 1H), 12.15(s, 1H), 13.05(br, 1H) |
| XI-094 | (4-(carboxymethoxy)-2-fluoro-phenyl) | DMSO-d6 1.06(t, 3H, J = 7.5), 2.23(s, 3H), 2.71(q, 2H, J = 7.5), 4.69(s, 2H), 5.48(s, 2H), 6.79(m, 1H), 6.96(dd, 1H, J = 2.7, 12.6), 7.13-7.22(m, 4H), 8.31(m, 1H), 8.37(s, 1H), 12.20(s, 1H), 13.04(br, 1H) |
| XI-095 | (1-carboxy-cyclohexylmethyl) | DMSO-d6 1.04(t, 3H, J = 7.5), 1.17-1.66(m, 8H), 1.80-1.96(m, 2H), 2.18(s, 3H), 2.58-2.74(m, 2H), 3.46(d, 2H, J = 6.0), 5.40(s, 2H), 7.11-7.20(m, 4H), 8.23(s, 1H), 9.92(t, 1H, J = 6.0), 12.35(br, 1H) |
| XI-096 | (4-carboxymethyl-3-fluoro-phenyl) | DMSO-d6 1.07(t, 3H, J = 7.4), 2.49(s, 3H), 2.71(q, 2H, J = 7.4), 3.57(s, 2H), 5.48(br s, 2H), 7.17-7.28(m, 6H), 7.78(d, 1H, J = 12.9), 8.37(s, 1H), 12.25(br s, 2H) |

TABLE 121

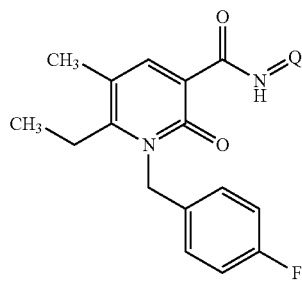

| Comp. No. | Q | ¹H-NMR(CDCl₃/TMS) δ |
|---|---|---|
| XI-098 | (3-F phenyl-CH₂COOH) | DMSO-d6 1.07(t, 3H, J = 7.4), 2.22(s, 3H), 2.70(q, 2H, J = 7.8), 3.59(s, 2H), 5.46(br s, 2H), 7.15-7.29(m, 7H), 8.31(s, 1H), 11.36(s, 1H), 12.40(br s, 1H) |
| XI-099 | (5-F phenyl-CH₂COOH) | DMSO-d6 1.06(t, 3H, J = 7.5), 2.22(s, 3H), 2.69(q, 2H, J = 7.4), 3.67(s, 2H), 5.47(br s, 2H), 7.10-7.25(m, 6H), 7.99(dd, 1H, J = 8.6 and 5.6), 8.35(s, 1H), 11.89(s, 1H), 12.48(br s, 1H) |
| XI-103 | (CF₃ phenyl-CH₂COOH) | DMSO-d6 1.07(t, 3H, J = 7.5), 2.24(s, 3H), 2.72(q, 2H, J = 8.1), 3.74(s, 2H), 5.49(s, 2H), 7.12-7.28(m, 4H), 7.46(d, 1H, J = 8.4), 7.77(m, 1H), 8.25(m, 1H), 8.38(s, 1H), 12.33(s, 1H), 12.50(br s, 1H) |
| XI-104 | (4-methyl thiazole-CH₂COOH) | DMSO-d6 1.07(t, 3H, J = 7.5), 2.17(s, 3H), 2.24(s, 3H), 2.74(q, 2H, J = 7.5), 3.71(s, 2H), 5.48(s, 2H), 7.15-7.28(m, 4H), 8.38(s, 1H), 12.50(br, 1H), 13.17(s, 1H) |
| XI-107 | (CH₃)₂CF-CH₂CH(COOH)- | 1.16(t, 3H, J = 7.5), 1.43(dd, 6H, J = 8.1, 21.3), 2.21(s, 3H), 2.43(ddd, 2H, 4.2, 15.3, 25.8), 2.67(ddd, 2H, 2.4, 7.2, 15.0), 4.76(ddd, 1H, J = 4.2, 6, 9.3), 5.42(br, 2H), 7.07-6.98(m, 4H), 8.40(s, 1H), 10.58(d, 1H, J = 5.4) |
| XI-111 | (4,4-dimethylcyclohexyl-CH₂COOH) | DMSO-d6 0.83(s, 3H), 0.89(s, 3H), 1.04(t, 2H, J = 7.5), 1.15-1.18(m, 3H), 1.26-1.35(m, 2H), 1.61-1.68(m, 2H) 2.18(s, 3H), 2.20-2.14(m, 2H), 2.62-2.69(q, 2H, J = 7.5), 2.81(s, 2H), 5.42(br, 2H), 7.11-7.20(m, 4H), 8.20(s, 1H), 9.83(s, 1H), 11.87(br, 1H) |

TABLE 122
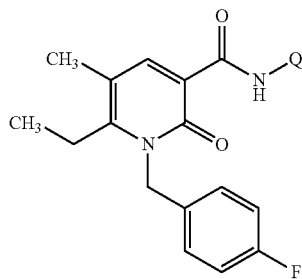
| Comp. No. | Q | ¹H-NMR(CDCl₃/TMS) δ |
|---|---|---|
| XI-112 | 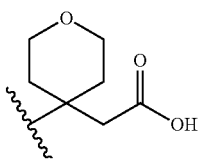 | DMSO-d6 1.04(t, 3H, J = 7.5), 1.72-1.84(m, 2H), 2.12-2.24(m, 5H), 2.62-2.74(q, 2H, J = 7.5), 2.84(s, 2H), 3.44-3.52(m, 2H), 3.62-3.73(m, 2H), 5.43(br, 2H), 7.12-7.22(m, 4H), 8.21(s, 1H), 9.99(s, 1H), 11.89(br, 1H) |
| XI-115 | 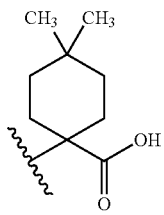 | DMSO-d6 0.86(s, 3H), 0.90(s, 3H), 1.06(t, 3H, J = 7.5), 1.23-1.37(m, 4H), 1.76-2.00(m, 4H), 2.18(s, 3H), 2.67(q, 2H, J = 7.5), 5.44(brs, 2H), 7.11-7.23(m, 4H), 8.19(s, 1H), 10.15(s, 1H), 12.23(brs, 1H) |
| XI-116 | 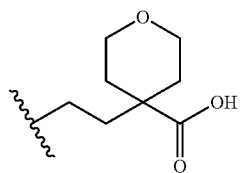 | DMSO-d6 1.04(t, 1H, J = 7.5), 1.40-2.00(m, 6H), 2.18(s, 3H), 2.67(q, 2H, J = 7.5), 3.20-3.75(m, 6H), 5.30-5.50(m, 2H), 7.10-7.20(m, 4H), 8.21(s, 1H), 9.70(t, 1H, J = 5.7) |
| XI-119 | 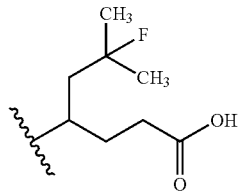 | DMSO-d6 1.04(t, 3H, J = 7.2), 1.30(dd, 6H, J = 5.7, 21.6), 1.5-1.7(m, 1H), 1.8-1.9(m, 1H), 1.84(dd, 2H), 1.84(dd, 2H, J = 6.3, 20.1), 2.18(s, 3H), 2.21(br, 2H), 2.66(brdd, 2H), 4.20(br, 1H), 5.41(s, 2H), 7.1-7.3(m, 4H), 8.22(s, 1H), 9.67(d, 1H, J = 8.7) |
| XI-146 | 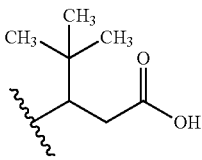 | DMSO-d6 0.88(s, 9H), 1.04(t, 3H, J = 5.4), 2.16(m, 1H), 2.18(s, 3H), 2.57(m, 1H), 2.65(m, 2H), 4.28(m, 1H), 5.42(m, 2H), 7.16(m, 4H), 8.22(s, 1H), 9.87(d, 1H, J = 7.2) |
| XI-209 | 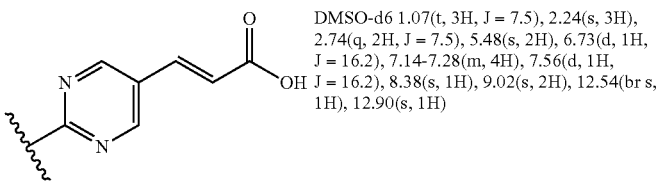 | DMSO-d6 1.07(t, 3H, J = 7.5), 2.24(s, 3H), 2.74(q, 2H, J = 7.5), 5.48(s, 2H), 6.73(d, 1H, J = 16.2), 7.14-7.28(m, 4H), 7.56(d, 1H, J = 16.2), 8.38(s, 1H), 9.02(s, 2H), 12.54(br s, 1H), 12.90(s, 1H) |

TABLE 123

[Structure: 5-methyl-6-ethyl-1-(4-fluorobenzyl)-2-oxo-1,2-dihydropyridine-3-carboxamide with N-Q substituent]

| Comp. No. | Q | $^1$H-NMR(CDCl$_3$/TMS) δ |
|---|---|---|
| XI-229 | [tetrahydropyran-4-yl with -CH$_2$CH$_2$COOH] | DMSO-d6 1.04(t, 3H, J = 7.5), 1.48-1.62(m, 2H), 1.98-2.20(m, 6H), 2.18(s, 3H), 2.66(q, 2H, J = 7.5), 3.40-3.52(m, 2H), 3.62-3.72(m, 2H), 5.43(brs, 2H), 7.12-7.23(m, 4H), 8.21(s, 1H), 9.86(s, 1H), 12.06(brs, 1H) |
| XI-241 | [4,4-difluorocyclohexyl-1-carboxylic acid] | DMSO-d6 1.05(t, 3H, J = 7.5), 1.9-2.3(m, 8H), 2.67(brq, J = 7.5), 5.45(s, 2H), 7.1-7.2(m, 4H), 8.21(s, 1H), 10.27(s, 1H) |
| XI-277 | [thiazol-4-yl-2-CH$_2$COOH] | DMSO-d6 1.07(t, 3H, J = 7.5), 2.23(s, 3H), 2.73(q, 2H, J = 7.5), 4.01(s, 2H), 5.47(s, 2H), 7.13-7.27(m, 4H), 7.63(s, 1H), 8.37(s, 1H), 12.64(s, 1H), 12.85(br s, 1H) |

TABLE 124

[Structure: 5-methyl-6-ethyl-1-(2,4-difluorobenzyl)-2-oxo-1,2-dihydropyridine-3-carboxamide with N-Q substituent]

| Comp. No. | Q | $^1$H-NMR(CDCl$_3$/TMS) δ |
|---|---|---|
| XI-063 | [cyclohexyl-1-carboxylic acid] | DMSO-d6 1.09(t, 3H, J = 7.4), 1.24-1.74(m, 8H), 2.01(d, 2H, J = 13.5), 2.21(s, 3H), 2.67(q, 2H, J = 7.3), 5.40(br s, 2H), 6.80(q, 1H, J = 8.0), 7.03(td, 1H, J = 8.6 and 2.6), 7.34(td, 1H, J = 8.5 and 2.6), 8.21(s, 1H), 10.04(s, 1H), 12.21(br s, 1H) |

TABLE 124-continued
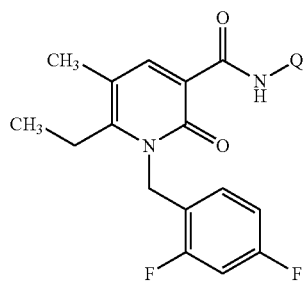
| Comp. No. | Q | $^1$H-NMR(CDCl$_3$/TMS) δ |
|---|---|---|
| XI-164 | 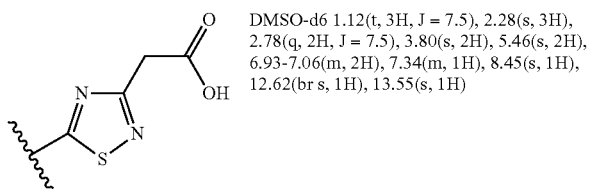 | DMSO-d6 0.84(dd, 6H, J = 6.5 and 2.6), 1.08(t, 3H, J = 7.5), 1.32(m, 2H), 1.55(m, 2H), 1.76(m, 1H), 2.18(t, 2H, J = 7.2), 2.20(s, 3H), 2.66(q, 2H, J = 7.3), 4.04(m, 1H), 5.36(br s, 2H), 6.79(q, 1H, J = 7.8), 7.01(td, 1H, J = 8.6 and 2.4), 7.32(td, 1H, J = 10.1 and 2.4), 8.24(s, 1H), 9.43(d, 1H, J = 9.0), 11.97(br s, 1H) |
| XI-183 | 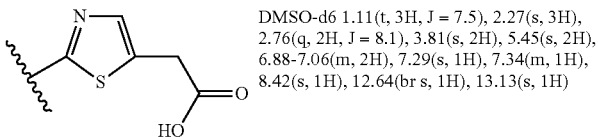 | DMSO-d6 1.12(t, 3H, J = 7.5), 2.28(s, 3H), 2.78(q, 2H, J = 7.5), 3.80(s, 2H), 5.46(s, 2H), 6.93-7.06(m, 2H), 7.34(m, 1H), 8.45(s, 1H), 12.62(br s, 1H), 13.55(s, 1H) |
| XI-184 | 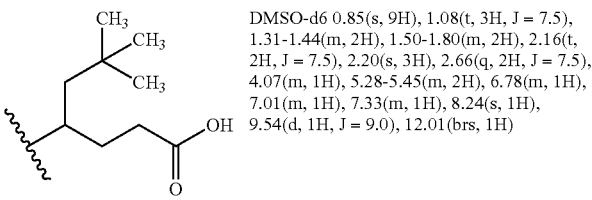 | DMSO-d6 1.11(t, 3H, J = 7.5), 2.27(s, 3H), 2.76(q, 2H, J = 8.1), 3.81(s, 2H), 5.45(s, 2H), 6.88-7.06(m, 2H), 7.29(s, 1H), 7.34(m, 1H), 8.42(s, 1H), 12.64(br s, 1H), 13.13(s, 1H) |
| XI-187 | 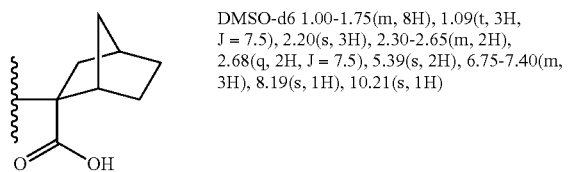 | DMSO-d6 0.85(s, 9H), 1.08(t, 3H, J = 7.5), 1.31-1.44(m, 2H), 1.50-1.80(m, 2H), 2.16(t, 2H, J = 7.5), 2.20(s, 3H), 2.66(q, 2H, J = 7.5), 4.07(m, 1H), 5.28-5.45(m, 2H), 6.78(m, 1H), 7.01(m, 1H), 7.33(m, 1H), 8.24(s, 1H), 9.54(d, 1H, J = 9.0), 12.01(brs, 1H) |
| XI-193 | | DMSO-d6 1.00-1.75(m, 8H), 1.09(t, 3H, J = 7.5), 2.20(s, 3H), 2.30-2.65(m, 2H), 2.68(q, 2H, J = 7.5), 5.39(s, 2H), 6.75-7.40(m, 3H), 8.19(s, 1H), 10.21(s, 1H) |

TABLE 125

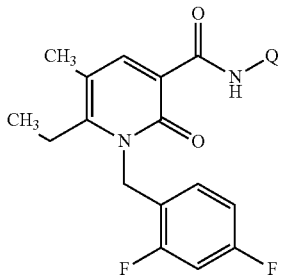

| Comp. No. | Q | ¹H-NMR(CDCl₃/TMS) δ |
|---|---|---|
| XI-196 | 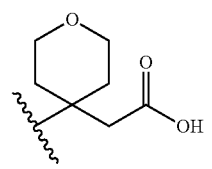 | DMSO-d6 1.08(t, 3H, J = 7.5), 1.70-2.25(m, 4H), 2.20(s, 3H), 2.26(q, 2H, J = 7.5), 2.84(s, 2H), 3.46(t, 2H, J = 10.8), 3.60-3.75(m, 2H), 5.39(s, 2H), 6.74-7.40(m, 3H), 8.22(s, 1H), 9.89(s, 1H) |
| XI-203 | 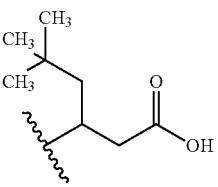 | DMSO-d6 0.85(d, 6H, J = 6.3), 1.08(t, 3H, J = 7.7), 1.31(m, 1H), 1.42-1.61(m, 2H), 2.20(s, 3H), 2.42(t, 2H, J = 6.2), 2.66(q, 2H, J = 7.5), 4.33(m, 1H), 5.36(dd, 2H, J = 24.0 and 17.1), 6.77(td, 1H, J = 8.9 and 6.3), 7.02(td, 1H, J = 8.4 and 1.9), 7.33(ddd, 1H, J = 10.5, 8.9 and 2.2), 8.24(s, 1H), 9.64(d, 1H, J = 8.7), 12.16(br s, 1H) |
| XI-204 | 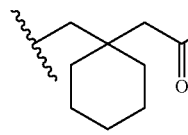 | DMSO-d6 0.86(s, 9H), 1.08(t, 3H, J = 7.5), 2.13(dd, 1H, J = 15.0 and 9.9), 2.20(s, 3H), 2.55(dd, 1H, J = 15.2 and 4.1), 2.65(qd, 2H, J = 7.4 and 2.7), 4.27(td, 1H, J = 9.8 and 3.9), 5.38(dd, 2H, J = 24.8 and 16.4), 6.78(td, 1H, J = 8.7 and 6.4), 7.02(tdd, 1H, J = 8.6, 2.9 and 1.1), 7.33(ddd, 1H, J = 11.2, 8.7 and 2.0), 8.23(s, 1H), 9.75(d, 1H, J = 9.9), 12.02(br s, 1H) |
| XI-208 | 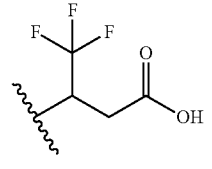 | DMSO-d6 1.08(t, 3H, J = 7.5), 1.24-1.58(m, 10H), 2.15(s, 2H), 2.20(s, 3H), 2.65(q, 2H, J = 7.3), 3.39(d, 2H, J = 6.3), 5.38(br s, 2H), 6.79(td, 1H, J = 8.9 and 6.4), 7.01(tdd, 1H, J = 8.5, 2.9 and 1.2), 7.33(ddd, 1H, J = 10.8, 9.2 and 2.6), 8.26(s, 1H), 9.83(t, 1H, J = 6.2), 12.15(br s, 1H) |
| XI-227 |  | DMSO-d6 1.09(t, 3H, J = 7.5), 2.22(m, 3H), 2.60-2.75(m, 3H), 2.82(dd, 1H, J = 4.8 and 16.5), 5.15(m, 1H), 5.37(s, 2H), 6.80(m, 1H), 7.01(m, 1H), 7.33(m, 1H), 8.29(s, 1H), 10.18(d, 1H, J = 9.0), 10.17(d, 1H, J = 9.0) |

TABLE 126

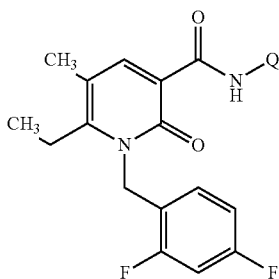

| Comp. No. | Q | ¹H-NMR(CDCl₃/TMS) δ |
|---|---|---|
| XI-232 | cyclohexyl-CH₂-COOH (1,1-disubstituted cyclohexane with CH₂COOH) | DMSO-d6 1.08(t, 3H, J = 7.0), 1.15-1.54(m, 8H), 2.12-2.22(m, 2H), 2.20(s, 3H), 2.65(q, 2H, J = 7.0), 2.79(s, 2H), 5.38(s, 2H), 6.78(m, 1H), 7.03(m, 1H), 7.32(m, 1H), 8.23(s, 1H), 9.71(s, 1H), 11.9(m, 1H) |
| XI-233 | cyclopentyl-CH₂-COOH | DMSO-d6 1.07(t, 3H, J = 7.0), 1.52-1.65(m, 4H), 1.69-1.80(m, 2H), 1.98-2.09(m, 2H), 2.19(s, 3H), 2.65(q, 2H, J = 7.0), 2.86(s, 2H), 5.35(s, 2H), 6.77(m, 1H), 7.02(m, 1H), 7.31(m, 1H), 8.21(s, 1H), 9.79(s, 1H) |
| XI-234 | cyclobutyl-CH₂-COOH | DMSO-d6 1.08(t, 3H, J = 7.0), 1.72-1.86(m, 2H), 2.13-2.24(m, 4H), 2.19(s, 3H), 2.66(q, 2H, J = 7.0), 2.81(s, 2H), 5.36(s, 2H), 6.80(m, 1H), 7.02(m, 1H), 7.32(m, 1H), 8.20(s, 1H), 9.85(s, 1H) |
| XI-254 | 6-pyridyl-CH₂-COOH | DMSO-d6 1.16(t, 3H, J = 7.2), 2.26(s, 3H), 2.75(q, 2H, J = 7.2), 3.59(s, 2H), 5.44(s, 2H), 6.86-7.08(m, 2H), 7.34(m, 1H), 7.72(dd, 1H, J = 2.4, 8.7), 8.16-8.26(m, 2H), 8.40(s, 1H), 12.36(s, 1H), 12.43(br s, 1H) |
| XI-262 | CH(CH₂CH(CH₃)₂)COOH | 0.97(d, 3H, J = 6.6), 1.19(t, 3H, J = 7.2), 1.61(m, 1H), 2.17(m, 1H), 2.22(3H, s), 2.72(q, 2H, J = 7.2), 4.54-4.60(m, 1H), 5.32-5.53(m, 2H), 6.81-6.94(m, 3H), 8.41(s, 1H), 10.40(d, 1H, J = 6.3) |
| XI-265 | 4,4-dimethylcyclohexyl-CH₂-COOH | DMSO-d6 0.83(s, 3H), 0.89(s, 3H), 1.06(t, 4H, J = 7.5), 1.10-1.36(m, 3H), 1.54-1.72(m, 2H), 2.02-2.16(m, 2H), 2.20(s, 3H), 2.65(q, 2H, J = 7.8), 2.79(s, 2H), 4.02(q, 2H, J = 7.5), 5.38(br, 2H), 6.78(m, 1H), 7.00(m, 1H), 7.33(m, 1H), 8.22(s, 1H), 9.73(s, 1H), 11.95(br, 1H) |

TABLE 127
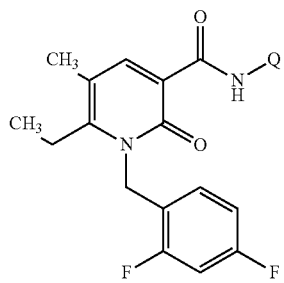
| Comp. No. | Q | $^1$H-NMR(CDCl$_3$/TMS) δ |
|---|---|---|
| XI-270 | 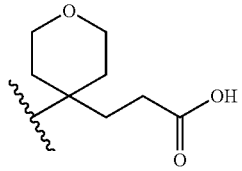 | DMSO-d6 1.08(t, 3H, J = 7.5), 1.48-1.62(m, 2H), 1.98-2.18(m, 6H), 2.20(s, 3H), 2.66(q, 2H, J = 7.5), 3.38-3.50(m, 2H), 3.60-3.72(m, 2H), 5.39(brs, 2H), 6.82(m, 1H), 7.03(m, 1H), 7.34(m, 1H), 8.23(s, 1H), 9.76(s, 1H), 12.00(brs, 1H) |
| XI-275 | 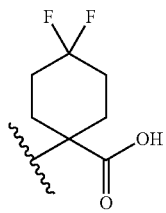 | DMSO-d6 1.09(t, 3H, J = 7.8), 1.7-2.3(m, 8H), 2.12(s, 3H), 2.64-2.74(br, 2H), 5.41(s, 2H), 6.8-6.9(m, 1H), 7.03(dt, 1H, J = 2.4, 8.4), 7.34(dt, 1H, J = 2.7, 9.3), 8.22(s, 1H), 10.17(s, 1H) |
| XI-278 | 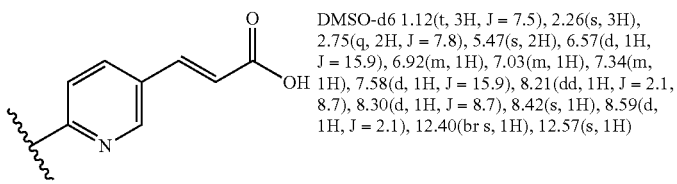 | DMSO-d6 1.12(t, 3H, J = 7.5), 2.26(s, 3H), 2.75(q, 2H, J = 7.8), 5.47(s, 2H), 6.57(d, 1H, J = 15.9), 6.92(m, 1H), 7.03(m, 1H), 7.34(m, 1H), 7.58(d, 1H, J = 15.9), 8.21(dd, 1H, J = 2.1, 8.7), 8.30(d, 1H, J = 8.7), 8.42(s, 1H), 8.59(d, 1H, J = 2.1), 12.40(br s, 1H), 12.57(s, 1H) |
| XI-293 | 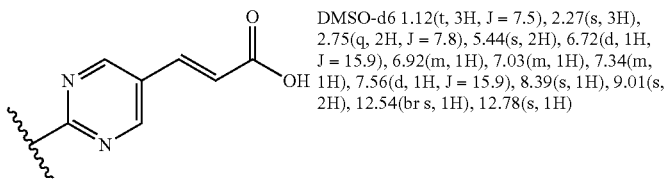 | DMSO-d6 1.12(t, 3H, J = 7.5), 2.27(s, 3H), 2.75(q, 2H, J = 7.8), 5.44(s, 2H), 6.72(d, 1H, J = 15.9), 6.92(m, 1H), 7.03(m, 1H), 7.34(m, 1H), 7.56(d, 1H, J = 15.9), 8.39(s, 1H), 9.01(s, 2H), 12.54(br s, 1H), 12.78(s, 1H) |
| XI-299 | 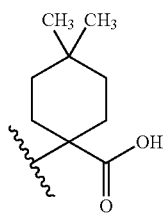 | DMSO-d6 0.82-0.92(br, 6H), 1.08(t, 3H, J = 7.2), 1.2-1.3(br, 4H), 1.7-1.9(m, 4H), 2.19(s, 3H), 2.6-2.7(br, 2H), 5.39(s, 2H), 6.75(m, 1H), 6.95-7.05(m, 1H), 7.28-7.36(m, 1H), 8.19(s, 1H), 10.04(s, 1H) |
| XI-303 | 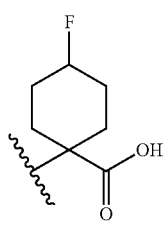 | DMSO-d6 1.19(t, 3H, J = 7.5), 1.62-2.36(m, 8H), 2.23(s, 3H), 2.65(q, 2H, J = 7.5), 4.79(d, 1H, 48), 5.44(s, 2H), 6.8-6.9(m, 3H), 8.41(s, 1H), 10.54(s, 1H) |

TABLE 128

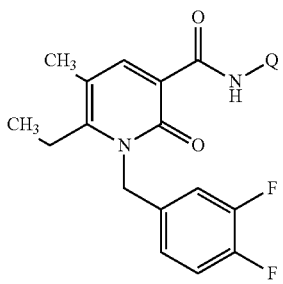

| Comp. No. | Q | $^1$H-NMR(CDCl$_3$/TMS) δ |
|---|---|---|
| XI-025 | (thiazol-2-yl with CH₂COOH at 4-position) | DMSO-d6 1.08(t, 3H, J = 7.5), 2.24(s, 3H), 2.74(q, 2H, J = 7.2), 3.60(s, 2H), 5.47(s, 2H), 7.02(m, 1H), 7.02(s, 1H), 7.30-7.47(m, 2H), 8.39(s, 1H), 12.40(br s, 1H), 13.25(s, 1H) |
| XI-027 | (1-carboxycyclohexyl) | DMSO-d6 1.06(t, 3H, J = 7.5), 1.25-1.74(m, 8H), 2.02(d, 2H, J = 13.2), 2.19(s, 3H), 2.67(q, 2H, J = 7.3), 5.43(br s, 2H), 6.89(m, 1H), 7.28(m, 1H), 7.41(m, 1H), 8.20(s, 1H), 10.10(s, 1H), 12.21(br s, 1H) |
| XI-122 | (1-(carboxymethyl)cyclohexyl) | DMSO-d6 1.05(t, 3H, J = 6.6), 1.10-1.58(m, 9H), 2.12-2.28(m, 4H), 2.54-2.72(m, 2H), 2.78(s, 2H), 5.41(br, 2H), 6.87-6.90(m, 1H), 7.21-7.32(m, 1H), 7.34-7.47(m, 1H), 8.21(s, 1H), 9.77(s, 1H), 11.86(br, 1H), |
| XI-142 | (2-(neopentyl)-CH(COOH)-) | DMSO-d6 0.91(s, 9H),1.06(t, 3H, J = 5.7), 1.55(m, 1H), 1.76(m, 1H), 2.20(s, 3H), 2.68(m, 2H), 4.50(m, 1H), 5.41(m, 2H), 6.91(m, 1H), 7.25(m, 1H), 7.40(m, 1H), 8.24(s, 1H), 10.02(d, 1H, J = 6.0) |
| XI-143 | (3-tert-butyl-3-CH₂COOH) | DMSO-d6 0.88(s, 9H), 1.06(t, 3H, J = 5.4), 2.17(m, 1H), 2.19(s, 3H), 2.52-2.73(m, 3H), 4.28(m, 1H), 5.42(m, 2H), 6.90(m, 1H), 7.26(m, 1H), 7.41(m, 1H), 8.23(s, 1H), 9.83(d, 1H, J = 7.2) |
| XI-151 | (thiazol-2-yl with CH₂COOH at 5-position) | DMSO-d6 1.08(t, 3H, J = 7.5), 2.25(s, 3H), 2.74(q, 2H, J = 7.5), 3.82(s, 2H), 5.48(s, 2H), 7.00(m, 1H), 7.30(s, 1H), 7.30-7.48(m, 2H), 8.40(s, 1H), 12.62(br s, 1H), 13.19(s, 1H) |
| XI-152 | (1,2,4-thiadiazol-5-yl with CH₂COOH) | DMSO-d6 1.08(t, 3H, J = 7.5), 2.25(s, 3H), 2.75(q, 2H, J = 7.8), 3.80(s, 2H), 5.49(s, 2H), 7.05(m, 1H), 7.30-7.50(m, 2H), 8.44(s, 1H), 12.63(br s, 1H), 13.61(s, 1H) |

TABLE 129

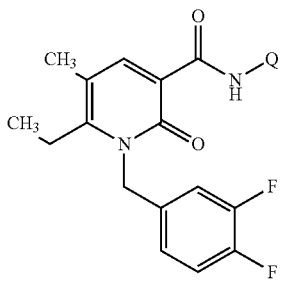

| Comp. No. | Q | $^1$H-NMR(CDCl$_3$/TMS) δ |
|---|---|---|
| XI-162 | ![structure: 4-isobutyl-pentanoic acid fragment] | DMSO-d6 0.86(dd, 6H, J = 6.6 and 3.0), 1.05(t, 3H, J = 7.5), 1.33(m, 2H), 1.56(m, 2H), 1.77(m, 1H), 2.19(s, 3H), 2.19(t, 2H, J = 7.5), 2.65(q, 2H, J = 7.6), 4.05(m, 1H), 5.39(br s, 2H), 6.90(m, 1H), 7.26(m, 1H), 7.39(dt, 1H, J = 10.8 and 8.4), 8.23(s, 1H), 9.49(d, 1H, J = 9.0), 11.99(br s, 1H) |
| XI-165 | ![structure: 3-isobutyl-butanoic acid fragment] | DMSO-d6 0.86(d, 6H, J = 6.6), 1.05(t, 3H, J = 7.4), 1.34(m, 1H), 1.46-1.57(m, 2H), 2.18(s, 3H), 2.43(t, 2H, J = 6.8), 2.65(q, 2H, J = 7.5), 4.34(m, 1H), 5.38(d, 2H, J = 8.1), 6.89(m, 1H), 7.25(m, 1H,), 7.39(dt, 1H, J = 10.5 and 8.6), 8.23(s, 1H), 9.70(d, 1H, J = 8.7), 12.13(br s, 1H) |
| XI-171 | ![structure: norbornane carboxylic acid fragment] | DMSO-d6 1.00-1.80(m, 8H), 1.06(t, 3H, J = 7.2), 2.19(s, 3H), 2.20-2.60(m, 2H), 2.67(q, 2H, J = 7.2), 5.25-5.55(m, 2H), 6.85-7.47(m, 3H), 8.17(s, 1H), 10.26(s, 1H) |
| XI-174 | ![structure: CF3 butanoic acid fragment] | DMSO-d6 1.06(t, 3H, J = 7.5), 2.21(s, 3H), 2.62-2.75(m, 3H), 2.85(dd, 2H, J = 16.5 and 5.1), 5.14(m, 1H), 5.21(br, 2H), 6.90(m, 1H), 7.27(m, 1H), 7.40(m, 1H), 8.28(s, 1H), 10.25(d, 1H, J = 9.0), 12.70(br, 1H) |
| XI-179 | ![structure: 4-tert-butyl pentanoic acid fragment] | DMSO-d6 0.86(s, 9H), 1.05(t, 3H, J = 7.5), 1.33-1.45(m, 2H), 1.51-1.81(m, 2H), 2.18(t, 2H, J = 7.5), 2.19(s, 3H), 2.66(q, 2H, J = 7.2), 4.08(m, 1H), 5.40(brs, 2H), 6.90(m, 1H), 7.24(m, 1H), 7.41(m, 1H), 8.23(s, 1H), 9.60(d, 1H, J = 9.0), 11.98(brs, 1H) |
| XI-205 | ![structure: cyclohexyl acetic acid fragment] | DMSO-d6 1.05(t, 3H, J = 7.5), 1.26-1.58(m, 10H), 2.17(s, 2H), 2.19(s, 3H), 2.65(q, 2H, J = 7.3), 3.40(d, 2H, J = 6.0), 5.41(br s, 2H), 6.89(m, 1H), 7.26(ddd, 1H, J = 11.7, 7.8 and 2.1), 7.39(dt, 1H, J = 10.7 and 8.5), 8.25(s, 1H), 9.89(t, 1H, J = 6.3), 12.18(br s, 1H) |

TABLE 130

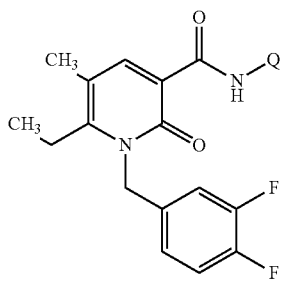

| Comp. No. | Q | ¹H-NMR(CDCl₃/TMS) δ |
|---|---|---|
| XI-218 | cyclopentyl-CH₂COOH | 1.15(t, 3H, J = 7.8), 1.75-1.89(m, 8H), 2.21(s, 3H), 2.66(q, 2H, J = 7.8), 3.05(s, 2H), 5.42(s, 2H), 7.01-7.07(m, 3H), 8.40(s, 1H), 10.42(s, 1H) |
| XI-221 | cyclobutyl-CH₂COOH | DMSO-d6 1.05(t, 3H, J = 7.5), 1.76-1.94(m, 2H), 2.14-2.30(m, 7H), 2.61-2.69(q, 2H, J = 8.1), 2.87(s, 2H), 5.38(br s, 2H), 6.88(m, 1H), 7.24(m, 1H), 7.39(m, 1H), 8.20(s, 1H), 9.93(s, 1H), 12.06(br, 1H) |
| XI-250 | pyridyl-CH₂COOH | DMSO-d6 1.08(t, 3H, J = 7.5), 2.24(s, 3H), 2.72(q, 2H, J = 7.5), 3.60(s, 2H), 5.46(s, 2H), 6.98(m, 1H), 7.28-7.48(m, 2H), 7.72(dd, 1H, J = 2.1, 8.4), 8.19(d, 1H, J = 2.4), 8.22(d, 1H, J = 9.0), 8.39(s, 1H), 12.43(br s, 1H), 12.43(s, 1H) |
| XI-264 | 4,4-dimethylcyclohexyl-CH₂COOH | DMSO-d6 0.83(s, 3H), 0.89(s, 3H), 1.05(t, 4H, J = 7.5), 1.10-1.36(m, 3H), 1.54-1.72(m, 2H), 2.02-2.16(m, 2H), 2.18(s, 3H), 2.65(q, 2H, J = 7.8), 2.82(s, 2H), 5.41(br, 2H), 6.93(m, 1H), 7.24(m, 1H), 7.40(m, 1H), 8.21(s, 1H), 9.80(s, 1H), 12.02(br, 1H) |
| XI-269 | tetrahydropyranyl-CH₂CH₂COOH | DMSO-d6 1.05(t, 3H, J = 7.5), 1.48-1.62(m, 2H), 1.99-2.18(m, 6H), 2.18(s, 3H), 2.65(q, 2H, J = 7.5), 3.40-3.52(m, 2H), 3.60-3.72(m, 2H), 5.42(brs, 2H), 6.92(m, 1H), 7.29(m, 1H), 7.40(m, 1H), 8.22(s, 1H), 9.82(s, 1H), 12.00(brs, 1H) |

TABLE 131
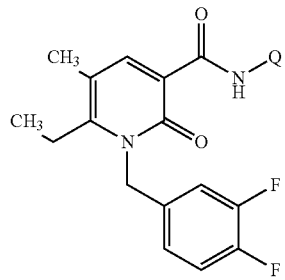
| Comp. No. | Q | ¹H-NMR(CDCl₃/TMS) δ |
|---|---|---|
| XI-284 | 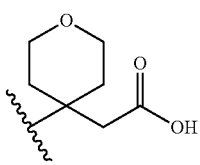 | DMSO-d6 1.05(t, 3H, J = 7.5), 1.70-1.82(m, 2H), 2.10-2.22(m, 2H), 2.19(s, 3H), 2.66(q, 2H, J = 7.5), 2.85(s, 2H), 3.48(t, 2H, J = 11), 3.60-3.75(m, 2H), 5.30-5.50(m, 2H), 6.85-7.45(m, 3H), 8.22(s, 1H), 9.95(s, 1H) |
| XI-288 | 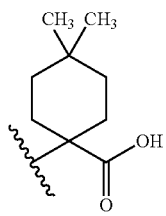 | DMSO-d6 0.86(s, 3H), 0.90(s, 3H), 1.06(t, 3H, J = 7.5), 1.23-1.35(m, 4H), 2.15-2.30(m, 2H), 2.16(s, 3H), 2.74(q, 2H, J = 7.5), 2.84(s, 2H), 3.50(t, 2H, J = 11.1), 3.60-4.20(m, 4H), 8.11(s, 1H), 10.09(s, 1H) |
| XI-292 | 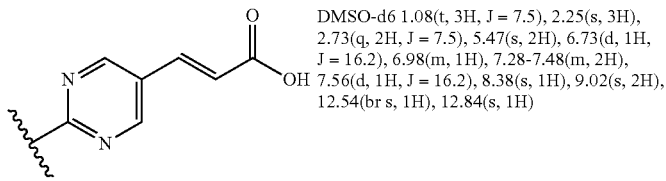 | DMSO-d6 1.08(t, 3H, J = 7.5), 2.25(s, 3H), 2.73(q, 2H, J = 7.5), 5.47(s, 2H), 6.73(d, 1H, J = 16.2), 6.98(m, 1H), 7.28-7.48(m, 2H), 7.56(d, 1H, J = 16.2), 8.38(s, 1H), 9.02(s, 2H), 12.54(br s, 1H), 12.84(s, 1H) |
| XI-295 | 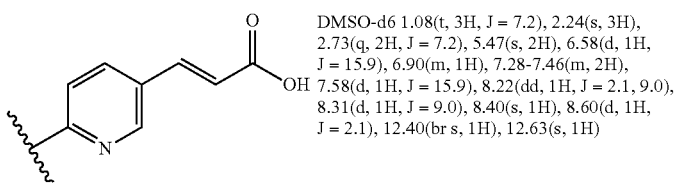 | DMSO-d6 1.08(t, 3H, J = 7.2), 2.24(s, 3H), 2.73(q, 2H, J = 7.2), 5.47(s, 2H), 6.58(d, 1H, J = 15.9), 6.90(m, 1H), 7.28-7.46(m, 2H), 7.58(d, 1H, J = 15.9), 8.22(dd, 1H, J = 2.1, 9.0), 8.31(d, 1H, J = 9.0), 8.40(s, 1H), 8.60(d, 1H, J = 2.1), 12.40(br s, 1H), 12.63(s, 1H) |

TABLE 132

| Comp. No. | Q | ¹H-NMR(CDCl₃/TMS) δ |
|---|---|---|
| XI-042 | cyclobutyl-CH₂-COOH | 1.00(t, 3H, J = 7.5), 1.10(t, 3H, J = 7.5), 1.20(t, 3H, J = 7.5), 1.40-1.78(m, 8H), 1.864-2.18(m, 3H), 2.35-2.41(m, 4H), 2.44-2.56(q, 2H, J = 7.5), 2.64-2.73(m, 2H), 3.08(s, 2H), 4.06-4.11(m, 2H), 8.33(s, 1H), 10.75(s, 1H) |
| XI-053 | tetrahydropyran-4-yl-CH₂- with COOH | DMSO-d6 0.94(t, 3H, J = 7.5), 1.03(t, 3H, J = 7.5), 1.12(t, 3H, J = 7.5), 1.32-1.66(m, 12H), 1.86-1.91(m, 2H), 2.66-2.71(m, 2H), 3.52(d, 2H, J = 6.3), 3.71-3.75(m, 2H), 4.00-4.04(m, 2H), 8.16(s, 1H), 10.56(t, 1H, J = 5.7), 12.55(br, 1H) |
| XI-132 | neopentyl-CH(COOH)-CH₂- | DMSO-d6 0.93(s, 9H), 0.94(t, 3H, J = 5.4), 1.03(t, 3H, J = 5.4), 1.12(t, 3H, J = 5.4), 1.39(m, 2H), 1.56(m, 5H), 1.77(m, 1H), 2.51(m, 2H), 2.70(m, 2H), 4.04(m, 2H), 4.49(m, 1H), 8.17(s, 1H), 10.16(d, 1H, J = 6.3) |
| XI-133 | tBu-CH(CH₂COOH)- | DMSO-d6 0.89(s, 9H), 0.94(t, 3H, J = 5.4), 1.03(t, 3H, J = 5.4), 1.12(t, 3H, J = 5.4), 1.41(m, 2H), 1.56(m, 4H), 1.77(m, 1H), 2.51(m, 2H), 2.70(m, 2H), 4.04(m, 2H), 4.49(m, 1H), 8.17(s, 1H), 10.16(d, 1H, J = 6.3) |
| XI-149 | 2-thiazolyl-5-CH₂COOH | DMSO-d6 0.96(t, 3H, J = 7.2), 1.05(t, 3H, J = 7.2), 1.16(t, 3H, J = 7.5), 1.34-1.50(m, 2H), 1.50-1.72(m, 4H), 2.48-2.53(m, 2H), 2.57(q, 2H, J = 7.5), 2.70-2.80(m, 2H), 3.82(s, 2H), 4.06-4.18(m, 2H), 7.31(s, 1H), 8.32(s, 1H), 12.63(br s, 1H), 13.37(s, 1H) |
| XI-154 | tBu-CH₂-CH(CH₂CH₂COOH)- | DMSO-d6 0.87(s, 9H), 0.91(t, 3H, J = 7.2), 1.03(t, 3H, J = 7.5), 1.12(t, 3H, J = 7.5), 1.32-1.80(m, 10H), 2.18(t, 2H, J = 7.5), 2.44-2.55(m, 2H), 2.64-2.74(m, 2H), 3.96-4.16(m, 3H), 8.16(s, 1H), 9.76(d, 1H, J = 9.3), 11.98(brs, 1H) |

TABLE 133
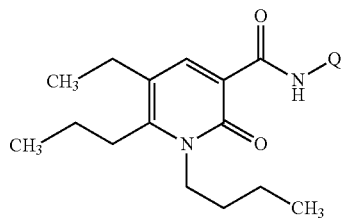
| Comp. No. | Q | $^1$H-NMR(CDCl$_3$/TMS) δ |
|---|---|---|
| XI-163 | 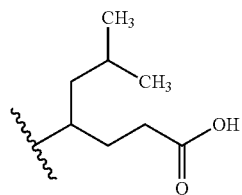 | DMSO-d6 0.86(t, 6H, J = 6.3), 0.94(t, 3H, J = 7.4), 1.03(t, 3H, J = 7.2), 1.12(t, 3H, J = 7.5), 1.24-1.45(m, 6H), 1.50-1.62(m, 6H), 1.78(m, 1H), 2.20(t, 2H, J = 7.5), 2.69(t, 2H, J = 8.3), 4.03(m, 1H), 5.39(br s, 2H), 8.16(s, 1H), 9.66(d, 1H, J = 9.0), 12.03(br s, 1H) |
| XI-167 | 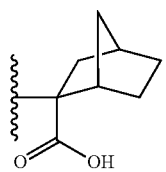 | DMSO-d6 0.95(t, 3H, J = 7.2), 1.03(t, 3H, J = 7.2), 1.12(t, 3H, J = 7.5), 1.10-1.80(m, 14H), 2.20-2.80(m, 6H), 3.95-4.20(m, 2H), 8.11(s, 1H), 10.43(s, 1H) |
| XI-189 | 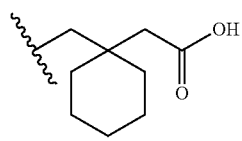 | DMSO-d6 0.94(t, 3H, J = 7.2), 1.03(t, 3H, 7.2), 1.12(t, 3H, J = 7.5), 2.19(s, 2H), 2.51(q, 2H, J = 7.4), 2.69(t, 2H, J = 7.8), 4.04(br, 2H), 8.17(s, 1H), 10.02(t, 1H, J = 5.7) |
| XI-210 | 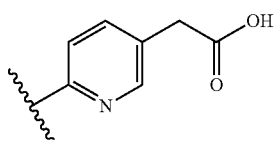 | DMSO-d6 0.96(t, 3H, J = 7.2), 1.05(t, 3H, J = 7.2), 1.16(t, 3H, J = 7.2), 1.43(m, 1H), 1.50-1.72(m, 2H), 2.55(q, 2H, J = 7.5), 2.68-2.80(m, 2H), 3.60(s, 2H), 4.04-4.17(m, 2H), 7.72(dd, 1H, J = 2.1, 8.4), 8.20-8.26(m, 2H), 8.32(s, 1H), 12.52(br s, 1H), 12.60(s, 1H) |
| XI-212 | 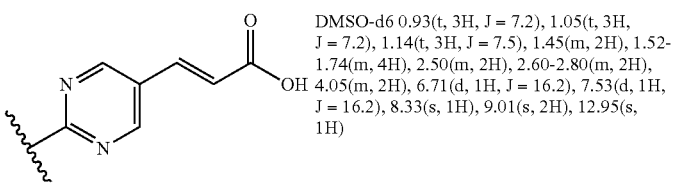 | DMSO-d6 0.93(t, 3H, J = 7.2), 1.05(t, 3H, J = 7.2), 1.14(t, 3H, J = 7.5), 1.45(m, 2H), 1.52-1.74(m, 4H), 2.50(m, 2H), 2.60-2.80(m, 2H), 4.05(m, 2H), 6.71(d, 1H, J = 16.2), 7.53(d, 1H, J = 16.2), 8.33(s, 1H), 9.01(s, 2H), 12.95(s, 1H) |

TABLE 134
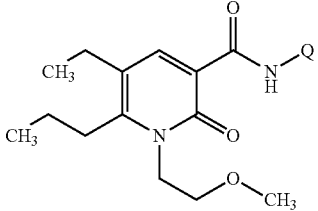
| Comp. No. | Q | ¹H-NMR(CDCl₃/TMS) δ |
|---|---|---|
| XI-065 | 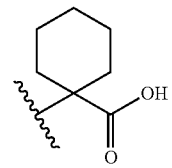 | DMSO-d6 1.03(t, 3H, J = 7.5), 1.12(t, 3H, J = 7.5), 1.14-1.78(m, 10H), 1.98-2.12(m, 2H), 2.48-2.55(m, 2H), 2.77-2.83(m, 2H), 3.24(s, 3H), 3.63(t, 2H, J = 5.4), 4.28(t, 2H, J = 5.4), 8.16(s, 1H), 10.20(s, 1H), 12.19(br, 1H) |
| XI-066 | 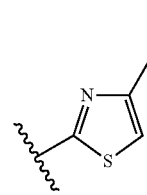 | DMSO-d6 1.04(t, 3H, J = 7.5), 1.16(t, 3H, J = 7.5), 1.53-1.60(m, 2H), 2.54-2.59(q, 2H, J = 7.5), 2.80-2.87(m, 2H), 3.24(s, 3H), 3.68(t, 2H, J = 5.4), 4.34(t, 2H, J = 5.4), 7.02(s, 1H), 8.32(s, 1H), 12.41(br, 1H), 13.34(s, 1H) |
| XI-121 | 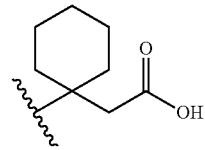 | DMSO-d6 1.01(t, 3H, J = 7.5), 1.12(t, 3H, J = 7.5), 1.35-1.60(m, 12H), 2.20-2.58(m, 2H), 2.70-2.85(m, 4H), 3.24(s, 3H), 3.61(t, 2H, J = 5.4), 4.25(t, 2H, J = 5.4), 8.17(s, 1H), 9.88(s, 1H), 11.88(br, 1H) |
| XI-197 | 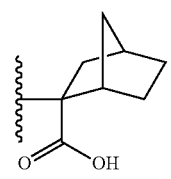 | DMSO-d6 1.02(t, 3H, J = 7.2), 1.05-1.80(m, 11H), 2.20-2.90(m, 8H), 3.24(s, 3H), 3.50-3.75(m, 2H), 4.20-4.40(m, 2H), 8.14(s, 1H), 10.37(s, 1H) |
| XI-219 | 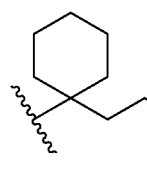 | 1.07(t, 3H, J = 7.5), 1.20(t, 3H, J = 7.2), 1.26-1.60(m, 10H), 2.19-2.27(m, 4H), 2.33-2.40(m, 2H), 2.50(q, 2H, J = 7.5), 2.79-2.85(m, 2H), 3.32(s, 3H), 3.70(t, 2H, J = 5.4), 4.32(t, 2H, J = 5.1), 8.40(s, 1H), 9.99(s, 1H) |

TABLE 135

| Comp. No. | Q | $^1$H-NMR(CDCl$_3$/TMS) δ |
|---|---|---|
| XI-067 | (cyclohexyl with -COOH) | DMSO-d6 0.94(t, 3H, J = 7.5), 1.21-1.52(m, 6H), 1.52-1.78(m, 9H), 3.79(s, 3H), 4.06-4.11(m, 2H), 4.56(s, 2H), 8.28(s, 1H), 10.40(s, 1H), 12.24(br, 1H) |
| XI-068 | (thiazol-2-yl-CH$_2$-COOH at 4-position) | DMSO-d6 0.95(t, 3H, J = 7.5), 1.37-1.47(q, 2H, J = 7.5), 1.65-1.75(m, 2H), 3.62(s, 3H), 3.85(s, 3H), 4.12-4.17(m, 2H), 4.60(s, 2H), 7.06(s, 1H), 8.45(s, 1H), 12.35(br, 1H), 13.58(s, 1H) |

TABLE 136

| Comp. No. | Q | $^1$H-NMR(CDCl$_3$/TMS) δ |
|---|---|---|
| X-186 | (1,2,4-thiadiazol-3-yl-CH$_2$-COOH) | DMSO-d6 0.94(t, 3H, J = 7.5 Hz), 1.16(t, 3H, J = 7.5 Hz), 1.38-1.46(m, 2H), 2.57(q, 2H, J = 7.5 Hz), 2.67-2.73(m, 2H), 3.79(s, 2H), 5.48(s, 2H), 7.13-7.28(m, 4H), 8.43(s, 1H), 13.63(s, 1H) |
| X-210 | (thiazol-2-yl-CH$_2$-COOH at 4-position) | DMSO-d6 0.96(t, 3H, J = 7.2), 1.17(t, 3H, J = 7.2), 1.36-1.52(m, 2H), 2.57(q, 2H, J = 7.5), 2.65-2.77(m, 2H), 5.48(s, 2H), 7.03(s, 1H), 7.13-7.30(m, 4H), 8.42(s, 1H), 12.39(br s, 1H), 13.30(s, 1H) |

TABLE 137

| Comp. No. | Q | ¹H-NMR(CDCl₃/TMS) δ |
|---|---|---|
| I-073 | (S)-CH(CH₃)-C(O)-O-CH₃ | 0.99(t, 3H, J = 7.2), 1.40-1.52(m, 2H), 1.52(d, 3H, J = 7.2), 1.63-1.74(m, 2H), 2.17(s, 3H), 2.41(s, 3H), 3.75(s, 3H), 4.10-4.15(m, 2H), 4.73(qd, 1H, J = 7.2 and 7.2), 8.28(s, 1H), 10.34(d, 1H, J = 7.2) |
| I-074 | CH(CH₂Ph)-C(O)-O-CH₃ | 0.99(t, 3H, J = 7.2 Hz), 1.39-1.51(m, 2H), 1.62-1.72(m, 2H), 2.15(s, 3H), 2.39(s, 3H), 3.11-3.28(m, 2H), 3.68(s, 3H), 4.09-4.14(m, 2H), 4.97(m, 1H), 7.17-7.29(m, 5H), 8.24(s, 1H), 10.45(d, 1H, J = 7.5 Hz) |
| I-075 | CH(iPr)-C(O)-O-CH₃ | 0.97-1.04(m, 9H), 1.40-1.52(m, 2H), 1.64-1.74(m, 2H), 2.16(s, 3H), 2.29(m, 1H), 2.41(s, 3H), 3.74(s, 3H), 4.10-4.16(m, 2H), 4.66(m, 1H), 8.28(s, 1H), 10.42(d, 1H, J = 8.1 Hz) |
| I-076 | CH(CH₂CH(CH₃)₂)-C(O)-O-CH₃ | 0.94-1.02(m, 9H), 1.40-1.52(m, 2H), 1.63-1.81(m, 5H), 2.16(s, 3H), 2.41(s, 3H), 3.73(s, 3H), 4.08-4.15(m, 2H), 4.75(m, 1H), 8.28(s, 1H), 10.26(d, 1H, J = 7.5 Hz) |
| I-077 | CH(CH(CH₃)(C₂H₅))-C(O)-O-CH₃ | 0.92-1.00(m, 9H), 1.23-1.72(m, 6H), 2.03(m, 1H), 2.16(s, 3H), 2.40(s, 3H), 3.74(s, 3H), 4.09-4.16(m, 2H), 4.72(m, 1H), 8.28(s, 1H), 10.41(d, 1H, J = 7.5 Hz) |
| I-078 | CH(iPr)-C(O)-O-CH₃ | 0.97-1.04(m, 9H), 1.40-1.52(m, 2H), 1.66-1.72(m, 2H), 2.16(s, 3H), 2.29(m, 1H), 2.41(s, 3H), 3.74(s, 3H), 4.10-4.16(m, 2H), 4.66(m, 1H), 8.28(s, 1H), 10.42(d, 1H, J = 7.8 Hz) |
| I-079 | CH(CH₂CH₂SCH₃)-C(O)-O-CH₃ | 1.00(t, 3H, J = 7.5 Hz), 1.40-1.52(m, 2H), 1.63-1.74(m, 2H), 2.10(s, 3H), 2.17(s, 3H), 2.05-2.31(m, 2H), 2.60(t, 2H, J = 7.5 Hz), 3.76(s, 3H), 4.88(m, 1H), 8.28(s, 1H), 10.43(d, 1H, J = 7.5 Hz) |

TABLE 138

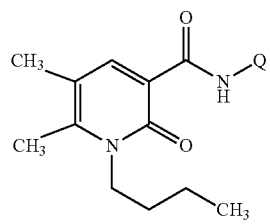

| Comp. No. | Q | ¹H-NMR(CDCl₃/TMS) δ |
|---|---|---|
| I-080 | (methyl ester —CH₂C(O)OCH₃) | 0.99(t, 3H, J = 7.2), 1.40-1.52(m, 2H), 1.63-1.73(m, 2H), 2.18(s, 3H), 2.42(s, 3H), 3.76(s, 3H), 4.13(q-like, 2H), 4.22(d, 2H, J = 5.7), 8.29(s, 1H), 10.38(brs, 1H) |
| IV-001 | (3-methyl-4-(N-isopropylcarbamoyl)phenyl) | 1.01(t, 3H, J = 7.4), 1.26(d, 6H, J = 6), 1.47(m, 2H), 1.71(m, 2H), 2.21(s, 3H), 2.45(s, 3H), 2.75(s, 3H), 4.18(m, 2H), 4.28(m, 1H), 5.91(d, 1H, J = 7.2), 7.55(dd, 1H, J = 8.4, 2.4), 7.67(d, 1H, J = 2.4), 8.48(d, 1H, J = 8.4), 12.25(brs, 1H) |
| IV-004 | (4-methoxycarbonylphenyl) | 1.02(t, 3H, J = 7.5), 1.42-1.56(m, 2H), 1.64-1.77(m, 2H), 2.22(s, 3H), 2.45(s, 3H), 3.90(s, 3H), 4.14-4.19(m, 2H), 7.84(d, 2H, J = 9.0), 8.02(d, 2H, J = 9.0), 8.39(s, 1H), 12.46(s, 1H) |
| IV-007 | (trans-4-methoxycarbonylcyclohexyl) | 0.99(t, 3H, J = 7.2), 1.23-1.74(m, 8H), 1.98-2.20(m, 4H), 2.17(s, 3H), 2.28(m, 1H), 2.40(s, 3H), 3.67(s, 3H), 3.93(m, 1H), 4.07-4.12(m, 2H), 8.30(s, 1H), 9.83(d, 1H, J = 7.8) |
| IV-014 | (4-carboxyphenyl) | DMSO-d6 0.95(t, 3H, J = 7.5), 1.34-1.48(m, 2H), 1.55-1.69(m, 2H), 2.19(s, 3H), 2.48(s, 3H), 4.14-4.19(m, 2H), 7.81(d, 2H, J = 9.0), 7.93(d, 2H, J = 9.0), 8.26(s, 1H), 12.59(s, 1H), 12.74(brs, 1H) |
| IV-017 | (trans-4-carboxycyclohexyl) | DMSO-d6 0.93(t, 3H, J = 7.2), 1.18-1.63(m, 8H), 1.86-1.97(m, 4H), 2.14(s, 3H), 2.21(m, 1H), 2.42(s, 3H), 3.70(m, 1H), 4.06-4.11(m, 2H), 8.11(s, 1H), 9.84(d, 1H, J = 7.8), 12.11(br, 1H) |
| V-004 | (4-methoxycarbonylbenzyl) | 0.99(t, 3H, J = 7.5), 1.38-1.52(m, 2H), 1.60-1.74(m, 2H), 2.19(s, 3H), 2.42(s, 3H), 3.90(s, 3H), 4.08-4.14(m, 2H), 4.69(d, 2H, J = 6.0), 7.66(d, 2H, J = 8.7), 7.98(d, 2H, J = 8.7), 8.34(s, 1H), 10.40(m, 1H) |

TABLE 139
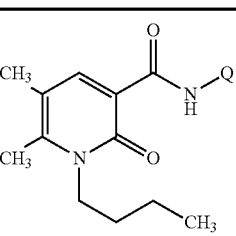
| Comp. No. | Q | $^1$H-NMR(CDCl$_3$/TMS) δ |
|---|---|---|
| V-010 | ~~CH$_2$-C$_6$H$_4$-COOH (para) | DMSO-d6 0.93(t, 3H, J = 7.3), 1.31-1.43(m, 2H), 1.52-1.62(m, 2H), 2.15(s, 3H), 2.44(s, 3H), 4.10(m, 2H), 4.59(d, 2H, J = 6.0), 7.41 (d, 2H, J = 8.4), 7.90(d, 2H, J = 8.4), 8.16(s, 1H), 10.33(1H, t, J = 6), 12.88(brs, 1H) |
TABLE 140
| Comp. No. | Q | $^1$H-NMR(CDCl$_3$/TMS) δ |
|---|---|---|
| I-085 | ~~CH(CH$_3$)C(O)OCH$_3$ | 1.06-1.28(m, 4H), 1.52(d, 3H, J = 7.2), 1.55-1.88(m, 7H), 2.16(s, 3H), 2.38(s, 3H), 3.75(s, 3H), 4.02(br, 2H), 4.72(m, 1H), 8.28(s, 1H) |
| I-086 | ~~CH(CH$_2$-indol-2-yl)C(O)OCH$_3$ | 1.06-1.29(m, 4H), 1.54-1.88(m, 7H), 2.15(s, 3H), 2.37(s, 3H), 3.36-3.42(m, 2H), 3.63(s, 3H), 3.86-4.16(m, 2H), 5.06(m, 1H), 7.02-7.18(m, 3H), 7.31(d, 1H, J = 8.1), 7.61(d, 1H, J = 7.8), 8.04(br, 1H), 8.27(s, 1H), 10.49(d, 1H, 7.2) |
| I-087 | ~~CH(CH$_2$Ph)C(O)OCH$_3$ | 1.06-1.29(m, 4H), 1.54-1.88(m, 7H), 2.15(s, 3H), 2.37(s, 3H), 3.10-3.30(m, 2H), 3.68(s, 3H), 3.86-4.16(m, 2H), 4.96(dd, 1H, J = 7.5 and 13.8), 7.17-7.30(m, 5H), 8.24(s, 1H), 10.46(d, 1H, 7.8) |

TABLE 140-continued

[Structure: 5-methyl-6-methyl-1-(cyclohexylmethyl)-2-oxo-1,2-dihydropyridine-3-carboxamide with N-H-Q]

| Comp. No. | Q | $^1$H-NMR(CDCl$_3$/TMS) δ |
|---|---|---|
| I-088 | [4-hydroxybenzyl substituted methyl ester] | 1.00-1.32(m, 4H), 1.54-1.95(m, 7H), 2.15(s, 3H), 2.38(s, 3H), 3.02(dd, 1H, J = 7.8 and 13.5), 3.16(dd, 1H, J = 5.4 and 13.5), 3.69(s, 3H), 4.02(br, 2H), 5.08(m, 1H), 5.83(br s, 1H), 6.66(d, 2H, J = 8.7), 7.04(d, 2H, 8.7), 8.24(s, 1H), 10.45(d, 1H, J = 7.8) |
| I-089 | [sec-butyl substituted methyl ester] | 0.92-1.38(m, 10H), 1.47-2.10(m, 10H), 2.16(s, 3H), 2.38(s, 3H), 3.74(s, 3H), 4.02(br, 2H), 4.70(dd, 1H, J = 7.8 and 8.4), 8.28(s, 1H), 10.40(d, 1H, J = 7.8) |
| I-090 | [hydroxymethyl substituted methyl ester] | 1.02-1.30(m, 4H), 1.58-1.94(m, 7H), 2.19(s, 3H), 2.42(s, 3H), 3.79(s, 3H), 3.80-4.20(m, 4H), 4.81(m, 1H), 8.28(s, 1H) |
| I-091 | [methyl ester CH$_2$CH$_2$] | 1.02-1.30(m, 4H), 1.57-1.94(m, 7H), 2.17(s, 3H), 2.39(s, 3H), 3.76(s, 3H), 4.02(br, 2H), 4.21(d, 2H, J = 5.7), 8.29(s, 1H), 10.36(m, 1H) |

TABLE 141

[Structure: same pyridinone core with N-H-Q amide]

| Comp. No. | Q | $^1$H-NMR(CDCl$_3$/TMS) δ |
|---|---|---|
| I-093 | [isobutyl substituted methyl ester] | 0.94-1.32(m, 10H), 1.56-1.96(m, 10H), 2.16(s, 3H), 2.38(s, 3H), 3.73(s, 3H), 4.00(br, 2H), 4.72(dd, 1H, J = 6.6 and 14.4), 8.29(s, 1H), 10.23(d, 1H, J = 7.5) |

TABLE 141-continued

[Structure: 5-methyl-6-methyl-1-(cyclohexylmethyl)-2-oxo-1,2-dihydropyridine-3-carboxamide with N-Q substituent]

| Comp. No. | Q | ¹H-NMR(CDCl₃/TMS) δ |
|---|---|---|
| V-003 | [4-(methoxycarbonyl)benzyl group] | 1.02-1.30(m, 4H), 1.56-1.90(m, 7H), 2.18(s, 3H), 2.40(s, 3H), 3.89(s, 3H), 4.01(br, 2H), 4.68(d, 2H, J = 6.0), 7.42(d, 2H, J = 8.4), 7.98(d, 2H, J = 8.4), 8.35(s, 1H), 10.40(m, 1H) |
| V-009 | [4-carboxybenzyl group] | DMSO-d6 1.02-1.30(m, 4H), 1.56-1.90(m, 7H), 2.16(s, 3H), 2.42(s, 3H), 3.92-4.10(m, 2H), 4.58(d, 2H, J = 6.0), 7.42(d, 2H, J = 8.4), 7.99(d, 2H, J = 8.4), 8.17(s, 1H), 10.31(t, 1H, J = 6.0), 12.86(br, 1H) |

30

TABLE 142

[Structure: 5-methyl-6-methyl-1-(4-fluorobenzyl)-2-oxo-1,2-dihydropyridine-3-carboxamide with N-Q substituent]

| Comp. No. | Q | ¹H-NMR(CDCl₃/TMS) δ |
|---|---|---|
| I-094 | [methyl 2-isopropyl-propanoate group] | 1.01-1.03(d, 6H, J = 6.9), 2.16(s, 3H), 2.29(s, 3H), 3.74(s, 3H), 4.66(dd, 1H, J = 5.4 and 8.1), 5.38-5.56(m, 2H), 6.99-7.15(m, 5H), 8.37(s, 1H), 10.31(d, 1h, J = 8.1) |
| X-145 | [1,2,4-thiadiazol-3-yl-acetic acid group] | DMSO-d6 2.19(s, 3H), 2.39(s, 3H), 3.80(s, 2H), 5.52(br-s, 2H), 7.13-7.31(m, 4H), 8.40(s, 1H), 13.69(s, 1H) |
| X-236 | [thiazol-4-yl-acetic acid group] | DMSO-d6 2.20(s, 3H), 2.39(s, 3H), 3.61(s, 2H), 5.51(s, 2H), 7.03(s, 1H), 7.18(t, 2H, J = 8.7), 7.28(dd, 2H, J = 5.7 and 9.0), 12.42(br s, 1H), 13.34(s, 1H) |

TABLE 142-continued
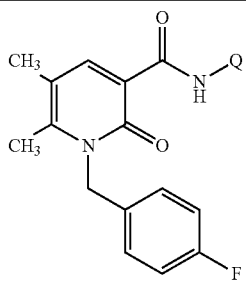
| Comp. No. | Q | ¹H-NMR(CDCl₃/TMS) δ |
|---|---|---|
TABLE 143
| Comp. No. | Structure |
|---|---|
| I-063 | 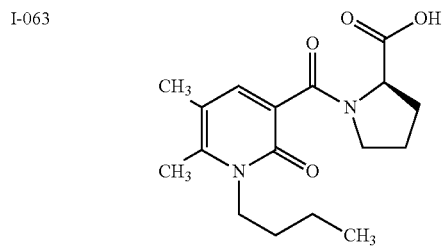 |
| I-064 | 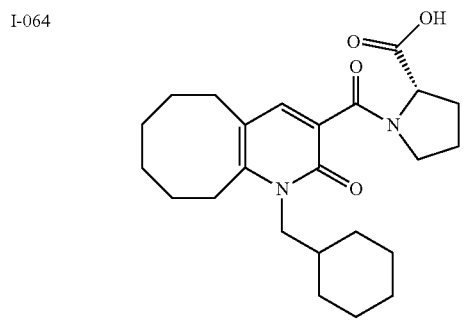 |
| I-065 | 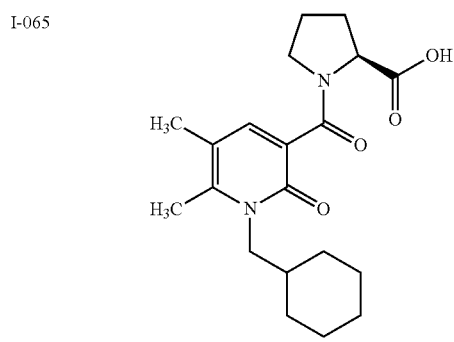 |
TABLE 143-continued
| Comp. No. | Structure |
|---|---|
| I-066 | 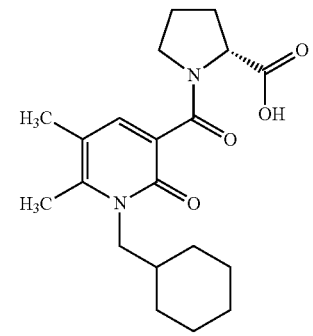 |
TABLE 144
| Comp. No. | Structure |
|---|---|
| I-067 | 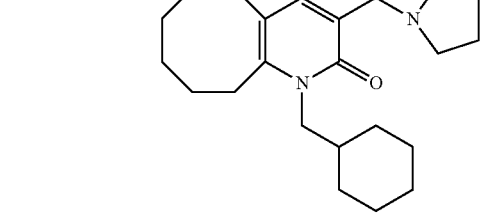 |
| I-068 | 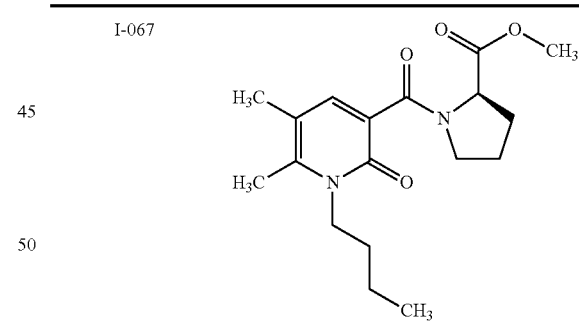 |

TABLE 144-continued

| Comp. No. | Structure |
|---|---|
| I-069 | 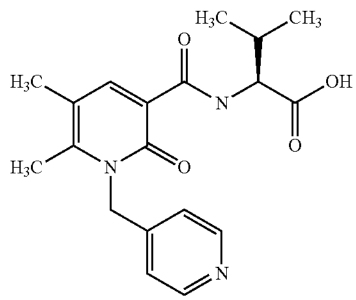 |
| I-070 | 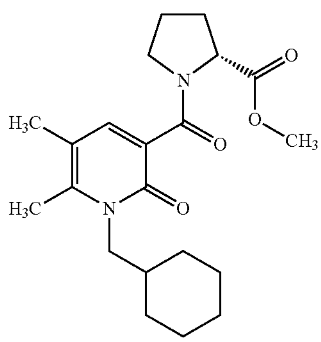 |

TABLE 145

| Comp. No. | Structure |
|---|---|
| I-092 | 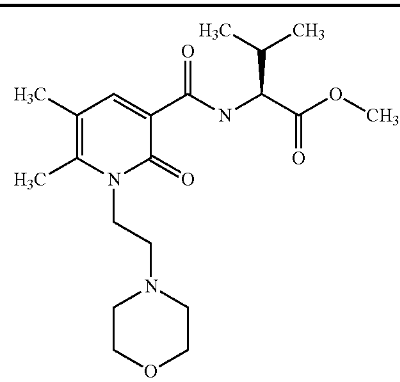 |
| I-095 | 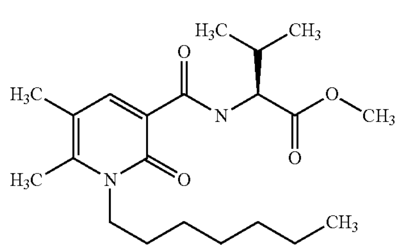 |

TABLE 145-continued

| Comp. No. | Structure |
|---|---|
| I-096 | 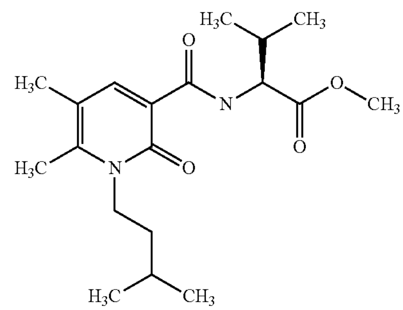 |
| I-097 | 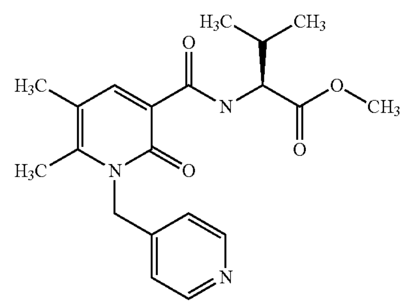 |

TABLE 146

| Comp. No. | Structure |
|---|---|
| I-098 | 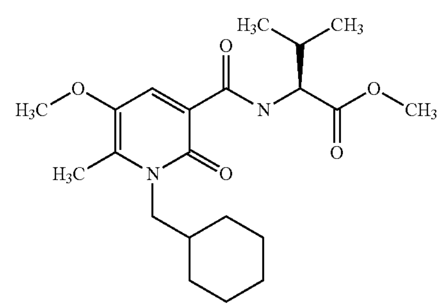 |
| I-099 | 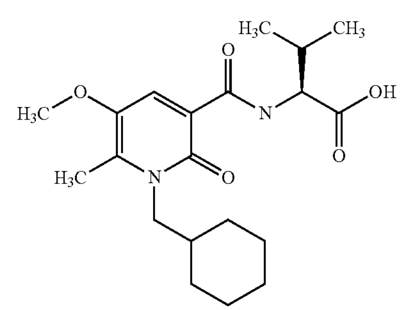 |

TABLE 146-continued
| Comp. No. | Structure |
|---|---|
| I-100 | 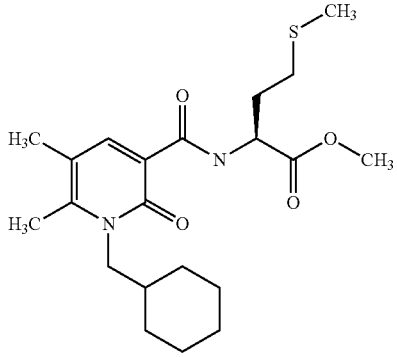 |
| I-101 | 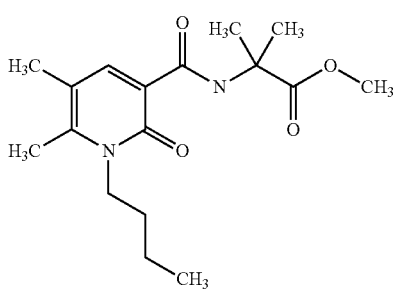 |
TABLE 147
| Comp. No. | Structure |
|---|---|
| I-102 | 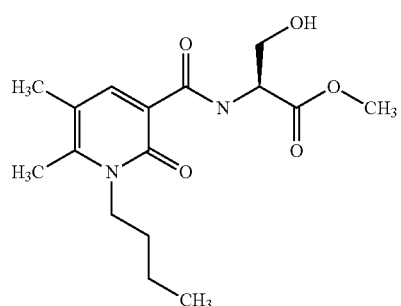 |
| I-103 | 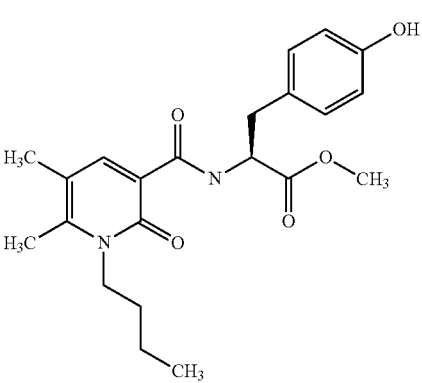 |
TABLE 147-continued
| Comp. No. | Structure |
|---|---|
| I-106 | 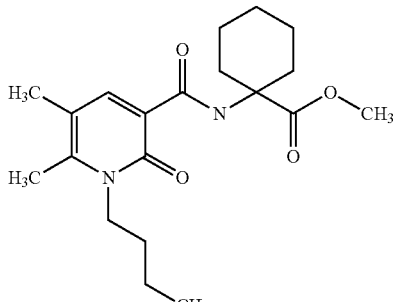 |
| I-107 | 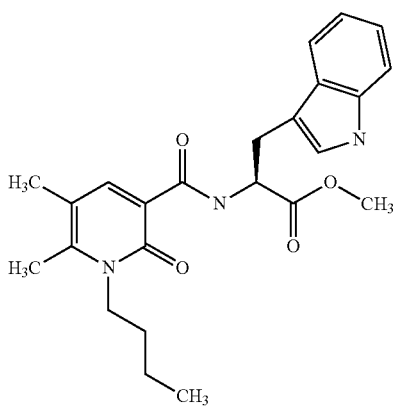 |
TABLE 148
| Comp. No. | Structure |
|---|---|
| I-108 | 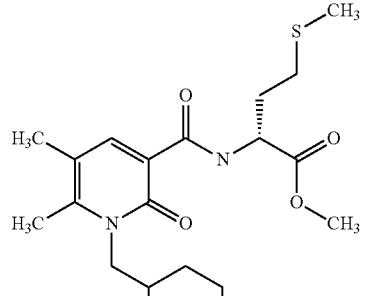 |
| I-109 | 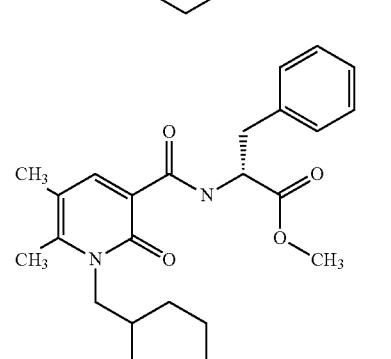 |

TABLE 148-continued

| Comp. No. | Structure |
|---|---|
| I-110 | (structure) |
| I-115 | (structure) |

TABLE 149

| Comp. No. | Structure |
|---|---|
| I-116 | (structure) |
| I-117 | (structure) |

TABLE 149-continued

| Comp. No. | Structure |
|---|---|
| I-118 | (structure) |
| I-120 | (structure) |

TABLE 150

| Comp. No. | Structure |
|---|---|
| I-121 | (structure) |
| I-122 | (structure) |

TABLE 150-continued
| Comp. No. | Structure |
|---|---|
| I-123 | 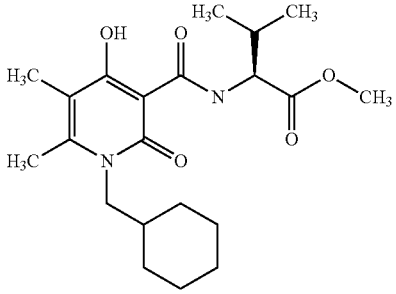 |
| I-125 | 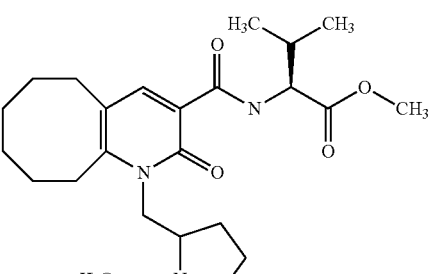 |
TABLE 151
| Comp. No. | Structure |
|---|---|
| I-126 | 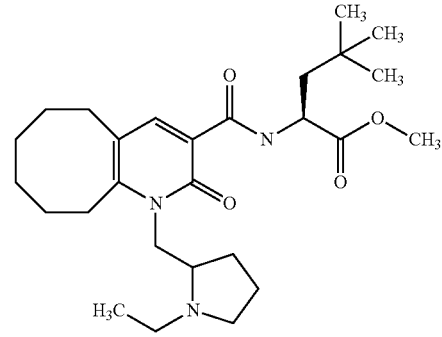 |
| I-127 | 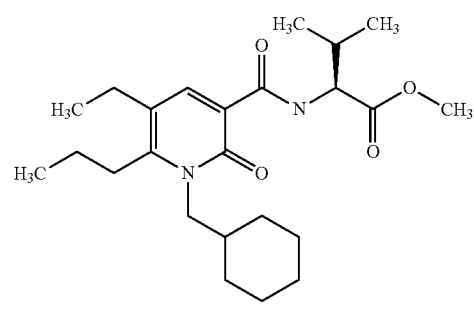 |
TABLE 151-continued
| Comp. No. | Structure |
|---|---|
| I-128 | 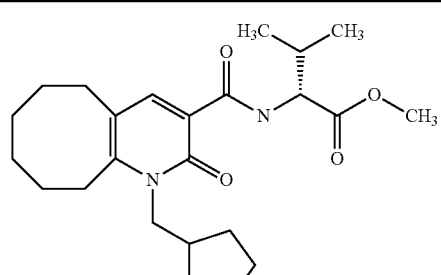 |
| I-133 | 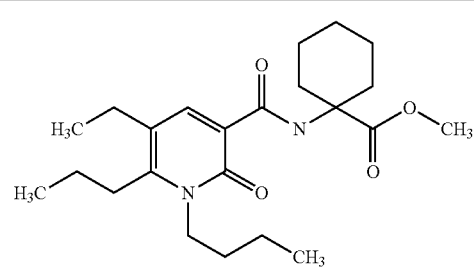 |
TABLE 152
| Comp. No. | Structure |
|---|---|
| I-138 | 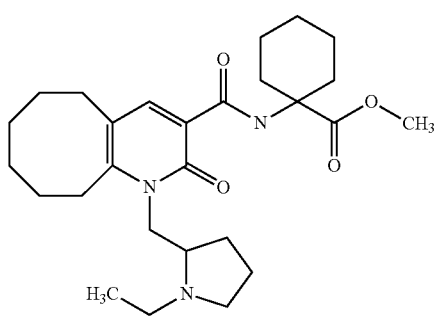 |
| I-139 | 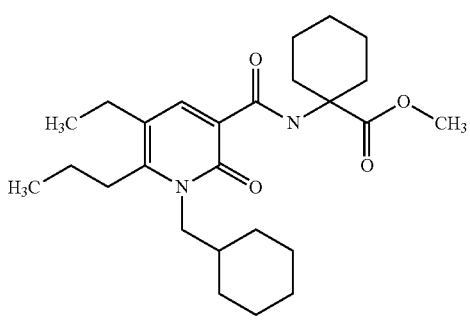 |

TABLE 152-continued

| Comp. No. | Structure |
|---|---|
| I-140 | 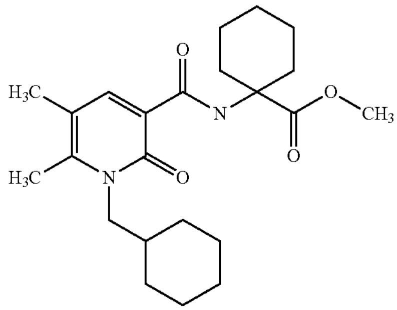 |
| I-141 | 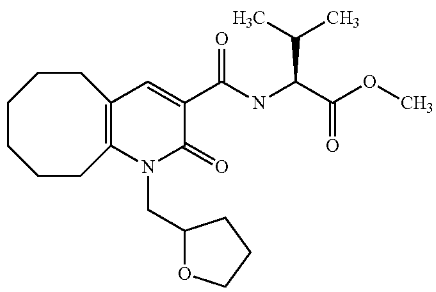 |

TABLE 153

| Comp. No. | Structure |
|---|---|
| I-142 | 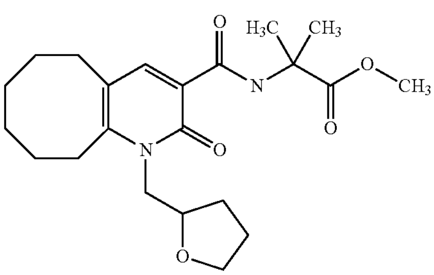 |
| I-143 | 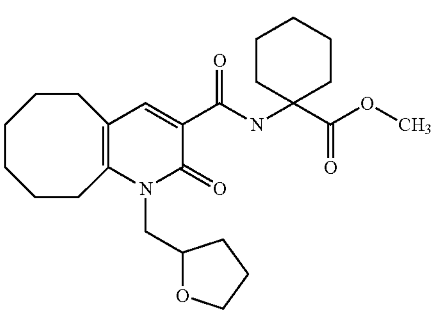 |

TABLE 153-continued

| Comp. No. | Structure |
|---|---|
| I-144 | 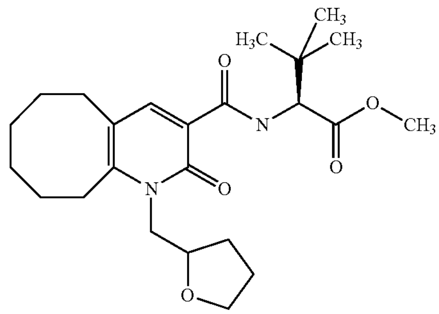 |
| I-147 | 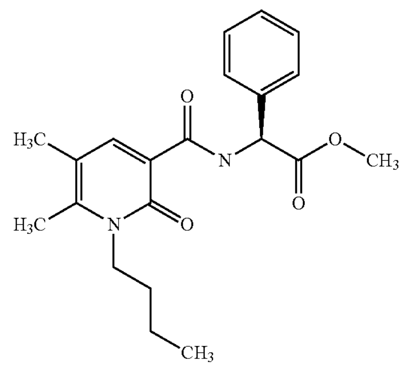 |

TABLE 154

| Comp. No. | Structure |
|---|---|
| I-148 | 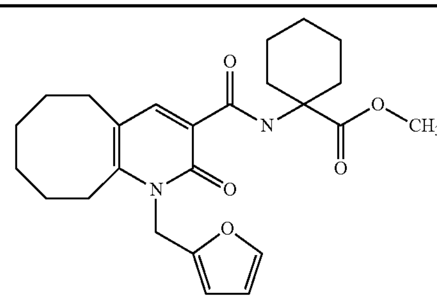 |
| I-154 | 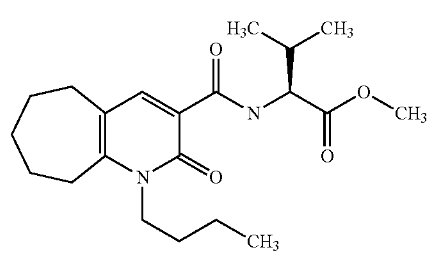 |

TABLE 154-continued
| Comp. No. | Structure |
|---|---|
| I-155 | 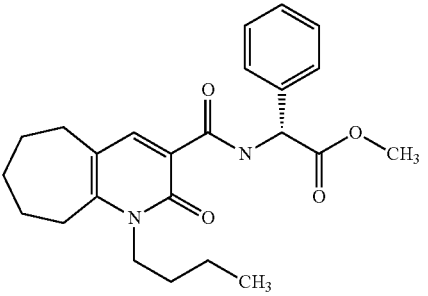 |
| I-158 | 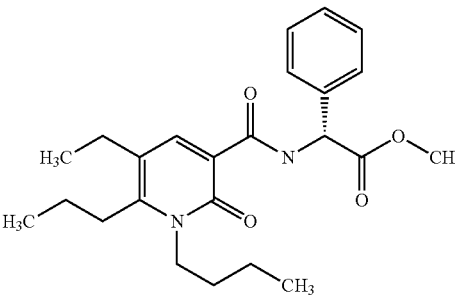 |
TABLE 155
| Comp. No. | Structure |
|---|---|
| I-160 | 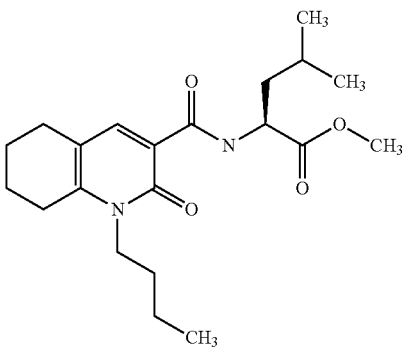 |
| I-161 | 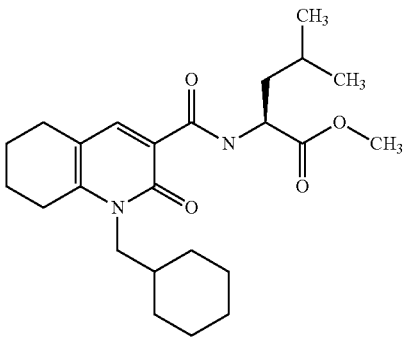 |
TABLE 155-continued
| Comp. No. | Structure |
|---|---|
| I-162 | 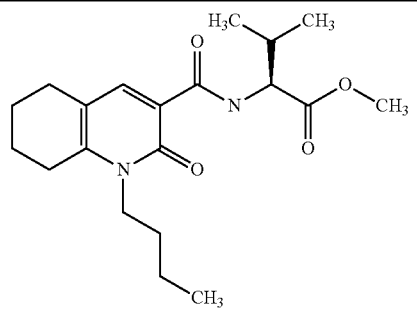 |
| I-163 | 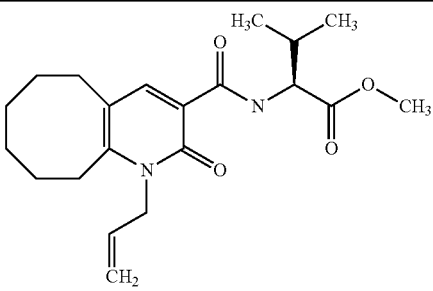 |
TABLE 156
| Comp. No. | Structure |
|---|---|
| I-164 | 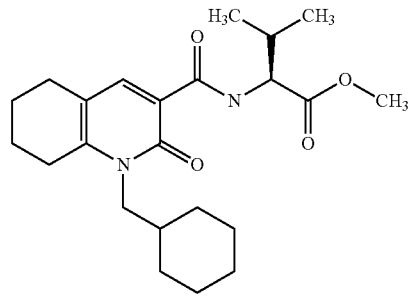 |
| I-165 | 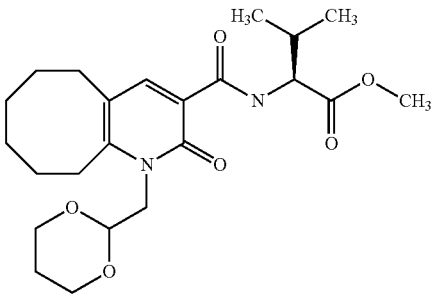 |

TABLE 156-continued

| Comp. No. | Structure |
|---|---|
| I-166 | (cyclooctane-fused pyridinone with N-CH2CHO substituent; C(O)NH-CH(iPr)-C(O)OCH3) |
| I-167 | (5,6,7,8-tetrahydroquinolin-2(1H)-one, N-butyl; C(O)NH-CH(CH2Ph)-C(O)OCH3) |

TABLE 157

| Comp. No. | Structure |
|---|---|
| I-168 | (5,6,7,8-tetrahydroquinolin-2(1H)-one, N-CH2-cyclohexyl; C(O)NH-CH(CH2Ph)-C(O)OCH3) |
| I-169 | (5,6,7,8-tetrahydroquinolin-2(1H)-one, N-butyl; C(O)NH-CH(sec-Bu)-C(O)OCH3) |

TABLE 157-continued

| Comp. No. | Structure |
|---|---|
| I-170 | (5,6,7,8-tetrahydroquinolin-2(1H)-one, N-CH2-cyclohexyl; C(O)NH-CH(sec-Bu)-C(O)OCH3) |
| I-171 | (cyclooctane-fused pyridinone, N-CH2-(1,3-dioxolan-2-yl); C(O)NH-CH(iPr)-C(O)OCH3) |

TABLE 158

| Comp. No. | Structure |
|---|---|
| I-172 | (cycloheptane-fused pyridinone, N-CH2-cyclohexyl; C(O)NH-CH(iPr)-C(O)OCH3) |
| I-173 | (cycloheptane-fused pyridinone, N-CH2-cyclohexyl; C(O)NH-CH(Ph)-C(O)OCH3) |

TABLE 158-continued
| Comp. No. | Structure |
|---|---|
| I-174 | 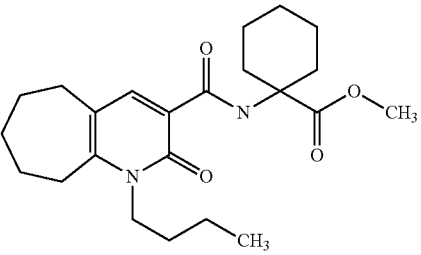 |
| I-175 | 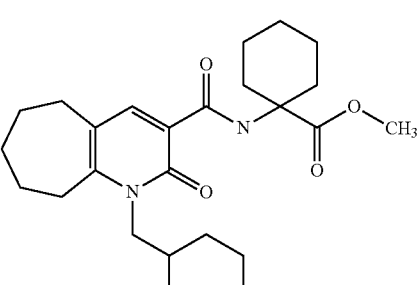 |
TABLE 159
| Comp. No. | Structure |
|---|---|
| I-176 | 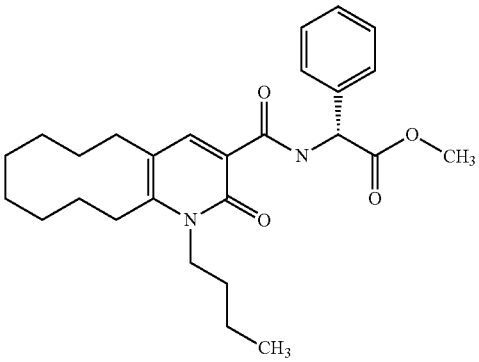 |
| I-177 | 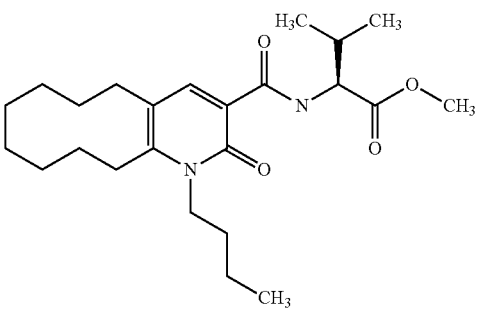 |
TABLE 159-continued
| Comp. No. | Structure |
|---|---|
| I-178 | 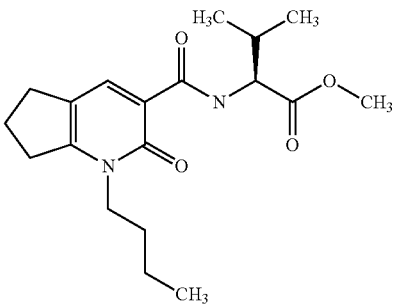 |
| I-179 | 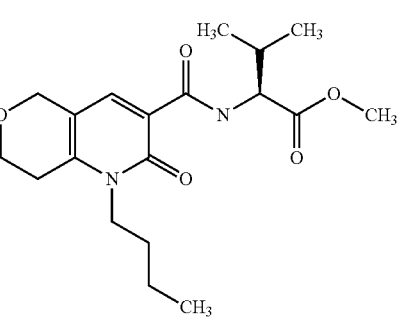 |
TABLE 160
| Comp. No. | Structure |
|---|---|
| I-181 | 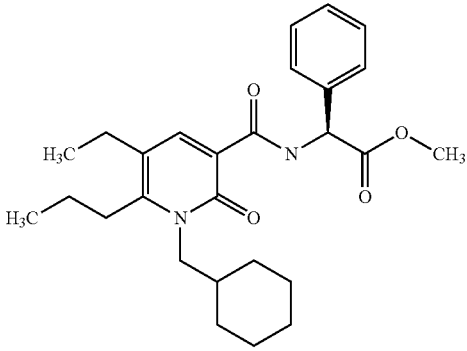 |
| I-183 | 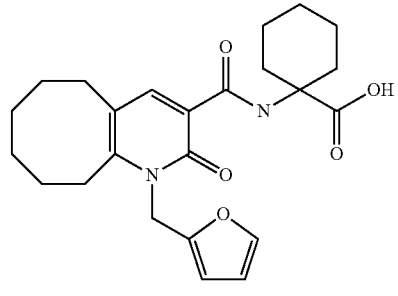 |

US 8,178,681 B2
TABLE 160-continued
| Comp. No. | Structure |
|---|---|
| I-186 | 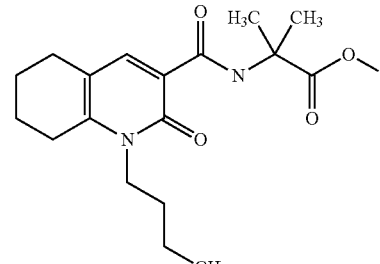 |
| I-187 | 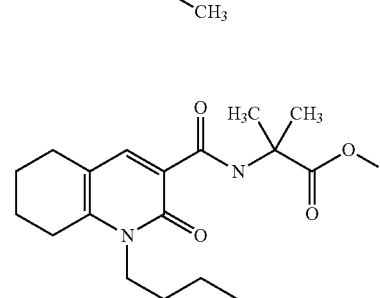 |
TABLE 161
| Comp. No. | Structure |
|---|---|
| I-188 | 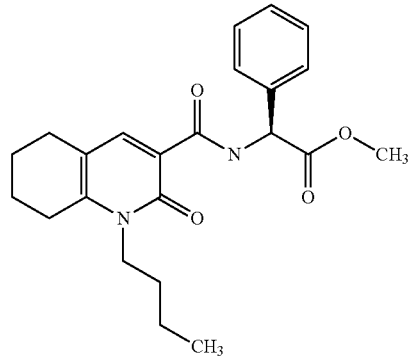 |
| I-189 | 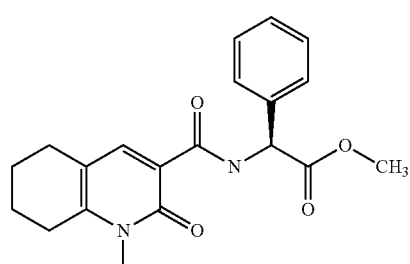 |
TABLE 161-continued
| Comp. No. | Structure |
|---|---|
| I-193 | 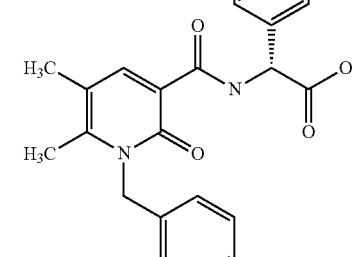 |
| I-194 | 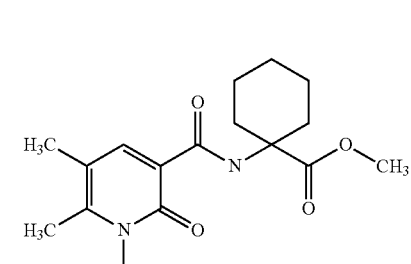 |
TABLE 162
| Comp. No. | Structure |
|---|---|
| I-196 | 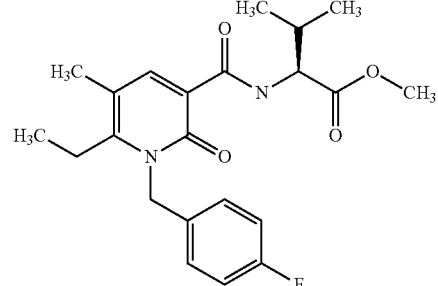 |
| I-197 | 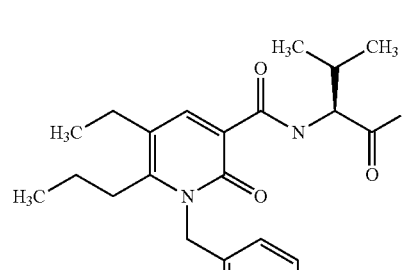 |

TABLE 162-continued

| Comp. No. | Structure |
|---|---|
| I-198 | 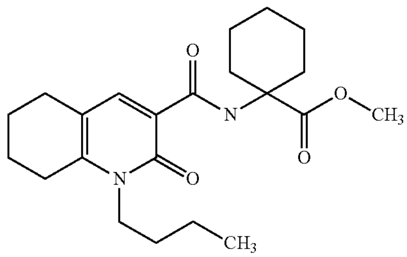 |
| I-199 | 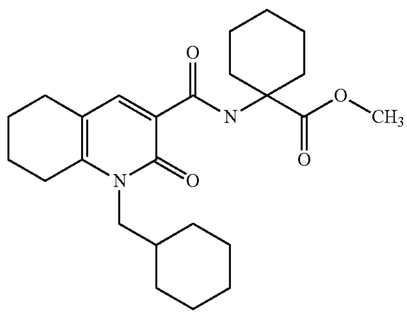 |

TABLE 163

| Comp. No. | Structure |
|---|---|
| I-200 | 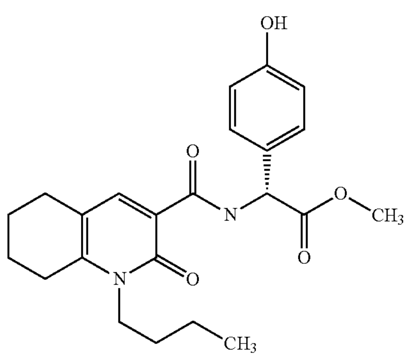 |
| I-201 | 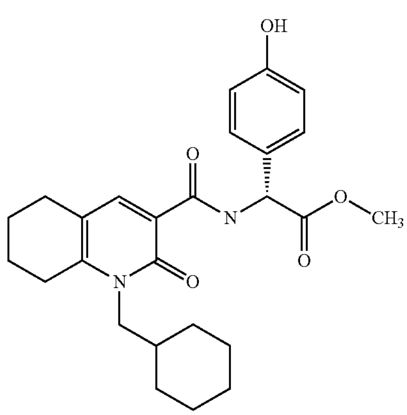 |

TABLE 163-continued

| Comp. No. | Structure |
|---|---|
| I-202 | 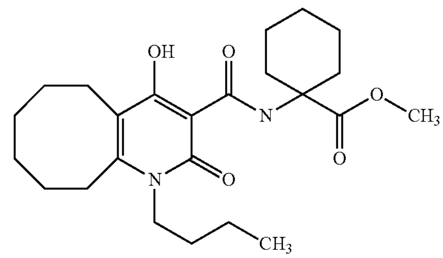 |
| I-205 | 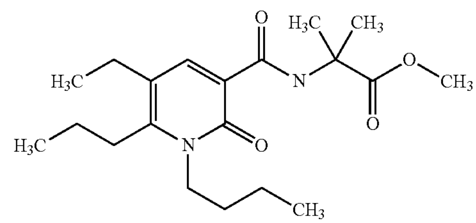 |

TABLE 164

| Comp. No. | Structure |
|---|---|
| I-206 | 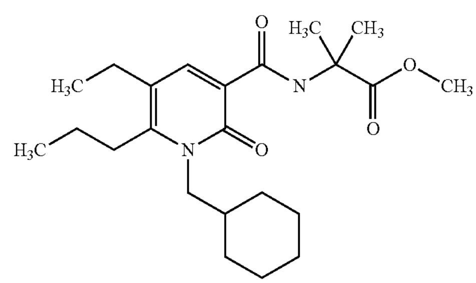 |
| I-207 | 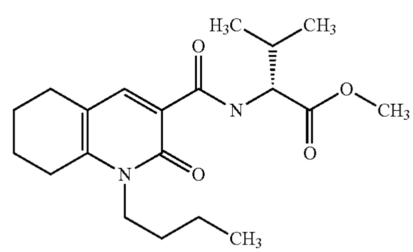 |
| I-208 | 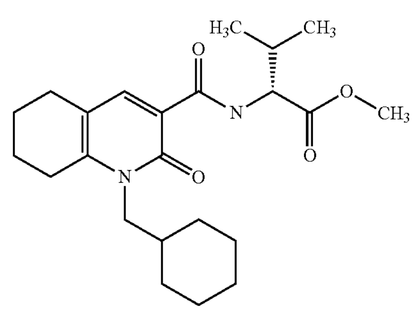 |

TABLE 164-continued
| Comp. No. | Structure |
|---|---|
| I-211 | 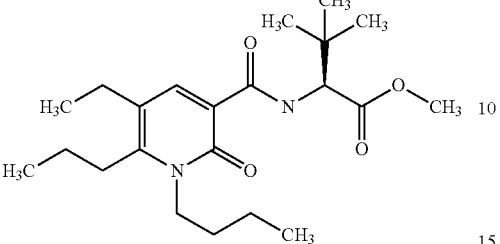 |
TABLE 165
| Comp. No. | Structure |
|---|---|
| I-212 | 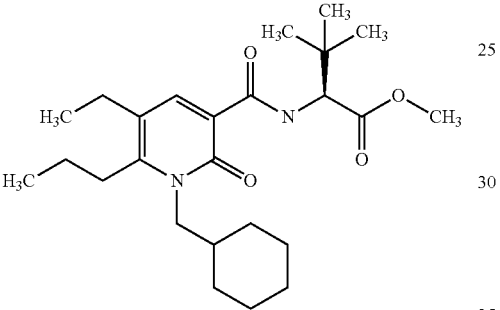 |
| I-213 | 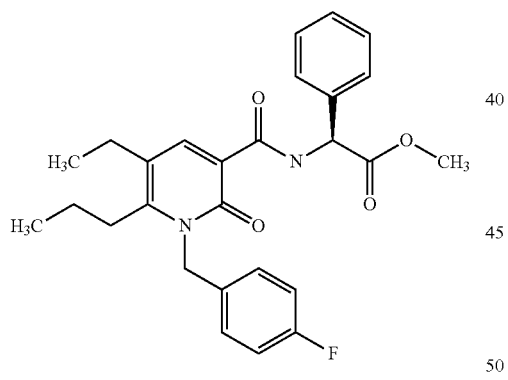 |
| I-214 | 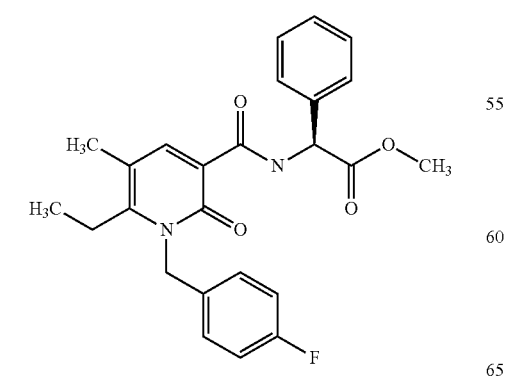 |
TABLE 165-continued
| Comp. No. | Structure |
|---|---|
| I-215 | 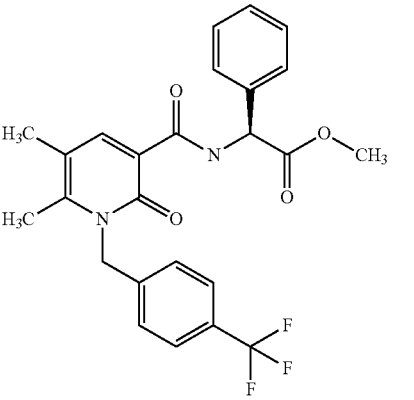 |
TABLE 166
| Comp. No. | Structure |
|---|---|
| I-216 | 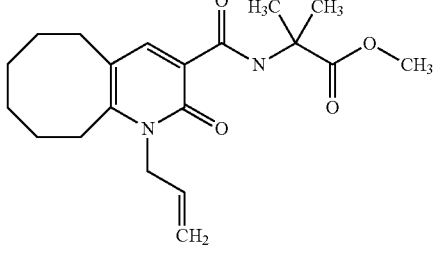 |
| I-217 | 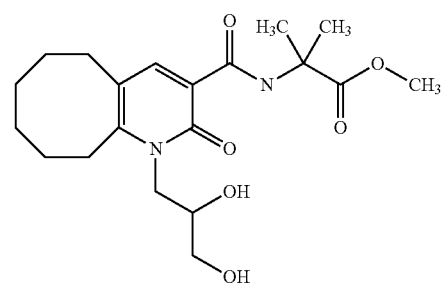 |
| I-218 | 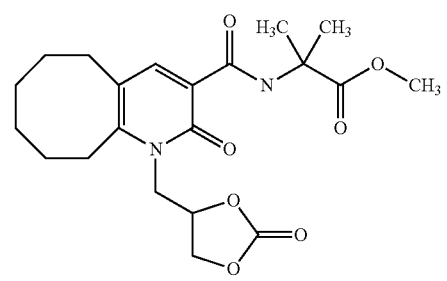 |

TABLE 166-continued
| Comp. No. | Structure |
|---|---|
| I-219 | 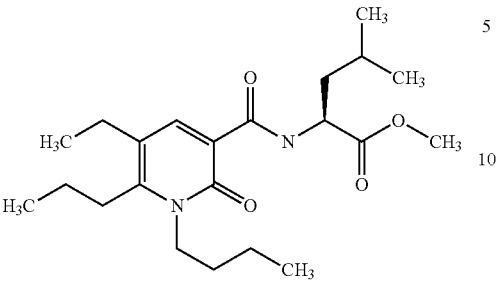 |
TABLE 167
| Comp. No. | Structure |
|---|---|
| I-220 | 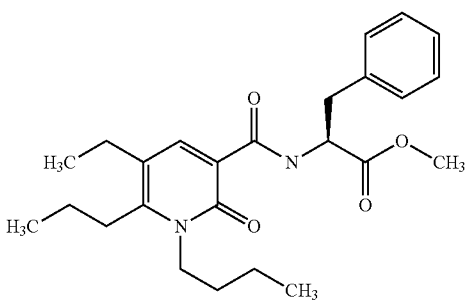 |
| I-221 | 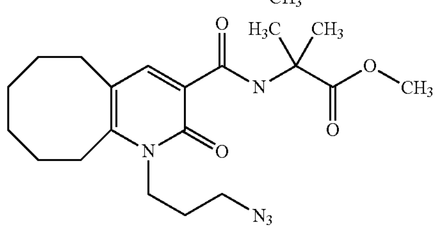 |
| I-222 | 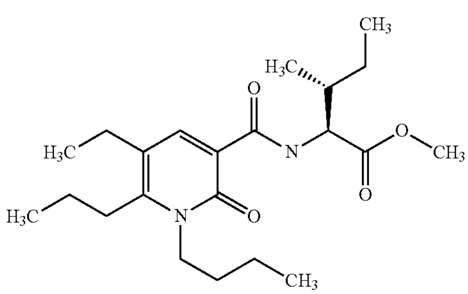 |
| I-223 | 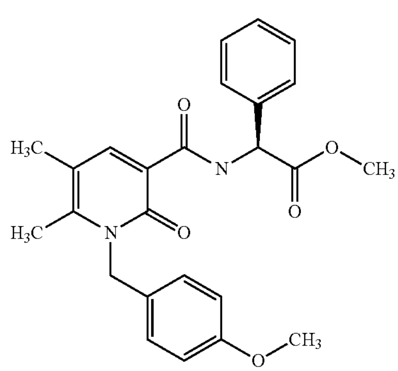 |
TABLE 168
| Comp. No. | Structure |
|---|---|
| I-224 | 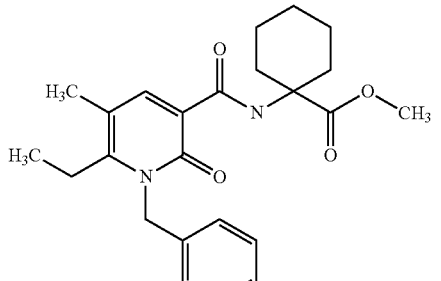 |
| I-225 | 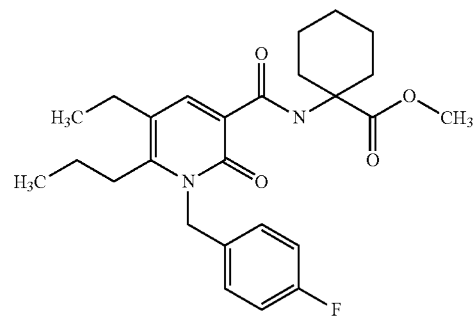 |
| I-226 | 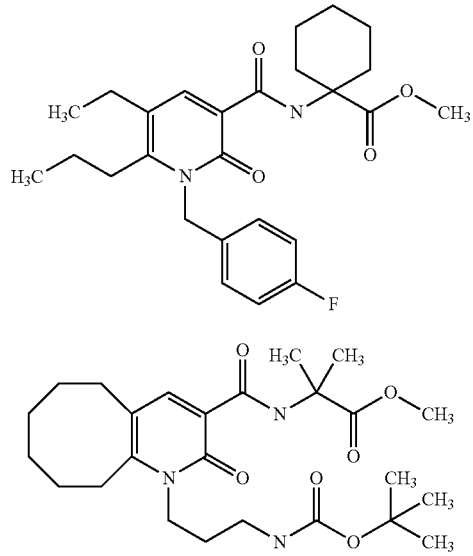 |
| I-227 | 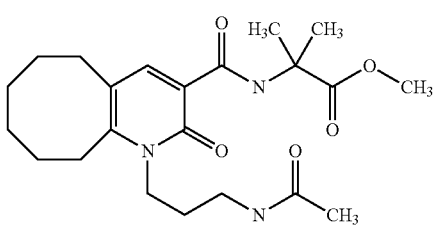 |
TABLE 169
| Comp. No. | Structure |
|---|---|
| I-228 | 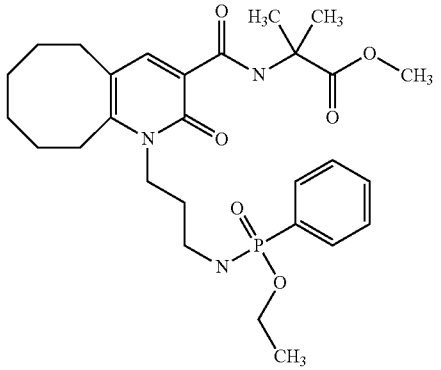 |

TABLE 169-continued

| Comp. No. | Structure |
|---|---|
| I-229 | 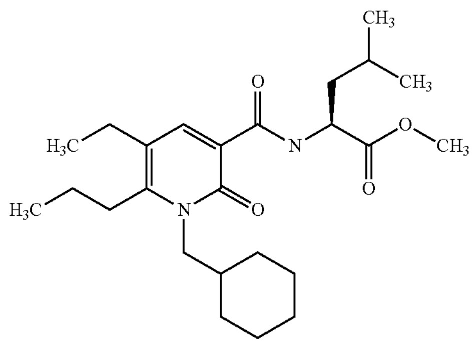 |
| I-230 | 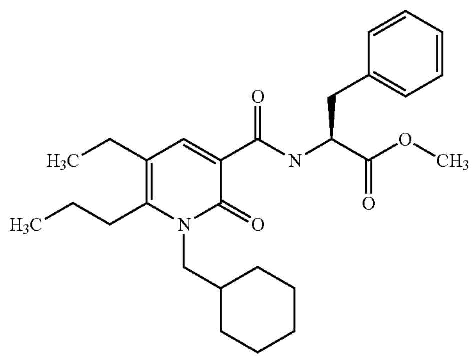 |
| I-231 | 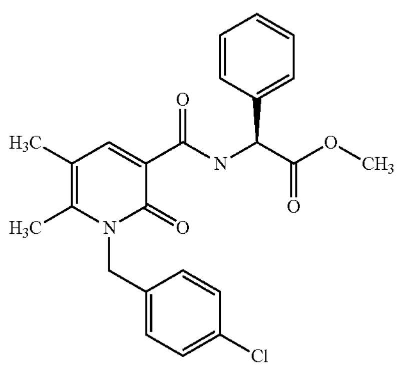 |

TABLE 170

| Comp. No. | Structure |
|---|---|
| I-232 | 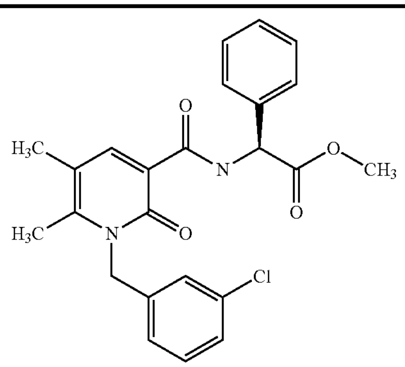 |

TABLE 170-continued

| Comp. No. | Structure |
|---|---|
| I-233 | 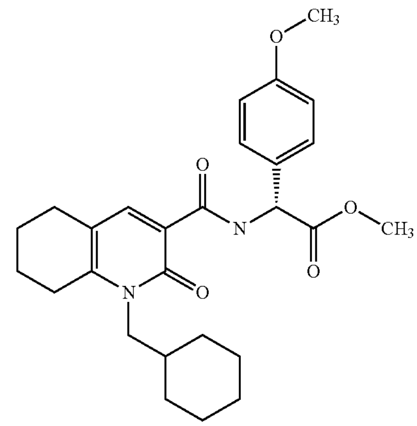 |
| I-234 | 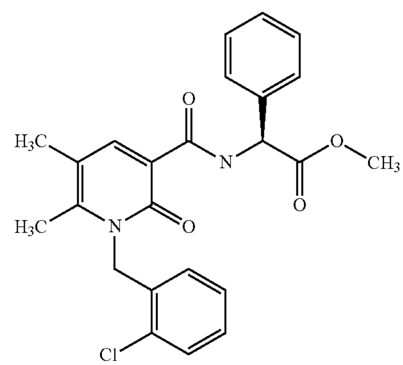 |
| I-236 | 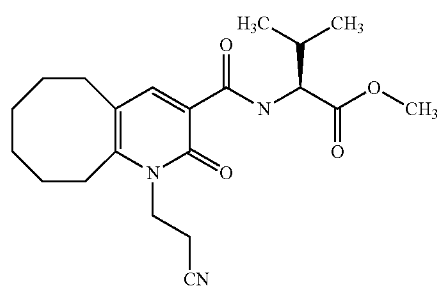 |

TABLE 171

| Comp. No. | Structure |
|---|---|
| I-237 | 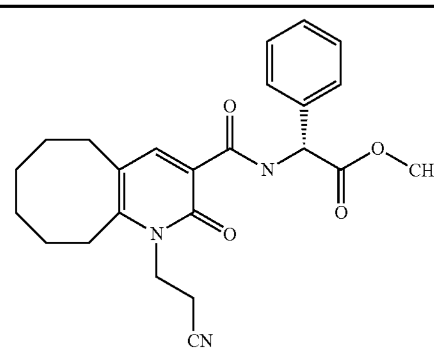 |

TABLE 171-continued

| Comp. No. | Structure |
|---|---|
| I-238 | (structure) |
| I-239 | (structure) |
| I-240 | (structure) |

TABLE 172

| Comp. No. | Structure |
|---|---|
| I-241 | (structure) |
| I-242 | (structure) |

TABLE 172-continued

| Comp. No. | Structure |
|---|---|
| I-245 | (structure) |
| I-246 | (structure) |

TABLE 173

| Comp. No. | Structure |
|---|---|
| I-247 | (structure) |
| I-249 | (structure) |
| I-250 | (structure) |

TABLE 173-continued
| Comp. No. | Structure |
|---|---|
| I-251 | 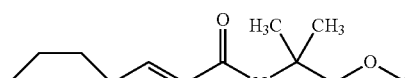 |
TABLE 174
| Comp. No. | Structure |
|---|---|
| I-256 | 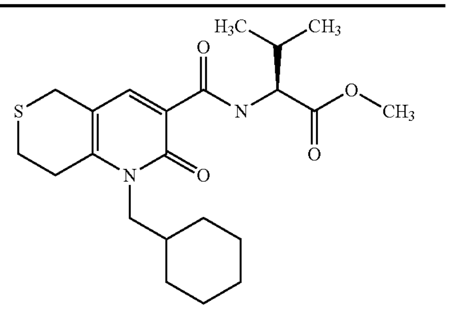 |
| I-257 | 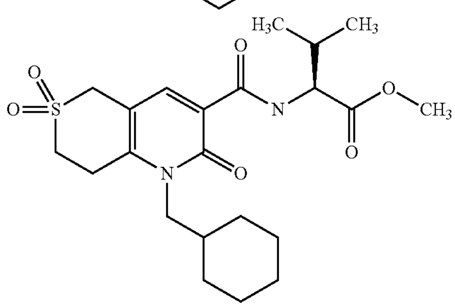 |
| I-258 | 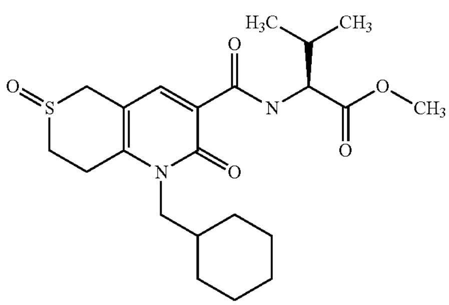 |
| I-261 | 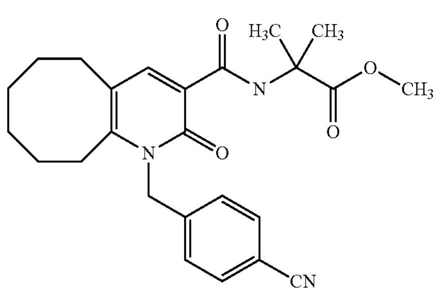 |
TABLE 175
| Comp. No. | Structure |
|---|---|
| I-266 | 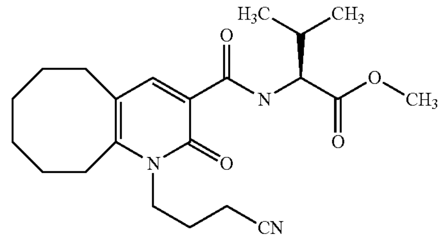 |
| I-267 | 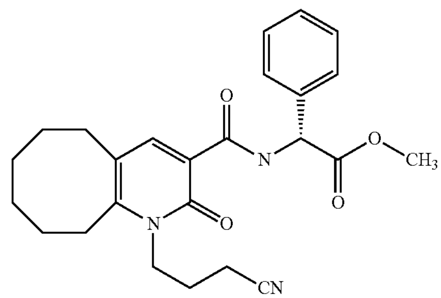 |
| I-271 | 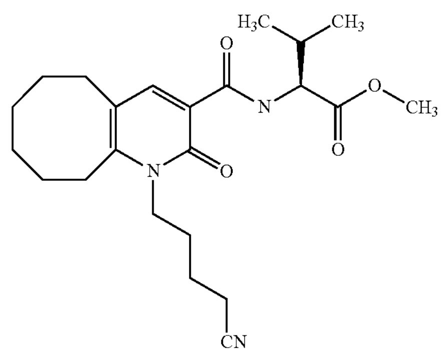 |
| I-272 | 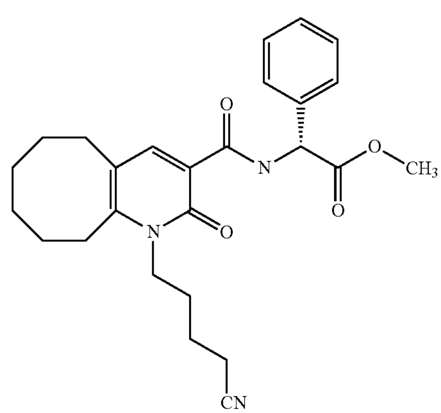 |

TABLE 176

| Comp. No. | Structure |
|---|---|
| I-273 | (structure) |
| I-278 | (structure) |
| I-279 | (structure) |
| I-280 | (structure) |

TABLE 177

| Comp. No. | Structure |
|---|---|
| I-281 | (structure) |
| I-282 | (structure) |
| I-283 | (structure) |
| I-285 | (structure) |

TABLE 178

| Comp. No. | Structure |
|---|---|
| I-287 | (cyclooctane-fused pyridinone, N-benzyl with 4-CF3, C3-carboxamide-NH-CH(iPr)-C(O)OCH3) |
| I-288 | (cyclooctane-fused pyridinone, N-benzyl with 4-CF3, C3-carboxamide-NH-CH(Ph)-C(O)OCH3) |
| I-289 | (cyclooctane-fused pyridinone, N-(3,4-methylenedioxybenzyl), C3-carboxamide-NH-CH(iPr)-C(O)OCH3) |
| I-290 | (cyclooctane-fused pyridinone, N-(3,4-methylenedioxybenzyl), C3-carboxamide-NH-CH(Ph)-C(O)OCH3) |

TABLE 179

| Comp. No. | Structure |
|---|---|
| I-292 | (cyclooctane-fused pyridinone, N-(4-methylbenzyl), C3-carboxamide-NH-CH(iPr)-C(O)OCH3) |
| I-293 | (cyclooctane-fused pyridinone, N-(4-methylbenzyl), C3-carboxamide-NH-CH(Ph)-C(O)OCH3) |
| I-294 | (cyclooctane-fused pyridinone, N-(4-chlorobenzyl), C3-carboxamide-NH-CH(iPr)-C(O)OCH3) |
| I-295 | (cyclooctane-fused pyridinone, N-(4-chlorobenzyl), C3-carboxamide-NH-CH(Ph)-C(O)OCH3) |

TABLE 180

| Comp. No. | Structure |
|---|---|
| I-298 | 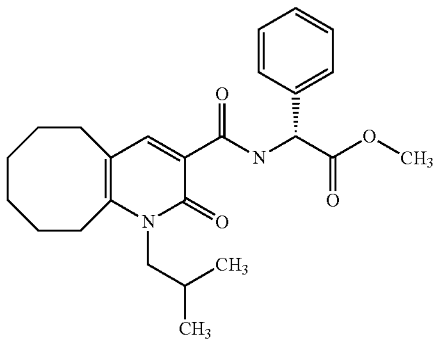 |
| I-330 | 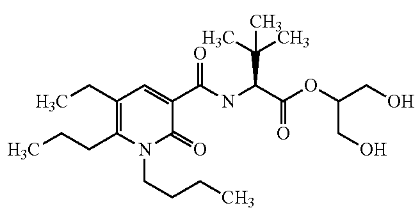 |
| I-347 | 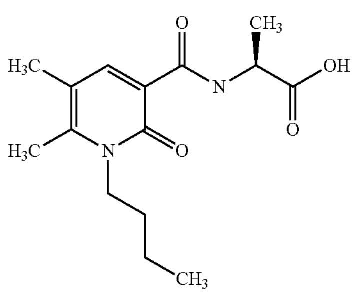 |
| I-348 | 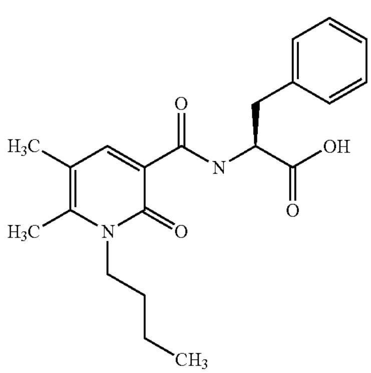 |

TABLE 181

| Comp. No. | Structure |
|---|---|
| I-349 | 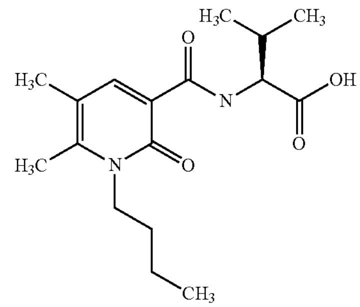 |
| I-350 | 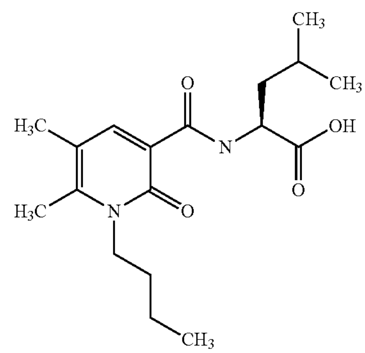 |
| I-351 | 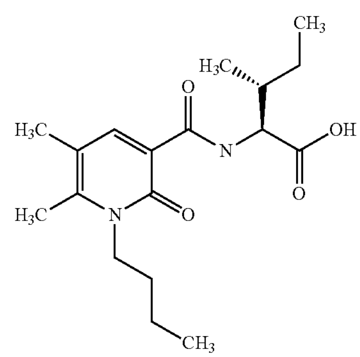 |
| I-352 | 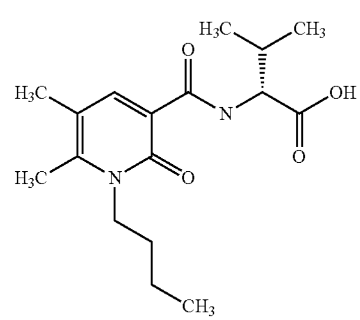 |

TABLE 182

| Comp. No. | Structure |
|---|---|
| I-353 | (5-methyl-6-methyl-1-butyl-2-oxo-1,2-dihydropyridine-3-carbonyl)-methionine |
| I-354 | (5-methyl-6-methyl-1-butyl-2-oxo-1,2-dihydropyridine-3-carbonyl)-glycine |
| I-359 | (5-methyl-6-methyl-1-cyclohexylmethyl-2-oxo-1,2-dihydropyridine-3-carbonyl)-alanine |
| I-360 | (5-methyl-6-methyl-1-cyclohexylmethyl-2-oxo-1,2-dihydropyridine-3-carbonyl)-tryptophan |

TABLE 183

| Comp. No. | Structure |
|---|---|
| I-361 | (5-methyl-6-methyl-1-cyclohexylmethyl-2-oxo-1,2-dihydropyridine-3-carbonyl)-tyrosine |
| I-362 | (5-methyl-6-methyl-1-cyclohexylmethyl-2-oxo-1,2-dihydropyridine-3-carbonyl)-phenylalanine |
| I-365 | (5-methyl-6-methyl-1-(2-morpholinoethyl)-2-oxo-1,2-dihydropyridine-3-carbonyl)-valine |
| I-366 | (5-methyl-6-methyl-1-(2-morpholinoethyl)-2-oxo-1,2-dihydropyridine-3-carbonyl)-valine |

TABLE 184
| Comp. No. | Structure |
|---|---|
| I-367 | 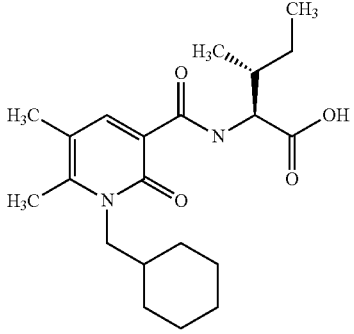 |
| I-368 | 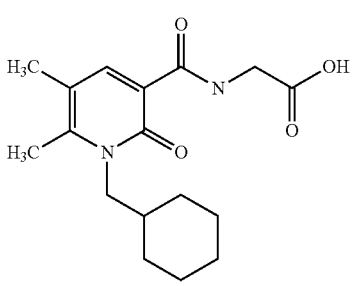 |
| I-369 | 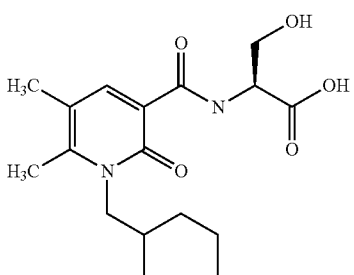 |
| I-370 | 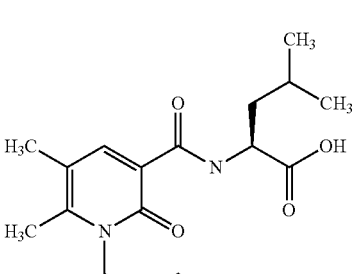 |
TABLE 185
| Comp. No. | Structure |
|---|---|
| I-371 | 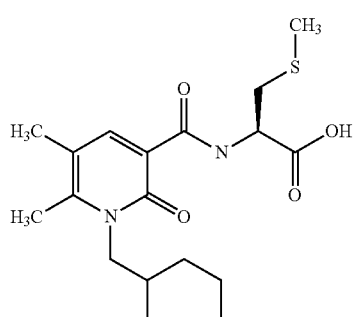 |
| I-372 | 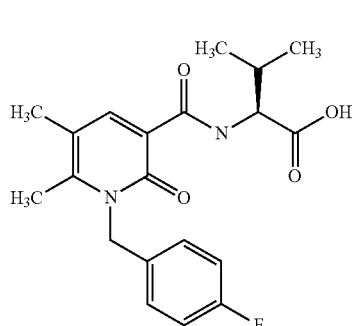 |
| I-373 | 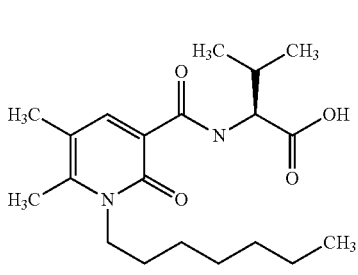 |
| I-374 | 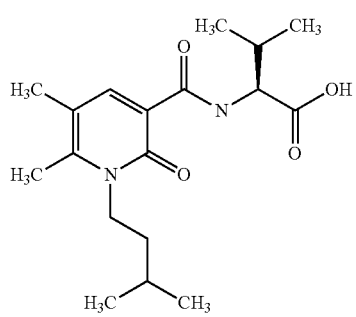 |

TABLE 186

| Comp. No | Structure |
|---|---|
| I-375 | (structure) |
| I-376 | (structure) |
| I-377 | (structure) |
| I-378 | (structure) |

TABLE 187

| Comp. No. | Structure |
|---|---|
| I-381 | (structure) |
| I-382 | (structure) |
| I-383 | (structure) |
| I-384 | (structure) |

TABLE 188
| Comp. No. | Structure |
|---|---|
| I-385 | 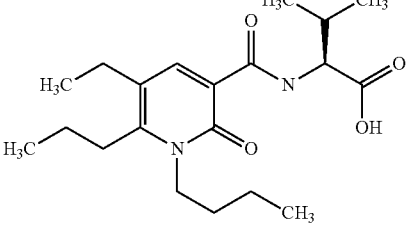 |
| I-387 | 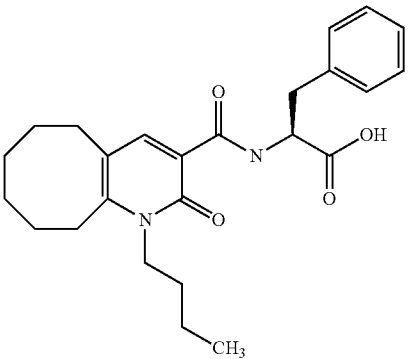 |
| I-388 | 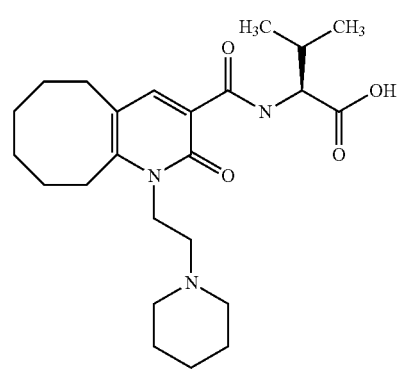 |
| I-389 | 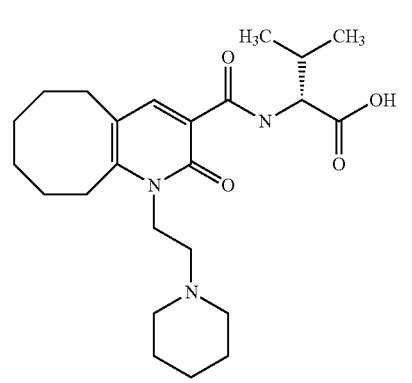 |
TABLE 189
| Comp. No. | Structure |
|---|---|
| I-390 | 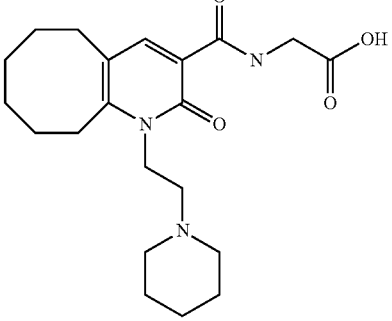 |
| I-391 | 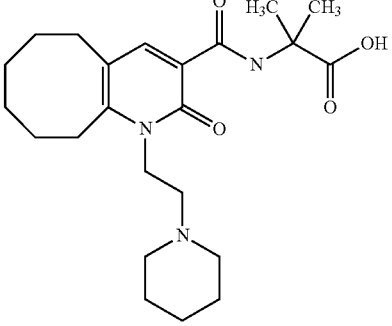 |
| I-393 | 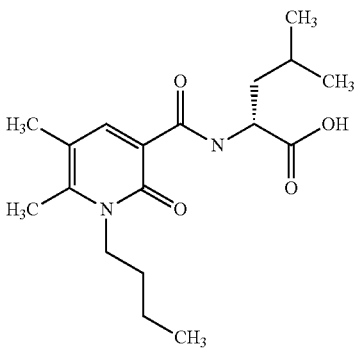 |
| I-394 | 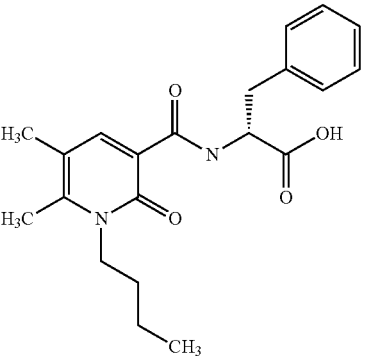 |

TABLE 190
| Comp. No. | Structure |
|---|---|
| I-395 | 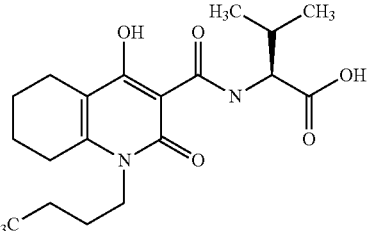 |
| I-396 | 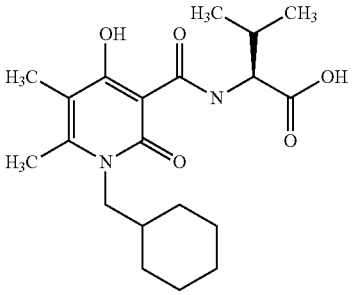 |
| I-398 | 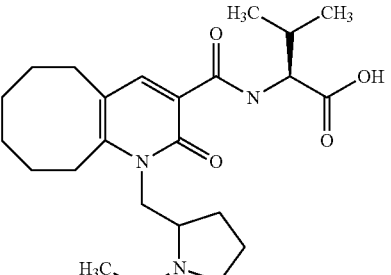 |
| I-399 | 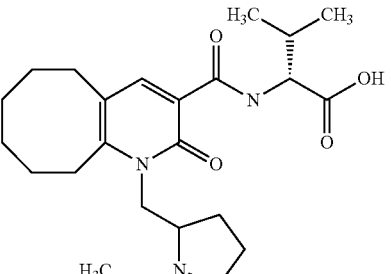 |
TABLE 191
| Comp. No. | Structure |
|---|---|
| I-400 | 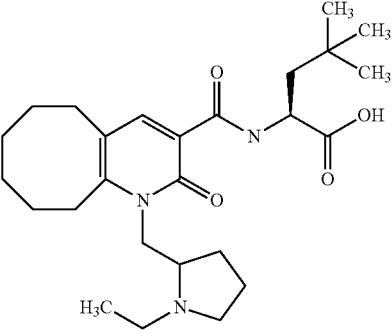 |
TABLE 191-continued
| Comp. No. | Structure |
|---|---|
| I-401 | 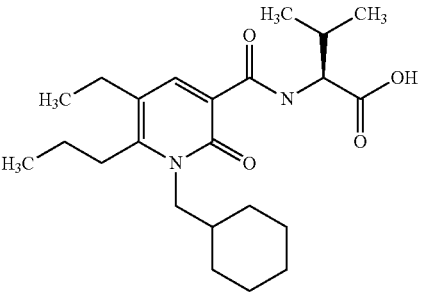 |
| I-406 | 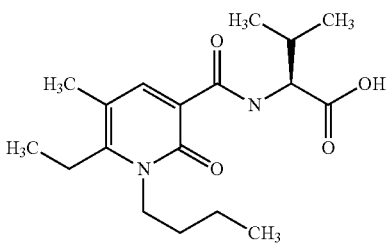 |
| I-408 | 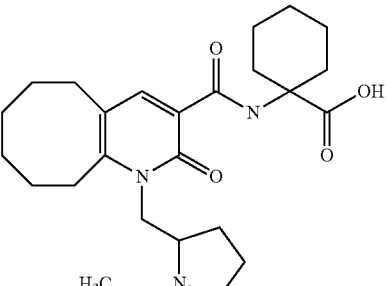 |
TABLE 192
| Comp. No. | Structure |
|---|---|
| I-411 | 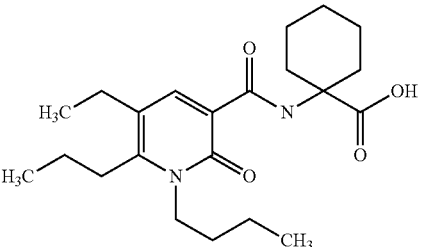 |

TABLE 192-continued

| Comp. No. | Structure |
|---|---|
| I-412 | 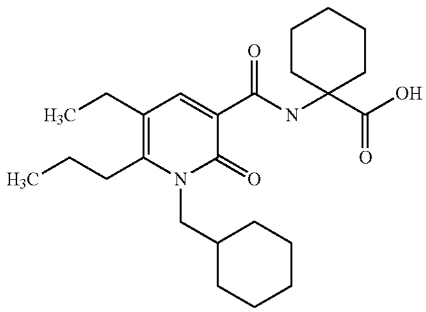 |
| I-413 | 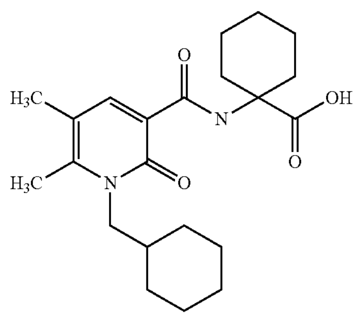 |
| I-414 | 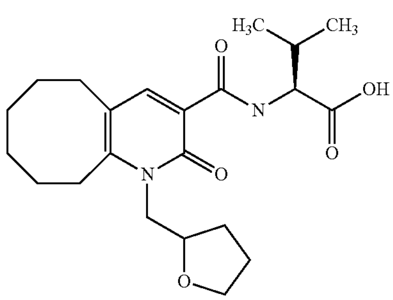 |

TABLE 193

| Comp. No. | Structure |
|---|---|
| I-415 | 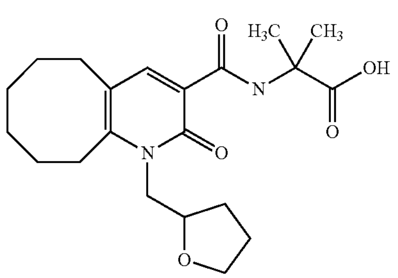 |

TABLE 193-continued

| Comp. No. | Structure |
|---|---|
| I-416 | 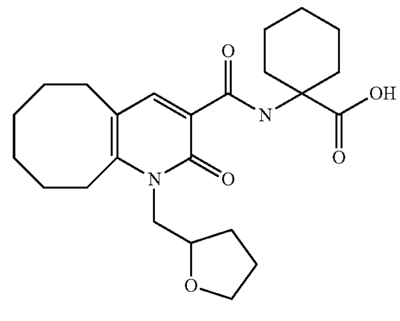 |
| I-417 | 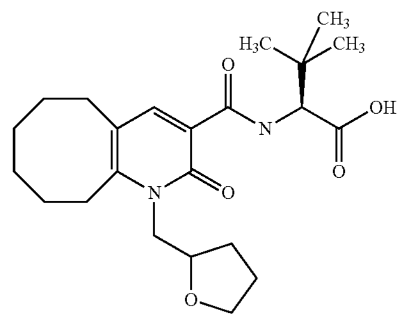 |
| I-420 | 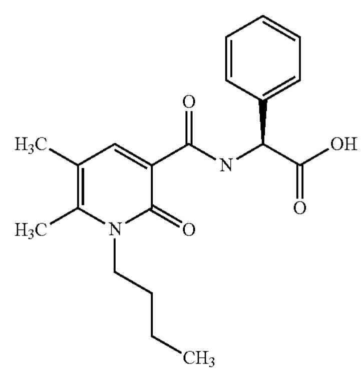 |

TABLE 194

| Comp. No. | Structure |
|---|---|
| I-427 | 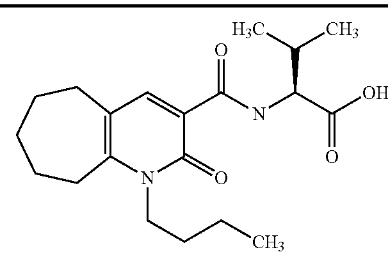 |

TABLE 194-continued

| Comp. No. | Structure |
|---|---|
| I-428 | 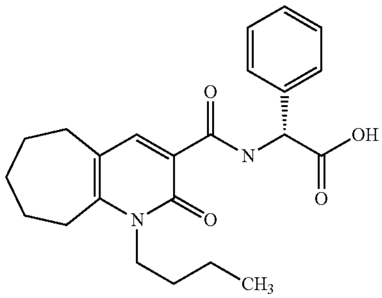 |
| I-431 | 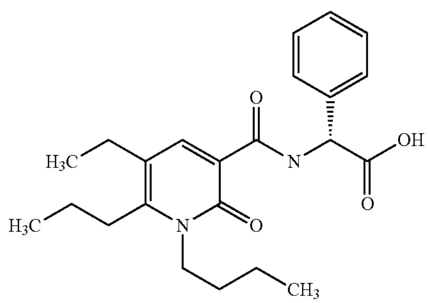 |
| I-433 | 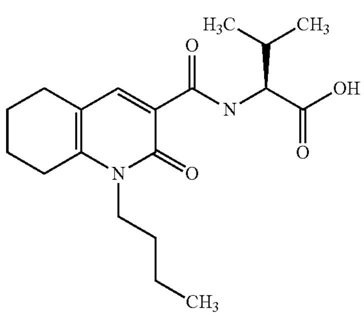 |

TABLE 195

| Comp. No. | Structure |
|---|---|
| I-434 | 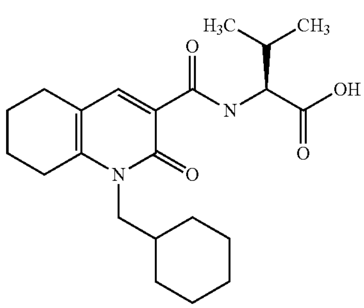 |

TABLE 195-continued

| Comp. No. | Structure |
|---|---|
| I-435 | 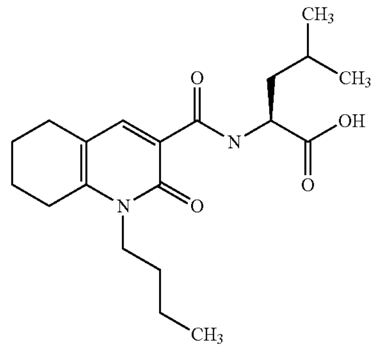 |
| I-436 | 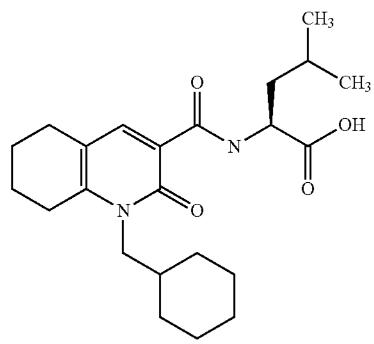 |
| I-437 | 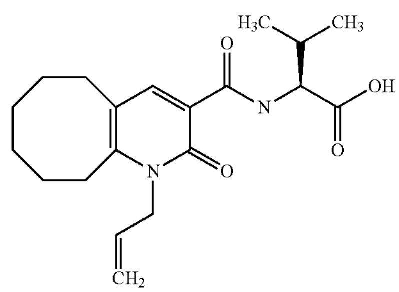 |

TABLE 196

| Comp. No. | Structure |
|---|---|
| I-439 | 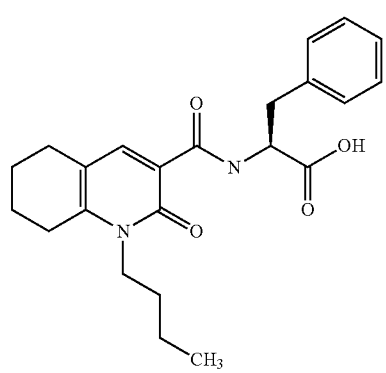 |

TABLE 196-continued

| Comp. No. | Structure |
|---|---|
| I-440 | 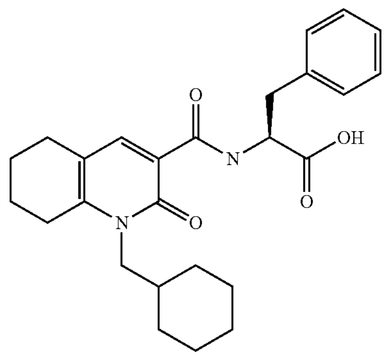 |
| I-441 | 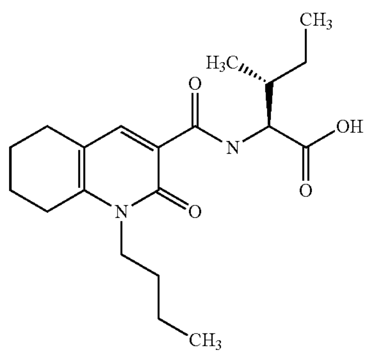 |
| I-442 | 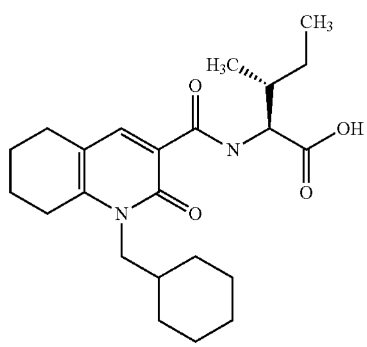 |

TABLE 197

| Comp. No. | Structure |
|---|---|
| I-444 | 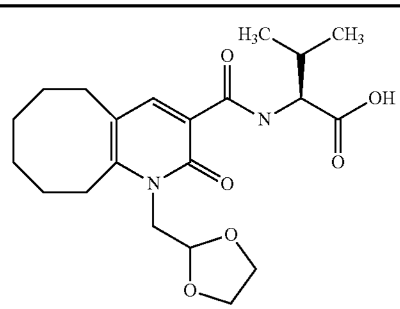 |

TABLE 197-continued

| Comp. No. | Structure |
|---|---|
| I-445 | 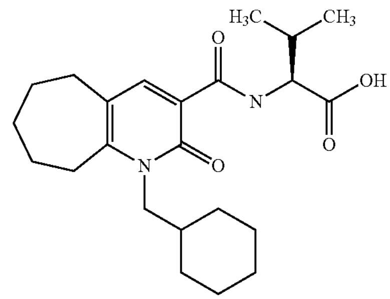 |
| I-446 | 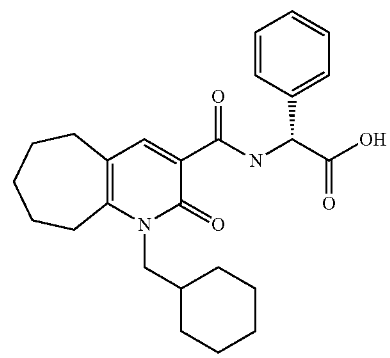 |
| I-447 | 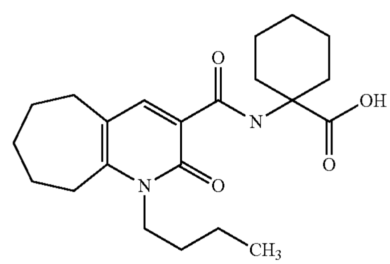 |

TABLE 198

| Comp. No. | Structure |
|---|---|
| I-448 | 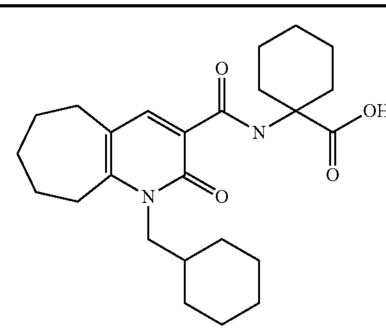 |

TABLE 198-continued

| Comp. No. | Structure |
|---|---|
| I-449 | (structure) |
| I-450 | (structure) |
| I-451 | (structure) |

TABLE 199

| Comp. No. | Structure |
|---|---|
| I-452 | (structure) |

TABLE 199-continued

| Comp. No. | Structure |
|---|---|
| I-453 | (structure) |
| I-457 | (structure) |
| I-458 | (structure) |

TABLE 200

| Comp. No. | Structure |
|---|---|
| I-459 | (structure) |

TABLE 200-continued

| Comp. No. | Structure |
|---|---|
| I-460 | (structure) |
| I-464 | (structure) |
| I-466 | (structure) |

TABLE 201

| Comp. No. | Structure |
|---|---|
| I-467 | (structure) |
| I-468 | (structure) |
| I-469 | (structure) |
| I-470 | (structure) |

TABLE 202

| Comp. No. | Structure |
|---|---|
| I-471 | (structure) |
| I-472 | (structure) |

TABLE 202-continued

| Comp. No. | Structure |
|---|---|
| I-473 | (structure) |
| I-477 | (structure) |

TABLE 203

| Comp. No. | Structure |
|---|---|
| I-478 | (structure) |
| I-479 | (structure) |
| I-480 | (structure) |

TABLE 203-continued

| Comp. No. | Structure |
|---|---|
| I-483 | (structure) |

TABLE 204

| Comp. No. | Structure |
|---|---|
| I-484 | (structure) |
| I-485 | (structure) |
| I-486 | (structure) |

TABLE 204-continued

| Comp. No. | Structure |
|---|---|
| I-487 | 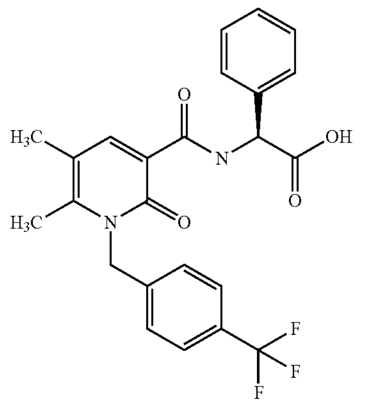 |

TABLE 205

| Comp. No. | Structure |
|---|---|
| I-488 | 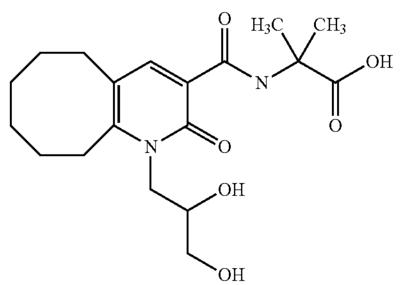 |
| I-489 | 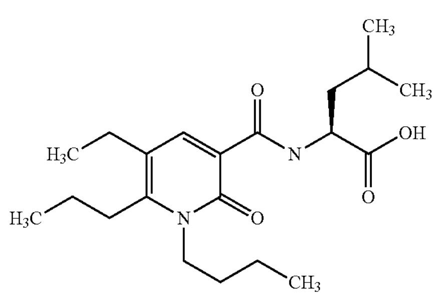 |
| I-490 | 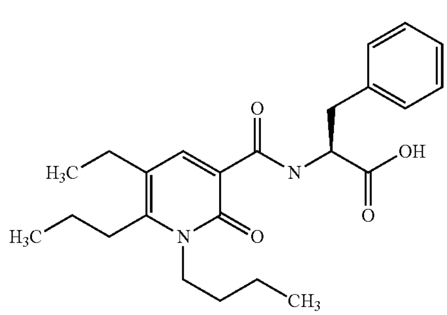 |
| I-491 | |

TABLE 206

| Comp. No. | Structure |
|---|---|
| I-492 | 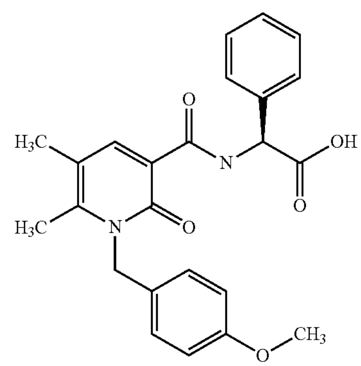 |
| I-493 | 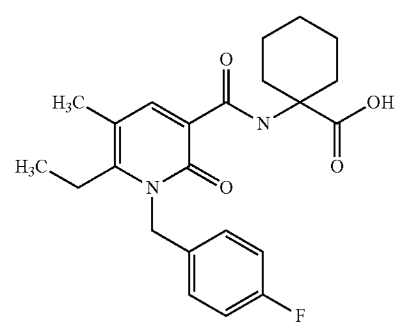 |
| I-494 | 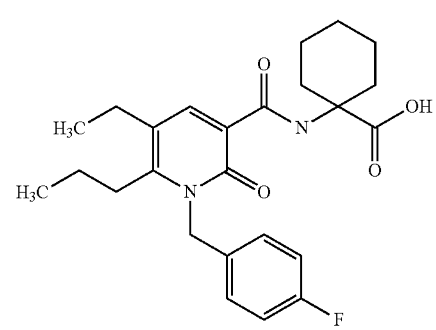 |

TABLE 206-continued
| Comp. No. | Structure |
|---|---|
| I-495 | 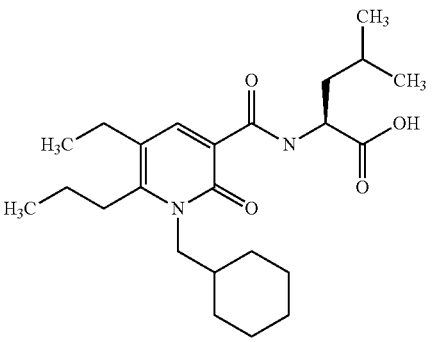 |
TABLE 207
| Comp. No. | Structure |
|---|---|
| I-496 | 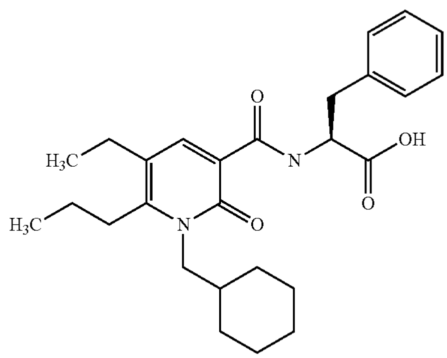 |
| I-497 | 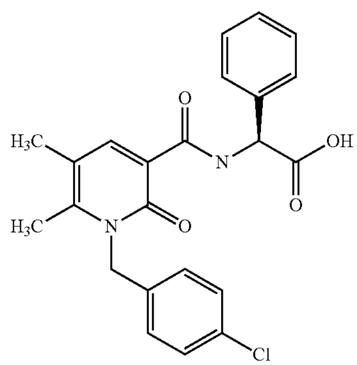 |
| I-498 | 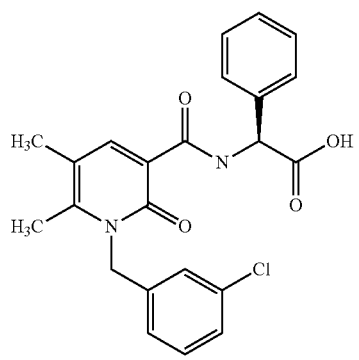 |
| I-499 | 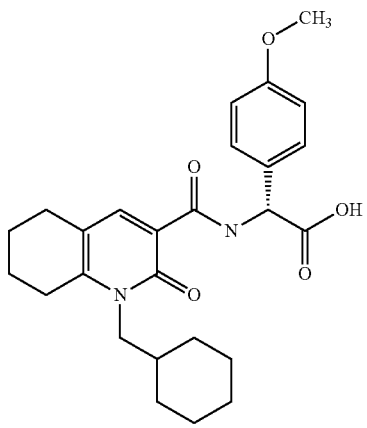 |
TABLE 208
| Comp. No. | Structure |
|---|---|
| I-500 | 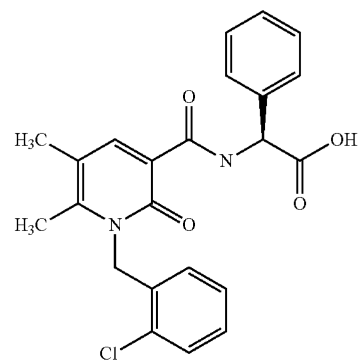 |
| I-502 | 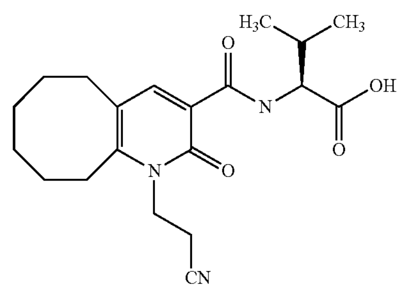 |
| I-503 | 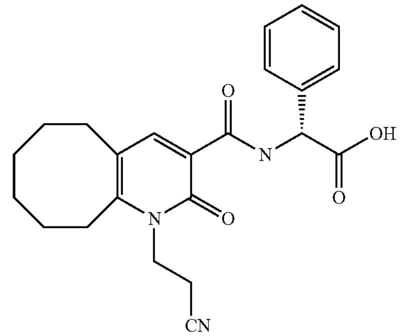 |

TABLE 208-continued

| Comp. No. | Structure |
|---|---|
| I-504 | (structure) |

TABLE 209

| Comp. No. | Structure |
|---|---|
| I-505 | (structure) |
| I-506 | (structure) |
| I-507 | (structure) |
| I-508 | (structure) |

TABLE 210

| Comp. No. | Structure |
|---|---|
| I-511 | (structure) |
| I-512 | (structure) |
| I-513 | (structure) |
| I-514 | (structure) |

TABLE 211

| Comp. No. | Structure |
|---|---|
| I-516 | (structure) |

TABLE 211-continued

| Comp. No. | Structure |
|---|---|
| I-517 | (structure) |
| I-518 | (structure) |
| I-520 | (structure) |

TABLE 212

| Comp. No. | Structure |
|---|---|
| I-521 | (structure) |
| I-522 | (structure) |
| I-523 | (structure) |
| I-524 | (structure) |

TABLE 213

| Comp. No. | Structure |
|---|---|
| I-527 | (structure) |
| I-531 | (structure) |

TABLE 213-continued

| Comp. No. | Structure |
|---|---|
| I-532 | (structure) |
| I-536 | (structure) |

TABLE 214

| Comp. No. | Structure |
|---|---|
| I-537 | (structure) |
| I-538 | (structure) |

TABLE 214-continued

| Comp. No. | Structure |
|---|---|
| I-543 | (structure) |
| I-544 | (structure) |

TABLE 215

| Comp. No. | Structure |
|---|---|
| I-545 | (structure) |
| I-546 | (structure) |

TABLE 215-continued
| Comp. No. | Structure |
|---|---|
| I-547 | 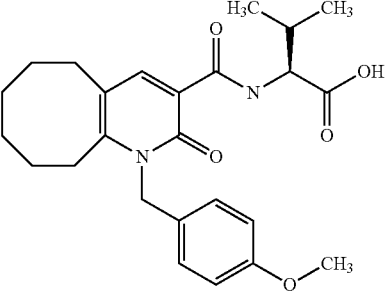 |
| I-548 | 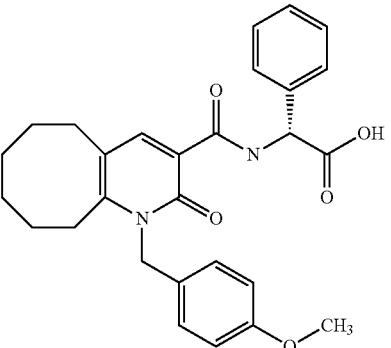 |
TABLE 216
| Comp. No. | Structure |
|---|---|
| I-550 | 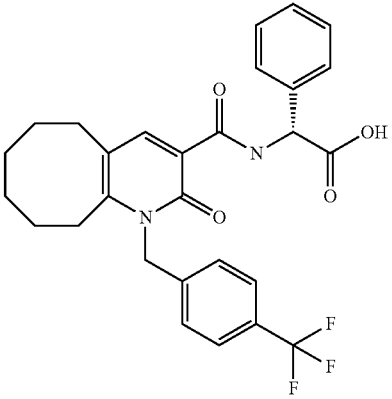 |
| I-552 | 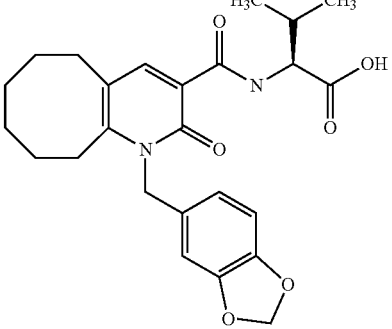 |
TABLE 216-continued
| Comp. No. | Structure |
|---|---|
| I-553 | 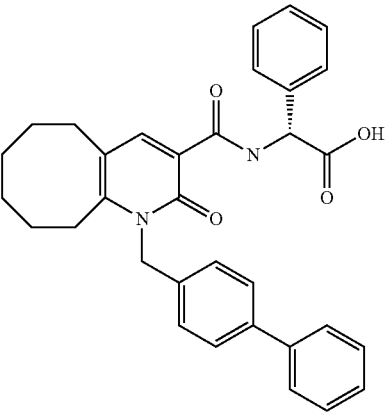 |
| I-554 | 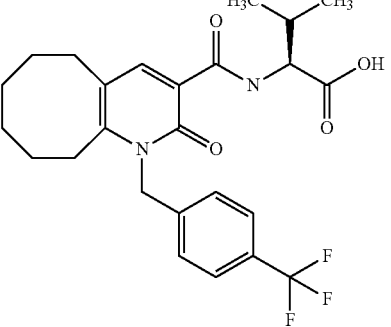 |
TABLE 217
| Comp. No. | Structure |
|---|---|
| I-555 | 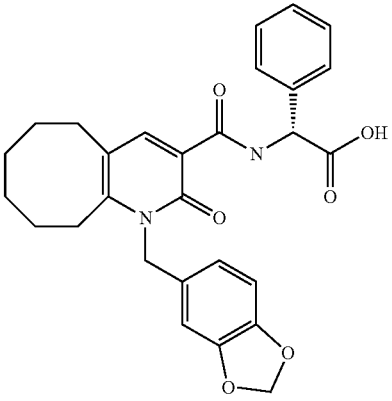 |
| I-557 | 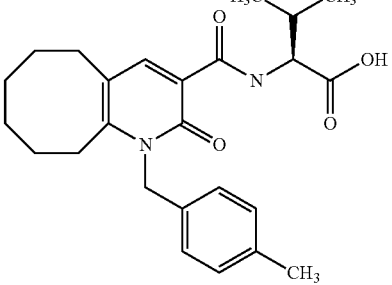 |

TABLE 217-continued
| Comp. No. | Structure |
|---|---|
| I-558 | 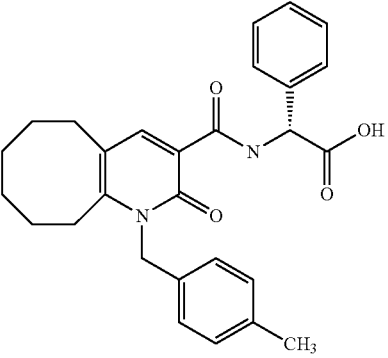 |
| I-559 | 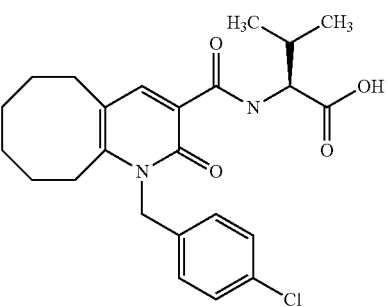 |
TABLE 218
| Comp. No. | Structure |
|---|---|
| I-560 | 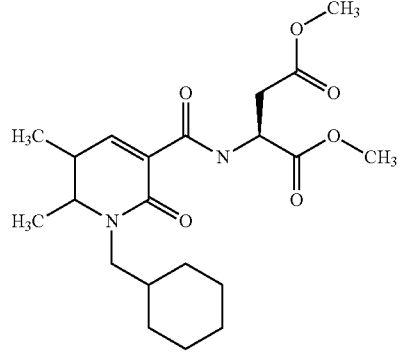 |
| I-563 | 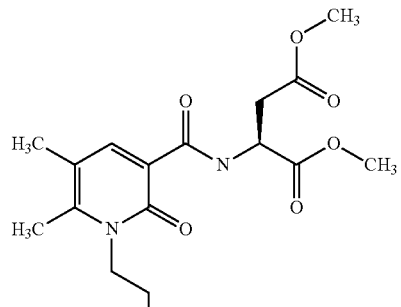 |
TABLE 218-continued
| Comp. No. | Structure |
|---|---|
| II-003 | 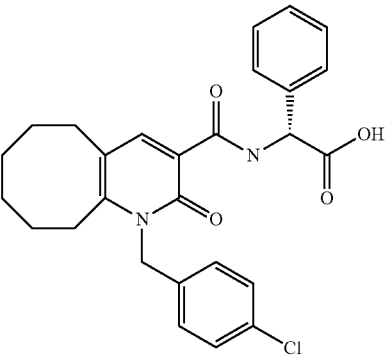 |
| II-004 | 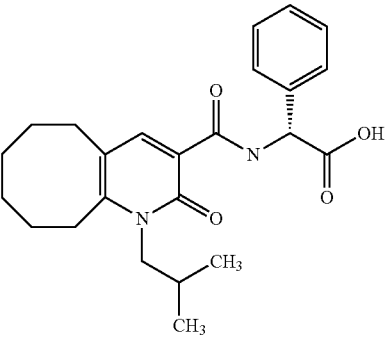 |
TABLE 219
| Comp. No. | Structure |
|---|---|
| II-005 | 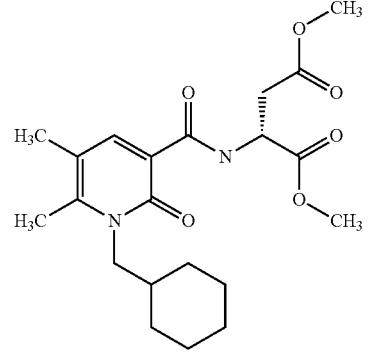 |
| II-006 | 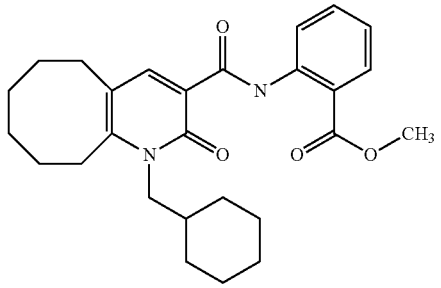 |

TABLE 219-continued
| Comp. No. | Structure |
|---|---|
| II-007 | 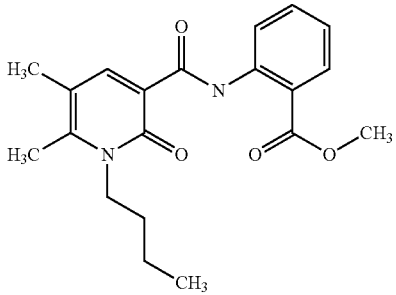 |
| II-008 | 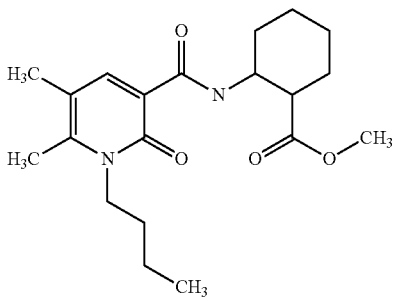 |
TABLE 220
| Comp. No. | Structure |
|---|---|
| II-011 | 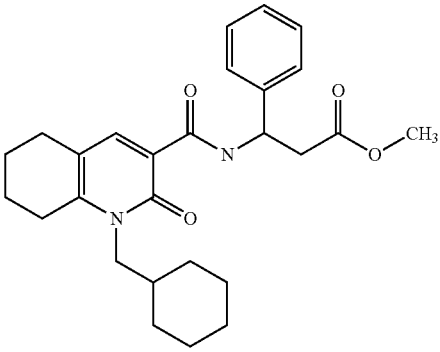 |
| II-012 | 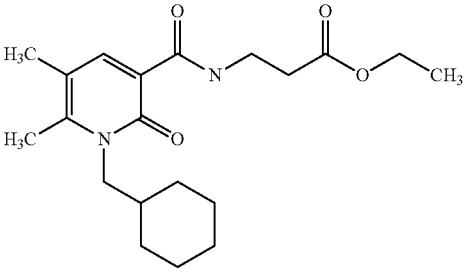 |
TABLE 220-continued
| Comp. No. | Structure |
|---|---|
| II-013 | 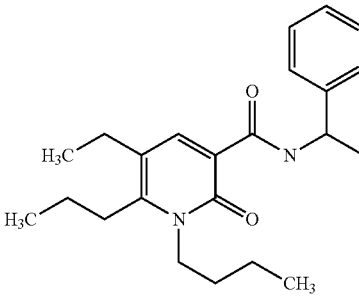 |
| II-018 | 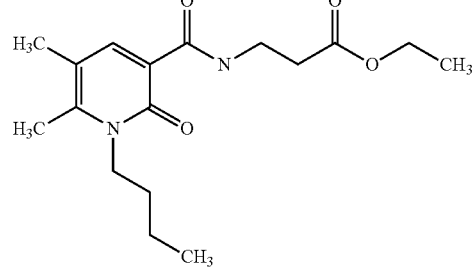 |
TABLE 221
| Comp. No. | Structure |
|---|---|
| II-019 | 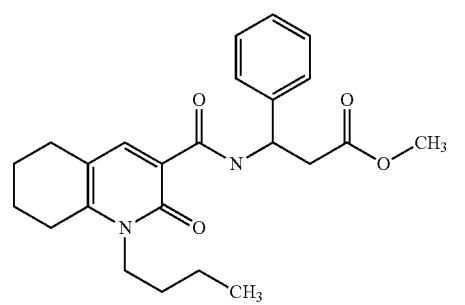 |
| II-020 | 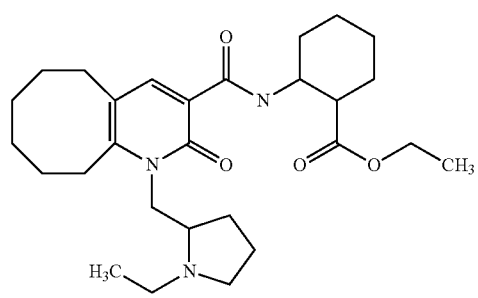 |

TABLE 221-continued

| Comp. No. | Structure |
|---|---|
| II-021 | (structure) |
| II-022 | (structure) |

TABLE 222

| Comp. No. | Structure |
|---|---|
| II-024 | (structure) |
| II-027 | (structure) |
| II-028 | (structure) |

TABLE 222-continued

| Comp. No. | Structure |
|---|---|
| II-029 | (structure) |

TABLE 223

| Comp. No. | Structure |
|---|---|
| II-030 | (structure) |
| II-031 | (structure) |
| II-032 | (structure) |
| II-033 | (structure) |

TABLE 224

| Comp. No. | Structure |
|---|---|
| II-036 | (structure) |
| II-037 | (structure) |
| II-040 | (structure) |
| II-041 | (structure) |

TABLE 225

| Comp. No. | Structure |
|---|---|
| II-043 | (structure) |
| II-044 | (structure) |
| II-045 | (structure) |
| II-046 | (structure) |

TABLE 226

| Comp. No. | Structure |
|---|---|
| II-047 | (structure) |

TABLE 226-continued

| Comp. No. | Structure |
|---|---|
| II-049 | (structure) |
| II-053 | (structure) |
| II-054 | (structure) |

Table 227

| Comp. No. | Structure |
|---|---|
| II-056 | (structure) |
| II-057 | (structure) |

Table 227-continued

| Comp. No. | Structure |
|---|---|
| II-058 | (structure) |
| II-059 | (structure) |

TABLE 228

| Comp. No. | Structure |
|---|---|
| II-060 | (structure) |
| II-061 | (structure) |

US 8,178,681 B2
TABLE 228-continued
| Comp. No. | Structure |
|---|---|
| II-062 | 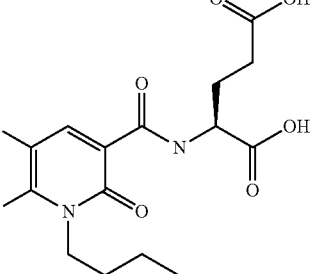 |
| II-063 | 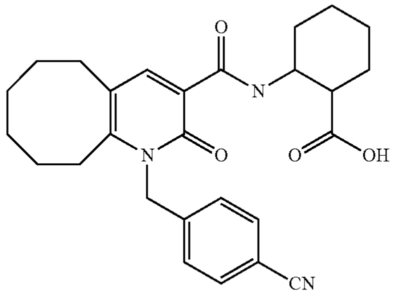 |
TABLE 229
| Comp. No. | Structure |
|---|---|
| III-002 | 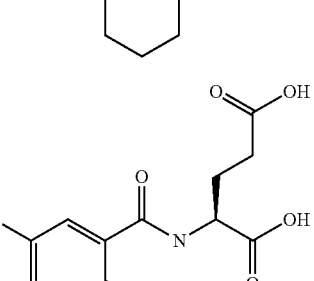 |
| III-003 | 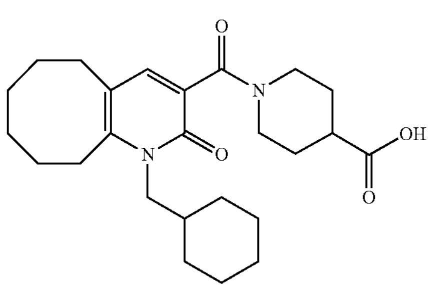 |
TABLE 229-continued
| Comp. No. | Structure |
|---|---|
| III-006 | 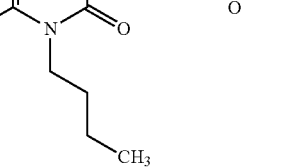 |
| III-007 | 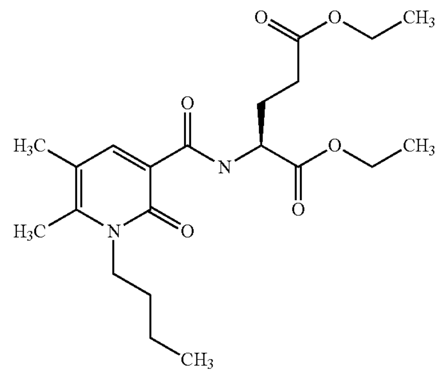 |
TABLE 230
| Comp. No. | Structure |
|---|---|
| III-009 | 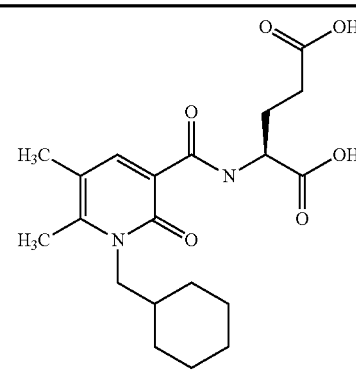 |
| III-010 | 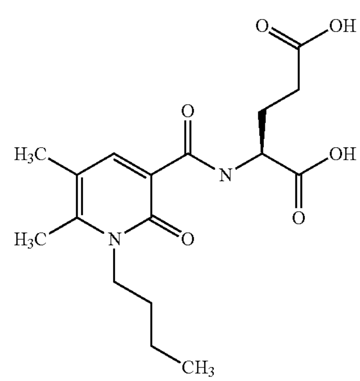 |

TABLE 230-continued
| Comp. No. | Structure |
|---|---|
| IV-005 | 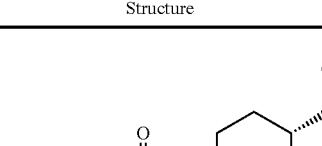 |
| IV-006 | 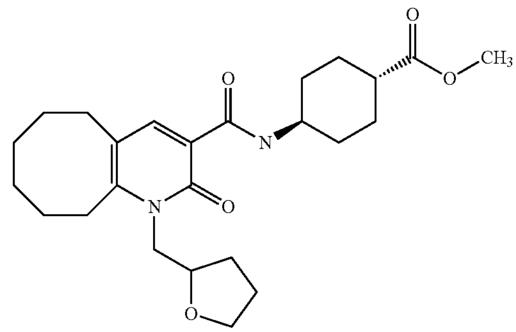 |
TABLE 231
| Comp. No. | Structure |
|---|---|
| IV-015 | 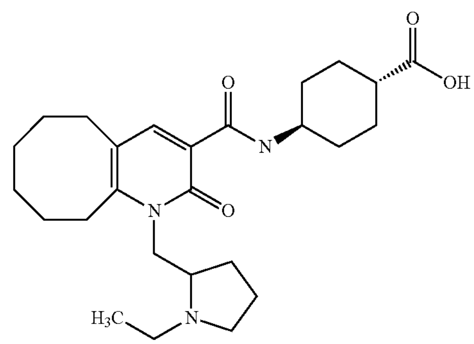 |
| IV-016 | 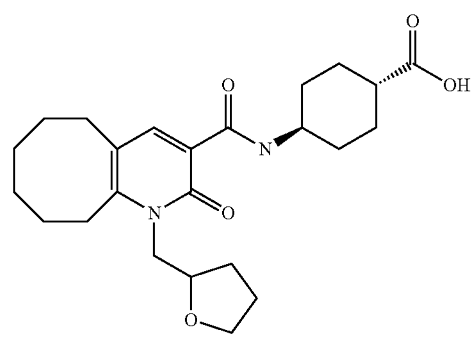 |
| IV-030 | 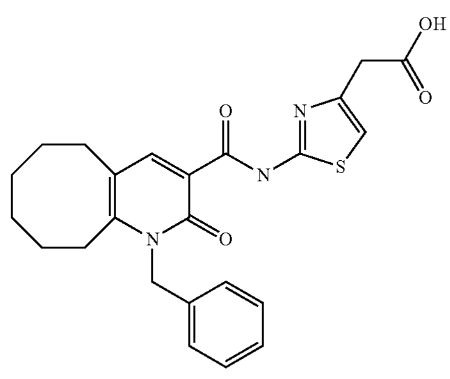 |

TABLE 231-continued
| Comp. No. | Structure |
|---|---|
| V-002 | 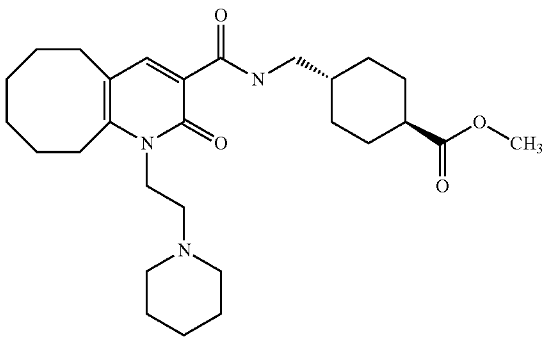 |
TABLE 232
| Comp. No. | Structure |
|---|---|
| V-008 | 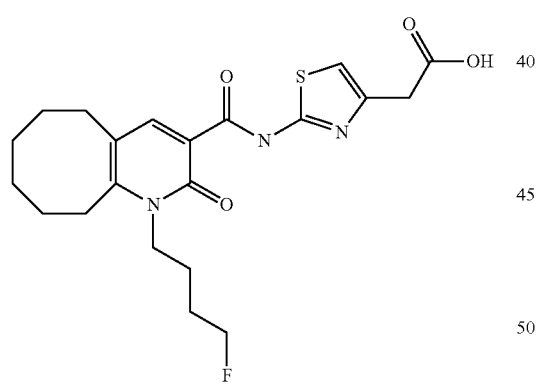 |
| X-35 | 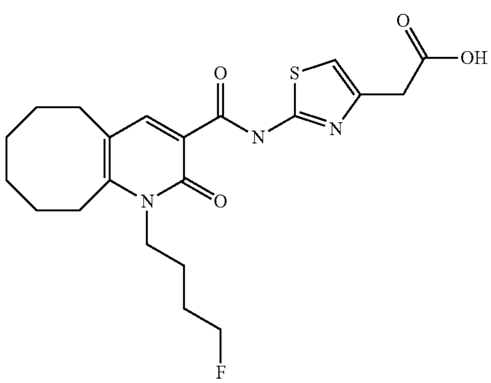 |
| X-50 | 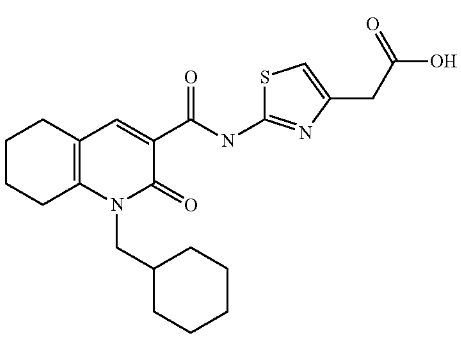 |
TABLE 232-continued
| Comp. No. | Structure |
|---|---|
| X-94 | 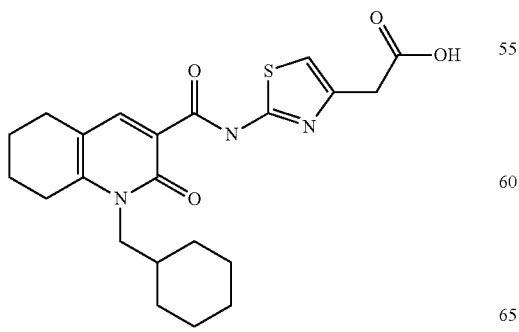 |
TABLE 233
| Comp. No. | Structure |
|---|---|
| X-107 | 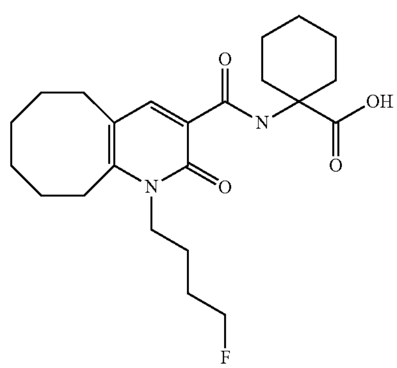 |

TABLE 233-continued

| Comp. No. | Structure |
|---|---|
| X-111 | 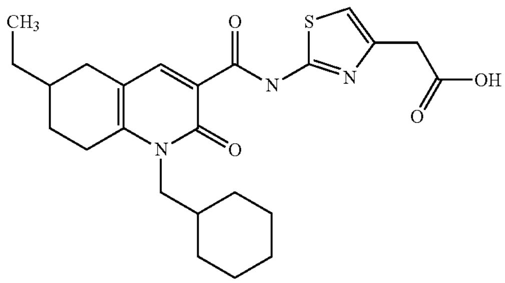 |
| X-113 | 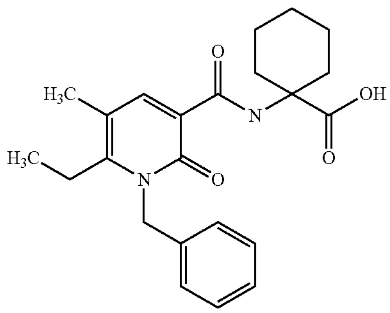 |
| X-118 | 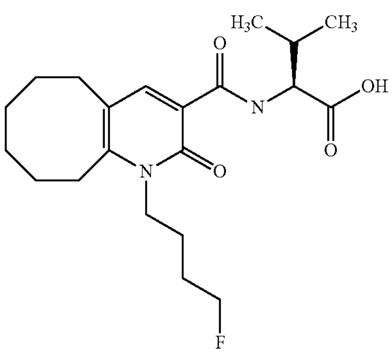 |

TABLE 234

| Comp. No. | Structure |
|---|---|
| X-140 | |
| X-141 | 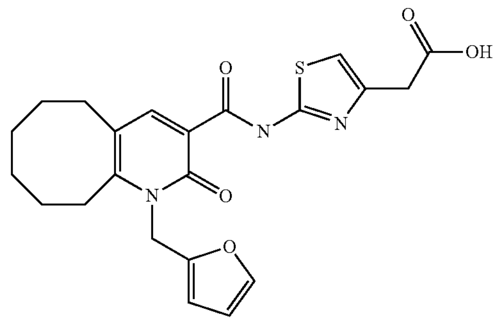 |
| X-142 | 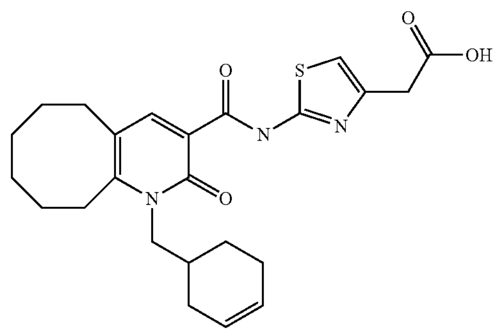 |
| X-143 | 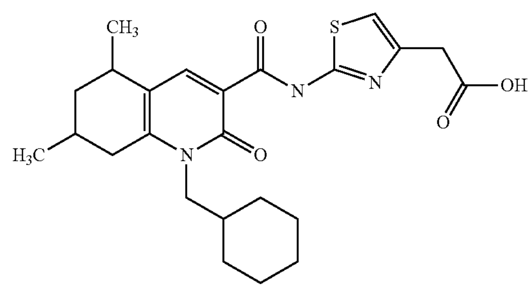 |

TABLE 235

| Comp. No. | Structure |
|---|---|
| X-145 | 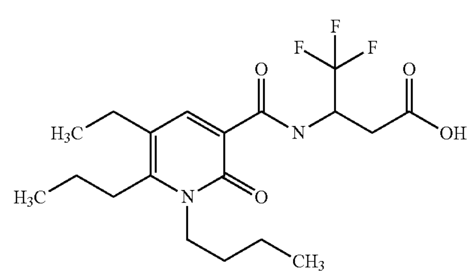 |

TABLE 235-continued

| Comp. No. | Structure |
|---|---|
| X-146 | (structure) |
| X-147 | (structure) |
| X-152 | (structure) |

TABLE 236

| Comp. No. | Structure |
|---|---|
| X-153 | (structure) |

TABLE 236-continued

| Comp. No. | Structure |
|---|---|
| X-161 | (structure) |
| X-174 | (structure) |
| X-175 | (structure) |

TABLE 237

| Comp. No. | Structure |
|---|---|
| X-176 | (structure) |
| X-178 | (structure) |

TABLE 237-continued
| Comp. No. | Structure |
|---|---|
| X-190 | 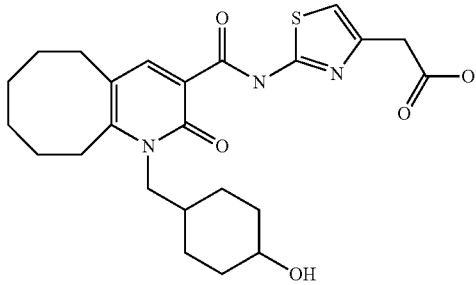 |
| X-196 | 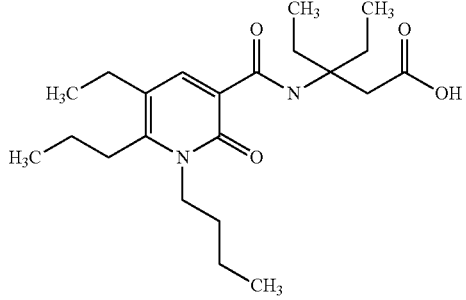 |
TABLE 238
| Comp. No. | Structure |
|---|---|
| X-198 | 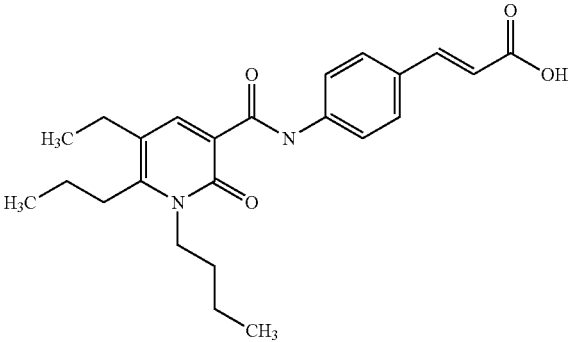 |
| X-207 | 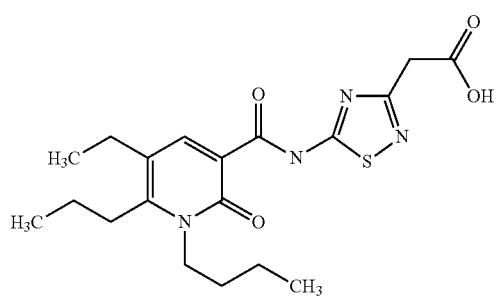 |
| X-208 | 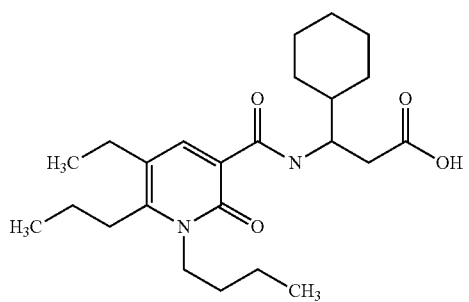 |

TABLE 238-continued
| Comp. No. | Structure |
|---|---|
| X-209 | 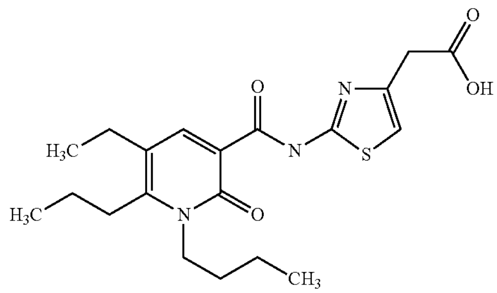 |
TABLE 239
| Comp. No. | Structure |
|---|---|
| X-211 | 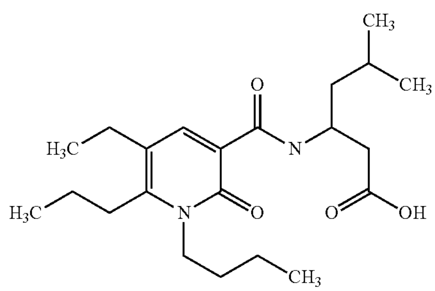 |
| X-215 | 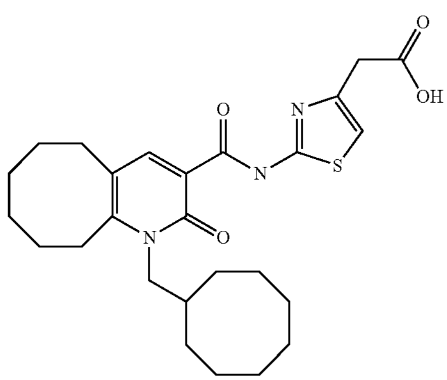 |
| X-223 | 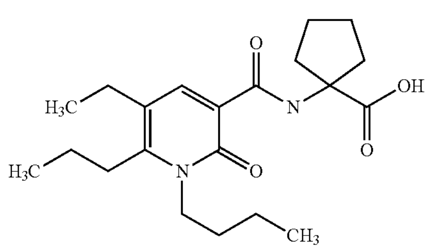 |
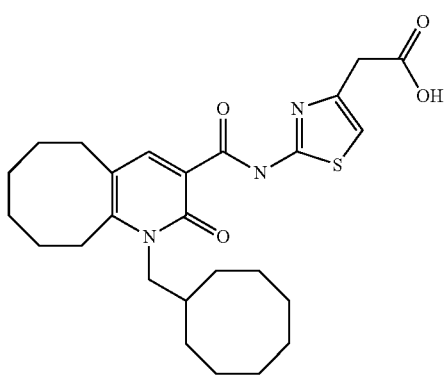
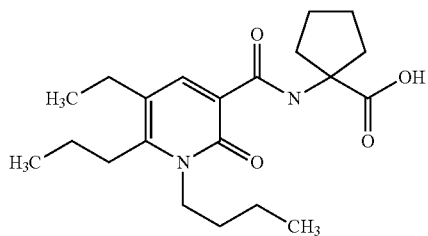

TABLE 239-continued
| Comp. No. | Structure |
|---|---|
| X-227 | 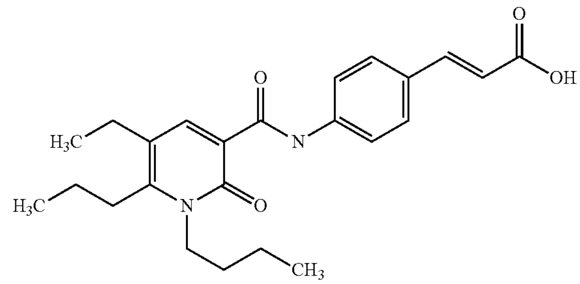 |
TABLE 240
| Comp. No. | Structure |
|---|---|
| X-229 | 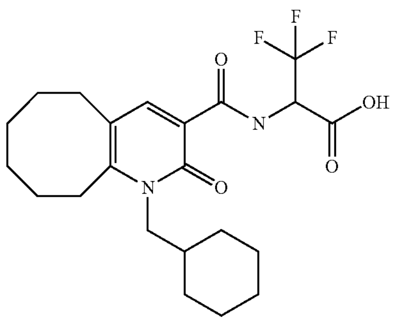 |
| X-230 | 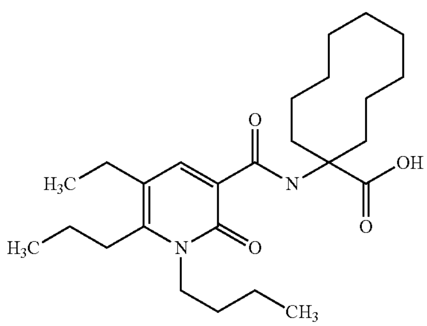 |
| X-233 | 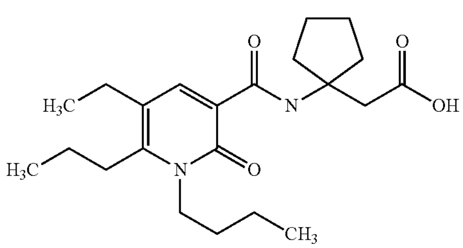 |
TABLE 240-continued
| Comp. No. | Structure |
|---|---|
| X-237 | 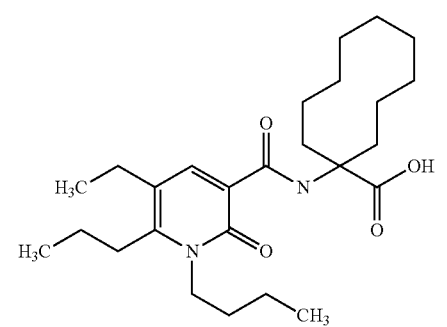 |
TABLE 241
| Comp. No. | Structure |
|---|---|
| X-241 | 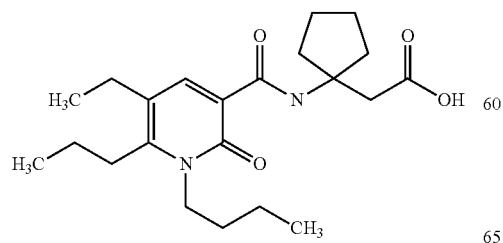 |
| XI-001 | 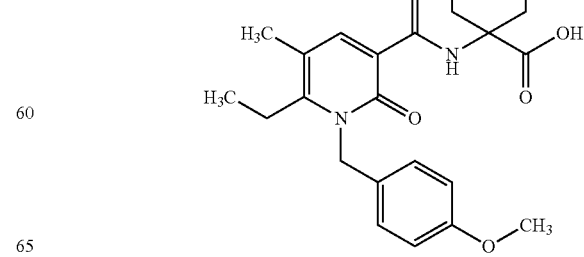 |

TABLE 241-continued

| Comp. No. | Structure |
|---|---|
| XI-005 | (structure) |
| XI-006 | (structure) |

TABLE 242

| Comp. No. | Structure |
|---|---|
| XI-007 | (structure) |
| XI-009 | (structure) |

TABLE 242-continued

| Comp. No. | Structure |
|---|---|
| XI-015 | (structure) |
| XI-016 | (structure) |

TABLE 243

| Comp. No. | Structure |
|---|---|
| XI-019 | (structure) |
| XI-024 | (structure) |

TABLE 243-continued

| Comp. No. | Structure |
|---|---|
| XI-026 | (structure) |
| XI-028 | (structure) |

TABLE 244

| Comp. No. | Structure |
|---|---|
| XI-029 | (structure) |
| XI-030 | (structure) |

TABLE 244-continued

| Comp. No. | Structure |
|---|---|
| XI-037 | (structure) |
| XI-038 | (structure) |

TABLE 245

| Comp. No. | Structure |
|---|---|
| XI-049 | (structure) |
| XI-060 | (structure) |

TABLE 245-continued
| Comp. No. | Structure |
|---|---|
| XI-061 | 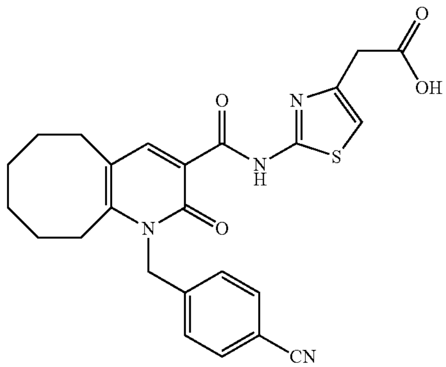 |
| XI-062 | 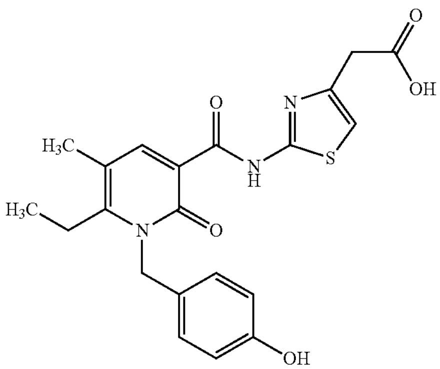 |
TABLE 246
| Comp. No. | Structure |
|---|---|
| XI-064 | 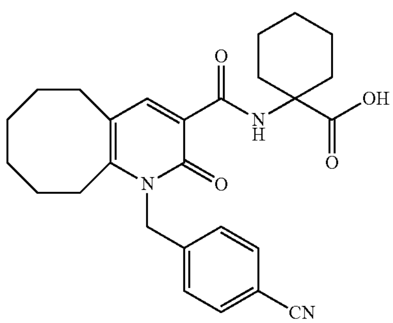 |
| XI-069 | 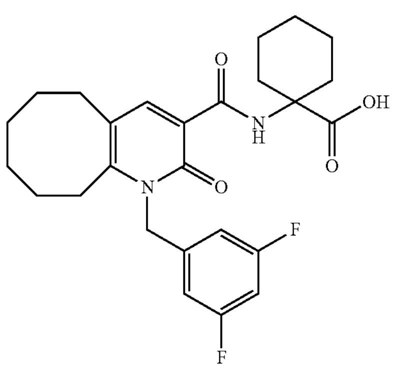 |
TABLE 246-continued
| Comp. No. | Structure |
|---|---|
| XI-238 | 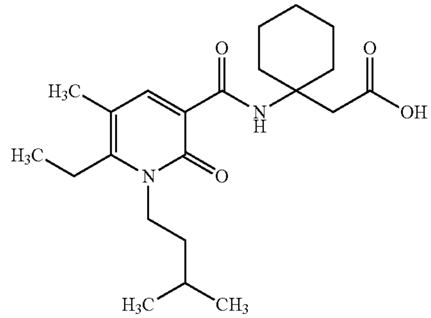 |
| XI-239 | 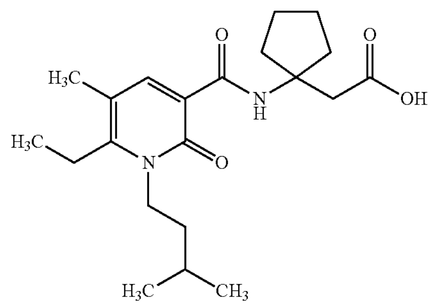 |
TABLE 247
| Comp. No. | Structure |
|---|---|
| XI-240 | 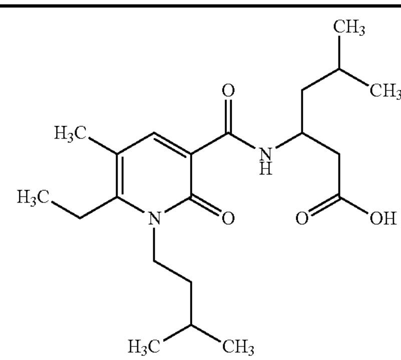 |
| XI-245 | 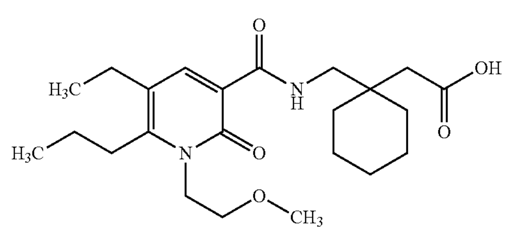 |
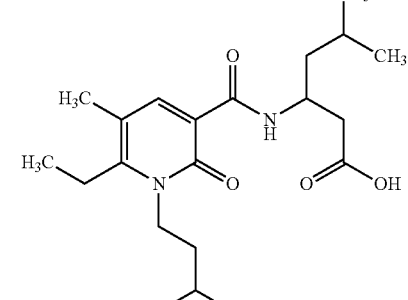
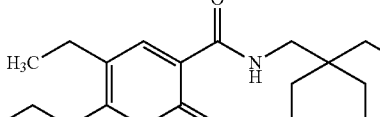

TABLE 247-continued

| Comp. No. | Structure |
|---|---|
| XI-248 | (structure) |
| XI-251 | (structure) |

TABLE 248

| Comp. No. | Structure |
|---|---|
| XI-255 | (structure) |
| XI-256 | (structure) |

TABLE 248-continued

| Comp. No. | Structure |
|---|---|
| XI-257 | (structure) |
| XI-258 | (structure) |

TABLE 249

| Comp. No. | Structure |
|---|---|
| XI-259 | (structure) |
| XI-268 | (structure) |

TABLE 249-continued
| Comp. No. | Structure |
|---|---|
| XI-271 | 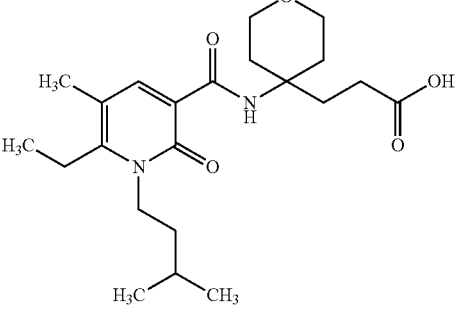 |
| XI-272 | 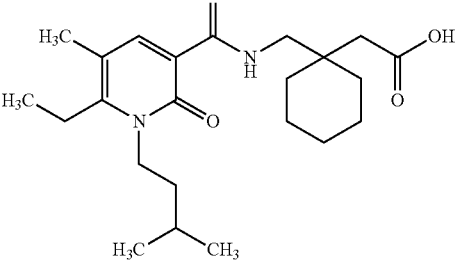 |
TABLE 250
| Comp. No. | Structure |
|---|---|
| XI-273 | 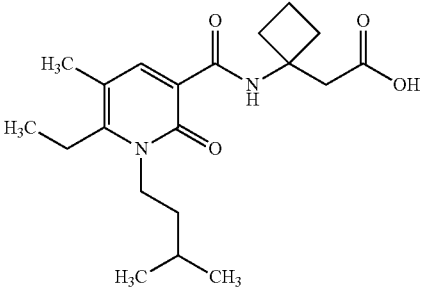 |
| XI-274 | 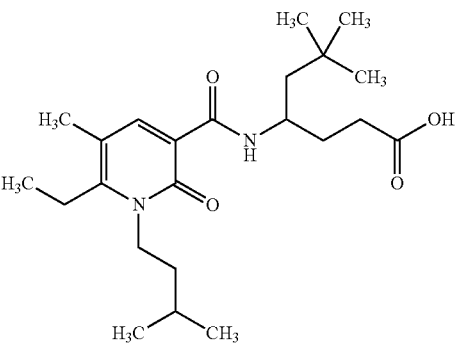 |
| XI-276 | 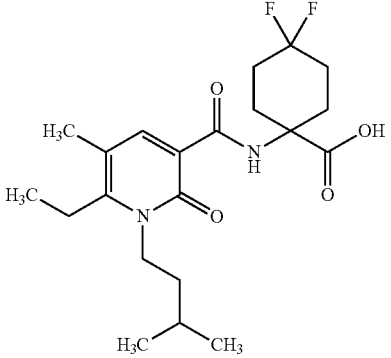 |

TABLE 250-continued
| Comp. No. | Structure |
|---|---|
| XI-281 | 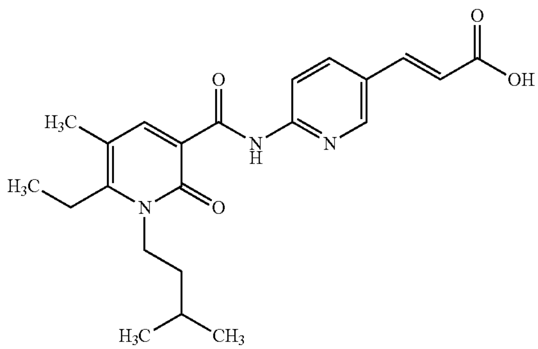 |
TABLE 251
| Comp. No. | Structure |
|---|---|
| XI-282 | 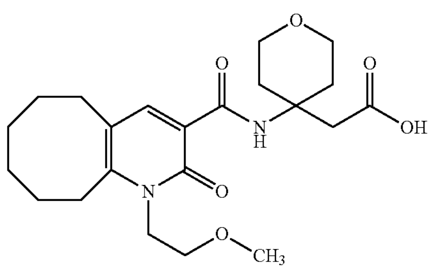 |
| XI-286 | 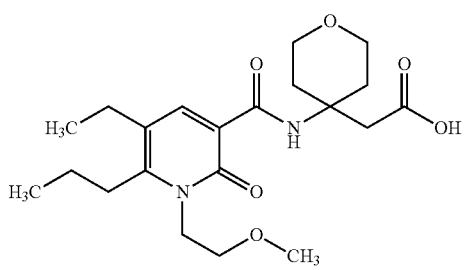 |
| XI-294 | 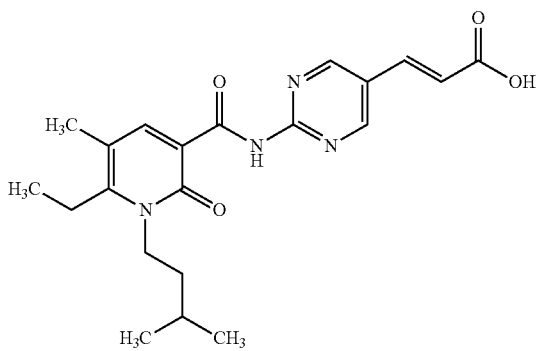 |

TABLE 251-continued
| Comp. No. | Structure |
|---|---|
| XI-296 | 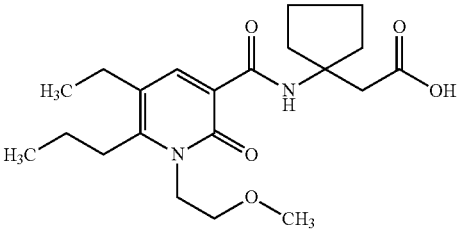 |
TABLE 252
| Comp. No. | Structure |
|---|---|
| XI-298 | 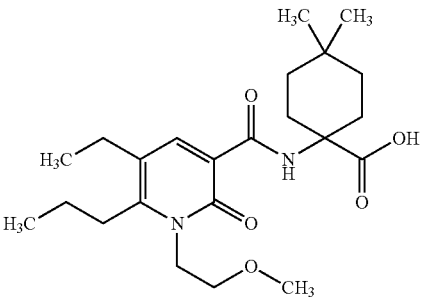 |
| XI-300 | 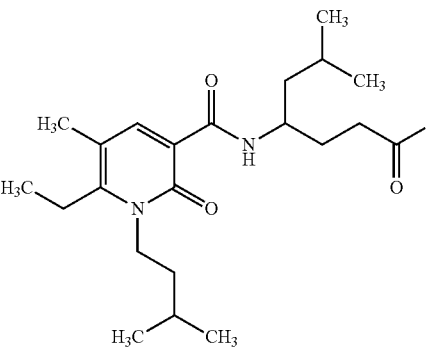 |
| XI-301 | 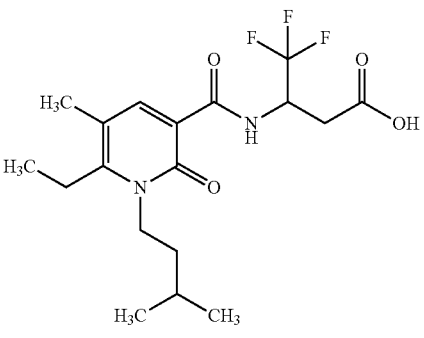 |
TABLE 252-continued
| Comp. No. | Structure |
|---|---|
| XI-302 | 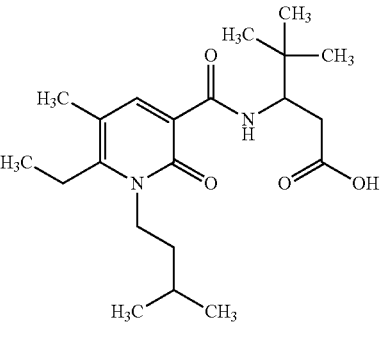 |
TABLE 253
| Comp. No. | Structure |
|---|---|
| XI-304 | 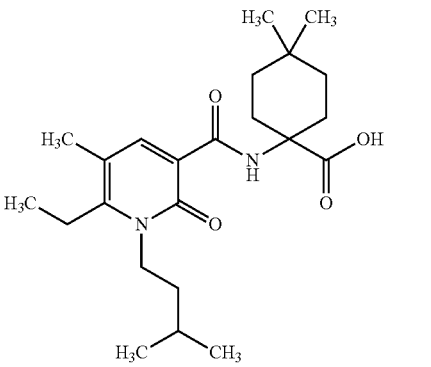 |
| XI-306 | 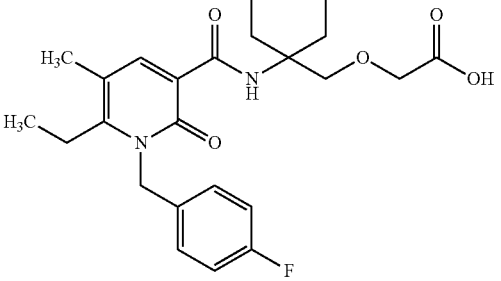 |

TABLE 253-continued

| Comp. No. | Structure |
|---|---|
| XI-307 | (structure: pyridinone with H3C-CH2, H3C-CH2-CH2 substituents, carboxamide linked to cyclohexane-COOH, N-substituted with CH2CH2CH(CH3)2) |

TABLE 254

| Comp. No. | ¹H-NMR(CDCl₃/TMS) δ |
|---|---|
| I-063 | DMSO-d6 0.92 and 0.93(each t, total 3H, J=7.2), 1.26-1.42(m, 2H), 1.46-1.60(m, 2H), 1.75-2.00(m, 3H), 2.03 and 2.07(each s, total 3H), 2.18(m, 1H), 2.34 and 2.36(each s, total 3H), 3.40-3.51(m, 2H), 3.96-4.12(m, 2H), 4.28 and 4.38(each m, total 1H), 7.25 and 7.29(each s, total 1H), 12.47(br, 1H) |
| I-064 | DMSO-d6 1.11-1.99(m, 23H), 2.16-2.57(m, 2H), 2.86(m, 2H), 3.35-3.51(m, 2H), 3.78-3.98(m, 2H), 4.28(m, 1H), 7.30(s, 1H), 12.48(s, 1H) |
| I-065 | DMSO-d6 0.98-1.27(m, 6H), 1.45-1.93(m, 8H), 2.03 and 2.07(s, 3H), 2.20(m, 1H), 2.32-2.34(s, 3H), 3.42-3.59(m, 2H), 3.84-4.50(m, 3H), 7.25 and 7.29(s, 1H), 12.44(br, 1H) |
| I-066 | DMSO-d6 0.98-1.27(m, 6H), 1.45-1.93(m, 8H), 2.03 and 2.07(s, 3H), 2.20(m, 1H), 2.32-2.34(s, 3H), 3.42-3.59(m, 2H), 3.84-4.50(m, 3H), 7.25 and 7.29(s, 1H), 12.35(br, 1H) |
| I-067 | 0.97(t, 3H, J=7.2), 1.39-1.49(m, 2H), 1.54-1.72(m, 2H), 1.86-2.06(m, 3H), 2.09 and 2.10(each s, total 3H), 2.27(m, 1H), 2.34 and 2.35(each s, total 3H), 3.48(m, 1H), 3.54 and 3.77(each s, total 3H), 3.74(m, 1H), 3.97-4.19(m, 2H), 4.61-4.70(m, 1H), 7.36 and 7.45(each s, total 1H) |
| I-068 | 1.14-2.05(m, 23H), 2.27(m, 1H), 2.51-2.57(m, 2H), 2.85-2.88(m, 2H), 3.74-3.76(m, 3H), 3.77(s, 3H), 4.02(m, 2H), 4.67(m, 1H), 7.45(s, 1H) |
| I-069 | DMSO-d6 0.84(d, 3H, J=4.5), 0.90(d, 3H, 4.5), 2.10-2.25(m, 4H), 2.29(s, 3H), 4.38(dd, 1H, J=4.5 and 8.4), 5.40-5.64(m, 2H), 7.10(d, 2H, J=5.4), 8.26(s, 1H), 8.53(d, 2H, J=5.4), 10.12(d, 1H, J=8.4), 12.67(br, 1H) |
| I-070 | 0.98-1.27(m, 4H), 1.55-1.88(m, 8H), 1.88-2.10(m, 2H), 2.06 and 2.09(s, 3H), 2.28(m, 1H), 2.31 and 2.33(s, 3H), 3.45(m, 1H), 3.55 and 3.76(s, 3H), 3.72-4.18(m, 2H), 4.60-4.76(m, 2H), 7.37 and 7.46(s, 1H) |
| I-092 | 1.02(d, 3H, J=6.9), 1.02(d, 3H, J=6.6), 2.17(s, 3H), 2.29(m, 1H), 2.46(s, 3H), 2.56(brt, 4H), 2.67(t, 2H, J=6.9), 3.71(t, 4H, J=4.5), 3.75(s, 3H), 4.28(br, 1H), 4.67(dd, 1H, J=5.1 and 8.1), 8.29(s, 1H), 10.35(d, 1H, J=8.1) |
| I-095 | 0.86-0.94(m, 3H), 1.00-1.04(dd, 6H, J=2.7 and 6.6), 1.24-1.48(m, 8H), 1.60-1.77(m, 2H), 2.16(s, 3H), 2.28(m, 1H), 2.40(s, 3H), 3.74(s, 3H), 4.10-4.38(m, 2H), 4.66(m, 1H), 8.28(s, 1H), 10.41(d, 1H, J=7.8) |
| I-096 | 1.00-1.04(m, 12H), 1.52-1.84(m, 3H), 2.16(s, 3H), 2.29(m, 1H), 2.40(s, 3H), 3.74(s, 3H), 4.10-4.26(m, 2H), 4.66(m, 1H), 8.27(s, 1H), 10.41(d, 1H, J=8.1) |
| I-097 | 1.00-1.04(dd, 6H, J=2.7 and 6.6), 2.16(s, 3H), 2.25(m, 1H), 2.26(s, 3H), 3.74(s, 3H), 4.66(dd, 1H, J=5.1 and 8.1), 5.47(br, 2H), 7.02(dd, 1H, J=1.5 and 4.5), 8.41(s, 1H), 8.57(dd, 1H, J=1.5 and 4.5), 10.20(d, 1H, J=8.1) |
| I-098 | 1.00-1.05(dd, 6H, J=2.7 and 6.9), 1.00-1.34(m, 4H), 1.58-1.98(m, 7H), 2.29(m, 1H), 2.41(s, 3H), 3.75(s, 3H), 3.78(s, 3H), 4.00(br, 2H), 4.63(dd, 1H, J=5.4 and 8.1), 8.37(s, 1H), 10.52(d, 1H, J=8.1) |

TABLE 255

| Comp. No. | ¹H-NMR(CDCl₃/TMS) δ |
|---|---|
| I-099 | DMSO-d6 0.92(d, 6H, J=6.9), 1.00-1.34(m, 4H), 1.46-1.94(m, 7H), 2.17(m, 1H), 2.42(s, 3H) 3.74(s, 3H), 3.90-4.15(m, 2H), 4.39(dd, 1H, J=5.1 and 8.4), 8.21(s, 1H), 10.37(d, 1H, J=8.4), 12.73(br, 1H) |
| I-100 | 1.02-1.30(m, 4H), 1.56-1.94(m, 7H), 2.04-2.36(m, 2H), 2.10(s, 3H), 2.16(s, 3H), 2.39(s, 3H), 2.59(t, 2H, J=7.8) 3.76(s, 3H), 4.05(br, 2H), 4.87(m, 1H), 8.28(s, 1H), 10.42(d, 1H, J=7.5) |
| I-101 | 1.00(t, 3H, J=7.2 Hz), 1.40-1.52(m, 2H), 1.62(s, 6H), 1.60-1.74(m, 2H), 2.15(s, 3H), 2.41(s, 3H), 3.74(s, 3H), 4.08-4.14(m, 2H), 8.27(s, 1H), 10.29(s, 1H) |
| I-102 | 1.00(t, 3H, J=7.2 Hz), 1.24-2.21(m, 15H), 2.15(s, 3H), 2.41(s, 3H), 3.72(s, 3H), 4.10-4.15(m, 2H), 8.26(s, 1H), 10.35(s, 1H) |
| I-103 | 0.98(t, 3H, J=7.2 Hz), 1.36-1.48(m, 2H), 1.59-1.69(m, 2H), 2.14(s, 3H), 2.38(s, 3H), 3.63(s, 3H), 4.51-4.10(m, 2H), 5.07(m, 1H), 7.03-7.64(m, 5H), 8.15(s, 1H), 8.26(s, 1H), 10.50(d, 1H, J=7.2 Hz) |
| I-106 | 0.99(t, 3H, J=7.2), 1.39-1.52(m, 2H), 1.63-1.74(m, 2H), 2.18(s, 3H), 2.42(s, 3H), 3.80(s, 3H), 4.01(dd, 1H, J=4.8 and 11.1), 4.06(dd, 1H, J=3.9 and 11.1), 4.06-4.20(m, 2H), 4.83(m, 1H), 8.29(s, 1H), 10.77(d, 1H, J=6.6) |
| I-107 | DMSO-d6 1.00(t, 3H, J=7.2 Hz), 1.24-2.21(m, 15H), 2.15(s, 3H), 2.41(s, 3H), 3.72(s, 3H), 4.10-4.15(m, 2H), 8.26(s, 1H), 10.35(s, 1H) |
| I-108 | 1.02-1.30(m, 4H), 1.56-1.94(m, 7H), 2.04-2.36(m, 2H), 2.10(s, 3H), 2.17(s, 3H), 2.39(s, 3H), 2.59(t, 2H, J=7.8), 3.76(s, 3H), 4.05(br, 2H), 4.87(m, 1H), 8.28(s, 1H), 10.42(d, 1H, J=7.5) |
| I-109 | 1.04-1.31(m, 4H), 1.54-1.88(m, 7H), 2.15(s, 3H), 2.37(s, 3H), 3.10-3.27(m, 2H), 3.68(s, 3H), 3.86-4.20(m, 2H), 4.96(dd, 1H, J=7.5 and 13.8), 7.17-7.30(m, 5H), 8.24(s, 1H), 10.46(d, 1H, 7.5) |
| I-110 | 0.97-1.10(m, 10H), 1.18(t, 2H, 7.5), 1.42-1.78(m, 9H), 2.28(m, 1H), 2.48(q, 2H, J=7.5), 2.61-2.65(m, 2H), 3.74(s, 3H), 4.08(br, 2H), 4.65(dd, 1H, J=5.4 and 8.1), 8.32(s, 1H), 10.43(d, 1H, J=8.1) |
| I-115 | 1.09-1.86(m, 19H), 2.69(t, 2H, J=5.4), 2.96(t, 2H, J=6.0), 3.84-4.21(m, 2H), 7.88(d, 2H, J=8.7), 8.09(d, 2H, J=9.0), 8.40(s, 1H), 12.54(s, 1H) |
| I-116 | 1.02(d, 3H, J=6.9), 1.04(d, 3H, J=6.9), 1.36-1.75(m, 14H), 2.28(m, 1H), 2.49-2.64(m, 8H), 2.96(t, 2H, J=6.6), 3.75(s, 3H), 4.29(m, 2H), 4.66(dd, 1H, J=5.1, 7.8), 8.27(s, 1H), 10.42(d, 1H, J=7.8) |
| I-117 | 1.36-1.76(m, 14H), 2.51-2.65(m, 8H), 2.95(t, 2H, J=6.3), 3.76(s, 3H), 4.22(d, 2H, J=5.7), 4.29(t, 2H, J=7.2), 8.29(s, 1H), 10.34(t, 1H, J=8.7) |
| I-118 | 1.26-1.76(m, 20H), 2.51-2.63(m, 8H), 2.95(t, 2H, J=6.6), 3.75(s, 3H), 4.27(t, 2H, J=7.2), 8.26(s, 1H), 10.28(s, 1H) |
| I-120 | 0.94-1.02(m, 9H), 1.40-1.52(m, 2H), 1.64-1.77(m, 5H), 2.16(s, 3H), 2.41(s, 3H), 3.73(s, 3H), 4.08-4.15(m, 2H), 4.76(m, 1H), 8.28(s, 1H), 10.24(d, 1H, J=7.8 Hz) |

TABLE 256

| Comp. No. | ¹H-NMR(CDCl₃/TMS) δ |
|---|---|
| I-121 | 0.99(t, 3H, J=7.2), 1.39-1.51(m, 2H), 1.62-1.72(m, 2H), 2.15(s, 3H), 2.39(s, 3H), 3.15(dd, 1H, J=7.2 and 13.8), 3.24(dd, 1H, J=6.3 and 13.8), 3.68(s, 3H), 4.11(t-like, 2H), 4.97(q-like, 1H), 7.17-7.29(m, 5H), 8.24(s, 1H), 10.45(d, 1H, J=7.8) |
| I-122 | 0.97(t, 3H, J=7.2), 1.02(d, 3H, J=6.9), 1.03(d, 3H, J=6.9), 1.40(m, 2H), 1.6-1.9(m, 6H), 2.28(m, 1H), 2.50(t, 2H, J=6.0), 2.67(t, 2H, J=6.0), 3.75(s, 3H), 3.93-3.98(m, 2H), 4.57(dd, 1H, J=5.1 and 8.1), 10.86(d, 1H, J=7.5), 16.00(s, 1H) |
| I-123 | 1.01-1.33(m, 10H), 1.60-1.90(4H, m), 2.03(s, 3H), 2.28(m, 1H), 2.36(s, 3H), 3.75(s, 3H), 3.93(brs, 1H), 4.57(dd, 1H, J=5.4 and 8.1), 10.90(d, 1H, J=7.8), 15.76(s, 1H) |
| I-125 | 0.89-1.14(m, 9H), 1.23-2.35(m, 13H), 2.62-2.66(m, 2H), 2.96-3.38(m, 5H), 3.75(s, 3H), 3.79-3.92(m, 3H), 4.33(m, 1H), 4.69(m, 1H), 8.28(s, 1H), 10.44(m, 1H) |
| I-126 | 0.89-1.14(m, 9H), 1.23-2.35(m, 13H), 2.62-2.66(m, 2H), 2.96-3.38(m, 5H), 3.75(s, 3H), 3.79-3.92(m, 3H), 4.33(m, 1H), 4.69(m, 1H), 8.28(s, 1H), 10.44(m, 1H) |

TABLE 256-continued

| Comp. No. | $^1$H-NMR(CDCl$_3$/TMS) δ |
|---|---|
| I-127 | 0.91-2.29(m, 25H), 2.61-2.65(m, 2H), 2.95-3.36(m, 5H), 3.73(s, 3H), 3.74-3.92(m, 3H), 4.33(m, 1H), 8.26(s, 1H), 10.39(s, 1H) |
| I-128 | 0.78-1.97(m, 17H), 0.99(s, 9H), 2.06-2.41(m, 2H), 2.58-2.69(m, 2H), 2.89-3.35(m, 5H), 3.73(s, 3H), 3.81-4.43(m, 2H), 4.79(m, 1H), 8.28(s, 1H), 10.27(s, 1H) |
| I-132 | 1.01-1.72(m, 19H), 1.09(s, 9H), 2.62(t, 2H, J=6.0), 2.91(t, 2H, J=6.3), 3.74(s, 3H), 3.92-4.16(m, 2H), 4.54(d, 1H, J=8.1), 8.26(s, 1H), 10.61(d, 1H, J=7.8) |
| I-133 | 1.00-1.31(m, 13H), 1.47-1.95(m, 12H), 2.28(m, 1H), 2.42-2.55(m, 2H), 2.64-2.75(m, 2H), 3.74(s, 3H), 4.01(br, 2H), 4.65(dd, 1H, J=4.8 and 8.1), 8.33(s, 1H), 10.43(d, 1H, J=7.8) |
| I-138 | 1.00(t, 3H, J=7.2), 1.08(t, 3H, J=7.2), 1.17(t, 3H, J=7.5), 1.40-1.86(m, 12H), 2.15-2.25(m, 8H), 2.45(q, 2H, J=7.8), 2.60-2.68(m, 2H), 3.72(s, 3H), 4.11(br, 2H), 8.31(s, 1H), 10.37(br, 1H) |
| I-139 | 1.00-1.96(m, 21H), 2.15-2.25(m, 8H), 2.47(q, 2H, J=7.2), 2.62-2.74(m, 2H), 3.72(s, 3H), 3.97(br, 2H), 8.31(s, 1H), 10.37(br, 1H) |
| I-140 | 1.06-1.42(m, 6H), 1.51-1.94(m, 15H), 2.14(s, 3H), 2.38(s, 3H), 3.72(s, 3H), 4.03(br, 2H), 8.26(s, 1H), 10.35(br, 1H) |
| I-141 | 1.01(d, 6H, J=8.1), 1.21-2.38(m, 13H), 2.58-2.71(m, 2H), 2.93-3.22(m, 2H), 3.67-3.98(m, 3H), 3.72(s, 3H), 4.26(m, 1H), 4.65-4.71(m, 2H), 8.29(s, 1H), 10.43(t, 1H, J=7.8) |
| I-142 | 1.22-2.20(m, 12H), 1.65(s, 6H), 2.59-2.71(m, 2H), 2.90-3.15(m, 2H), 3.68-3.92(m 3H), 3.75(s, 3H), 4.25(m, 1H), 4.59(m, 1H), 8.28(s, 1H), 10.26(s, 1H) |

TABLE 257

| Comp. No. | $^1$H-NMR(CDCl$_3$/TMS) δ |
|---|---|
| I-143 | 1.16-2.28(m, 22H), 2.59-2.63(m, 2H), 2.92-3.21(m, 2H), 3.73(s, 3H), 3.76(m, 1H), 3.84-3.92(m, 2H), 4.26(m, 1H), 4.60(dd, 1H, J=3.3, 12.3), 8.27(s, 1H), 10.33(s, 1H) |
| I-144 | 1.09-2.26(m, 12H), 1.08(s, 9H), 2.62-2.65(m, 2H), 2.92-3.27(m, 2H), 3.73(s, 3H), 3.72-3.94(m, 3H), 4.28(m, 1H), 4.50-4.69(m, 2H), 8.28(s, 1H), 10.58(t, 1H, J=6.6) |
| I-147 | 0.98(t, 3H, J=7.2 Hz), 1.39-1.51(m, 2H), 1.62-1.73(m, 2H), 2.15(s, 3H), 2.40(s, 3H), 3.74(s, 3H), 4.09-4.15(m, 2H), 5.73(d, 1H, J=6.6 Hz), 7.30-7.50(m, 5H), 8.26(s, 1H), 10.87(d, 1H, J=6.3 Hz) |
| I-148 | 1.23-1.93(m, 16H), 2.14-2.24(m, 2H), 2.61(t-like, 2H), 3.05(t-like, 2H), 3.73(s, 3H), 5.37(brs, 2H), 6.32(dd, 1H, J=0.6 and 3.3), 6.34(dd, 1H, J=1.8 and 3.3), 7.35(dd, 1H, J=0.9 and 1.8), 8.28(s, 1H), 10.27(brs, 1H) |
| I-154 | 0.95-1.08(m, 9H), 1.48(m, 1H), 1.56-1.74(m, 9H), 1.85(m, 1H), 2.69(t, 2H, J=5.4), 2.93(t, 2H, J=5.4), 3.74(s, 3H), 4.18(br, 2H), 4.66(dd, 1H, J=5.4 and 8.1), 8.26(s, 1H), 10.42(d, 1H, J=7.5) |
| I-155 | 0.95-1.08(m, 9H), 1.48(m, 1H), 1.56-1.74(m, 7H), 1.85(m, 1H), 2.69(t, 2H, J=5.4), 2.93(t, 2H, J=5.4), 3.74(s, 3H), 4.18(br, 2H), 4.66(dd, 1H, J=5.4 and 8.1), 8.26(s, 1H), 10.42(d, 1H, J=7.5) |
| I-158 | 0.98(t, 3H, J=7.5), 1.07(t, 3H, J=7.5), 1.16(t, 3H, J=7.5), 1.38-1.78(m, 8H), 2.47(q, 2H, J=7.5), 2.62-2.70(m, 2H), 3.74(s, 3H), 3.98-4.20(m, 2H), 5.73(d, 1H, J=7.2), 7.26-7.38(m, 3H), 7.46-7.53(m, 2H), 8.31(s, 1H), 10.89(d, 1H, J=6.9) |
| I-160 | 0.99-1.04(m, 9H), 1.38-1.51(m, 2H), 1.63-1.73(m, 4H), 1.82-1.91(m, 2H), 2.29(m, 1H), 2.60(t, 2H, J=6.0 Hz), 2.74(t, 2H, J=6.0 Hz), 3.74(s, 3H), 4.01-4.10(m, 2H), 4.66(m, 1H), 8.21(s, 1H), 10.43(d, 1H, J=8.4 Hz) |
| I-161 | 1.00-1.04(m, 6H), 1.09-1.90(m, 15H), 2.29(m, 1H), 2.61(t, 2H, J=6.0 Hz), 2.73(t, 2H, J=6.0 Hz), 3.75(s, 3H), 3.84-4.06(m, 2H), 4.65(m, 1H), 8.21(s, 1H), 10.44(d, 1H, J=7.8 Hz) |
| I-162 | 0.94-1.01(m, 9H), 1.39-1.51(m, 2H), 1.62-1.79(m, 7H), 1.83-1.91(m, 2H), 2.29(m, 1H), 2.60(t, 2H, J=6.0 Hz), 2.74(t, 2H, J=6.0 Hz), 3.74(s, 3H), 3.98-4.10(m, 2H), 4.76(m, 1H), 8.21(s, 1H), 10.27(d, 1H, J=7.2 Hz) |
| I-163 | 0.94-0.98(m, 6H), 1.00-1.25(m, 6H), 1.58-190(m, 12H), 2.61(t, 2H, J=6.0 Hz), 2.71(t, 2H, J=6.0 Hz), 3.74(s, 3H), 3.82-4.12(m, 2H), 4.75(m, 1H), 8.22(s, 1H), 10.26(d, 1H, J=7.2 Hz) |
| I-164 | 1.03(d, 6H, J=6.6), 1.36-1.79(m, 8H), 2.28(m, 1H), 2.64(t, 2H, J=6.3), 2.86(t, 2H, J=6.3), 3.74(s, 3H), 4.65(m, 1H), 4.85(br, 2H), 4.96(d, 1H, J=17.1), 5.21(d, 1H, J=13.5), 5.98(m, 1H), 8.32(s, 1H), 10.35(d, 1H, J=7.8) |

TABLE 258

| Comp. No. | $^1$H-NMR(CDCl$_3$/TMS) δ |
|---|---|
| I-165 | 1.03(d, 3H, J=6.9), 1.04(d, 3H, J=6.9), 1.30-1.79(m, 9H), 2.00-2.39(m, 2H), 2.63(t, 2H, J=6.0), 2.99-3.16(m, 2H), 3.75(s, 3H), 3.70-3.82(m, 2H), 4.03-4.37(m, 4H), 4.67(dd, 1H, J=5.4 and 7.8), 4.99(t, 1H, J=5.4), 8.29(s, 1H), 10.33(d, 1H, J=7.8) |
| I-166 | 1.00(d, 3H, J=6.9), 1.01(d, 3H, J=6.9), 1.36-1.77(m, 8H), 2.27(m, 1H), 2.63-2.76(m, 4H), 3.74(s, 3H), 4.66(dd, 1H, J=5.1 and 8.1), 4.98(ABq, 2H, J=17.7), 8.36(s, 1H), 9.70(s, 1H), 10.08(d, 1H, J=7.8) |
| I-167 | 0.99 (t, 3H, J=7.2 Hz), 1.38-1.50 (m, 2H), 1.60-1.76 (m, 4H), 1.83-1.90 (m, 2H), 2.59 (t, 2H, J=6.0 Hz), 2.73(t, 2H, J=6.0 Hz), 3.11-3.27 (m, 2H), 3.68 (s, 3H), 4.06-4.01 (m, 2H), 4.97 (m, 1H), 7.18-7.29 (m, 5H), 8.17 (s, 1H), 10.48 (d, 1H, J=7.5 Hz) |
| I-168 | 1.00-1.30 (m, 6H), 1.58-1.89 (m, 9H), 2.62 (t, 2H, J=6.0 Hz), 2.70 (t, 2H, J= 6.0 Hz), 3.11-3.27 (m,2H), 3.69 (s, 3H), 3.78-4.14 (m, 2H), 4.96 (m, 1H), 7.16-7.28 (m, 5H), 8.17 (s, 1H), 10.48 (d, 1H, J=7.8 Hz) |
| I-169 | 0.92-1.03 (m, 9H), 1.23-1.91 (m, 10H), 2.04 (m, 1H), 2.60 (t, 2H, J= 6.0 Hz), 2.74 (t, 2H, J=6.0 Hz), 3.74 (s, 3H), 4.00-4.08 (m, 2H), 4.72 (m, 1H), 8.21 (s, 1H), 10.43 (d, 1H, J=8.1 Hz) |
| I-170 | 0.92-1.00 (m, 6H), 1.02-1.94 (m, 17H), 2.04 (m,1H), 2.61 (t, 2H, J= 6.0 Hz), 2.71 (t, 2H, J=6.0 Hz), 3.74 (s, 3H), 3.80-4.17 (m, 2H), 4.72 (m, 1H), 8.21 (s, 1H), 10.43 (d, 1H, J=8.1 Hz) |
| I-171 | 1.02(d, 6H, J=6.6), 1.30-1.779(m, 8H), 2.28(m, 1H), 2.64(t, 2H, J=6.0), 3.06(t, 2H, J=6.3), 3.74(s, 3H), 3.86-4.05(m, 4H), 4.40(br, 2H), 4.66(dd, 1H, J=5.4 and 7.8), 5.21(t, 1H, J=4.5), 8.31(s, 1H), 10.32(d, 1H, J=8.4) |
| I-172 | 1.01(d, 3H, J=6.6), 1.03(d, 3H, J=6.6), 1.05-1.30(m, 4H), 1.50-1.90(m, 11H), 2.30(m, 1H), 2.67-2.71(m, 2H), 2.91-2.95(m, 2H), 3.74(s, 3H), 3.98(br, 2H), 4.65(dd, 1H, J=5.4 and 8.4), 8.26(s, 1H), 10.43(d, 1H, J=8.4) |
| I-173 | 1.00-1.30(m, 6H1), 1.50-1.97(m, 11H), 2.66-2.70(m, 2H), 2.89-2.95(m, 2H), 3.74(s, 3H), 4.22(br, 2H), 5.76(d, 1H, J=8.4), 7.32-7.40(m, 3H), 7.47-7.53(m, 2H), 8.25(s, 1H), 10.88(d, 1H, J=6.6) |

TABLE 258-continued

| Comp. No. | $^1$H-NMR(CDCl$_3$/TMS) δ |
|---|---|
| I-174 | 0.99(t, 3H, J=8.4), 1.20-2.32(m, 20H), 2.60-2.77(m, 2H), 2.85-3.00(m, 2H), 3.71(s, 3H), 4.18(br, 2H), 8.25(s, 1H), 10.36(br s, 1H) |
| I-175 | 0.99-1.95(m, 25H), 2.10-2.23(m, 2H), 2.60-2.75(m, 2H), 2.85-2.96(m, 2H), 3.72(s, 3H), 4.13(br, 2H), 8.25(s, 1H), 10.37(br s, 1H) |
| I-176 | 0.97(t, 3H, J=7.5), 1.20-1.90(m, 16H), 2.70(brt, 2H), 2.93(brt, 2H), 3.75(s, 3H), 4.13(br, 2H), 5.74(d, 1H, J=6.9), 7.28-7.51(m, 5H), 8.31(s, 1H), 10.93(d, 1H, J=6.9) |
| I-177 | 0.98(t, 3H, J=7.5), 1.03(d, 3H, J=6.9), 1.04(d, 3H, J=6.9), 1.22-1.90(m, 16H), 2.30(m, 1H), 2.71(brt, 2H), 2.94(brt, 2H), 3.75(s, 3H), 4.16(br, 2H), 4.66(dd, 1H, J=5.1 and 8.1), 8.31(s, 1H), 10.48(d, 10.48(d, 1H, J=8.1) |

TABLE 259

| Comp. No. | $^1$H-NMR(CDCl$_3$/TMS) δ |
|---|---|
| I-178 | 0.98(t, 3H, J=7.2), 1.02(d, 3H, J=6.9), 1.03(d, 3H, J=6.9), 1.36-1.48(m, 2H), 1.67-1.78(m, 2H), 2.13-2.34(m, 3H), 2.83(t, 2H, J=7.5), 3.00(t, 2H, J=7.5), 3.74(s, 3H), 3.93-4.09(m, 2H), 4.66(dd, 1H, J=5.1 and 8.1), 8.37(s, 1H), 10.43(d, 1H, J=8.1) |
| I-179 | 0.99(t, 3H, J=7.2), 1.02(d, 3H, J=7.2), 1.03(d, 3H, J=7.2), 1.39-1.51(m, 2H), 1.63-1.75(m, 2H), 2.29(m, 1H), 2.82(brt, 21), 3.75(s, 3H), 3.98-4.08(m, 41), 4.58(s, 2H), 4.66(dd, 1H, J=5.1 and 8.1), 8.15(s, 1H-), 10.35(d, 1H, J=8.1) |
| I-181 | 1.00-1.30(m, 10H), 1.45-1.93(m, 9H), 2.48(q, 2H, J=7.5), 2.67(t, 2H, J=8.1), 3.74(s, 3H), 3.99(br, 2H), 5.72(d, 1H, J=6.9), 7.25-7.40(m, 3H), 7.47-7.53(m, 2H), 8.32(s, 1H), 10.88(d, 1H, J=6.6) |
| I-183 | DMSO-d6 1.17-1.80(m, 16H), 2.00-2.10(br, 2H), 2.67(brt, 2H), 3.05(brt, 2H), 5.41(brs, 2H), 6.35(d, 1H, J=3.3), 6.43(dd, 1H, J=1.8 and 3.3), 7.61(dd, 1H, J=0.9 and 1.8), 8.13(s, 1H), 10.16(s, 1H), 12.21(brs, 1H) |
| I-186 | 0.99 (t, 3H, J=7.2 Hz), 1.34-1.51 (m, 2H), L62 (s, 6H), 1.83-1.91 (m, 2H), 2.59 (t, 2H, J=6.0 Hz), 2.74 (t, 2H, J=6.0 Hz), 3.74 (s, 3H), 4.01-4.06 (m, 2H), 8.20 (s, 1H), 10.30 (s,1H) |
| I-187 | 1.00-1.30 (m, 6H), 1.62 (s, 6H), 1.60-1.92 (m, 9H), 2.60 (t, 2H, J=6.3 Hz), 2.71 (t, 2H, J=6.3 Hz), 3.74 (s, 3H), 3.80-4.00 (m, 2H), 8.20 (s, 1H), 10.28 (s, 1H) |
| I-188 | 0.98 (t, 3H, J=7.2 Hz), 1.37-1.61 (m, 2H), 1.61-1.76 (m, 4H), 1.83-1.91 (m, 2H), 2.59 (t, 2H, J=6.0 Hz), 2.74 (t, 2H, J=6.0 Hz), 3.74 (s, 3H), 4.02-4.07 (m, 2H), 5.73 (d, 1H, J=6.6 Hz), 7.30-7.52 (m, 5H), 8.19 (s, 1H), 10.90 (d, 1H, J=6.9 Hz) |
| I-189 | 1.00-1.30 (m, 6H), 1.54-1.94 (m, 9H), 2.60 (t, 2H, J=6.3 Hz), 2.71 (t, 2H, J=6.3 Hz), 3.74 (s, 3H), 3.80-4.05 (m, 2H), 5.73 (d, 1H, J=6.3 Hz), 7.28-7.53 (m, 5H), 8.20 (s, 1H), 10.88 (d, 1H, J=6.6 Hz) |
| I-193 | 2.15(s, 3H), 2.29(s, 3H), 3.74(s, 3H), 5.45-5.50(br, 21), 5.73(d, 1H, J=6.6), 6.98-7.14(m, 41), 7.26-7.40(m, 3H), 7.46-7.52(m, 2H), 8.36(s, 1H), 10.76(d, 1H, J=6.6) |
| I-194 | 1.20-1.40(m, 2H), 1.40-1.76(m, 7H), 1.80-1.96(m, 2H), 2.14-2.25(m, 4H), 2.29(s, 3H), 3.74(s, 3H), 5.44(br s, 2H), 7.00-7.18(m, 4H), 8.36(s, 1H), 10.26(br s, 1H) |
| I-196 | 1.02(d, 6H, J=6.6), 1.14(t, 3H, J=7.5), 2.18(s, 3H), 2.25(m, 1H), 2.64(q, 2H, J=7.5), 3.74(s, 3H), 4.65(dd, 1H, J=5.1 and 8.1), 5.64(br, 2H), 6.96-7.16(m, 4H), 8.38(s, 1H), 10.30(d, 1H, J=8.1) |
| I-197 | 0.98-1.06(m, 6H), 1.19(t, 3H, J=7.5), 1.45-1.60(m, 2H), 2.28(m, 1H), 2.44-2.60(m, 5H), 3.74(s, 3H), 4.65(dd, 1H, J=5.4 and 8.1), 5.42(br, 2H), 6.96-7.12(m, 4H), 8.43(s, 1H), 10.31(d, 1H, J=8.1) |
| I-198 | 1.00 (t, 3H, J=7.2 Hz), 1.24-1.96 (m, 16H), 2.17-2.21 (m, 2H), 2.59 (t, 2H, J=6.0 Hz), 2.74 (t, 2H, J=6.0 Hz), 3.71 (s, 3H), 4.02-4.08 (m, 2H), 8.19 (s, 1H), 10.37 (s, 1H) |

TABLE 260

| Comp. No. | $^1$H-NMR(CDCl$_3$/TMS) δ |
|---|---|
| I-199 | 1.01-1.40 (m, 6H), 1.50-1.96 (m, 17H), 2.16-2.20 (m, 2H), 2.59 (t, 2H, J=6.0 Hz), 2.69 (t, 2H, J=6.0 Hz), 3.72 (s, 3H), 3.80-4.05 (m, 2H0, 8.19 (s, 1H), 10.38 (s, 1H) |

TABLE 260-continued

| Comp. No. | $^1$H-NMR(CDCl$_3$/TMS) δ |
|---|---|
| I-200 | 0.96 (t, 3H, J=7.2 Hz), 1.37-1.42 (m, 2H), 1.62-1.80 (m, 4H), 1.83-1.93 (m, 2H), 2.60 (t, 2H, J=6.0 Hz), 2.75 (t, 2H, J=6.0 Hz), 3.18 (s, 3H), 4.03-4.09 (m, 2H), 5.58 (d, 1H, J=6.3 Hz), 6.61-7.25 (m, 4H), 8.21 (s, 1H), 10.84 (d, 1H, J=6.6 Hz) |
| I-201 | DMSO-d6 0.90-1.20 (m, 6H), 1.44-1.84 (m, 9H), 2.58 (t, 2H, m, J=5.7 Hz), 2.78 (t, 2H, J=5.7 Hz), 3.62 (s, 3H), 3.75-4.02 (m, 2H), 5.40 (d, 1H, J=6.3 Hz), 6.76-7.22 (m, 4H), 8.04 (s, 1H), 9.66 (br, 1H), 10.53 (d, 1H, J=6.6 Hz) |
| I-205 | 1.00(t, 3H, J=7.5), 1.08(t, 3H, J=7.5), 1.18(t, 3H, J=7.5), 1.39-1.76(m, 6H), 1.61(s, 61), 2.47(q, 2H, J=7.5), 2.60-2.69(m, 2H), 3.74(s, 3H), 4.00-4.13(m, 2H), 8.32(s, 1H), 10.31(s, 1H) |
| I-206 | 1.05(t, 3H, J=7.5), 1.18(t, 3H, J=7.5), 1.00-1.31(m, 4H), 1.45-1.94(m, 9H), 1.61(s, 6H), 2.48(q, 2H, J=7.5), 2.63-2.73(m, 2H), 3.75(s, 3H), 3.98(br, 2H), 8.32(s, 1H), 10.28(s, 1H) |
| I-207 | 0.96 (m, 9H), 1.38-1.63 (m, 2H), 1.62-1.92 (m, 4H), 1.82-1.93 (m, 2H), 2.29 (m,1H), 2.60 (t, 2H, J=6.0 Hz), 2.72 (t, 2H, J=6.0 Hz), 3.74 (s, 3H), 4.00-4.13 (m, 2H), 4.66 (m,1H), 8.21 (s, 1H), 10.44 (d, 1H, J=8.1 Hz) |
| I-208 | 1.00-1.04 (m, 6H), 1.05-1.30 (m, 6H), 1.56-1.93 (m, 9H), 2.29 (m,1H), H), 2.61 (t, 2H, J=6.0 Hz), 2.71 (t, 2H, J=6.0 Hz), 3.74 (s, 3H), 3.80-4.08 (m, 2H), 4.65 (m, 1H), 8.21 (s, 1H), 10.44 (d, 1H, J=7.8 Hz) |
| I-211 | 1.00(t, 3H, J=7.5), 1.08(s, 9H), 1.08(t, 3H, J=7.5), 1.17(t, 3H, J=7.5), 1.38-1.78(m, 6H), 2.48(q, 2H, J=7.5), 2.60-2.69(m, 2H), 3.73(s, 3H), 4.01-4.15(m, 2H), 4.54(d, 1H, J=8.4), 8.32(s, 1H), 10.58(d, 1H, J=8.4) |
| I-212 | 0.98-1.31(m, 4H), 1.05(t, 3H, J=7.5), 1.08(s, 9H), 1.18(t, 3H, J=7.5), 1.45-1.90(m, 9H), 2.48(q, 2H, J=7.5), 2.62-2.73(m, 2H), 3.73(s, 3H), 3.98(br, 2H), 4.53(d, 1H, J=8.1), 8.32(s, 1H), 10.58(d, 1H, J=8.1) |
| I-213 | 1.01 (t, 3H, J=7.2 Hz), 1.18 (t, 3H, J=7.5 Hz), 1.45-1.56 (m, 2H), 2.45-2.60 (m, 4H), 3.73 (s, 3H), 5.25-5.58 (m, 2H), 5.72 (d, 1H, J=6.3 Hz), 6.98-7.50 (m, 9H), 8.42 (s, 1H), 10.75 (d, 1H, J=6.6 Hz) |
| I-214 | 1.14 (t, 3H, J=7.5 Hz), 2.18 (s, 3H), 2.64 (dd, 2H, J=7.5 and 17.1 Hz), 3.73 (s, 3H), 5.25-5.56 (m, 2H), 5.72 (d, 1H, J=6.6 Hz), 6.98-7.50 (m, 9H), 8.37 (s, 1H), 10.74 (d, 1H, J=6.6 Hz) |
| I-215 | 2.17 (s, 3H), 2.28 (s, 3H), 3.74 (s, 3H), 5.40-5.70 (m, 2H), 5.72 (d, 1H, J=6.6 Hz), 7.20-7.60 (m, 9H), 8.39 (s, 1H), 10.71 (d, 1H, J=6.9 Hz) |
| I-216 | 1.37-1.81(m, 8H), 1.61(s, 6H), 2.62(t, 2H, J=6.0), 2.85(t, 2H, J=6.3), 3.75(s, 3H), 4.82(br, 2H), 4.93(, d, 1H, J=17.1), 5.22(d, 1H, J=10.5), 5.99(m, 1H), 8.31(s, 1H), 10.24(s, 1H) |

TABLE 261

| Comp. No. | $^1$H-NMR(CDCl$_3$/TMS) δ |
|---|---|
| I-217 | 1.22-1.84(m, 8H), 1.62(s, 6H), 2.66(t, 2H, J=6.0), 2.99(brt, 2H), 3.54(dd, 1H, J=3.6 and 11.7), 3.68(dd, 1H, J=4.2 and 12.0), 3.75(s, 3H), 3.96(m, 1H), 4.21(dd, 1H, J=6.6 and 14.4), 4.44(dd, 1H, J=6.0 and 14.4), 8.33(s, 1H), 10.06(s, 1H) |
| I-218 | 1.40-1.90(m, 8H), 1.63(s, 6H), 2.58-3.10(m, 4H), 3.76(s, 3H),4.26(dd, 1H, J=6.9 and 14.4), 4.35(dd, 1H, J=7.5 and 9.3), 4.58(dd, 1H, J=3.0 and 14.4), 4.74(dd, 1H, J=8.1 and 9.0), 5.09(m, 1H), 8.34(s, 1H), 10.03(s, 1H) |
| I-219 | 0.92-1.00(m, 6H), 1.00(t, 3H, J=7.2), 1.08(t, 3H, J=7.2), 1.18(t, 3H, J=7.5), 1.39-1.85(m, 9H), 2.48(q, 2H, J=7.5), 2.60-2.70(m, 2H), 3.73(s, 3H), 3.96-4.18(m, 2H), 4.75(q, 1H, J=7.2), 8.33(s, 1H), 10.27(d, 1H, J=7.5) |
| I-220 | 1.00(t, 3H, J=7.5, 1.08(t, 3H, J=7.5), 1.17(t, 3H, J=7.5), 1.38-1.76(m, 6H), 2.47(q, 2H, J=7.5), 2.60-2.68(m, 2H), 3.10-3.17(m, 2H), 3.68(s, 1H), 3.98-4.13(m, 2H), 4.96(q, 2H, J=7.2), 7.17-7.31(m, 5H), 8.29(s, 1H), 10.48(d, 1H, J=7.5) |
| I-221 | 1.36-2.04(m, 10H), 1.62(s,6H), 2.62(t, 2H, J=6.0), 2.91(t, 2H, J=6.3), 3.46(t, 2H, J=6.3), 3.75(s, 3H), 4.20(brt, 2H), 8.28(s, 1H), 10.26(s, 1H) |
| I-222 | 0.91-1.05(m, 9H), 1.08(t, 3H, J=7.5), 1.18(t, 3H, J=7.5), 1.22-1.78(m, 8H), 2.04(m, 1H), 2.48(q, 2H, J=7.5), 2.61-2.69(m, 2H), 3.74(s, 3H), 4.00-4.18(m, 2H), 4.72(dd, 1H, J=5.4 and 8.1), 8.33(s, 1H), 10.43(d, 1H, J=7.5) |
| I-223 | 2.14 (s, 3H), 2.30 (s, 3H), 3.74 (s, 3H), 5.33-5.5 0 (m, 2H), 5.73 (d, 1H, J=6.9 Hz), 6.82-7.51 (m, 9H), 8.35 (s, 1H), 10.82 (d, 1H, J=6.3 Hz) |
| I-224 | 1.14 (t, 3H, J=7.8 Hz), 1.23-2.24 (m, 10H), 2.17 (s, 3H), 2.63 (dd, 2H, J=7.5 and 15 Hz), 3.73 (s, 3H), 5.30-5.55 (m, 2H), 6.99-7.10 (m, 4H), 8.37 (s, 1H), 10.24 (s, 1H) |
| I-225 | 1.01 (t, 3H, J=7.5 Hz), 1.19 (t, 3H, J=7.5 Hz), 1.23-1.70 (m, 8H), 1.80-1.93 (m, 2H), 2.14-2.23 (m, 2H), 2.44-2.59 (m,4H), 3.74 (s, 3H), 5.42 (br, 2H), 7.00-7.10 (m, 4H), 8.42 (s, 1H), 10.26 (s, 1H) |
| I-226 | 1.32-1.96(m, 10H), 1.46(s, 9H), 1.62(s, 6H), 2.61(t, 2H, J=6.0), 2.88(t, 2H, J=6.3), 3.20(brq, 2H), 3.75(s, 3H), 4.18(brt, 2H), 5.15(br, 1H), 8.27(s, 1H), 10.27(s, 1H) |

TABLE 261-continued

| Comp. No. | $^1$H-NMR(CDCl$_3$/TMS) δ |
|---|---|
| I-227 | 1.32-2.00(m, 10H), 1.64(s, 6H), 2.05(s, 3H), 2.62(t, 2H, J=6.0), 2.89(t, 2H, J=6.3), 3.27(brq, 2H), 3.76(s, 3H), 4.21(brt, 2H), 6.65(br, 1H), 8.30(s, 1H), 10.27(s, 1H) |
| I-228 | 1.35(t, 3H, J=7.2), 1.40-1.92(m, 10H), 1.61(s, 6H), 2.59(t, 2H, J-6.9), 2.84(t, 2H, J=6.3), 3.00(brq, 2H), 3.60(br, 1H), 3.75(s, 3H9, 4.02-4.30(m, 4H), 7.40-7.85(m, 5H), 8.26(s, 1H), 10.25(s, 1H) |
| I-229 | 0.92-1.31(m, 4H), 0.97(t, 61-1, J=6.0), 1.06(t, 3H, J=7.5), 1.18(t, 3H, J=7.5), 1.46-1.93(m, 12H), 2.49(q, 2H, J=7.5), 2.63-2.73(m, 2H), 3.74(s, 3H), 3.78-4.15(br, 2H), 4.75(q, 1H, J=7.5), 8.34(s, 1H), 10.26(d, 1H, J=7.2) |

TABLE 262

| Comp. No. | $^1$H-NMR(CDCl$_3$/TMS) δ |
|---|---|
| I-230 | 1.02-1.31(m, 4H), 1.06(t, 3H, J=7.5), 1.18(t, 3H, J=7.5), 1.45-1.88(m, 9H), 2.47(q, 2H, J=7.5), 2.58-2.74(m, 2H), 3.10-3.28(m, 2H), 3.68(s, 3H), 3.70-4.20(br, 2H), 4.96(q, 1H, J=7.5), 7.15-7.30(m, 5H), 8.29(s,1H), 10.49(d, 1H, J=7.5) |
| I-231 | 2.15 (s, 3H), 2.28 (s, 3H), 3.74 (s, 3H), 5.43 (br, 2H), 5.72 (d, 1H, J=6.6 Hz), 7.02-7.51 (m, 9H), 8.37 (s, 1H), 10.75 (d, 1H, J=6.3 Hz) |
| I-232 | 2.17 (s, 3H), 2.28 (s, 3H), 3.74 (s, 3H), 5.45 (br, 2H), 5.73 (d, 1H, J=6.3 Hz), 6.90-7.52 (m, 9H), 8.38 (s, 1H), 10.37 (d, 1H, J=6.0 Hz) |
| I-233 | 0.98-1.30 (m, 6H), 1.55-1.96 (m, 9H), 2.59 (t, J=6.0 Hz, 2H), 2.70 (t, J=6.0 Hz, 2H), 3.73 (s, 3H), 3.79 (s, 3H), 3.85-4.05 (m, 2H), 5.65 (d, J=6.6 Hz, 1H), 6.88-7.45 (m, 4H), 8.19 (s, 1H), 10.80 (d, J=6.9 Hz, 1H) |
| I-234 | 2.18 (s, 3H), 2.23(s, 3H), 3.73 (s, 3H), 5.46-5.58 (m, 2H), 5.72 (d, 1H, J=6.6 Hz), 6.62-7.50 (m, 9H), 8.41 (s, 1H), 10.71 (d, 1H, J=6.6 Hz) |
| I-236 | 1.02(d, 3H, J=6.9), 1.03(d, 3H, J=6.9), 1.34-1.56(m, 4H), 1.64-1.83(m, 4H), 2.29(m, 1H), 2.65(t, 2H, J=6.0), 2.91-3.03(m, 4H), 3.75(s, 3H), 4.42(t, 2H, J=6.6), 4.67(dd, 1H, J=5.1 and 8.1), 8.33(s, 1H), 10.18(d, 1H, J=8.1) |
| I-237 | 1.32-1.56(m, 4H), 1.56-1.84(m, 4H), 2.64(t, 2H, J=6.0), 2.90-3.06(m, 4H), 3.75(s, 3H), 4.41(t, 2H, J=6.6), 5.74(d, 1H, J=6.9), 7.28-7.44(m, 3H), 7.45-7.53(m, 2H), 8.32(s, 1H), 10.66(d, 1H, J=6.9) |
| I-238 | 1.02(dd, 6H, J=1.5 and 6.9), 1.30-1.54(m, 4H), 1.64-1.84(m, 4H), 1.95-2.07(m,2H), 2.29(m, 1H), 2.64(t, 2H, J=6.3), 2.84-2.95(m, 2H), 2.96(s, 3H), 3.00-3.22(m, 2H), 3.75(s, 3H), 4.16-4.50(m, 2H), 4.67(dd, 1H, J=5.1 and 8.1), 5.92(t, 1H, J=6.0), 8.32(s, 1H), 10.29(d, 1H, J=8.1) |
| I-239 | 1.32-1.54(m, 4H), 1.58-1.84(m, 4H), 1.94-2.06(m,2H), 2.63(t, 2H, J=5.7), 2.84-2.96(m, 2H), 2.90(s, 3H), 3.00-3.16(m, 2H), 3.74(s, 3H), 4.18-4.42(m, 2H), 5.75(d, 1H, J=7.2), 5.83(m, 1H), 7.28-7.50(m, 5H), 8.31(s, 1H), 10.78(d, 1H, J=7.2) |
| I-240 | 1.32-1.54(m, 4H), 1.60-1.84(m, 4H), 1.62(s, 6H), 1.95-2.06(m,2H), 2.62(t, 2H J=6.0) 2.86-2.94(m, 2H), 2.97(s, 3H), 3.06-3.18(m 2H), 3.76(s, 3H), 4.24-4.36(m, 2H), 5.74(t, 1H, J=6.0), 8.30(s, 1H), 10.17(s, 1H) |
| I-241 | 0.93-1.04 (m, 15H), 1.40-1.78 (m, 10H), 2.28 (m, 1H), 2.38-2.46 (m, 2H), 2.62-2.71 (m, 2H), 3.74 (s, 3H), 4.00-4.16 (m, 2H), 4.66 (m, 1H), 8.29 (s, 1H), 10.43 (d, 1H, J=7.8 Hz) |
| I-242 | 0.93-1.04 (m, 9H), 1.38-1.78 (m, 10H), 2.38-2.46 (m, 2H), 2.62-2.72 (m, 2H), 3.74 (s, 3H), 4.04-4.16 (m, 2H), 5.74 (d, 1H, J=6.6 Hz), 7.25-7.55 (m, 5H), 8.28 (s, 1H), 10.89 (d, 1H, J=6.9 Hz) |
| I-245 | 0.93-1.02 (m, 9H), 1.61 (s, 6H), 1.40-1.77 (m, 10H), 2.38-2.45 (m, 2H), 2.62-2.72 (m, 2H), 3.74 (s, 3H), 4.04-4.16 (m, 2H), 8.28 (s, 1H), 10.30 (s, H) |
| I-246 | 0.93-1.03 (m, 9H), 1.22-1.78 (m, 16H), 1.82-1.94 (m, 2H), 2.14-2.26 (m, 2H), 2.36-2.45 (m, 2H), 2.62-2.70 (m, 2H), 3.72 (s, 3H), 4.02-4.16 (m, 2H), 8.27 (s, 1H), 10.37 (s, 1H) |

TABLE 263

| Comp. No. | $^1$H-NMR(CDCl$_3$/TMS) δ |
|---|---|
| I-247 | 1.32-1.54(m, 4H), 1.61-1.82(m, 4H), 1.85-1.96(m, 2H), 2.01(s, 3H), 2.58-2.66(m, 2H), 2.85-2.94(m, 2H), 3.21-3.33(m, 2H), 3.75(s, 3H), 4.16-4.32(m, 2H), 5.74(d, 1H, J=6.9), 6.82(m, 1H), 7.28-7.53(m, 5H), 8.30(s, 1H), 10.85(d, 1H, J=6.9) |
| I-249 | 1.00(d, 3H, J=6.9), 1.01(d, 3H, J=6.9), 1.36-1.56(m, 4H), 1.62-1.78(m, 4H), 2.27(m, 1H), 2.65(t, 2H, J=6.0), 2.73(t, 2H, J=6.0), 3.75(s, 3H), 4.66(dd, |

TABLE 263-continued

| Comp. No. | ¹H-NMR(CDCl₃/TMS) δ |
|---|---|
| | 1H, J=5.1 and 8.1), 5.52(br, 2I), 7.20(d, 2H, J=8.4), 7.63(d, 2H, J=8.4), 8.40(s, 1H), 10.20(d, 1H, J=8.1) |
| I-250 | 1.45-1.56(m, 4H), 1.58-1.78(m, 4H), 2.65(t, 2H, J=6.0), 2.73(t, 2H, J=6.0), 3.75(s, 3H), 5.48(br, 2H), 5.72(d, 1H, J=6.9), 7.18(d, 2H, J=8.1), 7.26-7.40(m, 3H), 7.42-7.51(m, 2H), 7.61(d, 2H, J=8.1), 8.38(s, 1H), 10.65(d, 1H, J=6.6) |
| I-251 | 1.32-1.53(m, 4H), 1.60-1.80(m, 4H), 1.63(s; 6H), 1.86-1.97(m, 2H), 2.57-2.95(m, 2H), 2.84-2.93(m, 2H), 3.18-3.29(m, 2H), 3.69(s, 3H), 3.76(s, 3H), 4.15-4.27(m, 2H), 5.50(m, 1H), 8.28(s, 1H), 10.24(s,1H) |
| I-256 | 1.02(d, 3H, J=6.9), 1.03(d, 3H, J=6.9), 1.06-1.30(m, 5H), 1.57-1.91(m, 6H), 2.29(m, 1H), 2.94(brt, 2H), 3.02(brt, 2H), 3.66(s, 2H), 3.75(s, 3H), 4.01(br, 2H), 4.66(dd, 1H, J=5.4 and 8.1), 8.24(s, 1H), 10.34(d, 1H, J=8.1) |
| I-257 | 1.01(d, 3H, J=6.9), 1.02(d, 3H, J=6.9), 1.06-1.31(m, 5I), 1.56-1.90(m, 6H), 2.29(m, 1H), 3.31(brt, 2H), 3.45(brt, 2H), 3.76(s, 3H), 4.03(br, 2H), 4.11(d, 1H, J=18.0), 4.17(d, 11-1, J=18.0), 4.65(dd, 1H, J=5.1 and 8.1), 8.15(s, 1H), 10.13(d, 1H, J=8.1) |
| I-258 | 1.00-1.32(m, 11H), 1.58-1.94(m, 6H), 2.29(m, 1H), 2.87(m, 1H), 3.08(m, 1H), 3.29(m, 1H), 3.45(m, 1H), 3.75(s, 3H), 3.84(m, 2H), 4.06(m, 2H-1), 4.65(dd, 1H, J=5.1 and 8.1), 8.22(s, 1H), 10.20(brm, 1H) |
| I-261 | 1.34-1.54(m, 4H), 1.60(s, 6H), 1.62-1.78(m, 4H), 2.63(t, 2H, J=6.0), 2.73(t, 2H, J=6.0), 3.75(s, 3H), 5.42(br, 2H), 7.18(d, 2H, J=8.4), 7.64(d, 2H, J=8.4), 8.37(s, 1H), 10.08(br s, 1H) |
| I-266 | 1.02(d, 6H, J=6.9), 1.34-1.56(m, 4H), 1.62-1.85(m, 4H), 2.05-2.17(m, 2H), 2.28(m, 1H), 2.53(t, 2H, J=6.9), 2.63(t, 2H, J=6.0), 2.91(t, 2H, J=6.0), 3.75(s, 3H), 4.26(t, 2H, J=7.5), 4.67(dd, 1H, J=5.1 and 8.1), 8.03(s, 1H), 10.30(d, 1H, J=8.1) |
| I-267 | 1.34-1.56(m, 4H), 1.62-1.85(m, 4H), 2.05-2.17(m, 2H), 2.53(t, 2H, J=6.9), 2.63(t, 2H, =6.0), 2.91(t, 2H, J=6.0), 3.75(s, 3H), 4.26(t, 2H, J=7.5), 5.74(d, 1H, J=6.9), 7.20-7.39(m, 3H), 7.45-7.53(m, 2H), 8.03(s, 1H), 10.78(d, 1H, J=8.1) |
| I-271 | 1.02(d, 6H, J=7.2), 1.32-1.58(m, 4H), 1.60-1.96(m, 10H), 2.28(m, 1H), 2.46(t, 2H, J=6.9), 2.58-2.68(m, 2H), 2.89-3.00(m, 2H), 3.75(s, 3H), 4.10-4.24(m, 2H), 4.67(dd, 1H, J=5.1 and 8.1), 8.28(s, 1H), 10.35(d, 1H, J=8.1) |

TABLE 264

| Comp. No. | ¹H-NMR(CDCl₃/TMS) δ |
|---|---|
| I-272 | 1.32-1.58(m, 4H), 1.60-1.96(m, 10H), 2.46(t, 2H, J=6.9), 2.62(t, 2H, J=6.6), 2.89(t, 2H, J=6.6), 3.75(s, 3H), 4.10-4.24(m, 2H), 5.74(d, 1H, J=6.6), 7.60-7.41(m, 3H), 7.46-7.53(m, 2H), 8.27(s, 1H), 10.82(d, 1H, J=6.9) |
| I-273 | 1.14(t, 3H, J=7.5), 2.19(s, 3H), 2.65(q, 2H, J=7.5), 3.75(s, 3H), 5.43(br, 2H), 5.99(d, 1H, J=6.9), 6.96(dd, 1H, J=3.6 and 5.1), 6.98-7.09(m, 4H), 7.14(m, 1H), 7.24(dd, 1H, J=1.2 and 5.1), 8.38(s, 1H), 10.72(d, 1H, J=6.9) |
| I-278 | 1.34-1.80(m, 8H), 2.62(t-like, 2H), 3.06(t-like, 2H), 3.74(s, 3H), 5.32(d, 1H, J=15.9), 5.42(d, 1H, J=15.9), 5.72(d, 1H, J=6.9), 6.31-6.33(m, 2H), 7.28-7.39(m, 4H), 7.47-7.51(m, 2H), 8.29(s, 1H), 10.76(d, 1H, J=6.9) |
| I-279 | 1.28-1.74(m, 8H), 2.59(t-like, 2H), 2.72(t-like, 2H), 2.99(t-like, 2H), 3.76(s, 3H), 4.31(t-like, 2H), 5.77(d, 1H, J=6.9), 6.95-7.03(m, 2H), 7.14-7.21(m, 2H), 7.29-7.41(m, 3H), 7.49-7.53(m, 2H), 8.29(s, 1H), 10.91(d, 1H, J=6.9) |
| I-280 | 1.02(d, 3H, J=6.6), 1.03(d, 3H, J=6.6), 1.32-1.52(m, 4H), 1.60-1.76(m, 4H), 2.28(m, 1H), 2.63(t, 2H, J=6.0), 2.78(t, 2H, J=6.0), 3.74(t, 3H), 4.66(dd, 1H, J=5.1 and 8.1), 5.49(br, 2H), 7.07(d, 2H, J=6.6), 7.23-7.37(m, 3H), 8.37(s, 1H), 10.37(d, 1H, J=8.1) |
| I-281 | 1.32-1.52(m, 4H), 1.60-1.76(m, 4H), 2.63(t, 2H, J=6.0), 2.78(t, 2H, J=6.0), 3.74(t, 3H), 5.49(br, 2H), 5.72(d, 1H, J=6.3), 7.05(d, 2H, J=6.9), 7.21-7.39(m, 6H), 7.45-7.52(m, 2H), 8.37(s, 1H), 10.37(d, 1H, J=8.1) |
| I-282 | 1.02(d, 6H, J=6.9), 1.32-1.52(m, 4H), 1.60-1.76(m, 4H), 2.28(m, 1H), 2.62(t, 2H, J=6.0), 2.81(t, 2H, J=6.0), 3.75(s, 3H), 3.78(s, 3H), 4.66(dd, 1H, J=5.4 and 7.8), 5.42(br, 2H), 6.85(d, 2H, J=8.7), 7.03(d, 2H, J=8.7), 8.36(s, 1H), 10.39(d, 1H, J=8.1) |
| I-283 | 1.32-1.52(m, 4H), 1.60-1.76(m, 4H), 2.62(t, 2H, J=6.0), 2.81(t, 2H, J=6.0), 3.73(s, 3H), 3.77(s, 3H), 5.40(br, 2H), 5.72(d, 1H, J=6.6), 6.81-6.86(m, 2H), 7.01(d, 2H, J=8.7), 7.25-7.39(m, 3H), 7.46-7.52(m, 2H), 8.35(s, 1H), 10.80(d, 1H, J=8.1) |
| I-285 | 1.34-1.76(m, 8H), 2.64(t-like, 2H), 2.82(t-like, 2H), 3.74(s, 3H), 5.52(br, 2H), 5.73(d, 1H, J=6.6), 7.13(d, 2H, J=8.1), 7.27-7.56(m, 12H), 8.38(s, 1H), 10.79(d, 1H, J=6.6) |
| I-287 | 1.01(d, 3H, J=6.9), 1.02(d, 3H, J=6.9), 1.32-1.52(m, 4H), 1.60-1.76(m, 4H), 2.28(m, 1H), 2.64(t, 2H, J=6.0), 2.74(t, 2H, J=6.0), 3.74(s, 3H-1), 4.66(dd, 1H, J=5.1 and 8.1), 5.52(br, 2H), 7.19(d, 2H, J=8.1), 7.59(d, 2H, J=8.1), 8.40(s, 1H), 10.26(d, 1H, J=8.1) |

TABLE 264-continued

| Comp. No. | $^1$H-NMR(CDCl$_3$/TMS) δ |
|---|---|
| I-288 | 1.32-1.52(m, 4H), 1.60-1.76(m, 4H), 2.64(t, 2H, J=6.0), 2.74(t, 2H, J=6.0), 3.74(s, 3H), 5.53(br, 2H), 5.72(d, 1H, J=6.6), 7.17(d, 2H, J=6.9), 7.25-7.38(m, 3H), 7.48-7.52(m, 2H), 7.57(d, 2H, J=8.1), 8.38(s, 1H), 10.69(d, 1H, J=6.3) |

TABLE 265

| Comp. No. | $^1$H-NMR(CDCl$_3$/TMS) δ |
|---|---|
| I-289 | 1.02(d, 6H, J=6.9), 1.32-1.52(m, 4H), 1.60-1.76(m, 4H), 2.28(m, 1H), 2.62(t, 2H, J=6.0), 2.80(t, 2H, J=6.0), 3.74(s, 3H), 4.65(dd, 1H, J=5.1 and 8.1), 5.38(br, 2H), 5.94(s, 2H), 6.53-6.60(m, 2H), 6.75(d, 1H, J=8.1), 8.35(s, 1H), 10.33(d, 1H, J=8.1) |
| I-290 | 1.32-1.52(m, 4H), 1.60-1.76(m, 4H), 2.62(t, 2H, J=6.0), 2.80(t, 2H, J=6.0), 3.74(s, 3H), 5.38(br, 2H), 5.72(d, 1H, J=6.9), 5.93(s, 2H), 6.48-6.60(m, 2H), 6.75(d, 1H, J=8.1), 7.20-7.40(m, 3H), 7.48(d, 2H, J=6.9), 8.35(s, 1H), 10.77(d, 1H, J=8.1) |
| I-292 | 1.02(d, 6H, J=6.9), 1.32-1.52(m, 4H), 1.60-1.76(m, 4H), 2.26(m, 1H), 2.31(s, 3H), 2.62(t, 2H, J=6.0), 2.80(t, 2H, J=6.0), 3.74(s, 3H), 4.65(dd, 1H, J=5.1 and 8.1), 5.45(br, 2H), 6.96(d, 2H, J=8.1), 7.12(d, 2H, J=8.1), 8.36(s, 1H), 10.35(d, 1H, J=8.1) |
| I-293 | 1.32-1.52(m, 4H), 1.60-1.76(m, 4H), 2.31(s, 3H), 2.62(t, 2H, J=6.0), 2.80(t, 2H, J=6.0), 3.74(s, 3H), 5.45(br, 2H), 5.72(d, 1H, J=6.6), 6.94(d, 2H, J=8.1), 7.11(d, 2H, J=8.1), 7.26-7.39(m, 3H), 7.44-7.52(m, 2H), 8.35(s, 1H), 10.79(d, 1H, J=6.9) |
| I-294 | 1.02(d, 6H, J=6.9), 1.32-1.52(m, 4H), 1.60-1.76(m, 4H), 2.26(m, 1H), 2.63(t, 2H, J=6.0), 2.77(t, 2H, J=6.0), 3.74(s, 3H), 4.65(dd, 1H, J=5.1 and 8.1), 5.43(br, 2H), 7.02(d, 2H, J=8.1), 7.29(t, 2H, J=8.1), 8.38(s, 1H), 10.30(d, 1H, J=8.1) |
| I-295 | 1.32-1.52(m, 4H), 1.60-1.76(m, 4H), 2.63(t, 2H, J=6.0), 2.77(t, 2H, J=6.0), 3.74(s, 3H), 5.40(br, 2H), 5.73(d, 1H, 6.9), 7.00(d, 2H, J=8.1), 7.25-7.37(m, 5H), 7.45-7.50(m, 2H), 8.36(s, 1H), 10.73(d, 1H, J=6.6) |
| I-298 | 0.94(d, 3H, J=6.9), 0.95(d, 3H, J=6.9), 1.24-1.75(m, 8H1), 2.22(m, 1H), 2.62(t, 2H, J=6.0), 2.91(t-like, 2H), 3.74(s, 3H), 4.00(br, 2H), 5.75(d, 1H, J=6.6), 7.27-7.39(m, 3H), 7.47-7.51(m, 2H), 8.27(s, 1H), 10.90(d, 1H, J=6.6) |
| I-320 | 1.06-1.80(m, 19H), 2.01(s, 3H), 2.65(t, 2H, J=6.0), 2.94(t, 2H, J=6.0), 3.56(dd, 2H, J=5.7, 10.8), 3.97-4.18(m, 2H), 4.17(d, 2H, J=5.4), 4.27(m, 2H), 6.55(br, 1H), 8.27(s, 1H), 10.49(t, 1H, J=5.4) |
| I-330 | 1.00(t, 3H, J=7.5), 1.09(t, 3H, J=7.5), 1.14(s, 9H), 1.18(t, 3H, J=7.5), 1.39-1.75(m, 6H), 2.49(q, 2H, J=7.5), 2.62-2.72(m, 2H), 3.77-3.95(m, 4H), 3.96-4.20(m, 2H), 4.36(d, 1H, J=6.6), 4.99(m, 1H), 8.29(s, 1H), 10.75(d, 1H, J=6.6) |
| I-347 | 0.99(t, 3H, J=7.2), 1.40-1.52(m, 2H), 1.52(d, 3H, J=7.2), 1.63-1.74(m, 2H), 2.17(s, 3H), 2.41(s, 3H), 3.75(s, 3H), 4.10-4.15(m, 2H), 4.73(qd, 1H, J=7.2 and 7.2), 8.28(s, 1H), 10.34(d, 1H, J=7.2) |
| I-348 | DMSO-d6 0.94(t, 3H, J=7.2), 1.31-1.43(m, 2H), 1.51-1.61(m, 2H), 2.12(s, 3H), 2.42(s, 3H), 3.02(dd, 1H, J=7.2 and 13.8), 3.16(dd, 1H, J=5.7 and 13.8), 4.00-4.17(m, 2H), 4.71(m, 1H), 7.15-7.30(m, 5H), 8.09(s, 1H), 10.23(d, 1H, J=7.8), 12.91(br, 1H) |

TABLE 266

| Comp. No. | $^1$H-NMR(CDCl$_3$/TMS) δ |
|---|---|
| I-349 | DMSO-d6 0.92(d, 6H, J=6.6), 0.95(t, 3H, J=7.2), 1.33-1.45(m, 2H), 1.53-1.64(m, 2H), 2.15(s, 3H), 2.16(m, 1H), 2.44(s, 3H), 4.02-4.20(m, 2H), 4.40(dd, 1H, J=4.5 and 8.4), 8.12(s, 1H), 10.28(d, 1H, J=8.4), 12.75(br, 1H) |
| I-350 | DMSO-d6 0.88-0.97(m, 9H), 1.35-1.45(m, 2H), 1.53-1.69(m, 2H), 2.14(s, 3H), 2.44(s, 3H), 4.02-4.18(m, 2H), 4.47(m, 1H), 8.12(s, 1H), 10.16(d, 1H, J=7.8), 12.73(br, 1H) |
| I-351 | DMSO-d6 0.87-0.97 (m, 9H), 1.19 (m, 1H), 1.33-1.63 (m, 4H), 1.89 (m, 1H), 2.14 (s, 3H), 2.50 (s, 3H), 4.02-4-19 (m, 2H), 4.45 (dd, 1H, J=5.1, 8.4), 8.12 (s, 1H), 10.28 (d, 1H, J=8.4), 12.75 (brs, 1H) |

TABLE 266-continued

| Comp. No. | $^1$H-NMR(CDCl$_3$/TMS) δ |
|---|---|
| I-352 | DMSO-d6 0.94(t, 3H, J=7.2), 1.33-1.45(m, 2H), 1.53-1.63(m, 2H), 1.89-2.13(m, 2H), 2.04(s, 3H), 2.15(s, 3H), 2.44(s, 3H), 2.48(t, 2H, J=7.2), 4.04-4.18(m, 2H), 4.58(m, 1H), 8.12(s, 1H), 10.25(d, 1H, J=7.8), 12.90(br, 1H) |
| I-353 | DMSO-d6 0.94(t, 3H, J=7.2), 1.33-1.45(m, 2H), 1.53-1.63(m, 2H), 1.89-2.13(m, 2H), 2.04(s, 3H), 2.15(s, 3H), 2.44(s, 3H), 2.48(t, 2H, J=7.2), 4.04-4.18(m, 2H), 4.58(m, 1H), 8.12(s, 1H), 10.25(d, 1H, J=7.8), 12.90(br, 1H) |
| I-354 | DMSO-d6 0.94(t, 3H, J=7.2), 1.32-1.44(m, 2H), 1.53-1.63(m, 2H), 2.15(s, 3H), 2.44(s, 3H), 4.02(d, 2H, J=5.4), 4.11(t-like, 2H, 8.12(s, 1H), 10.12(t, 1H, J=5.4), 12.65(br, 1H) |
| I-359 | DMSO-d6 1.02-1.26(m, 4I), 1.37(d, 3H, J=7.2), 1.46-1.86(m, 7H), 2.15(s, 3H), 2.42(s, 3H), 3.90-4.16(m, 2H), 4.41(m, 1H), 8.12(s, 1H), 10.21(d, 1H, J=6.9) |
| I-360 | DMSO-d6 0.96-1.20(m, 4H), 1.42-1.80(m, 7H), 2.14(s, 3H), 2.41(s, 3H), 3.14-3.34(m, 2H), 3.90-4.07(m, 2H), 4.76(m, 1H), 6.88(m, 1H), 7.03(m, 1H), 7.10(d, 1H, J=2.7), 7.31(d, 1H, J=8.1), 7.48(d, 1H, J=7.8), 8.12(s, 1H), 10.27(d, 1H, J=8.1), 10.85(Br, 1H) |
| I-361 | DMSO-d6 1.00-1.32(m, 4H), 1.42-1.82(m, 7H), 2.14(s, 3H), 2.41(s, 3H), 2.90(dd, 1H, J=7.2 and 13.8), 3.01(dd, 1H, J=5.4 and 13.8), 4.02(br, 2H), 4.60(m, 1H), 6.60(d, 2H, J=8.4), 6.93(d, 2H, 8.4), 8.09(s, 1H), 9.20(br s, 1H), 10.20(d, 1H, J=7.8) |
| I-362 | DMSO-d6 1.02-1.32(m, 4H), 1.42-1.85(m, 7H), 2.13(s, 3H), 2.40(s, 3H), 3.01(dd, 1H, J=7.5 and 13.5), 3.16(dd, 1H, J=5.4 and 13.5), 3.91-4.12(m, 2H), 4.67(m, 1H), 7.12-7.26(m, 5H), 8.09(s, 1H), 10.23(d, 1H, J=7.5) |
| I-365 | DMSO-d6 0.92(d, 6H, J=6.9), 2.15(s, 3H), 2.16(m, 1H), 2.47-2.58(m, 6H), 3.57(t, 4H, J=4.2), 4.26(br, 1H), 4.41(dd, 1H, J=4.8 and 8.4), 8.14(s,1H), 10.23(d, 1H, J=8.7) |
| I-366 | DMSO-d6 0.92(d, 6H, J=6.9), 2.15(s, 3H), 2.16(m, 1H), 2.47-2.58(m, 6H), 3.57(t, 4H, J=4.2), 4.26(br, 1H), 4.41(dd, 1H, J=4.8 and 8.4), 8.14(s,1H), 10.23(d, 1H, J=8.7) |

TABLE 267

| Comp. No. | $^1$H-NMR(CDCl$_3$/TMS) δ |
|---|---|
| I-367 | DMSO-d6 0.85-1.97(m, 20H), 2.15(s, 3H), 2.42(s, 3H), 4.02(br, 2H), 4.44(dd, 1H, J=4.8 and 8.4), 8.12(s, 1H), 10.26(d, 1H, J=8.7), 12.72(br, 1H) |
| I-368 | DMSO-d6 1.00-1.29(m, 4H), 1.48-1.88(m, 7H), 2.15(s, 3H), 2.42(s, 3H), 3.93-4.10(m, 4H), 8.13(s, 1H), 10.10(t, 1H, J=5.4), 12.66(br s, 1H) |
| I-369 | DMSO-d6 1.00-1.28(m, 4H), 1.47-1.89(m, 7H), 2.15(s, 3H), 2.42(s, 3H), 3.67(dd, 1H, J=3.6 and 10.8), 3.82(dd, 1H, J=3.9 and 10.5), 4.02(br, 2H), 4.70(dd, 1H, J=7.8 and 8.4), 8.28(s, 1H), 10.40(d, 1H, J=7.8) |
| I-370 | DMSO-d6 0.85-1.32(m, 10H), 1.46-1.85(m, 10H), 2.15(s, 3H), 2.41(s, 3H), 4.04(br, 2H), 4.46(m, 1H), 8.13(s, 1H), 10.15(d, 1H, J=7.8), 12.72(br, 1H) |
| I-371 | DMSO-d6 1.00-1.32(m, 4H), 1.46-2.20(m, 11H), 2.03(s, 3H), 2.14(s, 3H), 2.47(s, 3H), 3.94-4.30(m, 2H), 4.56(m, 1H), 8.12(s, 1H), 10.23(d, 1H, J=7.5), 12.90(br, 1H) |
| I-372 | DMSO-d6 0.89-0.95(dd, 6H, J=2.7 and 6.9), 2.16(s, 3H), 2.31(s, 3H), 4.40(dd, 1H, J=4.8 and 8.4), 5.38-5.56(m, 2H), 6.99-7.15(m, 4H), 8.22(s, 1H), 10.18(d, 1h, J=8.1) |
| I-373 | DMS-d6 0.84-0.96(m, 9H), 1.22-1.42(m, 8H), 1.54-1.66(m, 2H), 2.12-2.24(m, 4H), 2.43(s, 3H), 4.00-4.18(m, 2H), 4.40(dd, 1H, J=4.8 and 8.4), 8.12(s, 1H), 10.27(d, 1H, J=8.4) |
| I-374 | DMSO-d6 0.91(d, 6H, J=6.9), 0.96(d, 6H, J=6.6), 1.44-1.55(m, 2H), 1.71(m, 1H), 2.08-2.24(m, 4H), 2.43(s, 3H), 4.00-4.25(m, 2H), 4.40(m, 1H), 8.12(s, 1H), 10.27(d, 1H, J=8.1) |
| I-375 | 0.98-1.27(m, 4H), 1.55-1.88(m, 8H), 1.88-2.10(m, 2H), 2.06 and 2.09(s, 3H), 2.28(m, 1H), 2.31 and 2.33(s, 3H), 3.45(m, 1H), 3.55 and 3.76(s, 3H), 3.72-4.18(m, 2H), 4.60-4.78(m, 2H), 7.37 and 7.46(s, 1H) |
| I-376 | DMSO-d6 0.94 (t, 3H, J=7.2), 1.32-1.45 (m, 2H), 1.47 (s, 6H), 1.52-1.63 (m, 2H), 2.14 (s, 3H), 2.43 (s, 3H), 4.09 (m, 2H), 8.08 (s, 1H), 10.23 (s, 1H), 12.37 (brs, 1H) |
| I-377 | DMSO-d6 0.95 (t, 3H, J=7.2 Hz), 1.22-2.06 (m, 15H), 2.14 (s, 3H), 2.44 (s, 3H), 4.09-4.14 (m, 2H), 8.07 (s, 1H), 10.27 (s, 1H) |
| I-378 | DMSO-d6 0.93(t, 3H, J=7.2), 1.30-1.42(m, 2H), 1.49-1.60(m, 2H), 2.13(s, 3H), 2.42(s, 3H), 3.14-3.31(m, 2), 4.06(t-like, 2H), 4.75(q-like, 1H), 6.91(td, 1H, J=8.1 and 1.2), 7.04(td, 1H, J=8.1 and 1.2), 7.10(d, 1H, J=2.4), 7.31(d, 1H, J=8.1), 7.50(d, 1H, J=8.1), 8.11(s, 1H), 10.86(d, 1H), 12.82(br, 1H) |
| I-381 | DMSO-d6 0.95(t, 3H, J=7.2), 1.33-1.45(m, 2H), 1.53-1.63(m, 2H), 2.14(s, 3H), 2.44(s, 3H), 3.68(dd, 1H, J=3.6 and 10.5), 3.83(dd, 1H, J=3.6 and 10.5), 4.10(t-like, 2H), 4.47(m, 1H), 8.12(s, 1H), 10.32(d, 1H, J=7.5), 12.57(br, 1H) |

TABLE 268

| Comp. No. | $^1$H-NMR(CDCl$_3$/TMS) δ |
|---|---|
| I-382 | DMSO-d6 0.94(t, 3H, J=7.2), 1.31-1.43(m, 2H), 1.51-1.61(m, 2H), 2.13(s, 3H), 2.42(s, 3H), 2.90(dd, 1H, J=6.6 and 13.8), 3.05(dd, 1H, J=5.1 and 13.8), 4.02-4.17(m, 2H), 4.62(q-like, 1H), 6.62(d, 2H, J=8.4), 6.95(d, 2H, J=8.4), 8.09(s, 1H), 9.23(br, 1H), 10.18(d, 1H, J=7.5), 12.79(br, 1H) |
| I-383 | DMSO-d6 1.00-1.32(m, 4H), 1.46-2.20(m, 11H), 2.03(s, 3H), 2.15(s, 3H), 2.47(s, 3H), 3.94-4.30(m, 2H), 4.56(m, 1H), 8.12(s, 1H), 10.23(d, 1H, J=7.5), 12.80(br, 1H) |
| I-384 | DMSO-d6 1.02-1.32(m, 4H), 1.42-1.85(m, 7H), 2.13(s, 3H), 2.40(s, 3H), 3.01(dd, 1H, J=7.5 and 13.5), 3.16(dd, 1H, J=5.4 and 13.5), 3.91-4.12(m, 2H), 4.67(m, 1H), 7.12-7.26(m, 5H), 8.09(s, 1H), 10.23(d, 1H, J=7.5), 12.8(br, 1H) |
| I-385 | DMSO-d6 0.90-0.98(m, 9H), 1.03(t, 3H, J=7.5), 1.12(t, 3H, 7.5), 1.36-1.68(m, 6H), 2.18(m, 1H), 2.40-2.50(m, 2H), 2.66-2.73(m, 2H), 3.94-4.14(m, 2H), 4.00(q, 1H, J=8.4 and 4.8), 8.17(s, 1H), 10.27(d, 1H, J=8.7), 12.70(br, 1H) |
| I-387 | 0.93(t, 3H, J=7.2), 1.22-1.78(m, 12H), 2.63(brt, 2H), 2.89(brt, 2H), 3.03(dd, 1H, J=7.8 and 13.8), 3.15(dd, 1H, J=5.4 and 13.8), 4.04(brt, 2H), 4.71(m, 1H), 7.16-7.29(m, 5H), 8.08(s, 1H), 10.23(d, 1H, J=7.5), 12.89(brs, 1H) |
| I-388 | 1.06(d, 6H, J=6.9), 1.39-2.39(m, 15H), 2.59-2.63(m, 2H), 2.81-2.85(m, 2H), 3.13-3.24(m, 4H), 3.66-3.76(m, 2H), 4.59(dd, 1H, J=5.4, 6.6), 4.72-4.78(m, 2H), 8.27(s, 1H), 12.12(m, 1H) |
| I-389 | 1.05(d, 6H, J=5.7), 1.26-3.18(m, 25H), 4.57(dd, 1H, J=8.1, 5.4), 4.61-4.69(m, 2H), 8.25(s, 1H), 10.18(d, 1H, J=8.1) |
| I-390 | 1.24-1.86(m, 14H), 2.61-2.68(m, 2H), 2.95-3.05(m, 8H), 4.12-4.14(m, 2H), 4.46-4.68(m, 2H), 8.28(s, 1H), 10.13(s, 1H) |
| I-391 | 1.36-2.17(m, 14H), 1.67(s, 6H), 2.64(t, 2H, J=5.4), 2.87-3.38(m, 8H), 4.61-4.82(m, 2H), 8.31(s, 1H), 10.40(s, 1H) |
| I-393 | DMSO-d6 0.88-0.97(m, 9H), 1.33-1.45(m, 2H), 1.53-1.69(m, 2H), 2.14(s, 3H), 2.44(s, 3H), 4.02-4.18(m, 2H), 4.47(m, 1H), 8.12(s, 1H), 10.17(d, 1H, J=7.8), 12.73(br, 1H) |
| I-394 | DMSO-d6 0.94(t, 3H, J=7.2), 1.31-1.42(m, 2H), 1.51-1.61(m, 2H), 2.13(s, 3H), 2.42(s, 3H), 3.02(dd, 1H, J=7.2 and 13.8), 3.16(dd, 1H, J=5.7 and 13.8), 4.00-4.17(m, 2H), 4.71(m, 1H), 7.15-7.30(m, 5H), 8.09(s, 1H), 10.22(d, 1H, J=7.8), 12.91(br, 1H) |
| I-395 | 0.97(t, 3H, J=7.2), 1.05(d, 3H, J=6.9), 1.07(d, 3H, J=6.9), 1.42(m, 2H), 1.56-1.9(m, 6H), 2.35(m, 1H), 2.51(t, 2H, J=6.0), 2.67(t, 2H, J=6.0), 3.94-3.99(m, 2H), 4.60(dd, 1H, J=5.1 and 8.1), 10.88(d, 1H, J=7.5) |
| I-396 | 1.03-1.80(17H, m), 2.04(s, 3H), 2.32(m, 1H), 2.33(s, 3H), 3.75(s, 3H), 3.95(brs, 1H), 4.58(dd, 1H, J=5.1 and 8.1), 10.94(d, 1H, J=8.1), 15.59 (s,1H) |

TABLE 269

| Comp. No. | $^1$H-NMR(CDCl$_3$/TMS) δ |
|---|---|
| I-398 | 1.05(d, 6H, J=6.0), 1.22-3.40(m, 22H), 3.78-4.28(m, 3H), 4.45-4.69(m, 2H), 4.70(m, 1H), 8.24(s, 1H), 10.30(d, 1H, J=7.8) |
| I-399 | 1.05(d, 6H, J=6.0), 1.22-3.40(m, 22H), 3.78-4.28(m, 3H), 4.45-4.69(m, 2H), 4.70(m, 1H), 8.24(s, 1H), 10.30(d, 1H, J=7.8) |
| I-400 | 1.22-2.37(m, 24H), 2.56-2.67(m, 2H), 3.14-3.38(m, 3H), 3.75-4.02(m, 2H), 4.68-4.99(m, 2H), 8.33(s, 1H), 10.41(s, 1H) |
| I-401 | 0.78-1.97(m, 17H), 0.99(s, 9H), 2.06-2.41(m, 2H), 2.58-2.69(m, 2H), 2.89-3.35(m, 5H), 3.81-4.43(m, 2H), 4.79(m, 1H), 8.28(s, 1H), 10.27(s, 1H) |
| I-406 | DMSO-d6 0.91(d, 6H, J=6.9), 1.01(t, 3H, 7.5), 1.07-1.32(m, 9H), 1.42-1.84(m, 9H), 2.17(m, 1H), 2.72(t, 2H, 7.7), 4.00(br, 2H), 4.39(dd, 1H, J=4.8 and 8.4), 8.15(s, 1H), 10.25(d, 1H, J=8.1), 12.35(br, 1H) |
| I-411 | DMSO-d6 0.94(t, 3H, J=7.8), 1.03(t, 3H, J=7.5), 1.12(t, 3H, J=7.5), 1.30-1.79(m, 16H), 1.97-2.10(m, 2H), 2.65-2.75(m, 2H), 4.00-4.11(m, 2H), 8.12(s, 1H), 10.27(br, 1H), 12.16(br, 1H) |
| I-412 | DMSO-d6 1.00-1.44(m, 13H), 1.44-2.04(m, 14H), 2.24-2.39(m, 2H), 2.52(q, 2H, J=7.5), 2.70(t, 2H, J=8.4), 4.03(br, 2H), 8.34(s, 1H), 10.76(br, 1H) |
| I-413 | DMSO-d6 1.00-1.48(m, 8H), 1.48-1.88(m, 11H), 2.14(s, 3H), 2.42(s, 3H), 4.02(br, 2H), 8.08(s, 1H), 10.26(br, 1H) |
| I-414 | 1.09(d, 6H, J=6.6), 1.08-2.73(m, 15H), 2.94-3.23(m, 2H), 3.69-3.98(m, 3H), 4.23(m, 1H), 4.45(m, 1H), 4.60(d, 1H, J=13.5), 8.30(s, 1H), 10.60(d, 1H, J=3.9) |
| I-415 | 1.14-2.25(m, 12H), 1.68(s, 6H), 2.64-2.69(m, 2H), 2.95-3.24(m, 2H), 3.71(dd, 1H, J=5.4, 13.8), 3.84-3.95(m, 2H), 4.24(m, 1H), 4.57(dd, 1H, J=2.7, 13.8), 8.31(s, 1H), 10.68(s, 1H) |
| I-416 | 1.15-2.39(m, 22H), 2.58-2.76(m, 2H), 2.97-3.23(m, 2H), 3.69-3.96(m, 3H), 4.24(m, 1H), 4.59(d, 1H, J=15.6), 8.30(s, 1H), 10.66(s, 1H) |

TABLE 269-continued

| Comp. No. | ¹H-NMR(CDCl₃/TMS) δ |
|---|---|
| I-417 | 1.05-2.18(m, 12H), 1.14(s, 9H), 2.64-3.21(m, 4H), 3.69-3.90(m, 3H), 4.28(m, 1H), 4.50(d, 1H, J=7.8), 4.63(d, 1H, J=14.4), 8.29(s, 1H), 10.66(t, 1H, J=7.2) |
| I-420 | DMSO-d6 0.94(t, 3H, J=7.2), 1.32-1.45(m, 2H), 1.51-1.65(m, 2H), 2.13(s, 3H), 2.43(s, 3H), 4.08-4.13(m 2H), 5.48(d, 1H, J=7.2) 7.30-7.43(m 5H), 8.10(s, 1H), 10.74(d, 1H, J=7.2), 13.08(brs, 1H) |
| I-427 | DMSO-d6 0.94-0.98(m, 9H), 1.34-1.88(m, 10H), 2.17(m, 1H), 2.66-2.72(m, 2H), 2.93-3.03(m 2H), 4.04-4.34(m 2H), 4.40(dd 1H, J=4.5 and 8.4), 8.10(s, 1H), 10.27(d, 1H, J=8.4), 12.79(br, 1H) |
| I-428 | DMSO-d6 0.93(t, 3H, J=7.2), 1.32-1.86(m, 8H), 2.68-2.71(m, 2H), 2.98-3.01(m, 2H), 4.18(br 2H), 4.10-4.28(m 2H), 5.48(d, 1H, J=6.9) 7.30-7.45(m, 5H), 8.08(s, 1H), 10.74(d, 1H, J=6.9) |

TABLE 270

| Comp. No. | ¹H-NMR(CDCl₃/TMS) δ |
|---|---|
| I-431 | DMSO-d6 0.94(t, 3H, J=7.5), 1.03(t, 3H, J=7.5), 1.19(t, 3H, J=7.5), 1.26-1.68(m, 8H1), 2.64-2.74(m, 2H), 4.01-4.07(m, 2H), 5.48(d, 1H, J=6.9), 7.25-7.42(m, 5H), 8.15(s, 1H), 10.73(d, 1H, J=6.9), 13.00(br, 1H) |
| I-433 | DMSO-d6 0.84-0.98(m, 9H), 1.31-1.46(m, 2H), 1.51-1.72(m, 4H), 1.73-1.85(m, 2H), 2.17(m, 1H), 2.57(t, 2H, J=5.7), 2.82(t, 2H, J=5.7), 3.94-4.13(m, 2H), 4.40(dd, 1H, J=4.8 and 8.4), 8.04(s, 1H), 10.28(d, 1H, J=8.4), 12.76(br, 1H) |
| I-434 | DMSO-d6 0.89-0.92 (m, 6H), 1.00-1.88 (m, 15H), 2.16 (m, 1H), 2.58 (t, 2H, J=6.0 Hz), 2.79 (t, 2H, J=6.0 Hz), 3.86-4.07 (m, 2H), 4.39 (m, 1H), 8.05 (s, 1H), 10.27 (d, 1H, J=8.4 Hz), 12.75 (br,1H) |
| I-435 | DMSO-d6: 0.87-1.00 (m, 9H), 1.32-1.44 (m, 2H), 1.52-1.81 (m, 9H), 2.57 (t, 2H, J=6.0 Hz), 2.82 (t, 2H, J=6.0 Hz), 3.94-4.10 (m, 2H), 4.47 (m, 1H), 8.03 (s, 1H), 10.17 (d, 1H, J=7.8 Hz), 12.73 (br,1H) |
| I-436 | DMSO-d6: 0.87-0.92 (m, 6H), 1.00-1.24 (m, 6H), 1.46-185 (m, 12H), 2.58 (t, 2H, J=6.0 Hz), 2.78 (t, 2H, J=6.0 Hz), 3.84-4.07 (m, 2H), 4.47 (m, 1H), 8.04 (s, 1H), 10.16 (d, 1H, J=7.8 Hz), 12.76 (br, 1H) |
| I-437 | 1.08(d, 6H, J=6.9), 1.37-1.80(m, 8H), 2.41(m, 1H), 2.65(t, 2H, J=6.0), 2.87(t, 2H, J=6.3), 4.50(dd, 1H, J=5.4 and 7.2), 4.84(br, 2H), 4.95(d, 1H, J=17.1), 5.22(d, 1H, J=10.5), 5.97(m, 1H), 8.33(s, 1H), 10.53(d, 1H, J=7.5) |
| I-439 | DMSO-d6 0.93 (t, 3H, J=7.5), 1.38 (m, 1H), 1.58-1.87 (m, 5H), 2.56 (t, 2H, J=6.0), 2.80 (t, 2H, J=6.0), 3.02 (dd, 1H, J=7.2 and 13.8), 3.16 (dd, 1H, J=7.2 and 13.8), 3.91-4.08 (m, 4H), 4.70 (dd, 1H, J=6.9 and 12.6), 7.13-7.28 (m, 5H), 8.01 (s, 1H), 10.22 (d, 1H, J=7.5), 12.84 (br, 1H) |
| I-440 | DMSO-d6: 0.98-1.22 (m, 6H), 1.40-1.82 (m, 9H), 2.57 (t, 2H, J=6.0 Hz), 2.77 (t, 2H, J=6.0 Hz), 2.98-3.19 (m,2H), 3.85-4.06 (m, 2H), 4.70 (m, 1H), 7.13-7.26 (m, 5H), 8.14 (s, 1H), 10.48 (d, 1H, J=7.8 Hz), 12.82 (br, 1H) |
| I-441 | DMSO-d6: 0.86-0.98 (m, 9H), 1.12-1.94 (m, 11H), 2.57 (t, 2H, J=6.0 Hz), 2.82 (t, 2H, J=6.0 Hz), 3.94-4.11 (m, 2H), 4.45 (m, 1H), 8.03 (s, 1H), 10.28 (d, 1H, J=8.7 Hz), 12.74 (s, 1H) |
| I-442 | DMSO-d6 0.88-0.92 (m, 6H), 1.00-1.93 (m, 18H), 2.58 (t, 2H, J=6.0 Hz), 2.79 (t, 2H, J=6.0 Hz), 3.84-4.07 (m, 2H), 4.44 (m, 1H), 8.04 (s, 1H), 10.27 (d, 1H, J=8.1 Hz), 12.82 (br,1H) |
| I-444 | 1.02(d, 6H, J=6.9), 1.30-1.79(m, 8H), 2.42(m, 1H), 2.66(t, 2H, J=6.0), 3.05(t, 2H, J=6 3) 3 82-4 03(m 4H), 4 39(br 2H), 4 51(dd 1H, J=5.4 and 7.5), 5.19(t, 1H, J=4.5), 8.31(s, 1H), 10.49(d, 1H, J=7.5) |
| I-445 | DMSO-d6 0.91(d, 6H, J=6.6), 1.00-1.23(m, 6H), 1.48-1.84(m, 11H), 2.14(m, 1H), 2.65-2.75(m, 2H), 2.95-3.07(m, 2H), 4.09(br, 2H), 4.37(dd, 1H, J=5.4 and 8.4), 8.26(s, 1H), 10.27(d, 1H, J=8.4), 12.80(br, 1H) |

TABLE 271

| Comp. No. | ¹H-NMR(CDCl₃/TMS) δ |
|---|---|
| I-446 | DMSO-d6 0.91-1.25(m, 5H), 1.40-1.82(m, 12H), 2.65-2.75(m, 2H), 2.93-3.07(m, 2H), 4.15(br, 2H), 5.44(d, 1H, J=8.4), 7.30-7.44(m, 5H), 8.08(s, 1H), 10.71(d, 1H, J=8.4), 13.05(br, 1H) |
| I-447 | DMSO-d6 0.93(t, 3H, J=8.4), 1.17-1.90(m, 18H), 1.98-2.03(m, 2H), 2.65-2.76(m, 2H), 2.98-3.05(m, 2H), 4.18(br s, 2H), 8.05(s, 1H), 10.26(br s, 1H), 12.18(br, 1H) |

TABLE 271-continued

| Comp. No. | $^1$H-NMR(CDCl$_3$/TMS) δ |
|---|---|
| I-448 | DMSO-d6 0.99-1.85(m, 25H), 1.96-2.10(m, 2H), 2.65-2.75(m, 2H), 2.95-3.06(m, 2H), 4.15(br, 2H), 8.05(s, 1H), 10.26(br s, 1H), 12.14(br, 1H) |
| I-449 | DMSO-d6 0.92(t, 3H, J=7.2), 1.24-1.82(m, 16H), 2.73(br, 2H), 2.98(br, 2H), 4.09(br, 2H), 5.49(d, 1H, J=6.9), 7.31-7.42(m, 5H), 8.12(s, 1H), 10.75(d, 1H, J=6.9), 13.10(br, 1H) |
| I-450 | DMSO-d6 0.91-0.95(m, 9H), 1.12-1.84(m, 16H), 2.17(m, 1H), 2.74(br, 2H), 2.99(br, 2H), 4.10(br, 2H), 4.40(dd, 1H, J=4.8 and 8.1), 8.13(s, 1H), 10.29(d, 1H, J=8.1), 12.77(br, 1H) |
| I-451 | DMSO-d6 1.00-1.20(m, 9H), 1.45-1.82(m, 5H), 2.17(s, 3H), 2.70-2.84(m, 2H), 4.01(br, 2H), 5.47(d, 1H, J=6.6), 7.29-7.39(m, 5H), 8.12(s, 1H), 10.69(d, 1H, J=8.4), 13.07(br) |
| I-452 | DMSO-d6 0.98-1.25(m, 12H), 1.40-1.83(m, 7H), 2.45-2.60(m, 2H), 2.65-2.79(m, 2H), 4.00(br, 2H), 5.47(d, 1H, J=6.9), 7.32-7.43(m, 5H), 8.15(s, 1H), 10.69(d, 1H, J=6.9), 13.09(br s, 1H) |
| I-453 | DMSO-d6 0.95(t, 3H, J=7.5), 1.37-1.50(m, 2H), 1.51-1.75(m, 7H), 1.78-1.90(m, 2H), 2.66-2.69(m, 2H), 2.91-2.95(m, 2H), 4.17(br, 2H), 5.73(d, 1H, J=6.6), 7.26-7.40(m, 3H), 7.48-7.54(m, 2H), 8.25(s, 1H), 11.00(d, 1H, J=6.6) |
| I-457 | DMSO-d6 0.93(t, 3H, J=7.5), 1.30-1.84(m, 14I), 2.56(t, 2H, J=6.0), 2.80(t, 2H, J=6.0), 4.01(t, 2H, J=7.8), 8.00(s, 1H), 10.24(s, 1H), 12.42(br, 1H) |
| I-458 | DMSO-d6 0.98-1.22(m, 4H), 1.40-1.86(m, 18H), 2.57(t, 2H, J=6.0), 2.78(t, 2H, J=6.0), 3.92(br, 2H), 8.01(s, 1H), 10.22(s, 1H), 12.48(br, 1H) |
| I-459 | DMSO-d6 0.93 (t, 3H, J=7.2 Hz), 1.32-1.44 (m, 2H), 1.50-1.70 (m, 4H), 1.72-1.84 (m, 2H), 2.56 (t, 2H, J=6.0 Hz), 2.82 (t, 2H, J=6.0 Hz), 4.00-4.05 (m, 2H), 5.48 (d, 1H, J=6.9 Hz), 7.25-7.42 (m, 5H), 8.02 (s, 1H), 10.75 (d, 1H, J=7.2 Hz) |
| I-460 | DMSO-d6 1.00-1.20 (m, 6H), 1.46-1.85 (m, 9H), 2.57 (t, 2H, J=6.3 Hz), 2.78 (t, 2H, J=6.3 Hz), 3.88-4.04 (m, 2H), 5.47 (d, 1H, J=6.9 Hz), 7.30-7.42 (m, 5H), 8.02 (s, 1H), 10.72 (d, 1H, J=6.9 Hz) |
| I-464 | DMSO-d6 2.14(s, 3H), 2.31(s, 3H), 5.45-5.51(m, 3H), 7.14(d, 4H, J=8.4), 7.26-7.45(m, 5H), 8.20(s, 1H), 10.67(d, 1H, J=6.6) |
| I-466 | DMSO-d6 1.14-1.48(m, 4H), 1.48-1.80(m, 6H), 2.15(s, 3H), 2.31(s, 3H), 5.43(br s, 2H), 7.18(d, 4H, J=7.5), 8.18(s, 1H), 10.17(s, 1H), 12.01(br, 1H) |

TABLE 272

| Comp. No. | $^1$H-NMR(CDCl$_3$/TMS) δ |
|---|---|
| I-467 | DMSO-d6 0.89(d, 3H, J=6.6), 0.90(d, 3H, J=6.9), 1.05(t, 3H, J=7.5), 2.10-2.22(m, 4H), 2.58-2.76(m, 2H), 4.00(dd, 1H, J=5.1 and 8.1), 5.30-5.60(m, 2H), 7.12-7.22(m, 4H), 8.23(s, 1H), 10.16(d, 1H, J=8.1), 12.71(br, 1H) |
| I-468 | DMSO-d6 0.84-1.00(m, 9H), 1.13(t, 3H, J=7.5), 1.35-1.52(m, 2H), 2.16(m, 1H), 2.50-2.68(m, 4H), 4.38(dd, 1H, J=5.4 and 8.1), 5.30-5.60(m, 2H), 7.12-7.22(m, 4H), 8.27(s, 1H), 10.15(d, 1H, J=8.1), 12.77(br, 1H) |
| I-469 | DMSO-d6 0.91-0.96(m, 9H), 1.30-1.42(m, 2H), 1.57-1.68(m, 2H), 2.04-2.22(m, 3H), 2.79(t, 2H, J=7.5), 3.08(t, 2H, J=7.5), 3.90-4.08(m, 2H), 4.40(dd, 1H, J=4.8 and 8.4), 8.22(s, 1H), 10.29(d, 1H, J=8.4), 12.74(br, 1H) |
| I-470 | DMSO-d6 0.94 (t, 3H, J=7.2 Hz), 1.20-1.8 6 (m, 16I), 2.00-2.10 (m, 2H), 2.57 (t, 2H, J=6.0 Hz), 2.82 (t, 2H, J=6.0 Hz), 4.01-4.08 (m, 2H), 7.99 (s, 1H), 10.27 (s, 1H), 12.17 (br, 1H) |
| I-471 | DMSO-d6 1.00-1.88 (m, 23H), 1.98-2.10 (m, 2H), 2.16-2.20 (m, 2H), 2.58 (t, 2H, J=6.0 Hz), 2.77 (t, 2H, J=6.0 Hz), 3.90-4.04 (m, 2H), 8.00 (s, 1H), 10.26(s, 1H), 12.20 (br, 1H) |
| I-472 | DMSO-d6 0.93(t, 3H, J=7.5), 1.38(m, 1H), 1.58-1.87(m, 9H), 2.56(t, 2H, J=6.0), 2.81(t, 2H, J=6.0), 4.01(t, 2H, J=8.7), 6.77(d, 2H, J=8.7), 7.19(d, 2H, J=8.7), 8.01(s, 1H), 10.57(d, 1H, J=7.5), 12.84(br, 1H) |
| I-473 | DMSO-d6 0.96(m, 4H), 1.44-1.86(m, 10H), 2.56(t, 2H, J=6.0), 2.78(t, 2H, J=6.0), 3.87-4.10(m, 2H), 5.32(d, 1H, J=6.9), 6.77(d, 2H, J=8.4), 7.18(d, 2H, J=8.4), 8.02(s, 1H), 10.54(d, 1H, J=6.9), 12.86(br, 1H) |
| I-477 | DMSO-d6 0.94(t, 3H, J=7.5), 1.03(t, 3H, J=7.5), 1.12(t, 3H, J=7.5), 1.33-1.66(m, 6H), 1.47(s, 6H), 2.42-2.55(m, 2H), 2.65-2.74(m, 2H), 3.99-4.08(m, 2H), 8.14(s, 1H), 10.23(s, 1H), 12.40(brs, 1H) |
| I-478 | DMSO-d6 1.01(t, 3H, J=7,2), 1.06-1.21(m, 4H), 1.12(t, 3H, J=7.5), 1.40-1.83(m, 9H), 1.47(s, 6H), 2.45-2.56(m, 2H), 2.67-2.77(m, 2H), 3.96(br, 2H), 8.14(s, 1H), 10.20(s, 1H), 12.42(brs, 1H) |
| I-479 | DMSO-d6 0.82-0.98(m, 9H), 1.30-1.48(m, 2H), 1.50-1.72(m, 4H), 1.72-1.86(m, 2H), 2.16(m, 1H), 2.57(t, 2H, J=6.0), 2.82(t, 2H, J=6.0), 3.91-4.14(m, 2H), 4.40(dd, 1H, J=4.8 and 8.4), 8.03(s, 1H), 10.27(d, 1H, J=8.4), 12.70(br, 1H) |
| I-480 | DMSO-d6 0.91(d, 6H, J=6.9), 1.00-1.24(m, 6H), 1.42-1.86(m, 8H), 2.16(m, 1H), 2.58(t, 2H, J=6.0), 2.79(t, 2H, J=6.0), 3.82-4.08(m, 2H), 4.40(dd, 1H, J=4.8 and 8.4), 8.05(s, 1H), 10.27(d, 1H, J=8.4), 12.77(br, 1H) |

TABLE 272-continued

| Comp. No. | $^1$H-NMR(CDCl$_3$/TMS) δ |
|---|---|
| I-483 | DMSO-d6 0.95(t, 3H, J=7.5), 0.99(s, 9H), 1.03(t, 3H, J=7.5), 1.12(t, 3H, J=7.5), 1.34-1.67(m, 6H), 2.45-2.56(m, 2H), 2.64-2.76(m, 2H), 3.93-4.17(m, 2H), 4.27(d, 1H, J=8.7), 8.16(s, 1H), 10.41(d, 1H, J=8.7), 12.66(brs, 1H) |

TABLE 273

| Comp. No. | $^1$H-NMR(CDCl$_3$/TMS) δ |
|---|---|
| I-484 | DMSO-d6 0.97-1.22(m, 4H), 0.99(s, 9H), 1.01(t, 3H, J=7,5), 1.15(t, 3H, J=7.5), 1.42-1.83(m, 9H), 2.47-2.56(m, 2H), 2.68-2.77(m, 2H), 3.98(br, 2H), 4.26(d, 1H, J=8.1), 8.17(s, 1H), 10.39(d, 1H, J=8.1), 12.65(br, 1H) |
| I-485 | DMSO-d6 0.93(t, 3H, J=7.2 Hz), 1.18(t, 3H, J=7.5 Hz), 1.35-1.50(m, 2H), 2.46-2.68(m, 4H), 5.45-5.50(m, 2H), 5.48(d, 1H, J=6.9 Hz), 7.12-7.44(m, 9H), 8.25(s, 1H), 10.63(d, 1H, J=6.9 Hz), 13.09(br, 1H) |
| I-486 | DMSO-d6 1.04(t, 3H, J=7.5 Hz), 2.18(s, 3H), 2.64(dd, 2H, J=7.2 and 14.7 Hz), 5.35-5.53(m, 2H), 5.49(d, 1H, J=6.6 Hz), 7.05-7.45(m, 9H), 8.22(s, 1H), 10.65(d, 1H, J=6.6 Hz), 13.13(br, 1H) |
| I-487 | DMSO-d6 2.16(s, 3H), 2.30(s, 3H), 5.48(d, 1H, J=6.6), 5.57(br, 2H), 7.32(d, 2H, J=8.1), 7.36-7.42(m, 4H), 7.72(d, 2H, J=8.1), 8.23(s, 1H), 10.61(d, 1H, J=6.6), 12.99(br, 1H) |
| I-488 | DMSO-d6 1.40-1.84(m, 8H), 1.48(s, 6H), 2.65(br, 2H), 2.95(m, 1H), 3.19-3.50(m, 5H), 3.83-3.95(m, 2H), 4.38(m, 1H), 4.78(br, 1H), 5.00(s, 1H), 10.24(s, 1H), 12.40(brs, 1H) |
| I-489 | DMSO-d6 0.90(dd, 6H, J=6.0 and 10.8), 0.95(t, 3H, J=7, 2), 1.03(t, 3H, J=7.2), 1.12(t, 3H, J=7.5), 1.33-1.70(m, 9H), 2.43-2.56(m, 2H), 2.66-2.78(m, 2H), 3.91-4.14(m, 2H), 4.47(m, 1H), 8.17(s, 1H), 10.16(d, 1H, J=7.8), 12.75(brs, 1H) |
| I-490 | DMSO-d6 0.94(t, 3H, J=7.2), 1.03(t, 3H, J=7,2), 1.11(t, 3H, J=7.5), 1.12(t, 3H, J=7.5), 1.32-1.64(m, 6H), 2.43-2.55(m, 2H), 2.62-2.77(m, 2H), 2.99-3.19(m, 2H), 3.91-4.13(m, 2H), 4.71(m, 1H), 7.16- 7.30(m, 5H), 8.14(s, 1H), 10.22(d, 1H, J=7.8), 12.90(brs, 1H) |
| I-491 | DMSO-d6 0.86-0.94(m, 6H), 0.95(t, 3H, J=7.5), 1.04(t, 3H, J=7,2), 1.12(t, 3H, J=7.5), 1.19(m, 1H), 1.34-1.68(m, 7H), 1.89(m, 1H), 2.44-2.57(m, 2H), 2.64-2.77(m, 2H), 3.92-4.17(m, 2H), 4.45(dd, 1H, J=4.8 and 8.4), 8.16(s,1H), 10.27(d, 1H, J=8.4), 12.77(brs, 1H) |
| I-492 | DMSO-d6 2.16(s, 3H), 2.30(s, 3H), 3.71(s, 3H), 5.40(br, 2H), 5.48(d, 1H, J=6.6), 6.90(d, 2H, J=8.7), 7.06(d, 2H, J=8.7), 7.30-7.44(m, 5H), 8.19(s, 1H), 10.70(d, 1H, J=6.6), 13.07(br, 1H) |
| I-493 | DMSO-d6 1.05(t, 3H, J=7.8 Hz), 1.15-2.10(m, 10H), 2.19(s, 3H), 2.67(dd, 2H, J=7.2 and 15 Hz), 5.42(s, 2H), 7.13-7.22(m, 4H), 8.19(s, 1H),10.14 (s, 1H), 12.17 (br, 1H) |
| I-494 | DMSO-d6 0.94(t, 3H, J=7.5 Hz), 1.14(t, 3H, J=7.5 Hz), 1.18-2.14(m, 10H), 1.98-2.08(m, 2H), 2.47-2.66(m, 4H), 5.43(br, 2H), 7.11-7.23(m,4H), 8.24(s, 1H), 10.15(s, 1H), 12.25(br, 1H) |
| I-495 | DMSO-d6 0.90(dd, 6H, J=6.0 and 11.4), 1.01(t, 3H, J=7.5), 1.06-1.24(m, 4H), 1.12(t, 3H, J=7,5), 1.40-1.84(m, 12H), 2.40-2.57(m, 2H), 2.67-2.78(m, 2H), 3.75-4.15(br, 2H), 4.46(q, 1H, J=7.5), 8.17(s, 1H), 10.13(d, 1H, J=7.5), 12.72(brs, 1H) |

TABLE 274

| Comp. No. | $^1$H-NMR(CDCl$_3$/TMS) δ |
|---|---|
| I-496 | DMSO-d6 1.01(t, 3H, J=7.2), 1.05-1.22(m, 4H), 1.11(t, 3H, J=7.5), 1.40-1.80(m, 9H), 2.43-2.55(m, 2H), 2.64-2.76(m, 2H), 2.96-3.20(m, 2H), 3.80-4.20(br, 2H), 4.70(m, 1H), 7.15-7.28(m, 5H), 8.14-8.19(s, 1H), 10.22(d, 1H, J=7.5), 12.89(brs, 1H) |
| I-497 | DMSO-d6 2.15(s, 3H), 2.30(s, 3H), 5.05(br, 2H), 5.48(d, 1H, J=6.9 Hz), 7.12-7.43(m, 9H), 8.21(s, 1H), 10.64(d, 1H, J=6.9 Hz) |
| I-498 | DMSO-d6 2.16(s, 3H), 2.30(s, 3H), 5.47-5.49(m, 4H), 7.03(m, 1H), 7.27-7.46(m, 8H), 8.21(s, 1H), 10.63(d, 1H, J=6.6) |
| I-499 | DMSO-d6 0.98-1.22(m, 6H), 1.44-1.85(m, 9H), 2.57(t, 2H, J=6.0 Hz), 2.77(t, 2H, J=6.0 Hz), 3.74(s, 3H), 3.88-4.04(m, 2H), 5.39(d, 1H, J= 6.6 Hz), 6.94-7.35(m, 4H), 8.03(s, 1H), 10.61(d, 1H, J=6.9 Hz) |
| I-500 | DMSO-d6 2.19(s, 3H), 2.28(s, 3H), 5.39-5.51(m, 4H), 6.58(d, 1H, J=7.5), 7.22-7.41(m, 7H), 7.55(m, 1H), 8.25(s, 1H), 10.55(d, 1H, J=6.6), 13.10(br, 1H) |
| I-502 | DMSO-d6 1.08(d, 3H, J=6.9), 1.34-1.58(m, 4H), 1.63-1.85(m, 4H), 2.40(m, 1H), 2.67(t, 2H, J=6.0), 2.88-3.09(m, 4H), 4.42(t, 2H, J=6.6), 4.58(dd, 1H, J=5.1 and 7.5), 8.35(s, 1H), 10.18(d, 1H, J=7.5) |
| I-503 | DMSO-d6 1.20-1.50(m, 4H), 1.52-1.78(m, 4H), 2.60-2.78(m, 2H), 2.95-3.03(m, 4H), 4.37(t, 2H, J=6.9), 5.48(d, 1H, J=7.2), 7.28-7.46(m, 5H), 8.14(s, 1H), 10.60(d, 1H, J=6.9) |
| I-504 | DMSO-d6 0.92(d, 6H, J=6.9), 1.25-1.90(m, 10H), 2.17(m, 1H), 2.62-2.72(m, 2H), 2.90-3.01(m, 2H), 2.92(s, 3H), 3.04-3.14(m, 2H), 4.06-4.22(m, 2H), 4.39(dd, 1H, J=4.8 and 8.4), 7.15(t, 1H, J=6.0), 8.12(s, 1H), 10.27(d, 1H, J=8.4), 12.95(brs, 1H) |
| I-505 | DMSO-d6 1.26-1.88(m, 10H), 2.60-2.70(m, 2H), 2.90-3.00(m, 2H), 2.91(s, 3H), 3.03-3.13(m, 2H), 4.08-4.19(m, 2H), 5.49(d, 1H, J=7.2), 7.14(t, 1H, J=6.0), 7.30-7.45(m, 5H), 8.31(s, 1H), 10.73(d, 1H, J=7.2), 13.12(brs, 1H) |
| I-506 | DMSO-d6 1.25-1.88(m, 10H), 1.48(s, 6H), 2.60-2.70(m, 2H), 2.90-3.01(m, 2H), 2.93(s, 3H), 3.03-3.12(m, 2H), 4.07-4.18(m, 2H), 7.15(t, 1H, J=6.0), 8.09(s, 1H), 10.22(s, 1H), 12.40(brs, 1H) |
| I-507 | DMSO-d6 0.84-1.00(m, 15H), 1.34-1.66(m, 10H), 2.16(m, 1H), 2.45(t, 2H, J=5.1), 2.64-2.76(m, 2H), 3.92-4.16(m, 2H), 4.40(q, 1H, J=4.5 and 8.1), 8.13(s, 1H), 10.27(d, 1H, J=8.1), 12.81(br, 1H) |

TABLE 274-continued

| Comp. No. | ¹H-NMR(CDCl₃/TMS) δ |
|---|---|
| I-508 | DMSO-d6 0.88-1.00(m, 9H), 1.34-1.68(m, 10H), 2.45(t, 2H, J=5.1), 2.64-2.76(m, 2H), 3.92-4.14(m, 2H), 5.48(d, 1H, J=8.4), 7.30-7.45(m, 5H), 8.13(s, 1H), 10.72(d, 1H, J=8.4), 13.08(br, 1H) |
| I-511 | DMSO-d6 0.88-1.00(m, 9H), 1.34-1.68(m, 16H), 2.45(t, 2H, J=5.1), 2.64-2.76(m, 2H), 3.92-4.10(m, 2H), 8.10(s, 1H), 10.22(s, 1H), 12.43(br, 1H) |

TABLE 275

| Comp. No. | ¹H-NMR(CDCl₃/TMS) δ |
|---|---|
| I-512 | DMSO-d6 0.90-0.98 (m, 9H), 1.16-1.78 (m, 16H), 2.00-2.08 (m, 2H), 2.42-2.54 (m, 4H), 2.61-2.77 (m, 2H), 4.02-4.12 (m, 2H), 8.10 (s, 1H), 10.26 (s, 1H), 12.23 (br, 1H) |
| I-513 | DMSO-d6 1.26-1.84(m, 10H), 1.48(s, 6H), 1.82(s, 3H), 2.60-2.68(m, 2H), 2.87-2.96(m, 2H), 3.00-3.20(m, 2H), 4.02-4.14(m, 2H), 7.99(t, 1H, J=5.7), 8.08(s, 1H), 10.23(s, 1H), 12.41(brs, 1H) |
| I-514 | DMSO-d6 1.26-1.82(m, 10H), 1.81(s, 3H), 2.60-2.70(m, 2H), 2.86-2.96(m, 2H), 3.10-3.20(m, 2H), 4.00-4.16(m, 2H), 5.48(d, 1H, J=6.9), 7.30-7.44(m, 5H), 7.99(m, 1H), 8.10(s, 1H), 10.73(d, 1H, J=6.9), 13.06(brs, 1H) |
| I-516 | DMSO-d6 0.88(d, 3H, J=6.9), 0.90(d, 3H, J=6.9), 1.26-1.50(m, 4H), 1.50-1.68(m, 4H), 2.27(m, 1H), 2.68(t, 2H, J=6.0), 2.80(t, 3H, J=6.0), 4.40(dd,1H, J=5.1 and 8.1), 5.51(br, 2H), 7.27(d, 2H, J=8.4), 7.82(d, 2H, J=8.4),8.24(s, 1H), 10.09(d, 1H, J=8.1), 12.75(br, 1H) |
| I-517 | DMSO-d6 1.20-1.52(m, 4H), 1.65-1.80(m, 4H), 2.67(t, 2H, J=6.0), 2.79(t,2H, J=6.0), 5.40-5.82(m, 3H), 7.27(d, 2H, J=8.1), 7.30-7.42(m, 5H), 7.81(d, 2H, J=8.1), 8.22(s, 1H), 10.56(d, 1H, J=6.6), 13.06(br, 1H) |
| I-518 | DMSO-d6 1.24-1.82(m, 10H), 1.48(s, 6H), 2.60-2.68(m, 2H), 2.86-2.96(m, 2H), 3.05-3.16(m, 2H), 3.53(s, 3H), 4.00-4.14(m, 2H), 7.27(m, 1H), 8.08(s, 1H), 10.21(s, 1H), 12.42(brs, 1H) |
| I-520 | DMSO-d6 1.07(d, 3H, J=6.6), 1.08(d, 3H, J=6.6), 1.34-1.52(m, 4H), 1.62-1.78(m, 4H), 2.41(m, 1H), 2.64(t, 2H, J=6.0), 2.82(t, 2H, J=6.0), 4.47(dd, 1H, J=5.4 and 7.5), 5.42(br, 2H), 6.94-7.10(m, 4H), 8.38(s, 1H), 10.52(d, 1H, J=7.5) |
| I-521 | DMSO-d6 1.34-1.54(m, 4H), 1.54-1.80(m, 4H), 2.62(t, 2H, J=6.0), 2.78(t, 2H, J=6.0), 5.42(br, 2H), 5.71(d, 1H, J=6.6), 6.92-7.12(m, 4H), 7.30-7.42(m, 3H), 7.49(d, 2H, J=6.6), 8.36(s, 1H), 10.84(d, 1H, J=6.9) |
| I-523 | DMSO-d6 0.91(d, 6H, J=6.9), 0.98-1.25(m, 5H), 1.46-1.86(m, 6H), 2.16(m,1H), 2.94(brt, 2H), 3.08(brt, 2H), 3.72(s, 2H), 4.02(br, 2H), 4.40(dd, 1H, J=4.8 and 8.4), 8.14(s, 1H), 10.22(d, 1H, J=8.4), 12.81(br, 1H) |
| I-524 | DMSO-d6 0.91(d, 6H, J=6.9), 1.00-1.26(m, 5H), 1.48-1.88(m, 6H), 2.17(m,1H), 3.06-3.28(m, 4H), 3.92(d, 1H, J=16.2), 4.03(d, 1H, J=16.2), 4.42(dd, 1H, J=4.5 and 8.1), 8.16(s, 1H), 10.16(d, 1H, J=8.1), 12.82(br, 1H) |
| I-527 | DMSO-d6 1.34-1.54(m, 4H), 1.60(s, 6H), 1.62-1.78(m, 4H), 2.67(t, 2H, J=6.0), 2.80(t, 2H, J=6.0), 5.50(br, 2H), 7.26(d, 2H, J=8.4), 7.82(d, 2H, J=8.4), 8.20(s, 1H), 10.08(br s, 1H), 12.44(br, 1H) |
| I-531 | DMSO-d6 0.93(d, 6H, J=6.9), 1.28-1.52(m, 4H), 1.54-1.79(m, 4H), 1.85-2.03(m, 2H), 2.26(m, 1H), 2.60-2.75(m, 4H), 2.88-3.00(m, 2H), 4.16(br, 2H), 4.35-4.44(m, 1H), 8.13(s, 1H), 10.27(d, 1H, J=6.9), 12.70(br, 1H) |

TABLE 276

| Comp. No. | ¹H-NMR(CDCl₃/TMS) δ |
|---|---|
| I-532 | DMSO-d6 1.34-1.56(m, 4H), 1.62-1.85(m, 4H), 1.85-2.00(m, 2H), 2.58-2.77(m, 4H), 2.87-3.00(m, 2H), 4.10-4.23(m, 2H), 5.47(d, 1H, J=6.9), 7.25-7.49(m, 5H), 8.11(s, 1H), 10.69(d, 1H, J=8.1), 13.16(br, 1H) |
| I-536 | DMSO-d6 1.08(d, 3H, J=6.6), 1.09(d, 3H, J=6.6), 1.34-1.58(m, 4H), 1.60-1.96(m, 8H), 2.37-2.50(m, 3H), 2.46(t, 2H, J=6.9), 2.58-2.68(m, 2H), 4.10-4.24(m, 3H), 4.53(dd, 1H, J=5.1 and 7.5), 8.30(s, 1H), 10.52(d, 1H, J=7.5) |
| I-537 | 1.32-1.58(m, 4H), 1.60-1.94(m, 10H), 2.23-2.46(m, 2H), 2.42(t, 2H, J=6.9), 2.89(t, 2H, J=6.6), 4.10-4.24(m, 4H), 5.73(d, 1H, J=6.6), 7.20-7.41(m, 3H), 7.46-7.53(m, 2H), 8.29(s, 1H), 10.89(d, 1H, J=6.6) |
| I-538 | DMSO-d6 1.05(t, 3H, J=7.5), 2.19(s, 3H), 2.67(q, 2H, J=7.5), 5.43(brs, 2H), 5.76(d, 1H, J=6.6), 7.01(dd, 1H, J=3.3 and 5.1), 7.11-7.21(m, 5H), 7.49(dd, 1H, J=1.2 and 5.1), 8.25(s, 1H), 10.62(d, 1H, J=6.9), 13.31(br, 1H) |
| I-543 | DMSO-d6 1.24-1.74(m, 8H), 2.65(brt, 2H), 3.04(brt, 2H), 5.34(d, 1H, J=16.2), 5.42(d, 1H, J=16.2), 5.49(d, 1H, J=6.9), 6.33(dd, 1H, J=0.6 and 3.3), 6.41(dd, 1H, J=1.8 and 3.3), 7.31-7.43(m, 5H), 7.60(dd, 1H, J=0.6 and 1.8), 8.15(s, 1H), 10.62(d, 1H, J=6.9), 13.10(br, 1H) |
| I-544 | DMSO-d6 1.22-1.76(m, 8H), 2.63(brt, 2H), 2.84(brt, 2H), 2.93(brt, 2H), 4.28(brt, 2H), 5.51(d, 1H, J=7.2), 7.10-7.18(m, 2H), 7.27-7.44(m, 7H), 8.12(s, 1H), 10.72(d, 1H, J=7.2), 13.10(brs, 1H) |
| I-545 | DMSO-d6 1.02-1.08(m, 6H), 1.24-1.47(m, 4H), 1.54-1.69(m, 4H), 2.15(m, 1H), 2.60-2.74(m, 2H), 2.75-2.88(m, 2H), 4.39(m, 1H), 5.45(br, 2H), 7.07(d, 2H, J=7.5), 7.20-7.40(m, 3H), 8.22(s, 1H), 10.19(d, 1H, J=8.4), 12.78(br, 1H) |
| I-546 | DMSO-d6 1.24-1.47(m, 4H), 1.54-1.69(m, 4H), 2.60-2.74(m, 2H), 2.75-2.88(m, 2H), 5.30-5.60(m, 3H), 7.06(d, 2H, J=6.9), 7.22-7.45(m, 8H), 8.20(s, 1H), 10.65(d, 1H, J=6.9), 13.09(br, 1H) |
| I-547 | DMSO-d6 0.91(d, 3H, J=6.6), 0.92(d, 3H, J=6.6), 1.24-1.48(m, 4H), 1.52-1.68(m, 4H), 2.16(m, 1H), 2.66(t, 2H, J=6.0), 2.81(t, 2H, J=6.0), 3.72(s, 3H), 4.39(dd, 1H, J=5.1 and 8.7), 5.38(br, 2H), 6.91(d, 2H, J=8.7), 7.03(d, 2H, J=8.7), 8.36(s, 1H), 10.39(d, 1H, J=8.1), 12.80(br, 1H) |

TABLE 276-continued

| Comp. No. | $^1$H-NMR(CDCl$_3$/TMS) δ |
|---|---|
| I-548 | DMSO-d6 1.24-1.48(m, 4H), 1.52-1.68(m, 4H), 2.66(t, 2H, J=6.0), 2.81(t, 2H, J=6.0), 3.71(s, 3H), 5.38(br, 2H), 6.91(d, 1H, J=8.7), 7.00(d, 2H, J=8.7), 7.03(d, 2H, J=8.7), 7.30-7.46(m, 5H), 8.16(s, 1H), 10.70(d, 1H, J=6.9), 13.08(br, 1H) |
| I-550 | DMSO-d6 1.22-1.74(m, 8H), 2.67(brt, 2H), 2.85(br, 2H), 5.49(br, 2H), 5.50(d, 1H, J=6.9), 7.16(d, 2H, J=8.4), 7.29-7.48(m, 8H), 7.62-7.65(m, 4H), 8.23(s, 1H), 10.69(d, 1H, J=6.9), 13.09(br, 1H) |

TABLE 277

| Comp. No. | $^1$H-NMR(CDCl$_3$/TMS) δ |
|---|---|
| I-552 | DMSO-d6 0.89(d, 6H, J=6.9), 1.22-1.50(m, 4H), 1.55-1.73(m, 4H), 2.16(m, 1H), 2.65-2.74(m, 2H), 2.74-2.89(m, 2H), 4.37(dd, 1H, J=5.1 and 8.1), 5.54(br, 2H), 7.29(d, 2H, J=8.1), 7.72(d, 2H, J=8.1), 8.24(s, 1H), 10.05(d, 1H, J=8.1), 12.65(br, 1H) |
| I-553 | DMSO-d6 1.22-1.50(m, 4H), 1.55-1.73(m, 4H), 2.65-2.74(m, 2H), 2.74-2.90(m, 2H), 5.48(d, 1H, J=6.9), 5.53(br, 2H), 7.28-7.44(m, 7H), 7.71(d, 2H, J=8.1), 8.24(s, 1H), 10.58(d, 1H, J=6.6), 13.05(br, 1H) |
| I-554 | DMSO-d6 0.90(d, 3H, J=6.9), 0.91(d, 3H, J=6.9), 1.22-1.47(m, 4H), 1.52-1.70(m, 4H), 2.18(m, 1H), 2.62-2.70(m, 2H), 2.76-2.90(m, 2H), 4.39(dd, 1H, J=5.1 and 8.1), 5.36(br, 2H), 5.99(s, 2H), 6.50(d, 1H, J=1.8 and 8.1), 6.73(d, 1H, J=1.8), 6.86(d, 1H, J=8.1), 8.20(s, 1H), 10.20(d, 1H, J=8.1), 12.62(br, 1H) |
| I-555 | DMSO-d6 1.22-1.47(m, 4H), 1.52-1.70(m, 4H), 2.62-2.70(m, 2H), 2.76-2.90(m, 2H), 5.35(br, 2H), 5.47(d, 1H, J=6.6), 5.99(s, 2H), 6.50(d, 1H, J=1.8 and 8.1), 6.73(d, 1H, J=1.8), 6.86(d, 1H, J=8.1), 7.30-7.46(m, 5H), 8.20(s, 1H), 10.20(d, 1H, J=8.1), 12.62(br, 1H) |
| I-557 | 1.07(d, 6H, J=6.9), 1.32-1.52(m, 4H), 1.60-1.76(m, 4H), 2.26(m, 1H), 2.31(s, 2H), 2.62(t, 2H, J=6.0), 2.80(t, 2H, J=6.0), 4.65(dd, 1H, J=5.1 and 8.1), 5.45(br, 2H), 6.95(d, 2H, J=8.1), 7.12(d, 2H, J=8.1), 8.37(s, 1H), 10.60(d, 1H, J=7.5), 14.41(br, 1H) |
| I-558 | 1.32-1.52(m, 4H), 1.60-1.76(m, 4H), 2.31(s, 3H), 2.62(t, 2H, J=6.0), 2.80(t, 2H, J=6.0), 5.45(br, 2H), 5.69(d, 1H, J=6.6), 6.92(d, 2H, J=8.1), 7.09(d, 2H, J=8.1), 7.26-7.39(m, 3H), 7.44-7.52(m, 2H), 8.35(s, 1H), 10.91(d, 1H, J=6.9) |
| I-559 | DMSO-d6 0.89(d, 3H, J=6.9), 0.91(d, 3H, J=6.9), 1.24-1.48(m, 4H), 1.54-1.67(m, 4H), 2.15(m, 1H), 2.60-2.69(m, 2H), 2.70-2.88(m, 2H), 4.39(dd, 1H, J=5.1 and 8.4), 5.45(br, 2H), 7.11(d, 2H, J=8.4), 7.41(d, 2H, J=8.4), 8.22(s, 1H), 10.15(d, 1H, J=8.4), 12.98(br, 1H) |
| I-560 | DMSO-d6 1.24-1.48(m, 4H), 1.54-1.67(m, 4H), 2.60-2.69(m, 2H), 2.70-2.88(m, 2H), 5.45(br, 2H), 5.47(d, 1H, J=6.9), 7.11(d, 2H, J=8.1), 7.30-7.43(m, 7H), 8.21(s, 1H), 10.62(d, 1H, J=6.9) |
| I-563 | DMSO-d6 0.88(d, 3H, J=6.9), 0.89(d, 3H, J=6.9), 1.15-1.74(m, 8H), 2.12(m, 1H), 2.65(brt, 2H), 2.96(brt, 2H), 3.98(br, 2H), 5.49(d, 1H, J=7.2), 7.31-7.41(m, 5H), 8.11(s, 1H), 10.73(d, 1H, J=7.2), 13.06(m, 1H) |
| II-003 | 1.00-1.30(m, 4H), 1.56-1.92(m, 7H), 2.16(s, 3H), 2.38(s, 3H), 3.00(dd, 2H, J=1.8 and 5.7), 3.70 (s, 3H), 3.77(s, 3H), 4.02(br, 2H), 4.72(m, 1H), 8.27(s, 1H), 10.65(d, 1H, J=7.5) |
| II-004 | 0.99(t, 3H, J=7.2), 1.39-1.51(m, 2H), 1.62-1.73(m, 2H), 2.17(s, 3H), 2.41(s, 3H), 2.96(dd, 1H, J=5.4 and 16.8), 3.04(dd, 1H, J=5.4 and 16.8), 3.71(s, 3H), 3.77(s, 3H), 4.13(q-like, 2H), 5.09(m, 1H), 8.27(s, 1H), 10.67(d, 1H, J=8.1) |

TABLE 278

| Comp. No. | $^1$H-NMR(CDCl$_3$/TMS) δ |
|---|---|
| II-005 | 1.00-1.30(m, 4H), 1.56-1.92(m, 7H), 2.16(s, 3H), 2.38(s, 3H), 3.00(dd, 2H, J=1.8 and 5.7), 3.71 (s, 3H), 3.77(s, 3H), 4.01(br, 2H), 5.08(m, 1H), 8.27(s, 1H), 10.65(d, 1H, J=7.5) |
| II-007 | 1.00(t, 3H, J=7.5), 1.41-1.55(m, 2H), 1.66-1.78(m, 2H), 2.20(s, 3H), 2.43(s, 3H), 3.99(s, 3H), 4.19-4.24(m, 2H), 7,12(m, 1H), 7.53(m, 1H), 8.03(m, 1H), 8.38(s, 1H), 8.64(m, 1H), 13.01(s, 1H) |

TABLE 278-continued

| Comp. No. | ¹H-NMR(CDCl₃/TMS) δ |
|---|---|
| II-008 | 0.99 (t, 3H, J= 7.2 Hz), 1.39-2.05 (m, 12H), 2.16 (s, 3H), 2.39 (s, 3H), 2.81 (m, 1H), 3.67 (s, 3H), 4.04-4.16 (m, 4H), 4.55 (m, 1H), 8.26 (s, 1H), 10.41 (d, 1H, J= 9.0 Hz) |
| II-011 | 1.00(t, 3H, J=7.2), 1.08(t, 3H, J=7.5), 1.17(t, 3H, J=7.5), 1.38-1.76(m, 6H), 2.47(q, 2H, J=7.5), 2.59-2.69(m, 2H), 2.85-3.08(m, 2H), 3.62(s, 3H), 4.00-4.12(m, 2H), 5.64(q, 1H, J=7.2), 7.19-7.44(m, 5H), 8.33(s, 1H), 10.63(d, 1H, J=8.4) |
| II-012 | 0.98 (t, 3H, J= 7.5 Hz), 1.38-1.50 (m, 2H), 1.60-1.95 (m, 6H), 2.59 (t, 2H, J= 6.0 Hz), 2.73 (t, 2H, J=6.0 Hz), 2.85-3.08 (m, 2H), 3.62 (s, 3H), 4.01-4.07 (m, 2H), 5.64 (m, 1H), 7.20-7.44 (m, 5H), 8.21 (s, 1H), 10.63 (d, 1H, J=7.8 Hz) |
| II-013 | 1.00-1.30 (m, 6H), 1.58-1.90 (m, 9H), 2.60 (t, 2H, J=6.0 Hz), 2.70 (t, 2H, J= 6.0 Hz), 2.86-3.08 (m, 2H), 3.62 (s, 3H), 3.80-4.06 (m, 2H), 5.64 (m, 1H), 7.20-7.45 (m, 5H), 8.22 (s, 1H), 10.62 (d, 1H, J=8.1 Hz) |
| II-018 | 1.04-1.31(m, 7H), 1.56-1.88(m, 7H), 2.17(s, 3H), 2.38(s, 3H), 2.64(t, 2H, J=6.9), 3.66-3.76(m, 2H), 4.01(br, 2H), 4.16(q, 2H, J=7.2), 8.30(s, 1H), 10.13(m, 1H) |
| II-019 | 0.99(t, 3H, J=7.2), 1.27(t, 3H, J=7.2), 1.39-1.51(m, 2H), 1.61-1.71(m, 2H), 2.17(s, 3H), 2.40(s, 3H), 2.64(q, 2H, J=7.2), 3.71(q-like, 2H), 4.11(t-like, 2H), 4.17(q, 1H, J=7.2), 8.29(s, 1H), 10.15(brs, 1H) |
| II-020 | 0.89-2.46(m, 20H), 2.62-2.66(m, 2H), 2.78-2.96(m, 2H), 3.15-3.32(m, 3H), 3.87-4.19(m, 5H), 4.33(m, 1H), 4.55(m, 1H), 8.27(s, 1H), 10.42(s, 1H) |
| II-021 | 1.13-2.20(m, 22H), 1.22(t, 3H, J=7.2), 2.61(m, 2H), 2.78(m, 1H), 2.91-3.19(m 2H), 3.72(dd, 1H, J=6.3, 3.6), 3.82-3.98(m, 2H), 4.07-4.65(m, 5H), 8.27(s, 1H), 10.38(t, 1H, J=8.4) |
| II-022 | 0.98(t, 3H, J=7.2 Hz, 3H), 1.22(t, J=7.2 Hz, 3H), 1.38-1.52(m, 2H), 1.59-2.05(m, 10H), 2.15(s, 3H), 2.38(s, 3H), 2.79(m, 1H), 4.05-4.19(m, 4H), 4.54(m, 1H), 8.26(s, 1H), 10.40(d, 1H, J=9.3 Hz) |
| II-024 | 0.98(t, 3H, J=7.2 Hz), 1.16(t, 3H, J=7.2 Hz), 1.37-1.51(m, 2H), 1.59-2.14(m, 8H), 2.16(s, 3H), 2.39(s, 3H), 3.11(m, 1H), 4.03-4.14(m, 4H), 4.71(m, 1H), 8.27(s, 1H), 10.15(d, 1H, J=6.8 Hz) |
| II-027 | 0.98(t, 3H, J=7.2 Hz), 1.23(t, 3H, J=6.9 Hz), 1.34-2.05(m, 16H), 2.60(t, 2H, J=6.0 Hz), 2.72(t, 2H, J=6.0 Hz), 2.79(m, 1H), 4.00-4.22(m, 4H), 4.55(m, 1H), 8.19(s, 1H), 10.41(d, 1H, J=8.4 Hz) |

TABLE 279

| Comp. No. | ¹H-NMR(CDCl₃/TMS) δ |
|---|---|
| II-028 | 0.99-1.23 (m, 6H), 1.22 (t, 3H, J= 7.2 Hz), 1.36-2.05 (m, 12H), 2.60 (t, 2H, J= 6.0 Hz), 2.69 (t, 2H, J= 6.0 Hz), 2.80 (m,1H), 3.85-4.04 (m, 2H), 4.13 (dd, 2H, J= 7.2 and 14.4 Hz), 4.53 (m, 1H), 8.19 (s, 1H), 10.40 (d, 1H, J= 9.0 Hz) |
| II-029 | 0.99(t, 3H, J=7.2), 1.07(t, 3H, J=7.5), 1.17(t, 3H, J=7.5), 1.23(t, 3H, J=7.2), 1.38-1.81(m, 12H), 1.86-2.07(m, 2H), 2.48(q, 2H, J=7.5), 2.59-2.68(m, 2H), 2.78(m, 1H), 3.96-4.23(m, 4H), 4.55(m, 1H), 8.30(s, 1H), 10.43(d, 1H, J=8.7) |
| II-030 | 0.99(t, 3H, J=7.5), 1.08(t, 3H, J=7.5), 1.19(t, 3H, J=7.5), 1.27(t, 3H, J=7.2), 1.38-1.74(m, 6H), 2.49(q, 2H, J=7.5), 2.60-2.69(m, 4H), 3.71(q, 2H, J=7.2), 4.00-4.12(m, 2H), 4.17(q, 2H, J=7.2), 8.33(s, 1H), 10.16(m, 1H) |
| II-031 | 1.21(t, 3H, J=7.2), 1.30-2.06(m, 18H), 2.06(s, 3H), 2.63(t, 2H, J=6.0), 2.78(m, 1H), 2.86-2.93(m, 2H), 3.06-3.38(m, 2H), 4.02-4.42(m, 4H), 4.53(m, 1H), 7.07(m, 1H), 8.30(s, 1H), 10.43(d, 1H, J=9.0) |
| II-032 | 1.23(t, 3H, J=7.2), 1.32-2.08(m, 18H), 2.57-2.66(m, 2H), 2.78(m, 1H), 2.84-2.92(m, 2H), 3.12-3.26(m, 2H), 3.68(s, 3H), 4.06-4.32(m, 4H), 4.53(m, 1H), 5.74(m, 1H), 8.28(s, 1H), 10.39(d, 1H, J=9.0) |
| II-033 | 1.18(t, 3H, J=6.9), 1.34-1.80(m, 11H), 1.60(s, 6H), 1.80-2.14(m, 3H), 4.00-4.20(m, 2H), 4.50-4.54(m, 2H), 5.52(br, 2H), 7.16(d, 2H, J=8.4), 7.62(d, 2H, J=8.4), 8.36(s, 1H), 10.22(br s, 1H) |
| II-036 | DMSO-d6 1.00-1.26(m, 4H), 1.47-1.85(m, 7H), 2.16(s, 3H), 2.42(s, 3H), 2.70-2.85(m, 2H), 3.90-4.12(m, 2H), 4.75(m, 1H), 8.13(s, 1H), 10.33(d, 1H, J=8.1), 12.57(br, 2H) |
| II-037 | DMSO-d6 0.94(t, 3H, J=7.2), 1.32-1.45(m, 2H), 1.52-1.62(m, 2H), 2.14(s, 3H)2.43(s, 3H), 2.74(dd, 1H, J=5.1 and 16.8), 2.84(dd, 1h, J=5.1 and 16.8), 4.06-4.12(m, 2H), 4.75(m, 1H), 8.12(s, 1H), 10.36(d, 1H, J=7.8), 12.64(br, 1H) |
| II-040 | DMSO-d6 1.00-1.26(m, 4H), 1.47-1.85(m, 7H), 2.15(s, 3H), 2.42(s, 3H), 2.6-2.86(m, 2H), 3.90-4.18(m, 2H), 4.74(m, 1H), 8.13(s, 1H), 10.33(d, 1H, J=8.1), 12.57(br, 2H) |
| II-041 | DMSO-d6 1.00-1.31(m, 4H), 1.46-1.88(m, 7H), 2.14(s, 3H), 2.40(s, 3H), 2.47(t, 2H, J=6.6), 3.39-3.60(m, 2H), 3.94-4.16(br, 2H), 8.12(s, 1H), 9.95(t, |

TABLE 279-continued

| Comp. No. | $^1$H-NMR(CDCl$_3$/TMS) δ |
|---|---|
| II-043 | DMSO-d6 0.93(t, 3H, J=7.2), 1.31-1.43(m, 2H), 1.51-1.61(m, 2H), 2.14(s, 3H), 2.42(s, 3H), 3.34(br, 2H), 3.48(q-like, 2H), 4.08(t-like, 2H), 8.12(s, 1H), 9.97(brt, 1H, J=6.0), 12.31(br, 1H) |
| II-044 | DMSO-d6 0.95(t, 3H, J=7.5), 1.32-1.46(m, 2H), 1.54-1.66(m, 2H), 2.17(s, 3H), 2.45(s, 3H), 4.10-4.15(m, 2H), 7.17(m, 1H), 7.56(m, 1H), 7.90(m, 1H), 8.22(s, 1H), 8.54(s, 1H), 12.86(s, 1H), 13.24(brs, 1H) |
| II-045 | 0.92-3.08(m, 29H), 3.36-3.92(m, 3H), 4.31-4.84(m, 3H), 8.23(s, 1H), 10.19(d, 1H, J=9.0) |
| II-046 | 1.13-2.16(m, 20H), 2.60-3.14(m, 5H), 3.74(m, 1H), 3.81-3.98(m, 2H), 4.27(m, 1H), 4.57-4.65(m, 2H), 8.29(s, 1H), 10.50(d, 1H, J=7.8) |

TABLE 280

| Comp. No. | $^1$H-NMR(CDCl$_3$/TMS) δ |
|---|---|
| II-047 | DMSO-d6: 0.94(t, 3H, J=7.2 Hz), 1.32-1.92(m, 12H), 2.14(s, 3H), 2.42(s, 3H), 2.63(m, 1H), 4.02-4.16(m, 4H), 4.39(m, 1H), 8.10(s, 1H), 10.24(d, 1H, J=9.0 Hz), 12.11(br, 1H) |
| II-049 | DMSO-d6 0.94(t, 3H, J=7.2), 1.30-2.10(m, 9H), 2.14(s, 3H), 2.42(s, 3H), 2.63(m, 1H), 2.91(m, 1H), 3.98-4.15(m, 2H), 4.38 and 4.54(m, total 1H), 8.11(s, 1H), 10.04(d, 1H, J=6.9), 12.15(br, 1H) |
| II-053 | DMSO-d6 0.93(t, 3H, J=6.6 Hz), 1.22-1.85(m, 16H), 2.56(t, 2H, J=6.0 Hz), 2.65(m, 1H), 2.80(t, 2H, J=6.0 Hz), 3.98-4.03(m, 2H), 4.40(m, 1H), 8.01(s, 1H), 10.24(d, 1H, J=9.0 Hz), 12.13(br, 1H) |
| II-054 | DMSO-d6 0.98-1.90(m, 23H), 2.57(t, 2H, J=6.3 Hz), 2.62(m, 1H), 2.77(t, 2H, J=6.3 Hz), 3.83-4.06(m, 2H), 4.38(m, 1H), 8.02(s, 1H), 10.22(d, 1H, J=9.0 Hz), 12.13(br,1H) |
| II-056 | DMSO-d6 0.94(t, 3H, J=7.2), 1.00(t, 3H, J=7,2), 1.11(t, 3H, J=7.5), 1.18-1.94(m, 14H), 2.53-2.75(m, 4H), 3.90-4.14(m, 3H), 4.41(m, 1H), 8.14(s, 1H), 10.24(d, 1H, J=9.0), 12.10(brs, 1H) |
| II-057 | DMSO-d6 0.94(t, 3H, J=7.5), 1.03(t, 3H, J=7.5), 1.12(t, 3H, J=7,2), 1.32-1.65(m, 6H), 2.43-2.55(m, 4H), 2.64-2.74(m, 2H), 3.48(q, 2H, J=6.3), 3.96-4.08(m, 2H), 8.16(s, 1H), 9.96(m, 1H), 12.28(brs, 1H) |
| II-058 | DMSO-d6 0.94(t, 3H, J=7.5), 1.03(t, 3H, J=7.2), 1.11(t, 3H, J=7,5), 1.33-1.66(m, 6H), 2.43-2.55(m, 2H), 2.63-2.74(m, 2H), 2.75-2.94(m, 2H), 3.96-4.08(m, 2H), 5.40(q, 1H, J=7.2), 7.18-7.40(m, 5H), 8.15(s, 1H), 10.43(d, 1H, J=8.1), 12.27(brs, 1H) |
| II-059 | DMSO-d6 0.93(t, 3H, J=7.2), 1.37(m, 2H), 1.51-1.65(m, 4H), 1.77(m, 2H), 4.00(2H, m), 5.40(1H, dd, J=7.8, 7.2), 7.22-7.38(m, 6H), 10.44(d, 1H, J=8.4), 12.25(brs, 1H) |
| II-060 | DMSO-d6 1.0-1.9(m, 4H), 1.4-1.8(m, 8H), 2.57(m, 2H), 2.7-2.87(m, 4H), 3.93(br, 2H), 5.39(dd, 1H, J=8.1, 6.9), 7.2-7.4(6H, m), 10.41(d, 1H, J=8.1), 12.33(br, 1H) |
| II-061 | DMSO-d6 1.24-1.96(m, 18H), 1.82(s, 3H), 2.58-2.68(m, 3H), 2.84-2.94(m, 2H), 3.08-3.19(m, 2H), 3.94-4.17(m, 2H), 4.42(m, 1H), 7.99(t, 1H, J=5.4), 8.09(s, 1H), 10.24(d, 1H, J=9.0), 12.11(brs, 1H) |
| II-062 | DMSO-d6 1.15-1.96(m, 18H), 2.50-2.70(m, 3H), 2.83-2.96(m, 2H), 3.03-3.17(m, 2H), 3.54(s, 3H), 3.92-4.18(m, 2H), 4.42(m, 1H), 7.28(m, 1H), 8.10(s, 1H), 10.24(d, 1H, J=8.7), 12.13(brs, 1H) |
| II-063 | DMSO-d6 1.10-1.84(m, 11H), 2.58-2.82(m, 6H), 1.80-2.14(m, 3H), 4.00-4.20(m, 2H), 5.40-5.60(br, 2H), 7.24(d, 2H, J=8.1), 7.82(d, 2H, J=8.1), 8.22(s, 1H), 10.08(d, 1H, J=5.7) |
| III-002 | 1.05-2.05(m, 26H), 2.49-2.57(m, 3H), 2.85(t, 2H, J=6.6), 2.97-3.14(m, 2H), 3.54(m, 1H), 3.95-4.02(m, 2H), 4.13(q, 2H, J=7.2), 4.49(m, 1H),7.32(s, 1H) |
| III-003 | DMSO-d6 1.09-1.91(m, 23H), 2.54-3.16(m, 8H), 3.76-3.96(m, 2H), 4.29(m, 1H), 7.26(s, 1H), 12.26(s, 1H) |
| III-006 | 1.00-1.38(m, 10H), 1.57-1.95(m, 7H), 2.17(s, 3H), 2.39(s, 3H), 3.90-4.26(m, 7H), 8.27(s, 1H), 10.20(d, 1H, J=7.8) |

TABLE 281

| Comp. No. | $^1$H-NMR(CDCl$_3$/TMS) δ |
|---|---|
| III-007 | 1.00 (t, 3H, J= 7.2 Hz), 1.22-1.31 (m, 8H), 1.40-1.52 (m, 2H), 1.63-1.73 (m, 2H), 2.13 (m, 1H), 2.17 (s, 3H), 2.39 (m, 1H), 2.45 (s, 3H), 4.08-4.25 (m, 6H), 4.79 (m, 1H), 8.27 (s, 1H), 10.43 (d, 1H, J= 7.8 Hz) |

TABLE 281-continued

| Comp. No. | ¹H-NMR(CDCl₃/TMS) δ |
|---|---|
| III-009 | DMSO-d6 1.00-1.38(m, 4H), 1.50-2.34(m, 9H), 2.14(s, 3H), 2.42(s, 3H), 3.84-4.20(m, 4H), 4.48(m, 1H), 8.12(s, 1H), 10.20(d, 1H, J=7.5), 12.54(br, 2H) |
| III-010 | DMSO-d6 0.94(t, 3H, J=7.2), 1.33-1.45(m, 2H), 1.53-1.64(m, 2H), 1.90(m, 1H), 2.08(m, 1H), 2.15(s, 3H), 2.20-2.32(m, 2H), 2.44(s, 3H), 4.03-4.18(m, 2H), 4.50(m, 1H), 8.11(s, 1H), 10.23(d, 1H, J=7.8), 12.48(br, 1H) |
| IV-005 | 0.89-2.33(m, 23H), 2.59-2.65(m, 2H), 2.94(m, 1H), 3.03-3.26(m, 2H), 3.35(m, 1H), 3.68(s, 3H), 3.79-4.02(m, 2H), 4.29(m, 1H), 8.30(s, 1H), 9.85(d, 1H, J=7.2) |
| IV-006 | 1.62-2.32(m, 21H), 2.58-2.72(m, 2H), 2.92-3.26(m, 2H), 3.68(s, 3H), 3.73-3.95(m 4H), 4.23(m, 1H), 4.56(dd, 1H, J=2.7, 13.8), 8.31(s, 1H), 9.79(d, 1H, J=7.8) |
| IV-015 | 1.22-2.34(m, 21H), 2.59-2.71(m, 3H), 3.04-4.02(m, 5H), 4.12-4.82(m, 3H), 8.33(s, 1H), 9.68(m, 1H) |
| IV-016 | 1.13-2.38(m, 23H), 2.57-2.73(m, 2H), 2.91-3.21(m, 2H), 3.73(dd, 1H, J=7.5, 15.0), 3.84-4.06(m, 2H), 4.25(m, 1H), 4.56(dd, 1H, J=2.7, 13.8), 8.32(s, 1H), 9.83(d, 1H, J=8.4) |
| IV-030 | DMSO-d6 1.24-1.48 (m, 4H), 1.53-1.73 (m, 4H), 2.65-2.79 (m, 2H), 2.82-2.97 (m, 2H), 3.60 (s, 2H), 5.14 (s, 2H), 7.02 (s, 1H), 7.12-7.19 (m, 2H), 7.24-7.39 (m, 3H), 8.38 (s, 1H), 12.00-12.80 (br, 1H), 13.23 (s, 1H) |
| V-002 | 1.02-2.95(m, 24H), 2.26(m, 1H), 2.51-2.66(m, 8H), 2.96(t, 2H, J=5.7), 3.30(t, 2H, J=8.1), 3.66(s, 3H), 4.28(m, 1H), 8.29(s, 1H), 9.96(m, 1H) |
| V-008 | 1.04-2.06(m, 23H), 2.25(m, 1H), 2.61-3.00(m, 8H), 3.31(t, 2H, J=6.6), 3.17-3.40(m, 2H), 4.34-4.48(m, 2H), 8.31(s, 1H), 9.87(t, 1H, J=5.7) |
| X-35 | DMSO-d6 1.30-1.85 (m, 12H), 2.71 (br, 2H), 2.99 (br, 2H), 3.61 (s, 2H), 4.19 (brs, 2H), 4.43 (brs, 1H), 4.59 (t, 1H, J=5.6), 7.01 (s, 1H), 8.28 (s, 1H), 13.45 (s, 1H) |
| X-50 | DMSO-d6 1.01-1.90(m, 15H), 2.64(t-like, 2H), 2.85(t-like, 2H), 3.61(s, 2H), 4.02(brd, 2H), 7.02(s, 1H), 8.20(s, 1H), 12,40(br, 1H), 13.50(s, 1H) |
| X-94 | DMSO-d6 1.16-1.94(m, 18H), 2.65-2.80(m, 2H), 2.90-3.09(m, 2H), 3.20(s, 3H), 3.62(s, 2H), 3.90-4.20(br, 2H), 7.02(s, 1H), 8.29(s, 1H), 12.10-12.60(br, 1H), 13.47(s, 1H) |
| X-107 | DMSO-d6 1.20-2.06 (m, 22H), 2.65 (br, 2H), 2.94 (t, 2H, J= 6.0), 4.12 (br, 2H), 4.42 (t, 1H, J= 5.4), 4.58 (t, 1H, 5.7), 8.08 (s, 1H), 10.26 (s,1H), 12.24 (br, 1H) |
| X-111 | DMSO-d6 0.94(t, 3H, J=7.5), 1.00-2.05(m, 16H), 2.78(m, 1H), 2.70-3.05(m, 3H), 3.61(s, 2H), 3.90-4.10(m, 2H), 7.02(s, 1H), 8.20(s, 1H), 12.41(br s, 1H), 13.51(s, 1H) |

TABLE 282

| Comp. No. | ¹H-NMR(CDCl₃/TMS) δ |
|---|---|
| X-113 | DMSO-d6 1.06(t, 3H, J=7.4), 1.24-1.74(m, 8H), 2.02(d, 2H, J=13.5), 2.19(s, 3H), 2.58(q, 2H, J=7.4), 5.47(s, 2H), 7.09(d, 2H, J=7.4), 7.25-7.38(m, 3H), 8.20(s, 1H), 10.17(s, 1H), 12.23(s, 1H) |
| X-118 | DMSO-d6 0.91(d, 6H, J=6.6), .125-1.83(m, 12H), 2.15(m, 1H), 2.63(br, 2H), 2.92(br, 2H), 4.10(br, 2H), 4.35-4.43(m, 2H), 4.56(t, 1H, J=5.7), 8.10(s, 1H), 10.24(d, 1H, J=8.7), 12.70(br, 1H) |
| X-140 | DMSO-d6 1.04-2.16(m, 12H), 2.60-2.80(m, 2H), 2.94-3.22(m, 2H), 3.50-3.70(m, 3H), 3.72-3.84(m, 1H), 4.00-4.24(m, 2H), 4.38-4.52(m, 1H), 7.02(s, 1H), 8.30(s, 1H), 12.39(br s, 1H), 13.40(s, 1H) |
| X-141 | DMSO-d6 1.26-1.84(m, 8H), 2.65-2.78(m, 2H), 3.05-3.20(m, 2H), 3.62(s, 2H), 5.44(s, 2H), 6.40-6.50(m, 2H), 7.03(s, 1H), 7.62(d, 1H, J=0.9), 8.32(s, 1H), 12.41(br, 1H), 13.29(s, 1H) |
| X-142 | DMSO-d6 1.30-2.14(m, 15H), 2.60-2.80(m, 2H), 2.90-3.10(m, 2H), 3.61(s, 2H), 4.05-4.30(br, 2H), 5.55-5.70(m, 2H), 7.02(s, 1H), 8.30(s, 1H), 12.40(br s, 1H), 13.46(s, 1H) |
| X-143 | DMSO-d6 1.00-1.30(m, 6H), 1.07(d, 3H, J=6.3), 1.25(d, 3H, J=6.6), 1.50-1.94(m, 8H), 2.39(dd, 1H, J=11.4 and 17.4), 2.82(m, 1H), 2.98(m, 1H), 3.61(s, 2H), 3.90-4.15(m, 2H), 7.03(s, 1H), 8.41(s, 1H), 12.41(br s, 1H), 13.49(s, 1H) |
| X-145 | DMSO-d6 0.94(t, 3H, J=7.2), 1.04(t, 3H, J=7.2), 1.13(t, 3H, J=7.5), 1.32-1.66(m, 6H), 2.47-2.57(m, 2H), 2.63-2.78(m, 3H), 2.87(dd, 1H, J=5.1 and 16.5), 3.95-4.10(m, 2H), 5.16(m, 1H), 8.21(s, 1H), 10.44(d, 1H, J=9.3), 12.69(s, 1H) |
| X-146 | DMSO-d6 2.19(s, 3H), 2.39(s, 3H), 3.80(s, 3H), 5.52(br-s, 2H), 7.13-7.31(m, 4H), 8.40(s, 1H), 13.69(s, 1H) |
| X-147 | DMSO-d6 1.12-1.18(m, 4H), 1.51-18.9(m, 11H), 2.66(br-s, 2H), 2.87(br-s, 2H), 3.81(s, 2H), 4.04(br-s, 2H), 8.25(s, 1H), 12.66(br-s, 1H), 13.88(s, 1H) |

TABLE 282-continued

| Comp. No. | $^1$H-NMR(CDCl$_3$/TMS) δ |
|---|---|
| X-152 | DMSO-d6 1.12-1.84(m, 8H), 2.60-2.80(m, 2H), 3.00-3.15(m, 2H), 3.63(s, 2H), 5.60(s, 2H), 6.98(dd, 1H, J=3.6 and 5.1), 7.04(s, 1H), 7.22(m, 1H), 7.45(dd, 1H, J=1.2 and 5.1), 8.34(s, 1H), 12.44(br s, 1H), 13.33(s, 1H) |
| X-153 | DMSO-d6 0.50-0.60(m, 4H), 1.12-1.84(m, 9H), 2.67-2.78(m, 2H), 2.97-3.09(m, 2H), 3.62(s, 2H), 4.16(d, 2H, J=6.6), 7.02(s, 1H), 8.29(s, 1H), 12.40(br s, 1H), 13.43(s, 1H) |
| X-161 | DMSO-d6 1.20-1.80(m, 16H), 2.76(m, 1H), 2.65-2.77(m, 2H), 2.90-3.10(m, 2H), 3.62(s, 2H), 4.20(d, 2H, J=7.2), 7.02(s, 1H), 8.29(s, 1H), 11.80-12.80(m, 1H), 13.48(s, 1H) |
| X-174 | DMSO-d6 0.94(t, 3H, J=7.5), 1.03(t, 3H, J=7.5), 1.12(t, 3H, J=7.5), 1.30-1.64(m, 14H), 2.18-2.30(m, 2H), 2.42-2.56(m, 2H), 2.62-2.74(m, 2H), 2.77(s, 2H), 3.95-4.08(m, 2H), 8.17(s, 1H), 9.94(s, 1H), 11.90(br, 1H) |
| X-175 | DMSO-d6 1.15-1.95(m, 16H), 2.65-2.92(m, 4H), 2.97-3.10(m, 2H), 3.61(s, 2H), 4.27(m, 1H), 7.01(s, 1H), 8.25(s, 1H), 12.46(br s, 1H), 13.51(s, 1H) |
| X-176 | DMSO-d6 1.26-2.04(m, 16H), 2.65-2.76(m, 2H), 2.80-2.95(m, 2H), 3.61(s, 2H), 4.60-4.80(br, 2H), 4.97(m, 1H), 7.02(s, 1H), 8.32(s, 1H), 12.40(br s, 1H), 13.40(s, 1H) |

TABLE 283

| Comp. No. | $^1$H-NMR(CDCl$_3$/TMS) δ |
|---|---|
| X-178 | DMSO-d6 0.93(t, 3H, J=7.5), 1.03(t, 3H, J=7.5), 1.12(t, 3H, J=7.5), 1.32-1.46(m, 2H), 1.48-1.68(m, 9H), 2.18-2.30(m, 2H), 2.42-2.56(m, 2H), 2.63-2.74(m, 2H), 2.76-2.84(m, 2H), 4.01(t, 2H, J=7.2), 8.13(s, 1H), 12.56(br, 1H) |
| X-190 | DMSO-d6 1.10-1.94(m, 16H), 2.65-2.80(m, 2H), 2.90-3.10(m, 2H), 3.62(s, 2H), 3.76(br s, 1H), 3.90-4.20(br, 2H), 4.20-4.40(br, 1H), 7.02(s, 1H), 8.29(s, 1H), 12.00-12.60(br, 1H), 13.49(s, 1H) |
| X-196 | DMSO-d6 0.80(t, 6H, J=7.5), 0.94(t, 3H, J=7.5), 1.03(t, 3H, J=7.5), 1.12(t, 3H, J=7.5), 1.32-1.46(q, 2H, J=7.5), 1.46-1.66(m, 4H), 1.66-1.81(m, 2H), 1.81-1.96(m, 2H), 2.44-2.56(m, 2H), 2.64-2.76(m, 2H), 2.76(s, 2H), 3.93-4.09(m, 2H), 8.15(s, 1H), 9.82(s, 1H), 11.94(br, 1H) |
| X-198 | DMSO-d6 0.96(t, 3H, J=7.5), 1.05(t, 3H, J=7.5), 1.16(t, 3H, J=7.5), 1.36-1.68(m, 6H), 2.56(q, 2H, J=7.5), 2.71-2.77(brm, 2H), 4.08-4.13(brm, 2H), 6.58(d, 1H, J=16.2), 7.59(d, 1H, J=15.9), 8.21(dd, 1H, J=2.4, 9.0), 8.30(d, 1H, J=8.7), 8.33(s, 1H), 8.61(d, 1H, J=2.1), 12.43(br, 1H), 12.80(s, 1H) |
| X-207 | DMSO-d6 0.96(t, 3H, J=7.2), 1.06(t, 3H, J=7.2), 1.17(t, 3H, J=7.2), 1.34-1.50(m, 2H), 1.52-1.72(m, 4H), 2.58(q, 2H, J=7.5), 2.72-2.83(m, 2H), 3.82(s, 2H), 4.10-4.20(m, 2H), 8.35(s, 1H), 12.68(br s, 1H), 13.81(s, 1H) |
| X-208 | DMSO-d6 0.96-1.38(m, 12H), 1.38-1.92(m, 13H), 2.10-2.24(m, 2H), 2.40-2.56(q, 2H, J=7.5), 2.56-2.76(m, 4H), 3.93-4.11(m, 3H), 8.37(s, 1H), 10.58(d, 1H, J=6.6) |
| X-209 | DMSO-d6 0.96(t, 3H, J=7.2), 1.05(t, 3H, J=7.5), 1.16(t, 3H, J=7.8), 1.34-1.50(m, 2H), 1.50-1.72(m, 4H), 2.56(q, 2H, J=7.5), 2.70-2.80(m, 2H), 3.62(s, 2H), 4.05-4.20(br, 2H), 7.02(s, 1H), 8.32(s, 1H), 12.40(br s, 1H), 13.45(s, 1H) |
| X-211 | DMSO-d6 0.87(dd, 6H, J=3.6 and 6.3), 0.94(t, 3H, J=7.5), 1.03(t, 3H, J=7.5), 1.12(t, 3H, J=7.5), 1.20-1.66(m, 9H), 2.35-2.55(m, 4H), 2.63-2.75(m, 2H), 3.93-4.10(m, 2H), 4.34(m, 1H), 8.16(s, 1H), 9.84(d, 1H, J=8.7), 12.10(brs, 1H) |
| X-215 | DMSO-d6 1.20-1.80(m, 22H), 2.00-2.15(m, 1H), 2.67-2.78(m, 2H), 2.93-3.07(m, 2H), 3.62(s, 2H), 3.90-4.20(br, 2H), 7.02(s, 1H), 8.30(s, 1H), 12.41(br s, 1H), 13.47(s, 1H) |
| X-223 | DMSO-d6 0.94(t, 3H, J=7.5), 1.02(t, 3H, J=7.5), 1.12(t, 3H, J=7.5), 1.32-1.78(m, 10H), 1.84-1.96(m, 2H), 2.10-2.24(m, 2H), 2.44-2.56(m, 2H), 2.64-2.76(m, 2H), 3.93-4.09(m, 2H), 8.13(s, 1H), 10.20(s, 1H), 12.29(br, 1H) |
| X-227 | DMSO-d6 0.96(t, 3H, J=7.5), 1.05(t, 3H, J=7.5), 1.16(t, 3H, J=7.5), 1.35-1.72(m, 6H), 2.56(q, 2H, J=7.5), 2.68-2.79(m, 2H), 4.00-4.16(m, 2H), 6.45(d, 1H, J=15.9), 7.55(d, 1H, J=15.9), 7.68(d, 2H, J=8.7), 7.76(d, 2H, J=8.7), 8.31(s, 1H), 12.30(brs, 1H), 12.44(s, 1H) |
| X-229 | DMSO-d6 1.02-1.86(m, 19H), 2.62-2.75(m, 2H), 2.92-3.05(m, 2H), 3.85-4.15(br, 2H), 5.43(m, 1H), 8.18(s, 1H), 10.83(d, 1H, J=9.0), 14.22(brs, 1H) |

TABLE 284

| Comp. No. | ¹H-NMR(CDCl₃/TMS) δ |
|---|---|
| X-230 | DMSO-d6 0.95(t, 3H, J=7.5), 1.03(t, 3H, J=7.5), 1.14(t, 3H, J=7.5), 1.32-1.68(m, 20H), 1.80-1.96(m, 2H), 2.08-2.20(m, 2H), 2.44-2.55(m, 2H), 2.64-2.76(m, 2H), 3.93-4.09(m, 2H), 8.12(s, 1H), 10.03(s, 1H), 12.19(br, 1H) |
| X-233 | DMSO-d6 0.94(t, 3H, J=7.5), 1.03(t, 3H, J=7.5), 1.12(t, 3H, J=7.5), 1.30-1.82(m, 12H), 2.00-2.15(m, 2H), 2.42-2.56(m, 2H), 2.60-2.74(m, 2H), 2.87(s, 2H), 3.93-4.09(m, 2H), 8.14(s, 1H), 9.93(s, 1H), 11.90(br, 1H) |
| X-237 | DMSO-d6 1.25-1.50(m, 4H), 1.55-1.75(m, 4H), 2.64-2.78(m, 2H), 2.84-2.98(m, 2H), 3.61(s, 2H), 5.41(br s, 2H), 6.00(s, 2H), 6.60(d, 1H, J=8.1), 6.81(s, 1H), 6.86(d, 1H, J=8.4), 7.02(s, 1H), 8.36(s, 1H), 12.40(br s, 1H) |
| X-241 | DMSO-d6 0.95(t, 3H, J=7.2), 1.03(t, 3H, J=7.5), 1.11(t, 3H, J=7.5), 1.33-1.66(m, 16H), 1.91-2.17(m, 4H), 2.44-2.56(m, 2H), 2.63-6(m, 2H), 3.96-4.10(m, 2H), 8.11(s, 1H), 10.14(s, 1H), 12.17(brs, 1H) |
| XI-001 | DMSO-d6 1.05(t, 3H, J=7.5), 1.25-1.91(m, 8H), 2.03(d, 2H, J=13.5), 2.18(s, 3H), 2.68(q, 2H, J=7.4), 3.72(s, 3H), 5.39(br s, 2H), 6.91(d, 2H, J=9.0), 7.04(d, 2H, J=9.0), 8.18(s, 1H), 10.19(s, 1H), 12.17(br s, 1H) |
| XI-005 | DMSO-d6 1.06(t, 3H, J=7.4), 1.24-1.73(m, 8H), 2.02(d, 2H, J=13.8), 2.18(s, 3H), 2.27(s, 3H), 2.66(q, 2H, J=7.4), 5.42(br s, 2H), 6.97(d, 2H, J=8.1), 7.16(d, 2H, J=8.1), 8.18(s, 1H), 10.17(s, 1H), 12.18(br s, 1H) |
| XI-006 | DMSO-d6 1.02-1.32(m, 6H), 1.40-2.08(m, 9H), 3.20-3.40(m, 2H), 3.45(m, 1H), 3.73(m, 1H), 3.89(dd, 1H, J=8.7, 12.9), 4.18(dd, 1H, J=6.0, 12.9), 6.99(s, 1H), 8.35(s, 1H), 12.37(br s, 1H), 13.49(s, 1H) |
| XI-007 | DMSO-d6 1.03(s, 6H), 1.28(s, 6H), 0.90-1.90(m, 11H), 2.69(s, 2H), 3.62(s, 2H), 4.00-4.15(m, 2H), 7.04(s, 1H), 8.49(s, 1H), 12.40(br, 1H), 13.49(s, 1H) |
| XI-009 | DMSO-d6 1.26-1.50(m, 4H), 1.56-1.74(m, 4H), 2.68-2.78(m, 2H), 2.85-2.95(m, 2H), 3.60(s, 2H), 5.52(s, 2H), 6.96(d, 1H, J=7.8), 7.02(s, 1H), 7.05-7.16(m, 2H), 7.39(m, 1H), 8.39(s, 1H), 12.42(br s, 1H), 13.27(s, 1H) |
| XI-015 | DMSO-d6 1.13(t, 3H, J=6.9), 1.27-1.75(m, 8H), 2.05(d, 2H, J=14.1), 2.16(s, 3H), 2.70(q, 2H, J=7.4), 2.95(t, 2H, J=7.5), 4.28(t, 2H, J=8.1), 7.14(t, 2H, J=8.9), 7.31(dd, 2H, J=8.9 and 5.6), 8.11(s, 1H), 10.23(s, 1H), 12.18(br s, |
| XI-016 | DMSO-d6 1.05(t, 3H, J=7.7), 1.24-1.73(m, 8H), 2.01(d, 2H, J=14.7), 2.19(s, 3H), 2.65(q, 2H, J=7.2), 5.45(br s, 2H), 7.12(d, 2H, J=8.4), 7.42(d, 2H, J=8.7), 8.20(s, 1H), 10.12(s, 1H), 12.21(br s, 1H) |
| XI-019 | DMSO-d6 1.20-1.50(m, 4H), 1.58-1.74(m, 4H), 2.70-2.80(m, 2H), 2.87-2.97(m, 2H), 3.59(s, 2H), 5.50(s, 2H), 6.85(m, 1H), 7.02(s, 1H), 7.13(m, 1H), 7.23-7.42(m, 2H), 8.40(s, 1H), 12.38(br s, 1H), 13.23(s, 1H) |
| XI-024 | DMSO-d6 1.07(t, 3H, J=7.5), 2.24(s, 3H), 2.74(q, 2H, J=6.9), 3.60(s, 2H), 5.49(s, 2H), 7.02(s, 1H), 7.22(d, 2H, J=8.4), 7.41(d, 2H, J=8.4), 8.40(s, 1H), 12.40(br s, 1H), 13.28(s, 1H) |
| XI-026 | DMSO-d6 1.07(t, 3H, J=7.5), 2.24(s, 3H), 2.74(q, 2H, J=7.5), 3.60(s, 2H), 5.52(s, 2H), 7.02(s, 1H), 7.14-7.20(m, 2H), 7.24-7.39(m, 3H), 8.40(s, 1H), 12.41(br s, 1H), 13.33(s, 1H) |

TABLE 285

| Comp. No. | ¹H-NMR(CDCl₃/TMS) δ |
|---|---|
| XI-028 | DMSO-d6 1.07(t, 3H, J=7.5), 1.24-1.73(m, 8H), 2.01(d, 2H, J=13.8), 2.21(s, 3H), 2.63(q, 2H, J=7.4), 5.46(br s, 2H), 7.08(d, 2H, J=5.7), 8.22(s, 1H), 8.52(d, 2H, J=6.0), 10.05(s, 1H), 12.18(br s, 1H) |
| XI-029 | DMSO-d6 1.06(t, 3H, J=7.4), 1.25-1.73(m, 8H), 2.02(d, 2H, J=12.9), 2.19(s, 3H), 2.66(q, 2H, J=7.4), 5.45(br s, 2H), 6.88(d, 1H, J=8.1), 6.98(d, 1H, J=9.9), 7.12(td, 1H, J=8.6 and 2.3), 7.40(m, 1H), 8.20(s, 1H), 10.11(s, 1H), 12.20(brs 1H) |
| XI-030 | DMSO-d6 1.08(t, 3H, J=7.7), 2.25(s, 3H), 2.74(q, 2H, J=7.6), 3.59(s, 2H), 5.51(br s, 2H), 6.97-7.15(m, 4H), 7.39(m, 1H), 8.40(s, 1H), 12.37(br s, 1H), 13.26(s, 1H) |
| XI-037 | DMSO-d6 1.09(t, 3H, J=7.5), 1.24-1.69(m, 8H), 2.01(d, 2H, J=13.8), 2.21(s, 3H), 2.66(q, 2H, J=7.5), 5.45(br s, 2H), 6.72(t, 1H, J=7.4), 7.15(t, 1H, J=7.5), 7.25-7.39(m, 2H), 8.21(s, 1H), 10.06(s, 1H), 12.18(br s, 1H) |
| XI-038 | DMSO-d6 1.11(t, 3H, J=7.4), 2.27(s, 3H), 2.76(q, 2H, J=7.4), 3.59(s, 2H), 5.50(br s, 2H), 6.86(t, 1H, J=8.0), 7.11(s, 1H), 7.14(t, 1H, J=7.5), 7.25-7.37(m, 2H), 8.42(s, 1H), 12.34(br s, 1H), 13.22(s, 1H) |
| XI-049 | DMSO-d6 1.04(t, 3H, J=7.5), 1.22-1.74(m, 8H), 2.03(d, 2H, J=13.5), 2.17(s, 3H), 2.68(q, 2H, J=7.2), 5.34(br s, 2H), 6.73(d, 2H, J=8.4), 6.92(d, 2H, J=8.4), 8.16(s, 1H), 9.39(s, 1H), 10.21(s, 1H), 12.17(br s, 1H) |
| XI-060 | DMSO-d6 1.25-1.50(m, 4H), 1.55-1.75(m, 4H), 2.67-2.80(m, 2H), 2.82-2.95(m, 2H), 3.60(s, 2H), 5.50(s, 2H), 6.85-6.97(m, 2H), 7.02(s, 1H), 7.16(m, 1H), 8.38(s, 1H), 12.38(br s, 1H), 13.21(s, 1H) |
| XI-061 | DMSO-d6 1.33(br s, 2H), 1.43(br s, 2H), 1.63(br s, 4H), 2.74(br s, 2H), 2.89(br s, 2H), 3.59(s, 2H), 5.58(br s, 2H), 7.02(s, 1H), 7.35(d, 2H, J=8.1), 7.81(d, 2H, J=8.1), 8.40(s, 1H), 12.38(br s, 1H), 13.21(s, 1H) |

TABLE 285-continued

| Comp. No. | $^1$H-NMR(CDCl$_3$/TMS) δ |
|---|---|
| XI-062 | DMSO-d6 1.07(t, 3H, J=7.5), 2.23(s, 3H), 2.77(q, 2H, J=7.4), 3.60(s, 2H), 5.39(br s, 2H), 6.72(d, 2H, J=8.4), 7.01-7.04(m, 3H), 8.37(s, 1H), 9.42(br s, 1H), 12.34(br s, 1H), 13.38(s, 1H) |
| XI-064 | DMSO-d6 1.25-1.74(m, 16H), 2.01(d, 2H, J=13.2), 2.68(br s, 2H), 2.80(br s, 2H), 5.54(br s, 2H), 7.27(d, 2H, J=8.4), 7.83(d, 2H, J=8.4), 8.20(s, 1H), 10.08(s, 1H), 12.21(br s, 1H) |
| XI-069 | DMSO-d6 1.16-1.80(m, 16H), 1.96-2.08(m, 2H), 2.63-2.74(m, 2H), 2.77-2.88(m, 2H), 5.46(s, 2H), 6.76-6.88(m, 2H), 7.17(m, 1H), 8.19(s, 1H), 10.09(s, 1H), 12.24(br s, 1H) |
| XI-238 | DMSO-d6 0.96(d, 6H, J=7.0), 1.16(t, 3H, J=7.0), 1.18-1.28(m, 2H), 1.30-1.53(m, 8H), 1.60-1.78(m, 3H), 2.14(s, 3H), 2.17-2.24(m, 2H), 2.43(s, 2H), 2.72(q, 2H, J=7.0), 3.97-4.13(m, 2H), 8.08(s, 1H), 9.73(s, 1H) |
| XI-239 | DMSO-d6 0.94(d, 6H, J=6.5), 1.14(t, 3H, J=7.5), 1.40-1.93(m, 10H), 2.02(m, 1H), 2.12(s, 3H), 2.40(s, 2H), 2.69(q, 2H, J=7.5), 3.97-4.09(m, 2H), 8.04(s, 1H), 9.76(s, 1H) |
| XI-240 | DMSO-d6 0.85-0.88(m, 6H), 0.96(d, 6H, J=6.5), 1.17(t, 3H, J=7.0), 1.33(m, 1H), 1.45-1.65(m, 4H), 1.72(m, 1H), 2.16(s, 3H), 2.44(t, 2H, J=6.5), 2.73(q, 2H, J=7.0), 3.96-4.15(m, 2H), 4.34(m, 1H), 8.12(s, 1H), 9.82(d, 1H, J=9.0) |

TABLE 286

| Comp. No. | $^1$H-NMR(CDCl$_3$/TMS) δ |
|---|---|
| XI-245 | DMSO-d6 1.01(t, 3H, J=7.2), 1.12(t, 3H, J=7.5), 1.26-1.59(m, 12H), 2.19(s, 2H), 2.52(t, 2H, J=7.5), 2.79(t, 2H, J=8.3), 3.23(s, 3H), 3.40(d, 2H, J=6.0), 3.61(t, 2H, J=5.4), 4.26(t, 2H, J=5.3), 8.20(s, 1H), 9.97(t, 1H, J=6.0), 12.16(br s, 1H) |
| XI-248 | DMSO-d6 0.98(d, 6H, J=6.6), 1.21(t, 3H, J=7.5), 1.48-1.62(m, 2H), 1.76(m, 1H), 2.24(s, 3H), 2.82(q, 1H, J=7.8), 3.81(s, 2H), 4.10-4.22(m, 2H), 8.34(s, 1H), 12.66(br s, 1H), 13.84(s, 1H) |
| XI-251 | DMSO-d6 0.98(d, 6H, J=6.6), 1.21(t, 3H, J=7.5), 1.48-1.60(m, 2H), 1.75(m, 1H), 2.23(s, 3H), 2.80(q, 2H, J=7.8), 3.82(s, 2H), 4.10-4.20(m, 2H), 7.31(s, 1H), 8.30(s, 1H), 12.64(br s, 1H), 13.39(s, 1H) |
| XI-255 | DMSO-d6 0.99(d, 6H, J=6.6), 1.20(t, 3H, J=7.5), 1.46-1.60(m, 2H), 1.76(m, 1H), 2.22(s, 3H), 2.79(q, 1H, J=7.5), 3.60(s, 2H), 4.08-4.20(m, 2H), 7.72(dd, 1H, J=2.1, 8.7), 8.19-8.24(m, 2H), 8.28(s, 1H), 12.45(br s, 1H), |
| XI-256 | DMSO-d6 0.95(t, 3H, J=7.5), 1.04(t, 3H, J=7.2), 1.13(t, 3H, J=7.2), 1.30-1.82(m, 8H), 2.14-2.74(m, 6H), 2.84(s, 2H), 3.50(t, 2H, J=10.5), 3.60-4.15(m, 4H), 8.15(s, 1H), 10.12(s, 1H) |
| XI-257 | DMSO-d6 0.96(s, 3H), 0.98(s, 3H), 1.15-1.80(m, 9H), 1.71(t, 3H, J=7.2), 2.16(s, 3H), 2.20-2.65(m, 4H), 2.74(q, 2H, J=7.2), 3.95-4.15(m, 2H), 8.07(s, 1H), 10.40(s, 1H) |
| XI-258 | DMSO-d6 0.95(s, 3H), 0.98(s, 3H), 1.18(t, 3H, J=7.5), 1.40-1.85(m, 5H), 2.15-2.30(m, 2H), 2.16(s, 3H), 2.74(q, 2H, J=7.5), 2.84(s, 2H), 3.50(t, 2H, J=11.1), 3.60-4.20(m, 4H), 8.11(s, 1H), 10.09(s, 1H) |
| XI-259 | DMSO-d6 0.92(s, 9H), 0.95(s, 3H), 0.97(s, 3H), 1.17(t, 3H, J=7.5), 1.40-1.82(m, 4H), 2.17(s, 3H), 2.74(q, 2H, J=7.5), 3.95-4.20(m, 2H), 4.44-4.56(m, 1H), 8.12(s, 1H), 10.15(d, 1H, J=8.4) |
| X1-268 | DMSO-d6 0.83(s, 3H), 0.89(s, 3H), 1.05(t, 4H, J=7.5), 1.10-1.36(m, 3H), 1.54-1.72(m, 2H), 2.02-2.16(m, 2H), 2.18(s, 3H), 2.65(q, 2H, J=7.8), 2.82(s, 2H), 5.41(br, 2H), 6.93(m, 1H), 7.24(m, 1H), 7.40(m, 1H), 8.21(s, 1H), 9.80(s, 1H), 12.02(br, 1H) |
| XI-271 | DMSO-d6 0.96(d, 6H, J=6.6), 1.18(t, 3H, J=7.5), 1.45-1.62(m, 4H), 1.73(m, 1H), 2.00-2.16(m, 6H), 2.16(s, 3H), 2.74(q, 2H, J=7.5), 3.40-3.52(m, 2H), 3.62-3.74(m, 2H), 4.00-4.14(m, 2H), 8.11(s, 1H), 9.96(s, 1H), 12.01(brs, |
| XI-272 | DMSO-d6 0.96(d, 6H, J=7.0), 1.17(t, 3H, J=7.0), 1.21-1.56(m, 12H), 1.72(m, 1H), 2.17(s, 3H), 2.19(s, 2H), 2.74(q, 2H, J=7.0), 3.40(d, 2H, J=6.5), 4.02-4.12(m, 2H), 8.14(s, 1H), 10.0(s, 1H), 12.1(s, 1H) |
| XI-273 | DMSO-d6 0.97(d, 6H, J=7.0), 1.17(t, 3H, J=7.0), 1.43-1.52(m, 2H), 1.73(m, 1H), 1.80-1.91(m, 2H), 2.16(s, 3H), 2.16-2.30(m, 4H), 2.74(q, 2H, J=7.0), 2.89(s, 2H), 4.00-4.10(m, 2H), 8.15(s, 1H), 10.1(s, 1H), 12.0(s, 1H) |
| XI-274 | DMSO-d6 0.87(s, 9H), 0.96(d, 6H, J=7.0), 1.17(t, 3H, J=7.0), 1.43-1.54(m, 2H), 1.59(m, 1H), 1.65-1.80(m, 2H), 2.16(s, 3H), 2.18(t, 2H, J=7.5), 2.74(q, 2H, J=7.0), 4.01-4.15(m, 3H), 8.13(s, 1H), 9.74(d, 1H, J=9.5), 12.0(s, 1H) |

TABLE 287

| Comp. No. | $^1$H-NMR(CDCl$_3$/TMS) δ |
|---|---|
| XI-276 | DMSO-d6 0.97(d, 6H, J=6.6), 1.18(t, 3H, J=7.5), 1.51(brdt, 2H, J=6.3), 1.7-2.3(m, 9H), 2.17(s, 3H), 2.76(q, 2H, J=7.2), 4.05-4.5(br, 2H), 8.10(s, 1H), 10.36(s, 1H) |
| XI-281 | DMSO-d6 0.99(d, 6H, J=6.6), 1.21(t, 3H, J=7.5), 1.47-1.60(m, 2H), 1.76(m, 1H), 2.22(s, 3H), 2.79(q, 1H, J=7.5), 4.06-4.22(m, 2H), 6.58(d, 1H, J=16.2), 7.59(d, 1H, J=15.9), 8.21(dd, 1H, J=2.4, 8.7), 8.30(d, 1H, J=8.7), 8.30(s, 1H), 8.61(d, 1H, J=2.1), 12.81(s, 1H) |
| XI-282 | DMSO-d6 1.20-1.85(m, 10H), 2.10-2.25(m, 2H), 2.60-2.75(m, 2H), 2.85(s, 2H), 2.95-3.05(m, 2H), 3.24(s, 3H), 3.50(t, 2H, J=11), 3.61(t, 2H, J=5.4), 3.64-3.74(m, 2H), 4.16-4.4(m, 2H), 8.11(s, 1H), 10.06(s, 1H) |
| XI-286 | DMSO-d6 1.02(t, 3H, J=7.5), 1.12(t, 3H, J=7.2), 1.45-2.90(m, 10H), 2.84(s, 2H), 3.24(s, 3H), 3.50(t, 2H, J=11), 3.61(t, 2H, J=5.3), 4.26(t, 2H, J=5.4), 8.17(s, 1H), 10.05(s, 1H) |
| XI-294 | DMSO-d6 0.99(d, 6H, J=6.6), 1.21(t, 3H, J=7.5), 1.48-1.70(m, 2H), 1.76(m, 1H), 2.27(s, 3H), 2.79(q, 2H, J=7.5), 4.08-4.22(m, 2H), 6.73(d, 1H, J=16.5), 7.57(d, 1H, J=15.9), 8.27(s, 1H), 9.02(s, 2H), 12.54(br s, 1H), 13.04(s, 1H) |
| XI-296 | 1.08(t, 3H, J=7.5), 1.20(t, 3H, J=7.5), 1.55(m, 2H), 1.78-1.87(m, 6H), 2.20(m, 2H), 2.51(q, 2H, J=7.5), 2.79-2.85(m, 2H), 3.05(s, 2H), 3.30(s, 3H), 3.67-3.71(m, 2H), 4.31(t, 2H, J=5.1), 8.37(s, 1H), 10.47(s, 1H) |
| XI-298 | 0.92(s, 3H), 0.96(s, 3H), 1.09(t, 3H, J=7.5), 1.22(t, 3H, J=7.5), 1.35-1.65(m, 6H), 2.05-2.24(m, 4H), 2.53(q, 2H, 7.5), 2.82-2.88(m, 2H), 3.30(s, 3H), 3.70(t, 2H, J=5.4), 4.34(t, 2H, J=5.4), 8.37(s, 1H), 10.66(1H, s) |
| XI-300 | DMSO-d6 0.85(d, 3H, J=7.0), 0.87(d, 3H, J=7.0), 0.96(d, 6H, J=7.0), 1.17(t, 3H, J=7.0), 1.29(m, 1H), 1.36-1.65(m, 5H), 1.65-1.82(m, 2H), 2.17(s, 3H), 2.20(t, 2H, J=7.0), 2.24(q, 2H, J=7.0), 4.00-4.10(m, 2H), 8.13(s, 1H), 9.64(d, 1H, J=9.0), 12.0(s, 1H) |
| XI-301 | DMSO-d6 0.95(d, 6H, J=7.0), 1.16(t, 3H, J=7.0), 1.42-1.52(m, 2H), 1.71(m, 1H), 2.17(s, 3H), 2.27(dd, 1H, J=9.0 and 15.5), 2.48(dd, 1H, J=7.5 and 15.5), 2.74(q, 2H, J=7.0), 4.00-4.10(m, 2H), 5.18(m, 1H), 8.17(s, 1H), |
| XI-302 | DMSO-d6 0.88(s, 9H), 0.96(d, 6H, J=6.5), 1.17(t, 3H, J=7.0), 1.41-1.55(m, 2H), 1.72(m, 1H), 2.16(s, 3H), 2.16(m, 1H), 2.56(m, 1H), 2.74(m, 2H), 3.98-4.16(m, 2H), 4.26(m, 1H), 8.13(s, 1H), 9.95(d, 1H, J=9.0) |
| XI-304 | 0.92(s, 3H), 0.96(s, 3H), 1.01(t, 6H, J=6.6), 1.26(t, 3H, 7.5), 1.38-1.61(m, 6H), 1.73-1.81(m, 1H), 2.21(s, 3H), 2.05-2.24(m, 4H), 2.77(q, 2H, 7.5), 4.14(m, 1H), 8.30(s, 1H), 10.75(1H, s) |
| XI-306 | DMSO-d6 1.04(t, 3H, J=7.5), 1.14-1.59(m, 8H), 2.09(m, 2H), 2.18(s, 3H), 2.65(q, 2H, J=7.2), 3.71(s, 2H), 3.96(s, 2H), 5.42(br s, 2H), 7.11-7.21(m, 4H), 8.21(s, 1H), 9.74(s, 1H), 12.51(br s, 1H) |
| XI-307 | DMSO-d6 0.98(d, 6H, J=6.6), 1.04(t, 3H, J=7.2), 1.12(t, 3H, J=7.5), 1.16-1.80(m, 13H), 1.98-2.10(m, 2H), 2.45-2.55(m, 2H), 2.63-2.75(m, 2H), 4.00-4.14(m, 2H), 8.13(s, 1H), 10.25(s, 1H), 12.19(br s, 1H) |

The testing examples of the above-mentioned compounds of the present invention are shown below.

Testing Example 1

Human Cannabinoid Receptor Bonding Inhibition Test

The human cannabinoid receptor used the membrane preparation (fraction) of the CHO cell which had made CB1 or CB2 receptor reveal stably. A prepared membrane sample product and a compound being tested, and [$^3$H] CP55940 of 38,000 dpm (the final concentration 0.5 nM: manufactured by NEN Life Science Products Corp.) were incubated in an assay buffer solution (50 mM tris-HCl buffer solution (pH 7.4) containing serum albumin of cattle, 1 nM EDTA, 3 mM MgCl$_2$) at 25° C. for 2 hours. After the incubation, they were filtered by a glass filter which had been processed with 1% polyethylene imine, and washed with 50 mM Tris-HCl buffer solution (pH 7.4), and then the radiation activity on the glass filter was found in the liquid scintillation counter. The non-specific bonding was measured in the presence of WIN55212-2 of 10 μM (a cannabinoid receptor agonist described in U.S. Pat. No. 5,081,122, manufactured by Sigma Corp.), and 50% inhibition concentration of the compound being tested (IC$_{50}$ value) to specific bonding was obtained. The Ki value of the compound being tested was calculated from the obtained IC$_{50}$ value and the Kd value of 3H CP55940. The results are shown in a table.

Testing Example 2 cAMP Formation Inhibition Experiment Through a Cannabinoid Receptor

A compound being tested was added in the CHO cell which had mad human CB1 or CB2 receptor reveal and incubated for 15 minutes, and then forskolin (the final concentration 4 μM, and manufactured by SIGMA Corp.) was added and the mixture was incubated for 20 minutes. After the reaction had been stopped by adding 1M hydrochloric acid, the amount of cAMP in the supernatant was measured with the use of Cyclic AMP kit (made by the CIS Diagnostic Corp.). The cAMP formation by the forskolin stimulation was assumed to be 100% to that with no forskolin stimulation, and the concentration (IC$_{50}$ value) of the compound being tested which showed the depressant effect of 50% was obtained. The compound being tested showed the agonist effect to the CB1 or CB2 receptor as shown in the table.

The results of Testing example 1 and Testing example 2 were shown in the following tables.

TABLE 288

| The numbers of the compounds | Binding activity (nM) | | Agonist activity (nM) | |
|---|---|---|---|---|
| | CB1 | CB2 | CB1 | CB2 |
| I-001 | <2 | <2 | <2 | |
| I-002 | 48 | 7.1 | 11 | 4.4 |
| I-019 | 2.9 | <2 | 8.1 | |
| I-038 | 7.1 | <2 | 34 | <2 |
| I-048 | 118 | 2.6 | 328 | 17 |
| I-052 | 32 | 7.3 | 49 | 8.1 |
| I-054 | 11 | 6 | 51 | 15 |
| I-084 | <2 | <2 | <2 | <2 |
| I-089 | <2 | <2 | <2 | <2 |
| I-094 | <2 | <2 | 9.0 | <2 |
| I-111 | 3.5 | <2 | <2 | |
| I-124 | 3.6 | <2 | <2 | |
| I-133 | 5.0 | <2 | 4.0 | |
| I-134 | <2 | <2 | <2 | |
| I-196 | <2 | <2 | <2 | |
| I-203 | <2 | <2 | <2 | |
| I-211 | 2.4 | <2 | <2 | |
| I-252 | <2 | <2 | <2 | |
| I-253 | <2 | <2 | <2 | |
| I-255 | 2.1 | <2 | <2 | |
| I-263 | <2 | <2 | <2 | |
| I-266 | 12 | <2 | 12.0 | |
| I-300 | <2 | <2 | <2 | |
| I-301 | <2 | <2 | <2 | |
| I-305 | <2 | <2 | <2 | |
| I-306 | <2 | <2 | <2 | |
| I-402 | 34 | <2 | >2000 | 5.7 |
| I-411 | >2000 | 382 | >2000 | 556 |
| I-424 | 357 | 3 | >2000 | 5.9 |
| I-493 | >2000 | 36 | >2000 | 24 |
| I-530 | 7 | <2 | 305 | |
| I-533 | 21 | <2 | >2000 | <2 |
| I-551 | 50 | 2.2 | 135 | <2 |
| I-556 | 8.1 | <2 | 357 | 3.5 |
| I-570 | 68 | 11 | 709 | 12 |
| I-572 | 39 | 4.4 | 397 | 2.4 |
| I-579 | 158 | 7.3 | 431 | 27 |
| I-580 | 24 | 7.4 | 41 | 48 |
| I-588 | 41 | 10 | 72 | 5.7 |
| I-590 | 66 | 16 | 51 | 2.4 |
| I-595 | 354 | 9.5 | 1208 | 30 |
| I-596 | 341 | 22 | 312 | 30 |
| I-599 | 37 | 4 | 37 | 13 |
| I-601 | 47 | 3.9 | 186 | 6.3 |
| I-604 | 16 | 2.5 | 55 | 4.8 |
| I-606 | 60 | 4.4 | 118 | 8.7 |

TABLE 289

| The numbers of the compounds | Binding activity (nM) | | Agonist activity (nM) | |
|---|---|---|---|---|
| | CB1 | CB2 | CB1 | CB2 |
| I-608 | 527 | 11 | >2000 | 3.5 |
| I-617 | 295 | 6.6 | 79 | 18 |
| II-031 | >2000 | 2.5 | | 9.9 |
| II-067 | >2000 | 13 | 685 | 4.9 |
| II-069 | 88 | 3.4 | 5.6 | 2.1 |
| II-073 | 88 | 6.2 | 11 | 0.2 |
| II-075 | 652 | 48 | 290 | 4.6 |
| II-076 | >2000 | 41 | >2000 | 1.2 |
| II-078 | 1452 | 27 | 252 | <2 |
| III-017 | 149 | 15 | 322 | 35 |
| IV-023 | 425 | 22 | 398 | 11 |
| IV-029 | 1318 | 43 | 606 | 22 |
| X-21 | 1767 | 3.3 | >2000 | 30 |
| X-54 | 93 | <2 | >2000 | 3.7 |
| X-64 | 580 | 18 | 454 | 15 |
| X-66 | >2000 | 92 | 549 | 50 |
| X-67 | >2000 | 96 | >2000 | 40 |
| X-115 | 1216 | 3.3 | >2000 | 8.6 |
| X-126 | 873 | 31 | 131 | 35 |
| X-128 | 608 | 10 | 152 | 3 |
| X-133 | >2000 | 5.5 | >2000 | <2 |
| X-138 | >2000 | 42 | >2000 | 30 |
| X-157 | 270 | 3.4 | 268 | <2 |
| X-174 | >2000 | 8.9 | >2000 | 9.8 |
| X-196 | >2000 | 31 | >2000 | 45 |
| X-197 | 1264 | 41 | 708 | 7.2 |
| X-202 | 1182 | 46 | >2000 | 81 |
| X-216 | 1767 | 3.3 | >2000 | 30 |
| X-220 | 555 | 18 | 1550 | 231 |
| X-222 | 1621 | 43 | >2000 | 57 |
| X-229 | 482 | 12 | 369 | 27 |
| X-231 | >2000 | 38 | >2000 | 35 |
| X-232 | >2000 | 15 | >2000 | 29 |
| X-233 | >2000 | 24 | >2000 | 15 |
| X-234 | 482 | 4 | 375 | 6.1 |
| X-235 | 950 | 3.7 | 270 | 4.7 |
| X-239 | 1420 | 10 | >2000 | 3.6 |
| X-240 | 793 | 6.2 | 468 | <2 |
| X-241 | >2000 | 57 | >2000 | 26 |
| XI-017 | 441 | 6.6 | 127 | 11 |
| XI-025 | 1361 | 54 | >2000 | 209 |
| XI-027 | 1361 | 54 | >2000 | 209 |
| XI-035 | >2000 | 31 | >2000 | 47 |
| Comparative compounds | | | | |
| 4-101*1 | 890 | 1.9 | | |
| 10-035*1 | 19 | 0.2 | | |

*1: The numbers of the compounds described in WO 02/053543.

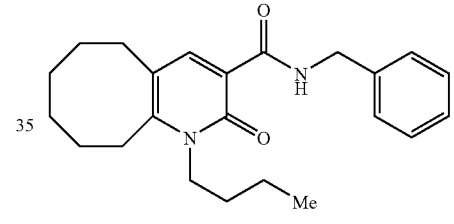

4-101

10-035

Testing Example 3

Anti-Pruritic Activity Test by Application

1) Preparation of the compound and the reagent: The compound being tested was dissolved in acetone (SIGMA). Compound 48/80 (SIGMA) was dissolved in physiological saline (m by Otsuka Pharmaceutical Co., Ltd.) so as to be 60 μg/mL.
2) Animals: Female Crj: CD-1 (ICR) mice of 6 to 10 age in week (Japan Charles Liver) were used as laboratory animals. The animals were fed in the barrier breeding room where 23±3° C. in room temperature, 30 to 70% in humidity, and the light and shade condition existed every 12 hours and feed (CE-2: Japan Crea) and the drinking water were freely taken. The hair of dorsa (from the cervical region of the back to the center of the back) of the animals were cut with a hair clipper two days or more before the anti-pruritic activity is evaluated, those with no wound, rubefaction, and thickening of the skin on the dehaired part were chosen and supplied to the experiment on the day of the evaluation.

3) Evaluation procedures: The acetone solution of the compound being tested was applied by 50 μL on the dehaired parts of the mice with a pipeter. On the mice of the control group, 50 μL of acetone was applied. The 15 minutes later, 50 μL (corresponding to 3 μg) of Compound 48/80 solution was injected intradermally in the compound applied parts with the use of a injector (Terumo Corporation), the mice were individually put in five observation cages made of acrylate resin at once, and the scratching action (action of scratching the injection part by the hind leg) frequency during 30 minutes was measured. The evaluation was carried out in one group of 5 to 7 mice.

4) Data processing: The experiment results were shown by the mean values. The test of the significant difference of the compound applying group to the control group was conducted with Welch's t-test, and $p<0.05$ was assumed to be significant.

The results were shown in the following table.

TABLE 290

| The numbers of the compounds | Itching inhibition ratio % (Concentration %) | The numbers of the compounds | Itching inhibition ratio % (Concentration %) | The numbers of the compounds | Itching inhibition ratio % (Concentration %) |
|---|---|---|---|---|---|
| I-001 | 53 (0.5) | I-002 | 68 (2.5) | I-019 | 74 (1.0) |
| I-038 | 67 (3.0) | I-048 | 58 (3.0) | I-052 | 80 (3.0) |
| I-054 | 63 (2.0) | I-084 | 60 (0.1) | I-089 | 65 (0.5) |
| I-094 | 60 (0.5) | I-111 | 55 (0.1) | I-124 | 49 (0.5) |
| I-133 | 56 (0.5) | I-134 | 91 (0.5) | I-196 | 47 (0.5) |
| I-203 | 86 (0.5) | I-211 | 70 (1.5) | I-252 | 96 (1.5) |
| I-253 | 70 (1.5) | I-255 | 93 (1.5) | I-263 | 57 (1.5) |
| I-266 | 64 (2.0) | I-300 | 41 (0.5) | I-301 | 39 (0.5) |
| I-305 | 61 (0.5) | I-306 | 83 (0.5) | I-402 | 59 (3.0) |
| I-411 | 80 (0.5) | I-424 | 62 (3.0) | I-530 | 74 (2.0) |
| I-533 | 73 (3.0) | I-551 | 51 (2.0) | I-556 | 76 (3.0) |
| I-570 | 84 (3.0) | I-572 | 97 (1.0) | I-579 | 99 (3.0) |
| I-580 | 98 (3.0) | I-588 | 81 (1.0) | I-590 | 75 (3.0) |
| I-595 | 108 (3.0) | I-596 | 60 (3.0) | I-599 | 67 (0.5) |
| I-601 | 67 (1.0) | I-604 | 95 (3.0) | I-606 | 86 (1.0) |
| I-608 | 75 (3.0) | I-617 | 96 (1.0) | II-031 | 55 (2.0) |
| II-067 | 68 (3.0) | II-069 | 84 (3.0) | II-073 | 58 (3.0) |
| II-075 | 95 (3.0) | II-076 | 86 (3.0) | II-078 | 94 (3.0) |
| III-017 | 76 (3.0) | IV-023 | 116 (3.0) | IV-029 | 93 (1.0) |
| X-21 | 106 (1.0) | X-54 | 100 (1.0) | X-64 | 99 (1.0) |
| X-66 | 71 (1.0) | X-67 | 79 (1.0) | X-115 | 67 (0.5) |
| X-216 | 106 (1.0) | X-220 | 97 (0.5) | X-229 | 105 (0.5) |
| XI-035 | 69 (0.5) | | | | |
| Comparative compounds | | 4-101*1 | 7.5 (5.0) | 10-035*1 | 22 (5.0) |

*1: The numbers of the compounds described in WO02/053543.
The above-mentioned compounds of the present invention except 4-101 and 10-035 described in WO 02/053543 showed significant differences by being $p < 0.05$.

Testing Example 4

Anti-Pruritic Activity Test by Oral Administration

1) Preparation of the compound and the reagent: The compound being tested was suspended in 0.5% aqueous solution of methyl cellulose (Kanto Chemicals Co., Ltd.). Compound 48/80 (SIGMA) was dissolved in physiological saline (m by Otsuka Pharmaceutical Co., Ltd.) so as to be 60 μg/mL.

2) Animals: Female Crj:CD-1 (ICR) mice of 6 to 10 age in weeks (Japan Charles Liver) were used as laboratory animals. The animals were fed in the barrier breeding room where 23±3° C. in room temperature, 30 to 70% in humidity, and the light and shade condition existed every 12 hours and feed (CE-2: Japan Crea) and the drinking water were freely taken. The hair of dorsa (from the cervical region of the back to the center of the back) of the animals were cut with a hair clipper two days or more before the anti-pruritic activity is evaluated, those with no wound, rubefaction, and thickening of the skin on the dehaired part were chosen and supplied to the experiment on the day of the evaluation.

3) Evaluation procedures: The suspension of the compound being tested was orally administered by volume of 5 mL/kg on the dehaired parts of the mice with an oral sound. To the mice of the control group, methyl cellulose was orally administered by volume of 5 mL/kg. The 30 minutes later, 50 mL (corresponding to 3 μg) of Compound 48/80 solution was injected intradermally in the back dehaired regions with the use of a injector (Terumo Corporation), the mice were individually put in five observation cages made of acrylate resin at once, and the scratching action (action of scratching the injection part by the hind leg) frequency during 30 minutes was measured. The evaluation was carried out in one group of 4 to 8 mice.

4) Data processing: The experiment results were shown by the mean values. The test of the significant difference of the compound administration group to the control group was made with Welch's t-test, and $p<0.05$ was assumed to be significant.

Testing Example 5

Test with a Rat OVA Asthma Model

Egg albumin (OVA) of 0.1 mg/mL and aluminum hydroxide gel of 1 mg were administered in the abdominal cavity of Brown Norway (BN) rat, and the rat was sensitized to them. On 12, 19, 26, and 33 days after the sensitization, 1% OVA solution was made an aerosol with ultrasonic nebulizer (NE-U17), the rat which had put in the chamber for the exposure was subjected to the inhalation exposure of this aerosol for 30 minutes. A compound of the present invention was orally administered by 10 mg/kg once a day continuously for three days since one hour before an antigen exposure of the fourth times. To the control group, 0.5% methyl cellulose was administered instead of a compound of the present invention.

On the three days after the antigen exposure of the fourth times, under the pentobarbital anesthesia (80 mg/kg, i.p.), acetylcholine (3.9, 7.8, 15.6, 31.3, 62.5, 125, 250 and 500 µg/kg) was injected in the cervix region vein of the rat with one by one in five minutes from a low dosage, and the airway shrinkage reaction (increase in insufflation pressure) caused immediately after the injection was measured by Konnzett & Rossler method partly modified. The depressant rate of airway hyperreactivity exacerbation to the control group was calculated from the area under the curve (AUC) calculated from the concentration reaction curve of the acetylcholine.

After the measurement of the airway hyperreactivity had ended, the bronchus alveoli of the rat were washed three times with the physiological saline of 5 mL, the total cell count in the cleaning solution was counted by using the hemacytometer under an optical microscope, and the depressant rate of the inflammatory cellular infiltration to the control group was calculated. In addition, the mucin in the airway cleaning solution is measured by the ELISA method using jacalin which is mucin binding lectin, and the depressant rate of the mucus secretion to the control group was calculated.

Testing Example 6

Test with a Guinea Pig Nasal Congestion Model

The methods of measuring the nasal resistance and evaluating the nasal decongestion with the use of a guinea pig are shown below. One percent egg albumin (OVA) solution was made an aerosol, and this aerosol was made to be inhaled in a Hartley male guinea pig for ten minutes for each twice every week and the guinea pig was sensitized to it. On the seven days later, the antigen was exposed and the reaction was caused. Under the pentobarbital anesthesia (30 mg/kg, i.p.), the guinea pig's trachea was incised and cannulas were installed in the nasal cavity side and the lung side respectively, and on the lung side, an artificial respirator, which supplies with air 60 times per minute and 4 mL each time, was connected. After guinea pig's spontaneous respiration had been stopped with galamine (2 mg/kg, i.v.), the air of 70 times per minute and 4 mL once was sent to the nasal rostrum from the cannula on the nasal cavity side with the artificial respirator, and air pressure necessary for the air supplying was measured by transducer which installed in the side branch and the pressure was assumed the index of the nasal resistance. The antigen was exposed by generating the aerosol of 3% OVA solution for three minutes between the artificial respirator and the nasal cavity cannula. A compound of the present invention was injected in the vein ten minutes before the antigen exposure. As for the result, the nasal resistance was continuously measured during 30 minutes from 0, and the depressant rate to the vehicle was obtained based on the index of the AUC (nasal resistance (cm $H_2O$) in the vertical axis and time (0 to 30 minutes) in the horizontal axis) of the 30 minutes.

Testing Example 7

Influence of Cigarette Smoke Exposure on the Deterioration of Guinea Pig's Breath Function (a COPD Model)

The main current smoke of a cigarette with a filter tip commercially available (Highlight, nicotine 1.4 mg content, and tar 17 mg content, Japan Tabaco Inc.) was exposed to the nose and the mouth of a Hartley guinea pig (obtained from Japan SLC Co., Ltd.) at the rate of 30 pieces of the cigarettes a day for five days a week during 30 days with a cigarette smoke exposure device for an animal (manufactured by Thinker N Co., Ltd.). (Wright J L, Churg A. Cigarette smoke causes physiologic and morphologic changes of emphysema in the guinea pig Am. Rev. Respir. Dis. 1990 142:1422-8.).

The compound (1) was suspended in 0.5% methyl cellulose, and orally administered at the rate of 10 mg/kg three times a day. To the medium group, 0.5% methyl cellulose of 5 ml/kg was orally administered three times a day.

After 16 to 24 hours had passed from the final cigarette smoke exposure, the trachea incision of the guinea pig was conducted under urethane (100 mg/kg, i.p.) anesthesia, and a cannula was incubated and installed in a respiratory function measuring device system, a maneuver (manufactured by Baxco Co., Ltd.) for small animals. The respiratory function of the guinea pig was measured according to the protocol of the maneuver.

In the medium administered control group and the medicine administered group, the amount of a functional residual air, the increase in the total lung capacity, and the decrease in the dynamic lung compliance by the cigarette smoke exposure were compared and the test of the significant difference was conducted. The data will be shown by the average±the standard deviation. The statistical test was conducted by the two-tailed test of the t-test method of Student, and judged to be a significant difference at $P<0.05$.

The compound (1) showed a significant difference of $P<0.05$ to the increase in the amount of a functional residual air by administering 30 mg/kg a day.

The compound (1) showed a significant difference of $P<0.05$ to the increase in the total lung capacity by administering 30 mg/kg a day.

Testing Example 8

Depression Effect on the Formalin Nociceptive Stimulus in ICR Mouse

The depression effect of a compound of the present invention on the formalin nociceptive stimulus is examined by using a ICR male mouse (five age in week) for the examination. The compound being tested is dissolved in sesame oil, and the solution is orally administered in the mouse two hours before the formalin administration, then formalin (2%, 20 µL) is subcutaneously administered in the right hind leg. In this experiment, the measurement is conducted for 30 minutes after the administration of formalin, and the measurement will be divided in two phases of 5 minutes immediately after the administration of formalin (the first phase) and 20 minutes from 10 to 30 minutes after the administration (the second phase). As for the strength of the pain, the depression effect of the compound being tested is measured based on the index of the total time of licking action and biting action to the right hind leg, and the ED50 value is calculated.

Testing Example 9

Dermatitis Model Inducing DNFB

Female BALB/cmouse was used for the test. 30 μL of 0.5% acetone solution of 1-fluoro-2,4-dinitrobenzene (DNFB) was applied on the mouse abdomen once a day for two days. On 6, 8, and 10 days after the first sensitization, 10 μL of 0.3% acetone solution of DNFB was applied on the inside and outside of both ears. The compound was suspended in the 0.5% methyl cellulose solution and orally administered once a day on 6 to 12 days after the first sensitization. The thickness of the pinnae of the mouse (the degree of the edema) was measured with calipers (a micrometer) every day during the experiment from the sixth day of the sensitization. Each data will be shown by the average±the standard error. The statistical test was conducted by the t-test method of Welch, and judged to be a significant difference at $P<0.05$.

FORMULATION EXAMPLES

The following formulation examples of 1 to 10 are nothing but exemplification and do not intend any ranges of the invention to be limited. The term of "active constituent" means the compound of the present invention, a pharmaceutically acceptable salt or a solvate thereof.

Formulation Example 1

The Hard Gelatin Capsule is Manufactured by the Use of the Following Constituents

|  | Dosage (mg/capsule) |
|---|---|
| Active constituent | 250 |
| Starch (dried) | 200 |
| Magnesium stearate | 10 |
| Total | 460 mg |

Formulation Example 2

The Tablet is Manufactured by the Use of the Following Constituents

|  | Dosage (mg/tablet) |
|---|---|
| Active ingredient | 250 |
| Cellulose (microcrystal) | 400 |
| Silicon dioxide (fume) | 10 |
| Stearic acid | 5 |
| Total | 665 mg |

The constituents are mixed and compressed to make the tablet of 665 mg in weight each.

Formulation Example 3

An Aerosol Solution Containing the Following Constituents is Manufactured

|  | Weight |
|---|---|
| Active ingredient | 0.25 |
| Ethanol | 25.75 |
| Propellant (chlorodifluoromethane) | 74.00 |
| Total | 100.00 |

The active constituent is mixed with ethanol, and this mixture is added in part of propellant 22 and cools to −30° C., and then the mixture moves to the filling device. After that, the necessary amount is supplied to a stainless steel container and diluted with the remaining propellant. A bubble unit is installed in the container.

Formulation Example 4

Tablets Containing 60 mg of an Active Constituent are Manufactured as Follows

| Active ingredient | 60 mg |
|---|---|
| Starch | 45 mg |
| Microcrystalline cellulose | 35 mg |
| Polyvinyl pyrrolidone (10% aqueous solution) | 4 mg |
| Sodium carboxymethyl starch | 4.5 mg |
| Magnesium stearate | 0.5 mg |
| Talc | 1 mg |
| Total | 150 mg |

The active ingredient, the starch, and the cellulose are passed through No. 45 meshes U.S. sieve and mixed enough. The aqueous solution containing the poly vinylpyrrolidone is mixed with the obtained powder, and then the mixture is passed through No. 14 mesh U.S. sieve. Thus obtained granules are dried at 50° C. and passed through No. 18 mesh U.S. sieve. The sodium carboxymethyl starch, the magnesium stearate, and the talc, all of which have been passed through No. 60 mesh U.S. sieve in advance, are added to the granules and mixed, and then the mixture is compressed with a tableting machine and tablets of 150 mg in weight each are obtained.

Formulation Example 5

Capsules Containing 80 mg of an Active Constituent are Manufactured as Follows

| Active ingredient | 80 mg |
|---|---|
| Starch | 59 mg |
| Microcrystalline cellulose | 59 mg |
| Magnesium stearate | 2 mg |
| Total | 200 mg |

The active ingredient, the starch, the cellulose, and the magnesium stearate are mixed and passed through No. 45 mesh U.S. sieve, and then the mixture is filled to the hard gelatin capsule by 200 mg each.

Formulation Example 6

Suppositories Containing 225 mg of an Active Constituent are Manufactured as Follows

| Active ingredient | 225 mg |
|---|---|
| Saturated fatty acid glyceride | 2000 mg |
| Total | 2225 mg |

The active ingredient is passed through No. 60 mesh U.S. sieve, and suspended in the saturated fatty acid glyceride which has been melted by being heated to the minimum necessary in advance Then, this mixture is put in a mold of 2 g in appearance and cooled.

Formulation Example 7

A Suspension Agent Containing 50 mg of an Active Constituent is Manufactured as Follows

| Active ingredient | 50 mg |
|---|---|
| Sodium carboxymethyl cellulose | 50 mg |
| Syrup | 1.25 ml |
| Benzoic acid solution | 0.10 ml |
| Perfume | q.v. |
| Coloring matter | q.v. |
| Total after adding refined water | 5 ml |

The active ingredient is passed through No. 45 mesh U.S. sieve and mixed with sodium carboxymethyl cellulose and syrup to make a smooth paste. The benzoic acid solution and the perfume are diluted with part of the water, and they are added in the paste and stirred. Then, the sufficient quantity of water is added to make the necessary volume.

Formulation Example 8

A Drug Product for a Vein is Manufactured as Follow

| Active ingredient | 100 mg |
|---|---|
| Saturated fatty acid glyceride | 1000 ml |

The solution of the above-mentioned constituents is usually administered to the patient at the speed of one ml per minute in the vein.

Formulation Example 9

A Gel Agent is Manufactured as Follows

| Active ingredient | 100 mg |
|---|---|
| Isoptopanol | 500 mg |
| Partially hydrophobic hydroxymethyl celloulose | 150 mg |
| Total after adding refined water | 10000 mg |

The active ingredient is dissolved in the isopropanol, and the solution is added in partially hydrophobic hydroxymethyl cellulose which has been uniformly dispersed. In addition, water is added, and then the mixture is uniformly mixed with a stirrer to dissolve all constituents.

Formulation Example 10

A Droplet Distributed Ointment is Manufactured as Follows

| Active ingredient | 100 mg |
|---|---|
| Benzyl alcohol | 400 mg |
| Sorbitan sesquistearate | 400 mg |
| Liquid paraffin | 500 mg |
| White petrolatum | 8600 mg |
| Total | 10000 mg |

The active ingredient is dissolved in benzyl alcohol, and the solution is added in the mixture of the sorbitan sesquistearate, the liquid paraffin, and the white petrolatum and mixed with a stirrer to adjust.

INDUSTRIAL APPLICABILITY

Such 3-carbamoyl-2-pyridone derivatives were found that have a strong agonistic activity to the cannabinoid receptor, are low in inhibition activity for enzyme (CYP) and in the central nerve side effects, are excellent in photostability, and/or have excellent transdermal absorbency or oral absorbency. Moreover, the pharmaceutical composition, which contains the said compound as an active ingredient, was found showing anti-pruritic effect, especially excellent anti-pruritic effect as a drug for external use.

The invention claimed is:

1. A compound of the formula (I):

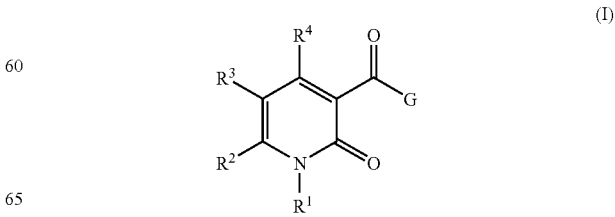

wherein, $R^1$ is C1-C8 alkyl optionally substituted with one to three halogen or C3-C8 cycloalkyl;
$R^2$ and $R^3$ taken together with the adjacent carbon atoms form a non-aromatic 8 membered carbon ring;
$R^4$ is hydrogen;
G is a group represented by formula:

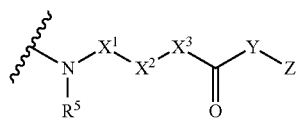

wherein $R^5$ is hydrogen;
$X^1$ is a single bond;
$X^2$ is heteroaryldiyl;
$X^3$ is C1-C3 alkylene;
Y is —O—;
Z is hydrogen;
or a pharmaceutically acceptable salt thereof.

2. The compound according to claim 1, wherein the compound is a group selected from the groups represented by the formulas:

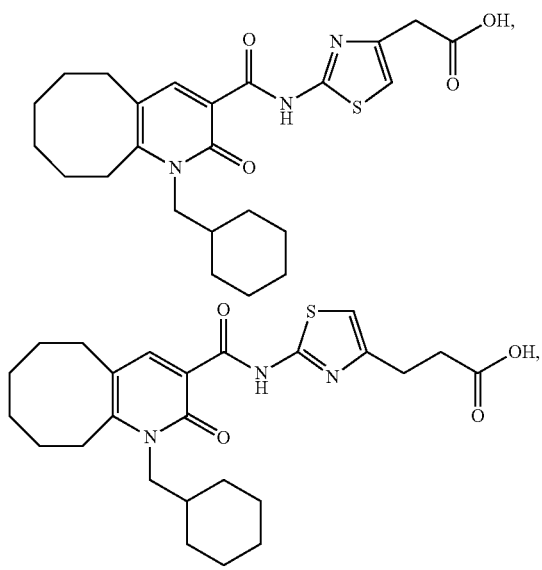

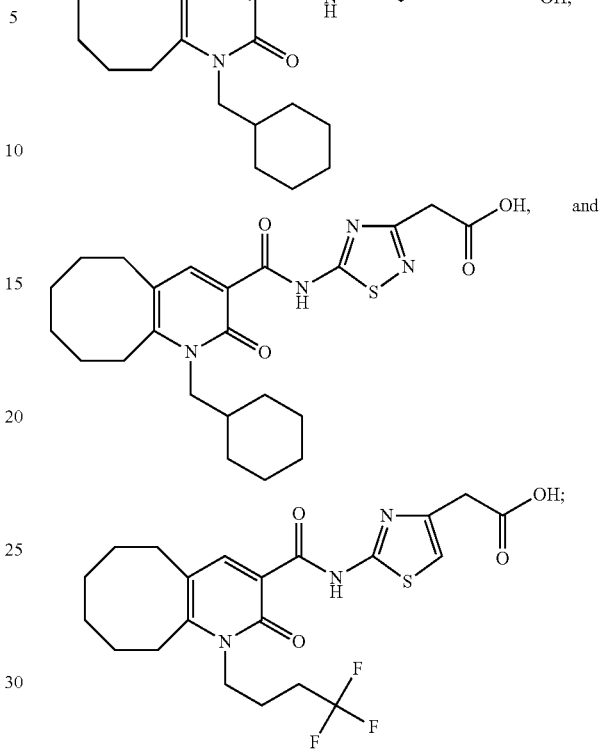

or a pharmaceutically acceptable salt thereof.

3. A pharmaceutical composition comprising the compound, or a pharmaceutically acceptable salt thereof, according to any one of claims 1 and 2 as an active ingredient.

4. The pharmaceutical composition according to claim 3, comprising the active ingredient in an amount effective as an anti-pruritus agent.

5. A method of alleviating itching in a mammal, which comprises administering to said mammal a therapeutically effective amount of a compound, or a pharmaceutically acceptable salt thereof, according to anyone of claims 1 and 2.

* * * * *

UNITED STATES PATENT AND TRADEMARK OFFICE
CERTIFICATE OF CORRECTION

| | | |
|---|---|---|
| PATENT NO. | : 8,178,681 B2 | Page 1 of 1 |
| APPLICATION NO. | : 11/628804 | |
| DATED | : May 15, 2012 | |
| INVENTOR(S) | : Natsuki Ishizuka et al. | |

It is certified that error appears in the above-identified patent and that said Letters Patent is hereby corrected as shown below:

Title page, item (57), line 7 of ABSTRACT,
"taken together with may form" should read --taken together with the adjacent carbon atoms may form--.

Title page, item (57), line 10 of ABSTRACT,
"an the like" should read --and the like--.

Title page, item (57), line 15 of ABSTRACT,
"and the like, and the like;" should read --and the like;--.

Title page, item (57), line 20 of ABSTRACT,
"for oral used" should read --for oral use--.

Signed and Sealed this
Eleventh Day of September, 2012

David J. Kappos
*Director of the United States Patent and Trademark Office*